US010675355B2

(12) United States Patent
Rich et al.

(10) Patent No.: US 10,675,355 B2
(45) Date of Patent: Jun. 9, 2020

(54) VAR2CSA-DRUG CONJUGATES

(71) Applicants: ZYMEWORKS INC., Vancouver (CA); VAR2 PHARMACEUTICALS APS, Copenhagen N (DK)

(72) Inventors: James R. Rich, Vancouver (CA); John Babcook, Vancouver (CA); Ali El-Salanti, Farum (DK); Mads Daugaard, Vancouver (CA); Madeleine Dahlback, Svedala (SE); Bradley J. Hedberg, Sooke (CA); Geoffrey C. Winters, Vancouver (CA); Alexander L. Mandel, Vancouver (CA); Elyse Marie Josée Bourque, Etang-du-Nord (CA); Tom Han Hsiao Hsieh, Vancouver (CA)

(73) Assignees: VAR2 PHARMACEUTICALS APS, Copenhagen (DK); ZYMEWORKS INC., Vancouver, BC (CA)

( * ) Notice: Subject to any disclaimer, the term of this patent is extended or adjusted under 35 U.S.C. 154(b) by 383 days.

(21) Appl. No.: 15/108,258

(22) PCT Filed: Dec. 29, 2014

(86) PCT No.: PCT/CA2014/000919
§ 371 (c)(1),
(2) Date: Jun. 24, 2016

(87) PCT Pub. No.: WO2015/095952
PCT Pub. Date: Jul. 2, 2015

(65) Prior Publication Data
US 2017/0246310 A1 Aug. 31, 2017
US 2018/0117163 A9 May 3, 2018

Related U.S. Application Data

(60) Provisional application No. 61/921,242, filed on Dec. 27, 2013, provisional application No. 62/051,886, filed on Sep. 17, 2014, provisional application No. 62/051,899, filed on Sep. 17, 2014.

(51) Int. Cl.
*A61K 47/64* (2017.01)
*C07K 14/445* (2006.01)
*A61K 38/05* (2006.01)
*A61K 47/54* (2017.01)

(52) U.S. Cl.
CPC .............. *A61K 47/64* (2017.08); *A61K 38/05* (2013.01); *A61K 47/54* (2017.08); *C07K 14/445* (2013.01)

(58) Field of Classification Search
CPC .................. A61K 38/05; A61K 47/48246
See application file for complete search history.

(56) References Cited

U.S. PATENT DOCUMENTS

| | | |
|---|---|---|
| 5,349,066 A | 9/1994 | Kaneko et al. |
| 5,502,032 A | 3/1996 | Haupt et al. |
| 5,635,483 A | 6/1997 | Pettit et al. |
| 5,663,149 A | 9/1997 | Pettit et al. |
| 5,780,588 A | 7/1998 | Pettit et al. |
| 6,124,431 A | 9/2000 | Sakakibara et al. |
| 6,153,590 A | 11/2000 | Anderson et al. |
| 6,323,315 B1 | 11/2001 | Pettit et al. |
| 6,569,834 B1 | 5/2003 | Pettit et al. |
| 6,870,028 B1 | 3/2005 | Andersen et al. |
| 6,884,869 B2 | 4/2005 | Pettit et al. |
| 7,064,211 B2 | 6/2006 | Kowalczyk et al. |
| 7,078,562 B2 | 7/2006 | Furukawa et al. |
| 7,078,572 B2 | 7/2006 | Kendall |
| 7,098,308 B2 | 8/2006 | Senter et al. |
| 7,192,972 B2 | 3/2007 | Kowalczyk et al. |
| 7,211,696 B2 | 5/2007 | Werbovetz et al. |
| 7,256,257 B2 | 8/2007 | Doronina et al. |
| 7,390,910 B2 | 6/2008 | Zask et al. |
| 7,410,951 B2 | 8/2008 | Andersen et al. |
| 7,423,116 B2 | 9/2008 | Doronina et al. |
| 7,498,298 B2 | 3/2009 | Doronina et al. |
| 7,528,152 B2 | 5/2009 | Kowalczyk et al. |
| 7,579,323 B1 | 8/2009 | Andersen et al. |
| 7,585,976 B2 | 9/2009 | Campagna et al. |
| 7,626,023 B2 | 12/2009 | Zask et al. |
| 7,659,241 B2 | 2/2010 | Senter et al. |
| 7,745,394 B2 | 6/2010 | Doronina et al. |
| 7,772,397 B2 | 8/2010 | Andersen et al. |
| 7,851,437 B2 | 12/2010 | Senter et al. |

(Continued)

FOREIGN PATENT DOCUMENTS

| | | |
|---|---|---|
| EP | 2620433 A1 | 7/2013 |
| WO | WO 1996/14856 A1 | 5/1996 |

(Continued)

OTHER PUBLICATIONS

Clausen (Structural and Functional Insight into How the Plasmodium falciparum VAR2CSA Protein Mediates Binding to Chondroitin Sulfate A in Placental Malaria, JBC Jul. 6, 2012, 287:23332-23345) (Year: 2012).*
Chen (Fusion Protein Linkers: Property, Design and Functionality, Adv Drug Deliv Rev. 2013, 65:1357-1369). (Year: 2013).*
Alexander-Bryant et al., "Bioengineering Strategies for Designing Targeted Cancer Therapies," Adv Cancer Res, vol. 118, pp. 1-59 (2013).
Bongo et al., "Efficient approach for profiling photoaffinity labeled peptides with a cleavable biotinyl photoprobe," Bioorganic & Medicinal Chemistry Letters, vol. 20, pp. 1834-1836 (2010).

(Continued)

*Primary Examiner* — Amber D Steele
(74) *Attorney, Agent, or Firm* — Squire Patton Boggs (US) LLP; Todd A. Lorenz; David H. Goetz

(57) ABSTRACT

VAR2CSA-drug conjugates having biological activity are disclosed. Methods associated with preparation and use of such conjugates, as well as pharmaceutical compositions comprising such conjugates, are also disclosed.

43 Claims, 24 Drawing Sheets

Specification includes a Sequence Listing.

(56) References Cited

U.S. PATENT DOCUMENTS

| | | | |
|---|---|---|---|
| 8,097,648 B2 | 1/2012 | Littlefield et al. | |
| 8,129,407 B2 | 3/2012 | Kowalczyk et al. | |
| 8,394,922 B2 | 3/2013 | Cheng et al. | |
| 8,609,105 B2 | 12/2013 | Senter et al. | |
| 8,633,224 B2 | 1/2014 | Kowalczyk et al. | |
| 8,992,932 B2 | 3/2015 | Lerchen et al. | |
| 9,522,876 B2 | 12/2016 | Winters et al. | |
| 9,801,951 B2 * | 10/2017 | Miao | C07D 207/08 |
| 9,879,086 B2 | 1/2018 | Winters et al. | |
| 2004/0121965 A1 | 6/2004 | Greenberger et al. | |
| 2005/0171014 A1 | 8/2005 | Tarasova et al. | |
| 2006/0106082 A1 | 5/2006 | Del Soldato et al. | |
| 2007/0026478 A1 | 2/2007 | Greenberger et al. | |
| 2008/0300192 A1 | 2/2008 | Doronina et al. | |
| 2008/0108820 A1 | 5/2008 | Campagna et al. | |
| 2008/0305044 A1 | 12/2008 | McDonagh et al. | |
| 2009/0155289 A1 | 6/2009 | Roberts et al. | |
| 2009/0264487 A1 | 10/2009 | Anderson et al. | |
| 2011/0020343 A1 | 1/2011 | Senter et al. | |
| 2011/0027274 A1 | 2/2011 | Cheng et al. | |
| 2011/0293704 A1 * | 12/2011 | Holst | A61K 39/0011 424/450 |
| 2012/0041196 A1 | 2/2012 | Raffaella et al. | |
| 2013/0095123 A1 | 4/2013 | Lerchen et al. | |
| 2013/0129753 A1 | 5/2013 | Doroski et al. | |
| 2013/0190248 A1 | 7/2013 | Mendelsohn et al. | |
| 2013/0231320 A1 | 9/2013 | Kawaminami et al. | |
| 2014/0315954 A1 | 10/2014 | Winters et al. | |
| 2015/0105540 A1 | 4/2015 | Miao et al. | |
| 2015/0141646 A1 | 5/2015 | Miao et al. | |
| 2015/0250896 A1 | 9/2015 | Zhao | |
| 2015/0284416 A1 | 10/2015 | Zhao | |
| 2016/0038606 A1 | 2/2016 | Winters et al. | |
| 2016/0075735 A1 | 3/2016 | Winters et al. | |
| 2016/0130299 A1 | 5/2016 | Perez et al. | |
| 2016/0311853 A1 | 10/2016 | Geirstanger et al. | |
| 2017/0029490 A1 | 2/2017 | Winters et al. | |
| 2017/0247408 A1 | 8/2017 | Winters et al. | |

FOREIGN PATENT DOCUMENTS

| | | | |
|---|---|---|---|
| WO | WO 1996/33211 A1 | 10/1996 | |
| WO | WO 1999/32509 A2 | 7/1999 | |
| WO | WO 2001/18032 A2 | 3/2001 | |
| WO | WO 2002/088172 A2 | 11/2002 | |
| WO | WO 2003/072754 A2 | 9/2003 | |
| WO | WO 2003/082268 A2 | 10/2003 | |
| WO | WO 2004/010957 A2 | 2/2004 | |
| WO | WO 2004/026293 A2 | 4/2004 | |
| WO | WO 2004/026814 A2 | 4/2004 | |
| WO | WO 2005/026169 A1 | 3/2005 | |
| WO | WO 2005/030794 A2 | 4/2005 | |
| WO | WO 2005/039492 A2 | 5/2005 | |
| WO | WO 2006/027711 A2 | 3/2006 | |
| WO | WO 2006/039652 A2 | 4/2006 | |
| WO | WO 2006/132670 A2 | 12/2006 | |
| WO | WO 2007/008603 A1 | 1/2007 | |
| WO | WO 2007/008848 A2 | 1/2007 | |
| WO | WO 2009/047264 A2 | 4/2009 | |
| WO | WO 2009/059309 A2 | 5/2009 | |
| WO | WO 2009/095447 A1 | 8/2009 | |
| WO | WO 2009/117531 A1 | 9/2009 | |
| WO | WO 2010/115981 A1 | 10/2010 | |
| WO | WO 2011/154359 A1 | 12/2011 | |
| WO | WO 2012/014073 A2 | 2/2012 | |
| WO | WO 2012/113847 A1 | 8/2012 | |
| WO | WO 2012/123957 A1 | 9/2012 | |
| WO | WO 2012/135440 A1 | 10/2012 | |
| WO | WO 2013/068874 A1 | 5/2013 | |
| WO | WO 2013/117705 A1 | 8/2013 | |
| WO | WO-2013117705 A1 * | 8/2013 | C07K 14/445 |
| WO | WO 2013/173391 A1 | 11/2013 | |
| WO | WO 2013/173392 A1 | 11/2013 | |
| WO | WO 2013/173393 A1 | 11/2013 | |
| WO | WO 2013/185117 A1 | 12/2013 | |
| WO | WO 2013/192360 A1 | 12/2013 | |
| WO | WO 2014/004376 A2 | 1/2014 | |
| WO | WO 2014/080251 A1 | 5/2014 | |
| WO | WO 2014/100762 A1 | 6/2014 | |
| WO | WO 2014/126836 A1 | 9/2014 | |
| WO | WO 2014/144871 A1 | 9/2014 | |
| WO | WO-2014144871 A1 * | 9/2014 | C07D 211/60 |
| WO | WO 2015/095301 A2 | 6/2015 | |
| WO | WO 2015/095952 A1 | 7/2015 | |
| WO | WO 2015/095953 A1 | 7/2015 | |
| WO | WO 2016/041082 A1 | 3/2016 | |

OTHER PUBLICATIONS

Cancer-prevention, http://www.mcancer.org/cancer-prevention, downloaded Nov. 10, 2017.

Cheng-Bin Yim et al., "Spacer Effects on in vivo Properties of DOTA-Conjugated Dimeric [Tyr3]Octreotate Peptides Synthesized by a "Cul-Click" and "Sulfo-Click" Ligation Method," Chembiochem, vol. 12, No. 5, pp. 750-760 (2011).

Govindaraju et al., "Supporting Information Surface Immobilization of Biomolecules by Click Sulfonamide Reaction," Supplemental Material (ESI) for Chemical Communications, The Royal Society of Chemistry (2008) Downloaded from: (http://www.rsc.org/suppdata/cc/b8/b80674c/b806764c.pdf).

Li et al., "Immunotoxins and Cancer Therapy," Cellular & Molecular Immunology, vol. 6, No. 2, pp. 106-112 (2005).

Matsuoka et al., "Preparation of peptides or analogs containing substituted phenethylamine moiety as motilin receptor antagonists," caplus an, PCT Int. Appl., p. 403, 2000:535162.

Sigmund, F. and Wesseley, F., "Untersuchungen über α-Amino-N-Carbonsäureanhydride. II.," Z. Physiol. Chem, vol. 157, pp. 91-105 (1926).

Dahlback M et al., "The Chondroitin Sulfate A-binding Site of the VAR2CSA Protein Involves Multiple N-terminal Domains," J. Biol. Chem., vol. 286, No. 18, pp. 15908-15917 (2011).

Zakeri B et al., "Peptide tag forming a rapid covalent bond to a protein, through enginerering a bacterial adhesin," Proc. Natl. Acad. Sci. USA, vol. 109, No. 12, pp. E690-E697 (2012).

Alley et al., "Contribution of Linker Stability to the Activities of Anticancer Immunoconjugates," Bioconjugate Chem., vol. 19, pp. 759-765 (2008).

Badescu et al, "Bridging Disulfides for Stable and Defined Antibody Drug Conjugates," Bioconjugate Chem., vol. 25 (6), pp. 1124-1136 (2014).

Bai et al., "Interactions of the Sponge-Derived Antimitotic Tripeptide Hemiasterlin with Tubulin: Comparison with Dolastatin 10 and Cyrpotphycin 1," Biochemistry, vol. 38, pp. 14302-14310 (1999).

Baldwin, A. D. and Kiick, K. L., "Tunable Degradation of Maleimide-Thiol Adducts in Reducing Environments," Bioconjugate Chem., Vo. 22, pp. 1946-1953 (2011).

Beaulieu, P.L. et al., "Allosteric N-acetamide-indole-6-carboxylic acid thumb pocket 1 inhibitors of hepatitis C virus Nssb polymerase—Acylsulfonamides and acylsulfamides as carboxylic acid replacements," Can J. Chem., vol. 91, pp. 66-81 (2013).

Burke et al., "Design, Synthesis and Biological Evaluation of Antibody-Drug Conjugates Comprised of Potent Camptothecin Analogues," Bioconjugate Chem., vol. 20, pp. 1242-1250 (2009).

Burke et al., "Novel immunoconjugates comprised of streptonigrin and 17-amino-geldanamycin attached via dipeptide-p-aminobenzylamine linker system," Biorg. Med. Chem. Lett., vol. 19, pp. 2650-2653 (2009).

Chakraborty et al., "Nucleation of β-Hairpin Structures with Cis Amide Bonds in E-Vinylogous Proline-Containing Peptides," J. Org. Chem., vol. 68, pp. 6459-6462 (2003).

Chan et al., "Mitosis-targeted anti-cancer therapies: where they stand," Cell Death and Disease, vol. 3, pp. 1-11 (2012).

Chen, J. et al., "The Bcl-2/Bcl-XL/Bcl-w Inhibitor, Navitoclax, Enhances the Activity of Chemotherapeutic Agents In Vitro and In Vivo," Mol Cancer Ther, 10(12), pp. 2340-2349, (2011).

Choi, K.Y., "Protease-Activated Drug Development," Theranostics, 2(2), pp. 156-178, (2012).

(56) References Cited

OTHER PUBLICATIONS

Clausen TM et al., "Structural and Functional Insight into How the Plasmodium falciparum VAR2CSA Protein Mediates Binding to Chondroitin Sulfate A in Placental Malaria," J. Biol. Chem., vol. 287, No. 28, pp. 23332-23345 (2012).
Coleman et al., "Cytotoxic Peptides from the Marine Sponge *Cymbastella* sp.," Tetrahedron vol. 51, No. 39, pp. 10653-10662 (1995).
Doronina et al., "Development of potent monoclonal antibody auristatin conjugates for cancer therapy," Nature Biotechnology, vol. 21, No. 7, pp. 778-784 (2003).
Doronina et al., "Enhanced Activity of Monomethylauristatin F through Monoclonal Antibody Delivery: Effects of Linker Technology on Efficacy and Toxicity," Bioconjugate Chem., vol. 17, pp. 114-124 (2006).
Doronina et al., "Novel Peptide Linkers for Highly Potent Antibody—Auristatin Conjugate," Bioconjugate Chem., vol. 19, pp. 1960-1963 (2008).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem., vol. 13, pp. 855-869 (2002).
"Expert Scientific Group on Phase One Clinical Trails Final Report" Nov. 30, 2006, pp. C1, C35-C38.
Fennell et al., "Effects of the antimitotic natural product dolastatin 10, and related peptides, on the human malarial parasite Plasmodium falciparum," Antimicrob. Chemother., vol. 51, pp. 833-841 (2003).
Francisco et al., "cAC10-vcMMAE, and anti-CD30-monomethyl auristatin E conjugate with potent and selective antitumor activity," Blood, vol. 102, No. 4, pp. 1458-1465 (2003).
Gajula et al., "A Synthetic Dolastatin 10 Analgoue Supresses Mictrotubule Dynamics, Inhibits Cell Proliferation, and Induces Apoptotic Cell Death," J. Med. Chem, vol. 56, pp. 2235-2245 (2013).
Grison, C. et al., "Stereoselective synthesis of vinylogous peptides," Tetrahedron, 57, pp. 4903-4923 (2001).
Grison et al., "Structural Investigation of "cis" and "trans" Vinylogous Peptides: cis-Vinylog Turn in Folded cis-Vinylogous Peptides, an Excelletn Mimic of the Natural β-Turn," J. Org. Chem. vol. 70, pp. 10753-10764 (2005).
Gura, T.,"Cancer Models: Systems for Identifiying New Drugs Are Often Faulty," Science 7, vol. 278, No. 5340, pp. 1041-1042 (2007).
Haba, K., "Single-Triggered Trimeric Prodrugs," Angew. Chem. Int. Ed., vol. 44, pp. 716-720 (2005).
Hadaschik, B.A. et al., "Intravesical Chemotherapy of High-Grade Bladder Cancer with HTI-286, A Synthetic Analogue of the Marine Sponge Product Hemiasterlin," Clin Cancer Res., vol. 14, pp. 1510-1518 (2008).
Huang, S. et al., "Synthesis and evaluation of N-acyl sulfonamides as potential prodrugs of cyclin-dependent kinase inhibitor JNJ-7706621," Bioorganic & Medicinal Chemistry Letters, vol. 16, pp. 3639-3641 (2006).
Ishikawa et al, "Preparation of endothelin antagonistic peptide derivatives," caplus an Eur. Pat. Appl., p. 121, 1992:256053.
Jeffrey et al., "Design, Synthesis, and in Vitro Evaluation of Dipeptide-Based Antibody Minor Groove Binder Conjugates," J. Med. Chem., vol. 48, pp. 1344-1358 (2005).
Jeffrey et al., "Dipeptide-based highly potent doxorubicin antibody conjugates," Biorg. Med. Chem. Lett. vol. 16, pp. 358-362 (2006).
Jeffrey et al., "Expanded Utility of the β-Glucuronide Linker: ADCs That Deliver Phenolic Cytotoxic Agents," ACS Med. Chem. lett., vol. 1, pp. 277-280 (2010).
Jiang, Y. et al., "Discovery of Danoprevir (ITMN-191/R7227), a Highly Selective and Potent Inhibitor of Hepatitis C Virus (HCV) NS3/4A Protease," J. Med. Chem., vol. 57, pp. 1753-1769 (2014).
Johansson, A. et al., "Acyl Sulfonamides as Potent Protease Inhibitors of the Hepatitis C Virus Full-Length NS3 (Protease-Helicase/NTPase): A Comparative Study of Different C-Terminals," Bioorganic & Medicinal Chemistry, 11, pp. 2551-2568 (2003).
Kamb, A., "What's wrong with our cancer models?," Nature Reviews Drug Discovery 4, vol. 4, pp. 161-165 (2005).
Koniev, O. et al, "Selective Irreversible Chemical Tagging of Cysteine with 3-Arylpropiolonitriles," Bioconjugate Chem., vol. 25 (2), pp. 202-206 (2014).
Kuznetsov et al., "Tubulin-based antimitotic mechanism of E7974, a novel analogue of the marine sponge natural product hemiasterlin," Mol Cancer Ther, 8(10), pp. 2852-2860 (2009).
Leaf, C., "Why Are We Losing The War on Cancer (and How to Win It)," Health Administrator vol. XVII, No. 1, pp. 172-183 (2005).
Lesma, et al., "Hemiasterlin Analogues Incorporating an Aromatic, and Heterocyclic Type C-terminus: Design, Synthesis and Biological Evaluation," Mol Divers.,18(2), pp. 357-373 (2004).
Li L et al., "Structural Analysis and Optimization of the Covalent Association between SpyCatcher and a Peptide Tag," J. Mol. Biol., vol. 426(2), pp. 309-317 (2014).
Loganzo et al., "HTI-286 , a Synthetic Analogue of the Tripeptide Hemiasterlin, Is a Potent Antimicrotubule Agent that Circumvents P-Glycoprotein-mediated Resistance in Vitro and in Vivo," Cancer Res, 63, pp. 1838-1845 (2003).
Luo et al., "Principle of Cancer Therapy: Oncogen and Non-oncogene Addiction," Cell vol. 136, pp. 823-837 (2009).
Mader, M.M. et al., "Acyl sulfonamide anti-proliferatives. Part 2: Activity of heterocyclic sulfonamide derivatives," Bioorganic & Medicinal Chemistry Letters, 15, pp. 617-620 (2005).
Marzo et al., "Antimitotic drugs in cancer chemotherapy: Promises and pitfalls," Biochemical Pharmacology, Vo. 86, pp. 703-710 (2013).
Matsuoka et al., "Preparation of peptids or analogs containing substituted phenethylamine moiety as motilin receptor antagonists," caplus an, PCT Int. Appl., p. 403, 2000:535162.
Merkx et al., "Resin-bound sulfonyl-azides: Efficient loading and activation strategy for the preparation of the N-acyl sulfonamide linker," J. Org. Chem., vol. 72, pp. 4574-4577 (2007).
Melnyk, O. et al, "Phenylthiocarbamate or N-Carbothiophenyl Group Chemistry in Peptide Synthesis and Bioconjugation," Bioconjugate Chem., vol. 25, pp. 629-639 (2014).
Mitra, A. and Sept D., "Localization of the Antimitotic Peptide and Depsipeptide Binding Site on B-tubulin," Biochemistry, 43, pp. 13955-13962 (2004).
Miyazawa, T. et al, "Effect of copper(II) chloride on suppression of racemization in peptide synthesis by the carbodiimide method," Int. J. Peptide Protein Res., vol. 39, pp. 237-244 (1992).
Neidle, S., "Failure Modes in Clinical Development," Cancer Drug Design and Discovery, ed. (Elsevier/Academic Press) pp. 427-431 (2008).
Niu et al., "Absolute configurations of tubulin inhibitors taltobulin (HTI-286) and HTI-042 characterized by X-ray diffraction analysis and NMR studies," Bioorganic & Medicinal Chmistry Letters, 20, pp. 1535-1538 (2010).
Otani et al., "TZT-1027, an antimicrotubule agent, attacks tumor vasculature and induces tumor cell death," Jpn. J. Cancer Res., vol. 91, pp. 837-844 (2000).
Papisov et al., "Semisynthetic Hydrophilic Polyals," Biomacromolecules,vol. 6, pp. 2659-2670 (2005).
Pettit et al., "Antineoplastic agents 337. Synthesis of dolastatin 10 structural modifications," Anti-Cancer Drug Des., vol. 10, pp. 529-544 (1995).
Pettit et al., "Specific activities of dolastatin 10 and peptide derivatives against *Cryptococcus neoformans*," Antimicrob. Agents Chemother., vol. 42, pp. 2961-2965 (1998).
Pettit et al., "Antineoplastic agents 365. Dolastatin 10 SAR probes," Anti-Cancer Drug Des., vol. 13, pp. 243-277 (1998).
Pettit et al., "Antineoplastic agents. 592. Highly effective cancer cell growth inhibitory structural modifications of dolastatin 10," J. Nat. Prod., vol. 74, pp. 962-968 (2011).
Ratain et al., "Phase I and pharmacological study of HTI-286, a novel antimicrotubule agent: correlation of neutropenia with time above a threshold serum concentration," Proc. Am. Soc. Clin. Oncol., vol. 22, p. 129 (2003).

(56) References Cited

OTHER PUBLICATIONS

Ravi M. et al., "Structure-Based Identification of the Binding Site for the Hemiasterlin Analogue HTI-286 on Tubulin," Biochemistry, 44, pp. 15871-15879 (2005).
Rocha-Lima et al., "A Phase 1 Trial of E7974 Administrated on Day 1 of a 21 Day Cycle in Patients with Advanced Solid Tumors," Cancer, pp. 4262-4270, Sep. 1, 2012.
Salanti et al., "Targeting Human Cancer by a Glycosaminoglycan Binding Malaria Protein," Cancer Cell., vol. 28(4), pp. 500-514 (2015).
Schumacher, F.F. et al, "In Situ Maleimide Bridging of Disulfides and a New Approach to Protein Pegylation," Bioconjugate Chem., vol. 22, pp. 132-136 (2011).
Scola, P.M. et al., "The Discovery of Asunaprevir (BMS-650032), An Orally Efficacious NS3 Protease Inhibitor for the Treatment of Hepatitis C Virus Infection," J. Med. Chem., 57, pp. 1730-1752 (2014).
Shabat et al., "In vivo activity in a catalytic antibody-prodrug system: Antibody catalyzed etoposide prodrug activation for selective chemotherapy," PNAS, vol. 98, No. 13, pp. 7528-7533 (2001).
Shannon et al., "Investigating the Proteome Reactivity and Selectivity of Aryl Halides," J. Am. Chem. Soc., vol. 136, pp. 3330-3333 (2014).
Shnyder et al., "Auristatin PYE, a novel synthetic derivative of dolastatin 10, is highly effective in human colon tumour models," Int. J. Oncol., vol. 31, pp. 353-360 (2007).
Sockolosky JT et al., "Engineering neonatal Fc receptor-mediated recycling and transcytosis in recombinant proteins by short terminal peptide extensions," Proc. Natl. Acad. Sci. USA, vol. 109, No. 40, pp. 16095-16100 (2012).
Steiner, M. et al., "Spacer length shapes drug release and therapeutic efficacy of traceless disulfide-linked ADCs targeting the tumor neovasculature," Chem. Sci., vol. 4, pp. 297-302 (2013).
Strop P et al., "Location Matters: Site of Conjugation Modulates Stability and Pharmacokinetics of Antibody Drug Conjugates," Chem Biol. vol. 20(2), pp. 161-167 (2013).
Sutherland, M.S.K., et al., "Lysosomal Trafficking and Cysteine Protease Metabolism Confer Target-specific Cytotoxicity by Peptide-linked Anti-CD30-Auristatin Conjugates," Journal of Biological Chemistry, Vo. 281, No. 15, pp. 10540-10547 (2006).
Talpir et al., "Hemiasterlin and Geodiamolide TA; Two New Cytotoxic Peptides from the Marine Sponge Hemiasterella Minor (Kirkpatrick)," Tetrahedron Letters, vol. 35, No. 25, pp. 4453-4456 (1994).
Temming et al., "Improved Efficacy of αvβ3-Targeted Albumin Conjugates by Conjugation of a Novel Auristatin Derivative," Molecular Pharmaceutics, vol. 4, No. 5, pp. 686-694 (2007).
Thomssen et al., "Prognostic value of the cysteine proteases cathepsins B and cathepsin L in human breast cancer," Clinical Cancer Research, vol. 1, pp. 741-746 (1995).
Toki et al., "Protease-Mediated Fragmentation of p-Aminobenzyl Ethers: A New Strategy for the Activation of Anticancer Prodrugs," J. Org. Chem., vol. 67, pp. 1866-1872 (2002).
Toure, B.C. et al., "The Role of the Acidity of N-Heteroaryl Sulfonamides as Inhibitors of Bcl-2 Family Protein—Protein Interactions," ACS Med. Chem. Lett., vol. 4, pp. 186-190 (2013).
Uehling, D.E. et al., "Synthesis and Evaluation of Potent and Selective β3 Adrenergic Receptor Agonists Containing Acylsulfonamide, Sulfonylsulfonamide, and Sulfonylurea Carboxylic Acid Isosteres," J. Med. Chem., vol. 45, pp. 567-583 (2002).
Vedejs, et al., "A Total Synthesis of (−)-Hemiasterlin Using N-Bts Methodology," J. Org. Chem., vol. 66, pp. 7355-7364 (2001).
Walker et al., "Monoclonal antibody mediated intracellular targeting of tallysomycin S10b," Bioorganic & Medicinal Chemistry Letters, vol. 14, pp. 4323-4327 (2004).
Werboretz et al., "Selective Antimicrotubule Activity of N1-Phenyl-3-5-dinitro- 4,N-4-di-n-propylsulfanilamide (GB-II-5) against Kinetoplastid Parasites," Mol. Pharmacol., vol. 64, pp. 1325-1333 (2003).
Woyke et al., "In vitro activities and postantifungal effects of the potent dolastatin 10 derivative Auristatin PHE," Antimicrob. Agents Chemother., vol. 45, pp. 3580-3584 (2001).
Yamashita et al., "Synthesis and Activity of Novel Analogs of Hemiasterlin as Inhibitors of Tubulin Polymerization: Modification of the a Segment," Bioorganic and Medicinal Chemistry Letters, vol. 14, pp. 5317-5322 (2004).
Yan, S. et al., "Thiazolone-acylsulfonamides as novel HCV NS5B polymerase allosteric inhibitors: convergence of structure-based drug design and X-ray crystallographic study," Bioorganic & Medicinal Chemistry Letters, vol. 17, pp. 1991-1995 (2007).
Yurkovestkiy et al., "Synthesis of a Macromolecular Camptothecin Conjugate with Dual Phase Drug Release," Mol Pharm., vol. 1:5, pp. 375-382 (2004).
Zask et al., "D-piece Modifications of the Hemiasterlin Analog HTI-286 Produce Potent Tubulin Inhibitors," Bioorganic & Medicinal Chemistry Letters, vol. 14, pp. 4353-4358 (2004).
Zask et al., "Synthesis and Biological Activity of Analogues of the Antimicrotubule Agent N,β, β-Trimethyl-l-phenylalanyl-N1-[(1S,26)-3-carboxy-1-isopropylbut-2-enyl]- N1,3-dimethyl-l-valinamide (HTI-286)," J. Med. Chem., vol. 47, pp. 4774-4786 (2004).
Alkhalil A, et al. "Structural requirements for the adherence of Plasmodium falciparum-infected erythrocytes to chondroitin sulfate proteoglycans of human placenta." J. Biol. Chem., vol. 275 (51), pp. 40357-40364 (2000).
Cancer-Prevention, http://www.cancerresearchuk.org/about-cancer/causes-of-cancer-be-prevented, downloaded Jan. 8, 2018.
CAS RN 1350253-85-8, STN Entry Date: Dec. 7, 2011.
Fried and Duffy, "Adherence of Plasmodium falciparum to chondroitin sulfate A in the human placenta," Science, vol. 272(5267), pp. 1502-1504 (1996).
Hamada et al., caplus an 2008:324765.
Nieman et al., "Synthesis and Antimitotic/Cytotoxic Activity of Hemiasterlin Analogues." J. Nat. Prod., 2003, 66 (2), pp. 183-199.
Olsen et al., caplus an 2010:213501.
Rich, J.R., et al., CAPLUS AN 2015:1087487.
Rogerson, et al., "Chondroitin sulfate A is a cell surface receptor for Plasmodium falciparum-infected erythrocytes," J Exp Med., vol. 182(1), pp. 15-20 (1995).
Salanti, et al. "Evidence for the involvement of VAR2CSA in pregnancy-associated malaria," J Exp Med., vol. 200(9), pp. 1197-1203 (2004).
Wilkinson et al., "Synthesis of MUC1 glycopeptide thioesters and ligation via direct aminolysis," Biopolymers, vol. 96(2), pp. 137-146 (2011).
Winters, G., et al., CAPLUS AN 2015:1087672.
Restriction Requirement dated Aug. 29, 2016 in U.S. Appl. No. 14/776,654.
Non-final Office Action dated Nov. 16, 2016 in U.S. Appl. No. 14/776,654.
Final Office Action dated May 9, 2017 in U.S. Appl. No. 14/776,654.
Advisory Action dated Jul. 14, 2017 in U.S. Appl. No. 14/776,654.
Non-final Office Action dated Sep. 15, 2017 in U.S. Appl. No. 14/776,654.
Notice of Allowance dated Feb. 5, 2018 in U.S. Appl. No. 14/776,654.
Non-final Office Action dated Oct. 2, 2015 in U.S. Appl No .14/213,504.
Final Office Action dated May 18, 2016 in U.S. Appl. No. 14/213,504.
Notice of Allowance dated Aug. 23, 2016 in U.S. Appl. No. 14/213,504.
Restriction Requirement dated Aug. 30, 2016 in U.S. Appl. No. 14/857,733.
Non-final Office Action dated Nov. 14, 2016 in U.S. Appl. No. 14/857,733.
Non-final Office Action dated Jun. 6, 2017 in U.S. Appl. No. 14/857,733.
Notice of Allowance dated Sep. 14, 2017 in U.S. Appl. No. 14/857,733.
Restriction Requirement dated Jun. 4, 2018 in U.S. Appl. No. 15/108,247.
Non-final Office Action dated Dec. 14, 2018 in U.S. Appl. No. 15/108,247.
Final Office Action dated Jul. 29, 2019 in U.S. Appl. No. 15/108,247.

(56) References Cited

OTHER PUBLICATIONS

Restriction Requirement dated Sep. 11, 2017 in U.S. Appl. No. 15/512,030.
Non-final Office Action dated Jan. 19, 2018 in U.S. Appl. No. 15/512,030.
Final Office Action dated Jun. 8, 2018 in U.S. Appl. No. 15/512,030.
Non-final Office Action dated Nov. 27, 2018 in U.S. Appl. No. 15/512,030.
Notice of Allowance dated May 16, 2019 in U.S. Appl. No. 15/512,030.
Restriction Requirement dated Jul. 27, 2018 in U.S. Appl. No. 15/724,763.
Non-final Office Action dated Feb. 7, 2019 in U.S. Appl. No. 15/724,763.
Notice of Allowance dated Aug. 15, 2019 in U.S. Appl. No. 15/724,763.
Restriction Requirement dated May 16, 2018 in U.S. Appl. No. 15/872,642.
Non-final Office Action dated Sep. 13, 2018 in U.S. Appl. No. 15/872,642.
Notice of Allowance dated Apr. 4, 2019 in U.S. Appl. No. 15/872,642.

\* cited by examiner

Colo205 Cell Viability

- VAR2CSA-toxin
- toxin-linker alone

Figure 18

U-138 MG Cell Viability

●— VAR2CSA-toxin
◆ VAR2CSA

SEQUENCE LISTING

```
<160> NUMBER OF SEQ ID NOS: 127

<210> SEQ ID NO 1
<211> LENGTH: 640
<212> TYPE: PRT
<213> ORGANISM: Artificial Sequence
<220> FEATURE:
<223> OTHER INFORMATION: ID1 domain of FCR3, DBL2Xb domain of FCR3 and
      ID2a

<400> SEQUENCE: 1

Asn Tyr Ile Lys Gly Asp Pro Tyr Phe Ala Glu Tyr Ala Thr Lys Leu
1               5                   10                  15

Ser Phe Ile Leu Asn Pro Ser Asp Ala Asn Asn Pro Ser Gly Glu Thr
            20                  25                  30

Ala Asn His Asn Asp Glu Ala Cys Asn Cys Asn Glu Ser Gly Ile Ser
        35                  40                  45

Ser Val Gly Gln Ala Gln Thr Ser Gly Pro Ser Ser Asn Lys Thr Cys
    50                  55                  60

Ile Thr His Ser Ser Ile Lys Thr Asn Lys Lys Glu Cys Lys Asp
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Asp Ser Cys Asp Asn Lys Asn Gln Asp Glu Cys Gln Lys
    130                 135                 140

Lys Leu Glu Lys Val Phe Ala Ser Leu Thr Asn Gly Tyr Lys Cys Asp
145                 150                 155                 160

Lys Cys Lys Ser Gly Thr Ser Arg Ser Lys Lys Lys Trp Ile Trp Lys
                165                 170                 175

Lys Ser Ser Gly Asn Glu Glu Gly Leu Gln Glu Glu Tyr Ala Asn Thr
            180                 185                 190

Ile Gly Leu Pro Pro Arg Thr Gln Ser Leu Tyr Leu Gly Asn Leu Pro
        195                 200                 205

Lys Leu Glu Asn Val Cys Glu Asp Val Lys Asp Ile Asn Phe Asp Thr
    210                 215                 220

Lys Glu Lys Phe Leu Ala Gly Cys Leu Ile Val Ser Phe His Glu Gly
225                 230                 235                 240

Lys Asn Leu Lys Lys Arg Tyr Pro Gln Asn Lys Asn Ser Gly Asn Lys
                245                 250                 255

Glu Asn Leu Cys Lys Ala Leu Glu Tyr Ser Phe Ala Asp Tyr Gly Asp
            260                 265                 270

Leu Ile Lys Gly Thr Ser Ile Trp Asp Asn Glu Tyr Thr Lys Asp Leu
        275                 280                 285

Glu Leu Asn Leu Gln Asn Asn Phe Gly Lys Leu Phe Gly Lys Tyr Ile
    290                 295                 300

Lys Lys Asn Asn Thr Ala Glu Gln Asp Thr Ser Tyr Ser Ser Leu Asp
305                 310                 315                 320
```

```
Glu Leu Arg Glu Ser Trp Trp Asn Thr Asn Lys Lys Tyr Ile Trp Thr
            325                 330                 335

Ala Met Lys His Gly Ala Glu Met Asn Ile Thr Thr Cys Asn Ala Asp
        340                 345                 350

Gly Ser Val Thr Gly Ser Gly Ser Cys Asp Asp Ile Pro Thr Ile
    355                 360                 365

Asp Leu Ile Pro Gln Tyr Leu Arg Phe Leu Gln Glu Trp Val Glu Asn
370                 375                 380

Phe Cys Glu Gln Arg Gln Ala Lys Val Lys Asp Val Ile Thr Asn Cys
385                 390                 395                 400

Lys Ser Cys Lys Glu Ser Gly Asn Lys Cys Lys Thr Glu Cys Lys Thr
                405                 410                 415

Lys Cys Lys Asp Glu Cys Glu Lys Tyr Lys Lys Phe Ile Glu Ala Cys
            420                 425                 430

Gly Thr Ala Gly Gly Ile Gly Thr Ala Gly Ser Pro Trp Ser Lys
        435                 440                 445

Arg Trp Asp Gln Ile Tyr Lys Arg Tyr Ser Lys His Ile Glu Asp Ala
    450                 455                 460

Lys Arg Asn Arg Lys Ala Gly Thr Lys Asn Cys Gly Thr Ser Ser Thr
465                 470                 475                 480

Thr Asn Ala Ala Ala Ser Thr Asp Glu Asn Lys Cys Val Gln Ser Asp
                485                 490                 495

Ile Asp Ser Phe Phe Lys His Leu Ile Asp Ile Gly Leu Thr Thr Pro
            500                 505                 510

Ser Ser Tyr Leu Ser Asn Val Leu Asp Asp Asn Ile Cys Gly Ala Asp
        515                 520                 525

Lys Ala Pro Trp Thr Thr Tyr Thr Thr Tyr Thr Thr Glu Lys Cys
530                 535                 540

Asn Lys Glu Arg Asp Lys Ser Lys Ser Gln Ser Ser Asp Thr Leu Val
545                 550                 555                 560

Val Val Asn Val Pro Ser Pro Leu Gly Asn Thr Pro Tyr Arg Tyr Lys
                565                 570                 575

Tyr Ala Cys Gln Cys Lys Ile Pro Thr Asn Glu Glu Thr Cys Asp Asp
            580                 585                 590

Arg Lys Glu Tyr Met Asn Gln Trp Ser Cys Gly Ser Ala Arg Thr Met
        595                 600                 605

Lys Arg Gly Tyr Lys Asn Asp Asn Tyr Glu Leu Cys Lys Tyr Asn Gly
    610                 615                 620

Val Asp Val Lys Pro Thr Thr Val Arg Ser Asn Ser Ser Lys Leu Asp
625                 630                 635                 640

<210> SEQ ID NO 2
<211> LENGTH: 341
<212> TYPE: PRT
<213> ORGANISM: Plasmodium falciparum

<400> SEQUENCE: 2

Lys Cys Asp Lys Cys Lys Ser Gly Thr Ser Arg Ser Arg Lys Ile Trp
1               5                   10                  15

Thr Trp Arg Lys Ser Ser Gly Asn Lys Glu Gly Leu Gln Glu Glu Tyr
            20                  25                  30

Ala Asn Thr Ile Gly Leu Ser Pro Arg Thr Gln Leu Leu Tyr Leu Gly
        35                  40                  45

Asn Leu Arg Lys Leu Glu Asn Val Cys Glu Asp Val Thr Asp Ile Asn
    50                  55                  60
```

```
Phe Asp Thr Lys Glu Lys Phe Leu Ala Gly Cys Leu Ile Ala Ala Phe
 65                  70                  75                  80

His Glu Gly Lys Asn Leu Lys Lys Arg Tyr Leu Glu Lys Lys Lys Gly
                 85                  90                  95

Asp Asn Asn Ser Lys Leu Cys Asp Leu Lys Tyr Ser Phe Ala Asp
            100                 105                 110

Tyr Gly Asp Leu Ile Lys Gly Thr Ser Ile Trp Asp Asn Asp Phe Thr
            115                 120                 125

Lys Asp Leu Glu Leu Asn Leu Gln Gln Ile Phe Gly Lys Leu Phe Arg
130                 135                 140

Lys Tyr Ile Lys Lys Asn Ile Ser Thr Glu Gln Asp Thr Ser Tyr
145                 150                 155                 160

Ser Ser Leu Asp Glu Leu Arg Glu Ser Trp Trp Asn Thr Asn Lys Lys
                165                 170                 175

Tyr Ile Trp Leu Ala Met Lys His Gly Ala Gly Met Asn Ser Thr Thr
                180                 185                 190

Cys Ser Cys Ser Gly Asp Ser Ser Gly Glu Asn Gln Thr Asn Ser
            195                 200                 205

Cys Asp Asp Ile Pro Thr Ile Asp Leu Ile Pro Gln Tyr Leu Arg Phe
210                 215                 220

Leu Gln Glu Trp Val Glu His Phe Cys Glu Gln Arg Gln Ala Lys Val
225                 230                 235                 240

Lys Asp Val Ile Thr Asn Cys Asn Ser Cys Lys Glu Ser Gly Gly Thr
                245                 250                 255

Cys Asn Ser Asp Cys Glu Lys Lys Cys Asn Lys Cys Asp Ala Tyr
            260                 265                 270

Lys Thr Phe Ile Glu Asp Cys Lys Gly Val Gly Gly Thr Gly Thr Ala
            275                 280                 285

Gly Ser Ser Trp Val Lys Arg Trp Tyr Gln Ile Tyr Met Arg Tyr Ser
290                 295                 300

Lys Tyr Ile Glu Asp Ala Lys Arg Asn Arg Lys Ala Gly Thr Lys Ser
305                 310                 315                 320

Cys Gly Thr Ser Ser Thr Thr Asn Val Ser Val Ser Thr Asp Glu Asn
                325                 330                 335

Lys Cys Val Gln Ser
            340
```

<210> SEQ ID NO 3
<211> LENGTH: 656
<212> TYPE: PRT
<213> ORGANISM: Artificial Sequence
<220> FEATURE:
<223> OTHER INFORMATION: M24 745 amino acids

<400> SEQUENCE: 3

```
Asp Tyr Ile Lys Gly Asp Pro Tyr Phe Ala Glu Tyr Ala Thr Lys Leu
1                5                   10                  15

Ser Phe Ile Leu Asn Ser Ser Asp Ala Asn Asn Pro Ser Gly Glu Thr
                 20                  25                  30

Ala Asn His Asn Asp Glu Val Cys Asn Pro Asn Glu Ser Glu Ile Ser
            35                  40                  45

Ser Val Gly Gln Ala Gln Thr Ser Asp Pro Ser Ser Asn Lys Thr Cys
        50                  55                  60

Asn Thr His Ser Ser Ile Lys Ala Asn Lys Lys Val Cys Lys His
 65                  70                  75                  80
```

Val Lys Leu Gly Ile Asn Asn Asp Lys Val Leu Arg Val Cys Val
                85                  90                  95

Ile Glu Asp Thr Ser Leu Ser Gly Val Glu Asn Cys Cys Phe Lys Asp
            100                 105                 110

Leu Leu Gly Ile Leu Gln Glu Asn Cys Ser Asp Asn Lys Ser Gly Ser
        115                 120                 125

Ser Ser Asn Gly Ser Cys Asn Asn Lys Asn Gln Glu Ala Cys Glu Lys
130                 135                 140

Asn Leu Glu Lys Val Leu Ala Ser Leu Thr Asn Cys Tyr Lys Cys Asp
145                 150                 155                 160

Lys Cys Lys Ser Gly Thr Ser Thr Val Asn Lys Asn Trp Ile Trp Lys
                165                 170                 175

Lys Ser Ser Gly Asn Lys Glu Gly Leu Gln Lys Glu Tyr Ala Asn Thr
            180                 185                 190

Ile Gly Leu Pro Pro Arg Thr His Ser Leu Tyr Leu Gly Asn Leu Pro
        195                 200                 205

Lys Leu Glu Asn Val Cys Glu Asp Val Lys Asp Ile Asn Phe Asp Thr
210                 215                 220

Lys Glu Lys Phe Leu Ala Gly Cys Leu Ile Ala Ala Phe His Glu Gly
225                 230                 235                 240

Lys Asn Leu Lys Lys Arg Tyr Pro Gln Asn Lys Asn Asp Asn Asn
                245                 250                 255

Ser Lys Leu Cys Lys Ala Leu Glu Tyr Ser Phe Ala Asp Tyr Gly Asp
            260                 265                 270

Leu Ile Lys Gly Thr Ser Ile Trp Asp Asn Glu Tyr Thr Lys Asp Leu
        275                 280                 285

Glu Leu Asn Leu Gln Gln Ile Phe Gly Lys Leu Phe Arg Lys Tyr Ile
290                 295                 300

Lys Lys Asn Ile Ser Thr Glu Gln Asp Thr Leu Tyr Ser Ser Leu Asp
305                 310                 315                 320

Glu Leu Arg Glu Ser Trp Trp Asn Thr Asn Lys Lys Tyr Ile Trp Leu
                325                 330                 335

Ala Met Lys His Gly Ala Gly Met Asn Ile Thr Thr Cys Cys Gly Asp
            340                 345                 350

Gly Ser Val Thr Gly Ser Gly Ser Ser Cys Asp Asp Ile Pro Thr Ile
        355                 360                 365

Asp Leu Ile Pro Gln Tyr Leu Arg Phe Leu Gln Glu Trp Val Glu His
370                 375                 380

Phe Cys Lys Gln Arg Gln Glu Lys Val Lys Asp Val Ile Asn Ser Cys
385                 390                 395                 400

Asn Ser Cys Lys Asn Thr Ser Ser Lys Thr Lys Leu Gly Asp Thr Cys
                405                 410                 415

Asn Ser Asp Cys Glu Lys Lys Cys Lys Ile Glu Cys Glu Lys Tyr Lys
            420                 425                 430

Lys Phe Ile Glu Glu Cys Arg Thr Ala Val Gly Thr Ala Gly Ser
        435                 440                 445

Ser Trp Ser Lys Arg Trp Asp Gln Ile Tyr Lys Met Tyr Ser Lys His
450                 455                 460

Ile Glu Asp Ala Lys Arg Asn Arg Lys Ala Gly Thr Lys Asn Cys Gly
465                 470                 475                 480

Ile Thr Thr Gly Thr Ile Ser Gly Glu Ser Gly Ala Asn Ser Gly
                485                 490                 495

-continued

```
Val Thr Thr Thr Glu Asn Lys Cys Val Gln Ser Asp Ile Asp Ser Phe
            500                 505                 510

Phe Lys His Leu Ile Asp Ile Gly Leu Thr Thr Pro Ser Ser Tyr Leu
        515                 520                 525

Ser Ile Val Leu Asp Asp Asn Ile Cys Gly Asp Asp Lys Ala Pro Trp
    530                 535                 540

Thr Thr Tyr Thr Thr Tyr Thr Thr Tyr Thr Thr Thr Glu Lys Cys Asn
545                 550                 555                 560

Lys Glu Arg Asp Lys Ser Lys Ser Gln Gln Ser Asn Thr Ser Val Val
                565                 570                 575

Val Asn Val Pro Ser Pro Leu Gly Asn Thr Pro His Gly Tyr Lys Tyr
            580                 585                 590

Ala Cys Gln Cys Lys Ile Pro Thr Asn Glu Glu Thr Cys Asp Asp Arg
        595                 600                 605

Lys Glu Tyr Met Asn Gln Trp Ile Ser Asp Thr Ser Lys Asn Pro Lys
    610                 615                 620

Gly Ser Gly Ser Thr Asn Asn Asp Tyr Glu Leu Tyr Thr Tyr Asn Gly
625                 630                 635                 640

Val Lys Glu Thr Lys Leu Pro Lys Lys Leu Asn Ser Pro Lys Leu Asp
                645                 650                 655

<210> SEQ ID NO 4
<211> LENGTH: 643
<212> TYPE: PRT
<213> ORGANISM: Artificial Sequence
<220> FEATURE:
<223> OTHER INFORMATION: KMWII 745 amino acids

<400> SEQUENCE: 4

Asp Tyr Ile Lys Asp Asp Pro Tyr Ser Lys Glu Tyr Thr Thr Lys Leu
1               5                   10                  15

Ser Phe Ile Leu Asn Ser Ser Asp Ala Asn Thr Ser Ser Gly Glu Thr
            20                  25                  30

Ala Asn His Asn Asp Glu Ala Cys Asn Cys Asn Glu Ser Glu Ile Ser
        35                  40                  45

Ser Val Gly Gln Ala Gln Thr Ser Gly Pro Ser Ser Asn Lys Thr Cys
    50                  55                  60

Ile Thr His Ser Phe Ile Lys Ala Asn Lys Lys Val Cys Lys Asp
65                  70                  75                  80

Val Lys Leu Gly Val Arg Glu Asn Asp Lys Val Leu Arg Val Cys Val
                85                  90                  95

Ile Glu Asp Thr Ser Leu Ser Gly Val Asp Asn Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Gly Ser Cys Asn Asn Lys Asn Gln Asp Glu Cys Gln Lys
    130                 135                 140

Lys Leu Glu Lys Val Phe Val Ser Leu Thr Asn Gly Tyr Lys Cys Asp
145                 150                 155                 160

Lys Cys Lys Ser Gly Thr Ser Thr Val Asn Lys Lys Trp Ile Trp Lys
                165                 170                 175

Lys Ser Ser Gly Asn Glu Lys Gly Leu Gln Lys Glu Tyr Ala Asn Thr
            180                 185                 190

Ile Gly Leu Pro Pro Arg Thr Gln Ser Leu Tyr Leu Gly Asn Leu Pro
        195                 200                 205
```

-continued

Lys Leu Gly Asn Val Cys Glu Asp Val Thr Asp Ile Asn Phe Asp Thr
210              215                 220

Lys Glu Lys Phe Leu Ala Gly Cys Leu Ile Ala Ala Phe His Glu Gly
225              230                 235                 240

Lys Asn Leu Lys Ile Ser His Glu Lys Lys Gly Asp Asn Gly Lys
                 245                 250                 255

Lys Leu Cys Lys Ala Leu Glu Tyr Ser Phe Ala Asp Tyr Gly Asp Leu
                 260                 265                 270

Ile Lys Gly Thr Ser Ile Trp Asp Asn Glu Tyr Thr Lys Asp Leu Glu
                 275                 280                 285

Leu Asn Leu Gln Lys Ala Phe Gly Lys Leu Phe Gly Lys Tyr Ile Lys
                 290                 295                 300

Lys Asn Ile Ala Ser Asp Glu Asn Thr Ser Tyr Ser Ser Leu Asp Glu
305              310                 315                 320

Leu Arg Glu Ser Trp Trp Asn Thr Asn Lys Lys Tyr Ile Trp Thr Ala
                 325                 330                 335

Met Lys His Gly Ala Glu Met Asn Ser Thr Met Cys Asn Ala Asp Gly
                 340                 345                 350

Ser Val Thr Gly Ser Gly Ser Ser Cys Asp Asp Ile Pro Thr Thr Asp
                 355                 360                 365

Phe Ile Pro Gln Tyr Leu Arg Phe Leu Gln Glu Trp Val Glu His Phe
                 370                 375                 380

Cys Lys Gln Arg Gln Glu Lys Val Asn Ala Val Ile Glu Asn Cys Asn
385              390                 395                 400

Ser Cys Lys Asn Thr Ser Gly Glu Arg Lys Ile Gly Gly Thr Cys Asn
                 405                 410                 415

Gly Asp Cys Lys Thr Glu Cys Lys Asn Lys Cys Glu Ala Tyr Lys Asn
                 420                 425                 430

Phe Ile Glu Asp Cys Lys Gly Gly Asp Gly Thr Ala Gly Ser Ser Trp
                 435                 440                 445

Val Lys Arg Trp Asp Gln Ile Tyr Lys Arg Tyr Ser Lys His Ile Glu
                 450                 455                 460

Asp Ala Lys Arg Asn Arg Lys Ala Gly Thr Lys Ser Cys Gly Pro Ser
465              470                 475                 480

Ser Ile Thr Asn Ala Ser Val Ser Thr Asp Glu Asn Lys Cys Val Gln
                 485                 490                 495

Ser Asp Ile Asp Ser Phe Phe Lys His Leu Ile Asp Ile Gly Leu Thr
                 500                 505                 510

Thr Pro Ser Ser Tyr Leu Ser Ile Val Leu Asp Glu Asn Asn Cys Gly
                 515                 520                 525

Glu Asp Asn Ala Pro Trp Thr Thr Tyr Thr Thr Tyr Thr Thr Thr Glu
530              535                 540

Lys Cys Asn Lys Asp Lys Lys Ser Lys Ser Gln Ser Cys Asn Thr
545              550                 555                 560

Ala Val Val Val Asn Val Pro Ser Pro Leu Gly Asn Thr Pro His Glu
                 565                 570                 575

Tyr Lys Tyr Ala Cys Gln Cys Lys Ile Pro Thr Thr Glu Glu Thr Cys
                 580                 585                 590

Asp Asp Arg Lys Glu Tyr Met Asn Gln Trp Ile Ser Asp Thr Ser Lys
                 595                 600                 605

Lys Gln Lys Gly Ser Gly Ser Thr Asn Asn Asp Tyr Glu Leu Tyr Thr
610              615                 620

Tyr Thr Gly Val Lys Glu Thr Lys Leu Pro Lys Lys Leu Asn Ser Pro

Lys Leu Asp

<210> SEQ ID NO 5
<211> LENGTH: 640
<212> TYPE: PRT
<213> ORGANISM: Artificial Sequence
<220> FEATURE:
<223> OTHER INFORMATION: 1248 745 amino acids

<400> SEQUENCE: 5

| | | | | | | | | | | | | | | |
|---|---|---|---|---|---|---|---|---|---|---|---|---|---|---|
| Ser | Tyr | Val | Lys | Asn | Asp | Pro | Tyr | Ser | Lys | Glu | Tyr | Val | Thr | Lys | Leu |
| 1 | | | | 5 | | | | | 10 | | | | | 15 | |
| Ser | Phe | Ile | Leu | Asn | Pro | Ser | Asp | Ala | Asn | Asn | Pro | Ser | Gly | Glu | Thr |
| | | | 20 | | | | | 25 | | | | | 30 | | |
| Ala | Asn | His | Asn | Asp | Glu | Ala | Cys | Asn | Pro | Asn | Glu | Ser | Glu | Ile | Ala |
| | | | 35 | | | | | 40 | | | | | 45 | | |
| Ser | Val | Gly | Gln | Ala | Gln | Thr | Ser | Asp | Arg | Leu | Ser | Gln | Lys | Ala | Cys |
| | | 50 | | | | | 55 | | | | | 60 | | | |
| Ile | Thr | His | Ser | Phe | Ile | Gly | Ala | Asn | Lys | Lys | Ile | Val | Cys | Lys | Asp |
| 65 | | | | | 70 | | | | | 75 | | | | | 80 |
| Val | Lys | Leu | Gly | Val | Arg | Glu | Lys | Asp | Lys | Asp | Leu | Lys | Ile | Cys | Val |
| | | | | 85 | | | | | 90 | | | | | 95 | |
| Ile | Glu | Asp | Asp | Ser | Leu | Arg | Gly | Val | Glu | Asn | Cys | Cys | Phe | Lys | Asp |
| | | | 100 | | | | | 105 | | | | | 110 | | |
| Leu | Leu | Gly | Ile | Leu | Gln | Glu | Asn | Cys | Ser | Asp | Asn | Lys | Ser | Gly | Ser |
| | | | 115 | | | | | 120 | | | | | 125 | | |
| Ser | Ser | Asn | Gly | Ser | Cys | Asn | Asn | Lys | Asn | Gln | Asp | Glu | Cys | Gln | Lys |
| | | 130 | | | | | 135 | | | | | 140 | | | |
| Lys | Leu | Asp | Glu | Ala | Leu | Ala | Ser | Leu | His | Asn | Gly | Tyr | Lys | Cys | Asp |
| 145 | | | | | 150 | | | | | 155 | | | | | 160 |
| Lys | Cys | Lys | Ser | Gly | Thr | Ser | Arg | Ser | Lys | Lys | Ile | Trp | Thr | Trp | Arg |
| | | | | 165 | | | | | 170 | | | | | 175 | |
| Lys | Phe | Pro | Gly | Asn | Gly | Glu | Gly | Leu | Gln | Lys | Glu | Tyr | Ala | Asn | Thr |
| | | | 180 | | | | | 185 | | | | | 190 | | |
| Ile | Gly | Leu | Pro | Pro | Arg | Thr | Gln | Ser | Leu | Tyr | Leu | Gly | Asn | Leu | Arg |
| | | | 195 | | | | | 200 | | | | | 205 | | |
| Lys | Leu | Glu | Asn | Val | Cys | Lys | Gly | Val | Thr | Asp | Ile | Asn | Phe | Asp | Thr |
| | | 210 | | | | | 215 | | | | | 220 | | | |
| Lys | Glu | Lys | Phe | Leu | Ala | Gly | Cys | Leu | Ile | Ala | Ala | Phe | His | Glu | Gly |
| 225 | | | | | 230 | | | | | 235 | | | | | 240 |
| Lys | Asn | Leu | Lys | Ile | Ser | Asn | Lys | Lys | Asn | Asp | Asp | Asn | Gly | Lys | |
| | | | | 245 | | | | | 250 | | | | | 255 | |
| Lys | Leu | Cys | Lys | Asp | Leu | Lys | Tyr | Ser | Phe | Ala | Asp | Tyr | Gly | Asp | Leu |
| | | | 260 | | | | | 265 | | | | | 270 | | |
| Ile | Lys | Gly | Thr | Ser | Ile | Trp | Asp | Asn | Glu | Tyr | Thr | Lys | Asp | Leu | Glu |
| | | | 275 | | | | | 280 | | | | | 285 | | |
| Leu | Asn | Leu | Gln | Lys | Ile | Phe | Gly | Lys | Leu | Phe | Arg | Lys | Tyr | Ile | Lys |
| | | 290 | | | | | 295 | | | | | 300 | | | |
| Lys | Asn | Ile | Ala | Ser | Asp | Glu | Asn | Thr | Leu | Tyr | Ser | Ser | Leu | Asp | Glu |
| 305 | | | | | 310 | | | | | 315 | | | | | 320 |
| Leu | Arg | Glu | Ser | Trp | Trp | Asn | Thr | Asn | Lys | Lys | Tyr | Ile | Trp | Leu | Ala |
| | | | | 325 | | | | | 330 | | | | | 335 | |
| Met | Lys | His | Gly | Thr | Thr | Cys | Ser | Ser | Gly | Ser | Gly | Asp | Asn | Gly | Asp |
| | | | 340 | | | | | 345 | | | | | 350 | | |

-continued

Gly Ser Val Thr Gly Ser Gly Ser Cys Asp Asp Met Ser Thr Ile
            355                 360                 365

Asp Leu Ile Pro Gln Tyr Leu Arg Phe Leu Gln Glu Trp Val Glu His
            370                 375                 380

Phe Cys Lys Gln Arg Gln Glu Lys Val Lys Asp Val Ile Glu Asn Cys
385                 390                 395                 400

Lys Ser Cys Lys Asn Thr Ser Gly Glu Arg Ile Ile Gly Gly Thr Cys
                405                 410                 415

Gly Ser Asp Cys Lys Thr Lys Cys Lys Gly Glu Cys Asp Ala Tyr Lys
            420                 425                 430

Asn Phe Ile Glu Glu Cys Lys Arg Gly Asp Gly Thr Ala Gly Ser Pro
            435                 440                 445

Trp Ser Lys Arg Trp Asp Gln Ile Tyr Met Arg Tyr Ser Lys Tyr Ile
            450                 455                 460

Glu Asp Ala Lys Arg Asn Arg Lys Ala Gly Thr Lys Asn Cys Gly Thr
465                 470                 475                 480

Ser Ser Thr Thr Asn Ala Ala Glu Asn Lys Cys Val Gln Ser Asp Ile
                485                 490                 495

Asp Ser Phe Phe Lys His Leu Ile Asp Ile Gly Leu Thr Thr Pro Ser
            500                 505                 510

Ser Tyr Leu Ser Ile Val Leu Asp Glu Asn Ile Cys Gly Asp Asp Lys
            515                 520                 525

Ala Pro Trp Thr Thr Tyr Thr Thr Tyr Thr Thr Glu Lys Cys Asn
            530                 535                 540

Lys Glu Thr Asp Lys Ser Lys Ser Gln Ser Cys Asn Thr Ala Val Val
545                 550                 555                 560

Val Asn Val Pro Ser Pro Leu Gly Asn Thr Pro His Gly Tyr Lys Tyr
                565                 570                 575

Ala Cys Glu Cys Lys Ile Pro Thr Thr Glu Glu Thr Cys Asp Asp Arg
            580                 585                 590

Lys Glu Tyr Met Asn Gln Trp Ile Ser Asp Thr Ser Lys Lys Pro Lys
            595                 600                 605

Gly Gly Arg Ser Thr Asn Asn Asp Tyr Glu Leu Tyr Thr Tyr Asn Gly
            610                 615                 620

Val Lys Glu Thr Lys Leu Pro Lys Lys Ser Ser Ser Lys Leu Asp
625                 630                 635                 640

<210> SEQ ID NO 6
<211> LENGTH: 358
<212> TYPE: PRT
<213> ORGANISM: Plasmodium falciparum

<400> SEQUENCE: 6

Lys Cys Glu Lys Cys Lys Ser Glu Gln Ser Lys Lys Asn Asn Asn Ile
1               5                   10                  15

Trp Ile Trp Arg Lys Phe Pro Gly Asn Gly Gly Leu Gln Lys Glu
            20                  25                  30

Tyr Ala Asn Thr Ile Gly Leu Pro Pro Arg Thr His Ser Leu Tyr Leu
            35                  40                  45

Gly Asn Leu Pro Lys Leu Glu Asn Val Cys Lys Asp Val Lys Asp Ile
            50                  55                  60

Asn Phe Asp Thr Lys Glu Lys Phe Leu Ala Gly Cys Leu Ile Ala Ala
65                  70                  75                  80

Phe His Glu Gly Lys Asn Leu Lys Thr Thr Tyr Pro Gln Asn Lys Asn

```
                    85                  90                  95
Ala Asp Asn Asn Ser Lys Leu Cys Lys Asp Leu Lys Tyr Ser Phe Ala
                   100                 105                 110

Asp Tyr Gly Asp Leu Ile Lys Gly Thr Ser Ile Trp Asp Asn Asp Phe
               115                 120                 125

Thr Lys Asp Leu Glu Leu Asn Leu Gln Lys Ile Phe Gly Lys Leu Phe
           130                 135                 140

Arg Lys Tyr Ile Lys Lys Asn Ile Ala Ser Asp Glu Asn Thr Leu Tyr
145                 150                 155                 160

Ser Ser Leu Asp Glu Leu Arg Glu Ser Trp Trp Asn Thr Asn Lys Lys
               165                 170                 175

Tyr Ile Trp Leu Ala Met Lys His Gly Ala Glu Met Asn Ser Thr Met
               180                 185                 190

Cys Asn Gly Asp Gly Ser Val Thr Gly Ser Ser Asp Ser Gly Ser Thr
               195                 200                 205

Thr Cys Ser Gly Asp Asn Gly Ser Ile Ser Cys Asp Asp Ile Pro Thr
           210                 215                 220

Ile Asp Leu Ile Pro Gln Tyr Leu Arg Phe Leu Gln Glu Trp Val Glu
225                 230                 235                 240

His Phe Cys Lys Gln Arg Gln Glu Lys Val Lys Pro Val Ile Glu Asn
               245                 250                 255

Cys Lys Ser Cys Lys Asn Thr Ser Gly Glu Arg Ile Ile Gly Gly Thr
               260                 265                 270

Cys Gly Ser Asp Cys Glu Lys Lys Cys Lys Gly Glu Cys Asp Ala Tyr
               275                 280                 285

Lys Lys Phe Ile Glu Glu Cys Lys Gly Gly Gly Gly Thr Gly Thr
           290                 295                 300

Ala Gly Ser Pro Trp Ser Lys Arg Trp Asp Gln Ile Tyr Lys Arg Tyr
305                 310                 315                 320

Ser Lys Tyr Ile Glu Asp Ala Lys Arg Asn Arg Lys Ala Gly Thr Lys
               325                 330                 335

Ser Cys Gly Pro Ser Ser Thr Thr Asn Ala Ala Ala Ser Thr Thr Glu
               340                 345                 350

Ser Lys Cys Val Gln Ser
           355

<210> SEQ ID NO 7
<211> LENGTH: 333
<212> TYPE: PRT
<213> ORGANISM: Plasmodium falciparum

<400> SEQUENCE: 7

Lys Cys Asp Lys Cys Lys Ser Glu Gln Ser Lys Asn Asn Lys Asn
1               5                   10                  15

Trp Ile Trp Lys Gln Phe Pro Gly Asn Gly Glu Gly Leu Gln Lys Glu
               20                  25                  30

Tyr Ala Asn Thr Ile Gly Leu Pro Pro Arg Thr His Ser Leu Tyr Leu
           35                  40                  45

Gly Asn Leu Pro Lys Leu Glu Asn Val Cys Lys Gly Val Thr Asp Ile
50                  55                  60

Asn Phe Asp Thr Lys Glu Lys Phe Leu Ala Gly Cys Leu Ile Ala Ala
65                  70                  75                  80

Phe His Glu Gly Lys Asn Leu Thr Ser His Glu Lys Lys Lys Gly
               85                  90                  95
```

```
Asp Asn Gly Lys Lys Leu Cys Lys Asp Leu Lys Tyr Ser Phe Ala Asp
            100                 105                 110

Tyr Gly Asp Leu Ile Lys Gly Thr Ser Ile Trp Asp Asn Asp Phe Thr
        115                 120                 125

Lys Asp Leu Glu Leu Asn Leu Gln Gln Ile Phe Gly Lys Leu Phe Arg
    130                 135                 140

Lys Tyr Ile Lys Lys Asn Ile Ser Ala Glu Gln Asp Thr Ser Tyr Ser
145                 150                 155                 160

Ser Leu Asp Glu Leu Arg Glu Ser Trp Trp Asn Thr Asn Lys Lys Tyr
                165                 170                 175

Ile Trp Leu Ala Met Lys His Gly Thr Thr Cys Ser Ser Gly Ser Gly
            180                 185                 190

Asp Asn Gly Asp Gly Ser Val Thr Gly Ser Gly Ser Ser Cys Asp Asp
        195                 200                 205

Met Pro Thr Thr Asp Phe Ile Pro Gln Tyr Leu Arg Phe Leu Gln Glu
    210                 215                 220

Trp Val Glu His Phe Cys Lys Gln Arg Gln Glu Lys Val Asn Ala Val
225                 230                 235                 240

Ile Thr Asn Cys Lys Ser Cys Lys Glu Ser Gly Gly Thr Cys Asn Ser
                245                 250                 255

Asp Cys Glu Lys Lys Cys Lys Asp Glu Cys Glu Lys Tyr Lys Lys Phe
            260                 265                 270

Ile Glu Glu Cys Arg Thr Ala Ala Asp Gly Thr Ala Gly Ser Ser Trp
        275                 280                 285

Ser Lys Arg Trp Asp Gln Ile Tyr Lys Met Tyr Ser Lys His Ile Glu
    290                 295                 300

Asp Ala Lys Arg Asn Arg Lys Ala Gly Thr Lys Asn Cys Gly Thr Ser
305                 310                 315                 320

Ser Thr Thr Asn Ala Ala Glu Asn Lys Cys Val Gln Ser
                325                 330

<210> SEQ ID NO 8
<211> LENGTH: 269
<212> TYPE: PRT
<213> ORGANISM: Plasmodium falciparum

<400> SEQUENCE: 8

Asp Tyr Ile Lys Asp Asp Pro Tyr Ser Lys Glu Tyr Thr Thr Lys Leu
1               5                   10                  15

Ser Phe Ile Leu Asn Ser Ser Asp Ala Asn Thr Ser Ser Gly Glu Thr
            20                  25                  30

Ala Asn His Asn Asp Glu Ala Cys Asn Cys Asn Glu Ser Glu Ile Ala
        35                  40                  45

Ser Val Glu Gln Ala Ser Ile Ser Asp Arg Ser Ser Gln Lys Ala Tyr
    50                  55                  60

Ile Thr His Ser Ser Ile Lys Thr Asn Lys Lys Val Cys Lys Tyr
65                  70                  75              80

Val Lys Leu Gly Ile Asn Asn Asp Lys Val Leu Arg Val Cys Val
                85                  90                  95

Ile Glu Asp Thr Ser Leu Ser Gly Val Glu Asn Cys Cys Phe Lys Asp
            100                 105                 110

Leu Leu Gly Ile Leu Gln Glu Asn Cys Ser Asp Asn Lys Arg Gly Ser
        115                 120                 125

Ser Phe Asn Asp Ser Cys Asn Asn Asn Glu Glu Ala Cys Gln Lys
    130                 135                 140
```

```
Lys Leu Glu Lys Val Leu Ala Ser Leu Thr Asn Gly Tyr Lys Cys Glu
145                 150                 155                 160

Lys Cys Lys Ser Gly Thr Ser Arg Ser Lys Lys Trp Ile Trp Lys
            165                 170                 175

Lys Ser Ser Gly Lys Glu Gly Leu Gln Lys Glu Tyr Ala Asn Thr
            180                 185                 190

Ile Gly Leu Pro Pro Arg Thr Gln Ser Leu Tyr Leu Gly Asn Leu Pro
            195                 200                 205

Lys Leu Glu Asn Val Cys Lys Gly Val Thr Asp Ile Asn Phe Asp Thr
210                 215                 220

Lys Glu Lys Phe Leu Ala Gly Cys Leu Ile Ala Ala Phe His Glu Gly
225                 230                 235                 240

Lys Asn Leu Lys Pro Ser His Gln Asn Lys Asn Asp Asp Asn Ser
            245                 250                 255

Lys Leu Cys Lys Asp Leu Lys Tyr Ser Phe Ala Asp Tyr
            260                 265

<210> SEQ ID NO 9
<211> LENGTH: 333
<212> TYPE: PRT
<213> ORGANISM: Plasmodium falciparum

<400> SEQUENCE: 9

Lys Cys Asp Lys Cys Lys Ser Gly Thr Ser Arg Ser Lys Lys Lys Trp
1               5                   10                  15

Thr Trp Arg Lys Ser Ser Gly Asn Lys Glu Gly Leu Gln Lys Glu Tyr
                20                  25                  30

Ala Asn Thr Ile Gly Leu Pro Pro Arg Thr His Ser Leu Tyr Leu Gly
                35                  40                  45

Asn Leu Arg Lys Leu Glu Asn Val Cys Glu Asp Val Thr Asp Ile Asn
        50                  55                  60

Phe Asp Thr Lys Glu Lys Phe Leu Ala Gly Cys Leu Ile Ala Ala Phe
65                  70                  75                  80

His Glu Gly Lys Asn Leu Lys Thr Thr Tyr Pro Gln Asn Lys Asn Asp
                85                  90                  95

Asp Asn Ser Lys Leu Cys Lys Ala Leu Lys Tyr Ser Phe Ala Asp
            100                 105                 110

Tyr Gly Asp Leu Ile Lys Gly Thr Ser Ile Trp Asp Asn Asp Phe Thr
            115                 120                 125

Lys Asp Leu Glu Leu Asn Leu Gln Lys Ile Phe Gly Lys Leu Phe Arg
130                 135                 140

Lys Tyr Ile Lys Lys Asn Ile Ser Thr Glu Gln His Thr Ser Tyr Ser
145                 150                 155                 160

Ser Leu Asp Glu Leu Arg Glu Ser Trp Trp Asn Thr Asn Lys Lys Tyr
            165                 170                 175

Ile Trp Leu Ala Met Lys His Gly Ala Glu Met Asn Gly Thr Thr Cys
            180                 185                 190

Ser Cys Ser Gly Asp Ser Asp Asp Ile Pro Thr Ile Asp Leu Ile
            195                 200                 205

Pro Gln Tyr Leu Arg Phe Leu Gln Glu Trp Val Glu His Phe Cys Lys
            210                 215                 220

Gln Arg Gln Ala Lys Val Asn Ala Val Ile Asn Ser Cys Asn Ser Cys
225                 230                 235                 240

Lys Asn Thr Ser Gly Glu Arg Lys Leu Gly Gly Thr Cys Gly Ser Glu
```

```
                        245                 250                 255
Cys Lys Thr Glu Cys Lys Asn Lys Cys Asp Ala Tyr Lys Glu Phe Ile
            260                 265                 270

Asp Gly Thr Gly Ser Gly Gly Thr Gly Thr Ala Gly Ser Ser Trp
        275                 280                 285

Val Lys Arg Trp Asp Gln Ile Tyr Lys Arg Tyr Ser Lys Tyr Ile Glu
        290                 295                 300

Asp Ala Lys Arg Asn Arg Lys Ala Gly Ser Lys Asn Cys Gly Thr Ser
305                 310                 315                 320

Ser Thr Thr Asn Ala Ala Glu Ser Lys Cys Val Gln Ser
                325                 330

<210> SEQ ID NO 10
<211> LENGTH: 650
<212> TYPE: PRT
<213> ORGANISM: Artificial Sequence
<220> FEATURE:
<223> OTHER INFORMATION: hb31 745 amino acids

<400> SEQUENCE: 10

Ser Tyr Val Lys Asn Asn Pro Tyr Ser Ala Glu Tyr Val Thr Lys Leu
1               5                   10                  15

Ser Phe Ile Leu Asn Ser Ser Asp Ala Asn Thr Ser Ser Glu Thr Pro
            20                  25                  30

Ser Lys Tyr Tyr Asp Glu Val Cys Asn Cys Asn Glu Ser Glu Ile Ser
        35                  40                  45

Ser Val Gly Gln Ala Gln Thr Ser Gly Pro Ser Ser Asn Lys Thr Cys
    50                  55                  60

Ile Thr His Ser Ser Ile Lys Thr Asn Lys Lys Val Cys Lys Asp
65                  70                  75                  80

Val Lys Leu Gly Ile Asn Asn Asp Lys Val Leu Arg Val Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Lys Asn Gln Ser Gly
        115                 120                 125

Ser Ser Ser Asn Gly Ser Cys Asn Asn Lys Asn Gln Asp Glu Cys Gln
    130                 135                 140

Lys Lys Leu Glu Lys Val Phe Ala Ser Leu Thr Asn Gly Tyr Lys Cys
145                 150                 155                 160

Asp Lys Cys Lys Ser Gly Thr Ser Arg Ser Lys Lys Trp Ile Trp
                165                 170                 175

Arg Lys Ser Ser Gly Asn Glu Glu Gly Leu Gln Lys Glu Tyr Ala Asn
            180                 185                 190

Thr Ile Gly Leu Pro Pro Arg Thr Gln Ser Leu Tyr Leu Gly Asn Leu
        195                 200                 205

Arg Lys Leu Glu Asn Val Cys Lys Gly Val Thr Asp Ile Asn Phe Asp
    210                 215                 220

Thr Lys Glu Lys Phe Leu Ala Gly Cys Leu Ile Ala Ala Phe His Glu
225                 230                 235                 240

Gly Lys Asn Leu Lys Thr Thr Tyr Pro Gln Asn Lys Lys Leu Cys
                245                 250                 255

Lys Asp Leu Lys Tyr Ser Phe Ala Asp Tyr Gly Asp Leu Ile Lys Gly
            260                 265                 270

Thr Ser Ile Trp Asp Asn Glu Tyr Thr Lys Asp Leu Glu Leu Asn Leu
```

```
                275                 280                 285
Gln Lys Ala Phe Gly Lys Leu Phe Arg Lys Tyr Ile Lys Lys Asn Ile
            290                 295                 300
Ser Thr Glu Gln His Thr Leu Tyr Ser Ser Leu Asp Glu Leu Arg Glu
305                 310                 315                 320
Ser Trp Trp Asn Thr Asn Lys Lys Tyr Ile Trp Leu Ala Met Lys His
                325                 330                 335
Gly Ala Gly Met Asn Ser Thr Thr Cys Cys Gly Asp Gly Ser Val Thr
            340                 345                 350
Gly Ser Gly Ser Ser Cys Asp Asp Ile Pro Thr Ile Asp Leu Ile Pro
            355                 360                 365
Gln Tyr Leu Arg Phe Leu Gln Glu Trp Val Glu His Phe Cys Lys Gln
            370                 375                 380
Arg Gln Glu Lys Val Asn Ala Val Ile Glu Asn Cys Asn Ser Cys Lys
385                 390                 395                 400
Glu Cys Gly Asp Thr Cys Asn Gly Glu Cys Lys Thr Glu Cys Glu Lys
                405                 410                 415
Lys Cys Lys Ile Glu Cys Glu Lys Tyr Lys Thr Phe Ile Glu Glu Cys
            420                 425                 430
Val Thr Ala Val Gly Gly Thr Ser Gly Ser Pro Trp Ser Lys Arg Trp
            435                 440                 445
Asp Gln Ile Tyr Lys Arg Tyr Ser Lys Tyr Ile Glu Asp Ala Lys Arg
450                 455                 460
Asn Arg Lys Ala Gly Thr Lys Asn Cys Gly Ile Thr Thr Gly Thr Ile
465                 470                 475                 480
Ser Gly Glu Ser Ser Gly Ala Asn Ser Gly Val Thr Thr Glu Asn
                485                 490                 495
Lys Cys Val Gln Ser Asp Ile Asp Ser Phe Phe Lys His Leu Ile Asp
                500                 505                 510
Ile Gly Leu Thr Thr Pro Ser Ser Tyr Leu Ser Ile Val Leu Asp Asp
            515                 520                 525
Asn Ile Cys Gly Ala Asp Asn Ala Pro Trp Thr Thr Tyr Thr Thr Tyr
            530                 535                 540
Thr Thr Tyr Thr Thr Thr Lys Asn Cys Asp Ile Lys Lys Lys Thr Pro
545                 550                 555                 560
Lys Ser Gln Pro Ile Asn Thr Ser Val Val Asn Val Pro Ser Pro
                565                 570                 575
Leu Gly Asn Thr Pro His Gly Tyr Lys Tyr Ala Cys Gln Cys Lys Ile
            580                 585                 590
Pro Thr Thr Glu Glu Ser Cys Asp Asp Arg Lys Glu Tyr Met Asn Gln
            595                 600                 605
Trp Ile Ile Asp Thr Ser Lys Lys Gln Lys Gly Ser Gly Ser Thr Asn
            610                 615                 620
Asn Asp Tyr Glu Leu Tyr Thr Tyr Asn Gly Val Lys Glu Thr Lys Leu
625                 630                 635                 640
Pro Lys Lys Ser Ser Ser Ser Lys Leu Asp
                645                 650

<210> SEQ ID NO 11
<211> LENGTH: 643
<212> TYPE: PRT
<213> ORGANISM: Artificial Sequence
<220> FEATURE:
<223> OTHER INFORMATION: hb32 745 amino acids
```

<400> SEQUENCE: 11

```
Ser Tyr Val Lys Asp Asp Pro Tyr Ser Ala Glu Tyr Val Thr Lys Leu
1               5                   10                  15

Ser Phe Ile Leu Asn Ser Ser Asp Ala Asn Thr Ser Ser Glu Thr Pro
            20                  25                  30

Ser Lys Tyr Tyr Asp Glu Val Cys Asn Cys Asn Glu Ser Glu Ile Ser
        35                  40                  45

Ser Val Gly Gln Ala Gln Thr Ser Gly Pro Ser Ser Asn Lys Thr Cys
    50                  55                  60

Ile Thr His Ser Ser Ile Lys Thr Asn Lys Lys Val Cys Lys Asp
65                  70                  75                  80

Val Lys Leu Gly Ile Asn Asn Asn Asp Lys Val Leu Arg Val Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Lys Asn Gln Ser Gly
        115                 120                 125

Ser Ser Ser Asn Gly Ser Cys Asn Asn Lys Asn Gln Asp Glu Cys Gln
    130                 135                 140

Lys Lys Leu Glu Lys Val Phe Ala Ser Leu Thr Asn Gly Tyr Lys Cys
145                 150                 155                 160

Asp Lys Cys Lys Ser Gly Thr Ser Arg Ser Lys Lys Trp Ile Trp
                165                 170                 175

Arg Lys Ser Ser Gly Asn Glu Glu Gly Leu Gln Lys Glu Tyr Ala Asn
            180                 185                 190

Thr Ile Gly Leu Pro Pro Arg Thr Gln Ser Leu Tyr Leu Gly Asn Leu
        195                 200                 205

Pro Lys Leu Glu Asn Val Cys Lys Gly Val Thr Asp Ile Ile Tyr Asp
    210                 215                 220

Thr Lys Glu Lys Phe Leu Ser Gly Cys Leu Ile Ala Ala Phe His Glu
225                 230                 235                 240

Gly Lys Asn Leu Lys Thr Ser His Glu Lys Lys Asn Asp Asp Asn Gly
                245                 250                 255

Lys Lys Leu Cys Lys Ala Leu Glu Tyr Ser Phe Ala Asp Tyr Gly Asp
            260                 265                 270

Leu Ile Lys Gly Thr Ser Ile Trp Asp Asn Asp Phe Thr Lys Asp Leu
        275                 280                 285

Glu Leu Asn Leu Gln Lys Ile Phe Gly Lys Leu Phe Arg Lys Tyr Ile
    290                 295                 300

Lys Lys Asn Asn Thr Ala Glu Gln Asp Thr Ser Tyr Ser Ser Leu Asp
305                 310                 315                 320

Glu Leu Arg Glu Ser Trp Trp Asn Thr Asn Lys Lys Tyr Ile Trp Thr
                325                 330                 335

Ala Met Lys His Gly Ala Gly Met Asn Ser Thr Thr Cys Ser Gly Asp
            340                 345                 350

Gly Ser Val Thr Gly Ser Gly Ser Cys Asp Asp Met Pro Thr Ile
        355                 360                 365

Asp Leu Ile Pro Gln Tyr Leu Arg Phe Leu Gln Glu Trp Val Glu His
    370                 375                 380

Phe Cys Lys Gln Arg Gln Glu Lys Val Lys Asp Val Ile Thr Asn Cys
385                 390                 395                 400

Asn Ser Cys Lys Glu Cys Gly Asp Thr Cys Asn Gly Glu Cys Lys Thr
                405                 410                 415
```

```
Glu Cys Lys Thr Lys Cys Lys Gly Glu Cys Lys Tyr Lys Asn Phe
            420                 425                 430

Ile Glu Glu Cys Asn Gly Thr Ala Asp Gly Thr Ser Gly Ser Ser
            435                 440                 445

Trp Ser Lys Arg Trp Asp Gln Ile Tyr Lys Arg Tyr Ser Lys Tyr Ile
    450                 455                 460

Glu Asp Ala Lys Arg Asn Arg Lys Ala Gly Thr Lys Asn Cys Gly Thr
465                 470                 475                 480

Ser Ser Thr Thr Asn Ala Ala Ala Ser Thr Thr Glu Asn Lys Cys Val
                485                 490                 495

Gln Ser Asp Ile Asp Ser Phe Phe Lys His Leu Ile Asp Ile Gly Leu
            500                 505                 510

Thr Thr Pro Ser Ser Tyr Leu Ser Asn Val Leu Asp Asp Asn Ile Cys
            515                 520                 525

Gly Glu Asp Lys Ala Pro Trp Thr Thr Tyr Thr Thr Tyr Thr Thr Lys
            530                 535                 540

Asn Cys Asp Ile Gln Lys Lys Thr Pro Lys Pro Gln Ser Cys Asp Thr
545                 550                 555                 560

Leu Val Val Val Asn Val Pro Ser Pro Leu Gly Asn Thr Pro His Gly
                565                 570                 575

Tyr Lys Tyr Val Cys Glu Cys Lys Ile Pro Thr Thr Glu Glu Thr Cys
            580                 585                 590

Asp Asp Arg Lys Glu Tyr Met Asn Gln Trp Ile Ile Asp Thr Ser Lys
            595                 600                 605

Lys Gln Lys Gly Ser Gly Ser Thr Asn Asn Asp Tyr Glu Leu Tyr Thr
            610                 615                 620

Tyr Asn Gly Val Gln Ile Lys Gln Ala Ala Gly Thr Leu Lys Asn Ser
625                 630                 635                 640

Lys Leu Asp

<210> SEQ ID NO 12
<211> LENGTH: 269
<212> TYPE: PRT
<213> ORGANISM: Plasmodium falciparum

<400> SEQUENCE: 12

Asn Tyr Ile Lys Gly Asp Pro Tyr Ser Ala Glu Tyr Ala Thr Lys Leu
1               5                   10                  15

Ser Phe Ile Leu Asn Ser Ser Asp Thr Glu Asn Ala Ser Glu Lys Ile
            20                  25                  30

Gln Lys Asn Asn Asp Glu Val Cys Asn Cys Asn Glu Ser Glu Ile Ala
            35                  40                  45

Ser Val Glu Gln Ala Pro Ile Ser Asp Arg Ser Ser Gln Lys Ala Cys
    50                  55                  60

Ile Thr His Ser Ser Ile Lys Ala Asn Lys Lys Val Cys Lys His
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Asn Lys Ser Gly Ser
            115                 120                 125

Ser Ser Asn Gly Ser Cys Asn Asn Asn Glu Glu Ile Cys Gln Lys
            130                 135                 140
```

Lys Leu Glu Lys Val Leu Ala Ser Leu Thr Asn Gly Tyr Lys Cys Asp
145                 150                 155                 160

Lys Cys Lys Ser Gly Thr Ser Thr Val Asn Lys Asn Trp Ile Trp Lys
                165                 170                 175

Lys Tyr Ser Gly Lys Glu Gly Gly Leu Gln Glu Glu Tyr Ala Asn Thr
            180                 185                 190

Ile Gly Leu Pro Pro Arg Thr Gln Ser Leu Tyr Leu Gly Asn Leu Pro
        195                 200                 205

Lys Leu Glu Asn Val Cys Glu Asp Val Lys Asp Ile Asn Phe Asp Thr
210                 215                 220

Lys Glu Lys Phe Leu Ala Gly Cys Leu Ile Ala Ala Phe His Glu Gly
225                 230                 235                 240

Lys Asn Leu Lys Thr Ser Asn Lys Lys Asn Asp Asp Asn Asn Ser
                245                 250                 255

Lys Leu Cys Lys Ala Leu Lys Tyr Ser Phe Ala Asp Tyr
            260                 265

<210> SEQ ID NO 13
<211> LENGTH: 344
<212> TYPE: PRT
<213> ORGANISM: Plasmodium falciparum

<400> SEQUENCE: 13

Lys Cys Asp Lys Cys Lys Ser Gly Thr Ser Thr Val Asn Lys Lys Trp
1               5                   10                  15

Ile Trp Lys Lys Tyr Ser Gly Thr Glu Gly Gly Leu Gln Glu Glu Tyr
            20                  25                  30

Ala Asn Thr Ile Ala Leu Pro Pro Arg Thr Gln Ser Leu Tyr Leu Gly
                35                  40                  45

Asn Leu Pro Lys Leu Glu Asn Val Cys Lys Asp Val Thr Asp Ile Asn
50                  55                  60

Phe Asp Thr Lys Glu Lys Phe Leu Ala Gly Cys Leu Ile Ala Ala Phe
65                  70                  75                  80

His Glu Gly Lys Asn Leu Lys Thr Thr Tyr Leu Glu Lys Lys Lys Gly
                85                  90                  95

Asp Asn Gly Lys Lys Asn Asp Asp Asn Asn Ser Lys Leu Cys Lys Ala
                100                 105                 110

Leu Lys Tyr Ser Phe Ala Asp Tyr Gly Asp Leu Ile Lys Gly Thr Ser
            115                 120                 125

Ile Trp Asp Asn Asp Phe Thr Lys Asp Leu Glu Leu Asn Leu Gln Gln
        130                 135                 140

Ile Phe Gly Lys Leu Phe Arg Lys Tyr Ile Lys Lys Asn Ile Ala Ser
145                 150                 155                 160

Asp Glu Asn Thr Leu Tyr Ser Ser Leu Asp Glu Leu Arg Glu Ser Trp
                165                 170                 175

Trp Asn Thr Asn Lys Lys Tyr Ile Trp Leu Ala Met Lys His Gly Ala
            180                 185                 190

Gly Met Asn Ser Thr Met Cys Asn Ala Asp Gly Ser Val Thr Gly Ser
        195                 200                 205

Gly Ser Ser Cys Asp Asp Ile Pro Thr Ile Asp Leu Ile Pro Gln Tyr
        210                 215                 220

Leu Arg Phe Leu Gln Glu Trp Val Glu His Phe Cys Lys Gln Arg Gln
225                 230                 235                 240

Ala Lys Val Lys Asp Val Ile Thr Asn Cys Asn Ser Cys Lys Glu Cys

```
            245                 250                 255
Gly Gly Thr Cys Asn Gly Glu Cys Lys Thr Glu Cys Glu Lys Lys Cys
            260                 265                 270

Lys Gly Glu Cys Asp Ala Tyr Lys Lys Phe Ile Glu Glu Cys Lys Gly
            275                 280                 285

Lys Ala Asp Glu Gly Thr Ser Gly Ser Ser Trp Ser Lys Arg Trp Asp
            290                 295                 300

Gln Ile Tyr Lys Arg Tyr Ser Lys Tyr Ile Glu Asp Ala Lys Arg Asn
305                 310                 315                 320

Arg Lys Ala Gly Thr Lys Asn Cys Gly Pro Ser Ser Thr Thr Ser Thr
                325                 330                 335

Ala Glu Ser Lys Cys Val Gln Ser
            340

<210> SEQ ID NO 14
<211> LENGTH: 334
<212> TYPE: PRT
<213> ORGANISM: Plasmodium falciparum

<400> SEQUENCE: 14

Lys Cys Asp Lys Cys Lys Ser Glu Gln Ser Lys Lys Asn Asn Asn Ile
1               5                   10                  15

Trp Ile Trp Lys Lys Ser Ser Gly Thr Glu Gly Gly Leu Gln Lys Glu
            20                  25                  30

Tyr Ala Asn Thr Ile Ala Leu Pro Pro Arg Thr Gln Ser Leu Tyr Leu
        35                  40                  45

Gly Asn Leu Arg Lys Leu Glu Asn Val Cys Glu Asp Val Lys Asp Ile
    50                  55                  60

Asn Phe Asp Thr Lys Glu Lys Phe Leu Ala Gly Cys Leu Ile Ala Ala
65                  70                  75                  80

Phe His Glu Gly Lys Asn Leu Lys Lys Arg Tyr Leu Glu Lys Lys Asn
                85                  90                  95

Gly Asp Asn Asn Ser Lys Leu Cys Lys Ala Leu Lys Tyr Ser Phe Ala
            100                 105                 110

Asp Tyr Gly Asp Leu Ile Lys Gly Thr Ser Ile Trp Asp Asn Glu Tyr
        115                 120                 125

Thr Lys Asp Leu Glu Leu Asn Leu Gln Lys Ile Phe Gly Lys Leu Phe
    130                 135                 140

Arg Lys Tyr Ile Lys Lys Asn Asn Thr Ala Glu Gln His Thr Ser Tyr
145                 150                 155                 160

Ser Ser Leu Asp Glu Leu Arg Glu Ser Trp Trp Asn Thr Asn Lys Lys
                165                 170                 175

Tyr Ile Trp Leu Ala Met Lys His Gly Thr Thr Cys Ser Ser Gly Ser
            180                 185                 190

Gly Asp Asn Gly Ser Ile Ser Cys Asp Asp Ile Pro Thr Ile Asp Leu
        195                 200                 205

Ile Pro Gln Tyr Leu Arg Phe Leu Gln Glu Trp Val Glu His Phe Cys
    210                 215                 220

Glu Gln Arg Gln Gly Lys Val Asn Ala Val Ile Glu Asn Cys Asn Ser
225                 230                 235                 240

Cys Lys Asn Thr Ser Ser Lys Thr Lys Leu Gly Gly Thr Cys Asn Gly
                245                 250                 255

Glu Cys Lys Thr Glu Cys Lys Gly Glu Cys Asp Ala Tyr Lys Glu Phe
            260                 265                 270
```

```
Ile Glu Lys Cys Lys Gly Thr Ala Ala Glu Gly Thr Ser Gly Ser Ser
            275                 280                 285

Trp Val Lys Arg Trp Tyr Gln Ile Tyr Met Arg Tyr Ser Lys Tyr Ile
    290                 295                 300

Glu Asp Ala Lys Arg Asn Arg Lys Ala Gly Thr Lys Asn Cys Gly Thr
305                 310                 315                 320

Ser Ser Thr Thr Ser Thr Ala Glu Ser Lys Cys Val Gln Ser
                325                 330

<210> SEQ ID NO 15
<211> LENGTH: 332
<212> TYPE: PRT
<213> ORGANISM: Plasmodium falciparum

<400> SEQUENCE: 15

Lys Cys Asp Lys Cys Lys Ser Glu Gln Ser Lys Asn Asn Asn Asn Ile
1               5                   10                  15

Trp Ile Trp Lys Lys Ser Ser Gly Thr Glu Gly Gly Leu Gln Lys Glu
            20                  25                  30

Tyr Ala Asn Thr Ile Ala Leu Pro Pro Arg Thr Gln Ser Leu Tyr Leu
        35                  40                  45

Gly Asn Leu Arg Lys Leu Glu Asn Val Cys Glu Asp Val Lys Asp Ile
    50                  55                  60

Asn Phe Asp Thr Lys Glu Lys Phe Leu Ala Gly Cys Leu Ile Ala Ala
65                  70                  75                  80

Phe His Glu Gly Lys Asn Leu Lys Lys Arg Tyr Leu Glu Lys Lys Asn
                85                  90                  95

Gly Asp Asn Asn Ser Lys Leu Cys Lys Ala Leu Lys Tyr Ser Phe Ala
            100                 105                 110

Asp Tyr Gly Asp Leu Ile Lys Gly Thr Ser Ile Trp Asp Asn Glu Tyr
        115                 120                 125

Thr Lys Asp Leu Glu Leu Asn Leu Gln Lys Ile Phe Gly Lys Leu Phe
    130                 135                 140

Arg Lys Tyr Ile Lys Lys Asn Asn Thr Ala Glu Gln Asp Thr Ser Tyr
145                 150                 155                 160

Ser Ser Leu Asp Glu Leu Arg Glu Ser Trp Trp Asn Thr Asn Lys Lys
                165                 170                 175

Tyr Ile Trp Thr Ala Met Lys His Gly Thr Thr Cys Ser Ser Gly Ser
            180                 185                 190

Gly Asp Asn Gly Ser Ile Ser Cys Asp Asp Ile Pro Thr Ile Asp Leu
        195                 200                 205

Ile Pro Gln Tyr Leu Arg Phe Leu Gln Glu Trp Val Glu His Phe Cys
    210                 215                 220

Glu Gln Arg Gln Glu Lys Val Lys Asp Val Ile Lys Asn Cys Asn Ser
225                 230                 235                 240

Cys Lys Glu Cys Gly Gly Thr Cys Asn Gly Glu Cys Lys Thr Glu Cys
                245                 250                 255

Lys Asn Lys Cys Lys Asp Glu Cys Asp Ala Tyr Lys Lys Phe Ile Glu
            260                 265                 270

Glu Cys Glu Gly Lys Ala Ala Glu Gly Thr Ser Gly Ser Ser Trp Ser
        275                 280                 285

Lys Arg Trp Asp Gln Ile Tyr Lys Arg Tyr Ser Lys Tyr Ile Glu Asp
    290                 295                 300

Ala Lys Arg Asn Arg Lys Ala Gly Thr Lys Asn Cys Gly Thr Ser Ser
305                 310                 315                 320
```

```
Thr Thr Ser Thr Ala Glu Asn Lys Cys Val Gln Ser
            325                 330

<210> SEQ ID NO 16
<211> LENGTH: 267
<212> TYPE: PRT
<213> ORGANISM: Plasmodium falciparum

<400> SEQUENCE: 16

Asn Tyr Ile Lys Asp Asp Pro Tyr Ser Ala Glu Tyr Thr Thr Lys Leu
1               5                   10                  15

Ser Phe Ile Leu Asn Ser Ser Asp Thr Glu Asn Ala Ser Glu Lys Ile
            20                  25                  30

Gln Lys Asn Asn Asp Glu Val Cys Asn Pro Asn Glu Ser Gly Ile Ala
        35                  40                  45

Cys Val Glu Leu Ala Gln Thr Ser Gly Ser Ser Asn Lys Thr Cys
    50                  55                  60

Asn Thr His Ser Phe Ile Lys Ala Asn Lys Lys Val Cys Lys Asp
65                  70                  75                  80

Val Lys Leu Gly Ile Asn Lys Lys Asp Lys Asp Leu Lys Ile Cys Val
                85                  90                  95

Ile Glu Asp Asp Ser Leu Arg Gly Val Asp Asn Cys Cys Gln Asp
            100                 105                 110

Leu Leu Gly Ile Leu Gln Glu Asn Cys Ser Asp Lys Asn Gln Ser Gly
            115                 120                 125

Ser Ser Ser Asn Gly Ser Cys Asn Asn Lys Asn Gln Glu Ala Cys Gln
        130                 135                 140

Lys Lys Leu Glu Asn Val Phe Ala Ser Leu Thr Asn Gly Tyr Lys Cys
145                 150                 155                 160

Glu Lys Cys Lys Ser Glu Gln Ser Lys Lys Asn Asn Lys Asn Trp Ile
                165                 170                 175

Trp Lys Lys Tyr Ser Val Lys Glu Glu Gly Leu Gln Lys Glu Tyr Ala
            180                 185                 190

Asn Thr Ile Ala Leu Pro Pro Arg Thr Gln Ser Leu Tyr Leu Gly Asn
        195                 200                 205

Leu Pro Lys Leu Gly Asn Val Cys Lys Gly Val Thr Asp Ile Asn Phe
    210                 215                 220

Asp Thr Lys Glu Lys Phe Leu Ala Gly Cys Leu Ile Ala Ala Phe His
225                 230                 235                 240

Glu Gly Lys Asn Leu Lys Thr Thr Tyr Leu Gln Asn Lys Lys Lys Leu
                245                 250                 255

Cys Lys Ala Leu Lys Tyr Ser Phe Ala Asp Tyr
            260                 265

<210> SEQ ID NO 17
<211> LENGTH: 263
<212> TYPE: PRT
<213> ORGANISM: Plasmodium falciparum

<400> SEQUENCE: 17

Asp Tyr Ile Lys Gly Asp Pro Tyr Phe Ala Glu Tyr Ala Thr Lys Leu
1               5                   10                  15

Ser Phe Ile Leu Asn Ser Ser Asp Ala Asn Thr Ser Ser Gly Glu Thr
            20                  25                  30

Ala Asn His Asn Asp Glu Ala Cys Asn Pro Asn Glu Ser Glu Ile Ala
        35                  40                  45
```

Ser Val Glu Gln Ala Ser Ile Ser Asp Arg Ser Ser Gln Lys Ala Cys
    50                  55                  60

Asn Thr His Ser Ser Ile Lys Ala Asn Lys Lys Glu Cys Lys His
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Gly Ser Cys Asp Lys Asn Ser Glu Glu Ile Cys Gln Lys
130                 135                 140

Lys Leu Asp Glu Ala Leu Ala Ser Leu His Asn Gly Tyr Lys Asn Gln
145                 150                 155                 160

Lys Cys Lys Ser Glu Gln Ser Lys Lys Asn Lys Asn Lys Trp Ile Trp
                165                 170                 175

Lys Lys Ser Ser Gly Asn Glu Lys Gly Leu Gln Lys Glu Tyr Ala Asn
            180                 185                 190

Thr Ile Gly Leu Pro Pro Arg Thr Gln Ser Leu Tyr Leu Gly Asn Leu
        195                 200                 205

Pro Lys Leu Glu Asn Val Cys Glu Asp Val Thr Asp Ile Asn Phe Asp
210                 215                 220

Thr Lys Glu Lys Phe Leu Ala Gly Cys Leu Ile Ala Ala Phe His Glu
225                 230                 235                 240

Gly Lys Asn Leu Lys Thr Thr Tyr Pro Gln Asn Lys Asn Asp Asp Asn
                245                 250                 255

Gly Lys Lys Leu Cys Lys Asp
            260

<210> SEQ ID NO 18
<211> LENGTH: 338
<212> TYPE: PRT
<213> ORGANISM: Plasmodium falciparum

<400> SEQUENCE: 18

Lys Cys Asp Lys Cys Lys Ser Glu Gln Ser Lys Lys Asn Lys Asn Ile
1               5                   10                  15

Trp Ile Trp Lys Lys Ser Ser Gly Asn Lys Lys Gly Leu Gln Lys Glu
                20                  25                  30

Tyr Ala Asn Thr Ile Gly Leu Pro Pro Arg Thr Gln Ser Leu Tyr Leu
            35                  40                  45

Gly Asn Leu Pro Lys Leu Glu Asn Val Cys Lys Asp Val Thr Asp Ile
        50                  55                  60

Asn Phe Asp Thr Lys Glu Lys Phe Leu Ala Gly Cys Leu Ile Ala Ala
65                  70                  75                  80

Phe His Glu Gly Lys Asn Leu Lys Ile Ser Glu Lys Lys Asn Asp
                85                  90                  95

Asp Asn Gly Lys Lys Leu Cys Lys Asp Leu Lys Tyr Ser Phe Ala Asp
            100                 105                 110

Tyr Gly Asp Leu Ile Lys Gly Thr Ser Ile Trp Asp Asn Glu Tyr Thr
        115                 120                 125

Lys Asp Leu Glu Leu Asn Leu Gln Asn Asn Phe Gly Lys Leu Phe Arg
130                 135                 140

Lys Tyr Ile Lys Lys Asn Asn Thr Ala Glu Gln His Thr Leu Tyr Ser

```
145                 150                 155                 160
Ser Leu Asp Glu Leu Arg Glu Ser Trp Trp Asn Thr Asn Lys Lys Tyr
                165                 170                 175

Ile Trp Leu Ala Met Lys His Gly Thr Thr Cys Ser Ser Gly Ser Gly
            180                 185                 190

Asp Asn Gly Asp Gly Ser Val Thr Gly Ser Gly Ser Ser Cys Asp Asp
        195                 200                 205

Met Ser Thr Ile Asp Leu Ile Pro Gln Tyr Leu Arg Phe Leu Gln Glu
    210                 215                 220

Trp Val Glu His Phe Cys Lys Gln Arg Gln Glu Lys Val Asn Ala Val
225                 230                 235                 240

Ile Glu Asn Cys Asn Ser Cys Lys Asn Thr Ser Ser Lys Thr Lys Leu
                245                 250                 255

Gly Gly Thr Cys Asn Gly Glu Cys Lys Thr Glu Cys Glu Lys Lys Cys
            260                 265                 270

Lys Asp Glu Cys Glu Lys Tyr Lys Glu Phe Ile Glu Glu Cys Lys Arg
        275                 280                 285

Gly Asp Gly Thr Ala Gly Ser Pro Trp Val Lys Arg Trp Asp Gln Ile
    290                 295                 300

Tyr Met Arg Tyr Ser Lys Tyr Ile Glu Asp Ala Lys Arg Asn Arg Lys
305                 310                 315                 320

Ala Gly Thr Lys Ser Cys Gly Thr Ser Ala Ala Glu Asn Lys Cys Val
                325                 330                 335

Gln Ser

<210> SEQ ID NO 19
<211> LENGTH: 341
<212> TYPE: PRT
<213> ORGANISM: Plasmodium falciparum

<400> SEQUENCE: 19

Lys Cys Asp Lys Cys Lys Ser Glu Gln Ser Lys Asn Asn Asn Asn Ile
1               5                   10                  15

Trp Ile Trp Lys Lys Ser Ser Gly Asp Glu Lys Gly Leu Gln Lys Glu
            20                  25                  30

Tyr Ala Asn Thr Ile Ala Leu Pro Pro Arg Thr Gln Ser Leu Tyr Leu
        35                  40                  45

Gly Asn Leu Pro Lys Leu Glu Asn Val Cys Lys Asp Val Thr Asp Ile
    50                  55                  60

Asn Phe Asp Thr Lys Glu Lys Phe Leu Ala Gly Cys Leu Ile Ala Ala
65                  70                  75                  80

Phe His Glu Gly Lys Asn Leu Lys Thr Ser His Gln Asn Lys Asn Ala
                85                  90                  95

Asp Asn Gly Lys Lys Asn Asp Asn Gly Lys Lys Leu Cys Lys Ala
            100                 105                 110

Leu Lys Tyr Ser Phe Ala Asp Tyr Gly Asp Leu Ile Lys Gly Thr Ser
        115                 120                 125

Ile Trp Asp Asn Glu Tyr Thr Lys Asp Leu Glu Leu Asn Leu Gln Gln
    130                 135                 140

Ile Phe Gly Lys Leu Phe Arg Lys Tyr Ile Lys Arg Asn Asn Thr Ala
145                 150                 155                 160

Glu Gln His Thr Leu Tyr Ser Ser Leu Asp Glu Leu Arg Glu Ser Trp
                165                 170                 175

Trp Asn Thr Asn Lys Lys Tyr Ile Trp Leu Ala Met Lys His Gly Thr
```

```
                180                 185                 190
Thr Cys Ser Ser Gly Ser Gly Asp Asn Gly Asp Gly Ser Val Thr Gly
            195                 200                 205

Ser Gly Ser Ser Cys Asp Asp Met Ser Thr Ile Asp Leu Ile Pro Gln
        210                 215                 220

Tyr Leu Arg Phe Leu Gln Glu Trp Val Glu His Phe Cys Lys Gln Arg
225                 230                 235                 240

Gln Glu Lys Val Lys Asp Val Ile Thr Asn Cys Asn Ser Cys Lys Glu
                245                 250                 255

Cys Gly Gly Thr Cys Gly Ser Asp Cys Lys Thr Lys Cys Glu Ala Tyr
            260                 265                 270

Lys Lys Phe Ile Glu Glu Cys Asn Gly Thr Ala Asp Gly Gly Thr Ser
        275                 280                 285

Gly Ser Ser Trp Ser Lys Arg Trp Asp Gln Ile Tyr Lys Arg Tyr Ser
    290                 295                 300

Lys Tyr Ile Glu Asp Ala Lys Arg Asn Arg Lys Ala Gly Thr Lys Asn
305                 310                 315                 320

Cys Gly Pro Ser Ser Gly Ala Asn Ser Gly Val Thr Thr Glu Asn
                325                 330                 335

Lys Cys Val Gln Ser
            340

<210> SEQ ID NO 20
<211> LENGTH: 352
<212> TYPE: PRT
<213> ORGANISM: Plasmodium falciparum

<400> SEQUENCE: 20

Lys Cys Glu Lys Cys Glu Ser Glu Gln Ser Lys Lys Asn Asn Lys Tyr
1               5                   10                  15

Trp Ile Trp Lys Lys Ser Ser Gly Asn Gly Glu Gly Leu Gln Glu Glu
                20                  25                  30

Tyr Ala Asn Thr Ile Ala Leu Pro Pro Arg Thr His Ser Leu Cys Leu
            35                  40                  45

Val Cys Leu His Glu Lys Glu Gly Lys Lys Thr Gln Glu Leu Lys Asn
        50                  55                  60

Ile Arg Thr Asn Ser Glu Leu Leu Lys Glu Arg Ile Ile Ala Ala Phe
65                  70                  75                  80

His Glu Gly Lys Asn Leu Lys Thr Ser Pro Gln Asn Lys Asn Asp Asn
                85                  90                  95

Gly Lys Lys Leu Cys Lys Asp Leu Lys Tyr Ser Phe Ala Asp Tyr Gly
            100                 105                 110

Asp Leu Ile Lys Gly Thr Ser Ile Trp Asp Asn Glu Tyr Thr Lys Asp
        115                 120                 125

Leu Glu Leu Asn Leu Gln Lys Ile Phe Gly Lys Leu Phe Arg Lys Tyr
    130                 135                 140

Ile Lys Lys Asn Asn Thr Ala Glu Gln His Thr Leu Tyr Ser Ser Leu
145                 150                 155                 160

Asp Glu Leu Arg Glu Ser Trp Trp Asn Thr Asn Lys Lys Tyr Ile Trp
                165                 170                 175

Leu Ala Met Lys His Gly Ala Gly Met Asn Ser Thr Met Cys Asn Ala
            180                 185                 190

Asp Gly Ser Val Thr Gly Ser Ser Asp Ser Gly Ser Thr Thr Cys Cys
        195                 200                 205
```

```
Gly Asp Asn Gly Ser Ile Ser Cys Asp Asp Met Pro Thr Ile Asp Leu
        210                 215                 220

Ile Pro Gln Tyr Leu Arg Phe Leu Gln Glu Trp Val Glu His Phe Cys
225                 230                 235                 240

Glu Gln Arg Gln Glu Lys Val Asn Ala Val Ile Thr Asn Cys Lys Ser
                245                 250                 255

Cys Lys Glu Cys Gly Gly Thr Cys Asn Ser Asp Cys Glu Lys Lys Cys
            260                 265                 270

Lys Ala Tyr Lys Glu Phe Ile Glu Lys Cys Lys Gly Gly Thr Glu
            275                 280                 285

Gly Thr Ser Gly Ser Ser Trp Ser Lys Arg Trp Asp Gln Ile Tyr Lys
290                 295                 300

Arg His Ser Lys His Ile Glu Asp Ala Lys Arg Asn Arg Lys Ala Gly
305                 310                 315                 320

Thr Lys Asn Cys Gly Ile Thr Gly Thr Ile Ser Gly Glu Ser Ser
                325                 330                 335

Gly Ala Asn Ser Gly Val Thr Thr Glu Asn Lys Cys Val Gln Ser
            340                 345                 350

<210> SEQ ID NO 21
<211> LENGTH: 344
<212> TYPE: PRT
<213> ORGANISM: Plasmodium falciparum

<400> SEQUENCE: 21

Lys Cys Asp Lys Cys Lys Ser Gly Thr Ser Arg Ser Arg Lys Ile Trp
1               5                   10                  15

Thr Trp Arg Lys Phe Arg Gly Asn Gly Glu Gly Leu Gln Lys Glu Tyr
                20                  25                  30

Ala Asn Thr Ile Gly Leu Ser Pro Arg Thr Gln Leu Leu Tyr Leu Val
            35                  40                  45

Cys Leu His Glu Lys Gly Lys Lys Thr Gln Glu Leu Lys Asn Ile Ser
        50                  55                  60

Thr Asn Ser Glu Leu Leu Lys Glu Trp Ile Ile Ala Ala Phe His Glu
65                  70                  75                  80

Gly Lys Asn Leu Lys Thr Thr Tyr Pro Gln Lys Lys Asn Asp Asp Asn
                85                  90                  95

Gly Lys Lys Leu Cys Lys Ala Leu Lys Tyr Ser Phe Ala Asp Tyr Gly
            100                 105                 110

Asp Leu Ile Lys Gly Thr Ser Ile Trp Asp Asn Asp Phe Thr Lys Asp
        115                 120                 125

Leu Glu Leu Asn Leu Gln Lys Ile Phe Gly Lys Leu Phe Arg Lys Tyr
    130                 135                 140

Ile Lys Lys Asn Ile Ala Ser Asp Glu Asn Thr Ser Tyr Ser Ser Leu
145                 150                 155                 160

Asp Glu Leu Arg Glu Ser Trp Trp Asn Thr Asn Lys Lys Tyr Ile Trp
                165                 170                 175

Thr Ala Met Lys His Gly Ala Gly Met Asn Gly Thr Thr Cys Cys Gly
            180                 185                 190

Asp Gly Ser Val Thr Gly Ser Ser Asp Ser Gly Ser Thr Thr Cys Cys
        195                 200                 205

Gly Asp Gly Ser Val Thr Gly Ser Gly Ser Ser Cys Asp Asp Ile Pro
    210                 215                 220

Thr Ile Asp Leu Ile Pro Gln Tyr Leu Arg Phe Leu Gln Glu Trp Val
225                 230                 235                 240
```

-continued

Glu His Phe Cys Glu Gln Arg Gln Lys Val Lys Asp Val Ile Thr
            245                 250                 255

Asn Cys Lys Ser Cys Lys Glu Ser Lys Lys Cys Lys Asn Lys Cys
            260                 265                 270

Asp Ala Tyr Lys Glu Phe Ile Asp Gly Thr Gly Ser Gly Gly Thr
            275                 280                 285

Gly Thr Ala Gly Ser Ser Trp Ser Lys Arg Trp Asp Gln Ile Tyr Met
290                 295                 300

Arg Tyr Ser Lys Tyr Ile Glu Asp Ala Lys Arg Asn Arg Lys Ala Gly
305                 310                 315                 320

Thr Lys Asn Cys Gly Thr Ser Ser Gly Ala Asn Ser Gly Val Thr Thr
            325                 330                 335

Thr Glu Asn Lys Cys Val Gln Ser
            340

<210> SEQ ID NO 22
<211> LENGTH: 350
<212> TYPE: PRT
<213> ORGANISM: Plasmodium falciparum

<400> SEQUENCE: 22

Lys Cys Glu Lys Cys Lys Ser Glu Gln Ser Lys Lys Asn Asn Lys Ile
1               5                   10                  15

Trp Thr Trp Arg Lys Phe Pro Gly Asn Gly Gly Leu Gln Lys Glu
            20                  25                  30

Tyr Ala Asn Thr Ile Gly Leu Ser Pro Arg Thr Gln Leu Leu Tyr Leu
            35                  40                  45

Val Cys Leu His Glu Lys Gly Lys Lys Thr Gln His Lys Thr Ile Ser
    50                  55                  60

Thr Asn Ser Glu Leu Leu Lys Glu Trp Ile Ile Ala Ala Phe His Glu
65                  70                  75                  80

Gly Lys Asn Leu Lys Lys Arg Tyr Leu Glu Lys Lys Gly Asp Asn
                85                  90                  95

Asn Ser Lys Leu Cys Lys Asp Leu Lys Tyr Ser Phe Ala Asp Tyr Gly
            100                 105                 110

Asp Leu Ile Lys Gly Thr Ser Ile Trp Asp Asn Asp Phe Thr Lys Asp
            115                 120                 125

Leu Glu Leu Asn Leu Gln Gln Ile Phe Gly Lys Leu Phe Arg Lys Tyr
            130                 135                 140

Ile Lys Lys Asn Ile Ala Ser Asp Glu Asn Thr Ser Tyr Ser Ser Leu
145                 150                 155                 160

Asp Glu Leu Arg Glu Ser Trp Trp Asn Thr Asn Lys Lys Tyr Ile Trp
                165                 170                 175

Thr Ala Met Lys His Gly Ala Gly Met Asn Ser Thr Met Cys Asn Gly
            180                 185                 190

Asp Gly Ser Val Thr Gly Ser Ser Asp Ser Gly Ser Thr Thr Cys Ser
            195                 200                 205

Gly Asp Asn Gly Ser Ile Ser Cys Asp Asp Ile Pro Thr Ile Asp Leu
210                 215                 220

Ile Pro Gln Tyr Leu Arg Phe Leu Gln Glu Trp Val Glu His Phe Cys
225                 230                 235                 240

Glu Gln Arg Gln Glu Lys Val Lys Asp Val Ile Lys Asn Cys Asn Ser
            245                 250                 255

Cys Lys Glu Cys Gly Gly Thr Cys Asn Gly Glu Cys Lys Thr Glu Cys

```
                 260                 265                 270
Lys Asn Lys Cys Lys Asp Glu Cys Glu Lys Tyr Lys Asn Phe Ile Glu
            275                 280                 285

Val Cys Thr Gly Gly Asp Gly Thr Ala Gly Ser Pro Trp Ser Lys Arg
        290                 295                 300

Trp Tyr Gln Ile Tyr Met Arg Tyr Ser Lys Tyr Ile Glu Asp Ala Lys
305                 310                 315                 320

Arg Asn Arg Lys Ala Gly Thr Lys Ser Cys Gly Thr Ser Ser Gly Ala
                325                 330                 335

Asn Ser Gly Val Thr Thr Thr Glu Ser Lys Cys Val Gln Ser
            340                 345                 350

<210> SEQ ID NO 23
<211> LENGTH: 359
<212> TYPE: PRT
<213> ORGANISM: Plasmodium falciparum

<400> SEQUENCE: 23

Lys Cys Glu Lys Cys Lys Ser Glu Gln Ser Lys Lys Asn Asn Lys Asn
1               5                   10                  15

Trp Ile Trp Arg Lys Phe Pro Gly Asn Gly Glu Gly Leu Gln Lys Glu
            20                  25                  30

Tyr Ala Asn Thr Ile Gly Leu Pro Pro Arg Thr His Ser Leu Tyr Leu
        35                  40                  45

Val Cys Leu His Glu Lys Gly Lys Lys Thr Gln Glu Leu Lys Asn Ile
    50                  55                  60

Arg Thr Asn Ser Glu Leu Leu Lys Glu Trp Ile Ala Ala Phe His
65                  70                  75                  80

Glu Gly Lys Asn Leu Lys Lys Arg Tyr His Gln Asn Asn Asn Ser Gly
                85                  90                  95

Asn Lys Lys Lys Leu Cys Lys Ala Leu Glu Tyr Ser Phe Ala Asp Tyr
            100                 105                 110

Gly Asp Leu Ile Lys Gly Thr Ser Ile Trp Asp Asn Glu Tyr Thr Lys
        115                 120                 125

Asp Leu Glu Leu Asn Leu Gln Gln Ile Phe Gly Lys Leu Phe Arg Lys
    130                 135                 140

Tyr Ile Lys Lys Asn Ile Ser Thr Glu Gln Asp Thr Leu Tyr Ser Ser
145                 150                 155                 160

Leu Asp Glu Leu Arg Glu Ser Trp Trp Asn Thr Asn Lys Lys Tyr Ile
                165                 170                 175

Trp Leu Ala Met Lys His Gly Ala Gly Met Asn Ser Thr Thr Cys Cys
            180                 185                 190

Gly Asp Gly Ser Val Thr Gly Ser Ser Asp Ser Gly Ser Thr Thr Cys
        195                 200                 205

Ser Gly Asp Asn Gly Ser Ile Ser Cys Asp Asp Met Pro Thr Ile Asp
    210                 215                 220

Leu Ile Pro Gln Tyr Leu Arg Phe Leu Gln Glu Trp Val Glu His Phe
225                 230                 235                 240

Cys Glu Gln Arg Gln Glu Lys Val Lys Asp Val Ile Glu Asn Cys Lys
                245                 250                 255

Ser Cys Lys Asn Thr Ser Gly Glu Arg Ile Ile Gly Gly Thr Cys Asn
            260                 265                 270

Gly Glu Cys Lys Thr Glu Cys Glu Lys Lys Cys Lys Ala Ala Cys Glu
        275                 280                 285
```

```
Ala Tyr Lys Thr Phe Ile Glu Glu Cys Glu Gly Lys Ala Ala Glu Gly
    290                 295                 300

Thr Ser Gly Ser Ser Trp Ser Lys Arg Trp Tyr Gln Ile Tyr Met Arg
305                 310                 315                 320

Tyr Ser Lys Tyr Ile Glu Asp Ala Lys Arg Asn Arg Lys Ala Gly Thr
                325                 330                 335

Lys Asn Cys Gly Lys Ser Ser Gly Ala Asn Ser Gly Val Thr Thr Thr
            340                 345                 350

Glu Asn Lys Cys Val Gln Ser
            355
```

```
<210> SEQ ID NO 24
<211> LENGTH: 270
<212> TYPE: PRT
<213> ORGANISM: Plasmodium falciparum

<400> SEQUENCE: 24
```

```
Asn Tyr Ile Lys Asp Asp Pro Tyr Ser Lys Glu Tyr Val Thr Lys Leu
1               5                   10                  15

Ser Phe Ile Pro Asn Ser Ser Asp Ala Asn Asn Pro Ser Gly Glu Thr
            20                  25                  30

Ala Asn His Asn Asp Glu Val Cys Asn Pro Asn Glu Ser Glu Ile Ser
        35                  40                  45

Ser Val Glu His Ala Gln Thr Ser Val Leu Leu Ser Gln Lys Ala Tyr
    50                  55                  60

Ile Thr His Ser Ser Ile Lys Ala Asn Lys Lys Val Cys Lys Tyr
65                  70                  75                  80

Val Lys Leu Gly Val Arg Glu Asn Asp Lys Asp Leu Lys Ile Cys Val
                85                  90                  95

Ile Glu Asp Asp Ser Leu Arg Gly Val Glu Asn Cys Cys Phe Lys Asp
            100                 105                 110

Phe Leu Arg Ile Leu Gln Glu Asn Cys Ser Asp Asn Lys Arg Glu Ser
        115                 120                 125

Ser Ser Asn Gly Ser Cys Asn Asn Asn Glu Glu Ala Cys Glu Lys
    130                 135                 140

Asn Leu Asp Glu Ala Leu Ala Ser Leu Thr Asn Cys Tyr Lys Asn Gln
145                 150                 155                 160

Lys Cys Lys Ser Gly Thr Ser Thr Val Asn Asn Lys Trp Ile Trp
                165                 170                 175

Lys Lys Ser Ser Gly Lys Glu Gly Gly Leu Gln Lys Glu Tyr Ala Asn
            180                 185                 190

Thr Ile Gly Leu Pro Pro Arg Thr Gln Ser Leu Cys Leu Val Val Cys
        195                 200                 205

Leu Asp Glu Lys Glu Gly Lys Thr Gln Glu Leu Lys Asn Ile Arg Thr
    210                 215                 220

Asn Ser Glu Leu Leu Lys Glu Trp Ile Ile Ala Ala Phe His Glu Gly
225                 230                 235                 240

Lys Asn Leu Lys Lys Arg Tyr His Gln Asn Lys Asn Asp Asp Asn Asn
                245                 250                 255

Ser Lys Leu Cys Lys Ala Leu Lys Tyr Ser Phe Ala Asp Tyr
            260                 265                 270
```

```
<210> SEQ ID NO 25
<211> LENGTH: 334
<212> TYPE: PRT
<213> ORGANISM: Plasmodium falciparum
```

<400> SEQUENCE: 25

```
Lys Cys Asp Lys Cys Lys Ser Glu Gln Ser Lys Lys Asn Asn Lys Tyr
1               5                   10                  15

Trp Ile Trp Lys Lys Tyr Ser Val Lys Glu Gly Gly Leu Gln Lys Glu
            20                  25                  30

Tyr Ala Asn Thr Ile Ala Leu Pro Pro Arg Thr Gln Ser Leu Cys Leu
        35                  40                  45

Val Val Cys Leu Asp Glu Lys Glu Gly Lys Thr Gln Glu Leu Lys Asn
    50                  55                  60

Ile Arg Thr Asn Ser Glu Leu Leu Lys Glu Arg Ile Ile Ala Ala Phe
65                  70                  75                  80

His Glu Gly Lys Asn Leu Lys Thr Tyr His Glu Lys Lys Gly Asp
                85                  90                  95

Asp Gly Lys Lys Leu Cys Lys Asp Leu Lys Tyr Ser Phe Ala Asp Tyr
            100                 105                 110

Gly Asp Leu Ile Lys Gly Thr Ser Ile Trp Asp Asn Asp Phe Thr Lys
            115                 120                 125

Asp Leu Glu Leu Asn Leu Gln Lys Ile Phe Gly Lys Leu Phe Arg Lys
130                 135                 140

Tyr Ile Lys Lys Asn Asn Thr Ala Glu Gln His Thr Ser Tyr Ser Ser
145                 150                 155                 160

Leu Asp Glu Leu Arg Glu Ser Trp Trp Asn Thr Lys Lys Tyr Ile
            165                 170                 175

Trp Thr Ala Met Lys His Gly Ala Glu Met Asn Gly Thr Thr Cys Ser
            180                 185                 190

Cys Ser Gly Asp Ser Ser Asn Asp Ile Pro Thr Ile Asp Leu Ile Pro
            195                 200                 205

Gln Tyr Leu Arg Phe Leu Gln Glu Trp Val Glu His Phe Cys Glu Gln
210                 215                 220

Arg Gln Ala Lys Val Asn Ala Val Ile Lys Asn Cys Lys Ser Cys Lys
225                 230                 235                 240

Glu Cys Gly Gly Thr Cys Asn Gly Glu Cys Lys Thr Glu Cys Lys Thr
            245                 250                 255

Lys Cys Lys Gly Glu Cys Glu Lys Tyr Lys Glu Phe Ile Glu Lys Cys
            260                 265                 270

Glu Gly Gln Ala Ala Glu Gly Thr Ser Gly Ser Ser Trp Ser Lys Arg
            275                 280                 285

Trp Tyr Gln Ile Tyr Met Arg Tyr Ser Lys Tyr Ile Glu Asp Ala Lys
290                 295                 300

Arg Asn Arg Lys Ala Gly Thr Lys Asn Cys Gly Thr Ser Ser Gly Ala
305                 310                 315                 320

Asn Ser Gly Val Thr Thr Thr Glu Asn Lys Cys Val Gln Ser
            325                 330
```

<210> SEQ ID NO 26
<211> LENGTH: 351
<212> TYPE: PRT
<213> ORGANISM: Plasmodium falciparum

<400> SEQUENCE: 26

```
Lys Cys Asp Lys Cys Lys Ser Glu Gln Ser Lys Lys Asn Asn Lys Asn
1               5                   10                  15

Trp Ile Trp Lys Lys Tyr Ser Gly Thr Glu Gly Gly Leu Gln Lys Glu
            20                  25                  30
```

Tyr Ala Asn Thr Ile Ala Leu Pro Pro Arg Thr Gln Ser Leu Tyr Leu
            35                  40                  45

Val Cys Leu His Glu Lys Glu Lys Thr Gln Glu Leu Lys Asn Ile
 50                  55                  60

Ser Thr Asn Ser Glu Leu Leu Lys Glu Trp Ile Ile Ala Ala Phe His
 65                  70                  75                  80

Glu Gly Lys Asn Leu Lys Ile Ser Pro Gln Asn Lys Asn Asp Asn Gly
                85                  90                  95

Lys Asn Leu Cys Lys Asp Leu Lys Tyr Ser Phe Ala Asp Tyr Gly Asp
                100                 105                 110

Leu Ile Lys Gly Thr Ser Ile Trp Asp Asn Asp Phe Thr Lys Asp Leu
            115                 120                 125

Glu Leu Asn Leu Gln Gln Ile Phe Gly Lys Leu Phe Arg Lys Tyr Ile
        130                 135                 140

Lys Lys Asn Asn Thr Ala Glu Gln Asp Thr Leu Tyr Ser Ser Leu Asp
145                 150                 155                 160

Glu Leu Arg Glu Ser Trp Trp Asn Thr Asn Lys Lys Tyr Ile Trp Thr
                165                 170                 175

Ala Met Lys His Gly Ala Gly Met Asn Gly Thr Thr Cys Cys Gly Asp
                180                 185                 190

Gly Ser Val Thr Gly Ser Ser Asp Ser Gly Ser Thr Thr Cys Cys Gly
            195                 200                 205

Asp Gly Ser Val Thr Gly Ser Gly Ser Ser Cys Asp Asp Ile Pro Thr
        210                 215                 220

Ile Asp Leu Ile Pro Gln Tyr Leu Arg Phe Leu Gln Glu Trp Val Glu
225                 230                 235                 240

His Phe Cys Glu Gln Arg Gln Ala Lys Val Lys Asp Val Ile Lys Asn
                245                 250                 255

Cys Asn Ser Cys Lys Glu Cys Gly Gly Thr Cys Asn Gly Glu Cys Lys
                260                 265                 270

Thr Glu Cys Glu Lys Lys Cys Lys Gly Glu Cys Glu Ala Tyr Lys Lys
            275                 280                 285

Phe Ile Glu Lys Cys Asn Gly Gly Gly Gly Gly Thr Ser Gly Ser
        290                 295                 300

Ser Trp Ser Lys Arg Trp Asp Gln Ile Tyr Met Arg Tyr Ser Lys Tyr
305                 310                 315                 320

Ile Glu Asp Ala Lys Arg Asn Arg Lys Ala Gly Thr Lys Asn Cys Gly
                325                 330                 335

Thr Ser Ser Thr Thr Asn Ala Ala Glu Asn Lys Cys Val Gln Ser
            340                 345                 350

<210> SEQ ID NO 27
<211> LENGTH: 353
<212> TYPE: PRT
<213> ORGANISM: Plasmodium falciparum

<400> SEQUENCE: 27

Lys Cys Asp Lys Cys Lys Ser Gly Thr Ser Thr Val Asn Lys Lys Trp
1               5                   10                  15

Ile Trp Lys Lys Phe Pro Gly Lys Glu Gly Gly Leu Gln Glu Glu Tyr
            20                  25                  30

Ala Asn Thr Ile Ala Leu Pro Pro Arg Thr Gln Ser Leu Cys Leu Val
            35                  40                  45

Val Cys Leu Asp Glu Lys Glu Gly Lys Thr Gln His Lys Thr Ile Ser

Thr Asn Ser Glu Leu Leu Lys Glu Trp Ile Ile Ala Ala Phe His Glu
65                  70                  75                  80

Gly Lys Asn Leu Lys Ile Ser Asn Lys Lys Asn Asp Glu Asn Asn
    85                  90                  95

Ser Lys Leu Cys Lys Asp Leu Lys Tyr Ser Phe Ala Asp Tyr Gly Asp
            100                 105                 110

Leu Ile Lys Gly Thr Ser Ile Trp Asp Asn Asp Phe Thr Lys Asp Leu
        115                 120                 125

Glu Leu Asn Leu Gln Lys Ile Phe Gly Lys Leu Phe Arg Lys Tyr Ile
    130                 135                 140

Lys Lys Asn Asn Thr Ala Glu Gln Asp Thr Ser Tyr Ser Ser Leu Asp
145                 150                 155                 160

Glu Leu Arg Glu Ser Trp Trp Asn Thr Asn Lys Lys Tyr Ile Trp Leu
            165                 170                 175

Ala Met Lys His Gly Thr Thr Cys Ser Ser Gly Ser Gly Asp Asn Gly
            180                 185                 190

Asp Gly Ser Val Thr Gly Ser Ser Asp Ser Gly Ser Thr Thr Cys Cys
        195                 200                 205

Gly Asp Gly Ser Val Thr Gly Ser Gly Ser Ser Cys Asp Asp Ile Pro
    210                 215                 220

Thr Ile Asp Leu Ile Pro Gln Tyr Leu Arg Phe Leu Gln Glu Trp Val
225                 230                 235                 240

Glu His Phe Cys Lys Gln Arg Gln Ala Lys Val Lys Asp Val Ile Glu
            245                 250                 255

Asn Cys Lys Ser Cys Lys Asn Thr Ser Ser Lys Thr Lys Leu Gly Asp
            260                 265                 270

Thr Cys Asn Ser Asp Cys Lys Thr Lys Cys Lys Val Ala Cys Glu Lys
        275                 280                 285

Tyr Lys Glu Phe Ile Glu Lys Cys Val Ser Ala Ala Gly Gly Thr Ser
    290                 295                 300

Gly Ser Ser Trp Val Lys Arg Trp Asp Gln Ile Tyr Met Arg Tyr Ser
305                 310                 315                 320

Lys Tyr Ile Glu Asp Ala Lys Arg Asn Arg Lys Ala Gly Thr Lys Asn
            325                 330                 335

Cys Gly Pro Ser Ser Thr Thr Ser Thr Ala Glu Ser Lys Cys Val Gln
            340                 345                 350

Ser

<210> SEQ ID NO 28
<211> LENGTH: 327
<212> TYPE: PRT
<213> ORGANISM: Plasmodium falciparum

<400> SEQUENCE: 28

Lys Cys Asp Lys Cys Lys Ser Gly Thr Ser Thr Val Asn Lys Lys Trp
1               5                   10                  15

Ile Trp Lys Lys Tyr Ser Gly Lys Glu Gly Gly Leu Gln Lys Glu Tyr
            20                  25                  30

Ala Asn Thr Ile Gly Leu Pro Pro Arg Thr Gln Ser Leu Cys Leu Val
        35                  40                  45

Cys Leu His Glu Lys Glu Gly Lys Thr Gln Glu Leu Lys Asn Ile Ser
    50                  55                  60

Thr Asn Ser Glu Leu Leu Lys Glu Trp Ile Ile Ala Ala Phe His Glu

```
                65                  70                  75                  80
        Gly Lys Asn Leu Lys Ile Ser Asn Lys Lys Asn Asp Asp Asn Gly
                        85                  90                  95

Lys Lys Leu Cys Lys Asp Leu Lys Tyr Ser Phe Ala Asp Tyr Gly Asp
                        100                 105                 110

Leu Ile Lys Gly Thr Ser Ile Trp Asp Asn Asp Phe Thr Lys Asp Leu
                        115                 120                 125

Glu Leu Asn Leu Gln Lys Ile Phe Gly Lys Leu Phe Arg Lys Tyr Ile
                        130                 135                 140

Lys Lys Asn Asn Thr Ala Glu Gln Asp Thr Leu Tyr Ser Ser Leu Asp
        145                 150                 155                 160

Glu Leu Arg Glu Ser Trp Trp Asn Thr Asn Lys Lys Tyr Ile Trp Thr
                        165                 170                 175

Ala Met Lys His Gly Ala Gly Met Asn Ser Thr Thr Cys Ser Cys Ser
                        180                 185                 190

Gly Asp Ser Ser Asn Asp Ile Pro Thr Ile Asp Leu Ile Pro Gln Tyr
                        195                 200                 205

Leu Arg Phe Leu Gln Glu Trp Val Glu His Phe Cys Lys Gln Arg Gln
                        210                 215                 220

Glu Lys Val Asn Ala Val Ile Thr Asn Cys Lys Ser Cys Lys Glu Ser
        225                 230                 235                 240

Gly Gly Thr Cys Asn Ser Asp Cys Glu Lys Cys Lys Ile Glu Cys
                        245                 250                 255

Glu Lys Tyr Lys Asn Phe Ile Glu Lys Cys Val Thr Ala Ala Gly Gly
                        260                 265                 270

Thr Ser Gly Ser Ser Trp Ser Lys Arg Trp Asp Gln Ile Tyr Lys Met
                        275                 280                 285

Tyr Ser Lys Tyr Ile Glu Asp Ala Lys Arg Asn Arg Lys Ala Gly Thr
                        290                 295                 300

Lys Asn Cys Gly Pro Ser Ser Thr Thr Asn Ala Ala Ala Ser Thr Asp
        305                 310                 315                 320

Glu Asn Lys Cys Val Gln Ser
                        325

<210> SEQ ID NO 29
<211> LENGTH: 628
<212> TYPE: PRT
<213> ORGANISM: Artificial Sequence
<220> FEATURE:
<223> OTHER INFORMATION: dd2full 745 amino acids

<400> SEQUENCE: 29

Asn Tyr Ile Lys Gly Asp Pro Tyr Phe Ala Glu Tyr Ala Thr Lys Leu
        1               5                   10                  15

Ser Phe Ile Leu Asn Ser Ser Asp Thr Glu Asn Ala Ser Glu Thr Pro
                        20                  25                  30

Ser Lys Tyr Tyr Asp Glu Ala Cys Asn Cys Asn Glu Ser Glu Ile Ala
                        35                  40                  45

Ser Val Gly Gln Ala Gln Thr Ser Gly Pro Ser Ser Asn Lys Thr Cys
                        50                  55                  60

Ile Thr His Ser Ser Ile Lys Thr Asn Lys Lys Lys Glu Cys Lys Asp
        65                  70                  75                  80

Val Lys Leu Gly Ile Asn Asn Asn Asp Lys Val Leu Arg Val Cys Val
                        85                  90                  95

Ile Glu Asp Thr Ser Leu Ser Gly Val Asp Asn Cys Cys Cys Gln Asp
```

```
            100             105             110
Leu Leu Gly Ile Leu Gln Glu Asn Cys Ser Asp Asn Lys Arg Gly Ser
        115                 120             125

Ser Ser Asn Gly Ser Cys Asp Lys Asn Ser Glu Glu Ile Cys Gln Lys
    130                 135             140

Lys Leu Glu Lys Val Phe Ala Ser Leu Thr Asn Gly Tyr Lys Cys Asp
145                 150                 155                 160

Lys Cys Lys Ser Gly Thr Ser Arg Ser Lys Lys Trp Ile Trp Lys
                165                 170             175

Lys Ser Ser Gly Asn Glu Glu Gly Leu Gln Lys Glu Tyr Ala Asn Thr
                180                 185                 190

Ile Gly Leu Pro Pro Arg Thr Gln Ser Leu Cys Leu Val Cys Leu His
        195                 200                 205

Glu Lys Glu Gly Lys Thr Gln His Lys Thr Ile Ser Thr Asn Ser Glu
        210                 215                 220

Leu Leu Lys Glu Trp Ile Ile Ala Ala Phe His Glu Gly Lys Asn Leu
225                 230                 235                 240

Lys Thr Ser His Glu Lys Lys Asn Asp Asp Asn Gly Lys Lys Leu Cys
                245                 250                 255

Lys Ala Leu Glu Tyr Ser Phe Ala Asp Tyr Gly Asp Leu Ile Lys Gly
                260                 265                 270

Thr Ser Ile Trp Asp Asn Glu Tyr Thr Lys Asp Leu Glu Leu Asn Leu
            275                 280                 285

Gln Lys Ile Phe Gly Lys Leu Phe Arg Lys Tyr Ile Lys Lys Asn Asn
        290                 295                 300

Thr Ala Glu Gln His Thr Ser Tyr Ser Ser Leu Asp Glu Leu Arg Glu
305                 310                 315                 320

Ser Trp Trp Asn Thr Asn Lys Lys Tyr Ile Trp Thr Ala Met Lys His
                325                 330                 335

Gly Ala Gly Met Asn Gly Thr Thr Cys Ser Cys Ser Gly Asp Ser Ser
                340                 345                 350

Asn Asp Met Pro Thr Ile Asp Leu Ile Pro Gln Tyr Leu Arg Phe Leu
                355                 360                 365

Gln Glu Trp Val Glu His Phe Cys Lys Gln Arg Gln Glu Lys Val Asn
        370                 375                 380

Ala Val Ile Glu Asn Cys Asn Ser Cys Lys Glu Ser Gly Gly Thr Cys
385                 390                 395                 400

Asn Ser Asp Cys Lys Thr Glu Cys Lys Asn Lys Cys Glu Ala Tyr Lys
                405                 410                 415

Glu Phe Ile Glu Asp Cys Lys Gly Gly Gly Thr Gly Thr Ala Gly Ser
                420                 425                 430

Pro Trp Ser Lys Arg Trp Asp Gln Ile Tyr Lys Arg Tyr Ser Lys His
                435                 440                 445

Ile Glu Asp Ala Lys Arg Asn Arg Lys Ala Gly Thr Lys Asn Cys Gly
450                 455                 460

Thr Ser Ser Thr Thr Asn Ala Ala Ser Thr Asp Glu Asn Lys Cys
465                 470                 475                 480

Val Gln Ser Asp Val Asp Ser Phe Phe Lys His Leu Ile Asp Ile Gly
                485                 490                 495

Leu Thr Thr Pro Ser Ser Tyr Leu Ser Asn Val Leu Asp Asp Asn Ile
                500                 505                 510

Cys Gly Ala Asp Lys Ala Pro Trp Thr Thr Tyr Thr Thr Tyr Thr Thr
                515                 520                 525
```

```
Thr Lys Asn Cys Asp Ile Gln Lys Lys Thr Pro Lys Ser Gln Ser Cys
    530                 535                 540

Asp Thr Leu Val Val Asn Val Pro Ser Pro Leu Gly Asn Thr Pro
545                 550                 555                 560

His Glu Tyr Lys Tyr Ala Cys Glu Cys Lys Ile Pro Thr Thr Glu Glu
                565                 570                 575

Thr Cys Asp Asp Arg Lys Glu Tyr Met Asn Gln Trp Ser Cys Gly Ser
            580                 585                 590

Ala Gln Thr Val Arg Gly Arg Ser Gly Lys Asp Asp Tyr Glu Leu Tyr
        595                 600                 605

Thr Tyr Asn Gly Val Lys Glu Thr Lys Pro Leu Gly Thr Leu Lys Asn
    610                 615                 620

Ser Lys Leu Asp
625

<210> SEQ ID NO 30
<211> LENGTH: 350
<212> TYPE: PRT
<213> ORGANISM: Plasmodium falciparum

<400> SEQUENCE: 30

Lys Cys Glu Lys Cys Lys Ser Glu Gln Ser Lys Lys Asn Asn Lys Asn
1               5                   10                  15

Trp Ile Trp Arg Lys Phe Arg Gly Thr Glu Gly Gly Leu Gln Glu Glu
                20                  25                  30

Tyr Ala Asn Thr Ile Gly Leu Pro Pro Arg Thr Gln Ser Leu Cys Leu
            35                  40                  45

Val Val Cys Leu Asp Glu Lys Gly Lys Lys Thr Gln Glu Leu Lys Asn
        50                  55                  60

Ile Arg Thr Asn Ser Glu Leu Leu Lys Glu Trp Ile Ile Ala Ala Phe
65                  70                  75                  80

His Glu Gly Lys Asn Leu Lys Pro Ser His Gln Asn Lys Asn Ser Gly
                85                  90                  95

Asn Lys Glu Asn Leu Cys Lys Ala Leu Lys Tyr Ser Phe Ala Asp Tyr
            100                 105                 110

Gly Asp Leu Ile Lys Gly Thr Ser Ile Trp Asp Asn Asp Phe Thr Lys
        115                 120                 125

Asp Leu Glu Leu Asn Leu Gln Lys Ile Phe Gly Lys Leu Phe Arg Lys
    130                 135                 140

Tyr Ile Lys Lys Asn Asn Thr Ala Glu Gln His Thr Ser Tyr Ser Ser
145                 150                 155                 160

Leu Asp Glu Leu Arg Glu Ser Trp Trp Asn Thr Asn Lys Lys Tyr Ile
                165                 170                 175

Trp Thr Ala Met Lys His Gly Ala Glu Met Asn Gly Thr Thr Cys Asn
            180                 185                 190

Ala Asp Gly Ser Val Thr Gly Ser Ser Asp Ser Gly Ser Thr Thr Cys
        195                 200                 205

Ser Gly Asp Asn Gly Ser Ile Ser Cys Asp Asp Ile Pro Thr Ile Asp
    210                 215                 220

Leu Ile Pro Gln Tyr Leu Arg Phe Leu Gln Glu Trp Val Glu His Phe
225                 230                 235                 240

Cys Lys Gln Arg Gln Glu Lys Val Asn Ala Val Ile Asn Ser Cys Asn
                245                 250                 255

Ser Cys Lys Asn Thr Ser Ser Lys Thr Lys Leu Gly Asp Thr Cys Asn
```

```
                    260                 265                 270
Ser Asp Cys Lys Thr Lys Cys Lys Ile Glu Cys Glu Lys Tyr Lys Thr
            275                 280                 285

Phe Ile Glu Lys Cys Val Thr Ala Ala Gly Gly Thr Ser Gly Ser Pro
            290                 295                 300

Trp Ser Lys Arg Trp Asp Gln Ile Tyr Lys Arg Tyr Ser Lys Tyr Ile
305                 310                 315                 320

Glu Asp Ala Lys Arg Asn Arg Lys Ala Gly Thr Lys Asn Cys Gly Pro
                325                 330                 335

Ser Ser Thr Thr Ser Thr Ala Glu Ser Lys Cys Val Gln Ser
            340                 345                 350

<210> SEQ ID NO 31
<211> LENGTH: 330
<212> TYPE: PRT
<213> ORGANISM: Plasmodium falciparum

<400> SEQUENCE: 31

Lys Cys Asp Lys Cys Lys Ser Glu Gln Ser Lys Lys Asn Asn Lys Asn
1               5                   10                  15

Trp Ile Trp Arg Lys Tyr Ser Gly Asn Gly Glu Gly Leu Gln Lys Glu
            20                  25                  30

Tyr Ala Asn Thr Ile Gly Leu Pro Pro Arg Thr His Ser Leu Tyr Leu
        35                  40                  45

Val Cys Leu His Glu Lys Gly Lys Thr Gln Glu Leu Lys Asn Ile
    50                  55                  60

Arg Thr Asn Ser Glu Leu Leu Lys Glu Trp Ile Ala Ala Phe His
65                  70                  75                  80

Glu Gly Lys Asn Leu Lys Thr Thr Tyr Leu Glu Asn Lys Asn Asp Glu
                85                  90                  95

Asn Lys Lys Lys Leu Cys Lys Ala Leu Lys Tyr Ser Phe Ala Asp Tyr
            100                 105                 110

Gly Asp Leu Ile Lys Gly Thr Ser Ile Trp Asp Asn Asp Phe Thr Lys
            115                 120                 125

Asp Leu Glu Leu Asn Leu Gln Lys Ile Phe Gly Lys Leu Phe Arg Lys
        130                 135                 140

Tyr Ile Lys Lys Asn Ile Ala Ser Asp Glu Asn Thr Leu Tyr Ser Ser
145                 150                 155                 160

Leu Asp Glu Leu Arg Glu Ser Trp Trp Asn Thr Asn Lys Lys Tyr Ile
                165                 170                 175

Trp Thr Ala Met Lys His Gly Ala Glu Met Asn Gly Thr Thr Cys Ser
            180                 185                 190

Ser Gly Ser Gly Asp Asn Gly Ser Ile Ser Cys Asp Asp Ile Pro Thr
        195                 200                 205

Ile Asp Leu Ile Pro Gln Tyr Leu Arg Phe Leu Gln Glu Trp Val Gly
    210                 215                 220

His Phe Cys Lys Gln Arg Gln Glu Lys Val Asn Ala Val Ile Thr Asn
225                 230                 235                 240

Cys Asn Ser Cys Lys Glu Ser Gly Gly Thr Cys Asn Ser Asp Cys Glu
                245                 250                 255

Lys Lys Cys Lys Ile Glu Cys Glu Lys Tyr Lys Lys Phe Ile Glu Glu
            260                 265                 270

Cys Arg Thr Ala Ala Gly Gly Thr Ser Gly Ser Pro Trp Ser Lys Arg
        275                 280                 285
```

```
Trp Asp Gln Ile Tyr Lys Met Tyr Ser Lys Tyr Ile Glu Asp Ala Lys
            290                 295                 300

Arg Asn Arg Lys Ala Gly Thr Lys Asn Cys Gly Pro Ser Ser Thr Thr
305                 310                 315                 320

Ser Thr Ala Glu Ser Lys Cys Val Gln Ser
                325                 330

<210> SEQ ID NO 32
<211> LENGTH: 334
<212> TYPE: PRT
<213> ORGANISM: Plasmodium falciparum

<400> SEQUENCE: 32

Lys Cys Asp Lys Cys Lys Ser Glu Gln Ser Lys Lys Asn Asn Lys Asn
1               5                   10                  15

Trp Ile Trp Arg Lys Tyr Ser Gly Asn Gly Glu Gly Leu Gln Lys Glu
            20                  25                  30

Tyr Ala Asn Thr Ile Gly Leu Pro Pro Arg Thr His Ser Leu Tyr Leu
            35                  40                  45

Val Cys Leu His Glu Lys Glu Gly Lys Thr Gln His Lys Thr Ile Ser
        50                  55                  60

Thr Asn Ser Glu Leu Leu Lys Glu Trp Ile Ile Ala Ala Phe His Glu
65                  70                  75                  80

Gly Lys Asn Leu Lys Lys Arg Tyr Pro Gln Asn Asn Ser Gly Asn
                85                  90                  95

Lys Lys Lys Leu Cys Lys Asp Leu Lys Tyr Ser Phe Ala Asp Tyr Gly
                100                 105                 110

Asp Leu Ile Lys Gly Thr Ser Ile Trp Asp Asn Glu Tyr Thr Lys Asp
            115                 120                 125

Leu Glu Leu Asn Leu Gln Lys Ala Phe Gly Lys Leu Phe Arg Lys Tyr
130                 135                 140

Ile Lys Lys Asn Ile Ala Ser Asp Glu Asn Thr Leu Tyr Ser Ser Leu
145                 150                 155                 160

Asp Glu Leu Arg Glu Ser Trp Trp Asn Thr Asn Lys Lys Tyr Ile Trp
                165                 170                 175

Leu Ala Met Lys His Gly Ala Glu Met Asn Gly Thr Met Cys Asn Ala
            180                 185                 190

Asp Gly Ser Val Thr Gly Ser Gly Ser Ser Cys Asp Asp Met Ser Thr
        195                 200                 205

Ile Asp Leu Ile Pro Gln Tyr Leu Arg Phe Leu Gln Glu Trp Val Glu
210                 215                 220

His Phe Cys Glu Gln Arg Gln Ala Lys Val Lys Asp Val Ile Asn Ser
225                 230                 235                 240

Cys Lys Ser Cys Lys Glu Ser Gly Asp Thr Cys Asn Ser Asp Cys Glu
                245                 250                 255

Lys Lys Cys Lys Asn Lys Cys Asp Ala Tyr Lys Thr Phe Ile Glu Glu
            260                 265                 270

Phe Cys Thr Ala Asp Gly Gly Thr Ala Gly Ser Pro Trp Ser Lys Arg
        275                 280                 285

Trp Asp Gln Ile Tyr Lys Arg Tyr Ser Lys Tyr Ile Glu Asp Ala Lys
            290                 295                 300

Arg Asn Arg Lys Ala Gly Thr Lys Asn Cys Gly Thr Ser Ser Gly Ala
305                 310                 315                 320

Asn Ser Gly Val Thr Thr Thr Glu Asn Lys Cys Val Gln Ser
                325                 330
```

```
<210> SEQ ID NO 33
<211> LENGTH: 350
<212> TYPE: PRT
<213> ORGANISM: Plasmodium falciparum

<400> SEQUENCE: 33

Lys Cys Asp Lys Cys Lys Ser Gly Thr Ser Thr Val Asn Lys Asn Trp
 1               5                  10                  15

Ile Trp Lys Lys Tyr Ser Gly Lys Glu Glu Gly Leu Gln Lys Glu Tyr
            20                  25                  30

Ala Asn Thr Ile Ala Leu Pro Pro Arg Thr His Ser Leu Tyr Leu Val
        35                  40                  45

Cys Leu His Glu Lys Gly Lys Lys Thr Gln Glu Leu Lys Asn Ile Arg
    50                  55                  60

Thr Asn Ser Glu Leu Leu Lys Glu Trp Ile Ile Ala Ala Phe His Glu
65                  70                  75                  80

Gly Lys Asn Leu Lys Thr Ser Pro Gln Asn Asn Asn Ser Gly Asn Lys
                85                  90                  95

Lys Lys Leu Cys Lys Ala Leu Lys Tyr Ser Phe Ala Asp Tyr Gly Asp
            100                 105                 110

Leu Ile Lys Gly Thr Ser Ile Trp Asp Asn Asp Phe Thr Lys Asp Leu
        115                 120                 125

Glu Leu Asn Leu Gln Lys Ile Phe Gly Lys Leu Phe Arg Lys Tyr Ile
    130                 135                 140

Lys Lys Asn Asn Thr Ala Glu Gln His Thr Ser Tyr Ser Ser Leu Asp
145                 150                 155                 160

Glu Leu Arg Glu Ser Trp Trp Asn Thr Asn Lys Lys Tyr Ile Trp Leu
                165                 170                 175

Ala Met Lys His Gly Ala Glu Met Asn Gly Thr Thr Cys Cys Gly Asp
            180                 185                 190

Gly Ser Val Thr Gly Ser Ser Asp Ser Gly Ser Thr Thr Cys Ser Gly
        195                 200                 205

Asp Asn Gly Ser Ile Ser Cys Asp Asp Met Pro Thr Thr Asp Phe Ile
    210                 215                 220

Pro Gln Tyr Leu Arg Phe Leu Gln Glu Trp Val Glu His Phe Cys Lys
225                 230                 235                 240

Gln Arg Gln Glu Lys Val Lys His Val Met Glu Ser Cys Lys Ser Cys
                245                 250                 255

Lys Glu Cys Gly Asp Thr Cys Asn Gly Glu Cys Lys Thr Glu Cys Glu
            260                 265                 270

Lys Lys Cys Lys Asn Lys Cys Glu Ala Tyr Lys Thr Phe Ile Glu Lys
        275                 280                 285

Cys Val Ser Ala Asp Gly Gly Thr Gly Ser Ser Trp Ser Lys Arg
    290                 295                 300

Trp Asp Gln Ile Tyr Met Arg Tyr Ser Lys Tyr Ile Glu Asp Ala Lys
305                 310                 315                 320

Arg Asn Arg Lys Ala Gly Thr Lys Asn Cys Gly Thr Ser Ser Thr Thr
                325                 330                 335

Asn Ala Ala Ala Ser Thr Ala Glu Asn Lys Cys Val Gln Ser
            340                 345                 350

<210> SEQ ID NO 34
<211> LENGTH: 647
<212> TYPE: PRT
```

<213> ORGANISM: Artificial Sequence
<220> FEATURE:
<223> OTHER INFORMATION: P13 745 amino acids

<400> SEQUENCE: 34

```
Asp Tyr Ile Lys Asp Asp Pro Tyr Ser Ala Glu Tyr Ala Thr Lys Leu
1               5                   10                  15

Ser Phe Ile Leu Asn Pro Ser Asp Ala Asn Thr Ser Ser Gly Glu Thr
            20                  25                  30

Ala Asn His Asn Asp Glu Val Cys Asn Cys Asn Glu Ser Glu Ile Ala
        35                  40                  45

Ser Val Glu Leu Ala Pro Ile Ser Asp Ser Ser Asn Lys Thr Cys
    50                  55                  60

Ile Thr His Ser Phe Ile Gly Ala Asn Lys Lys Glu Cys Lys Asp
65                  70                  75                  80

Val Lys Leu Gly Val Arg Glu Lys Asp Leu Lys Ile Cys Val
                85                  90                  95

Ile Glu Asp Asp Ser Leu Arg Gly Val Glu Asn Cys Cys Cys Gln Asp
            100                 105                 110

Leu Leu Gly Ile Leu Gln Glu Asn Cys Ser Asp Asn Lys Ser Gly Ser
        115                 120                 125

Ser Ser Asn Gly Ser Cys Asp Lys Asn Ser Glu Asp Glu Cys Gln Lys
    130                 135                 140

Lys Leu Glu Asn Val Phe Ala Ser Leu Lys Asn Gly Tyr Lys Cys Asp
145                 150                 155                 160

Lys Cys Lys Ser Gly Thr Ser Thr Val Asn Lys Lys Trp Ile Trp Arg
                165                 170                 175

Lys Tyr Ser Gly Asn Gly Glu Gly Leu Gln Lys Glu Tyr Ala Asn Thr
            180                 185                 190

Ile Gly Leu Pro Pro Arg Thr His Ser Leu Tyr Leu Val Cys Leu His
        195                 200                 205

Glu Lys Glu Gly Lys Thr Gln His Lys Thr Ile Ser Thr Asn Ser Glu
210                 215                 220

Leu Leu Lys Glu Trp Ile Ile Ala Ala Phe His Glu Gly Lys Asn Leu
225                 230                 235                 240

Lys Thr Ser His Gln Asn Asn Ser Gly Asn Lys Lys Leu Cys
                245                 250                 255

Lys Ala Leu Lys Tyr Ser Phe Ala Asp Tyr Gly Asp Leu Ile Lys Gly
            260                 265                 270

Thr Ser Ile Trp Asp Asn Asp Phe Thr Lys Asp Leu Glu Leu Asn Leu
        275                 280                 285

Gln Lys Ile Phe Gly Lys Leu Phe Arg Lys Tyr Ile Lys Lys Asn Ile
    290                 295                 300

Ala Ser Asp Glu Asn Thr Ser Tyr Ser Ser Leu Asp Glu Leu Arg Glu
305                 310                 315                 320

Ser Trp Trp Asn Thr Asn Lys Lys Tyr Ile Trp Leu Ala Met Lys His
                325                 330                 335

Gly Ala Glu Met Asn Ser Thr Met Cys Asn Gly Asp Gly Ser Val Thr
            340                 345                 350

Gly Ser Ser Asp Ser Gly Ser Thr Cys Ser Gly Asp Asn Gly Ser
        355                 360                 365

Ile Ser Cys Asp Asp Ile Pro Thr Ile Asp Leu Ile Pro Gln Tyr Leu
    370                 375                 380

Arg Phe Leu Gln Glu Trp Val Glu His Phe Cys Lys Gln Arg Gln Glu
```

```
            385                 390                 395                 400
Lys Val Lys Asp Val Ile Thr Asn Cys Lys Ser Cys Lys Glu Ser Gly
                405                 410                 415

Asp Thr Cys Asn Ser Asp Cys Glu Lys Cys Lys Asn Lys Cys Glu
            420                 425                 430

Ala Tyr Lys Lys Phe Ile Glu Arg Arg Thr Ala Ala Gln Gly Thr
            435                 440                 445

Ala Glu Ser Ser Trp Val Lys Arg Trp Asp Gln Ile Tyr Met Arg Tyr
450                 455                 460

Ser Lys Tyr Ile Glu Asp Ala Lys Arg Asn Arg Lys Ala Gly Thr Lys
465                 470                 475                 480

Ser Cys Gly Pro Ser Ser Thr Asn Ala Ala Ser Thr Ala Glu
                485                 490                 495

Asn Lys Cys Val Gln Ser Asp Ile Asp Ser Phe Phe Lys His Leu Ile
                500                 505                 510

Asp Ile Gly Leu Thr Thr Pro Ser Ser Tyr Leu Ser Ile Val Leu Asp
                515                 520                 525

Asp Asn Ile Cys Gly Ala Asp Asn Ala Pro Trp Thr Thr Tyr Thr Thr
530                 535                 540

Tyr Thr Thr Thr Lys Asn Cys Asp Ile Lys Lys Thr Pro Lys Pro
545                 550                 555                 560

Gln Ser Cys Asp Thr Leu Val Val Asn Val Pro Ser Pro Leu Gly
                565                 570                 575

Asn Thr Pro His Glu Tyr Lys Tyr Ala Cys Gln Cys Arg Thr Pro Asn
                580                 585                 590

Lys Gln Glu Ser Cys Asp Asp Arg Lys Glu Tyr Met Asn Gln Trp Ser
                595                 600                 605

Ser Gly Ser Ala Gln Thr Val Arg Gly Arg Ser Thr Asn Asn Asp Tyr
610                 615                 620

Glu Leu Tyr Thr Tyr Asn Gly Val Lys Glu Thr Lys Pro Leu Gly Thr
625                 630                 635                 640

Leu Lys Asn Ser Lys Leu Asp
                645

<210> SEQ ID NO 35
<211> LENGTH: 341
<212> TYPE: PRT
<213> ORGANISM: Plasmodium falciparum

<400> SEQUENCE: 35

Lys Cys Asp Lys Cys Lys Ser Gly Thr Ser Thr Val Asn Lys Lys Trp
1               5                   10                  15

Ile Trp Arg Lys Ser Ser Gly Asn Lys Glu Gly Leu Gln Lys Glu Tyr
                20                  25                  30

Ala Asn Thr Ile Gly Leu Pro Pro Arg Thr Gln Ser Leu Tyr Leu Gly
            35                  40                  45

Asn Leu Pro Lys Leu Glu Asn Val Cys Glu Asp Val Lys Asp Ile Asn
50                  55                  60

Phe Asp Thr Lys Glu Lys Phe Leu Ala Gly Cys Leu Ile Val Ser Phe
65                  70                  75                  80

His Glu Gly Lys Asn Leu Lys Thr Ser His Glu Lys Lys Asn Asp Asp
                85                  90                  95

Asn Gly Lys Lys Leu Cys Lys Ala Leu Glu Tyr Ser Phe Ala Asp Tyr
            100                 105                 110
```

Gly Asp Leu Ile Lys Gly Thr Ser Ile Trp Asp Asn Glu Tyr Thr Lys
            115                 120                 125

Asp Leu Glu Leu Asn Leu Gln Lys Ile Phe Gly Lys Leu Phe Arg Lys
        130                 135                 140

Tyr Ile Lys Lys Asn Asn Thr Ala Glu Gln Asp Thr Ser Tyr Ser Ser
145                 150                 155                 160

Leu Asp Glu Leu Arg Glu Ser Trp Trp Asn Thr Asn Lys Lys Tyr Ile
                165                 170                 175

Trp Thr Ala Met Lys His Gly Ala Gly Met Asn Ile Thr Thr Cys Cys
            180                 185                 190

Gly Asp Gly Ser Ser Gly Glu Asn Gln Thr Asn Ser Cys Asp Asp Ile
        195                 200                 205

Pro Thr Ile Asp Leu Ile Pro Gln Tyr Leu Arg Phe Leu Gln Glu Trp
210                 215                 220

Val Glu His Phe Cys Lys Gln Arg Gln Glu Lys Val Asn Ala Val Val
225                 230                 235                 240

Thr Asn Cys Lys Ser Cys Lys Glu Ser Gly Gly Thr Cys Asn Gly Glu
                245                 250                 255

Cys Lys Thr Lys Cys Lys Asn Lys Cys Glu Val Tyr Lys Thr Phe Ile
            260                 265                 270

Asp Asn Val Gly Asp Gly Thr Ala Gly Ser Pro Trp Val Lys Arg Trp
        275                 280                 285

Asp Gln Ile Tyr Lys Arg Tyr Ser Lys His Ile Glu Asp Ala Lys Arg
290                 295                 300

Asn Arg Lys Ala Gly Thr Lys Asn Cys Gly Ile Thr Thr Gly Thr Ile
305                 310                 315                 320

Ser Gly Glu Ser Ser Gly Ala Thr Ser Gly Val Thr Thr Glu Asn
                325                 330                 335

Lys Cys Val Gln Ser
            340

<210> SEQ ID NO 36
<211> LENGTH: 632
<212> TYPE: PRT
<213> ORGANISM: Artificial Sequence
<220> FEATURE:
<223> OTHER INFORMATION: 7g8 745 amino acids

<400> SEQUENCE: 36

Asn Tyr Ile Lys Asp Asp Pro Tyr Ser Lys Glu Tyr Val Thr Lys Leu
1               5                   10                  15

Ser Phe Ile Pro Asn Ser Ser Asp Ala Asn Thr Ser Ser Glu Lys Ile
            20                  25                  30

Gln Lys Asn Asn Asp Glu Val Cys Asn Pro Asn Glu Ser Gly Ile Ser
        35                  40                  45

Ser Val Glu Gln Ala Gln Thr Ser Gly Pro Ser Ser Asn Lys Thr Cys
    50                  55                  60

Ile Thr His Ser Ser Ile Lys Ala Asn Lys Lys Glu Cys Lys Asp
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Gln Asp
            100                 105                 110

Leu Leu Gly Ile Leu Gln Glu Asn Cys Ser Asp Asn Lys Arg Gly Ser
        115                 120                 125

-continued

```
Ser Ser Asn Asp Ser Cys Asp Asn Lys Asn Gln Asp Glu Cys Gln Lys
    130                 135                 140

Lys Leu Asp Glu Ala Leu Glu Ser Leu His Asn Gly Tyr Lys Asn Gln
145                 150                 155                 160

Lys Cys Lys Ser Gly Thr Ser Thr Val Asn Lys Lys Trp Ile Trp Lys
                165                 170                 175

Lys Ser Ser Gly Asn Lys Glu Gly Leu Gln Lys Glu Tyr Ala Asn Thr
            180                 185                 190

Ile Gly Leu Pro Pro Arg Thr Gln Ser Leu Tyr Leu Gly Asn Leu Pro
        195                 200                 205

Lys Leu Glu Asn Val Ser Lys Gly Val Thr Asp Ile Ile Tyr Asp Thr
210                 215                 220

Lys Glu Lys Phe Leu Ala Gly Cys Leu Ile Val Ser Phe His Glu Gly
225                 230                 235                 240

Lys Asn Leu Lys Thr Ser His Glu Lys Lys Asn Asp Asn Gly Lys
                245                 250                 255

Lys Leu Cys Lys Ala Leu Glu Tyr Ser Phe Ala Asp Tyr Gly Asp Leu
            260                 265                 270

Ile Lys Gly Thr Ser Ile Trp Asp Asn Glu Tyr Thr Lys Asp Leu Glu
        275                 280                 285

Leu Asn Leu Gln Lys Ala Phe Gly Lys Leu Phe Arg Lys Tyr Ile Lys
290                 295                 300

Lys Asn Ile Ser Ala Glu Gln Asp Thr Ser Tyr Ser Ser Leu Asp Glu
305                 310                 315                 320

Leu Arg Glu Ser Trp Trp Asn Thr Asn Lys Lys Tyr Ile Trp Ile Ala
                325                 330                 335

Met Lys His Gly Ala Gly Met Asn Gly Thr Thr Cys Cys Gly Asp Gly
            340                 345                 350

Ser Ser Gly Glu Asn Gln Thr Asn Ser Cys Asp Asp Ile Pro Thr Ile
        355                 360                 365

Asp Leu Ile Pro Gln Tyr Leu Arg Phe Leu Gln Glu Trp Val Glu His
370                 375                 380

Phe Cys Glu Gln Arg Gln Ala Lys Val Lys Asp Val Ile Thr Asn Cys
385                 390                 395                 400

Lys Ser Cys Lys Asn Thr Ser Gly Glu Arg Lys Ile Gly Gly Thr Cys
                405                 410                 415

Asn Gly Glu Cys Lys Thr Lys Cys Lys Asn Lys Cys Glu Ala Tyr Lys
            420                 425                 430

Thr Phe Ile Glu His Cys Lys Gly Gly Asp Gly Thr Ala Gly Ser Ser
        435                 440                 445

Trp Val Lys Arg Trp Asp Gln Ile Tyr Lys Arg Tyr Ser Lys His Ile
450                 455                 460

Glu Asp Ala Lys Arg Asn Arg Lys Ala Gly Thr Lys Ser Cys Gly Thr
465                 470                 475                 480

Ser Thr Ala Glu Asn Lys Cys Val Gln Ser Asp Ile Asp Ser Phe Phe
                485                 490                 495

Lys His Leu Ile Asp Ile Gly Leu Thr Thr Pro Ser Ser Tyr Leu Ser
            500                 505                 510

Ile Val Leu Asp Glu Asn Cys Gly Glu Asp Lys Ala Pro Trp Thr
        515                 520                 525

Thr Tyr Thr Thr Thr Lys Asn Cys Asp Ile Gln Lys Asp Lys Ser Lys
530                 535                 540

Ser Gln Ser Ser Asp Thr Leu Val Val Val Asn Val Pro Ser Pro Leu
```

|     |     |     |     |     |     |     |
| --- | --- | --- | --- | --- | --- | --- |
| 545 |     | 550 |     | 555 |     | 560 |

Gly Asn Thr Pro His Gly Tyr Lys Tyr Ala Cys Gln Cys Lys Ile Pro
                565                 570                 575

Thr Thr Glu Glu Thr Cys Asp Asp Arg Lys Glu Tyr Met Asn Gln Trp
            580                 585                 590

Ser Cys Gly Ser Ala Arg Thr Met Lys Arg Gly Tyr Lys Asn Asp Asn
        595                 600                 605

Tyr Glu Leu Cys Lys Tyr Asn Gly Val Asp Val Lys Pro Thr Thr Val
    610                 615                 620

Arg Ser Ser Thr Lys Leu Asp
625                 630

<210> SEQ ID NO 37
<211> LENGTH: 639
<212> TYPE: PRT
<213> ORGANISM: Artificial Sequence
<220> FEATURE:
<223> OTHER INFORMATION: Indo 745 amino acids

<400> SEQUENCE: 37

Asp Tyr Ile Lys Gly Asp Pro Tyr Ser Ala Glu Tyr Val Thr Lys Leu
1               5                   10                  15

Ser Phe Ile Pro Asn Ser Ser Asp Ala Asn Asn Pro Ser Glu Lys Ile
                20                  25                  30

Gln Lys Asn Asn Asp Glu Val Cys Asn Cys Asn Glu Ser Glu Ile Ser
            35                  40                  45

Ser Val Gly Gln Ala Ser Ile Ser Asp Pro Ser Ser Asn Lys Thr Cys
50                  55                  60

Asn Thr His Ser Ser Ile Lys Ala Asn Lys Lys Val Cys Lys Asp
65                  70                  75                  80

Val Lys Leu Gly Val Arg Glu Asn Asp Lys Val Leu Lys Ile Cys Val
                85                  90                  95

Ile Glu His Thr Ser Leu Arg Gly Val Asp Asn Cys Cys Phe Lys Asp
            100                 105                 110

Leu Leu Gly Ile Leu Gln Glu Pro Arg Ile Asp Lys Asn Gln Ser Gly
        115                 120                 125

Ser Ser Ser Asn Gly Ser Cys Asp Lys Asn Ser Glu Glu Ala Cys Glu
    130                 135                 140

Lys Asn Leu Glu Lys Val Leu Ala Ser Leu Thr Asn Gly Tyr Lys Cys
145                 150                 155                 160

Asp Lys Cys Lys Ser Gly Thr Ser Arg Ser Lys Lys Trp Ile Trp
                165                 170                 175

Lys Lys Tyr Ser Gly Lys Glu Gly Leu Gln Glu Glu Tyr Ala Asn
            180                 185                 190

Thr Ile Gly Leu Pro Pro Arg Thr Gln Ser Leu Cys Leu Val Val Cys
        195                 200                 205

Leu Asp Glu Lys Glu Gly Lys Thr Gln Glu Leu Lys Asn Ile Ser Thr
    210                 215                 220

Asn Ser Glu Leu Leu Lys Glu Trp Ile Ile Ala Ala Phe Pro Glu Gly
225                 230                 235                 240

Lys Asn Leu Lys Pro Ser Pro Glu Lys Lys Gly Asp Asn Gly Lys
                245                 250                 255

Lys Leu Cys Lys Asp Leu Lys Tyr Ser Phe Ala Asp Tyr Gly Asp Leu
            260                 265                 270

Ile Lys Gly Thr Ser Ile Trp Asp Asn Glu Tyr Thr Lys Asp Leu Glu

```
              275                 280                 285
Leu Asn Leu Gln Lys Ile Phe Gly Lys Leu Phe Arg Lys Tyr Ile Lys
    290                 295                 300
Lys Asn Ile Ala Ser Asp Glu Asn Thr Leu Tyr Ser Ser Leu Asp Glu
305                 310                 315                 320
Leu Arg Glu Ser Trp Trp Asn Thr Asn Lys Tyr Ile Trp Leu Ala
                325                 330                 335
Met Lys His Gly Ala Gly Met Asn Ser Thr Met Cys Asn Ala Asp Gly
            340                 345                 350
Ser Val Thr Gly Ser Gly Ser Ser Cys Asp Asp Met Pro Thr Ile Asp
                355                 360                 365
Leu Ile Pro Gln Tyr Leu Arg Phe Leu Gln Glu Trp Val Glu His Phe
    370                 375                 380
Cys Lys Gln Arg Gln Glu Lys Val Lys Pro Val Ile Glu Asn Cys Asn
385                 390                 395                 400
Ser Cys Lys Asn Thr Ser Ser Glu Arg Lys Ile Gly Gly Thr Cys Asn
                405                 410                 415
Ser Asp Cys Lys Thr Glu Cys Lys Asn Lys Cys Glu Val Tyr Lys Lys
            420                 425                 430
Phe Ile Glu Asp Cys Lys Gly Gly Asp Gly Thr Ala Gly Ser Ser Trp
                435                 440                 445
Ser Lys Arg Trp Asp Gln Ile Tyr Lys Arg Tyr Ser Lys Tyr Ile Glu
    450                 455                 460
Asp Ala Lys Arg Asn Arg Lys Ala Gly Thr Lys Asn Cys Gly Pro Ser
465                 470                 475                 480
Ser Thr Thr Asn Ala Ala Glu Asn Lys Cys Val Gln Ser Asp Ile Asp
                485                 490                 495
Ser Phe Phe Lys His Leu Ile Asp Ile Gly Leu Thr Thr Pro Ser Ser
            500                 505                 510
Tyr Leu Ser Thr Val Leu Asp Asp Asn Ile Cys Gly Glu Asp Asn Ala
    515                 520                 525
Pro Trp Thr Thr Tyr Thr Thr Tyr Thr Thr Lys Asn Cys Asp Lys
530                 535                 540
Asp Lys Lys Ser Lys Ser Gln Ser Cys Asp Thr Leu Val Val Val
545                 550                 555                 560
Asn Val Pro Ser Pro Leu Gly Asn Thr Pro His Glu Tyr Lys Tyr Ala
                565                 570                 575
Cys Glu Cys Arg Thr Pro Asn Lys Gln Glu Ser Cys Asp Asp Arg Lys
            580                 585                 590
Glu Tyr Met Asn Gln Trp Ile Ser Asp Asn Thr Lys Asn Pro Lys Gly
                595                 600                 605
Ser Gly Ser Gly Lys Asp Tyr Tyr Glu Leu Tyr Thr Tyr Asn Gly Val
    610                 615                 620
Asp Val Lys Pro Thr Thr Val Arg Ser Ser Thr Lys Leu Asp
625                 630                 635

<210> SEQ ID NO 38
<211> LENGTH: 655
<212> TYPE: PRT
<213> ORGANISM: Artificial Sequence
<220> FEATURE:
<223> OTHER INFORMATION: MC 745 amino acids

<400> SEQUENCE: 38

Asp Tyr Ile Lys Gly Asp Pro Tyr Phe Ala Glu Tyr Ala Thr Lys Leu
```

-continued

```
1               5                   10                  15
Ser Phe Ile Leu Asn Ser Ser Asp Ala Asn Thr Ser Ser Gly Glu Thr
            20                  25                  30
Ala Asn His Asn Asp Glu Ala Cys Asn Cys Asn Glu Ser Glu Ile Ser
            35                  40                  45
Ser Val Glu His Ala Ser Ile Ser Asp Pro Ser Ser Asn Lys Thr Cys
        50                  55                  60
Asn Thr His Ser Ser Ile Lys Ala Asn Lys Lys Val Cys Lys His
65                  70                  75                  80
Val Lys Leu Gly Val Arg Glu Asn Asp Lys Asp Leu Arg Val Cys Val
                85                  90                  95
Ile Glu His Thr Ser Leu Ser Gly Val Glu Asn Cys Cys Phe Lys Asp
            100                 105                 110
Phe Leu Arg Ile Leu Gln Glu Asn Cys Ser Asp Asn Lys Ser Gly Ser
            115                 120                 125
Ser Ser Asn Gly Ser Cys Asp Lys Asn Asn Glu Glu Ala Cys Glu Lys
130                 135                 140
Asn Leu Glu Lys Val Phe Ala Ser Leu Thr Asn Cys Tyr Lys Cys Glu
145                 150                 155                 160
Lys Cys Lys Ser Glu Gln Ser Lys Lys Asn Asn Lys Lys Trp Thr Trp
                165                 170                 175
Arg Lys Ser Ser Gly Asn Lys Gly Gly Leu Gln Glu Glu Tyr Ala Asn
            180                 185                 190
Thr Ile Gly Leu Pro Pro Arg Thr Gln Ser Leu Cys Leu Val Val Cys
            195                 200                 205
Leu Asp Glu Lys Glu Gly Lys Lys Thr Gln Glu Leu Lys Asn Ile Arg
210                 215                 220
Thr Asn Ser Glu Leu Leu Lys Glu Trp Ile Ile Ala Ala Phe His Glu
225                 230                 235                 240
Gly Lys Asn Leu Lys Pro Ser His Glu Lys Lys Asn Asp Asp Asn Gly
                245                 250                 255
Lys Lys Asn Asp Asp Asn Asn Ser Lys Leu Cys Lys Asp Leu Lys Tyr
            260                 265                 270
Ser Phe Ala Asp Tyr Gly Asp Leu Ile Lys Gly Thr Ser Ile Trp Asp
            275                 280                 285
Asn Glu Tyr Thr Lys Asp Leu Glu Leu Asn Leu Gln Lys Ile Phe Gly
            290                 295                 300
Lys Leu Phe Arg Lys Tyr Ile Lys Lys Asn Ile Ala Ser Asp Glu Asn
305                 310                 315                 320
Thr Leu Tyr Ser Ser Leu Asp Glu Leu Arg Glu Ser Trp Trp Asn Thr
                325                 330                 335
Asn Lys Lys Tyr Ile Trp Leu Ala Met Lys His Gly Ala Glu Met Asn
            340                 345                 350
Gly Thr Thr Cys Asn Ala Asp Gly Ser Val Thr Gly Ser Gly Ser Ser
            355                 360                 365
Cys Asp Asp Ile Pro Thr Ile Asp Leu Ile Pro Gln Tyr Leu Arg Phe
            370                 375                 380
Leu Gln Glu Trp Val Glu His Phe Cys Lys Gln Arg Gln Ala Lys Val
385                 390                 395                 400
Lys Asp Val Ile Glu Asn Cys Lys Ser Cys Lys Glu Ser Gly Asn Lys
                405                 410                 415
Cys Lys Thr Glu Cys Lys Asn Lys Cys Glu Ala Tyr Lys Lys Phe Ile
            420                 425                 430
```

Glu Asn Cys Lys Gly Gly Asp Gly Thr Ala Gly Ser Ser Trp Val Lys
            435                 440                 445

Arg Trp Asp Gln Ile Tyr Met Arg Tyr Ser Lys Tyr Ile Glu Asp Ala
    450                 455                 460

Lys Arg Asn Arg Lys Ala Gly Thr Lys Asn Cys Gly Pro Ser Ser Ile
465                 470                 475                 480

Thr Asn Val Ser Ala Ser Thr Asp Glu Asn Lys Cys Val Gln Ser Asp
            485                 490                 495

Ile Asp Ser Phe Phe Lys His Leu Ile Asp Ile Gly Leu Thr Thr Pro
            500                 505                 510

Ser Ser Tyr Leu Ser Ile Val Leu Asp Asp Asn Ile Cys Gly Asp Asp
            515                 520                 525

Lys Ala Pro Trp Thr Thr Tyr Thr Thr Tyr Thr Thr Tyr Thr Thr Tyr
            530                 535                 540

Thr Thr Tyr Thr Thr Tyr Thr Thr Tyr Thr Thr Lys Asn Cys Asp
545                 550                 555                 560

Lys Glu Arg Asp Lys Ser Lys Ser Gln Ser Cys Asn Thr Ala Val Val
            565                 570                 575

Val Asn Val Pro Ser Pro Leu Gly Asn Thr Pro His Glu Tyr Lys Tyr
            580                 585                 590

Ala Cys Glu Cys Arg Thr Pro Ser Asn Lys Glu Leu Cys Asp Asp Arg
            595                 600                 605

Lys Glu Tyr Met Asn Gln Trp Ser Ser Gly Ser Ala Gln Thr Val Arg
            610                 615                 620

Asp Arg Ser Gly Lys Asp Tyr Tyr Glu Leu Tyr Thr Tyr Asn Gly Val
625                 630                 635                 640

Lys Glu Thr Lys Leu Pro Lys Lys Leu Asn Ser Ser Lys Leu Asp
            645                 650                 655

<210> SEQ ID NO 39
<211> LENGTH: 347
<212> TYPE: PRT
<213> ORGANISM: Plasmodium falciparum

<400> SEQUENCE: 39

Lys Cys Asp Lys Cys Lys Ser Glu Gln Ser Lys Lys Asn Asn Lys Tyr
1               5                   10                  15

Trp Ile Trp Lys Lys Ser Ser Val Lys Glu Gly Leu Gln Lys Glu
            20                  25                  30

Tyr Ala Asn Thr Ile Ala Leu Pro Pro Arg Thr His Ser Leu Cys Leu
            35                  40                  45

Val Val Cys Leu Asp Glu Lys Gly Lys Lys Thr Gln Glu Leu Lys Asn
    50                  55                  60

Ile Ser Thr Asn Ser Glu Leu Leu Lys Glu Arg Ile Ile Ala Ala Phe
65              70                  75                  80

His Glu Gly Lys Asn Leu Lys Thr Thr Tyr Leu Glu Lys Lys Asn Ala
            85                  90                  95

Asp Asn Asn Ser Lys Leu Cys Lys Ala Leu Lys Tyr Ser Phe Ala Asp
            100                 105                 110

Tyr Gly Asp Leu Ile Lys Gly Thr Ser Ile Trp Asp Asn Glu Tyr Thr
            115                 120                 125

Lys Asp Leu Glu Leu Asn Leu Gln Gln Ile Phe Gly Lys Leu Phe Arg
            130                 135                 140

Lys Tyr Ile Lys Lys Asn Asn Thr Ala Glu Gln His Thr Leu Tyr Ser

```
                145                 150                 155                 160
Ser Leu Asp Glu Leu Arg Glu Ser Trp Trp Asn Thr Asn Lys Lys Tyr
                    165                 170                 175

Ile Trp Leu Ala Met Lys His Gly Ala Gly Met Asn Gly Thr Thr Cys
                    180                 185                 190

Cys Gly Asp Gly Ser Val Thr Gly Ser Ser Asp Ser Gly Ser Thr Thr
                    195                 200                 205

Cys Ser Gly Asp Asn Gly Ser Ile Ser Cys Asp Met Pro Thr Thr
    210                 215                 220

Asp Phe Ile Pro Gln Tyr Leu Arg Phe Leu Gln Glu Trp Val Glu His
225                 230                 235                 240

Phe Cys Lys Gln Arg Gln Glu Lys Val Lys Asp Val Ile Glu Asn Cys
                    245                 250                 255

Asn Ser Cys Lys Asn Asn Leu Gly Lys Thr Glu Ile Asn Glu Lys Cys
                    260                 265                 270

Lys Thr Glu Cys Lys Asn Lys Cys Glu Ala Tyr Lys Asn Phe Ile Glu
                    275                 280                 285

Lys Phe Cys Thr Ala Asp Gly Thr Ser Gly Ser Pro Trp Ser Lys
    290                 295                 300

Arg Trp Asp Gln Ile Tyr Lys Arg Tyr Ser Lys Tyr Ile Glu Asp Ala
305                 310                 315                 320

Lys Arg Asn Arg Lys Ala Gly Thr Lys Asn Cys Gly Thr Ser Ser Thr
                    325                 330                 335

Thr Ser Thr Ala Glu Asn Lys Cys Val Gln Ser
                340                 345

<210> SEQ ID NO 40
<211> LENGTH: 335
<212> TYPE: PRT
<213> ORGANISM: Plasmodium falciparum

<400> SEQUENCE: 40

Lys Cys Glu Lys Cys Lys Ser Gly Thr Ser Thr Val Asn Lys Tyr Trp
1               5                   10                  15

Ile Trp Arg Lys Ser Ser Gly Asn Lys Glu Gly Leu Gln Lys Glu Tyr
                    20                  25                  30

Ala Asn Thr Ile Ala Leu Pro Pro Arg Thr His Ser Leu Cys Leu Val
                    35                  40                  45

Val Cys Leu Asp Glu Lys Glu Gly Lys Thr Gln Glu Leu Lys Asn Ile
    50                  55                  60

Ser Thr Asn Ser Glu Leu Leu Lys Glu Arg Ile Ile Ala Ala Phe His
65                  70                  75                  80

Glu Gly Glu Asn Leu Lys Thr Ser His Glu Lys Lys Lys Gly Asp Asp
                    85                  90                  95

Gly Lys Lys Asn Ala Asp Asn Ser Lys Leu Cys Lys Ala Leu Lys
                    100                 105                 110

Tyr Ser Phe Ala Asp Tyr Gly Asp Leu Ile Lys Gly Thr Ser Ile Trp
                    115                 120                 125

Asp Asn Glu Tyr Thr Lys Asp Leu Glu Leu Asn Leu Gln Lys Ile Phe
    130                 135                 140

Gly Lys Leu Phe Arg Lys Tyr Ile Lys Lys Asn Ile Ala Ser Asp Glu
145                 150                 155                 160

Asn Thr Ser Tyr Ser Ser Leu Asp Glu Leu Arg Glu Ser Trp Trp Asn
                    165                 170                 175
```

```
Thr Asn Lys Lys Tyr Ile Trp Leu Ala Met Lys His Gly Ala Gly Met
            180                 185                 190

Asn Gly Thr Thr Cys Ser Cys Ser Gly Asp Ser Ser Asp Asp Met Pro
            195                 200                 205

Thr Thr Asp Phe Ile Pro Gln Tyr Leu Arg Phe Leu Gln Glu Trp Val
            210                 215                 220

Glu His Phe Cys Lys Gln Arg Gln Glu Asn Val Asn Ala Val Ile Glu
225                 230                 235                 240

Asn Cys Asn Ser Cys Lys Glu Cys Gly Gly Thr Cys Asn Ser Asp Cys
            245                 250                 255

Glu Lys Lys Cys Lys Thr Glu Cys Lys Asn Lys Cys Glu Ala Tyr Lys
            260                 265                 270

Asn Phe Ile Glu Lys Phe Cys Thr Ala Asp Gly Gly Thr Ser Gly Tyr
            275                 280                 285

Ser Trp Ser Lys Arg Trp Asp Gln Ile Tyr Lys Arg Tyr Ser Lys Tyr
            290                 295                 300

Ile Glu Asp Ala Lys Arg Asn Arg Lys Ala Gly Thr Lys Ser Cys Gly
305                 310                 315                 320

Thr Ser Ser Thr Thr Ser Thr Ala Glu Ser Lys Cys Val Gln Ser
            325                 330                 335

<210> SEQ ID NO 41
<211> LENGTH: 667
<212> TYPE: PRT
<213> ORGANISM: Artificial Sequence
<220> FEATURE:
<223> OTHER INFORMATION: ghana2 745 amino acids

<400> SEQUENCE: 41

Ser Tyr Val Lys Asn Asn Pro Tyr Ser Lys Glu Tyr Val Thr Lys Leu
1               5                   10                  15

Ser Phe Ile Leu Asn Pro Ser Asp Ala Asn Asn Pro Ser Glu Thr Pro
            20                  25                  30

Ser Lys Tyr Tyr Asp Glu Val Cys Asn Cys Asn Glu Ser Gly Ile Ala
            35                  40                  45

Cys Val Gly Gln Ala Gln Thr Ser Gly Pro Ser Ser Asn Lys Thr Cys
        50                  55                  60

Ile Thr His Ser Phe Ile Gly Ala Asn Lys Lys Val Cys Lys Asp
65                  70                  75                  80

Val Lys Leu Gly Val Arg Glu Lys Asp Lys Asp Leu Lys Ile Cys Val
            85                  90                  95

Ile Glu Asp Thr Tyr Leu Ser Gly Val Asp Asn Cys Cys Phe Lys Asp
            100                 105                 110

Phe Leu Gly Met Leu Gln Glu Asn Cys Ser Asp Asn Lys Ser Gly Ser
            115                 120                 125

Ser Ser Asn Gly Ser Cys Asn Asn Lys Asn Gln Asp Glu Cys Glu Lys
        130                 135                 140

Asn Leu Asp Glu Ala Leu Ala Ser Leu Thr Asn Gly Tyr Lys Cys Glu
145                 150                 155                 160

Lys Cys Lys Ser Gly Thr Ser Thr Val Asn Lys Tyr Trp Ile Trp Arg
            165                 170                 175

Lys Ser Ser Gly Asn Lys Glu Gly Leu Gln Lys Glu Tyr Ala Asn Thr
            180                 185                 190

Ile Ala Leu Pro Pro Arg Thr His Ser Leu Cys Leu Val Val Cys Leu
            195                 200                 205
```

```
Asp Glu Lys Glu Gly Lys Thr Gln His Lys Thr Ile Ser Thr Asn Ser
    210                 215                 220
Glu Leu Leu Lys Glu Trp Ile Ile Ala Ala Phe His Glu Gly Lys Asn
225                 230                 235                 240
Leu Lys Thr Ser His Glu Lys Lys Gly Asp Asp Gly Lys Lys Asn
            245                 250                 255
Ala Asp Asn Asn Ser Lys Leu Cys Lys Ala Leu Lys Tyr Ser Phe Ala
            260                 265                 270
Asp Tyr Gly Asp Leu Ile Lys Gly Thr Ser Ile Trp Asp Asn Asp Phe
        275                 280                 285
Thr Lys Asp Leu Glu Leu Asn Leu Gln Lys Ile Phe Gly Lys Leu Phe
        290                 295                 300
Arg Lys Tyr Ile Lys Lys Asn Ile Ala Ser Asp Glu Asn Thr Ser Tyr
305                 310                 315                 320
Ser Ser Leu Asp Glu Leu Arg Glu Ser Trp Trp Asn Thr Asn Lys Lys
                325                 330                 335
Tyr Ile Trp Leu Ala Met Lys His Gly Ala Gly Met Asn Ser Thr Thr
                340                 345                 350
Cys Cys Gly Asp Gly Ser Val Thr Gly Ser Ser Asp Ser Gly Ser Thr
            355                 360                 365
Thr Cys Cys Gly Asp Gly Ser Val Thr Gly Ser Gly Ser Ser Cys Asp
    370                 375                 380
Asp Met Pro Thr Thr Asp Phe Ile Pro Gln Tyr Leu Arg Phe Leu Gln
385                 390                 395                 400
Glu Trp Val Glu His Phe Cys Lys Gln Arg Gln Glu Asn Val Asn Ala
                405                 410                 415
Val Ile Glu Asn Cys Asn Ser Cys Lys Glu Cys Gly Gly Thr Cys Asn
            420                 425                 430
Ser Asp Cys Glu Lys Lys Cys Lys Thr Glu Cys Lys Gly Glu Cys Asp
            435                 440                 445
Ala Tyr Lys Glu Phe Ile Glu Lys Cys Asn Gly Gly Ala Ala Glu Gly
    450                 455                 460
Thr Ser Gly Ser Ser Trp Ser Lys Arg Trp Asp Gln Ile Tyr Lys Arg
465                 470                 475                 480
Tyr Ser Lys Tyr Ile Glu Asp Ala Lys Arg Asn Arg Lys Ala Gly Thr
                485                 490                 495
Lys Asn Cys Gly Thr Ser Ser Thr Ser Thr Ala Glu Ser Lys Cys
            500                 505                 510
Val Gln Ser Asp Ile Asp Ser Phe Phe Lys His Leu Ile Asp Ile Gly
    515                 520                 525
Leu Thr Thr Pro Ser Ser Tyr Leu Ser Ile Val Leu Asp Glu Asn Ile
    530                 535                 540
Cys Gly Ala Asp Asn Ala Pro Trp Thr Thr Tyr Thr Thr Tyr Thr Thr
545                 550                 555                 560
Tyr Thr Thr Tyr Thr Thr Thr Glu Lys Cys Asn Lys Glu Thr Asp Lys
                565                 570                 575
Ser Lys Leu Gln Gln Cys Asn Thr Ser Val Val Asn Val Pro Ser
            580                 585                 590
Pro Leu Gly Asn Thr Pro His Gly Tyr Lys Tyr Val Cys Glu Cys Arg
            595                 600                 605
Thr Pro Asn Lys Gln Glu Thr Cys Asp Asp Arg Lys Glu Tyr Met Asn
    610                 615                 620
Gln Trp Ile Ser Asp Asn Thr Lys Asn Pro Lys Gly Ser Arg Ser Thr
```

```
                    625                 630                 635                 640
Asn Asn Asp Tyr Glu Leu Tyr Thr Tyr Asn Gly Val Gln Ile Lys Pro
                645                 650                 655
Thr Thr Val Arg Ser Asn Ser Thr Lys Leu Asp
                660                 665

<210> SEQ ID NO 42
<211> LENGTH: 348
<212> TYPE: PRT
<213> ORGANISM: Plasmodium falciparum

<400> SEQUENCE: 42

Lys Cys Asp Lys Cys Lys Ser Glu Gln Ser Lys Lys Asn Asn Lys Asn
1               5                   10                  15

Trp Ile Trp Lys Lys Ser Ser Gly Asn Glu Lys Gly Leu Gln Lys Glu
                20                  25                  30

Tyr Ala Asn Thr Ile Gly Leu Pro Pro Arg Thr Gln Ser Leu Cys Leu
            35                  40                  45

Val Val Cys Leu Asp Glu Lys Glu Gly Lys Thr Gln Glu Leu Lys Asn
        50                  55                  60

Ile Arg Thr Asn Ser Glu Leu Leu Lys Glu Trp Ile Ile Ala Ala Phe
65                  70                  75                  80

His Glu Gly Lys Asn Leu Lys Thr Ser His Glu Lys Lys Lys Gly Asp
                85                  90                  95

Asn Asn Ser Lys Leu Cys Lys Asp Leu Lys Tyr Ser Phe Ala Asp Tyr
            100                 105                 110

Gly Asp Leu Ile Lys Gly Thr Ser Ile Trp Asp Asn Glu Tyr Thr Lys
        115                 120                 125

Asp Leu Glu Leu Asn Leu Gln Asn Asn Phe Gly Lys Leu Phe Arg Lys
    130                 135                 140

Tyr Ile Lys Lys Asn Ile Ala Ser Asp Glu Asn Thr Ser Tyr Ser Ser
145                 150                 155                 160

Leu Asp Glu Leu Arg Glu Ser Trp Trp Asn Thr Asn Lys Lys Tyr Ile
                165                 170                 175

Trp Leu Ala Met Lys His Gly Ala Gly Met Asn Ser Thr Thr Cys Ser
            180                 185                 190

Ser Gly Ser Gly Ser Thr Thr Cys Ser Ser Gly Ser Gly Ser Thr Thr
        195                 200                 205

Cys Ser Ser Gly Ser Gly Asp Ser Cys Asp Asp Met Pro Thr Ile Asp
    210                 215                 220

Leu Ile Pro Gln Tyr Leu Arg Phe Leu Gln Glu Trp Val Glu His Phe
225                 230                 235                 240

Cys Lys Gln Arg Gln Glu Lys Val Asn Ala Val Ile Lys Asn Cys Asn
                245                 250                 255

Ser Cys Lys Glu Ser Gly Gly Thr Cys Asn Gly Glu Cys Lys Thr Glu
            260                 265                 270

Cys Lys Asn Lys Cys Glu Ala Tyr Lys Thr Phe Ile Glu Glu Phe Cys
        275                 280                 285

Thr Ala Asp Gly Gly Thr Ser Gly Ser Pro Trp Ser Lys Arg Trp Asp
    290                 295                 300

Gln Ile Tyr Lys Met Tyr Ser Lys His Ile Glu Asp Ala Lys Arg Asn
305                 310                 315                 320

Arg Lys Ala Gly Thr Lys Asn Cys Gly Pro Ser Ser Thr Thr Asn Val
                325                 330                 335
```

```
Ser Val Ser Thr Asp Glu Asn Lys Cys Val Gln Ser
            340                 345
```

<210> SEQ ID NO 43
<211> LENGTH: 652
<212> TYPE: PRT
<213> ORGANISM: Artificial Sequence
<220> FEATURE:
<223> OTHER INFORMATION: ghana1 745 amino acids

<400> SEQUENCE: 43

```
Asp Tyr Ile Lys Asp Asp Pro Tyr Phe Ala Glu Tyr Val Thr Lys Leu
1               5                   10                  15

Ser Phe Ile Leu Asn Ser Ser Asp Ala Asn Asn Pro Ser Gly Glu Thr
            20                  25                  30

Ala Asn His Asn Asp Glu Val Cys Asn Pro Asn Glu Ser Gly Ile Ala
        35                  40                  45

Ser Val Glu Gln Ala Gln Thr Ser Asp Pro Ser Ser Asn Lys Thr Cys
    50                  55                  60

Asn Thr His Ser Ser Ile Lys Ala Asn Lys Lys Val Cys Lys His
65                  70                  75                  80

Val Lys Leu Gly Val Arg Glu Asn Asp Lys Asp Leu Lys Ile Cys Val
                85                  90                  95

Ile Glu His Thr Ser Leu Ser Gly Val Glu Asn Cys Cys Gln Asp
            100                 105                 110

Phe Leu Arg Ile Leu Gln Glu Asn Cys Ser Asp Asn Lys Ser Gly Ser
        115                 120                 125

Ser Ser Asn Gly Ser Cys Asn Lys Asn Gln Glu Ala Cys Glu Lys
    130                 135                 140

Asn Leu Glu Lys Val Leu Ala Ser Leu Thr Asn Cys Tyr Lys Cys Asp
145                 150                 155                 160

Lys Cys Lys Ser Glu Gln Ser Lys Lys Asn Asn Lys Asn Trp Ile Trp
                165                 170                 175

Lys Lys Ser Ser Gly Asn Glu Lys Gly Leu Gln Lys Glu Tyr Ala Asn
            180                 185                 190

Thr Ile Gly Leu Pro Pro Arg Thr Gln Ser Leu Cys Leu Val Val Cys
        195                 200                 205

Leu Asp Glu Lys Glu Gly Lys Thr Gln Glu Leu Lys Asn Ile Arg Thr
    210                 215                 220

Asn Ser Glu Leu Leu Lys Glu Trp Ile Ile Ala Ala Phe His Glu Gly
225                 230                 235                 240

Lys Asn Leu Lys Lys Arg Tyr Pro Gln Asn Lys Asn Asp Asp Asn Asn
                245                 250                 255

Ser Lys Leu Cys Lys Asp Leu Lys Tyr Ser Phe Ala Asp Tyr Gly Asp
            260                 265                 270

Leu Ile Lys Gly Thr Ser Ile Trp Asp Asn Glu Tyr Thr Lys Asp Leu
        275                 280                 285

Glu Leu Asn Leu Gln Asn Asn Phe Gly Lys Leu Phe Arg Lys Tyr Ile
    290                 295                 300

Lys Lys Asn Ile Ser Thr Glu Gln Asp Thr Leu Tyr Ser Ser Leu Asp
305                 310                 315                 320

Glu Leu Arg Glu Ser Trp Trp Asn Thr Asn Lys Lys Tyr Ile Trp Leu
                325                 330                 335

Ala Met Lys His Gly Ala Gly Met Asn Ser Thr Thr Cys Ser Ser Gly
            340                 345                 350
```

Ser Gly Ser Thr Thr Cys Ser Ser Gly Ser Gly Ser Thr Cys Ser
                355                 360                 365

Ser Gly Ser Gly Asp Ser Cys Asp Asp Met Pro Thr Thr Asp Phe Ile
            370                 375                 380

Pro Gln Tyr Leu Arg Phe Leu Gln Glu Trp Val Glu His Phe Cys Lys
385                 390                 395                 400

Gln Arg Gln Glu Lys Val Asn Ala Val Ile Lys Asn Cys Asn Ser Cys
                405                 410                 415

Lys Glu Ser Gly Gly Thr Cys Asn Gly Glu Cys Lys Thr Glu Cys Lys
            420                 425                 430

Asn Lys Cys Glu Ala Tyr Lys Thr Phe Ile Glu Glu Phe Cys Thr Ala
                435                 440                 445

Asp Gly Gly Thr Ser Gly Ser Pro Trp Ser Lys Arg Trp Asp Gln Ile
            450                 455                 460

Tyr Lys Met Tyr Ser Lys His Ile Glu Asp Ala Lys Arg Asn Arg Lys
465                 470                 475                 480

Ala Gly Thr Lys Asn Cys Gly Pro Ser Thr Thr Asn Val Ser Val
                485                 490                 495

Ser Thr Asp Glu Asn Lys Cys Val Gln Ser Asp Ile Asp Ser Phe Phe
                500                 505                 510

Lys His Leu Ile Asp Ile Gly Leu Thr Thr Pro Ser Ser Tyr Leu Ser
            515                 520                 525

Ile Val Leu Asp Asp Asn Ile Cys Gly Glu Asp Lys Ala Pro Trp Thr
            530                 535                 540

Thr Tyr Thr Thr Tyr Thr Thr Thr Lys Lys Cys Asn Lys Glu Thr Asp
545                 550                 555                 560

Lys Ser Lys Ser Gln Ser Cys Asn Thr Ala Val Val Asn Val Pro
                565                 570                 575

Ser Pro Leu Gly Asn Thr Pro His Gly Tyr Lys Tyr Ala Cys Glu Cys
            580                 585                 590

Lys Ile Pro Thr Thr Glu Glu Thr Cys Asp Asp Arg Lys Glu Tyr Met
            595                 600                 605

Asn Gln Trp Ile Ile Asp Thr Ser Lys Lys Gln Lys Gly Ser Gly Ser
            610                 615                 620

Gly Lys Asp Asp Tyr Glu Leu Tyr Thr Tyr Asn Gly Val Asp Val Lys
625                 630                 635                 640

Pro Thr Thr Val Arg Ser Asn Ser Thr Lys Leu Asp
                645                 650

<210> SEQ ID NO 44
<211> LENGTH: 628
<212> TYPE: PRT
<213> ORGANISM: Artificial Sequence
<220> FEATURE:
<223> OTHER INFORMATION: V1S1 745 amino acids

<400> SEQUENCE: 44

Asp Tyr Ile Lys Asp Asp Pro Tyr Ser Ala Gln Tyr Thr Thr Lys Leu
1               5                   10                  15

Ser Phe Ile Leu Asn Pro Ser Asp Ala Asn Thr Ser Ser Glu Lys Ile
            20                  25                  30

Gln Lys Asn Asn Asp Glu Ala Cys Asn Cys Asn Glu Ser Gly Ile Ser
        35                  40                  45

Ser Val Gly Gln Ala Gln Thr Ser Gly Pro Ser Ser Asn Lys Thr Cys
    50                  55                  60

-continued

```
Ile Thr His Ser Ser Ile Lys Ala Asn Lys Lys Val Cys Lys Asp
 65                  70                  75                  80

Val Lys Leu Gly Ile Asn Asn Asn Asp Lys Val Leu Arg Val Cys Val
                 85                  90                  95

Ile Glu Asp Thr Ser Leu Ser Gly Val Asp Asn Cys Cys Gln Asp
                100                 105                 110

Leu Leu Gly Ile Leu Gln Glu Asn Cys Ser Asp Asn Lys Arg Gly Ser
                115                 120                 125

Ser Ser Asn Gly Ser Cys Asn Asn Asn Glu Glu Ala Cys Glu Lys
    130                 135                 140

Asn Leu Asp Glu Ala Pro Ala Ser Leu His Asn Gly Tyr Lys Asn Gln
145                 150                 155                 160

Lys Cys Lys Ser Gly Thr Ser Arg Ser Lys Lys Trp Ile Trp Lys
                165                 170                 175

Lys Ser Ser Gly Asn Glu Lys Gly Leu Gln Glu Glu Tyr Ala Asn Thr
                180                 185                 190

Ile Gly Leu Pro Pro Arg Thr Gln Ser Leu Cys Leu Val Cys Leu His
                195                 200                 205

Glu Lys Glu Gly Lys Thr Gln His Lys Thr Ile Ser Thr Asn Ser Glu
    210                 215                 220

Leu Leu Lys Glu Trp Ile Ile Ala Ala Phe His Glu Gly Lys Asn Leu
225                 230                 235                 240

Lys Thr Ser His Glu Lys Lys Asn Asp Asn Gly Lys Lys Leu Cys
                245                 250                 255

Lys Ala Leu Glu Tyr Ser Phe Ala Asp Tyr Gly Asp Leu Ile Lys Gly
                260                 265                 270

Thr Ser Ile Trp Asp Asn Glu Tyr Thr Lys Asp Leu Glu Leu Asn Leu
                275                 280                 285

Gln Lys Ala Phe Gly Lys Leu Phe Arg Lys Tyr Ile Lys Lys Asn Asn
    290                 295                 300

Thr Ala Glu Gln Asp Thr Ser Tyr Ser Ser Leu Asp Glu Leu Arg Glu
305                 310                 315                 320

Ser Trp Trp Asn Thr Asn Lys Lys Tyr Ile Trp Ile Ala Met Lys His
                325                 330                 335

Gly Ala Gly Met Asn Gly Thr Thr Cys Ser Cys Ser Gly Asp Ser Ser
                340                 345                 350

Asn Asp Met Pro Thr Ile Asp Leu Ile Pro Gln Tyr Leu Arg Phe Leu
                355                 360                 365

Gln Glu Trp Val Glu His Phe Cys Glu Gln Arg Gln Ala Lys Val Lys
    370                 375                 380

Asp Val Ile Thr Asn Cys Lys Ser Cys Lys Glu Ser Gly Asn Lys Cys
385                 390                 395                 400

Lys Thr Glu Cys Lys Thr Lys Cys Lys Asp Glu Cys Glu Lys Tyr Lys
                405                 410                 415

Thr Phe Ile Glu Asp Cys Asn Gly Gly Thr Gly Thr Ala Gly Ser
                420                 425                 430

Ser Trp Val Lys Arg Trp Asp Gln Ile Tyr Lys Arg Tyr Ser Lys His
                435                 440                 445

Ile Glu Asp Ala Lys Arg Asn Arg Lys Ala Gly Thr Lys Asn Cys Gly
                450                 455                 460

Pro Ser Ser Ile Thr Asn Ala Ala Ala Ser Thr Asp Glu Asn Lys Cys
465                 470                 475                 480

Val Gln Ser Asp Ile Asp Ser Phe Phe Lys His Leu Ile Asp Ile Gly
```

```
                       485                 490                 495
Leu Thr Thr Pro Ser Ser Tyr Leu Ser Asn Val Leu Asp Glu Asn Ser
                500                 505                 510

Cys Gly Asp Asp Lys Ala Pro Trp Thr Thr Tyr Thr Thr Tyr Thr Thr
                515                 520                 525

Thr Lys Asn Cys Asp Ile Gln Lys Asp Lys Ser Lys Ser Gln Pro Ile
            530                 535                 540

Asn Thr Ser Val Val Asn Val Pro Ser Pro Leu Gly Asn Thr Pro
545                 550                 555                 560

Tyr Arg Tyr Lys Tyr Ala Cys Glu Cys Lys Ile Pro Thr Thr Glu Glu
                565                 570                 575

Ser Cys Asp Asp Arg Lys Glu Tyr Met Asn Gln Trp Ser Cys Gly Ser
                580                 585                 590

Ala Arg Thr Met Lys Arg Gly Tyr Lys Asn Asp Asn Tyr Glu Leu Cys
                595                 600                 605

Lys Tyr Asn Gly Val Asp Val Lys Pro Thr Thr Val Arg Ser Asn Ser
                610                 615                 620

Ser Lys Leu Asp
625

<210> SEQ ID NO 45
<211> LENGTH: 653
<212> TYPE: PRT
<213> ORGANISM: Artificial Sequence
<220> FEATURE:
<223> OTHER INFORMATION: raj116_var25 745 amino acids

<400> SEQUENCE: 45

Asp Tyr Ile Lys Gly Asp Pro Tyr Phe Ala Glu Tyr Ala Thr Lys Leu
1               5                   10                  15

Ser Phe Ile Leu Asn Pro Ser Asp Thr Glu Asn Ala Ser Glu Thr Pro
                20                  25                  30

Ser Lys Tyr Tyr Asp Glu Ala Cys Asn Pro Asn Glu Ser Glu Ile Ala
            35                  40                  45

Ser Val Glu Gln Ala Gln Thr Ser Gly Pro Ser Ser Asn Lys Thr Cys
        50                  55                  60

Ile Thr His Ser Ser Ile Lys Thr Asn Lys Lys Glu Cys Lys Asp
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Phe Lys Asp
            100                 105                 110

Leu Leu Gly Ile Leu Gln Glu Asn Cys Ser Asp Asn Lys Arg Gly Ser
        115                 120                 125

Ser Ser Asn Asp Ser Cys Asn Asn Asn Glu Glu Ala Cys Glu Lys
    130                 135                 140

Asn Leu Asp Glu Ala Leu Ala Ser Leu Thr Asn Gly Tyr Lys Cys Asp
145                 150                 155                 160

Lys Cys Lys Ser Gly Thr Ser Thr Val Asn Lys Lys Trp Thr Trp Arg
                165                 170                 175

Lys Ser Ser Gly Asn Glu Glu Gly Leu Gln Lys Glu Tyr Ala Asn Thr
            180                 185                 190

Ile Gly Leu Pro Pro Arg Thr Gln Ser Leu Cys Leu Val Cys Leu His
        195                 200                 205

Glu Lys Glu Gly Lys Thr Lys His Lys Thr Ile Ser Thr Asn Ser Glu
```

```
              210                 215                 220
Leu Leu Lys Glu Trp Ile Ile Ala Ala Phe His Glu Gly Lys Asn Leu
225                 230                 235                 240

Lys Thr Ser His Glu Lys Lys Asn Asp Asp Asn Gly Lys Lys Leu Cys
                245                 250                 255

Lys Ala Leu Glu Tyr Ser Phe Ala Asp Tyr Gly Asp Leu Ile Lys Gly
                260                 265                 270

Thr Ser Ile Trp Asp Asn Glu Tyr Thr Lys Asp Leu Glu Leu Asn Leu
                275                 280                 285

Gln Lys Ala Phe Gly Lys Leu Phe Arg Lys Tyr Ile Lys Lys Asn Asn
    290                 295                 300

Thr Ala Glu Gln Asp Thr Ser Tyr Ser Ser Leu Asp Glu Leu Arg Glu
305                 310                 315                 320

Ser Trp Trp Asn Thr Asn Lys Lys Tyr Ile Trp Thr Ala Met Lys His
                325                 330                 335

Gly Ala Glu Met Asn Gly Thr Thr Cys Ser Ser Gly Ser Gly Asp Asn
                340                 345                 350

Gly Asp Ser Ser Ile Thr Gly Ser Ser Asp Ser Gly Ser Thr Thr Cys
                355                 360                 365

Ser Gly Asp Asn Gly Ser Ile Ser Cys Asp Asp Ile Pro Thr Thr Asp
                370                 375                 380

Phe Ile Pro Gln Tyr Leu Arg Phe Leu Gln Glu Trp Val Glu His Phe
385                 390                 395                 400

Cys Glu Gln Arg Gln Ala Lys Val Lys Asp Val Ile Asn Ser Cys Asn
                405                 410                 415

Ser Cys Asn Glu Ser Gly Gly Thr Cys Asn Gly Glu Cys Lys Thr Lys
                420                 425                 430

Cys Lys Asp Glu Cys Glu Lys Tyr Lys Lys Phe Ile Glu Asp Cys Asn
                435                 440                 445

Gly Gly Asp Gly Thr Ala Gly Ser Ser Trp Val Lys Arg Trp Asp Gln
                450                 455                 460

Ile Tyr Lys Arg Tyr Ser Lys His Ile Glu Asp Ala Lys Arg Asn Arg
465                 470                 475                 480

Lys Ala Gly Thr Lys Asn Cys Gly Pro Ser Ser Ile Thr Asn Ala Ala
                485                 490                 495

Ala Ser Thr Asp Glu Asn Lys Cys Val Gln Ser Asp Val Asp Ser Phe
                500                 505                 510

Phe Lys His Leu Ile Asp Ile Gly Leu Thr Thr Pro Ser Ser Tyr Leu
                515                 520                 525

Ser Ile Val Leu Asp Glu Asn Ser Cys Gly Asp Asp Lys Ala Pro Trp
530                 535                 540

Thr Thr Tyr Thr Thr Tyr Thr Thr Glu Lys Cys Asn Lys Glu Arg
545                 550                 555                 560

Asp Lys Ser Lys Ser Gln Ser Ser Asp Thr Leu Val Val Asn Val
                565                 570                 575

Pro Ser Pro Leu Gly Asn Thr Pro His Glu Tyr Lys Tyr Ala Cys Glu
                580                 585                 590

Cys Lys Ile Pro Thr Asn Glu Glu Thr Cys Asp Asp Arg Lys Asp Tyr
                595                 600                 605

Met Asn Gln Trp Ile Ser Asp Thr Ser Lys Lys Gln Lys Gly Ser Gly
                610                 615                 620

Ser Gly Lys Asp Tyr Tyr Glu Leu Tyr Thr Tyr Asn Gly Val Gln Ile
625                 630                 635                 640
```

Lys Gln Ala Ala Gly Arg Ser Ser Thr Lys Leu Asp
              645                 650

<210> SEQ ID NO 46
<211> LENGTH: 490
<212> TYPE: PRT
<213> ORGANISM: Plasmodium falciparum

<400> SEQUENCE: 46

Lys Cys Asp Lys Cys Lys Ser Glu Gln Ser Lys Lys Asn Asn Asn Lys
1               5                   10                  15

Trp Ile Trp Lys Lys Tyr Ser Gly Asn Gly Glu Gly Leu Gln Lys Glu
            20                  25                  30

Tyr Ala Asn Thr Ile Gly Leu Pro Pro Arg Thr Gln Ser Leu Cys Leu
        35                  40                  45

Val Cys Leu His Glu Lys Glu Gly Lys Thr Gln His Lys Thr Ile Ser
    50                  55                  60

Thr Asn Ser Glu Leu Leu Lys Glu Trp Ile Ile Ala Ala Phe His Glu
65                  70                  75                  80

Gly Lys Asn Leu Lys Lys Arg Tyr Pro Gln Asn Lys Asn Asp Asp Asn
                85                  90                  95

Asn Ser Lys Leu Cys Lys Ala Leu Glu Tyr Ser Phe Ala Asp Tyr Gly
            100                 105                 110

Asp Leu Ile Lys Gly Thr Ser Ile Trp Asp Asn Glu Tyr Thr Lys Asp
        115                 120                 125

Leu Glu Leu Asn Leu Gln Lys Ala Phe Gly Lys Leu Phe Arg Lys Tyr
130                 135                 140

Ile Lys Lys Asn Asn Thr Ala Glu Gln Asp Thr Ser Tyr Ser Ser Leu
145                 150                 155                 160

Asp Glu Leu Arg Glu Ser Trp Trp Asn Thr Asn Lys Lys Tyr Ile Trp
                165                 170                 175

Thr Ala Met Lys His Gly Ala Glu Met Asn Gly Thr Thr Cys Ser Ser
            180                 185                 190

Gly Ser Gly Asp Asn Gly Asp Ser Ser Cys Asp Asp Ile Pro Thr Ile
        195                 200                 205

Asp Leu Ile Pro Gln Tyr Leu Arg Phe Leu Gln Glu Trp Val Glu His
210                 215                 220

Phe Cys Lys Gln Arg Gln Ala Lys Val Lys Asp Val Ile Asn Ser Cys
225                 230                 235                 240

Asn Ser Cys Lys Asn Thr Ser Gly Glu Arg Lys Ile Gly Gly Thr Cys
                245                 250                 255

Asn Ser Asp Cys Glu Lys Lys Cys Lys Val Ala Cys Asp Ala Tyr Lys
            260                 265                 270

Thr Phe Ile Glu Glu Cys Arg Thr Ala Val Gly Gly Thr Ala Gly Ser
        275                 280                 285

Ser Trp Val Lys Arg Trp Asp Gln Ile Tyr Lys Arg Tyr Ser Lys His
    290                 295                 300

Ile Glu Asp Ala Lys Arg Asn Arg Lys Ala Gly Thr Lys Asn Cys Gly
305                 310                 315                 320

Pro Ser Ser Thr Thr Asn Ala Ala Glu Asn Lys Cys Val Gln Ser Asp
                325                 330                 335

Ile Asp Ser Phe Phe Lys His Leu Ile Asp Ile Gly Leu Thr Thr Pro
            340                 345                 350

Ser Ser Tyr Leu Ser Asn Val Leu Asp Glu Asn Ser Cys Gly Ala Asp

```
                355                 360                 365
Lys Ala Pro Trp Thr Thr Tyr Thr Thr Tyr Thr Thr Tyr Thr Thr Tyr
370                 375                 380

Thr Thr Tyr Thr Thr Thr Glu Lys Cys Asn Lys Glu Arg Asp Lys Ser
385                 390                 395                 400

Lys Ser Gln Gln Ser Asn Thr Ser Val Val Asn Val Pro Ser Pro
                405                 410                 415

Leu Gly Asn Thr Pro His Glu Tyr Lys Tyr Ala Cys Glu Cys Lys Ile
                420                 425                 430

Pro Thr Thr Glu Glu Thr Cys Asp Asp Arg Lys Glu Tyr Met Asn Gln
                435                 440                 445

Trp Ile Ile Asp Asn Thr Lys Asn Pro Lys Gly Ser Gly Ser Thr Asp
                450                 455                 460

Asn Asp Tyr Glu Leu Tyr Thr Tyr Asn Gly Val Gln Ile Lys Gln Ala
465                 470                 475                 480

Ala Gly Arg Ser Ser Ser Thr Lys Leu Asp
                485                 490

<210> SEQ ID NO 47
<211> LENGTH: 335
<212> TYPE: PRT
<213> ORGANISM: Plasmodium falciparum

<400> SEQUENCE: 47

Lys Cys Glu Lys Cys Lys Ser Gly Thr Ser Thr Val Asn Asn Lys Trp
1               5                   10                  15

Ile Trp Arg Lys Ser Ser Gly Lys Glu Gly Gly Leu Gln Lys Glu Tyr
                20                  25                  30

Ala Asn Thr Ile Gly Leu Pro Pro Arg Thr Gln Ser Leu Tyr Leu Gly
                35                  40                  45

Asn Leu Pro Lys Leu Glu Asn Val Cys Lys Gly Val Thr Asp Ile Ile
                50                  55                  60

Tyr Asp Thr Lys Glu Lys Phe Leu Ser Gly Cys Leu Ile Ala Ala Phe
65              70                  75                  80

His Glu Gly Lys Asn Leu Lys Thr Thr Tyr Leu Glu Lys Lys Asn Asp
                85                  90                  95

Asp Asn Gly Lys Lys Leu Cys Lys Ala Leu Glu Tyr Ser Phe Ala Asp
                100                 105                 110

Tyr Gly Asp Leu Ile Lys Gly Thr Ser Ile Trp Asp Asn Glu Tyr Thr
                115                 120                 125

Lys Asp Leu Glu Leu Asn Leu Gln Lys Ile Phe Gly Lys Leu Phe Arg
                130                 135                 140

Lys Tyr Ile Lys Lys Asn Asn Thr Ala Glu Gln Asp Thr Ser Tyr Ser
145                 150                 155                 160

Ser Leu Asp Glu Leu Arg Glu Ser Trp Trp Asn Thr Asn Lys Lys Tyr
                165                 170                 175

Ile Trp Ile Ala Met Lys His Gly Ala Gly Met Asn Gly Thr Thr Cys
                180                 185                 190

Ser Ser Gly Ser Gly Asp Ser Ser Asn Asp Ile Pro Thr Thr Asp Phe
                195                 200                 205

Ile Pro Gln Tyr Leu Arg Phe Leu Gln Glu Trp Val Glu Asn Phe Cys
                210                 215                 220

Glu Gln Arg Gln Ala Lys Val Lys Pro Val Ile Glu Asn Cys Asn Ser
225                 230                 235                 240
```

Cys Lys Glu Ser Gly Gly Thr Cys Asn Gly Glu Cys Lys Thr Lys Cys
                245                 250                 255

Lys Val Ala Cys Asp Ala Tyr Lys Phe Ile Asp Gly Thr Gly Ser
            260                 265                 270

Gly Gly Gly Ser Arg Pro Thr Gly Ile Ala Gly Ser Ser Trp Ser Lys
            275                 280                 285

Arg Trp Asp Gln Ile Tyr Lys Arg Tyr Ser Lys His Ile Glu Asp Ala
        290                 295                 300

Lys Arg Asn Arg Lys Ala Gly Thr Lys Asn Cys Gly Pro Ser Ser Ile
305                 310                 315                 320

Thr Asn Val Ser Val Ser Thr Asp Glu Asn Lys Cys Val Gln Ser
                325                 330                 335

<210> SEQ ID NO 48
<211> LENGTH: 637
<212> TYPE: PRT
<213> ORGANISM: Artificial Sequence
<220> FEATURE:
<223> OTHER INFORMATION: T2C6 745 amino acids

<400> SEQUENCE: 48

Asn Tyr Ile Lys Asp Asp Pro Tyr Ser Lys Glu Tyr Val Thr Lys Leu
1               5                   10                  15

Ser Phe Ile Pro Asn Ser Ser Asp Ala Asn Thr Ser Ser Glu Lys Ile
            20                  25                  30

Gln Lys Asn Asn Asp Glu Val Cys Asn Pro Asn Glu Ser Gly Ile Ser
        35                  40                  45

Ser Val Glu Gln Ala Gln Thr Ser Asp Pro Ser Ser Asn Lys Thr Cys
    50                  55                  60

Ile Thr His Ser Ser Ile Lys Ala Asn Lys Lys Glu Cys Lys Asp
65                  70                  75                  80

Val Lys Leu Gly Val Arg Glu Asn Asp Lys Asp Leu Lys Ile Cys Val
                85                  90                  95

Ile Glu His Thr Ser Leu Ser Gly Val Asp Asn Cys Cys Phe Lys Asp
            100                 105                 110

Phe Leu Arg Met Leu Gln Glu Pro Arg Ile Asp Lys Asn Gln Arg Gly
        115                 120                 125

Ser Ser Ser Asn Gly Ser Cys Asp Lys Asn Ser Glu Glu Ala Cys Glu
    130                 135                 140

Lys Asn Leu Asp Glu Ala Leu Ala Ser Leu Thr Asn Gly Tyr Lys Cys
145                 150                 155                 160

Asp Lys Cys Lys Ser Glu Gln Ser Lys Lys Asn Asn Lys Trp Ile
                165                 170                 175

Trp Lys Lys Phe Pro Gly Lys Glu Gly Gly Leu Gln Glu Glu Tyr Ala
            180                 185                 190

Asn Thr Ile Gly Leu Pro Pro Arg Thr Gln Tyr Leu Cys Leu Val Val
        195                 200                 205

Cys Leu Asp Glu Lys Glu Gly Lys Thr Gln Glu Leu Lys Asn Ile Arg
    210                 215                 220

Thr Asn Ser Glu Leu Leu Lys Glu Trp Ile Ile Ala Ala Phe His Glu
225                 230                 235                 240

Gly Lys Asn Leu Lys Thr Thr Tyr Pro Gln Lys Lys Asn Asp Asn
                245                 250                 255

Gly Lys Lys Leu Cys Lys Asp Leu Lys Tyr Ser Phe Ala Asp Tyr Gly
            260                 265                 270

```
Asp Leu Ile Lys Gly Thr Ser Ile Trp Asp Asn Glu Tyr Thr Lys Asn
        275                 280                 285

Val Glu Leu Asn Leu Gln Asn Asn Phe Gly Lys Leu Phe Arg Lys Tyr
    290                 295                 300

Ile Lys Lys Asn Asn Thr Ala Glu Gln Asp Thr Ser Tyr Ser Ser Leu
305                 310                 315                 320

Asp Glu Leu Arg Glu Ser Trp Trp Asn Thr Asn Lys Lys Tyr Ile Trp
                325                 330                 335

Leu Ala Met Lys His Gly Ala Glu Met Asn Ser Thr Thr Cys Cys Gly
            340                 345                 350

Asp Gly Ser Val Thr Gly Ser Gly Ser Ser Cys Asp Asp Ile Pro Thr
        355                 360                 365

Ile Asp Leu Ile Pro Gln Tyr Leu Arg Phe Leu Gln Glu Trp Val Glu
370                 375                 380

His Phe Cys Lys Gln Arg Gln Ala Lys Val Lys Asp Val Ile Thr Asn
385                 390                 395                 400

Cys Asn Ser Cys Lys Glu Ser Gly Asn Lys Cys Lys Thr Glu Cys Lys
                405                 410                 415

Asn Lys Cys Lys Asp Glu Cys Glu Lys Tyr Lys Lys Phe Ile Glu Ala
                420                 425                 430

Cys Gly Thr Ala Val Gly Gly Thr Gly Thr Ala Gly Ser Pro Trp Ser
            435                 440                 445

Lys Arg Trp Asp Gln Ile Tyr Lys Arg Tyr Ser Lys His Ile Glu Asp
    450                 455                 460

Ala Lys Arg Asn Arg Lys Ala Gly Thr Lys Asn Cys Gly Pro Ser Ser
465                 470                 475                 480

Thr Thr Asn Ala Ala Glu Asn Lys Cys Val Gln Ser Asp Ile Asp Ser
                485                 490                 495

Phe Phe Lys His Leu Ile Asp Ile Gly Leu Thr Thr Pro Ser Ser Tyr
                500                 505                 510

Leu Ser Ile Val Leu Asp Asp Asn Ile Cys Gly Ala Asp Lys Ala Pro
            515                 520                 525

Trp Thr Thr Tyr Thr Thr Tyr Thr Thr Glu Asn Cys Asp Ile Gln Lys
    530                 535                 540

Lys Thr Pro Lys Ser Gln Ser Cys Asp Thr Leu Val Val Asn Val
545                 550                 555                 560

Pro Ser Pro Leu Gly Asn Thr Pro His Gly Tyr Lys Tyr Ala Cys Gln
                565                 570                 575

Cys Arg Thr Pro Asn Lys Gln Glu Ser Cys Asp Asp Arg Lys Glu Tyr
                580                 585                 590

Met Asn Gln Trp Ile Ile Asp Asn Thr Lys Asn Pro Lys Gly Ser Gly
                595                 600                 605

Ser Gly Lys Asp Tyr Tyr Glu Leu Cys Lys Tyr Asn Gly Val Lys Glu
        610                 615                 620

Thr Lys Pro Leu Gly Thr Leu Lys Asn Ser Lys Leu Asp
625                 630                 635

<210> SEQ ID NO 49
<211> LENGTH: 330
<212> TYPE: PRT
<213> ORGANISM: Plasmodium falciparum

<400> SEQUENCE: 49

Lys Cys Asp Lys Cys Lys Ser Glu Gln Ser Lys Lys Asn Asn Asn Lys
1               5                   10                  15
```

Trp Ile Trp Arg Lys Phe Pro Gly Lys Glu Gly Gly Leu Gln Lys Glu
            20                  25                  30

Tyr Ala Asn Thr Ile Gly Leu Pro Pro Arg Thr Gln Ser Leu Cys Leu
        35                  40                  45

Val Cys Leu His Glu Lys Glu Gly Lys Thr Gln His Lys Thr Ile Ser
 50                  55                  60

Thr Asn Ser Glu Leu Leu Lys Glu Trp Ile Ile Ala Ala Phe His Glu
 65                  70                  75                  80

Gly Lys Asn Leu Lys Thr Thr Tyr Leu Glu Lys Lys Asn Ala Glu Asn
                85                  90                  95

Lys Lys Lys Leu Cys Lys Ala Leu Lys Tyr Ser Phe Ala Asp Tyr Gly
            100                 105                 110

Asp Leu Ile Lys Gly Thr Ser Ile Trp Asp Asn Glu Tyr Thr Lys Asp
        115                 120                 125

Leu Glu Leu Asn Leu Gln Lys Ile Phe Gly Lys Leu Phe Arg Lys Tyr
130                 135                 140

Ile Lys Lys Asn Asn Thr Ala Glu Gln Asp Thr Ser Tyr Ser Ser Leu
145                 150                 155                 160

Asp Glu Leu Arg Glu Ser Trp Trp Asn Thr Asn Lys Lys Tyr Ile Trp
                165                 170                 175

Thr Ala Met Lys His Gly Ala Gly Met Asn Gly Thr Met Cys Asn Ala
            180                 185                 190

Asp Gly Ser Val Thr Gly Ser Gly Ser Ser Cys Asp Asp Met Pro Thr
        195                 200                 205

Thr Asp Phe Ile Pro Gln Tyr Leu Arg Phe Leu Gln Glu Trp Val Glu
210                 215                 220

His Phe Cys Lys Gln Arg Gln Ala Lys Val Lys Asp Val Ile Glu Asn
225                 230                 235                 240

Cys Lys Ser Cys Lys Glu Ser Gly Asn Lys Cys Lys Thr Glu Cys Lys
                245                 250                 255

Asn Lys Cys Asp Ala Tyr Lys Thr Phe Ile Glu Glu Cys Gly Thr Ala
            260                 265                 270

Val Gly Gly Thr Ala Gly Ser Ser Trp Val Lys Arg Trp Asp Gln Ile
        275                 280                 285

Tyr Lys Arg Tyr Ser Lys His Ile Glu Asp Ala Lys Arg Asn Arg Lys
290                 295                 300

Ala Gly Thr Lys Asn Cys Gly Thr Ser Ser Thr Thr Asn Ala Ala Ala
305                 310                 315                 320

Ser Thr Ala Glu Asn Lys Cys Val Gln Ser
                325                 330

<210> SEQ ID NO 50
<211> LENGTH: 269
<212> TYPE: PRT
<213> ORGANISM: Plasmodium falciparum

<400> SEQUENCE: 50

Asn Tyr Ile Lys Asp Asp Pro Tyr Ser Lys Glu Tyr Val Thr Lys Leu
1               5                   10                  15

Ser Phe Ile Leu Asn Ser Ser Asp Ala Glu Asn Ala Ser Glu Thr Pro
            20                  25                  30

Ser Lys Tyr Tyr Asp Glu Ala Cys Asn Cys Asn Glu Ser Gly Ile Ser
        35                  40                  45

Ser Val Glu Gln Ala Ser Ile Ser Asp Arg Ser Ser Gln Lys Ala Cys

```
Asn Thr His Ser Phe Ile Gly Ala Asn Lys Lys Val Cys Lys His
65                  70                  75                  80

Val Lys Leu Gly Val Arg Glu Asn Asp Lys Asp Leu Lys Ile Cys Val
                85                  90                  95

Ile Glu Asp Asp Ser Leu Arg Gly Val Glu Asn Cys Cys Phe Lys Asp
            100                 105                 110

Phe Leu Arg Met Leu Gln Glu Pro Arg Ile Asp Lys Asn Gln Arg Gly
        115                 120                 125

Ser Ser Ser Asn Asp Ser Cys Asn Asn Asn Glu Glu Ala Cys Glu
    130                 135                 140

Lys Asn Leu Asp Glu Ala Leu Ala Ser Leu His Asn Gly Tyr Lys Asn
145                 150                 155                 160

Gln Lys Cys Lys Ser Glu Gln Ser Lys Lys Asn Asn Lys Trp Ile
                165                 170                 175

Trp Lys Lys Ser Ser Gly Lys Glu Gly Gly Leu Gln Lys Glu Tyr Ala
                180                 185                 190

Asn Thr Ile Gly Leu Pro Pro Arg Thr Gln Ser Leu Cys Leu Val Cys
                195                 200                 205

Leu His Glu Lys Glu Gly Lys Thr Gln His Lys Thr Ile Ser Thr Asn
    210                 215                 220

Ser Glu Leu Leu Lys Glu Trp Ile Ile Asp Ala Phe His Glu Gly Lys
225                 230                 235                 240

Asn Leu Lys Thr Thr Tyr Leu Glu Lys Lys Gly Asp Asn Gly Lys
                245                 250                 255

Lys Leu Cys Lys Ala Leu Lys Tyr Ser Phe Ala Asp Tyr
                260                 265

<210> SEQ ID NO 51
<211> LENGTH: 347
<212> TYPE: PRT
<213> ORGANISM: Plasmodium falciparum

<400> SEQUENCE: 51

Lys Cys Asp Lys Cys Lys Ser Glu Gln Ser Lys Asn Asn Lys Asn
1               5                   10                  15

Trp Ile Trp Lys Lys Ser Ser Gly Lys Glu Gly Gly Leu Gln Lys Glu
                20                  25                  30

Tyr Ala Asn Thr Ile Ala Leu Pro Pro Arg Thr Gln Ser Leu Cys Leu
            35                  40                  45

Val Val Cys Leu His Glu Lys Glu Gly Lys Thr Gln His Lys Thr Ile
    50                  55                  60

Ser Thr Asn Ser Glu Leu Leu Lys Glu Trp Ile Ile Asp Ala Phe His
65                  70                  75                  80

Glu Gly Lys Asn Leu Lys Thr Thr Tyr Leu Glu Lys Gln Asn Ala Asp
                85                  90                  95

Asn Gly Lys Lys Asn Ala Asp Asn Ser Lys Leu Cys Lys Asp Leu
            100                 105                 110

Lys Tyr Ser Phe Ala Asp Tyr Gly Asp Leu Ile Lys Gly Thr Ser Ile
        115                 120                 125

Trp Asp Asn Glu Tyr Thr Lys Asp Leu Glu Leu Asn Leu Gln Gln Ile
        130                 135                 140

Phe Gly Lys Leu Phe Arg Lys Tyr Ile Lys Lys Asn Ile Ala Ser Asp
145                 150                 155                 160
```

```
Glu Asn Thr Leu Tyr Ser Ser Leu Asp Glu Leu Arg Glu Ser Trp Trp
                165                 170                 175

Asn Thr Asn Lys Lys Tyr Ile Trp Thr Ala Met Lys His Gly Ala Glu
        180                 185                 190

Met Asn Gly Thr Thr Cys Ser Ser Gly Ser Gly Asp Ser Ser Ser Gly
        195                 200                 205

Glu Asn Gln Thr Asn Ser Cys Asp Asp Ile Pro Thr Ile Asp Leu Ile
        210                 215                 220

Pro Gln Tyr Leu Arg Phe Leu Gln Glu Trp Val Glu His Phe Cys Glu
225                 230                 235                 240

Gln Arg Gln Ala Lys Val Lys Asp Val Ile Thr Asn Cys Lys Ser Cys
                245                 250                 255

Lys Glu Ser Gly Gly Thr Cys Asn Ser Asp Cys Lys Thr Lys Cys Lys
                260                 265                 270

Gly Glu Cys Glu Lys Tyr Lys Lys Phe Ile Glu Lys Cys Lys Gly Gly
                275                 280                 285

Gly Thr Glu Gly Thr Ser Gly Ser Ser Trp Val Lys Arg Trp Tyr Gln
        290                 295                 300

Ile Tyr Met Arg Tyr Ser Lys Tyr Ile Glu Asp Ala Lys Arg Asn Arg
305                 310                 315                 320

Lys Ala Gly Thr Lys Ser Cys Gly Thr Ser Ser Gly Ala Asn Ser Gly
                325                 330                 335

Val Thr Thr Thr Glu Ser Lys Cys Val Gln Ser
                340                 345

<210> SEQ ID NO 52
<211> LENGTH: 269
<212> TYPE: PRT
<213> ORGANISM: Plasmodium falciparum

<400> SEQUENCE: 52

Asp Tyr Ile Lys Asp Asp Pro Tyr Ser Lys Glu Tyr Thr Thr Lys Leu
1               5                   10                  15

Ser Phe Ile Leu Asn Ser Ser Asp Ala Asn Thr Ser Ser Glu Lys Ile
                20                  25                  30

Gln Lys Asn Asn Asp Glu Val Cys Asn Pro Asn Glu Ser Glu Ile Ser
            35                  40                  45

Ser Val Glu Gln Ala Gln Thr Ser Arg Pro Ser Ser Asn Lys Thr Cys
    50                  55                  60

Ile Thr His Ser Ser Ile Lys Ala Asn Lys Lys Val Cys Lys Asp
65                  70                  75                  80

Val Lys Leu Gly Val Arg Glu Asn Asp Lys Val Leu Arg Val Cys Val
                85                  90                  95

Ile Glu His Thr Ser Leu Ser Gly Val Glu Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Gly Ser Cys Asp Lys Asn Ser Glu Glu Ala Cys Glu Lys
    130                 135                 140

Asn Leu Asp Glu Ala Leu Ala Ser Leu Thr Asn Cys Tyr Lys Asn Gln
145                 150                 155                 160

Lys Cys Lys Ser Glu Gln Ser Lys Lys Asn Asn Lys Trp Ile Trp
                165                 170                 175

Lys Lys Ser Ser Gly Asn Glu Lys Gly Leu Gln Lys Glu Tyr Ala Asn
            180                 185                 190
```

```
Thr Ile Gly Leu Pro Pro Arg Thr Gln Ser Leu Cys Leu Val Cys Leu
            195                 200                 205

His Glu Lys Glu Gly Lys Thr Gln Glu Leu Lys Asn Ile Ser Thr Asn
210                 215                 220

Ser Glu Leu Leu Lys Glu Trp Ile Ile Ala Ala Phe His Glu Gly Lys
225                 230                 235                 240

Asn Leu Lys Thr Thr Tyr Pro Gln Asn Lys Asn Asp Asp Asn Gly Lys
            245                 250                 255

Lys Leu Phe Lys Asp Leu Lys Tyr Ser Phe Ala Asp Tyr
            260                 265

<210> SEQ ID NO 53
<211> LENGTH: 646
<212> TYPE: PRT
<213> ORGANISM: Artificial Sequence
<220> FEATURE:
<223> OTHER INFORMATION: MTS1 745 amino acids

<400> SEQUENCE: 53

Asp Tyr Ile Lys Asp Asp Pro Tyr Ser Lys Glu Tyr Thr Thr Lys Leu
1               5                   10                  15

Ser Phe Ile Leu Asn Ser Ser Asp Ala Asn Thr Ser Ser Glu Lys Ile
                20                  25                  30

Gln Lys Asn Asn Asp Glu Val Cys Asn Pro Asn Glu Ser Glu Ile Ser
            35                  40                  45

Ser Val Glu Gln Ala Gln Thr Ser Arg Pro Ser Ser Asn Lys Thr Cys
50                  55                  60

Ile Thr His Ser Ser Ile Lys Ala Asn Lys Lys Val Cys Lys Asp
65                  70                  75                  80

Val Lys Leu Gly Val Arg Glu Asn Asp Lys Val Leu Arg Val Cys Val
                85                  90                  95

Ile Glu His Thr Ser Leu Ser Gly Val Glu Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Gly Ser Cys Asp Lys Asn Ser Glu Glu Ala Cys Glu Lys
130                 135                 140

Asn Leu Asp Glu Ala Leu Ala Ser Leu Thr Asn Cys Tyr Lys Asn Gln
145                 150                 155                 160

Lys Cys Lys Ser Glu Gln Ser Lys Lys Asn Asn Asn Lys Trp Ile Trp
                165                 170                 175

Lys Lys Ser Ser Gly Lys Glu Gly Gly Leu Gln Lys Glu Tyr Ala Asn
            180                 185                 190

Thr Ile Gly Leu Pro Pro Arg Thr Gln Ser Leu Tyr Leu Gly Asn Leu
        195                 200                 205

Pro Lys Leu Glu Asn Val Cys Lys Gly Val Thr Asp Ile Asn Phe Asp
210                 215                 220

Thr Lys Glu Lys Phe Leu Ala Gly Cys Leu Ile Ala Ala Phe His Glu
225                 230                 235                 240

Gly Lys Asn Leu Lys Thr Thr Tyr Leu Glu Lys Asn Asp Asp Asn
                245                 250                 255

Gly Lys Lys Leu Cys Lys Ala Leu Glu Tyr Ser Phe Ala Asp Tyr Gly
            260                 265                 270

Asp Leu Ile Lys Gly Thr Ser Ile Trp Asp Asn Glu Tyr Thr Lys Asp
        275                 280                 285
```

Leu Glu Leu Asn Leu Gln Lys Ala Phe Gly Lys Leu Phe Arg Lys Tyr
            290                 295                 300

Ile Lys Lys Asn Asn Thr Ala Glu Gln Asp Thr Ser Tyr Ser Ser Leu
305                 310                 315                 320

Asp Glu Leu Arg Glu Ser Trp Trp Asn Thr Asn Lys Lys Tyr Ile Trp
                325                 330                 335

Thr Ala Met Lys His Gly Ala Gly Met Asn Gly Thr Thr Cys Ser Ser
            340                 345                 350

Gly Ser Gly Asp Ser Ser Asn Asp Ile Pro Thr Thr Asp Phe Ile Pro
                355                 360                 365

Gln Tyr Leu Arg Phe Leu Gln Glu Trp Val Glu Asn Phe Cys Glu Gln
370                 375                 380

Arg Gln Ala Lys Val Lys Asp Val Ile Glu Asn Cys Asn Ser Cys Lys
385                 390                 395                 400

Asn Thr Ser Gly Glu Arg Lys Ile Gly Asp Thr Cys Asn Ser Asp Cys
                405                 410                 415

Glu Lys Lys Cys Lys Asp Glu Cys Glu Lys Tyr Lys Lys Phe Ile Glu
                420                 425                 430

Asp Cys Lys Gly Asp Gly Thr Ala Gly Ser Ser Trp Val Lys Arg
            435                 440                 445

Trp Asp Gln Ile Tyr Lys Arg Tyr Ser Lys His Ile Glu Asp Ala Lys
450                 455                 460

Arg Asn Arg Lys Ala Gly Thr Lys Asn Cys Gly Ile Thr Thr Gly Thr
465                 470                 475                 480

Ile Ser Gly Glu Ser Ser Gly Ala Thr Ser Gly Val Thr Thr Thr Glu
                485                 490                 495

Asn Lys Cys Val Gln Ser Asp Ile Asp Ser Phe Phe Lys His Leu Ile
            500                 505                 510

Asp Ile Gly Leu Thr Thr Pro Ser Ser Tyr Leu Ser Asn Val Leu Asp
            515                 520                 525

Asp Asn Ile Cys Gly Glu Asp Asn Ala Pro Trp Thr Thr Tyr Thr Thr
530                 535                 540

Tyr Thr Thr Glu Lys Cys Asn Lys Glu Thr Asp Lys Ser Lys Ser Gln
545                 550                 555                 560

Gln Ser Asn Thr Ala Val Val Val Asn Val Pro Ser Pro Leu Gly Asn
                565                 570                 575

Thr Pro His Gly Tyr Lys Tyr Ala Cys Glu Cys Lys Ile Pro Thr Thr
            580                 585                 590

Glu Glu Thr Cys Asp Asp Arg Lys Glu Tyr Met Asn Gln Trp Ser Cys
                595                 600                 605

Gly Ser Ala Gln Thr Val Arg Asp Arg Ser Gly Lys Asp Asp Tyr Glu
610                 615                 620

Leu Cys Lys Tyr Asn Gly Val Gln Ile Lys Gln Ala Ala Gly Thr Leu
625                 630                 635                 640

Lys Asn Ser Lys Leu Asp
            645

<210> SEQ ID NO 54
<211> LENGTH: 632
<212> TYPE: PRT
<213> ORGANISM: Plasmodium falciparum

<400> SEQUENCE: 54

Asn Tyr Ile Lys Gly Asp Pro Tyr Phe Ala Glu Tyr Ala Thr Lys Leu

-continued

```
1               5                   10                  15
Ser Phe Ile Leu Asn Ser Ser Asp Ala Asn Pro Ser Glu Lys Ile
                20                  25                  30
Gln Lys Asn Asn Asp Glu Val Cys Asn Cys Asn Glu Ser Gly Ile Ala
                35                  40                  45
Ser Val Glu Gln Glu Gln Ile Ser Asp Pro Ser Ser Asn Lys Thr Cys
    50                  55                  60
Ile Thr His Ser Ser Ile Lys Ala Asn Lys Lys Val Cys Lys His
65                  70                  75                  80
Val Lys Leu Gly Val Arg Glu Asn Asp Lys Asp Leu Arg Val Cys Val
                85                  90                  95
Ile Glu His Thr Ser Leu Ser Gly Val Glu Asn Cys Cys Gln Asp
                100                 105                 110
Phe Leu Arg Ile Leu Gln Glu Asn Cys Ser Asp Asn Lys Ser Gly Ser
                115                 120                 125
Ser Ser Asn Gly Ser Cys Asn Asn Lys Asn Gln Glu Ala Cys Glu Lys
    130                 135                 140
Asn Leu Glu Lys Val Leu Ala Ser Leu Thr Asn Cys Tyr Lys Cys Asp
145                 150                 155                 160
Lys Cys Lys Ser Glu Gln Ser Lys Asn Asn Lys Asn Trp Ile Trp
                165                 170                 175
Lys Lys Ser Ser Gly Lys Glu Gly Leu Gln Lys Glu Tyr Ala Asn
                180                 185                 190
Thr Ile Gly Leu Pro Pro Arg Thr Gln Ser Leu Cys Leu Val Val Cys
                195                 200                 205
Leu Asp Glu Lys Gly Lys Lys Thr Gln Glu Leu Lys Asn Ile Arg Thr
    210                 215                 220
Asn Ser Glu Leu Leu Lys Glu Trp Ile Ile Ala Ala Phe His Glu Gly
225                 230                 235                 240
Lys Asn Leu Lys Pro Ser His Glu Lys Lys Asn Asp Asp Asn Gly Lys
                245                 250                 255
Lys Leu Cys Lys Ala Leu Glu Tyr Ser Phe Ala Asp Tyr Gly Asp Leu
                260                 265                 270
Ile Lys Gly Thr Ser Ile Trp Asp Asn Glu Tyr Thr Lys Asp Leu Glu
                275                 280                 285
Leu Asn Leu Gln Lys Ile Phe Gly Lys Leu Phe Arg Lys Tyr Ile Lys
    290                 295                 300
Lys Asn Asn Thr Ala Glu Gln Asp Thr Ser Tyr Ser Ser Leu Asp Glu
305                 310                 315                 320
Leu Arg Glu Ser Trp Trp Asn Thr Asn Lys Lys Tyr Ile Trp Leu Ala
                325                 330                 335
Met Lys His Gly Ala Gly Met Asn Ser Thr Thr Cys Cys Gly Asp Gly
                340                 345                 350
Ser Val Thr Gly Ser Gly Ser Ser Cys Asp Asp Ile Pro Thr Ile Asp
    355                 360                 365
Leu Ile Pro Gln Tyr Leu Arg Phe Leu Gln Glu Trp Val Glu His Phe
                370                 375                 380
Cys Lys Gln Arg Gln Glu Lys Val Lys Pro Val Ile Glu Asn Cys Lys
385                 390                 395                 400
Ser Cys Lys Glu Ser Gly Gly Thr Cys Asn Gly Glu Cys Lys Thr Glu
                405                 410                 415
Cys Lys Asn Lys Cys Glu Val Tyr Lys Lys Phe Ile Glu Asp Cys Lys
                420                 425                 430
```

```
Gly Gly Asp Gly Thr Ala Gly Ser Ser Trp Val Lys Arg Trp Asp Gln
            435                 440                 445

Ile Tyr Lys Arg Tyr Ser Lys Tyr Ile Glu Asp Ala Lys Arg Asn Arg
    450                 455                 460

Lys Ala Gly Thr Lys Asn Cys Gly Pro Ser Ser Thr Thr Asn Ala Ala
465                 470                 475                 480

Glu Asn Lys Cys Val Gln Ser Asp Ile Asp Ser Phe Phe Lys His Leu
                485                 490                 495

Ile Asp Ile Gly Leu Thr Thr Pro Ser Ser Tyr Leu Ser Ile Val Leu
            500                 505                 510

Asp Asp Asn Ile Cys Gly Ala Asp Lys Ala Pro Trp Thr Thr Tyr Thr
        515                 520                 525

Thr Tyr Thr Thr Thr Glu Lys Cys Asn Lys Glu Thr Asp Lys Ser Lys
    530                 535                 540

Leu Gln Gln Cys Asn Thr Ala Val Val Val Asn Val Pro Ser Pro Leu
545                 550                 555                 560

Gly Asn Thr Pro His Gly Tyr Lys Tyr Ala Cys Gln Cys Lys Ile Pro
                565                 570                 575

Thr Asn Glu Glu Thr Cys Asp Asp Arg Lys Glu Tyr Met Asn Gln Trp
            580                 585                 590

Ser Cys Gly Ser Ala Arg Thr Met Lys Arg Gly Tyr Lys Asn Asp Asn
        595                 600                 605

Tyr Glu Leu Cys Lys Tyr Asn Gly Val Asp Val Lys Pro Thr Thr Val
    610                 615                 620

Arg Ser Asn Ser Ser Lys Leu Asp
625                 630

<210> SEQ ID NO 55
<211> LENGTH: 2730
<212> TYPE: PRT
<213> ORGANISM: Plasmodium falciparum

<400> SEQUENCE: 55

Met Asp Lys Ser Ser Ile Ala Asn Lys Ile Glu Ala Tyr Leu Gly Ala
1               5                   10                  15

Lys Ser Asp Asp Ser Lys Ile Asp Gln Ser Leu Lys Ala Asp Pro Ser
            20                  25                  30

Glu Val Gln Tyr Tyr Gly Ser Gly Asp Gly Tyr Tyr Leu Arg Lys
        35                  40                  45

Asn Ile Cys Lys Ile Thr Val Asn His Ser Asp Ser Gly Thr Asn Asp
50                  55                  60

Pro Cys Asp Arg Ile Pro Pro Tyr Gly Asp Asn Asp Gln Trp Lys
65                  70                  75                  80

Cys Ala Ile Ile Leu Ser Lys Val Ser Glu Lys Pro Glu Asn Val Phe
                85                  90                  95

Val Pro Pro Arg Arg Gln Arg Met Cys Ile Asn Asn Leu Glu Lys Leu
            100                 105                 110

Asn Val Asp Lys Ile Arg Asp Lys His Ala Phe Leu Ala Asp Val Leu
        115                 120                 125

Leu Thr Ala Arg Asn Glu Gly Glu Arg Ile Val Gln Asn His Pro Asp
    130                 135                 140

Thr Asn Ser Ser Asn Val Cys Asn Ala Leu Glu Arg Ser Phe Ala Asp
145                 150                 155                 160

Ile Ala Asp Ile Ile Arg Gly Thr Asp Leu Trp Lys Gly Thr Asn Ser
```

```
                165                 170                 175
Asn Leu Glu Gln Asn Leu Lys Gln Met Phe Ala Lys Ile Arg Glu Asn
                180                 185                 190

Asp Lys Val Leu Gln Asp Lys Tyr Pro Lys Asp Gln Asn Tyr Arg Lys
                195                 200                 205

Leu Arg Glu Asp Trp Trp Asn Ala Asn Arg Gln Lys Val Trp Glu Val
210                 215                 220

Ile Thr Cys Gly Ala Arg Ser Asn Asp Leu Leu Ile Lys Arg Gly Trp
225                 230                 235                 240

Arg Thr Ser Gly Lys Ser Asn Gly Asp Asn Lys Leu Glu Leu Cys Arg
                245                 250                 255

Lys Cys Gly His Tyr Glu Glu Lys Val Pro Thr Lys Leu Asp Tyr Val
                260                 265                 270

Pro Gln Phe Leu Arg Trp Leu Thr Glu Trp Ile Glu Asp Phe Tyr Arg
                275                 280                 285

Glu Lys Gln Asn Leu Ile Asp Asp Met Glu Arg His Arg Glu Glu Cys
                290                 295                 300

Thr Ser Glu Asp His Lys Ser Lys Glu Gly Thr Ser Tyr Cys Ser Thr
305                 310                 315                 320

Cys Lys Asp Lys Cys Lys Lys Tyr Cys Glu Cys Val Lys Lys Trp Lys
                325                 330                 335

Ser Glu Trp Glu Asn Gln Lys Asn Lys Tyr Thr Glu Leu Tyr Gln Gln
                340                 345                 350

Asn Lys Asn Glu Thr Ser Gln Lys Asn Thr Ser Arg Tyr Asp Asp Tyr
                355                 360                 365

Val Lys Asp Phe Phe Lys Lys Leu Glu Ala Asn Tyr Ser Ser Leu Glu
370                 375                 380

Asn Tyr Ile Lys Gly Asp Pro Tyr Phe Ala Glu Tyr Ala Thr Lys Leu
385                 390                 395                 400

Ser Phe Ile Leu Asn Ser Ser Asp Ala Asn Asn Pro Ser Glu Lys Ile
                405                 410                 415

Gln Lys Asn Asn Asp Glu Val Cys Asn Cys Asn Glu Ser Gly Ile Ala
                420                 425                 430

Ser Val Glu Gln Glu Gln Ile Ser Asp Pro Ser Ser Asn Lys Thr Cys
                435                 440                 445

Ile Thr His Ser Ser Ile Lys Ala Asn Lys Lys Val Cys Lys His
                450                 455                 460

Val Lys Leu Gly Val Arg Glu Asn Asp Lys Asp Leu Arg Val Cys Val
465                 470                 475                 480

Ile Glu His Thr Ser Leu Ser Gly Val Glu Asn Cys Cys Gln Asp
                485                 490                 495

Phe Leu Arg Ile Leu Gln Glu Asn Cys Ser Asp Asn Lys Ser Gly Ser
                500                 505                 510

Ser Ser Asn Gly Ser Cys Asn Asn Lys Asn Gln Glu Ala Cys Glu Lys
                515                 520                 525

Asn Leu Glu Lys Val Leu Ala Ser Leu Thr Asn Cys Tyr Lys Cys Asp
                530                 535                 540

Lys Cys Lys Ser Glu Gln Ser Lys Asn Asn Lys Asn Trp Ile Trp
545                 550                 555                 560

Lys Lys Ser Ser Gly Lys Glu Gly Gly Leu Gln Lys Glu Tyr Ala Asn
                565                 570                 575

Thr Ile Gly Leu Pro Pro Arg Thr Gln Ser Leu Cys Leu Val Val Cys
                580                 585                 590
```

-continued

```
Leu Asp Glu Lys Gly Lys Lys Thr Gln Glu Leu Lys Asn Ile Arg Thr
            595                 600                 605
Asn Ser Glu Leu Leu Lys Glu Trp Ile Ile Ala Ala Phe His Glu Gly
        610                 615                 620
Lys Asn Leu Lys Pro Ser His Glu Lys Lys Asn Asp Asp Asn Gly Lys
625                 630                 635                 640
Lys Leu Cys Lys Ala Leu Glu Tyr Ser Phe Ala Asp Tyr Gly Asp Leu
                645                 650                 655
Ile Lys Gly Thr Ser Ile Trp Asp Asn Glu Tyr Thr Lys Asp Leu Glu
            660                 665                 670
Leu Asn Leu Gln Lys Ile Phe Gly Lys Leu Phe Arg Lys Tyr Ile Lys
        675                 680                 685
Lys Asn Asn Thr Ala Glu Gln Asp Thr Ser Tyr Ser Ser Leu Asp Glu
690                 695                 700
Leu Arg Glu Ser Trp Trp Asn Thr Asn Lys Lys Tyr Ile Trp Leu Ala
705                 710                 715                 720
Met Lys His Gly Ala Gly Met Asn Ser Thr Thr Cys Cys Gly Asp Gly
                725                 730                 735
Ser Val Thr Gly Ser Gly Ser Ser Cys Asp Asp Ile Pro Thr Ile Asp
            740                 745                 750
Leu Ile Pro Gln Tyr Leu Arg Phe Leu Gln Glu Trp Val Glu His Phe
        755                 760                 765
Cys Lys Gln Arg Gln Glu Lys Val Lys Pro Val Ile Glu Asn Cys Lys
        770                 775                 780
Ser Cys Lys Glu Ser Gly Gly Thr Cys Asn Gly Glu Cys Lys Thr Glu
785                 790                 795                 800
Cys Lys Asn Lys Cys Glu Val Tyr Lys Lys Phe Ile Glu Asp Cys Lys
                805                 810                 815
Gly Gly Asp Gly Thr Ala Gly Ser Ser Trp Val Lys Arg Trp Asp Gln
            820                 825                 830
Ile Tyr Lys Arg Tyr Ser Lys Tyr Ile Glu Asp Ala Lys Arg Asn Arg
        835                 840                 845
Lys Ala Gly Thr Lys Asn Cys Gly Pro Ser Ser Thr Thr Asn Ala Ala
850                 855                 860
Glu Asn Lys Cys Val Gln Ser Asp Ile Asp Ser Phe Phe Lys His Leu
865                 870                 875                 880
Ile Asp Ile Gly Leu Thr Thr Pro Ser Ser Tyr Leu Ser Ile Val Leu
                885                 890                 895
Asp Asp Asn Ile Cys Gly Ala Asp Lys Ala Pro Trp Thr Thr Tyr Thr
            900                 905                 910
Thr Tyr Thr Thr Thr Glu Lys Cys Asn Lys Glu Thr Asp Lys Ser Lys
        915                 920                 925
Leu Gln Gln Cys Asn Thr Ala Val Val Val Asn Val Pro Ser Pro Leu
    930                 935                 940
Gly Asn Thr Pro His Gly Tyr Lys Tyr Ala Cys Gln Cys Lys Ile Pro
945                 950                 955                 960
Thr Asn Glu Glu Thr Cys Asp Asp Arg Lys Glu Tyr Met Asn Gln Trp
                965                 970                 975
Ser Cys Gly Ser Ala Arg Thr Met Lys Arg Gly Tyr Lys Asn Asp Asn
            980                 985                 990
Tyr Glu Leu Cys Lys Tyr Asn Gly Val Asp Val Lys Pro Thr Thr Val
        995                 1000                1005
```

```
Arg Ser Asn Ser Ser Lys Leu Asp Asp Lys Asp Val Thr Phe Phe
1010                1015                1020

Asn Leu Phe Glu Gln Trp Asn Lys Glu Ile Gln Tyr Gln Ile Glu
    1025                1030                1035

Gln Tyr Met Thr Asn Thr Lys Ile Ser Cys Asn Asn Glu Lys Asn
        1040                1045                1050

Val Leu Ser Arg Val Ser Asp Glu Ala Ala Gln Pro Lys Phe Ser
    1055                1060                1065

Asp Asn Glu Arg Asp Arg Asn Ser Ile Thr His Glu Asp Lys Asn
    1070                1075                1080

Cys Lys Glu Lys Cys Lys Cys Tyr Ser Leu Trp Ile Glu Lys Ile
    1085                1090                1095

Asn Asp Gln Trp Asp Lys Gln Lys Asp Asn Tyr Asn Lys Phe Gln
    1100                1105                1110

Arg Lys Gln Ile Tyr Asp Ala Asn Lys Gly Ser Gln Asn Lys Lys
    1115                1120                1125

Val Val Ser Leu Ser Asn Phe Leu Phe Phe Ser Cys Trp Glu Glu
    1130                1135                1140

Tyr Ile Gln Lys Tyr Phe Asn Gly Asp Trp Ser Lys Ile Lys Asn
    1145                1150                1155

Ile Gly Ser Asp Thr Phe Glu Phe Leu Ile Lys Lys Cys Gly Asn
    1160                1165                1170

Asp Ser Gly Asp Gly Glu Thr Ile Phe Ser Glu Lys Leu Asn Asn
    1175                1180                1185

Ala Glu Lys Lys Cys Lys Glu Asn Glu Ser Thr Asn Asn Lys Met
    1190                1195                1200

Lys Ser Ser Glu Thr Ser Cys Asp Cys Ser Glu Pro Ile Tyr Ile
    1205                1210                1215

Arg Gly Cys Gln Pro Lys Ile Tyr Asp Gly Lys Ile Phe Pro Gly
    1220                1225                1230

Lys Gly Gly Glu Lys Gln Trp Ile Cys Lys Asp Thr Ile Ile His
    1235                1240                1245

Gly Asp Thr Asn Gly Ala Cys Ile Pro Pro Arg Thr Gln Asn Leu
    1250                1255                1260

Cys Val Gly Glu Leu Trp Asp Lys Arg Tyr Gly Gly Arg Ser Asn
    1265                1270                1275

Ile Lys Asn Asp Thr Lys Glu Ser Leu Lys Gln Lys Ile Lys Asn
    1280                1285                1290

Ala Ile Gln Lys Glu Thr Glu Leu Leu Tyr Glu Tyr His Asp Lys
    1295                1300                1305

Gly Thr Ala Ile Ile Ser Arg Asn Pro Met Lys Gly Gln Lys Glu
    1310                1315                1320

Lys Glu Glu Lys Asn Asn Asp Ser Asn Gly Leu Pro Lys Gly Phe
    1325                1330                1335

Cys His Ala Val Gln Arg Ser Phe Ile Asp Tyr Lys Asn Met Ile
    1340                1345                1350

Leu Gly Thr Ser Val Asn Ile Tyr Glu Tyr Ile Gly Lys Leu Gln
    1355                1360                1365

Glu Asp Ile Lys Lys Ile Ile Glu Lys Gly Thr Thr Lys Gln Asn
    1370                1375                1380

Gly Lys Thr Val Gly Ser Gly Ala Glu Asn Val Asn Ala Trp Trp
    1385                1390                1395

Lys Gly Ile Glu Gly Glu Met Trp Asp Ala Val Arg Cys Ala Ile
```

-continued

```
              1400              1405              1410
Thr Lys Ile Asn Lys Lys Gln Lys Lys Asn Gly Thr Phe Ser Ile
    1415              1420              1425

Asp Glu Cys Gly Ile Phe Pro Pro Thr Gly Asn Asp Glu Asp Gln
    1430              1435              1440

Ser Val Ser Trp Phe Lys Glu Trp Ser Glu Gln Phe Cys Ile Glu
    1445              1450              1455

Arg Leu Gln Tyr Glu Lys Asn Ile Arg Asp Ala Cys Thr Asn Asn
    1460              1465              1470

Gly Gln Gly Asp Lys Ile Gln Gly Asp Cys Lys Arg Lys Cys Glu
    1475              1480              1485

Glu Tyr Lys Lys Tyr Ile Ser Glu Lys Lys Gln Glu Trp Asp Lys
    1490              1495              1500

Gln Lys Thr Lys Tyr Glu Asn Lys Tyr Val Gly Lys Ser Ala Ser
    1505              1510              1515

Asp Leu Leu Lys Glu Asn Tyr Pro Glu Cys Ile Ser Ala Asn Phe
    1520              1525              1530

Asp Phe Ile Phe Asn Asp Asn Ile Glu Tyr Lys Thr Tyr Tyr Pro
    1535              1540              1545

Tyr Gly Asp Tyr Ser Ser Ile Cys Ser Cys Glu Gln Val Lys Tyr
    1550              1555              1560

Tyr Glu Tyr Asn Asn Ala Glu Lys Lys Asn Asn Lys Ser Leu Cys
    1565              1570              1575

His Glu Lys Gly Asn Asp Arg Thr Trp Ser Lys Lys Tyr Ile Lys
    1580              1585              1590

Lys Leu Glu Asn Gly Arg Thr Leu Glu Gly Val Tyr Val Pro Pro
    1595              1600              1605

Arg Arg Gln Gln Leu Cys Leu Tyr Glu Leu Phe Pro Ile Ile Ile
    1610              1615              1620

Lys Asn Lys Asn Asp Ile Thr Asn Ala Lys Lys Glu Leu Leu Glu
    1625              1630              1635

Thr Leu Gln Ile Val Ala Glu Arg Glu Ala Tyr Tyr Leu Trp Lys
    1640              1645              1650

Gln Tyr His Ala His Asn Asp Thr Thr Tyr Leu Ala His Lys Lys
    1655              1660              1665

Ala Cys Cys Ala Ile Arg Gly Ser Phe Tyr Asp Leu Glu Asp Ile
    1670              1675              1680

Ile Lys Gly Asn Asp Leu Val His Asp Glu Tyr Thr Lys Tyr Ile
    1685              1690              1695

Asp Ser Lys Leu Asn Glu Ile Phe Asp Ser Ser Asn Lys Asn Asp
    1700              1705              1710

Ile Glu Thr Lys Arg Ala Arg Thr Asp Trp Trp Glu Asn Glu Ala
    1715              1720              1725

Ile Ala Val Pro Asn Ile Thr Gly Ala Asn Lys Ser Asp Pro Lys
    1730              1735              1740

Thr Ile Arg Gln Leu Val Trp Asp Ala Met Gln Ser Gly Val Arg
    1745              1750              1755

Lys Ala Ile Asp Glu Glu Lys Glu Lys Lys Lys Pro Asn Glu Asn
    1760              1765              1770

Phe Pro Pro Cys Met Gly Val Gln His Ile Gly Ile Ala Lys Pro
    1775              1780              1785

Gln Phe Ile Arg Trp Leu Glu Glu Trp Thr Asn Glu Phe Cys Glu
    1790              1795              1800
```

```
Lys Tyr Thr Lys Tyr Phe Glu Asp Met Lys Ser Asn Cys Asn Leu
1805                1810                1815

Arg Lys Gly Ala Asp Asp Cys Asp Asp Asn Ser Asn Ile Glu Cys
1820                1825                1830

Lys Lys Ala Cys Ala Asn Tyr Thr Asn Trp Leu Asn Pro Lys Arg
1835                1840                1845

Ile Glu Trp Asn Gly Met Ser Asn Tyr Tyr Asn Lys Ile Tyr Arg
1850                1855                1860

Lys Ser Asn Lys Glu Ser Glu Asp Gly Lys Asp Tyr Ser Met Ile
1865                1870                1875

Met Glu Pro Thr Val Ile Asp Tyr Leu Asn Lys Arg Cys Asn Gly
1880                1885                1890

Glu Ile Asn Gly Asn Tyr Ile Cys Cys Ser Cys Lys Asn Ile Gly
1895                1900                1905

Glu Asn Ser Thr Ser Gly Thr Val Asn Lys Lys Leu Gln Lys Lys
1910                1915                1920

Glu Thr Gln Cys Glu Asp Asn Lys Gly Pro Leu Asp Leu Met Asn
1925                1930                1935

Lys Val Leu Asn Lys Met Asp Pro Lys Tyr Ser Glu His Lys Met
1940                1945                1950

Lys Cys Thr Glu Val Tyr Leu Glu His Val Glu Glu Gln Leu Lys
1955                1960                1965

Glu Ile Asp Asn Ala Ile Lys Asp Tyr Lys Leu Tyr Pro Leu Asp
1970                1975                1980

Arg Cys Phe Asp Asp Lys Ser Lys Met Lys Val Cys Asp Leu Ile
1985                1990                1995

Gly Asp Ala Ile Gly Cys Lys His Lys Thr Lys Leu Asp Glu Leu
2000                2005                2010

Asp Glu Trp Asn Asp Val Asp Met Arg Asp Pro Tyr Asn Lys Tyr
2015                2020                2025

Lys Gly Val Leu Ile Pro Pro Arg Arg Arg Gln Leu Cys Phe Ser
2030                2035                2040

Arg Ile Val Arg Gly Pro Ala Asn Leu Arg Asn Leu Lys Glu Phe
2045                2050                2055

Lys Glu Glu Ile Leu Lys Gly Ala Gln Ser Glu Gly Lys Phe Leu
2060                2065                2070

Gly Asn Tyr Tyr Asn Glu Asp Lys Asp Lys Glu Lys Ala Leu Glu
2075                2080                2085

Ala Met Lys Asn Ser Phe Tyr Asp Tyr Glu Tyr Ile Ile Lys Gly
2090                2095                2100

Ser Asp Met Leu Thr Asn Ile Gln Phe Lys Asp Ile Lys Arg Lys
2105                2110                2115

Leu Asp Arg Leu Leu Glu Lys Glu Thr Asn Asn Thr Glu Lys Val
2120                2125                2130

Asp Asp Trp Trp Glu Thr Asn Lys Lys Ser Ile Trp Asn Ala Met
2135                2140                2145

Leu Cys Gly Tyr Lys Lys Ser Gly Asn Lys Ile Ile Asp Pro Ser
2150                2155                2160

Trp Cys Thr Ile Pro Thr Thr Glu Thr Pro Pro Gln Phe Leu Arg
2165                2170                2175

Trp Ile Lys Glu Trp Gly Thr Asn Val Cys Ile Gln Lys Glu Glu
2180                2185                2190
```

-continued

```
His Lys Glu Tyr Val Lys Ser Lys Cys Ser Asn Val Thr Asn Leu
2195                2200                2205

Gly Ala Gln Glu Ser Glu Ser Lys Asn Cys Thr Ser Glu Ile Lys
2210                2215                2220

Lys Tyr Gln Glu Trp Ser Arg Lys Arg Ser Ile Gln Trp Glu Ala
2225                2230                2235

Ile Ser Glu Gly Tyr Lys Lys Tyr Lys Gly Met Asp Glu Phe Lys
2240                2245                2250

Asn Thr Phe Lys Asn Ile Lys Glu Pro Asp Ala Asn Glu Pro Asn
2255                2260                2265

Ala Asn Glu Tyr Leu Lys Lys His Cys Ser Lys Cys Pro Cys Gly
2270                2275                2280

Phe Asn Asp Met Gln Glu Ile Thr Lys Tyr Thr Asn Ile Gly Asn
2285                2290                2295

Glu Ala Phe Lys Gln Ile Lys Glu Gln Val Asp Ile Pro Ala Glu
2300                2305                2310

Leu Glu Asp Val Ile Tyr Arg Leu Lys His His Glu Tyr Asp Lys
2315                2320                2325

Gly Asn Asp Tyr Ile Cys Asn Lys Tyr Lys Asn Ile Asn Val Asn
2330                2335                2340

Met Lys Lys Asn Asn Asp Asp Thr Trp Thr Asp Leu Val Lys Asn
2345                2350                2355

Ser Ser Asp Ile Asn Lys Gly Val Leu Leu Pro Pro Arg Arg Lys
2360                2365                2370

Asn Leu Phe Leu Lys Ile Asp Glu Ser Asp Ile Cys Lys Tyr Lys
2375                2380                2385

Arg Asp Pro Lys Leu Phe Lys Asp Phe Ile Tyr Ser Ser Ala Ile
2390                2395                2400

Ser Glu Val Glu Arg Leu Lys Lys Val Tyr Gly Glu Ala Lys Thr
2405                2410                2415

Lys Val Val His Ala Met Lys Tyr Ser Phe Ala Asp Ile Gly Ser
2420                2425                2430

Ile Ile Lys Gly Asp Asp Met Met Glu Asn Asn Ser Ser Asp Lys
2435                2440                2445

Ile Gly Lys Ile Leu Gly Asp Gly Val Gly Gln Asn Glu Lys Arg
2450                2455                2460

Lys Lys Trp Trp Asp Met Asn Lys Tyr His Ile Trp Glu Ser Met
2465                2470                2475

Leu Cys Gly Tyr Lys His Ala Tyr Gly Asn Ile Ser Glu Asn Asp
2480                2485                2490

Arg Lys Met Leu Asp Ile Pro Asn Asn Asp Asp Glu His Gln Phe
2495                2500                2505

Leu Arg Trp Phe Gln Glu Trp Thr Glu Asn Phe Cys Thr Lys Arg
2510                2515                2520

Asn Glu Leu Tyr Glu Asn Met Val Thr Ala Cys Asn Ser Ala Lys
2525                2530                2535

Cys Asn Thr Ser Asn Gly Ser Val Asp Lys Lys Glu Cys Thr Glu
2540                2545                2550

Ala Cys Lys Asn Tyr Ser Asn Phe Ile Leu Ile Lys Lys Lys Glu
2555                2560                2565

Tyr Gln Ser Leu Asn Ser Gln Tyr Asp Met Asn Tyr Lys Glu Thr
2570                2575                2580

Lys Ala Glu Lys Lys Glu Ser Pro Glu Tyr Phe Lys Asp Lys Cys
```

-continued

```
            2585               2590               2595
Asn Gly Glu Cys Ser Cys Leu Ser Glu Tyr Phe Lys Asp Glu Thr
            2600               2605               2610
Arg Trp Lys Asn Pro Tyr Glu Thr Leu Asp Asp Thr Glu Val Lys
            2615               2620               2625
Asn Asn Cys Met Cys Lys Pro Pro Pro Ala Ser Asn Asn Thr
            2630               2635               2640
Ser Asp Ile Leu Gln Lys Thr Ile Pro Phe Gly Ile Ala Leu Ala
            2645               2650               2655
Leu Gly Ser Ile Ala Phe Leu Phe Met Lys Lys Lys Pro Lys Thr
            2660               2665               2670
Pro Val Asp Leu Leu Arg Val Leu Asp Ile Pro Lys Gly Asp Tyr
            2675               2680               2685
Gly Ile Pro Thr Pro Lys Ser Ser Asn Arg Tyr Ile Pro Tyr Ala
            2690               2695               2700
Ser Asp Arg Tyr Lys Gly Lys Thr Tyr Ile Tyr Met Glu Gly Asp
            2705               2710               2715
Thr Ser Gly Asp Asp Asp Lys Tyr Ile Trp Asp Leu
            2720               2725               2730
```

<210> SEQ ID NO 56
<211> LENGTH: 2734
<212> TYPE: PRT
<213> ORGANISM: Artificial Sequence
<220> FEATURE:
<223> OTHER INFORMATION: FCR3 complete 2734 aa extracellular part (577
      aa highlighted corr. ID1- DBL2b)

<400> SEQUENCE: 56

```
Met Asp Ser Thr Ser Thr Ile Ala Asn Lys Ile Glu Glu Tyr Leu Gly
1               5                   10                  15
Ala Lys Ser Asp Asp Ser Lys Ile Asp Glu Leu Leu Lys Ala Asp Pro
                20                  25                  30
Ser Glu Val Glu Tyr Tyr Arg Ser Gly Gly Asp Gly Asp Tyr Leu Lys
            35                  40                  45
Asn Asn Ile Cys Lys Ile Thr Val Asn His Ser Asp Ser Gly Lys Tyr
        50                  55                  60
Asp Pro Cys Glu Lys Lys Leu Pro Tyr Asp Asp Asn Asp Gln Trp
65                  70                  75                  80
Lys Cys Gln Gln Asn Ser Ser Asp Gly Ser Gly Lys Pro Glu Asn Ile
                85                  90                  95
Cys Val Pro Pro Arg Arg Glu Arg Leu Cys Thr Tyr Asn Leu Glu Asn
            100                 105                 110
Leu Lys Phe Asp Lys Ile Arg Asp Asn Asn Ala Phe Leu Ala Asp Val
        115                 120                 125
Leu Leu Thr Ala Arg Asn Glu Gly Glu Lys Ile Val Gln Asn His Pro
    130                 135                 140
Asp Thr Asn Ser Ser Asn Val Cys Asn Ala Leu Glu Arg Ser Phe Ala
145                 150                 155                 160
Asp Leu Ala Asp Ile Ile Arg Gly Thr Asp Gln Trp Lys Gly Thr Asn
                165                 170                 175
Ser Asn Leu Glu Lys Asn Leu Lys Gln Met Phe Ala Lys Ile Arg Glu
            180                 185                 190
Asn Asp Lys Val Leu Gln Asp Lys Tyr Pro Lys Asp Gln Lys Tyr Thr
        195                 200                 205
```

```
Lys Leu Arg Glu Ala Trp Trp Asn Ala Asn Arg Gln Lys Val Trp Glu
210                 215                 220
Val Ile Thr Cys Gly Ala Arg Ser Asn Asp Leu Leu Ile Lys Arg Gly
225                 230                 235                 240
Trp Arg Thr Ser Gly Lys Ser Asp Arg Lys Asn Phe Glu Leu Cys
                245                 250                 255
Arg Lys Cys Gly His Tyr Glu Lys Glu Val Pro Thr Lys Leu Asp Tyr
                260                 265                 270
Val Pro Gln Phe Leu Arg Trp Leu Thr Glu Trp Ile Glu Asp Phe Tyr
                275                 280                 285
Arg Glu Lys Gln Asn Leu Ile Asp Asp Met Glu Arg His Arg Glu Glu
290                 295                 300
Cys Thr Arg Glu Asp His Lys Ser Lys Glu Gly Thr Ser Tyr Cys Ser
305                 310                 315                 320
Thr Cys Lys Asp Lys Cys Lys Lys Tyr Cys Glu Cys Val Lys Lys Trp
                325                 330                 335
Lys Thr Glu Trp Glu Asn Gln Glu Asn Lys Tyr Lys Asp Leu Tyr Glu
                340                 345                 350
Gln Asn Lys Asn Lys Thr Ser Gln Lys Asn Thr Ser Arg Tyr Asp Asp
                355                 360                 365
Tyr Val Lys Asp Phe Phe Glu Lys Leu Glu Ala Asn Tyr Ser Ser Leu
370                 375                 380
Glu Asn Tyr Ile Lys Gly Asp Pro Tyr Phe Ala Glu Tyr Ala Thr Lys
385                 390                 395                 400
Leu Ser Phe Ile Leu Asn Pro Ser Asp Ala Asn Asn Pro Ser Gly Glu
                405                 410                 415
Thr Ala Asn His Asn Asp Glu Ala Cys Asn Cys Asn Glu Ser Gly Ile
                420                 425                 430
Ser Ser Val Gly Gln Ala Gln Thr Ser Gly Pro Ser Ser Asn Lys Thr
                435                 440                 445
Cys Ile Thr His Ser Ser Ile Lys Thr Asn Lys Lys Glu Cys Lys
                450                 455                 460
Asp Val Lys Leu Gly Val Arg Glu Asn Asp Lys Asp Leu Lys Ile Cys
465                 470                 475                 480
Val Ile Glu Asp Thr Ser Leu Ser Gly Val Asp Asn Cys Cys Cys Gln
                485                 490                 495
Asp Leu Leu Gly Ile Leu Gln Glu Asn Cys Ser Asp Asn Lys Arg Gly
                500                 505                 510
Ser Ser Ser Asn Asp Ser Cys Asp Asn Lys Asn Gln Asp Glu Cys Gln
                515                 520                 525
Lys Lys Leu Glu Lys Val Phe Ala Ser Leu Thr Asn Gly Tyr Lys Cys
530                 535                 540
Asp Lys Cys Lys Ser Gly Thr Ser Arg Ser Lys Lys Trp Ile Trp
545                 550                 555                 560
Lys Lys Ser Ser Gly Asn Glu Glu Gly Leu Gln Glu Glu Tyr Ala Asn
                565                 570                 575
Thr Ile Gly Leu Pro Pro Arg Thr Gln Ser Leu Tyr Leu Gly Asn Leu
                580                 585                 590
Pro Lys Leu Glu Asn Val Cys Glu Asp Val Lys Asp Ile Asn Phe Asp
                595                 600                 605
Thr Lys Glu Lys Phe Leu Ala Gly Cys Leu Ile Val Ser Phe His Glu
610                 615                 620
Gly Lys Asn Leu Lys Lys Arg Tyr Pro Gln Asn Lys Asn Ser Gly Asn
```

```
625                 630                 635                 640
Lys Glu Asn Leu Cys Lys Ala Leu Glu Tyr Ser Phe Ala Asp Tyr Gly
                    645                 650                 655

Asp Leu Ile Lys Gly Thr Ser Ile Trp Asp Asn Glu Tyr Thr Lys Asp
                    660                 665                 670

Leu Glu Leu Asn Leu Gln Asn Asn Phe Gly Lys Leu Phe Gly Lys Tyr
                    675                 680                 685

Ile Lys Lys Asn Asn Thr Ala Glu Gln Asp Thr Ser Tyr Ser Ser Leu
                    690                 695                 700

Asp Glu Leu Arg Glu Ser Trp Trp Asn Thr Asn Lys Lys Tyr Ile Trp
705                 710                 715                 720

Thr Ala Met Lys His Gly Ala Glu Met Asn Ile Thr Cys Asn Ala
                    725                 730                 735

Asp Gly Ser Val Thr Gly Ser Gly Ser Ser Cys Asp Asp Ile Pro Thr
                    740                 745                 750

Ile Asp Leu Ile Pro Gln Tyr Leu Arg Phe Leu Gln Glu Trp Val Glu
                    755                 760                 765

Asn Phe Cys Glu Gln Arg Gln Ala Lys Val Lys Asp Val Ile Thr Asn
                    770                 775                 780

Cys Lys Ser Cys Lys Glu Ser Gly Asn Lys Cys Lys Thr Glu Cys Lys
785                 790                 795                 800

Thr Lys Cys Lys Asp Glu Cys Glu Lys Tyr Lys Lys Phe Ile Glu Ala
                    805                 810                 815

Cys Gly Thr Ala Gly Gly Gly Ile Gly Thr Ala Gly Ser Pro Trp Ser
                    820                 825                 830

Lys Arg Trp Asp Gln Ile Tyr Lys Arg Tyr Ser Lys His Ile Glu Asp
                    835                 840                 845

Ala Lys Arg Asn Arg Lys Ala Gly Thr Lys Asn Cys Gly Thr Ser Ser
                    850                 855                 860

Thr Thr Asn Ala Ala Ala Ser Thr Asp Glu Asn Lys Cys Val Gln Ser
865                 870                 875                 880

Asp Ile Asp Ser Phe Phe Lys His Leu Ile Asp Ile Gly Leu Thr Thr
                    885                 890                 895

Pro Ser Ser Tyr Leu Ser Asn Val Leu Asp Asp Asn Ile Cys Gly Ala
                    900                 905                 910

Asp Lys Ala Pro Trp Thr Thr Tyr Thr Thr Tyr Thr Thr Thr Glu Lys
                    915                 920                 925

Cys Asn Lys Glu Arg Asp Lys Ser Lys Ser Gln Ser Ser Asp Thr Leu
930                 935                 940

Val Val Val Asn Val Pro Ser Pro Leu Gly Asn Thr Pro Tyr Arg Tyr
945                 950                 955                 960

Lys Tyr Ala Cys Gln Cys Lys Ile Pro Thr Asn Glu Glu Thr Cys Asp
                    965                 970                 975

Asp Arg Lys Glu Tyr Met Asn Gln Trp Ser Cys Gly Ser Ala Arg Thr
                    980                 985                 990

Met Lys Arg Gly Tyr Lys Asn Asp Asn Tyr Glu Leu Cys Lys Tyr Asn
                    995                 1000                1005

Gly Val Asp Val Lys Pro Thr Thr Val Arg Ser Asn Ser Ser Lys
                1010                1015                1020

Leu Asp Gly Asn Asp Val Thr Phe Phe Asn Leu Phe Glu Gln Trp
                1025                1030                1035

Asn Lys Glu Ile Gln Tyr Gln Ile Glu Gln Tyr Met Thr Asn Ala
                1040                1045                1050
```

```
Asn Ile Ser Cys Ile Asp Glu Lys Glu Val Leu Asp Ser Val Ser
    1055                1060                1065

Asp Glu Gly Thr Pro Lys Val Arg Gly Gly Tyr Glu Asp Gly Arg
    1070                1075                1080

Asn Asn Asn Thr Asp Gln Gly Thr Asn Cys Lys Glu Lys Cys Lys
    1085                1090                1095

Cys Tyr Lys Leu Trp Ile Glu Lys Ile Asn Asp Gln Trp Gly Lys
    1100                1105                1110

Gln Lys Asp Asn Tyr Asn Lys Phe Arg Ser Lys Gln Ile Tyr Asp
    1115                1120                1125

Ala Asn Lys Gly Ser Gln Asn Lys Lys Val Val Ser Leu Ser Asn
    1130                1135                1140

Phe Leu Phe Phe Ser Cys Trp Glu Glu Tyr Ile Gln Lys Tyr Phe
    1145                1150                1155

Asn Gly Asp Trp Ser Lys Ile Lys Asn Ile Gly Ser Asp Thr Phe
    1160                1165                1170

Glu Phe Leu Ile Lys Lys Cys Gly Asn Asn Ser Ala His Gly Glu
    1175                1180                1185

Glu Ile Phe Asn Glu Lys Leu Lys Asn Ala Glu Lys Lys Cys Lys
    1190                1195                1200

Glu Asn Glu Ser Thr Asp Thr Asn Ile Asn Lys Ser Glu Thr Ser
    1205                1210                1215

Cys Asp Leu Asn Ala Thr Asn Tyr Ile Arg Gly Cys Gln Ser Lys
    1220                1225                1230

Thr Tyr Asp Gly Lys Ile Phe Pro Gly Lys Gly Glu Lys Gln
    1235                1240                1245

Trp Ile Cys Lys Asp Thr Ile Ile His Gly Asp Thr Asn Gly Ala
    1250                1255                1260

Cys Ile Pro Pro Arg Thr Gln Asn Leu Cys Val Gly Glu Leu Trp
    1265                1270                1275

Asp Lys Ser Tyr Gly Gly Arg Ser Asn Ile Lys Asn Asp Thr Lys
    1280                1285                1290

Glu Leu Leu Lys Glu Lys Ile Lys Asn Ala Ile His Lys Glu Thr
    1295                1300                1305

Glu Leu Leu Tyr Glu Tyr His Asp Thr Gly Thr Ala Ile Ile Ser
    1310                1315                1320

Lys Asn Asp Lys Lys Gly Gln Lys Gly Lys Asn Asp Pro Asn Gly
    1325                1330                1335

Leu Pro Lys Gly Phe Cys His Ala Val Gln Arg Ser Phe Ile Asp
    1340                1345                1350

Tyr Lys Asn Met Ile Leu Gly Thr Ser Val Asn Ile Tyr Glu His
    1355                1360                1365

Ile Gly Lys Leu Gln Glu Asp Ile Lys Lys Ile Glu Lys Gly
    1370                1375                1380

Thr Pro Gln Gln Lys Asp Lys Ile Gly Gly Val Gly Ser Ser Thr
    1385                1390                1395

Glu Asn Val Asn Ala Trp Trp Lys Gly Ile Glu Arg Glu Met Trp
    1400                1405                1410

Asp Ala Val Arg Cys Ala Ile Thr Lys Ile Asn Lys Lys Asn Asn
    1415                1420                1425

Asn Ser Ile Phe Asn Gly Asp Glu Cys Gly Val Ser Pro Pro Thr
    1430                1435                1440
```

-continued

Gly Asn Asp Glu Asp Gln Ser Val Ser Trp Phe Lys Glu Trp Gly
1445                     1450                1455

Glu Gln Phe Cys Ile Glu Arg Leu Arg Tyr Glu Gln Asn Ile Arg
1460                     1465                1470

Glu Ala Cys Thr Ile Asn Gly Lys Asn Glu Lys Cys Ile Asn
1475                     1480                1485

Ser Lys Ser Gly Gln Gly Asp Lys Ile Gln Gly Ala Cys Lys Arg
1490                     1495                1500

Lys Cys Glu Lys Tyr Lys Tyr Ile Ser Glu Lys Lys Gln Glu
1505                     1510                1515

Trp Asp Lys Gln Lys Thr Lys Tyr Glu Asn Lys Tyr Val Gly Lys
1520                     1525                1530

Ser Ala Ser Asp Leu Leu Lys Glu Asn Tyr Pro Glu Cys Ile Ser
1535                     1540                1545

Ala Asn Phe Asp Phe Ile Phe Asn Asp Asn Ile Glu Tyr Lys Thr
1550                     1555                1560

Tyr Tyr Pro Tyr Gly Asp Tyr Ser Ser Ile Cys Ser Cys Glu Gln
1565                     1570                1575

Val Lys Tyr Tyr Lys Tyr Asn Asn Ala Glu Lys Lys Asn Asn Lys
1580                     1585                1590

Ser Leu Cys Tyr Glu Lys Asp Asn Asp Met Thr Trp Ser Lys Lys
1595                     1600                1605

Tyr Ile Lys Lys Leu Glu Asn Gly Arg Ser Leu Glu Gly Val Tyr
1610                     1615                1620

Val Pro Pro Arg Arg Gln Gln Leu Cys Leu Tyr Glu Leu Phe Pro
1625                     1630                1635

Ile Ile Ile Lys Asn Glu Glu Gly Met Glu Lys Ala Lys Glu Glu
1640                     1645                1650

Leu Leu Glu Thr Leu Gln Ile Val Ala Glu Arg Glu Ala Tyr Tyr
1655                     1660                1665

Leu Trp Lys Gln Tyr Asn Pro Thr Gly Lys Gly Ile Asp Asp Ala
1670                     1675                1680

Asn Lys Lys Ala Cys Cys Ala Ile Arg Gly Ser Phe Tyr Asp Leu
1685                     1690                1695

Glu Asp Ile Ile Lys Gly Asn Asp Leu Val His Asp Glu Tyr Thr
1700                     1705                1710

Lys Tyr Ile Asp Ser Lys Leu Asn Glu Ile Phe Gly Ser Ser Asp
1715                     1720                1725

Thr Asn Asp Ile Asp Thr Lys Arg Ala Arg Thr Asp Trp Trp Glu
1730                     1735                1740

Asn Glu Thr Ile Thr Asn Gly Thr Asp Arg Lys Thr Ile Arg Gln
1745                     1750                1755

Leu Val Trp Asp Ala Met Gln Ser Gly Val Arg Tyr Ala Val Glu
1760                     1765                1770

Glu Lys Asn Glu Asn Phe Pro Leu Cys Met Gly Val Glu His Ile
1775                     1780                1785

Gly Ile Ala Lys Pro Gln Phe Ile Arg Trp Leu Glu Glu Trp Thr
1790                     1795                1800

Asn Glu Phe Cys Glu Lys Tyr Thr Lys Tyr Phe Glu Asp Met Lys
1805                     1810                1815

Ser Lys Cys Asp Pro Pro Lys Arg Ala Asp Thr Cys Gly Asp Asn
1820                     1825                1830

Ser Asn Ile Glu Cys Lys Lys Ala Cys Ala Asn Tyr Thr Asn Trp

-continued

```
        1835               1840               1845

Leu Asn Pro Lys Arg Ile Glu Trp Asn Gly Met Ser Asn Tyr Tyr
    1850               1855               1860

Asn Lys Ile Tyr Arg Lys Ser Asn Lys Glu Ser Glu Gly Gly Lys
    1865               1870               1875

Asp Tyr Ser Met Ile Met Ala Pro Thr Val Ile Asp Tyr Leu Asn
    1880               1885               1890

Lys Arg Cys His Gly Glu Ile Asn Gly Asn Tyr Ile Cys Cys Ser
    1895               1900               1905

Cys Lys Asn Ile Gly Ala Tyr Asn Thr Thr Ser Gly Thr Val Asn
    1910               1915               1920

Lys Lys Leu Gln Lys Lys Glu Thr Glu Cys Glu Glu Lys Gly
    1925               1930               1935

Pro Leu Asp Leu Met Asn Glu Val Leu Asn Lys Met Asp Lys Lys
    1940               1945               1950

Tyr Ser Ala His Lys Met Lys Cys Thr Glu Val Tyr Leu Glu His
    1955               1960               1965

Val Glu Glu Gln Leu Asn Glu Ile Asp Asn Ala Ile Lys Asp Tyr
    1970               1975               1980

Lys Leu Tyr Pro Leu Asp Arg Cys Phe Asp Asp Gln Thr Lys Met
    1985               1990               1995

Lys Val Cys Asp Leu Ile Ala Asp Ala Ile Gly Cys Lys Asp Lys
    2000               2005               2010

Thr Lys Leu Asp Glu Leu Asp Glu Trp Asn Asp Met Asp Leu Arg
    2015               2020               2025

Gly Thr Tyr Asn Lys His Lys Gly Val Leu Ile Pro Pro Arg Arg
    2030               2035               2040

Arg Gln Leu Cys Phe Ser Arg Ile Val Arg Gly Pro Ala Asn Leu
    2045               2050               2055

Arg Ser Leu Asn Glu Phe Lys Glu Glu Ile Leu Lys Gly Ala Gln
    2060               2065               2070

Ser Glu Gly Lys Phe Leu Gly Asn Tyr Tyr Lys Glu His Lys Asp
    2075               2080               2085

Lys Glu Lys Ala Leu Glu Ala Met Lys Asn Ser Phe Tyr Asp Tyr
    2090               2095               2100

Glu Asp Ile Ile Lys Gly Thr Asp Met Leu Thr Asn Ile Glu Phe
    2105               2110               2115

Lys Asp Ile Lys Ile Lys Leu Asp Arg Leu Leu Glu Lys Glu Thr
    2120               2125               2130

Asn Asn Thr Lys Lys Ala Glu Asp Trp Trp Lys Thr Asn Lys Lys
    2135               2140               2145

Ser Ile Trp Asn Ala Met Leu Cys Gly Tyr Lys Lys Ser Gly Asn
    2150               2155               2160

Lys Ile Ile Asp Pro Ser Trp Cys Thr Ile Pro Thr Thr Glu Thr
    2165               2170               2175

Pro Pro Gln Phe Leu Arg Trp Ile Lys Glu Trp Gly Thr Asn Val
    2180               2185               2190

Cys Ile Gln Lys Gln Glu His Lys Glu Tyr Val Lys Ser Lys Cys
    2195               2200               2205

Ser Asn Val Thr Asn Leu Gly Ala Gln Ala Ser Glu Ser Asn Asn
    2210               2215               2220

Cys Thr Ser Glu Ile Lys Lys Tyr Gln Glu Trp Ser Arg Lys Arg
    2225               2230               2235
```

```
Ser Ile Arg Trp Glu Thr Ile Ser Lys Arg Tyr Lys Lys Tyr Lys
    2240            2245                2250
Arg Met Asp Ile Leu Lys Asp Val Lys Glu Pro Asp Ala Asn Thr
    2255            2260                2265
Tyr Leu Arg Glu His Cys Ser Lys Cys Pro Cys Gly Phe Asn Asp
    2270            2275                2280
Met Glu Glu Met Asn Asn Glu Asp Asn Glu Lys Glu Ala Phe
    2285            2290                2295
Lys Gln Ile Lys Glu Gln Val Lys Ile Pro Ala Glu Leu Glu Asp
    2300            2305                2310
Val Ile Tyr Arg Ile Lys His His Glu Tyr Asp Lys Gly Asn Asp
    2315            2320                2325
Tyr Ile Cys Asn Lys Tyr Lys Asn Ile His Asp Arg Met Lys Lys
    2330            2335                2340
Asn Asn Gly Asn Phe Val Thr Asp Asn Phe Val Lys Lys Ser Trp
    2345            2350                2355
Glu Ile Ser Asn Gly Val Leu Ile Pro Pro Arg Arg Lys Asn Leu
    2360            2365                2370
Phe Leu Tyr Ile Asp Pro Ser Lys Ile Cys Glu Tyr Lys Lys Asp
    2375            2380                2385
Pro Lys Leu Phe Lys Asp Phe Ile Tyr Trp Ser Ala Phe Thr Glu
    2390            2395                2400
Val Glu Arg Leu Lys Lys Ala Tyr Gly Gly Ala Arg Ala Lys Val
    2405            2410                2415
Val His Ala Met Lys Tyr Ser Phe Thr Asp Ile Gly Ser Ile Ile
    2420            2425                2430
Lys Gly Asp Asp Met Met Glu Lys Asn Ser Ser Asp Lys Ile Gly
    2435            2440                2445
Lys Ile Leu Gly Asp Thr Asp Gly Gln Asn Glu Lys Arg Lys Lys
    2450            2455                2460
Trp Trp Asp Met Asn Lys Tyr His Ile Trp Glu Ser Met Leu Cys
    2465            2470                2475
Gly Tyr Arg Glu Ala Glu Gly Asp Thr Glu Thr Asn Glu Asn Cys
    2480            2485                2490
Arg Phe Pro Asp Ile Glu Ser Val Pro Gln Phe Leu Arg Trp Phe
    2495            2500                2505
Gln Glu Trp Ser Glu Asn Phe Cys Asp Arg Arg Gln Lys Leu Tyr
    2510            2515                2520
Asp Lys Leu Asn Ser Glu Cys Ile Ser Ala Glu Cys Thr Asn Gly
    2525            2530                2535
Ser Val Asp Asn Ser Lys Cys Thr His Ala Cys Val Asn Tyr Lys
    2540            2545                2550
Asn Tyr Ile Leu Thr Lys Lys Thr Glu Tyr Glu Ile Gln Thr Asn
    2555            2560                2565
Lys Tyr Asp Asn Glu Phe Lys Asn Lys Asn Ser Asn Asp Lys Asp
    2570            2575                2580
Ala Pro Asp Tyr Leu Lys Glu Lys Cys Asn Asp Asn Lys Cys Glu
    2585            2590                2595
Cys Leu Asn Lys His Ile Asp Asp Lys Asn Lys Thr Trp Lys Asn
    2600            2605                2610
Pro Tyr Glu Thr Leu Glu Asp Thr Phe Lys Ser Lys Cys Asp Cys
    2615            2620                2625
```

```
Pro Lys Pro Leu Pro Ser Pro Ile Lys Pro Asp Asp Leu Pro Pro
        2630            2635            2640
Gln Ala Asp Glu Pro Phe Asp Pro Thr Ile Leu Gln Thr Thr Ile
        2645            2650            2655
Pro Phe Gly Ile Ala Leu Ala Leu Gly Ser Ile Ala Phe Leu Phe
        2660            2665            2670
Met Lys Val Ile Tyr Ile Tyr Ile Tyr Val Cys Cys Ile Cys Met
        2675            2680            2685
Tyr Val Cys Met Tyr Val Cys Met Tyr Val Cys Met Tyr Val Cys
        2690            2695            2700
Met Tyr Val Cys Met His Val Cys Met Leu Cys Val Tyr Val Ile
        2705            2710            2715
Tyr Val Phe Lys Ile Cys Ile Tyr Ile Glu Lys Glu Lys Arg Lys
        2720            2725            2730
Lys
```

<210> SEQ ID NO 57
<211> LENGTH: 58
<212> TYPE: PRT
<213> ORGANISM: Artificial Sequence
<220> FEATURE:
<223> OTHER INFORMATION: BPTI, protease inhibitor

<400> SEQUENCE: 57

```
Arg Pro Asp Phe Cys Leu Glu Pro Pro Tyr Thr Gly Pro Cys Lys Ala
1               5                   10                  15
Arg Ile Ile Arg Tyr Phe Tyr Asn Ala Lys Ala Gly Leu Cys Gln Thr
            20                  25                  30
Phe Val Tyr Gly Gly Cys Arg Ala Lys Arg Asn Asn Phe Lys Ser Ala
        35                  40                  45
Glu Asp Cys Met Arg Thr Cys Gly Gly Ala
    50                  55
```

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

-continued

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76
<211> LENGTH: 18
<212> TYPE: DNA
<213> ORGANISM: Artificial Sequence
<220> FEATURE:
<223> OTHER INFORMATION: primer

<400> SEQUENCE: 76
aactacatca agggcgac                                             18

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
cttgttgata ttggtgtcgg t                                         21

<210> SEQ ID NO 78
<211> LENGTH: 18
<212> TYPE: DNA
<213> ORGANISM: Artificial Sequence
<220> FEATURE:
<223> OTHER INFORMATION: Primer

<400> SEQUENCE: 78
cacagcgata gcggcaag                                             18

<210> SEQ ID NO 79
<211> LENGTH: 18
<212> TYPE: DNA
<213> ORGANISM: Artificial Sequence
<220> FEATURE:
<223> OTHER INFORMATION: Primer

<400> SEQUENCE: 79
gtccagcttg ctggagtt                                             18

<210> SEQ ID NO 80
<211> LENGTH: 18
<212> TYPE: DNA
<213> ORGANISM: Artificial Sequence
<220> FEATURE:
<223> OTHER INFORMATION: Primer

<400> SEQUENCE: 80
aactacatca agggcgac                                             18

<210> SEQ ID NO 81
<211> LENGTH: 18
<212> TYPE: DNA
<213> ORGANISM: Artificial Sequence
<220> FEATURE:

<223> OTHER INFORMATION: Primer

<400> SEQUENCE: 81
gtccagcttg ctggagtt                                                 18

<210> SEQ ID NO 82
<211> LENGTH: 18
<212> TYPE: DNA
<213> ORGANISM: Artificial Sequence
<220> FEATURE:
<223> OTHER INFORMATION: Primer

<400> SEQUENCE: 82
aactacatca agggcgac                                                 18

<210> SEQ ID NO 83
<211> LENGTH: 18
<212> TYPE: DNA
<213> ORGANISM: Artificial Sequence
<220> FEATURE:
<223> OTHER INFORMATION: Primer

<400> SEQUENCE: 83
agcggcgttg gtggtgga                                                 18

<210> SEQ ID NO 84
<211> LENGTH: 18
<212> TYPE: DNA
<213> ORGANISM: Artificial Sequence
<220> FEATURE:
<223> OTHER INFORMATION: Primer

<400> SEQUENCE: 84
aactacatca agggcgac                                                 18

<210> SEQ ID NO 85
<211> LENGTH: 18
<212> TYPE: DNA
<213> ORGANISM: Artificial Sequence
<220> FEATURE:
<223> OTHER INFORMATION: Primer

<400> SEQUENCE: 85
gtacttgtac cggtaggg                                                 18

<210> SEQ ID NO 86
<211> LENGTH: 18
<212> TYPE: DNA
<213> ORGANISM: Artificial Sequence
<220> FEATURE:
<223> OTHER INFORMATION: Primer

<400> SEQUENCE: 86
cacagcgata gcggcaag                                                 18

<210> SEQ ID NO 87
<211> LENGTH: 18
<212> TYPE: DNA
<213> ORGANISM: Artificial Sequence
<220> FEATURE:
<223> OTHER INFORMATION: Primer

<400> SEQUENCE: 87
gtacttgtac cggtaggg                                                 18

<210> SEQ ID NO 88
<211> LENGTH: 18
<212> TYPE: DNA
<213> ORGANISM: Artificial Sequence
<220> FEATURE:
<223> OTHER INFORMATION: Primer

<400> SEQUENCE: 88
ctgaccaact gctacaag                                                 18

<210> SEQ ID NO 89
<211> LENGTH: 19
<212> TYPE: DNA
<213> ORGANISM: Artificial Sequence
<220> FEATURE:
<223> OTHER INFORMATION: Primer

<400> SEQUENCE: 89
ggtccagagg gtacagctt                                                19

<210> SEQ ID NO 90
<211> LENGTH: 18
<212> TYPE: DNA
<213> ORGANISM: Artificial Sequence
<220> FEATURE:
<223> OTHER INFORMATION: Primer

<400> SEQUENCE: 90
ctgtccttca tcctgaac                                                 18

<210> SEQ ID NO 91
<211> LENGTH: 21
<212> TYPE: DNA
<213> ORGANISM: Artificial Sequence
<220> FEATURE:
<223> OTHER INFORMATION: Primer

<400> SEQUENCE: 91
ttcagcgttg ttgtactcgt a                                             21

<210> SEQ ID NO 92
<211> LENGTH: 18
<212> TYPE: DNA
<213> ORGANISM: Artificial Sequence
<220> FEATURE:
<223> OTHER INFORMATION: Primer

<400> SEQUENCE: 92
ctgtccttca tcctgaac                                                 18

<210> SEQ ID NO 93
<211> LENGTH: 18
<212> TYPE: DNA
<213> ORGANISM: Artificial Sequence
<220> FEATURE:
<223> OTHER INFORMATION: Primer

<400> SEQUENCE: 93
gtccagaggg tacagctt                                                 18

<210> SEQ ID NO 94
<211> LENGTH: 18
<212> TYPE: DNA
<213> ORGANISM: Artificial Sequence
<220> FEATURE:
<223> OTHER INFORMATION: Primer

<400> SEQUENCE: 94
cactctgact ctggcacc                                         18

<210> SEQ ID NO 95
<211> LENGTH: 24
<212> TYPE: DNA
<213> ORGANISM: Artificial Sequence
<220> FEATURE:
<223> OTHER INFORMATION: Primer

<400> SEQUENCE: 95
agaggacttc atcttgttgt tggt                                  24

<210> SEQ ID NO 96
<211> LENGTH: 18
<212> TYPE: DNA
<213> ORGANISM: Artificial Sequence
<220> FEATURE:
<223> OTHER INFORMATION: Primer

<400> SEQUENCE: 96
ctgtccttca tcctgaac                                         18

<210> SEQ ID NO 97
<211> LENGTH: 24
<212> TYPE: DNA
<213> ORGANISM: Artificial Sequence
<220> FEATURE:
<223> OTHER INFORMATION: Primer

<400> SEQUENCE: 97
agaggacttc atcttgttgt tggt                                  24

<210> SEQ ID NO 98
<211> LENGTH: 18
<212> TYPE: DNA
<213> ORGANISM: Artificial Sequence
<220> FEATURE:
<223> OTHER INFORMATION: Primer

<400> SEQUENCE: 98
cactctgact ctggcacc                                         18

<210> SEQ ID NO 99
<211> LENGTH: 18
<212> TYPE: DNA
<213> ORGANISM: Artificial Sequence
<220> FEATURE:
<223> OTHER INFORMATION: Primer

<400> SEQUENCE: 99
gtccagctta gaggagtt                                         18

<210> SEQ ID NO 100
<211> LENGTH: 18
<212> TYPE: DNA
<213> ORGANISM: Artificial Sequence
<220> FEATURE:
<223> OTHER INFORMATION: Primer

<400> SEQUENCE: 100
ctgtccttca tcctgaac                                         18

<210> SEQ ID NO 101
<211> LENGTH: 18

```
<212> TYPE: DNA
<213> ORGANISM: Artificial Sequence
<220> FEATURE:
<223> OTHER INFORMATION: Primer

<400> SEQUENCE: 101
gtccagctta gaggagtt                                                 18

<210> SEQ ID NO 102
<211> LENGTH: 18
<212> TYPE: DNA
<213> ORGANISM: Artificial Sequence
<220> FEATURE:
<223> OTHER INFORMATION: Primer

<400> SEQUENCE: 102
cactctgact ctggcacc                                                 18

<210> SEQ ID NO 103
<211> LENGTH: 18
<212> TYPE: DNA
<213> ORGANISM: Artificial Sequence
<220> FEATURE:
<223> OTHER INFORMATION: Primer

<400> SEQUENCE: 103
ggcggcgttg gtggtaga                                                 18

<210> SEQ ID NO 104
<211> LENGTH: 18
<212> TYPE: DNA
<213> ORGANISM: Artificial Sequence
<220> FEATURE:
<223> OTHER INFORMATION: Primer

<400> SEQUENCE: 104
ctgtccttca tcctgaac                                                 18

<210> SEQ ID NO 105
<211> LENGTH: 18
<212> TYPE: DNA
<213> ORGANISM: Artificial Sequence
<220> FEATURE:
<223> OTHER INFORMATION: Primer

<400> SEQUENCE: 105
ggcggcgttg gtggtaga                                                 18

<210> SEQ ID NO 106
<211> LENGTH: 18
<212> TYPE: DNA
<213> ORGANISM: Artificial Sequence
<220> FEATURE:
<223> OTHER INFORMATION: Primer

<400> SEQUENCE: 106
cactctgact ctggcacc                                                 18

<210> SEQ ID NO 107
<211> LENGTH: 18
<212> TYPE: DNA
<213> ORGANISM: Artificial Sequence
<220> FEATURE:
<223> OTHER INFORMATION: Primer

<400> SEQUENCE: 107
```
gtacttgtat ccgtgggg                                                         18

<210> SEQ ID NO 108
<211> LENGTH: 18
<212> TYPE: DNA
<213> ORGANISM: Artificial Sequence
<220> FEATURE:
<223> OTHER INFORMATION: Primer

<400> SEQUENCE: 108
ctgtccttca tcctgaac                                                         18

<210> SEQ ID NO 109
<211> LENGTH: 18
<212> TYPE: DNA
<213> ORGANISM: Artificial Sequence
<220> FEATURE:
<223> OTHER INFORMATION: Primer

<400> SEQUENCE: 109
gtacttgtat ccgtgggg                                                         18

<210> SEQ ID NO 110
<211> LENGTH: 18
<212> TYPE: DNA
<213> ORGANISM: Artificial Sequence
<220> FEATURE:
<223> OTHER INFORMATION: Primer

<400> SEQUENCE: 110
cacagcgata gcggcaag                                                         18

<210> SEQ ID NO 111
<211> LENGTH: 36
<212> TYPE: DNA
<213> ORGANISM: Artificial Sequence
<220> FEATURE:
<223> OTHER INFORMATION: Primer

<400> SEQUENCE: 111
ggtgtcgaag ttgatgtcgg gcagattgcc caggta                                     36

<210> SEQ ID NO 112
<211> LENGTH: 18
<212> TYPE: DNA
<213> ORGANISM: Artificial Sequence
<220> FEATURE:
<223> OTHER INFORMATION: Primer

<400> SEQUENCE: 112
cacagcgata gcggcaag                                                         18

<210> SEQ ID NO 113
<211> LENGTH: 36
<212> TYPE: DNA
<213> ORGANISM: Artificial Sequence
<220> FEATURE:
<223> OTHER INFORMATION: Primer

<400> SEQUENCE: 113
agctgcggcc agattagcgc cctcgtggaa ggacac                                     36

<210> SEQ ID NO 114
<211> LENGTH: 18
<212> TYPE: DNA
<213> ORGANISM: Artificial Sequence

```
<220> FEATURE:
<223> OTHER INFORMATION: Primer

<400> SEQUENCE: 114
cacagcgata gcggcaag                                                 18

<210> SEQ ID NO 115
<211> LENGTH: 36
<212> TYPE: DNA
<213> ORGANISM: Artificial Sequence
<220> FEATURE:
<223> OTHER INFORMATION: Primer

<400> SEQUENCE: 115
agcgcattca gctgcggcgt tggtcttgat ggagct                             36

<210> SEQ ID NO 116
<211> LENGTH: 18
<212> TYPE: DNA
<213> ORGANISM: Artificial Sequence
<220> FEATURE:
<223> OTHER INFORMATION: Primer

<400> SEQUENCE: 116
cacagcgata gcggcaag                                                 18

<210> SEQ ID NO 117
<211> LENGTH: 18
<212> TYPE: DNA
<213> ORGANISM: Artificial Sequence
<220> FEATURE:
<223> OTHER INFORMATION: Primer

<400> SEQUENCE: 117
gtccagcttg ctggagtt                                                 18

<210> SEQ ID NO 118
<211> LENGTH: 36
<212> TYPE: DNA
<213> ORGANISM: Artificial Sequence
<220> FEATURE:
<223> OTHER INFORMATION: Primer

<400> SEQUENCE: 118
gctaatctgg ccgcagctta cccccagaat aagaac                             36

<210> SEQ ID NO 119
<211> LENGTH: 18
<212> TYPE: DNA
<213> ORGANISM: Artificial Sequence
<220> FEATURE:
<223> OTHER INFORMATION: Primer

<400> SEQUENCE: 119
gtccagcttg ctggagtt                                                 18

<210> SEQ ID NO 120
<211> LENGTH: 36
<212> TYPE: DNA
<213> ORGANISM: Artificial Sequence
<220> FEATURE:
<223> OTHER INFORMATION: Primer

<400> SEQUENCE: 120
gccgcagctg aatgcgctga cgtgaagctg ggcgtg                             36
```

<210> SEQ ID NO 121
<211> LENGTH: 18
<212> TYPE: DNA
<213> ORGANISM: Artificial Sequence
<220> FEATURE:
<223> OTHER INFORMATION: Primer

<400> SEQUENCE: 121
gtccagcttg ctggagtt                                                 18

<210> SEQ ID NO 122
<211> LENGTH: 18
<212> TYPE: DNA
<213> ORGANISM: Artificial Sequence
<220> FEATURE:
<223> OTHER INFORMATION: Primer

<400> SEQUENCE: 122
cacagcgata gcggcaag                                                 18

<210> SEQ ID NO 123
<211> LENGTH: 18
<212> TYPE: DNA
<213> ORGANISM: Artificial Sequence
<220> FEATURE:
<223> OTHER INFORMATION: Primer

<400> SEQUENCE: 123
gtccagcttg ctggagtt                                                 18

<210> SEQ ID NO 124
<211> LENGTH: 18
<212> TYPE: DNA
<213> ORGANISM: Artificial Sequence
<220> FEATURE:
<223> OTHER INFORMATION: Primer

<400> SEQUENCE: 124
cacagcgata gcggcaag                                                 18

<210> SEQ ID NO 125
<211> LENGTH: 18
<212> TYPE: DNA
<213> ORGANISM: Artificial Sequence
<220> FEATURE:
<223> OTHER INFORMATION: Primer

<400> SEQUENCE: 125
gtccagcttg ctggagtt                                                 18

<210> SEQ ID NO 126
<211> LENGTH: 18
<212> TYPE: DNA
<213> ORGANISM: Artificial Sequence
<220> FEATURE:
<223> OTHER INFORMATION: Primer

<400> SEQUENCE: 126
cacagcgata gcggcaag                                                 18

<210> SEQ ID NO 127
<211> LENGTH: 18
<212> TYPE: DNA
<213> ORGANISM: Artificial Sequence

```
<220> FEATURE:
<223> OTHER INFORMATION: Primer

<400> SEQUENCE: 127
gtccagcttg ctggagtt                                              18
```

VAR2CSA-DRUG CONJUGATES

CROSS REFERENCE TO RELATED APPLICATIONS

This application claims the benefit under 35 U.S.C. § 119(e) of U.S. Provisional Patent Application No. 61/921,242, U.S. Provisional Patent Application No. 62/051,886, filed Sep. 17, 2014, filed Dec. 27, 2013, and U.S. Provisional Patent Application No. 62/051,899, filed Sep. 17, 2014, which applications are incorporated herein by reference in their entireties.

BACKGROUND

Field

The invention relates to drug conjugates, compositions comprising the same, and methods of using such drug conjugates and compositions for the treatment of cancer and other diseases.

Description of the Related Art

VAR2CSA Protein

Proteoglycans are proteins conjugated to glycosaminoglycan (GAG) chains. These proteins are distributed inside cells, on the cell membrane and in the extracellular matrix serving a variety of functions: cartilage matrix formation; the structural organization of tissues; organizations of basement membranes; regulating the role of secretory vesicles; binding of cytokines, chemokines, growth factors, and morphogens; protease receptors and protease inhibitors; co-receptors, tyrosine-kinase-type growth factor receptors; as endocytic receptors; facilitate cell attachment, cell-cell interactions, and cell motility as well as cell migration.

The malaria parasite *Plasmodium falciparum* utilizes host cell proteoglycans in almost all stages of its complex life cycle. The sporozoite infects hepatocytes in the liver through surface-expressed circumsporozoite protein interacting with highly sulfated heparan sulfate proteoglycans (HSPG). Merozoite infection of the erythrocytes is mediated by EBA-175 binding to sialic acid on glycophorin A. In addition, a number of *Plasmodium falciparum* Erythrocyte Membrane Protein 1 (PfEMP1) proteins, mediating host endothelial adhesion, have been described as glycan-binding. One of these is VAR2CSA, which is a unique member of the PfEMP1 protein family. VAR2CSA binds with high affinity to a distinct form of chondroitin sulfate A (CSA), attached to proteoglycans, so called Chondroitin Sulfate Proteoglycan (CSPG), in the intervillous spaces of the placenta. This type of CSA is referred to as placental-like CSA (plCSA). VAR2CSA is a large multi-domain protein (350 kDa) expressed on the surface of *P. falciparum*-infected erythrocytes (IEs), and the VAR2CSA-plCSA interaction is responsible for placenta specific sequestration in placental malaria (PM). Importantly, recombinant full-length VAR2CSA ecto-domain from FCR3 and 3D7 type parasites has shown affinity for plCSA in the low nano-molar range.

CSA belongs to the family of glycosaminoglycans (GAGs), which are linear polymers of alternating amino sugars and hexuronic acid residues, attached to proteoglycans. There are several types of GAGs including: chondroitin sulfate (CS), dermatan sulfate (DS or CSB), heparan sulfate (HS) and heparin. While the polysaccharide backbone of these GAGs is simple, considerable diversity arises in modifications such as sulfation and uronate epimerization. This is the basis for the wide variety in domain structure and biological activities of different GAGs.

CS interacts with many important factors such as growth hormones, cytokines, chemokines, and adhesion molecules and is thought to be involved in structural stabilization, cytokinesis, cell proliferation, differentiation, cell migration, tissue morphogenesis, organogenesis, infection, and wound repair. CS chains are composed of alternating units of N-acetyl-D-galactosamine (GalNAc) and glucuronic acid residues. Glucuronic acid can be sulfated at its $C_2$ position and GalNAc can be sulfated at $C_4$ and/or $C_6$, giving rise to various disaccharide units. Varying modifications of the sugar backbone allows structural and functional heterogeneity of the CS chains.

Chondroitin sulfate proteoglycan 4 (CSPG4), also known as High Molecular Weight-Melanoma Associated Antigen (HMW-MAA) or melanoma-associated chondroitin sulfate proteoglycan (MSCP), is a cell surface proteoglycan which has been shown to be expressed by melanoma cells. CSPG4/MSCP/HMW-MAA is a large proteoglycan characterized by having CS chains on the protein backbone.

VAR2CSA retains its ability to bind with high affinity and specificity to certain chondroitin sulfate proteoglycans with minimal structural elements of the polypeptide sequence. The core plCSA-binding site lies within the DBL2X domain including small parts of the flanking interdomain regions. The binding does not depend on the ID2b region, or on the DBL1X or DBL3X flanking domains, as previously suggested. The minimal binding region is ID1-DBL2Xb, which binds CSPG with characteristics comparable to that of full-length VAR2CSA. The ID1-DBL2Xb minimal binding region is much smaller than full-length VAR2CSA, having a molecular weight of only 62 kDa. This VAR2CSA fragment and other VAR2CSA polypeptides bind with high and specific affinity to cancer cells and tissues, which binding is suggested to be through a specific interaction with chondroitin sulfate proteoglycans expressed on the surface of the cancer cells or in the surrounding extracellular matrix (Salanti et al., WO2013/117705). Accordingly, this specific and high affinity binding may be used for the targeting of cancer cells or other tissues or cells with high or otherwise expression, such as inappropriate expression, of this particular type of chondroitin sulfate proteoglycan.

In the medical field, there is a need for stable protein-drug conjugates that can release biologically active compounds selectively at desired target locations having high, or otherwise inappropriate, expression of chondroitin sulfate proteoglycans. The present disclosure fulfills these needs and provides further related advantages.

BRIEF SUMMARY

In brief, the present disclosure is directed to biologically active protein-drug conjugates and methods of using such protein-drug conjugates. Provided are protein-drug conjugates which are compounds of Formula I:

T-L-P            I wherein:

T is a targeting moiety comprising a VAR2CSA polypeptide;

L-P is selected from: $L^1$-$P^1$ or $L^2$-$P^2$;

$L^1$ is a linker, or $L^1$ is absent;

P¹ is a monovalent radical of a compound of Formula XIV

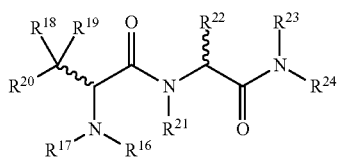

XIV wherein:
$R^{16}$ and $R^{17}$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO$_2$H, —CHO, —COSH, or —NO$_2$; or $R^{17}$ and $R^{20}$ are fused and form a ring;
$R^{18}$ and $R^{19}$ are independently selected from the group consisting of: H, $R^{25}$, and ArR$^{25}$—, or $R^{18}$ and $R^{19}$ are joined to form a ring;
$R^{20}$ is selected from the group consisting of: H, $R^{25}$, ArR$^{25}$—, and Ar; or $R^{20}$ and $R^{17}$ are fused and form a ring;
$R^{21}$ is selected from the group consisting of: H, $R^{25}$, and ArR$^{25}$—;
$R^{22}$ and $R^{23}$ are independently selected from the group consisting of: H, $R^{25}$, and ArR$^{25}$—;
$R^{24}$ is: —Y—(CO)NHSO$_2$—$R^{26}$
$R^{25}$ is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$^{28}$, —O$_2$CR$^{28}$, —SH, —SR$^{28}$, —SOCR$^{28}$, —NH$_2$, —NHR$^{28}$, —N(R$^{28}$)$_2$, —NHCOR$^{28}$, —NR$^{28}$COR$^{28}$, —I, —Br, —Cl, —F, —CN, —CO$_2$H, —CO$_2$R$^{28}$, —CHO, —COR$^{28}$, —CONH$_2$, —CONHR$^{28}$, —CON(R$^{28}$)$_2$, —COSH, —COSR$^{28}$, —NO$_2$, —SO$_3$H, —SOR$^{28}$, —SO$_2$R$^{28}$, wherein R$^{28}$ is a linear, branched or cyclic, one to ten carbon saturated or unsaturated alkyl group;
the ring formed by joining $R^{18}$ and $R^{19}$ is a three to seven member non-aromatic cyclic skeleton within the definition of $R^{25}$,
Y is defined as a moiety selected from the group consisting of: a linear, saturated or unsaturated, one to six carbon alkyl group, optionally substituted with $R^{25}$, ArR$^{25}$—, or X; and,
X is defined as a moiety selected from the group consisting of: —OH, —OR$^{25}$, =O, =S, —O$_2$CR$^{25}$, —SH, —SR$^{25}$, —SOCR$^{25}$, —NH$_2$, —NHR$^{25}$, —N(R$^{25}$)$_2$, —NHCOR$^{25}$, —NRCOR$^{25}$, —I, —Br, —Cl, —F, —CN, —CO$_2$H, —CO$_2$R$^{25}$, —CHO, —COR$^{25}$, —CONH$_2$, —CONHR$^{25}$, —CON(R$^{25}$)$_2$, —COSH, —COSR$^{25}$, —NO$_2$, —SO$_3$H, —SOR$^{25}$, and —SO$_2$R$^{25}$;
$R^{26}$ is selected from the group consisting of optionally substituted alkyl, optionally substituted alkylamino, optionally substituted cycloalkyl, optionally substituted aryl, optionally substituted heterocyclyl, optionally substituted heteroaryl, —COR$^{27}$, —CSR$^{27}$, —OR$^{27}$, and —NHR$^{27}$, wherein each R$^{27}$ is, independently, optionally substituted alkyl, optionally substituted alkylamino, optionally substituted cycloalkyl, optionally substituted aryl, optionally substituted heterocyclyl, or optionally substituted heteroaryl; and
$L^2$ is a linker, or $L^2$ is absent;
$P^2$ is a biologically active compound; and
$L^2$-$P^2$ has the following structure (III):

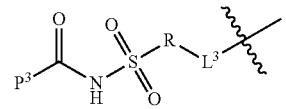

III wherein:
R is selected from the group consisting of optionally substituted alkyl, optionally substituted alkylamino, optionally substituted cycloalkyl, optionally substituted aryl, optionally substituted heterocyclyl, optionally substituted heteroaryl, —COR$^{27}$, —CSR$^{27}$, —OR$^{27}$, and —NHR$^{27}$, wherein each R$^{27}$ is, independently, optionally substituted alkyl, optionally substituted alkylamino, optionally substituted cycloalkyl, optionally substituted aryl, optionally substituted heterocyclyl, or optionally substituted heteroaryl, or R is absent;
$P^3$ is the remaining portion of compound $P^2$; and
$L^3$ is optionally the remaining portion of linker $L^2$ when $L^2$ is present.

In a preferred embodiment, R is selected from the group consisting of optionally substituted alkyl, optionally substituted alkylamino, optionally substituted cycloalkyl, optionally substituted aryl, optionally substituted heterocyclyl and optionally substituted heteroaryl, or R is absent.

In another embodiment, a method of using a compound of Formula I in therapy is provided. In particular, the present disclosure provides a method of treating cancer in a mammal comprising administering to a mammal in need thereof an effective amount of a compound of Formula I or a pharmaceutical composition comprising a compound of Formula I and a pharmaceutically acceptable carrier diluent or excipient.

In another embodiment, the present disclosure provides a method of inhibiting tumor growth in a mammal comprising administering to a mammal in need thereof an effective amount of a compound of Formula I or a pharmaceutical composition comprising a compound of Formula I and a pharmaceutically acceptable carrier, diluent or excipient.

In another embodiment, the present disclosure provides a method of killing cancer cells in vitro using a compound of construct. In another embodiment, the present disclosure provides a method of killing cancer cells in vivo in a mammal, comprising administering to a mammal in need thereof an effective amount of a compound of Formula I or a pharmaceutical composition comprising a compound of Formula I and a pharmaceutically acceptable carrier, diluent or excipient.

These and other aspects of the disclosure will be apparent upon reference to the following detailed description.

BRIEF DESCRIPTION OF THE DRAWINGS

Figure 14:
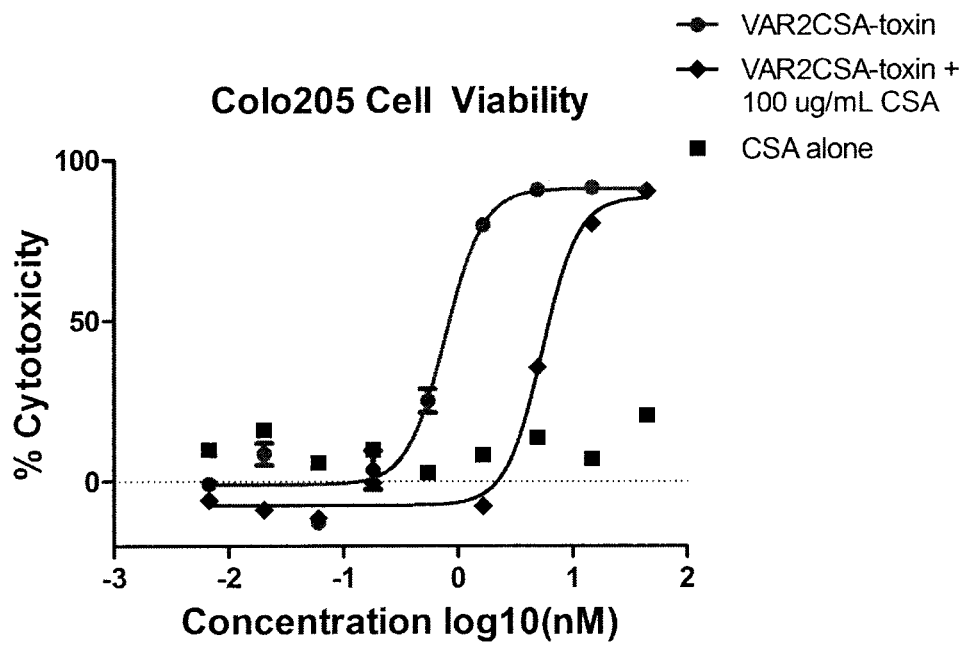

FIG. 14 shows the cytotoxicity of VAR2CSA drug conjugate against Colo205 cells. The VAR2 protein used was DBL1-ID2a. VAR2-Compound O—circles. VAR2-Compound O with added CSA (Sigma C9819)—diamonds. CSA alone—squares.

FIG. 16 shows the cytotoxicity of VAR2CSA drug conjugates against Colo205 cells. VAR2-Compound O—circles. Toxin-linker alone—squares.

Figure 18:
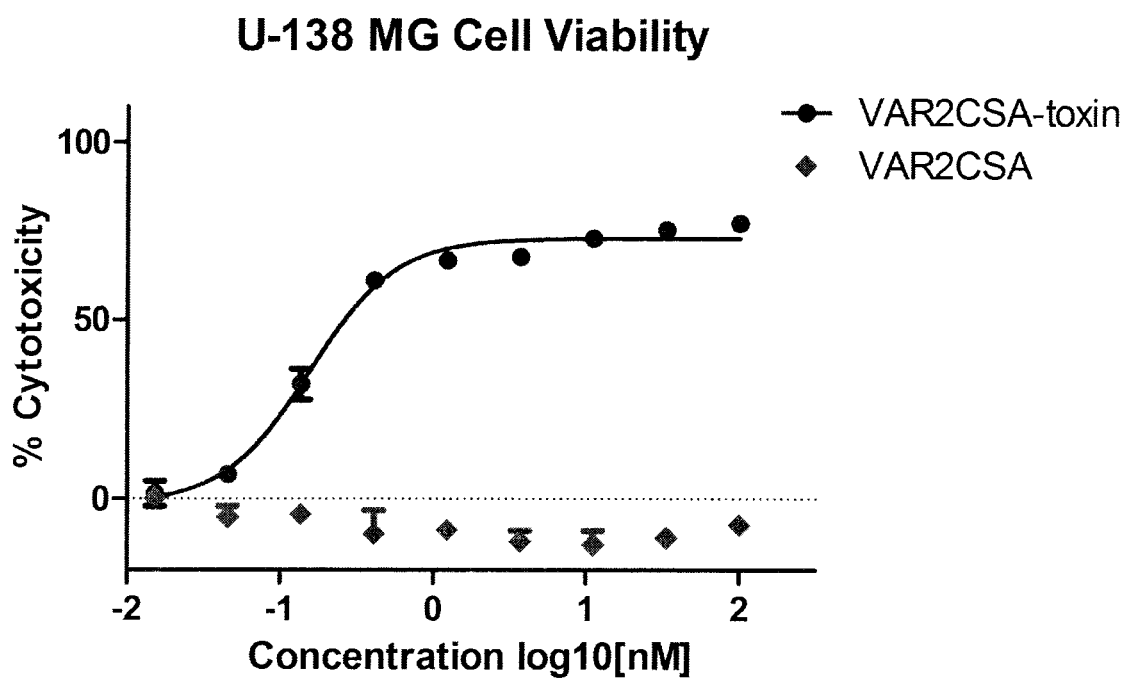

FIG. 18 shows the cytotoxicity of VAR2CSA drug conjugates against U138 MG Cells. VAR2-Compound O—circles. VAR2CSA alone—diamonds.

DETAILED DESCRIPTION

Figure 1:
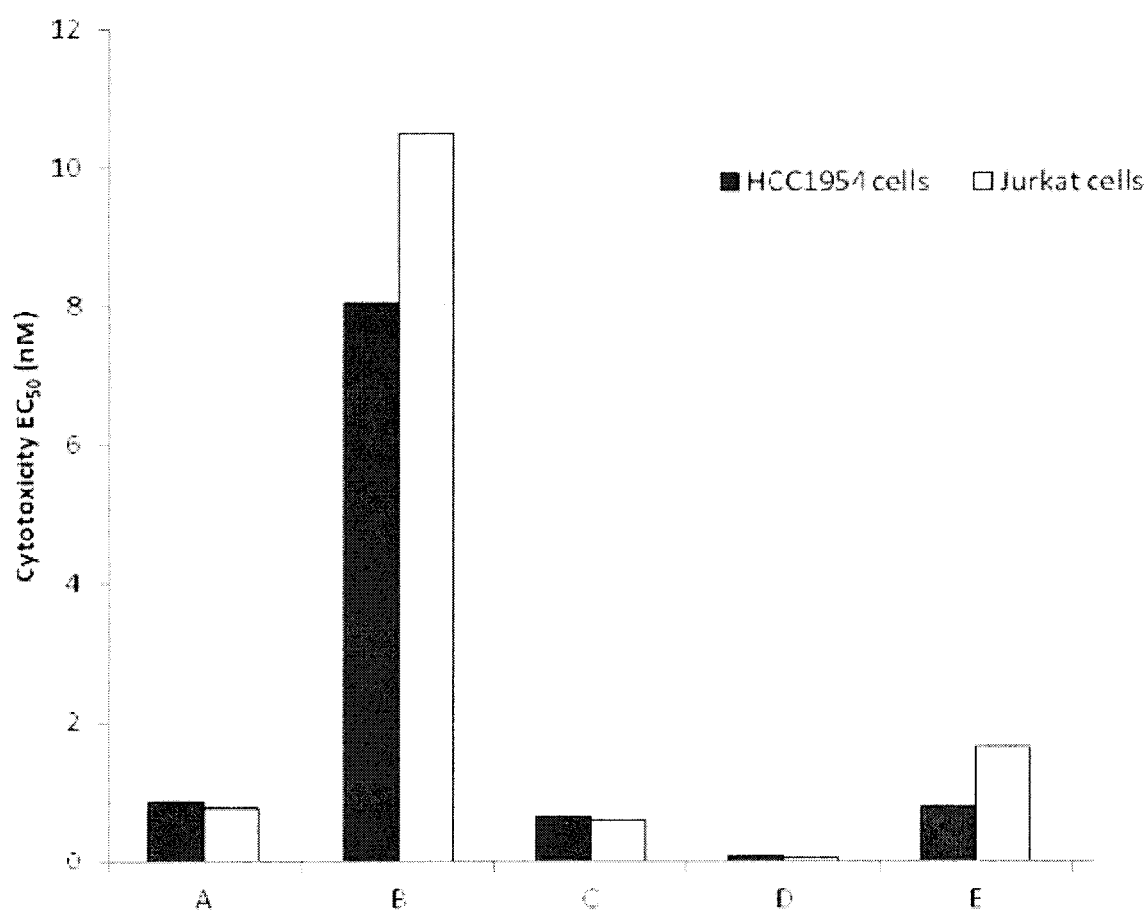
FIG. 1 shows summarized cytotoxicity data (EC$_{50}$) for each of Compounds A-E for two cell lines (HCC1954 and Jurkat)
Figure 2:
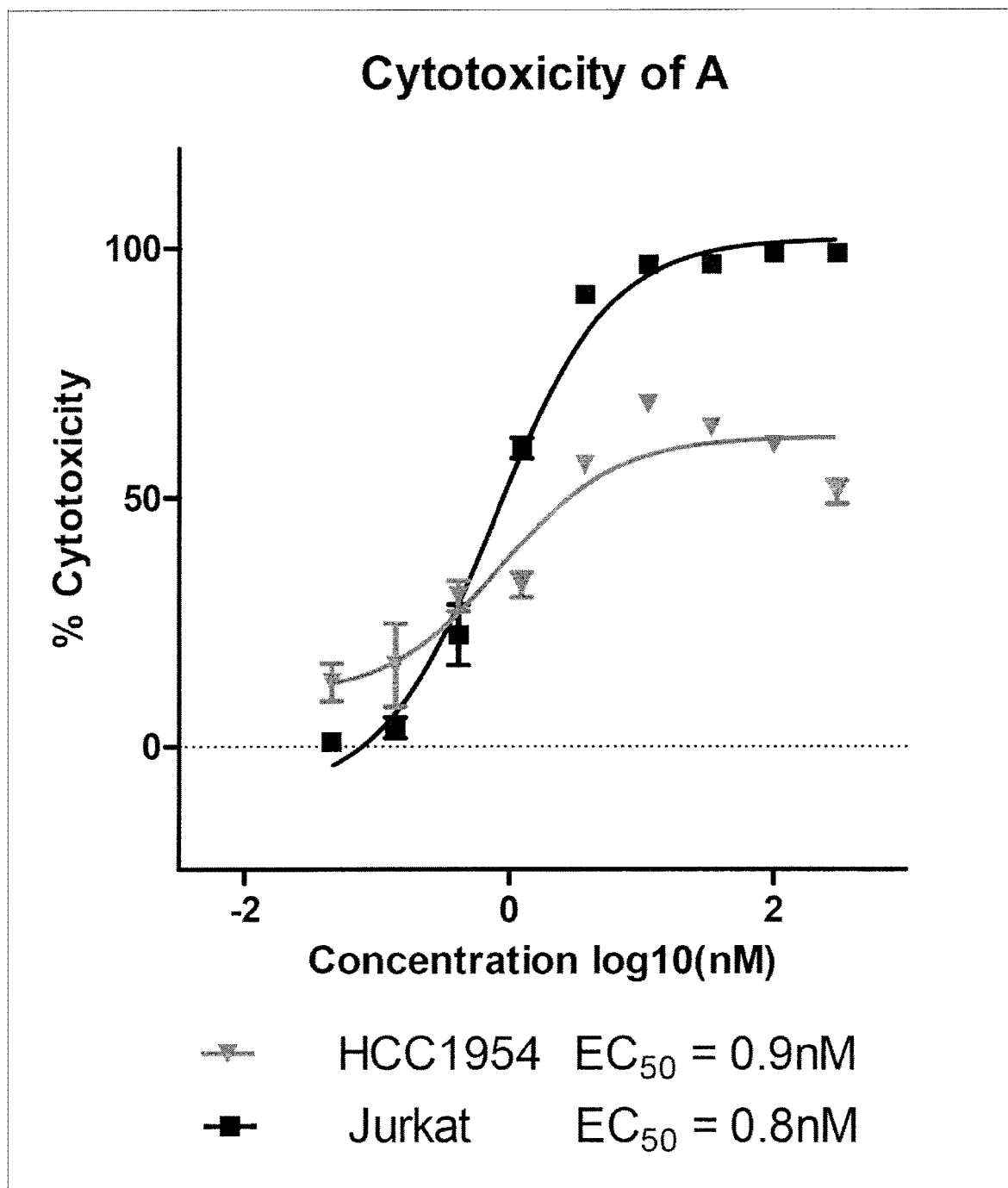
FIG. 2 shows a cytotoxicity data plot for Compound A on two cell lines (HCC1954 and Jurkat)
Figure 3:
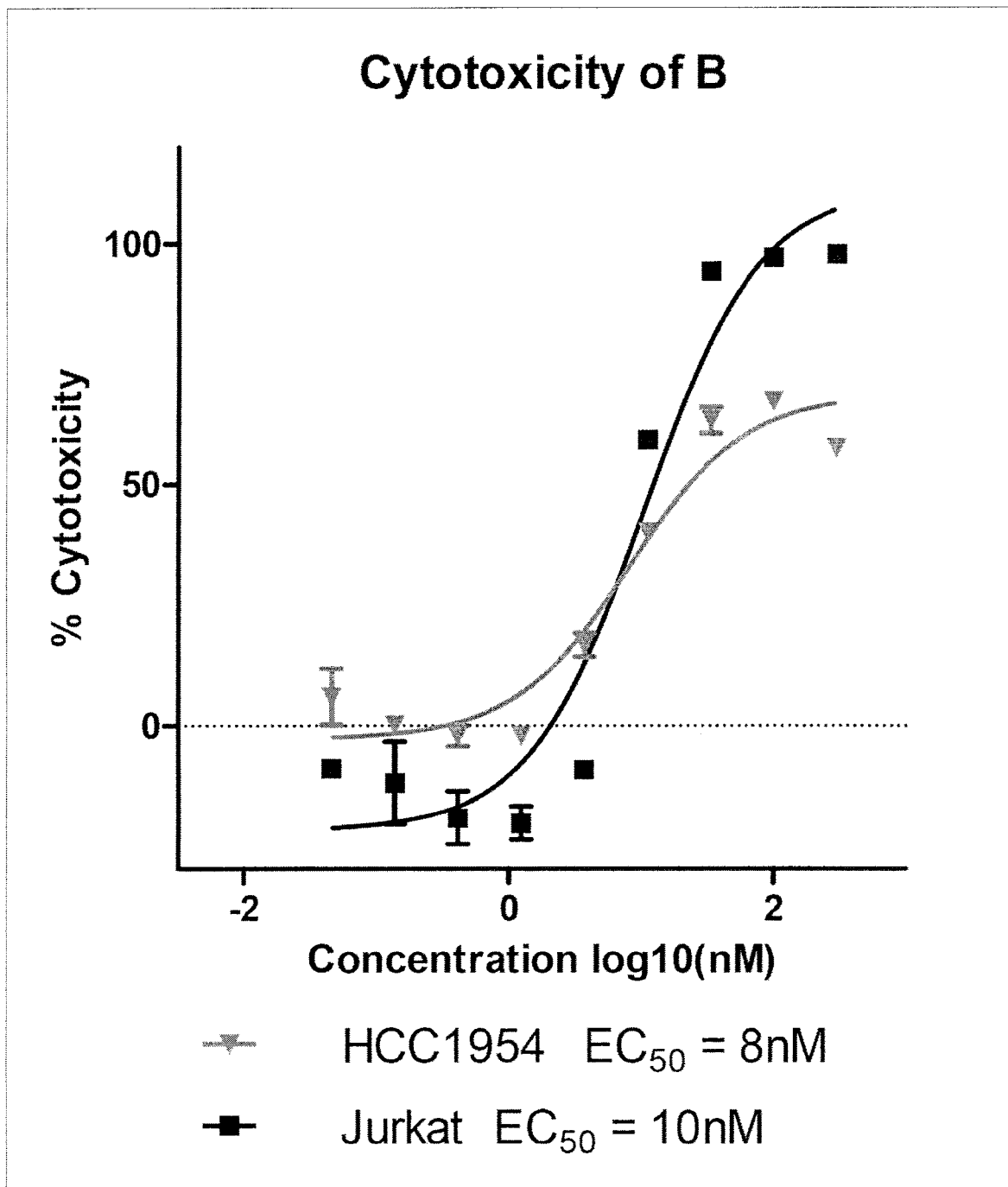
FIG. 3 shows a cytotoxicity data plot for Compound B on two cell lines (HCC1954 and Jurkat).
Figure 4:
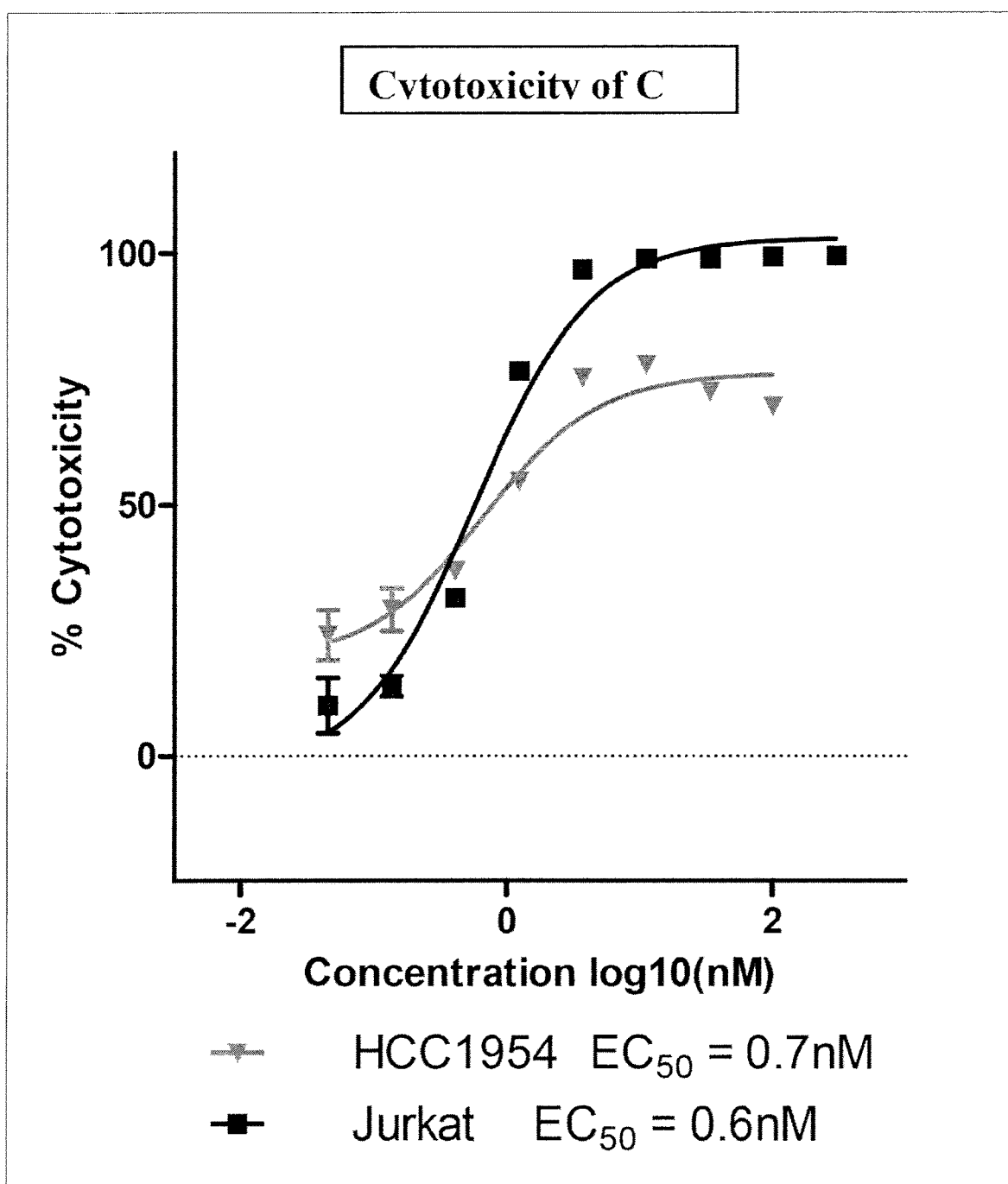
FIG. 4 shows a cytotoxicity data plot for Compound C on two cell lines (HCC1954 and Jurkat).
Figure 5:
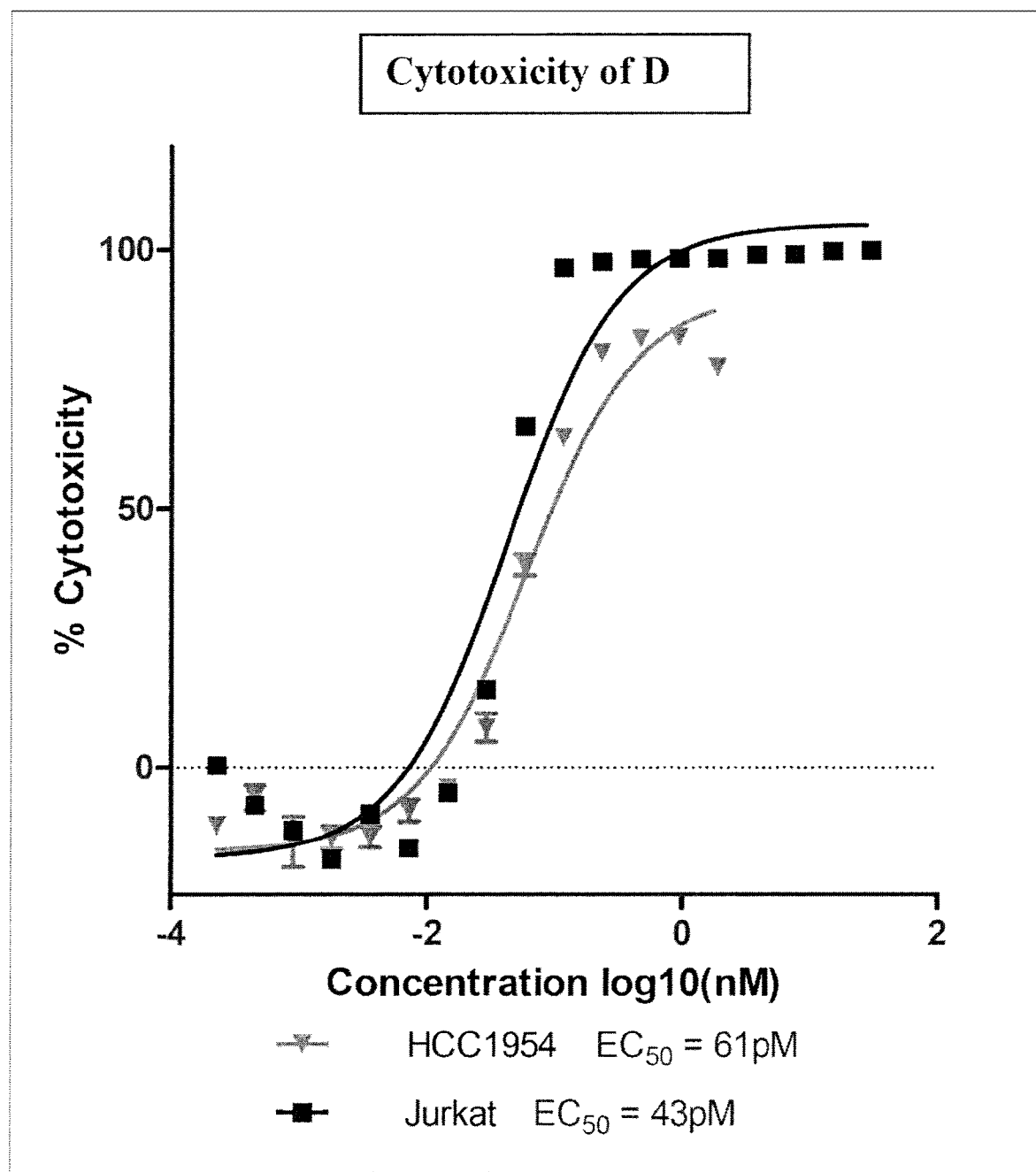
FIG. 5 shows a cytotoxicity data plot for Compound D on two cell lines (HCC1954 and Jurkat).
Figure 6:
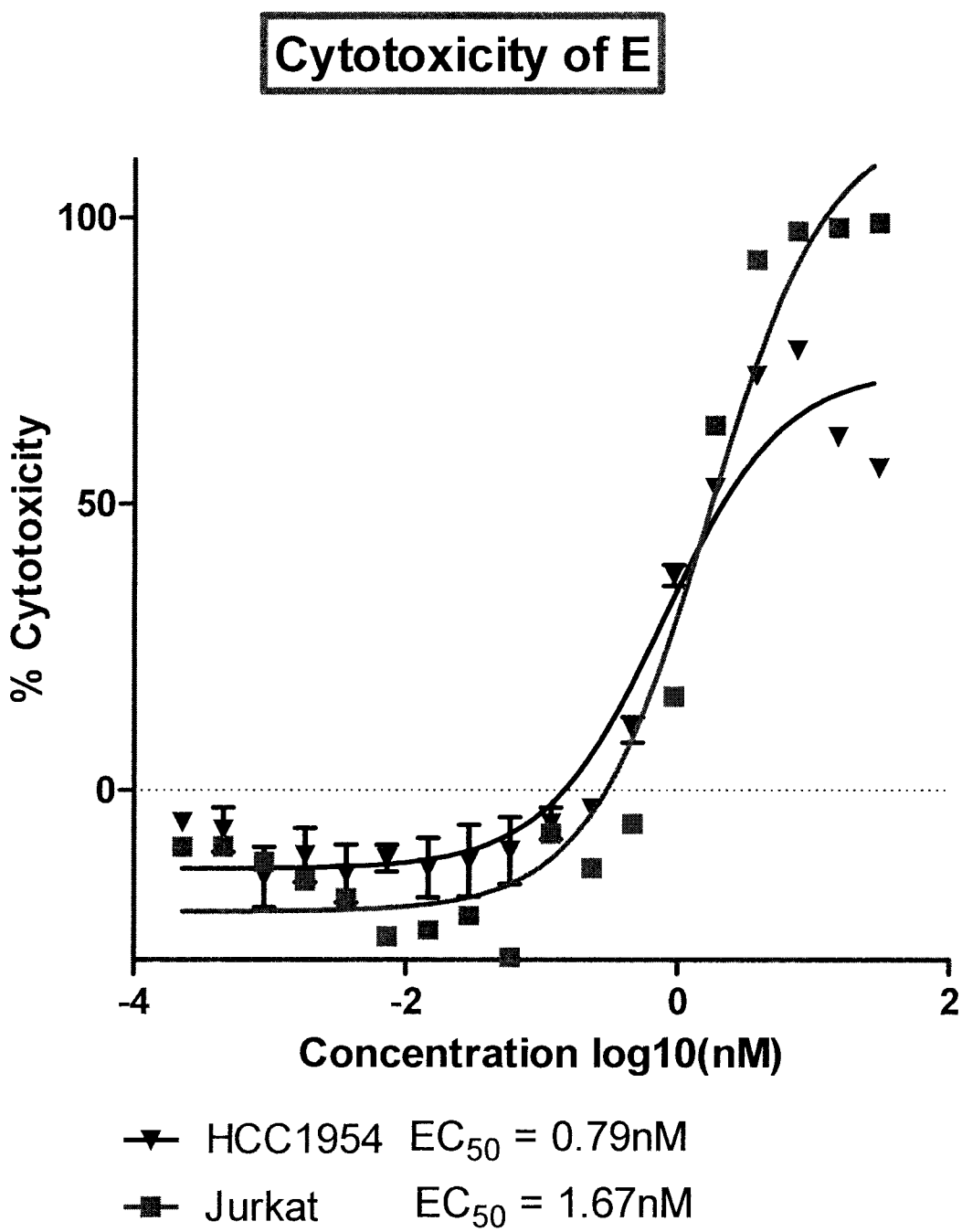
FIG. 6 shows a cytotoxicity data plot for Compound E on two cell lines (HCC1954 and Jurkat).

In the following description, certain specific details are set forth in order to provide a thorough understanding of various embodiments of the disclosure. However, one skilled in the art will understand that the disclosure may be practiced without these details.

Definitions

Unless stated otherwise, the following terms and phrases as used herein are intended to have the following meanings. When trade names are used herein, applicants intend to independently include the trade name product formulation, the generic drug, and the active pharmaceutical ingredient(s) of the trade name product.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination.

Chemical Groups

All combinations of the embodiments pertaining to the chemical groups represented by the variables (e.g., $R^1$-$R^{50}$, Q, X, Y, and Z) contained within the generic chemical formulae described herein, (e.g., II, XIV, XV, and XX) are specifically embraced by the present invention just as if each and every combination was individually explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein. In addition, in the event that a list of substituents is listed for any particular variable (e.g., $R^1$-$R^{50}$, Q, X, Y, and Z) in a particular embodiment and/or claim, it is understood that each individual substituent may be deleted from the particular embodiment and/or claim and that the remaining list of substituents will be considered to be within the scope of the present disclosure.

The term "acyloxy", as used herein, includes —OC(O)-alkyl, wherein alkyl is as defined herein. Examples of acyloxy include, but are not limited to: formyloxy, acetoxy, propionyloxy, isobutyryloxy, pivaloyloxy, and the like.

The term "acylthio", as used herein, refers to —SC(O)-alkyl, wherein alkyl is as defined herein. Examples of acylthio include, but are not limited to: formylthio, acetylthio, propionylthio, isobutyrylthio, pivaloylthio, and the like.

The term "alkoxycarbonyl", as used herein, refers to —C(O)O-alkyl. Examples of alkoxycarbonyl include, but are not limited to: methoxycarbonyl, ethoxycarbonyl, n-propoxycarbonyl, isopropoxycarbonyl, n-butoxycarbonyl, sec-butoxycarbonyl, isobutoxycarbonyl, t-butoxycarbonyl, pentyloxycarbonyl, isopentyloxycarbonyl, t-pentyloxycarbonyl, neo-pentyloxycarbonyl, 1-methylbutoxycarbonyl, 2-methylbutoxycarbonyl, n-hexyloxycarbonyl, and the like.

"Alkyl" refers to a straight or branched hydrocarbon chain substituent consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" or "alkyldiyl" refers to a straight or branched divalent hydrocarbon chain linking the rest of the molecule to a substituent group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the substituent group through a single or double bond. The points of attachment of the alkylene chain to the rest of the molecule and to the substituent group can be through one carbon or any two carbons within the chain. Unless stated otherwise specifically in the specification, an alkylene chain may be optionally substituted.

The term "alkenyldiyl", as used herein, refers to a straight or branched unsaturated hydrocarbon di-radical containing the specified number of carbon atoms, and one or more carbon-carbon double bonds, e.g., $C_2$-$C_6$ alkenyldiyl, $C_2$-$C_4$ alkenyldiyl, or $C_2$ alkenyldiyl. Examples of alkenyldiyl include, but are not limited to: ethenyldiyl, n-propenyldiyl, isopropenyldiyl, n-butenyldiyl, sec-butenyldiyl, isobutenyldiyl, t-butenyldiyl, pentenyldiyl, isopentenyldiyl, t-pentenyldiyl, neo-pentenyldiyl, 1-methylbutenyldiyl, 2-methylbutenyldiyl, n-hexenyldiyl, and the like.

"Alkoxy" refers to a substituent of the formula —$OR_a$ where $R_a$ is an alkyl substituent as defined above containing one to twelve carbon atoms. Unless stated otherwise specifically in the specification, an alkoxy group may be optionally substituted.

"Alkylamino" refers to a substituent of the formula —$NHR_a$ or —$NR_aR_a$ where each $R_a$ is, independently, an alkyl substituent as defined above containing one to twelve carbon atoms. Unless stated otherwise specifically in the specification, an alkylamino group may be optionally substituted.

"Amino" refers to the —$NH_2$ substituent.

The term "amino-cycloalkyl", as used herein, refers to a cycloalkyl group, substituted with one amino substituent, as those terms are defined herein. Examples of amino-cycloalkyl include, but are not limited to: aminocyclopropyl, aminocyclobutyl, aminocyclopentyl, aminocyclohexyl, and the like.

The term "amino-alkyl", as used herein, refers to an alkyl group, substituted with one amino substituent, as those terms are defined herein. Examples of amino-alkyl include, but are not limited to: aminomethyl, aminoethyl, amino-n-propyl, amino-isopropyl, amino-n-butyl, amino-sec-butyl, amino-isobutyl, amino-t-butyl, amino-pentyl, amino-isopentyl, amino-t-pentyl, amino-neo-pentyl, amino-1-methylbutyl, amino-2-methylbutyl, amino-n-hexyl, and the like.

The term "amino-aryl", as used herein, refers to an aryl group, substituted with one amino substituent, as those terms are defined herein. Examples of amino-aryl include, but are not limited to: amino-phenyl, amino-naphthalenyl, and the like.

"Aryl" refers to a hydrocarbon ring system substituent comprising hydrogen, 6 to 18 carbon atoms and at least one aromatic ring. For purposes of this disclosure, the aryl substituent may be a monocyclic, bicyclic, tricyclic or tetracyclic ring system, which may include fused or bridged ring systems. Aryl substituents include, but are not limited to, aryl substituents derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl substituents that are optionally substituted.

"Aralkyl" refers to a substituent of the formula —$R_b$—$R_c$ where $R_b$ is an alkylene chain as defined above and $R_c$ is one or more aryl substituents as defined above, for example, benzyl, diphenylmethyl and the like. Unless stated otherwise specifically in the specification, an aralkyl group may be optionally substituted.

The term "carboxamide", as used herein, refers to —C(O)$NH_2$.

The term "carboxyl", as used herein, refers to —C(O)OH.

"Cyano" refers to the —CN substituent.

"Cycloalkyl" or "carbocyclic ring" refers to a stable non-aromatic monocyclic or polycyclic hydrocarbon substituent consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic substituents include, for example, cyclopropyl, cyclobutyl, cyclopentyl, cyclohexyl, cycloheptyl, and cyclooctyl. Polycyclic substituents include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a substituent of the formula —$R_bR_d$ where $R_d$ is an alkylene chain as defined above and $R_g$ is a cycloalkyl substituent as defined above. Unless stated otherwise specifically in the specification, a cycloalkylalkyl group may be optionally substituted.

"Fused" refers to any ring structure described herein which is fused to an existing ring structure in the compounds of the disclosure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl substituent, as defined above, that is substituted by one or more halo substituents, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

The term "haloalkoxy", as used herein, refers to —O-haloalkyl, wherein haloalkyl is as defined herein. Examples of haloalkoxy include, but are not limited to: difluoromethoxy, trifluoromethoxy, 2,2,2-trifluoroethoxy, pentafluoroethoxy, and the like.

"Heteroaryl" refers to a 5- to 14-membered ring system substituent comprising hydrogen atoms, one to thirteen carbon atoms, one to six heteroatoms selected from the group consisting of nitrogen, oxygen and sulfur, and at least one aromatic ring. For purposes of this disclosure, the heteroaryl substituent may be a monocyclic, bicyclic, tricyclic or tetracyclic ring system, which may include fused or bridged ring systems; and the nitrogen, carbon or sulfur atoms in the heteroaryl substituent may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl substituent as defined above containing at least one nitrogen and where the point of attachment of the heteroaryl substituent to the rest of the molecule is through a nitrogen atom in the heteroaryl substituent. Unless stated otherwise specifically in the specification, an N-heteroaryl group may be optionally substituted.

"Heteroarylalkyl" refers to a substituent of the formula —$R_bR_f$ where $R_b$ is an alkylene chain as defined above and $R_f$ is a heteroaryl substituent as defined above. Unless stated otherwise specifically in the specification, a heteroarylalkyl group may be optionally substituted.

The term "heteroaryldiyl", as used herein, refers to a divalent radical derived from a 6- to 12-membered mono- or bicyclic ring system wherein at least one ring atom is a heteroatom and at least one ring is aromatic. Examples of a heteroatom include, but are not limited to: O, S, N, and the like. Examples of heteroaryldiyl include, but are not limited to: thiazolyldiyl, 2,4-thiazolyldiyl, triazolyldiyl, 1,2,3-triazolyl-1,4-diyl, pyridyldiyl, benzofuranyldiyl, pyrazinyldiyl, pyridazinyldiyl, pyrimidinyldiyl, triazinyldiyl, quinolinyldiyl, benzoxazolyldiyl, benzothiazolyldiyl, 1H-benzimidazolyldiyl, isoquinolinyldiyl, quinazolinyldiyl, quinoxalinyldiyl, pyrrolyldiyl, indolyldiyl, 1H-benzoimidazol-2-yldiyl, benzo[1,3]dioxol-5-yldiyl, 3,4-dihydro-2H-benzo[1,4]oxazin-7-yldiyl, 2,3-dihydro-benzofurn-7-yldiyl, 2,3-dihydro-indol-1-yldiyl, and the like. Examples of include, but are not limited to: and the like.

"Heterocyclyl" or "heterocyclic ring" refers to a stable 3- to 18-membered non-aromatic ring substituent which consists of two to twelve carbon atoms and from one to six heteroatoms selected from the group consisting of nitrogen, oxygen and sulfur. Unless stated otherwise specifically in the specification, the heterocyclyl substituent may be a monocyclic, bicyclic, tricyclic or tetracyclic ring system, which may include fused or bridged ring systems; and the nitrogen, carbon or sulfur atoms in the heterocyclyl substituent may be optionally oxidized; the nitrogen atom may be optionally quaternized; and the heterocyclyl substituent may be partially or fully saturated. Examples of such heterocyclyl substituents include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"N-heterocyclyl" refers to a heterocyclyl substituent as defined above containing at least one nitrogen and where the point of attachment of the heterocyclyl substituent to the rest of the molecule is through a nitrogen atom in the heterocyclyl substituent. Unless stated otherwise specifically in the specification, a N-heterocyclyl group may be optionally substituted.

"Heterocyclylalkyl" refers to a substituent of the formula —$R_bR_e$ where $R_b$ is an alkylene chain as defined above and $R_e$ is a heterocyclyl substituent as defined above, and if the heterocyclyl is a nitrogen-containing heterocyclyl, the heterocyclyl may be attached to the alkyl substituent at the nitrogen atom. Unless stated otherwise specifically in the specification, a heterocyclylalkyl group may be optionally substituted.

The term "heterocyclyldiyl", as used herein, refers to a divalent radical derived from a 3- to 12-membered mono- or bicyclic non-aromatic ring system wherein at least one ring atom is a heteroatom. Examples of a heteroatom include, but are not limited to: O, S, N, and the like. A heterocyclyldiyl substituent can be attached via any two of its available ring atoms, for example, ring carbons, or ring nitrogens. In some embodiments, the heterocyclyldiyl is a 3-, 4-, 5-, 6- or 7-membered containing ring. Examples of a heterocyclyldiyl group include, but are not limited to: aziridin-1-yldiyl, aziridin-2-yldiyl, azetidin-1-yldiyl, azetidin-2-yldiyl, azetidin-3-yldiyl, piperidin-1-yldiyl, piperidin-2-yldiyl, piperidin-3-yldiyl, piperidin-4-yldiyl, morpholin-2-yldiyl, morpholin-3-yldiyl, morpholin-4-yldiyl, piperazin-1-yldiyl, piperazin-2-yldiyl, piperazin-3-yldiyl, piperazin-4-yldiyl, pyrrolidin-1-yldiyl, pyrrolidin-2-yldiyl, pyrrolidin-3-yldiyl, [1,3]-dioxolan-2-yldiyl, thiomorpholin-4-yldiyl, [1,4]oxazepan-4-yldiyl, 1,1-dioxo-1λ6-thiomorpholin-4-yldiyl, azepan-1-yldiyl, azepan-2-yldiyl, azepan-3-yldiyl, azepan-4-yldiyl, octahydro-quinolin-1-yldiyl, octahydro-isoquinolin-2-yldiyl, and the like.

"Hydroxy" or "hydroxyl" refers to the —OH substituent.

The term "hydroxy-alkyl", as used herein, refers to an alkyl group, substituted with one hydroxy substituent, as those terms are defined herein. Examples of hydroxy-alkyl include, but are not limited to: hydroxymethyl, hydroxy-ethyl, hydroxy-n-propyl, hydroxy-isopropyl, hydroxy-n-butyl, hydroxy-sec-butyl, hydroxy-isobutyl, hydroxy-t-butyl, hydroxy-pentyl, hydroxy-isopentyl, hydroxy-t-pentyl, hydroxy-neo-pentyl, hydroxy-1-methylbutyl, hydroxy-2-methylbutyl, hydroxy-n-hexyl, and the like.

"Imino" refers to the =NH substituent.

"Thioalkyl" refers to a substituent of the formula —$SR_a$ where $R_a$ is an alkyl substituent as defined above containing one to twelve carbon atoms. Unless stated otherwise specifically in the specification, a thioalkyl group may be optionally substituted.

"Nitro" refers to the —$NO_2$ substituent.

"Oxo" refers to the =O substituent.

"Thiol" refers to the —SH substituent.

"Thioxo" refers to the =S substituent.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as azides, amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gC(=NR_g)NR_gR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The present disclosure also meant to encompass all pharmaceutically acceptable compounds of Formula I being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds are useful to help determine or measure the effectiveness of the compounds, by characterizing, for example, the site or mode of action, or binding affinity to pharmacologically important site of action. Certain isotopically-labelled compounds described herein, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds described herein can generally be prepared by conventional techniques known to those skilled in the art or by processes analogous to those described in the Preparations and Examples as set out below using an appropriate isotopically-labeled reagent in place of the non-labeled reagent previously employed.

The present disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the present disclosure includes compounds produced by a process comprising administering a compound of this disclosure to a mammal for a period of time sufficient to yield a metabolic product thereof. Such products are typically identified by administering a radiolabelled compound of the disclosure in a detectable dose to an animal, such as rat, mouse, guinea pig, monkey, or to human, allowing sufficient time for metabolism to occur, and isolating its conversion products from the urine, blood or other biological samples.

The compounds of the disclosure, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)-for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

Other Definitions

The term "amino acid" or "amino acid residue" as used herein includes any one of the twenty naturally occurring amino acids, the D-form of any one of the naturally occurring amino acids, non-naturally occurring amino acids, and derivatives, analogs, and mimetics thereof. Any amino acid, including naturally occurring amino acids, may be purchased commercially or synthesized by methods known in the art. Examples of non-naturally-occurring amino acids include citrulline ("Cit"), norleucine ("Nle"), norvaline ("Nva"), p-Alanine, L- or D-naphthalanine, ornithine ("Orn"), homoarginine (homoArg) and others well known in the peptide art, including those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984. Common amino acids may be referred to by their full name, standard single-letter notation, or standard three-letter notation for example: A, Ala, alanine; C, Cys, cysteine; D, Asp, aspartic; E, Glu, glutamic acid; F, Phe, phenylalanine; G, Gly, glycine; H, His, histidine; I, Ile isoleucine; K, Lys, lysine; L, Leu, leucine; M, Met, methionine; N, Asn, asparagine; P, Pro, proline; Q, Gln, glutamine; R, Arg, arginine; S, Ser, serine; T, Thr, threonine; V, Val, valine; W, Trp, tryptophan; X, Hyp, hydroxyproline; Y, Tyr, tyrosine. Any and all of the amino acids in the compositions herein can be naturally occurring, synthetic, and derivatives or mimetics thereof. When the amino acid residues contain one or more chiral centers, any of the D, L, meso, threo or erythro (as appropriate) racemates or mixtures thereof, fall within the scope of this invention.

The term "another amino acid" as used herein means one amino acid that is different from that amino acid naturally present at that position. This includes but is not limited to amino acids that can be encoded by a polynucleotide. In some embodiments the different amino acid is in natural L-form and can be encoded by a polynucleotide.

The term "construct" is intended to indicate a polynucleotide segment which may be based on a complete or partial naturally occurring nucleotide sequence encoding the polypeptide of interest. The construct may optionally contain other polynucleotide segments. In a similar way, the term "amino acids which can be encoded by polynucleotide constructs" covers amino acids which can be encoded by the polynucleotide constructs defined above, i.e. amino acids such as Ala, Val, Leu, Ile, Met, Phe, Trp, Pro, Gly, Ser, Thr, Cys, Tyr, Asn, Glu, Lys, Arg, His, Asp and Gln.

The term "DBL2Xb" as used herein refers to a domain of VAR2CSA characterized by having an amino acid sequence with at least 70% sequence identity to an amino acid sequence identified by 153-577 of SEQ ID NO:1.

The term "derivative" as used herein, is intended to designate a VAR2CSA polypeptide exhibiting substantially the same or improved biological activity relative to wild-type VAR2CSA identified by SEQ ID NO:55 or SEQ ID NO:56, or a fragment thereof, in which one or more of the amino acids of the parent peptide have been chemically modified, e.g. by alkylation, PEGylation, acylation, ester formation or amide formation or the like.

A "disease or condition of interest" includes diseases and conditions involving expression, such as inappropriate expression of CSA, such as in cancer, arthritis, arthrosis, multiple sclerosis, healing after neural damage, cartilage repair, wound healing, and in psoriasis.

"Effective amount" or "therapeutically effective amount" refers to that amount of a compound described herein which, when administered to a mammal, preferably a human, is sufficient to effect treatment, as defined below, of the particular indication (e.g., cancer or tumor cells in the mammal, preferably a human). The amount of a compound described herein which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

The phrases "functional variant", "functional fragment", and "functional derivatives" as used herein refers to variants, fragments, truncated versions, as well as derivatives of SEQ ID NO:55 or SEQ ID NO:56, such as any one of SEQ ID NO:1, 3-5, 10, 11, 29, 34, 36-38, 41, 43-45, 48, 53-56, which polypeptides comprises essential binding sequence parts of SEQ ID NO:55 or SEQ ID NO:56 and at least possess the ability to bind plCSA. Accordingly, such polypeptides are VAR2CSA polypeptides, as used herein. It is to be understood that a VAR2CSA functional variant or functional fragment may have two or three features selected from being a both a variant, and/or a fragment and/or a derivative. A functional variant or fragment of a VAR2CSA polypeptide encompass those that exhibit at least about 25%, such as at least about 50%, such as at least about 75%, such as at least about 90% of the binding affinity of wild-type VAR2CSA polypeptide that has been produced in the same cell type, when tested in the assays as described herein or in WO 2013/117705.

The term "immunologic fragment" as used herein refers to fragment of an amino acid sequence that possesses essentially the same functional activities and the same spatial orientation to be recognized by a targeting moiety. Accordingly a specific targeting moiety will bind both the polypeptide and immunologic fragments thereof.

The term "intracellular metabolite" refers to a compound resulting from a metabolic process or reaction inside a cell on a compound described herein (e.g., a VAR2CSA-drug conjugate). The metabolic process or reaction may be an enzymatic process such as proteolytic cleavage of a peptide linker of the subject compound, or hydrolysis of a functional group such as a hydrazone, ester, or amide within the subject compound, or degradation of a portion or all of a targeting moiety. In the context of conjugates, intracellular metabolites may include, but are not limited to, VAR2CSA polypeptides and free drug, which may have been separated intracellularly, i.e., after entry, diffusion, uptake or transport into a cell (e.g., by enzymatic cleavage of a conjugate by an intracellular enzyme, or degradation of VAR2CSA polypeptide).

In the context of conjugates, the terms "intracellularly cleaved" and "intracellular cleavage" refer to metabolic processes or reactions inside a cell on a compound described herein whereby the covalent attachment, e.g., the linker between the payload and the targeting moiety is broken, resulting in the free drug dissociated from targeting moiety inside the cell. In some embodiments, the cleaved moieties of the subject compounds are intracellular metabolites. Accordingly, in one embodiment, the invention provides compounds that are cleavage products of a compound of Formula I, which cleavage products include compounds of Formula II. Alternatively, drug may be liberated through the degradation or proteolysis of VAR2CSA polypeptide.

The term "extracellular cleavage" refers a metabolic process or reaction outside a cell on a compound described herein whereby the covalent attachment, e.g., the linker between the payload and the targeting moiety is broken, resulting in the free drug dissociated from the targeting moiety outside the cell. In some embodiments, the cleaved moieties of the subject compounds are initially extracellular metabolites, which may move intracellularly by diffusion and cell permeability or transport.

The term "isolated polypeptide" refers to a polypeptide described herein that (1) has been separated from at least about 50 percent of polynucleotides, lipids, carbohydrates or other materials (i.e., contaminants) with which it is naturally associated (not including post-translational modifications). Preferably, the isolated polypeptide is substantially free from any other contaminating polypeptides or other contaminants that are found in its natural environment, which would interfere with its therapeutic, diagnostic, prophylactic or research use.

The term "ID1" as used herein refers to a domain of VAR2CSA characterized by having an amino acid sequence with at least 70% sequence identity to an amino acid sequence identified by 1-152 of SEQ ID NO:1.

The term "ID2a" as used herein refers to a domain of VAR2CSA characterized by having an amino acid sequence of at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, or at least 62, such as the 63 consecutive amino acids from the N-terminal of amino acids 578-640 of SEQ ID NO:1 and with at least 70% sequence identity to such a sequence of consecutive amino acids. In some embodiments an amino acid sequence identity referred to herein of at least 70% of any one sequence identified by SEQ ID NO:1-57 or a fragment thereof, refers to a sequence with at least 71, 72, 73, 74, 75, 76, 77, 78, 79, 80, 81, 8, 83, 84, 85, 86, 87, 88, 89, 90, 91, 92, 93, 94, 95, 96, 97, 98, or 99% sequence identity to this sequence.

"Mammal" includes humans and both domestic animals such as laboratory animals and household pets (e.g., cats, dogs, swine, cattle, sheep, goats, horses, rabbits), and non-domestic animals such as wildlife and the like.

The term "microorganism" as used herein refers to bacteria, fungi, archaea, protists (such as green algae and plankton), planarians and amoebae. Included within this definition are pathogenic microorganisms.

A "native sequence" polypeptide is one which has the same amino acid sequence as a polypeptide derived from nature. Such native sequence polypeptides can be isolated from nature or can be produced by recombinant or synthetic means. Thus, a native sequence polypeptide can have the amino acid sequence of naturally-occurring human polypeptide, murine polypeptide, or polypeptide from any other mammalian species.

"Optional" or "optionally" means that the subsequently described event of circumstances may or may not occur, and that the description includes instances where said event or circumstance occurs and instances in which it does not. For example, "optionally substituted aryl" means that the aryl substituent may or may not be substituted and that the description includes both substituted aryl substituents and aryl substituents having no substitution.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Prodrug" is meant to indicate a compound that may be converted under physiological conditions or by solvolysis to a biologically active compound of the disclosure. Thus, the term "prodrug" refers to a metabolic precursor of a compound of the disclosure that is pharmaceutically acceptable. A prodrug may be inactive when administered to a subject in need thereof, but is converted in vivo to an active compound of the disclosure. Prodrugs are typically rapidly transformed in vivo to yield the parent compound of the disclosure, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987. Prodrugs of a compound of the disclosure may be prepared by modifying functional groups present in the compound of the disclosure in such a way that the modifications are cleaved, either in routine manipulation or in vivo, to the parent compound of the disclosure. Prodrugs include compounds of the disclosure wherein a hydroxy, amino or mercapto group is bonded to any group that, when the prodrug of the compound of the disclosure is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the disclosure and the like.

The term "protecting group", as used herein, refers to a labile chemical moiety which is known in the art to protect reactive groups including without limitation, hydroxyl and amino groups, against undesired reactions during synthetic procedures. Hydroxyl and amino groups which protected with a protecting group are referred to herein as "protected hydroxyl groups" and "protected amino groups", respectively. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999). Groups can be selectively incorporated into compounds of the present disclosure as precursors. For example an amino group can be placed into a compound of the disclosure as an azido group that can be chemically converted to the amino group at a desired point in the synthesis. Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72. Examples of "hydroxyl protecting groups" include, but are not limited to, t-butyl, t-butoxymethyl, methoxymethyl, tetrahydropyranyl, 1-ethoxyethyl, 1-(2-chloroethoxy) ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl (TBDPS), triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Examples of "amino protecting groups" include, but are not limited to, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide-protecting groups, such as 2-nitrobenzenesulfonyl; and imine and cyclic imide protecting groups, such as phthalimido and dithiasuccinoyl.

Often crystallizations produce a solvate of the compound of the disclosure. As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases, the compound of the disclosure may merely retain adventitious water or be a mixture of water plus some adventitious solvent.

"Stable compound" and "stable structure" are meant to indicate a compound that is sufficiently robust to survive isolation to a useful degree of purity from a reaction mixture, and formulation into an efficacious therapeutic agent.

The term "sequence identity" as known in the art, refers to a relationship between the sequences of two or more polypeptide molecules or two or more nucleic acid molecules, as determined by comparing the sequences. In the art, "identity" also means the degree of sequence relatedness between nucleic acid molecules or between polypeptides, as the case may be, as determined by the number of matches between strings of two or more nucleotide residues or two or more amino acid residues. "Identity" measures the percent of identical matches between the smaller of two or more sequences with gap alignments (if any) addressed by a particular mathematical model or computer program (i.e., "algorithms"). The term "similarity" is a related concept, but in contrast to "identity", refers to a sequence relationship that includes both identical matches and conservative substitution matches. Therefore, in cases where there are conservative substitutions, the degree of similarity between two polypeptides will be higher than the percent identity between those two polypeptides.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present disclosure includes tautomers of any said compounds.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition.

In one embodiment, the term "VAR2CSA polypeptide" as used herein refers to the extracellular part of a specific Erythrocyte Membrane Protein 1 (PfEMP1) protein expressed by *Plasmodium falciparum* interacting with chondroitin sulfate proteoglycans (CSPG) and characterized by having a sequence of SEQ ID NO:55 or SEQ ID NO:56, or fragments or variants or derivatives thereof with the ability to bind plCSA that could be presented on a proteoglycan (CSPG). In some embodiments, the VAR2CSA polypeptide at least comprises the protein fragment of VAR2CSA, which fragment consist of a sequential amino acid sequence of a) ID1, and b) DBL2Xb. In some embodiments, the VAR2CSA polypeptide at least comprises the protein fragment of VAR2CSA, which fragment consist of a sequential amino acid sequence of a) ID1, and b) DBL2Xb, and c) ID2a. In some embodiments, the VAR2CSA polypeptide competes for binding to plCSA with a VAR2CSA polypeptide consisting of sequential amino acid sequence of a) ID1, and b) DBL2Xb. In some embodiments, the VAR2CSA polypeptide competes for binding to plCSA with a VAR2CSA polypeptide consisting of sequential amino acid sequence of a) ID1, b) DBL2Xb and c) ID2a. In some embodiments, the VAR2CSA polypeptide competes for binding to plCSA with a VAR2CSA polypeptide comprising the amino acid sequence in SEQ ID NO:55 or SEQ ID NO:56. Included within the definition of a VAR2CSA polypeptide are polypeptides described in Salanti A. et al. Mol. Micro 2003 July; 49 (1):179-91; in Khunrae P. et al., J Mol Biol. 2010 Apr. 2; 397 (3):826-34, in Srivastava A. et al., Proc Natl Acad Sci USA. 2010 Mar. 16; 107 (11):4884-9, in Dahlbäck M. et al, J Biol Chem. 2011 May 6; 286 (18):15908-17, and in Srivastava A. et al., PLoS One. 2011; 6 (5):e20270.

The terms "variant" or "variants", as used herein, refer to a VAR2CSA polypeptide having an amino acid sequence of SEQ ID NO:55 or SEQ ID NO:56 or fragments of a VAR2CSA polypeptide comprising an amino acid sequence of SEQ ID NO:1-54, which fragments or variants retain the ability to bind plCSA on proteoglycans (CSPG), wherein one or more amino acids have been substituted by another amino acid and/or wherein one or more amino acids have been deleted and/or wherein one or more amino acids have been inserted in the polypeptide and/or wherein one or more amino acids have been added to the polypeptide. Such addition can take place either at the N-terminal end or at the C-terminal end or both. The "variant" or "variants" within this definition still have functional activity in terms of being able to bind plCSA. Accordingly, such polypeptides are VAR2CSA polypeptides, as used herein. In some embodiment a variant has at least 70%, such as at least 71, 72, 73, 74, 75, 76, 77, 78, 79, 80, 81, 8, 83, 84, 85, 86, 87, 88, 89, 90, 91, 92, 93, 94, 95, 96, 97, 98, or 99% sequence identity with the sequence of SEQ ID NO:1-57, such as the sequence of SEQ ID NO:1, 3-5, 10, 11, 29, 34, 36-38, 41, 43-45, 48, 53-56, 60-70, 72-75.

The term "vector", as used herein, means any nucleic acid entity capable of the amplification in a host cell. Thus, the vector may be an autonomously replicating vector, i.e. a vector, which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to plasmid vectors, phage vectors, viruses or cosmid vectors. Vectors usually contain a replication origin and at least one selectable gene, i.e., a gene which encodes a product which is readily detectable or the presence of which is essential for cell growth.

Compounds

Provided are protein-drug conjugates which are compounds of Formula I:

$$T\text{-}L\text{-}P \qquad \qquad I$$

wherein:

T is a targeting moiety comprising a VAR2CSA polypeptide;

L-P is selected from: $L^1\text{-}P^1$ or $L^2\text{-}P^2$;

$L^1$ is a linker, or $L^1$ is absent;

$P^1$ is a monovalent radical of a compound of Formula XIV

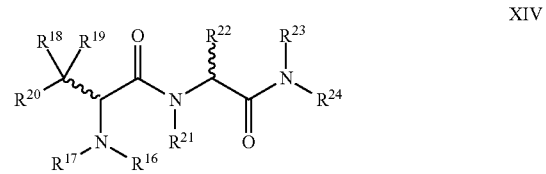

XIV wherein:

$R^{16}$ and $R^{17}$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO$_2$H, —CHO, —COSH, or —NO$_2$; or $R^{17}$ and $R^{20}$ are fused and form a ring;

$R^{18}$ and $R^{19}$ are independently selected from the group consisting of: H, $R^{25}$, and Ar$R^{25}$—, or $R^{18}$ and $R^{19}$ are joined to form a ring;

$R^{20}$ is selected from the group consisting of: H, $R^{25}$, Ar$R^{25}$—, and Ar; or $R^{20}$ and $R^{17}$ are fused and form a ring;

$R^{21}$ is selected from the group consisting of: H, $R^{25}$, and Ar$R^{25}$—;

$R^{22}$ and $R^{23}$ are independently selected from the group consisting of: H, $R^{25}$, and Ar$R^{25}$—;

$R^{24}$ is: —Y—(CO)NHSO$_2$—$R^{26}$ $R^{25}$ is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$^{28}$, —O$_2$CR$^{28}$, —SH, —SR$^{28}$, —SOCR$^{28}$, —NH$_2$, —NHR$^{28}$, —N(R$^{28}$)$_2$, —NHCOR$^{28}$, —NR$^{28}$COR$^{28}$, —I, —Br, —Cl, —F, —CN, —CO$_2$H, —CO$_2$R$^{28}$, —CHO, —COR$^{28}$, —CONH$_2$, —CONHR$^{28}$, —CON(R$^{28}$)$_2$, —COSH, —COSR$^{28}$, —NO$_2$, —SO$_3$H, —SOR$^{28}$, —SO$_2$R$^{28}$, wherein R$^{28}$ is a linear, branched or cyclic, one to ten carbon saturated or unsaturated alkyl group;

the ring formed by joining $R^{18}$ and $R^{19}$ is a three to seven member non-aromatic cyclic skeleton within the definition of $R^{25}$, Y is defined as a moiety selected from the group consisting of: a linear, saturated or unsaturated, one to six carbon alkyl group, optionally substituted with $R^{25}$, $ArR^{25}$—, or X; and, X is defined as a moiety selected from the group consisting of: —OH, —$OR^{25}$, =O, =S, —$O_2CR^{25}$, —SH, —$SR^{25}$, —$SOCR^{25}$, —$NH_2$, —$NHR^{25}$, —$N(R^{25})_2$, —$NHCOR^{25}$, —$NRCOR^{25}$, —I, —Br, —Cl, —F, —CN, —$CO_2H$, —$CO_2R^{25}$, —CHO, —$COR^{25}$, —$CONH_2$, —$CONHR^{25}$, —$CON(R^{25})_2$, —COSH, —$COSR^{25}$, —$NO_2$, —$SO_3H$, —$SOR^{25}$, and —$SO_2R^{25}$;

$R^{26}$ is selected from the group consisting of optionally substituted alkyl, optionally substituted alkylamino, optionally substituted cycloalkyl, optionally substituted aryl, optionally substituted heterocyclyl, optionally substituted heteroaryl, —$COR^{27}$, —$CSR^{27}$, —$OR^{27}$, and —$NHR^{27}$, wherein each $R^{27}$ is, independently, optionally substituted alkyl, optionally substituted alkylamino, optionally substituted cycloalkyl, optionally substituted aryl, optionally substituted heterocyclyl, or optionally substituted heteroaryl; and $L^2$ is a linker, or $L^2$ is absent;

$P^2$ is a biologically active compound; and $L^2$-$P^2$ has the following structure (III):

wherein:

R is selected from the group consisting of optionally substituted alkyl, optionally substituted alkylamino, optionally substituted cycloalkyl, optionally substituted aryl, optionally substituted heterocyclyl, optionally substituted heteroaryl, —$COR^{27}$, —$CSR^{27}$, —$OR^{27}$, and —$NHR^{27}$, wherein each $R^{27}$ is, independently, optionally substituted alkyl, optionally substituted alkylamino, optionally substituted cycloalkyl, optionally substituted aryl, optionally substituted heterocyclyl, optionally substituted heteroaryl, or R is absent;

$P^3$ is the remaining portion of compound $P^2$; and $L^3$ is optionally the remaining portion of linker $L^2$ when $L^2$ is present.

In a preferred embodiment, R is selected from the group consisting of optionally substituted alkyl, optionally substituted alkylamino, optionally substituted cycloalkyl, optionally substituted aryl, optionally substituted heterocyclyl and optionally substituted heteroaryl, or R is absent.

In some embodiments, $L^2$ is present and T and $L^2$ are linked via a peptide bond. In some embodiments, R is present and $L^2$ is present and $L^2$ and $P^2$ are linked via a peptide bond. In some embodiments, $L^2$ is absent, R is present, and T and $P^2$ are linked via a peptide bond.

In certain embodiments, one payload molecule is linked to one linker molecule. In certain embodiments, a plurality of payload molecules are linked to the same linker molecule. In certain embodiments, one linker molecule is linked to one targeting moiety. In certain embodiments, a plurality of linker molecules are linked to the same targeting moiety. "Drug-antibody ratio" or "DAR" is meant to indicate the number of drug moieties conjugated to a targeting moiety (an antibody).

Targeting Moiety (T)

A targeting moiety can form a bond to a linker unit (L) or a payload compound (P). A targeting moiety can form a bond to the linker moiety or the payload compound via a heteroatom of the targeting moiety. Heteroatoms that may be present on a targeting moiety include sulfur (in one embodiment, from a sulfhydryl group of T), oxygen (in one embodiment, from a carbonyl, carboxyl or hydroxyl group of T) and nitrogen (in one embodiment, from a primary or secondary amino group of T). These heteroatoms can be present on the targeting moiety in the targeting moiety's natural state, or can be introduced into the targeting moiety, for example by chemical modification or recombinant means.

In some embodiments, the targeting moiety has a sulfhydryl group and bonds to the linker moiety via the sulfhydryl group's sulfur atom. In another embodiment, the targeting moiety has one or more lysine residues that can be chemically modified to introduce one or more sulfhydryl groups. The targeting moiety bonds to the linker moiety via the sulfhydryl group. Reagents that can be used to modify lysines include, but are not limited to, N-succinimidyl S-acetylthioacetate (SATA) and 2-iminothiolane hydrochloride (Traut's Reagent).

In another embodiment, the linker moiety can have one or more carbohydrate groups that can be chemically modified to have one or more sulfhydryl groups. The targeting moiety bonds to the linker moiety via the sulfhydryl group's sulfur atom. In yet another embodiment, the targeting moiety can have one or more carbohydrate groups that can be oxidized to provide an aldehyde (—CHO) group (see, e.g., Laguzza et al., 1989, J. Med. Chem. 32 (3):548-55). The corresponding aldehyde can form a bond with a reactive site on a portion of a linker moiety. Reactive sites that can react with a carbonyl group on a targeting moiety include, but are not limited to, hydrazine and hydroxylamine. Other protocols for the modification of proteins for the attachment or association of payload compounds are described in Coligan et al., Current Protocols in Protein Science, vol. 2, John Wiley & Sons (2002).

Provided are compounds of Formula I:

T-L-P      I wherein T is a targeting moiety comprising a VAR2CSA polypeptide.

The targeting moiety described herein includes within its scope any molecule comprising a VAR2CSA polypeptide as defined herein. In a preferred embodiment, the targeting moiety is a protein comprising a VAR2CSA polypeptide. In another preferred embodiment, the targeting moiety consists essentially of a VAR2CSA polypeptide. In another preferred embodiment, the targeting moiety consists of a VAR2CSA polypeptide. In a preferred embodiment, the VAR2CSA polypeptide is a VAR2CSA polypeptide disclosed in WO2013/117705.

The VAR2CSA protein may be recombinantly produced from any number of host cell types, as will be recognized by one of reasonable skill in the art. In one embodiment, VAR2CSA polypeptide is produced recombinantly using a mammalian cell system. In another embodiment, VAR2CSA polypeptide is produced using a non-mammalian cell system. In one embodiment, VAR2CSA polypeptide is produced using an insect cell system. As will be appreciated by the reasonably skilled artisan, the glycosylation pattern of recombinant VAR2CSA polypeptide produced by different cell types may vary.

In some embodiments, the VAR2CSA polypeptide is not a minimal binding fragment. In some embodiments, the VAR2CSA polypeptide is a minimal binding fragment. In some embodiments, the VAR2CSA polypeptide consists of a sequential amino acid sequence of a) ID1, and b) DBL2Xb, and optionally c) ID2a. In some embodiments the VAR2CSA polypeptide comprises ID2a.

VAR2CSA, part of a malaria protein, can bind to a cancer-specific antigen and extra-cellular CSPG with very high specificity and very high binding strength. VAR2CSA mediates adhesion of parasite-infected cells exclusively to CSA attached to proteoglycans (CSPG) in the placenta of pregnant women. Recombinant protein has been shown to bind with unprecedented high affinity and specificity to plCSA. This may be due to an interaction with plCSA that is not only dependent on the charged sulfates but also on the CS backbone. CS present in the placenta is believed to be very similar to the CS presented on various cancer cells including cancer stem cells (Salanti et al., WO2013/117705). This is substantiated by the fact that VAR2CSA-expressing parasite infected cells adhere specifically to plCSA on C32 melanoma cells and to human brain cancer cells. By coupling VAR2CSA to an apoptotic or cytotoxic payload the compounds described herein can be used to specifically target and eliminate cancer cells and cancer stem cells. plCSA can be present on a number of protein backbones, e.g. CSPG4, CD44, biglycan, decorin, versican, aggrecan (the major CSPG in cartilage), perlecan, syndecan, and others listed in Table 1.

TABLE 1

Potential molecules targeted by a VAR2CSA polypeptide

| Protein ID 1 | Protein ID 2 | Gene name |
|---|---|---|
| NG2 | CSPG4 | cspg4 |
| Neuroglycan and Neuroglycan-C | CSPG5 | ngc 7 |
| Neuropilin-1 CS | NRP-1-CS | NRP1 |
| APLP2 and APP (and when plCSA is added the proteins are called Appicans) | amyloid precursor-like protein 2 | APLP2 |
| Snorc | | Snorc |
| Tomoregulin-1 | TENB1 | TMEFF1 |
| Tomoregulin-2 | TENB2 | TMEFF2 |
| Thrombomodulin | CD141 | THBD |
| Betaglycan | Transforming growth factor beta receptor III | TGFBR3 |
| Syndecan 1 | CD138 | SDC1 |
| Syndecan 2 | CD362 | SDC2 |
| Syndecan 3 | | SDC3 |
| Syndecan 4 | Amphiglycan | SDC4 |
| CSPG8 | CSPG8 | Cd44 |
| Glypican1-6 (kun 1 og 5) | | GPC1-6 |
| Brevican | CSPG7 | bcan |
| lubricin | Proteoglycan 4 | PRG4 |
| Dentin matrix protein 1 | | DMP1 |
| Neurocan | CSPG3 | ncan |
| Versican | CSPG2 | vcan |
| Aggrecan | CSPG1 | acan |
| Bamecan | CSPG6 | smc3 |
| SRPX2 | Sushi repeat-containing protein | SRPX2 |
| Serglycin | Hematopoietic proteoglycan core protein | SRGN |
| Decorin | Small leucine-rich proteoglycan (SLRP) family | dcn |
| Biglycan | Small leucine-rich proteoglycan (SLRP) family | bgn |
| Lumican | Small leucine-rich proteoglycan (SLRP) family | lum |

TABLE 1-continued

Potential molecules targeted by a VAR2CSA polypeptide

| Protein ID 1 | Protein ID 2 | Gene name |
|---|---|---|
| Fibromodulin | Small leucine-rich proteoglycan (SLRP) family | fmod |
| Keratocan | Small leucine-rich proteoglycan (SLRP) family | kera |
| Mimecan | osteoglycin | ogn |
| Testican 1-3 | BM-40/SPARC/osteonectin family of extracellular calcium-binding proteins | SPOCK1 |
| phosphacan | Receptor-type tyrosine-protein phosphatase zeta | PTPRZ1 |
| Leprecan | Leucine Proline-Enriched Proteoglycan 1 | LEPRE1 |
| Perlecan | basement membrane-specific heparan sulfate proteoglycan core protein | HSPG2 |

VAR2CSA binds plCSA in the intervillous spaces of the placenta with an affinity below 10 nM. Smaller recombinant parts of VAR2CSA have been produced that bind plCSA with characteristics similar to that of the full-length and native VAR2CSA protein. Table 2 lists the plCSA affinity of certain VAR2CSA polypeptides using biosensor technology. Affinity is given as a $K_D$ (nM) value determined in kinetics experiments using a quartz crystal microbalance biosensor (Attana A100). N/A: proteins for which no KD value could be determined, due to a lack of binding to plCSA.

TABLE 2 plCSA Binding Affinity of Certain VAR2CSA Polypeptides.

| VAR2CSA Fragment | FCR3 | | 3D7 |
| | Baculo | E. coli | Baculo |
|---|---|---|---|
| FV2 | 5.2* | | 8.2 |
| ID1-DBL4ε | 8.6* | | 9.4 |
| ID1-DBL3ε | 0.3* | | 8.5 |
| DBL2X-DBL4ε | 2.4* | | 1.2 |
| DBL1-ID2b | 1.5* | | |
| DBL1-ID2a | 8.0 | 3.5 | 29.5 |
| ID1-ID2a | 7.6 | 18.3 | 5.7 |
| DBL1X-DBL2Xb | | 14.6 | |
| DBL1X-DBL2Xa | N/A | | |
| ID1-DBL2Xb | | | 21.8 |
| ID1-DBL2Xa | | | N/A |

*Proteins published in (Dahlbäck et al., JBC, 2011)

Recombinant VAR2CSA protein does not bind other CS such as chondroitin sulfate C (C6S) or highly sulfated GAGs such as heparan sulfate (HS). Recombinant proteins can be produced to bind with high affinity to plCSA in various expression systems, e.g., S2 cells, T. ni cells, CHO cells, and E. coli strains including BL21 and SHuffle.

A number of VAR2CSA polypeptides smaller than full length VAR2CSA and which bind plCSA with very high affinity (nM) and high specificity have been identified (Salanti et al., WO2013/117705). As shown herein, such a representative VAR2CSA polypeptide (75 kDa) binds strongly at low concentrations to a wide range of cancer cell lines including cutaneous melanoma (C32, MeWo), lung carcinoma (A549), breast carcinoma (HCC1395), osteosarcoma (U205, MNNG/HOS), rhabdomyosarcoma (RH30) and cutaneous T-cell lymphoma (Tables 3 and 4). As a control molecule another VAR2CSA protein was used, which is identical to the minimal binding VAR2CSA construct except for a 151 amino acids truncation in the C-terminal part of the molecule. This truncation removes the plCSA binding. Recombinant VAR2CSA binds all CSPG4 expressing cell lines and cancer cell lines expressing other CSPG molecules having plCSA chains (e.g. T-cell lymphoma). Recombinant VAR2CSA protein fails to interact with human red blood cells and peripheral blood mononuclear cells (PBMC) (Table 3).

TABLE 3

Staining of Cancer Cell Lines and Negative Control Cells Using the Minimal Binding Domain of VAR2CSA (ID1-ID2a). Shown are the mean FITC 30 fluorescence values recorded from a minimum of 5000 cells using a FC500 flowcytometer (Becton Dickinson).

| Cell type | Blank | ID1-DBL2Xa | ID1-ID2a |
|---|---|---|---|
| C32 | 5.77 | 6.94 | 63.81 |
| MyLa 2059 | 5.61 | 5.61 | 145.35 |
| MyLa 1850 | 5.87 | 5.6 | 137.86 |
| Cho WT | 3.09 | 4.35 | 34.79 |
| Cho 745 | 4.24 | 4.29 | 4.38 |
| PBMC | 1.34 | 1.36 | 1.67 |
| Erythrocytes | 1.11 | 1.17 | 1.07 |

TABLE 4

Staining of cancer cell lines using recombinant VAR2CSA. Shown are the medium score of FITC fluorescence intensity recorded from a minimum of 4 high power field images using a HAL100 Zeiss microscope.

| Cell type | Blank | DBL1-ID2a |
|---|---|---|
| U2OS | NS | +++ |
| MG63 | NS | ++++ |
| MDA-MB-231 | NS | +++ |
| TC32 | NS | + |
| TC71 | NS | ++ |
| MNNG | NS | +++ |
| CHLA9 | NS | ++ |
| CHLA10 | NS | ++ |
| RH30 | NS | +++ |
| RH18 | NS | ++ |
| PC3 | NS | +++ |

NS: No staining;
+: weak;
++: medium;
+++: strong;
++++: Very strong.

Cells infected with malaria parasites adhere to C32 melanoma cells, probably through a specific interaction between CSPG4 and VAR2CSA. Thus, it is envisioned that the compounds described herein may be used as therapeutic compounds targeting plCSA on various cancer cells. The advantages of targeting plCSA on cancer cells with VAR2CSA polypeptides over other current therapies in development are numerous: 1) The interaction between VAR2CSA and plCSA is of unprecedented high affinity and highly specific; 2) VAR2CSA is an evolutionary refined malaria protein and it is thus unlikely that therapy will break tolerance and cause autoimmune reactions in the patient; 3) VAR2CSA is a stable protein that is well characterized and can be highly expressed in organisms compatible with large-scale protein production; 4) VAR2CSA is a polymorphic protein with a number of serovariants. Repeated therapy could be offered by different serovariants to avoid issues with neutralizing antibodies; 5) VAR2CSA is naturally exposed extracellularly on the *P. falciparum*-infected red blood cell and is thus by nature a stable protein in human serum and has been shown to be highly protease resistant.

The compounds described herein utilize the interaction between VAR2CSA polypeptides and plCSA. This interaction is a high affinity interaction and one use of such compounds is to target plCSA expressing cancer cells and cancer stem cells. Accordingly, the compounds described herein may be used to target cancer cells with minimal adverse toxicity to plCSA-negative tissue.

plCSA is also involved in other diseases and pathological conditions like for example arthritis, arthrosis, multiple sclerosis and healing after neural damage, cartilage repair, wound healing, and in psoriasis. Accordingly, the compounds described herein are useful in the treatment of any such disease or condition. For example, the compounds described herein are useful for targeting drugs that block protease mediated degradation of aggrecan during arthritis and arthrosis. The compounds described herein may also be used to target anti-inflammatory drugs to the affected tissues and to deliver inhibitors such as ADAMTS4 and -5 inhibitors. The compounds described herein may be used to target drugs that stimulate the production of aggrecan by chondrocytes.

The compounds described herein may be used to target drugs that degrade CSPG or inhibit CSPG production in affected neural tissue, such as chondroitinase ABC, which cut the sugar chains of the protein core of CSPG molecules; xylocides, which reduce CSPG production; and drugs that inhibit enzymes important for CSPG production such as chondroitin synthase or chondroitin polymerizing factor. Examples of such drugs include: 4-fluoro-glucosamine, p-nitrophenyl-beta-D-xyloxide, and 4-methyl-umbelliferyl-beta-D-xylopyranoside.

The compounds described herein may also be used to target and maintain cytokines such as IL1-alpha, which stimulate production of ADAMTS4, which subsequently cleave CSPG.

In some embodiments, the VAR2CSA polypeptide described herein consists of a sequential amino acid sequence of a) ID1, and b) DBL2Xb, and optionally c) ID2a.

In some embodiments, the VAR2CSA polypeptide described herein comprises ID2a.

In some embodiments, the VAR2CSA polypeptide described herein does not comprise ID2a.

In some embodiments, the VAR2CSA polypeptide described herein further comprises an amino acid sequence in the N- or C-terminal, or within the sequence of the protein fragment of VAR2CSA of not more than 100 amino acids, such as not more than 90 amino acids, such as not more than 80 amino acids, such as not more than 70 amino acids, such as not more than 60 amino acids, such as not more than 50 amino acids, such as not more than 40 amino acids, such as not more than 30 amino acids, such as not more than 20 amino acids, such as not more than 18 amino acids, such as not more than 16 amino acids, such as not more than 14 amino acids, such as not more than 12 amino acids, such as not more than 10 amino acids, such as not more than 8 amino acids, such as not more than 6 amino acids, such as not more than 4 amino acids, such as not more than 2 amino acids derived from any part of a VAR2CSA polypeptide as defined herein, which is not part of ID1, DBL2Xb, or ID2a.

In some embodiments, the VAR2CSA polypeptide described herein further comprises an amino acid sequence in the N- or C-terminal, or within the sequence of the protein fragment of VAR2CSA of not more than 100 amino acids, such as not more than 90 amino acids, such as not more than 80 amino acids, such as not more than 70 amino acids, such as not more than 60 amino acids, such as not more than 50 amino acids, such as not more than 40 amino acids, such as not more than 30 amino acids, such as not more than 20 amino acids, such as not more than 18 amino acids, such as not more than 16 amino acids, such as not more than 14 amino acids, such as not more than 12 amino acids, such as not more than 10 amino acids, such as not more than 8 amino acids, such as not more than 6 amino acids, such as not more than 4 amino acids, such as not more than 2 amino acids, which amino acid sequence is not derived from any part of a VAR2CSA polypeptide as defined herein.

In some embodiments, the VAR2CSA polypeptide described herein binds chondroitin sulfate A (CSA) on proteoglycans (CSPG) with an affinity as measured by a $K_D$ lower than 100 nM, such as lower than 80 nM, such as lower than 70 nM, such as lower than 60 nM, such as lower than 50 nM, such as lower than 40 nM, such as lower than 30 nM, such as lower than 26 nM, such as lower than 24 nM, such as lower than 22 nM, such as lower than 20 nM, such as lower than 18 nM, such as lower than 16 nM, such as lower than 14 nM, such as lower than 12 nM, such as lower than 10 nM, such as lower than 9 nM, such as lower than 8 nM, such as lower than 7 nM, such as lower than 6 nM, or lower than 4 nM.

In some embodiments, the VAR2CSA polypeptide described herein binds plCSA on proteoglycans (CSPG) with an affinity as measured by a $K_D$ lower than 100 nM, such as lower than 80 nM, such as lower than 70 nM, such as lower than 60 nM, such as lower than 50 nM, such as lower than 40 nM, such as lower than 30 nM, such as lower than 26 nM, such as lower than 24 nM, such as lower than 22 nM, such as lower than 20 nM, such as lower than 18 nM, such as lower than 16 nM, such as lower than 14 nM, such as lower than 12 nM, such as lower than 10 nM, such as lower than 9 nM, such as lower than 8 nM, such as lower than 7 nM, such as lower than 6 nM, or lower than 4 nM.

In some embodiments the VAR2CSA polypeptide described herein comprises an amino acid sequence having at least 70% sequence identity with any one amino acid sequence of 1-577 of SEQ ID NO:1, 1-592 of SEQ ID NO:3, 1-579 of SEQ ID NO:4, 1-576 of SEQ ID NO:5, 1-586 of SEQ ID NO:10, 1-579 of SEQ ID NO:11, 1-565 of SEQ ID NO:29, 1-584 of SEQ ID NO:34, 1-569 of SEQ ID NO:36, 1-575 of SEQ ID NO:37, 1-592 of SEQ ID NO:38, 1-603 of SEQ ID NO:41, 1-588 of SEQ ID NO:43, 1-565 of SEQ ID NO:44, 1-589 of SEQ ID NO:45, 1-573 of SEQ ID NO:48, 1-583 of SEQ ID NO:53, or 1-569 of SEQ ID NO:54.

In some embodiments the VAR2CSA polypeptide described herein comprises an amino acid sequence having at least 70% sequence identity with an amino acid sequence of 578-640 of SEQ ID NO:1, 593-656 of SEQ ID NO:3, 580-643 of SEQ ID NO:4, 577-640 of SEQ ID NO:5, 587-650 of SEQ ID NO:10, 580-643 of SEQ ID NO:11, 566-628 of SEQ ID NO:29, 585-647 of SEQ ID NO:34, 570-632 of SEQ ID NO:36, 576-639 of SEQ ID NO:37, 593-655 of SEQ ID NO:38, 604-667 of SEQ ID NO:41, 589-652 of SEQ ID NO:43, 566-628 of SEQ ID NO:44, 590-653 of SEQ ID NO:45, 574-637 of SEQ ID NO:48, 584-646 of SEQ ID NO:53, or 570-632 of SEQ ID NO:54.

In some embodiments the VAR2CSA polypeptide described herein comprises an amino acid sequence having at least 70% sequence identity with an amino acid sequence of SEQ ID NO:2, 6, 8, 9, 12, 13, 14, 15, 16, 17, 18, 19, 20, 21, 22, 23, 24, 25, 26, 27, 28, 30, 31, 32, 33, 35, 39, 40, 42, 46, 47, 49, 50, 51, or 52.

In some embodiments the VAR2CSA polypeptide described herein consists of an 30 amino acid sequence having at least 70% sequence identity with any one amino acid sequence of 1-577 of SEQ ID NO:1, 1-592 of SEQ ID NO:3, 1-579 of SEQ ID NO:4, 1-576 of SEQ ID NO:5, 1-586 of SEQ ID NO:10, 1-579 of SEQ ID NO:11, 1-565 of SEQ ID NO:29, 1-584 of SEQ ID NO:34, 1-569 of SEQ ID NO:36, 1-575 of SEQ ID NO:37, 1-592 of SEQ ID NO:38, 1-603 of SEQ ID NO:41, 1-588 of SEQ ID NO:43, 1-565 of SEQ ID NO:44, 1-589 of SEQ ID NO:45, 1-573 of SEQ ID NO:48, 1-583 of SEQ ID NO:53, or 1-569 of SEQ ID NO:54.

In some embodiments the VAR2CSA polypeptide described herein consists of an amino acid sequence selected from the list consisting of SEQ ID NO:1, 3-5, 10, 11, 29, 34, 36-38, 41, 43-45, 48, 53, and 54.

In some embodiments the VAR2CSA polypeptide described herein consists of an amino acid sequence having a length of less than 700 amino acids, such as less than 690 amino acids, such as less than 680 amino acids, such as less than 670 amino acids, such as less than 660 amino acids, such as less than 650 amino acids, such as less than 640 amino acids, such as less than 630 amino acids, such as less than 620 amino acids, such as less than 610 amino acids, such as less than 600 amino acids, such as less than 590 amino acids, such as less than 580 amino acids, such as less than 570 amino acids.

In some embodiments the VAR2CSA polypeptide described herein has a molecular mass of less than about 100 kDa under non-reducing conditions on an SDS-PAGE.

In some embodiments the VAR2CSA polypeptide described herein is a recombinant protein.

In some embodiments the VAR2CSA polypeptide described herein is non-glycosylated.

In some embodiments the VAR2CSA polypeptide described herein is glycosylated.

In some aspects of the present invention, the VAR2CSA polypeptide described herein comprises a sequence as defined by one or more sequences selected from SEQ ID NO 57 or a functional variant or fragment thereof.

In some embodiments the VAR2CSA polypeptide described herein comprises a protease inhibitor, such as basic pancreatic trypsin inhibitor (BPTI) in the terminal, such as the N-terminal of the protein sequence, such as a sequence defined by SEQ ID NO:57.

VAR2CSA Polypeptide Modifications

Conservative modifications to the amino acid sequence of SEQ ID NO: 1-56 (and the corresponding modifications to the encoding nucleotides) will produce VAR2CSA polypeptides having functional and chemical characteristics similar to those of naturally occurring VAR2CSA polypeptides. In contrast, substantial modifications in the functional and/or chemical characteristics of a VAR2CSA polypeptide may be accomplished by selecting substitutions in the amino acid sequence of SEQ ID NO: 1-56 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain. For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, Acta Physiol. Scand. Suppl. 643:55-67; Sasaki et al., 1998, Adv. Biophys. 35:1-24, which discuss alanine scanning mutagenesis). Desired amino acid substitutions (whether conservative or non-conservative) can be determined by those skilled in the art at the time such substitutions are desired. For example, amino acid substitutions can be used to identify important residues of a VAR2CSA polypeptide, or to increase or decrease the affinity of a VAR2CSA polypeptide described herein.

Naturally occurring residues may be divided into classes based on common side chain properties: 1) hydrophobic: norleucine, Met, Ala, Val, Leu, Ile; 2) neutral hydrophilic: Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe. Non-conservative substitutions may involve, for example, the exchange of a member of one of these classes for a member from another class. Such substituted residues may be introduced into regions of the *Plasmodium falciparum* VAR2CSA polypeptide that are homologous with non-*Plasmodium falciparum* VAR2CSA polypeptides, or into the non-homologous regions of the molecule. In making such changes, the hydropathic index of amino acids may be considered.

Each amino acid has been assigned a hydropathic index on the basis of its hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is understood in the art. Kyte et al., J. Mol. Biol., 157:105-131 (1982). It is known that certain amino acids may be substituted for other amino acids having a similar hydropathic index or score and still retain a similar biological activity. In making changes based upon the hydropathic index, the substitution of amino acids whose hydropathic indexes are within ±2 is preferred, those that are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those that are within ±1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable variants of the polypeptide as set forth in SEQ ID NO:1-57 using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a VAR2CSA polypeptide to such similar polypeptides. With such a comparison, one can identify residues and portions of the molecules that are conserved among similar polypeptides. It will be appreciated that changes in areas of a VAR2CSA polypeptide that are not conserved relative to such similar polypeptides would be less likely to adversely affect the biological activity and/or structure of the VAR2CSA polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a VAR2CSA polypeptide that correspond to amino acid residues that are important for activity or structure in similar polypeptides. One skilled in the art may opt for chemically similar amino acid substitutions for such predicted important amino acid residues of VAR2CSA polypeptides described herein. One skilled in the art can also analyze the three-dimensional structure and amino acid sequence in relation to that structure in similar polypeptides. In view of that information, one skilled in the art may predict the alignment of amino acid residues of a VAR2CSA polypeptide with respect to its three dimensional structure.

One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays as described herein. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7 (4):422-427 (1996), Chou et al., Biochemistry, 13 (2):222-245 (1974); Chou et al., Biochemistry, 113 (2):211-222 (1974); Chou et al., Adv. Enzymol. Relat. Areas Mol. Biol, 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins, which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., Nucl. Acid. Res., 27 (1):244-247 (1999). It has been suggested (Brenner et al., Curr. Op. Struct. Biol., 7 (3):369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7 (3):377-87 (1997); Sippl et al., Structure, 4 (1):15-9 (1996)), "profile analysis" (Bowie et al., Science, 253:164-170 (1991); Gribskov et al., Meth. Enzymol., 183:146-159 (1990); Gribskov et al., Proc. Nat. Acad. Sci., 84 (13):4355-4358 (1987)), and "evolutionary linkage" (See Home, supra, and Brenner, supra).

Identity and similarity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math., 48:1073 (1988).

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., Nucl. Acid. Res., 12:387 (1984); Genetics Computer Group, University of Wisconsin, Madison, Wis.), BLASTP, BLASTN, and FASTA (Altschul et al., J. Mol. Biol., 215:403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Accordingly, in a preferred embodiment, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually one tenth of the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., Proc. Natl. Acad. Sci USA, 89:10915-10919 (1992) for the BLOSUM 62 comparison matrix) is also used by the algorithm.

Preferred parameters for a polypeptide sequence comparison include the following: Algorithm: Needleman et al., J. Mol. Biol, 48:443-453 (1970); Comparison matrix: BLOSUM 62 from Henikoff et al., Proc. Natl. Acad. Sci. USA, 89:10915-10919 (1992); Gap Penalty: 12, Gap Length Penalty: 4, Threshold of Similarity: 0. The GAP program is useful with the above parameters. The aforementioned parameters are the default parameters for polypeptide comparisons (along with no penalty for end gaps) using the GAP algorithm. Preferred parameters for nucleic acid molecule sequence comparisons include the following: Algorithm: Needleman et al., J. Mol Biol., 48:443-453 (1970); Comparison matrix: matches=+10, mismatch=0, Gap Penalty: 50, Gap Length Penalty: 3. The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

The amino acid sequence alterations may be accomplished by a variety of techniques. Modification of the nucleic acid sequence may be by site-specific mutagenesis. Techniques for site-specific mutagenesis are well known in the art and are described in, for example, Zoller and Smith (DNA 3:479-488, 1984) or "Splicing by extension overlap", Horton et al., Gene 77, 1989, pp. 61-68. Thus, using the nucleotide and amino acid sequences of VAR2CSA, one may introduce the alteration(s) of choice. Likewise, procedures for preparing a DNA construct using polymerase chain reaction using specific primers are well known to persons skilled in the art (cf. PCR Protocols, 1990, Academic Press, San Diego, Calif., USA).

The polypeptides described herein can also comprise non-naturally occurring amino acid residues. Non-naturally occurring amino acids include, without limitation, beta-alanine, desaminohistidine, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, nor-valine, 2-azaphenylalanine, 3-azaphenylalanine, 4-azaphenylalanine, and 4-fluorophenylalanine. Several methods are known in the art for incorporating non-naturally occurring amino acid residues into polypeptides. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Polypeptides are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically aminoacylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

VAR2CSA Nucleic Acid Constructs

The VAR2CSA polypeptides described herein may be produced by means of recombinant nucleic acid techniques. In general, a cloned wild-type VAR2CSA nucleic acid sequence is modified to encode the desired protein. This modified sequence is then inserted into an expression vector, which is in turn transformed or transfected into host cells. Higher eukaryotic cells, in particular cultured mammalian cells, may be used as host cells. Procaryotic cells such as *Lactococcus lactis* or *E. coli* can also be used to express the polypeptides as long as these prokaryotes are able to produce disulfide bonds or the protein is or may be refolded correctly. In addition, Yeast strains can also be used to express the protein, here among *Saccharomyces cerevisiae* and *P. Pichia*.

The nucleic acid construct encoding the VAR2CSA polypeptides described herein may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., Molecular Cloning: A Laboratory Manual, 2nd. Ed. Cold Spring Harbor Laboratory, Cold Spring Harbor, N.Y., 1989).

The nucleic acid construct encoding a VAR2CSA polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesized, e.g. in an automatic DNA synthesizer, purified, annealed, ligated and cloned in suitable vectors. The DNA sequences encoding the *Plasmodium falciparum* VAR2CSA polypeptides described herein may also be prepared by polymerase chain reaction using specific primers, for instance as described in U.S. Pat. No. 4,683,202, Saiki et al., Science 239 (1988), 487-491, or Sambrook et al., supra.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct is preferably a DNA construct. DNA sequences for use in producing VAR2CSA polypeptides described herein will typically encode a pre-pro polypeptide at the amino-terminus of VAR2CSA to obtain proper posttranslational processing and secretion from the host cell.

The DNA sequences encoding the *Plasmodium falciparum* VAR2CSA polypeptides described herein are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the *Plasmodium falciparum* VAR2CSA polypeptides described herein is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the polypeptide.

Expression vectors for use in expressing VAR2CSA polypeptides described herein will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell.

Examples of suitable promoters for directing the transcription of the DNA encoding the *Plasmodium falciparum* VAR2CSA polypeptide in mammalian cells include the SV40 promoter (Subramani et al., Mol. Cell Biol. 1 (1981), 854-864), the MT-1 (metallothionein gene) promoter (Palmiter et al., Science 222 (1983), 809-814), the CMV promoter (Boshart et al., Cell 41:521-530, 1985) and the adenovirus 2 major late promoter (Kaufman and Sharp, Mol. Cell. Biol, 2:1304-1319, 1982).

Examples of a suitable promoter for use in insect cells include the polyhedrin promoter (U.S. Pat. No. 4,745,051; Vasuvedan et al., FEBS Lett. 311, (1992) 7-11), the P10 promoter (J. M. Vlak et al., J. Gen. Virology 69, 1988, pp. 765-776), the *Autographa californica* polyhedrosis virus basic protein promoter (EP 397 485), the baculovirus immediate early gene 1 promoter (U.S. Pat. Nos. 5,155,037, 5,162,222), and the baculovirus 39K delayed-early gene promoter (U.S. Pat. Nos. 5,155,037; 5,162,222).

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) and alcohol dehydrogenase genes (Young et al., in Genetic Engineering of Microorganisms for Chemicals (Hollaender et al, eds.), Plenum Press, New York, 1982), and the TPI1 (U.S. Pat. No. 4,599,311) and ADH2-4c (Russell et al., Nature 304 (1983), 652-654) promoters.

Examples of suitable promoters for use in filamentous fungus host cells include, for instance, the ADH3 promoter (McKnight et al., The EMBO J. 4 (1985), 2093-2099) and the tpiA promoter. Examples of other useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters. Suitable promoters are mentioned in, e.g. EP 238 023 and EP 383 779.

The DNA sequences encoding the *Plasmodium falciparum* VAR2CSA polypeptides described herein may also, if necessary, be operably connected to a suitable terminator, such as the human growth hormone terminator (Palmiter et al., Science 222, 1983, pp. 809-814) or the TPI1 (Alber and Kawasaki, J. Mol. Appl. Gen. 1, 1982, pp. 419-434) or ADH3 (McKnight et al., The EMBO J. 4, 1985, pp. 2093-2099) terminators. Expression vectors may also contain a set of RNA splice sites located downstream from the promoter and upstream from the insertion site for the VAR2CSA sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus E1b region, the human growth hormone gene terminator (DeNoto et al. Nucl. Acids Res. 9:3719-3730, 1981) and the polyadenylation signal from *Plasmodium falciparum*, human or bovine genes. The expression vectors may also include a noncoding viral leader sequence, such as the adenovirus 2 tripartite leader, located between the promoter and the RNA splice sites; and enhancer sequences, such as the SV40 enhancer.

To direct the *Plasmodium falciparum* VAR2CSA polypeptides described herein into the secretory pathway of the host cells, a secretory signal sequence (also known as a leader sequence, pre-pro sequence or pre sequence) may be provided in the recombinant vector. The secretory signal sequence is joined to the DNA sequences encoding the *Plasmodium falciparum* VAR2CSA polypeptides described herein in the correct reading frame. Secretory signal sequences are commonly positioned 5' to the DNA sequence encoding the peptide. The secretory signal sequence may be that normally associated with the protein, or may be from a gene encoding another secreted protein.

For secretion from yeast cells, the secretory signal sequence may encode any signal peptide, which ensures efficient direction of the expressed *Plasmodium falciparum* VAR2CSA polypeptides described herein into the secretory pathway of the cell. The signal peptide may be naturally occurring signal peptide, or a functional part thereof, or it may be a synthetic peptide. Suitable signal peptides have been found to be the alpha-factor signal peptide (cf. U.S. Pat. No. 4,870,008), the signal peptide of mouse salivary amylase (cf. O. Hagenbuchle et al., Nature 289, 1981, pp. 643-646), a modified carboxypeptidase signal peptide (cf. L. A. Valls et al., Cell 48, 1987, pp. 887-897), the yeast BAR1 signal peptide (cf. WO 87/02670), or the yeast aspartic protease 3 (YAP3) signal peptide (cf. M. Egel-Mitani et al., Yeast 6, 1990, pp. 127-137).

For efficient secretion in yeast, a sequence encoding a leader peptide may also be inserted downstream of the signal sequence and upstream of the DNA sequence encoding the *Plasmodium falciparum* VAR2CSA polypeptides described herein. The function of the leader peptide is to allow the expressed peptide to be directed from the endoplasmic reticulum to the Golgi apparatus and further to a secretory vesicle for secretion into the culture medium (i.e. exportation of the *Plasmodium falciparum* VAR2CSA polypeptides described herein across the cell wall or at least through the cellular membrane into the periplasmic space of the yeast cell). The leader peptide may be the yeast alpha-factor leader (the use of which is described in e.g. U.S. Pat. Nos. 4,546,082, 4,870,008, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral alpha-amylase, *A. niger* acid-stable amylase, or *A. niger* glucoamylase. Suitable signal peptides are disclosed in, e.g. EP 238 023 and EP 215 594.

For use in insect cells, the signal peptide may conveniently be derived from an insect gene (cf. WO 90/05783), such as the lepidopteran *Manduca sexta* adipokinetic hormone precursor signal peptide (cf. U.S. Pat. No. 5,023,328).

The procedures used to ligate the DNA sequences coding for the *Plasmodium falciparum* VAR2CSA polypeptides described herein, the promoter and optionally the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, N.Y., 1989).

Methods of transfecting mammalian cells and expressing DNA sequences introduced in the cells are described in e.g. Kaufman and Sharp, J. Mol. Biol. 159 (1982), 601-621; Southern and Berg, J. Mol. Appl. Genet. 1 (1982), 327-341; Loyter et al., Proc. Natl. Acad. Sci. USA 79 (1982), 422-426; Wigler et al., Cell 14 (1978), 725; Corsaro and Pearson, Somatic Cell Genetics 7 (1981), 603, Graham and van der Eb, Virology 52 (1973), 456; and Neumann et al., EMBO J. 1 (1982), 841-845.

Cloned DNA sequences are introduced into cultured mammalian cells by, for example, calcium phosphate-mediated transfection (Wigler et al., Cell 14:725-732, 1978; Corsaro and Pearson, Somatic Cell Genetics 7:603-616, 1981; Graham and Van der Eb, Virology 52d:456-467, 1973) or electroporation (Neumann et al., EMBO J. 1:841-845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (Mammalian Cell Technology, Butterworth Publishers, Stoneham, Mass.). The person skilled in the art will easily be able to choose suitable selectable markers.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1-2 days, to begin expressing the gene of interest. In this context, "appropriate growth medium" means a medium containing nutrients and other components required for the growth of cells and the expression of the Plasmodium falciparum VAR2CSA polypeptide of interest. Media generally include a carbon source, a nitrogen source, essential amino acids, essential sugars, vitamins, salts, phospholipids, protein and growth factors. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby in-creasing expression levels. Clones of stably transfected cells are then screened for expression of the Plasmodium falciparum VAR2CSA polypeptide of interest.

The host cell into which the DNA sequences encoding the Plasmodium falciparum VAR2CSA polypeptides described herein is introduced may be any cell which is capable of producing the posttranslational modified polypeptides, and includes yeast, fungi and higher eukaryotic cells.

Examples of mammalian cell lines for use in the present invention are the COS-1 (ATCC CRL 1650), baby hamster kidney (BHK) and 293 (ATCC CRL 1573; Graham et al., J. Gen. Virol. 36:59-72, 1977) cell lines. A preferred BHK cell line is the tk-ts13 BHK cell line (Waechter and Baserga, Proc. Natl. Acad. Sci. USA 79:1106-1110, 1982), hereinafter referred to as BHK 570 cells. The BHK 570 cell line has been deposited with the American Type Culture Collection, 12301 Parklawn Dr., Rockville, Md. 20852, under ATCC accession number CRL 10314. A tk-ts13 BHK cell line is also available from the ATCC under accession number CRL 1632. In addition, a number of other cell lines may be used within the present invention, including Rat Hep I (rat hepatoma; ATCC CRL 1600), Rat Hep II (rat hepatoma; ATCC CRL 1548), TCMK (ATCC CCL 139), human lung (ATCC HB 8065), NCTC 1469 (ATCC CCL 9.1), CHO (ATCC CCL 61) and DUKX cells (Urlaub and Chasin, Proc. Natl. Acad. Sci. USA 77:4216-4220, 1980).

Examples of suitable yeasts cells include cells of Saccharomyces spp. or Schizosaccharomyces spp., in particular strains of Saccharomyces cerevisiae or Saccharomyces kluyveri. Methods for transforming yeast cells with heterologous DNA and producing heterologous polypeptides there from are described, e.g. in U.S. Pat. Nos. 4,599,311, 4,931,373, 4,870,008, 5,037,743, and 4,845,075. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequences encoding the Plasmodium falciparum VAR2CSA polypeptides described herein may be preceded by a signal sequence and optionally a leader sequence, e.g. as described above. Further examples of suitable yeast cells are strains of Kluyveromyces, such as K. lactis, Hansenula, e.g. H. polymorpha, or Pichia, e.g. P. pastoris (cf. Gleeson et al., J. Gen. Microbiol. 132, 1986, pp. 3459-3465; U.S. Pat. No. 4,882, 279).

Examples of other fungal cells are cells of filamentous fungi, e.g. Aspergillus spp., Neurospora spp., Fusarium spp. or Trichoderma spp., in particular strains of A. oryzae, A. nidulans and A. niger. The use of Aspergillus spp. for the expression of proteins is described in, e.g., EP 272 277, EP 238 023, EP 184 438 The transformation of F. oxysporum may, for instance, be carried out as described by Malardier et al., 1989, Gene 78: 147-156. The transformation of Trichoderma spp. may be performed for instance as described in EP 244 234.

When a filamentous fungus is used as the host cell, it may be transformed with the DNA construct described herein, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. Nos. 4,745,051; 4,879,236; 5,155,037; 5,162, 222; and EP 397,485. The insect cell line used as the host may suitably be a Lepidoptera cell line, such as Spodoptera frugiperda cells or Trichoplusia ni cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting expression of the Plasmodium falciparum VAR2CSA polypeptide after which all or part of the resulting peptide may be recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The Plasmodium falciparum VAR2CSA polypeptide produced by the cells may then be recovered from the culture medium by conventional procedures including separating the host cells from the medium by centrifugation or filtration, precipitating the protein aqueous components of the supernatant or filtrate by means of a salt, e.g. ammonium sulfate, purification by a variety of chromatographic procedures, e.g. ion exchange chromatography, gel filtration chromatography, affinity chromatography, or the like, dependent on the type of polypeptide in question.

Transgenic animal technology may be employed to produce the VAR2CSA polypeptides described herein. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and biochemically well characterized. Furthermore, the major milk proteins are present in milk at high concentrations (typically from about 1 to 15 g/L).

From a commercial point of view, it is clearly preferable to use as the host a species that has a large milk yield. While smaller animals such as mice and rats can be used (and are preferred at the proof of principle stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk (see, for example, WO 88/00239 for a comparison of factors influencing the choice of host species). It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489), beta lactoglobulin, a lactalbumin, and whey acidic protein. The beta lactoglobulin (BLG) promoter is preferred. In the case of the ovine beta lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non coding portion of the beta lactoglobulin gene (see Whitelaw et al., Biochem. J. 286: 31 39 (1992)). Similar fragments of promoter DNA from other species are also suitable.

Other regions of the beta lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., Proc. Natl. Acad. Sci. USA 85: 836 840 (1988); Palmiter et al., Proc. Natl. Acad. Sci. USA 88: 478 482 (1991); Whitelaw et al., Transgenic Res. 1: 3 13 (1991); WO 89/01343; and WO 91/02318). In this regard, it is generally preferred, where possible, to use genomic sequences containing all or some of the native introns of a gene encoding the protein or polypeptide of interest, thus the further inclusion of at least some introns from, e.g, the beta lactoglobulin gene, is preferred. One such region is a DNA segment that provides for intron splicing and RNA polyadenylation from the 3' non coding region of the ovine beta lactoglobulin gene. When substituted for the natural 3' non coding sequences of a gene, this ovine beta lactoglobulin segment can both enhance and stabilize expression levels of the protein or polypeptide of interest. Within other embodiments, the region surrounding the initiation ATG of the VAR2CSA sequence is replaced with corresponding sequences from a milk specific protein gene. Such replacement provides a putative tissue specific initiation environment to enhance expression. It is convenient to replace the entire VAR2CSA pre pro and 5' non coding sequences with those of, for example, the BLG gene, although smaller regions may be replaced.

For expression of VAR2CSA polypeptides described herein in transgenic animals, a DNA segment encoding VAR2CSA is operably linked to additional DNA segments required for its expression to produce expression units. Such additional segments include the above mentioned promoter, as well as sequences that provide for termination of transcription and polyadenylation of mRNA. The expression units will further include a DNA segment encoding a secretory signal sequence operably linked to the segment encoding modified VAR2CSA. The secretory signal sequence may be a native secretory signal sequence or may be that of another protein, such as a milk protein (see, for example, von Heijne, Nucl. Acids Res. 14: 4683-90 (1986); and Meade et al., U.S. Pat. No. 4,873,316).

Construction of expression units for use in transgenic animals is conveniently carried out by inserting a VAR2CSA sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a VAR2CSA variant; thereby creating a gene fusion that includes the expression control sequences of the milk protein gene. In any event, cloning of the expression units in plasmids or other vectors facilitates the amplification of the VAR2CSA sequence. Amplification is conveniently carried out in bacterial (e.g. E. coli) host cells, thus the vectors will typically include an origin of replication and a selectable marker functional in bacterial host cells. The expression unit is then introduced into fertilized eggs (including early stage embryos) of the chosen host species. Introduction of heterologous DNA can be accomplished by one of several routes, including microinjection (e.g. U.S. Pat. No. 4,873,191), retroviral infection (Jaenisch, Science 240: 1468-74 (1988)) or site directed integration using embryonic stem (ES) cells (reviewed by Bradley et al., Biotechnology 10: 534-9 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art (see, for example, Hogan et al., Manipulating the Mouse Embryo: A Laboratory Manual, Cold Spring Harbor Laboratory, 1986; Simons et al., Biotechnology 6: 179-83 (1988); Wall et al., Biol. Reprod. 32: 645 651 (1985); Buhler et al., Biotechnology 8: 140-3 (1990); Ebert et al., Biotechnology 9: 835-8 (1991); Krimpenfort et al., Biotechnology 9: 844-7 (1991); Wall et al., J. Cell. Biochem. 49: 113-20 (1992); U.S. Pat. Nos. 4,873,191; 4,873,316; WO 88/00239, WO 90/05188, WO 92/11757; and GB 87/00458). Techniques for introducing foreign DNA sequences into mammals and their germ cells were originally developed in the mouse (see, e.g., Gordon et al., Proc. Natl. Acad. Sci. USA 77: 7380-84 (1980); Gordon and Ruddle, Science 214:1244-46 (1981); Palmiter and Brinster, Cell 41: 343-5 (1985); Brinster et al., Proc. Natl. Acad. Sci. USA 82: 4438-42 (1985); and Hogan et al. (ibid.)). These techniques were subsequently adapted for use with larger animals, including livestock species (see, e.g., WO 88/00239, WO 90/05188, and WO 92/11757; and Simons et al., Biotechnology 6: 179-83 (1988)). To summarize, in the most efficient route used to date in the generation of transgenic mice or livestock, several hundred linear molecules of the DNA of interest are injected into one of the pro nuclei of a fertilized egg according to established techniques. Injection of DNA into the cytoplasm of a zygote can also be employed.

Production in transgenic plants may also be employed. Expression may be generalized or directed to a particular organ, such as a tuber (see, Hiatt, Nature 344:469 479 (1990); Edelbaum et al., J. Interferon Res. 12:449 453 (1992); Sijmons et al., Biotechnology 8:217-21 (1990); and EP 0 255 378).

The VAR2CSA polypeptides described herein may be recovered from cell culture medium or milk. The VAR2CSA polypeptides described herein may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). Preferably, they may be purified by affinity chromatography on an anti-VAR2CSA antibody column. Additional purification may be achieved by conventional chemical purification means, such as high performance liquid chromatography. Other methods of purification, including barium citrate precipitation, are known in the art, and may be applied to the purification of the VAR2CSA polypeptides described herein (see, for example, Scopes, R., Protein Purification, Springer-Verlag, N.Y., 1982).

For therapeutic purposes it is preferred that the VAR2CSA polypeptides described herein are substantially pure. Thus, in a preferred embodiment, the VAR2CSA polypeptides described herein are purified to at least about 90 to 95% homogeneity, preferably to at least about 98% homogeneity. Purity may be assessed by e.g. gel electrophoresis and amino-terminal amino acid sequencing.

Linker Moiety $L^1$

Provided are compounds of Formula IV:

T-$L^1$-$P^1$     IV wherein:
T is a targeting moiety comprising a VAR2CSA polypeptide;
$L^1$ is a linker, or $L^1$ is absent; and
$P^1$ is a monovalent radical of a compound of Formula XIV

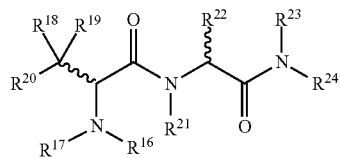

XIV wherein $R^{16}$, $R^{17}$, $R^{18}$, $R^{19}$, $R^{20}$, $R^{21}$, $R^{22}$, $R^{23}$, and $R^{24}$ are as defined herein supra and infra.

The linker moiety $L^1$ is a bifunctional compound which can be used to link payload $P^1$ and targeting moiety T to form a conjugate compound, T-$L^1$-$P^1$. Such conjugates allow the selective delivery of drugs to target cells (e.g., tumor cells). Linker moieties include a divalent substituent such as an alkyldiyl, an aryldiyl, a heteroaryldiyl, moieties such as: —$(CR_2)_nO(CR_2)_n$—, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide. The compounds described herein can be prepared using a linker moiety having a reactive site for binding to the payload and the targeting moiety.

In some embodiments, $L^1$ has a reactive site which has an electrophilic group that is reactive to a nucleophilic group present on T. Useful nucleophilic groups on T include but are not limited to sulfhydryl, hydroxyl and amino groups. The heteroatom of the nucleophilic group of T is reactive to an electrophilic group on $L^1$ and forms a covalent bond to $L^1$. Useful electrophilic groups include, but are not limited to maleimide and haloacetamide groups. The nucleophilic group on T provide a convenient site for attachment to $L^1$.

In some embodiments, $L^1$ has a reactive site which has a nucleophilic group that is reactive to an electrophilic group present on the targeting moiety. Useful electrophilic groups on the targeting moiety include, but are not limited to, aldehyde and ketone carbonyl groups. The heteroatom of a nucleophilic group of $L^1$ can react with an electrophilic group on the targeting moiety and form a covalent bond to the targeting moiety. Useful nucleophilic groups on $L^1$ include, but are not limited to, hydrazide, oxime, amino, hydrazine, thiosemicarbazone, hydrazine carboxylate, and arylhydrazide. The electrophilic group on the targeting moiety provides a convenient site for attachment to $L^1$.

Carboxylic acid functional groups and chloroformate functional groups are also useful reactive sites for $L^1$ because they can react, for example, with an amino group of $P^1$ to form an amide linkage. Also useful as a reactive site is a carbonate functional group on $L^1$, such as but not limited to p-nitrophenyl carbonate, which can react, for example, with an amino group of $P^1$ to form a carbamate linkage.

It will be appreciated that any linker moieties taught in the prior art, and particularly those taught for use in the context of drug delivery, may be used in the current invention. In some embodiments, linkers with features well suited to a particular use, such as susceptibility to enzymatic cleavage or chemical cleavage within a cell of interest, may be used.

Without limiting the scope of the preceding statement, in one embodiment, $L^1$ comprises a linker moiety disclosed in WO 2012/113847. In another embodiment, $L^1$ comprises a linker moiety disclosed in U.S. Pat. No. 8,288,352. In another embodiment, $L^1$ comprises a linker moiety disclosed in U.S. Pat. No. 5,028,697. In another embodiment, $L^1$ comprises a linker moiety disclosed in U.S. Pat. No. 5,006,652. In another embodiment, $L^1$ comprises a linker moiety disclosed in U.S. Pat. No. 5,094,849. In another embodiment, $L^1$ comprises a linker moiety disclosed in U.S. Pat. No. 5,053,394. In another embodiment, $L^1$ comprises a linker moiety disclosed in U.S. Pat. No. 5,122,368. In another embodiment, $L^1$ comprises a linker moiety disclosed in U.S. Pat. No. 5,387,578. In another embodiment, $L^1$ comprises a linker moiety disclosed in U.S. Pat. No. 5,547,667. In another embodiment, $L^1$ comprises a linker moiety disclosed in U.S. Pat. No. 5,622,929. In another embodiment, $L^1$ comprises a linker moiety disclosed in U.S. Pat. No. 5,708,146. In another embodiment, $L^1$ comprises a linker moiety disclosed in U.S. Pat. No. 6,468,522. In another embodiment, $L^1$ comprises a linker moiety disclosed in U.S. Pat. No. 6,103,236. In another embodiment, $L^1$ comprises a linker moiety disclosed in U.S. Pat. No. 6,638,509. In another embodiment, $L^1$ comprises a linker moiety disclosed in U.S. Pat. No. 6,214,345. In another embodiment, $L^1$ comprises a linker moiety disclosed in U.S. Pat. No. 6,759,509. In another embodiment, $L^1$ comprises a linker moiety disclosed in WO 2007/103288. In another embodiment, $L^1$ comprises a linker moiety disclosed in WO 2008/083312. In another embodiment, $L^1$ comprises a linker moiety disclosed in WO 2003/068144. In another embodiment, $L^1$ comprises a linker moiety disclosed in WO 2004/016801. In another embodiment, $L^1$ comprises a linker moiety disclosed in WO 2009/134976. In another embodiment, $L^1$ comprises a linker moiety disclosed in WO 2009/134952. In another embodiment, $L^1$ comprises a linker moiety disclosed in WO 2009/134977. In another embodiment, $L^1$ comprises a linker moiety disclosed in WO 2002/08180. In another embodiment, $L^1$ comprises a linker moiety disclosed in WO 2004/043493. In another embodiment, $L^1$ comprises a linker moiety disclosed in WO 2007/018431. In another embodiment, $L^1$ comprises a linker moiety disclosed in WO 2003/026577. In another embodiment, $L^1$ comprises a linker moiety disclosed in WO 2005/077090. In another embodiment, $L^1$ comprises a linker moiety disclosed in WO 2005/082023. In another embodiment, $L^1$ comprises a linker moiety disclosed in WO 2007/011968. In another embodiment, $L^1$ comprises a linker moiety disclosed in WO 2007/038658. In another embodiment, $L^1$ comprises a linker moiety disclosed in WO 2007/059404. In another embodiment, $L^1$ comprises a linker moiety disclosed in WO 2006/

110476. In another embodiment, L¹ comprises a linker moiety disclosed in WO 2005/112919. In another embodiment, L¹ comprises a linker moiety disclosed in WO 2008/103693. In another embodiment, L¹ comprises a linker moiety disclosed in U.S. Pat. No. 6,756,037. In another embodiment, L¹ comprises a linker moiety disclosed in U.S. Pat. No. 7,087,229. In another embodiment, L¹ comprises a linker moiety disclosed in U.S. Pat. No. 7,122,189. In another embodiment, L¹ comprises a linker moiety disclosed in U.S. Pat. No. 7,332,164. In another embodiment, L¹ comprises a linker moiety disclosed in U.S. Pat. No. 5,556,623. In another embodiment, L¹ comprises a linker moiety disclosed in U.S. Pat. No. 5,643,573. In another embodiment, L¹ comprises a linker moiety disclosed in U.S. Pat. No. 5,665,358. Linkers L¹ comprising a self-immolative component may also be used. For example, see U.S. Pat. No. 6,214,345. An example of a self-immolative component is p-aminobenzylcarbamoyl (PABC). Commercially available linkers may be used in the invention. For example, the commercially available cleavable linker sulfosuccinimidyl 6-[3'(2-pyridyldithio)-propionamido]hexanoate (sulfo-LC-SPDP: Thermo Pierce Cat #21650) and Non-cleavable linker succinimidyl 4-[N-maleimidomethyl]cyclohexane-1-carboxylate (SMCC: Thermo Pierce Cat #22360) may be used, as demonstrated herein. See also, WO2012171020, WO2010138719, the range of commercially available linkers, for example, from Concortis http://www.concortis.com/home. See also Kim et al., Bioconjugate Chemistry, 21 (8): 1513-1519 August 2010. See also EP2326349. See also copper-free click chemistry linkers, Angew. Chem. Int. Ed., 2010, 49, p. 9422-9425, ChemBioChem, 2011, 12, p. 1309-1312, http://www.synaffix.com/technology/.

In some embodiments, L¹ comprises: SPDP, SMCC, vcPABC, MCvcPABC, MTvc, ADvc, maleimide, NHS, biotin, streptavidin, NeutrAvidin, a glycoside, or a combination thereof.

In some embodiments, L¹ comprises SPDP.
In some embodiments, L¹ comprises SMCC.
In some embodiments, L¹ comprises vcPABC.
In some embodiments, L¹ comprises MCvcPABC.
In some embodiments, L¹ comprises MTvc.
In some embodiments, L¹ comprises ADvc.
In some embodiments, L¹ comprises maleimide.
In some embodiments, L¹ comprises NHS.
In some embodiments, L¹ comprises biotin.
In some embodiments, L¹ comprises streptavidin.
In some embodiments, L¹ comprises NeutrAvidin.
In some embodiments, L¹ comprises a glycoside.
In some embodiments, L¹ is absent.

Payload Moiety P¹

Talpir, R. et al. (1994) Tetrahedron Lett. 35:4453-6, describe the naturally occurring compound hemiasterlin, a stable tripeptide obtained from marine sponges that causes microtubule depolymerization and mitotic arrest in cells. Hemisasterlin consists of unusual and highly congested amino acids, features thought to contribute to its activity. A number of groups have modified particular structural elements of hemiasterlin to evaluate structure-activity relationships and assess the activity of hemiasterlin analogs. See for example Zask et al., Bioorganic & Medicinal Chemistry Letters, 14:4353-4358, 2004; Zask et al., J Med Chem, 47:4774-4786, 2004; Yamashita et al., Bioorganic & Medicinal Chemistry Letters, 14:5317-5322, 2004; PCT/GB96/00942; WO 2004/026293; WO96/33211; and U.S. Pat. No. 7,579,323.

Analogs of hemiasterlin with modifications in the "A-segment", or the amino terminal segment, have been described (see for example, Zask et al., J Med Chem, 47:4774-4786, 2004; Yamashita et al., Bioorganic & Medicinal Chemistry Letters, 14:5317-5322, 2004; U.S. Pat. No. 7,579,323). U.S. Pat. No. 7,579,323 discloses an analog of hemiasterlin, referred to as HTI-286, in which the indole moiety is replaced by a phenyl group. HTI-286 exhibits potent antimitotic activity and has been assessed in clinical trials for the treatment of cancer (Ratain et al., Proc Am Soc Clin Oncol, 22:129, 2003).

Analogs of hemiasterlin with modifications in the "D-segment", or the carboxy terminal segment, have also been reported (see, for example, WO 2004/026293; Zask et al., Bioorganic & Medicinal Chemistry Letters, 14:4353-4358, 2004; Zask et al., J Med Chem, 47:4774-4786, 2004). The majority of modifications at the carboxy terminus result in compounds with substantially decreased potency compared to parent carboxylic acids. See, for example, WO 2004/026293, particularly Table 12. Zask et al., (J Med Chem, 47:4774-4786, 2004) also report that amide analogs prepared using simple cyclic and acyclic amines exhibit significantly reduced potency (reductions of one to three orders of magnitude). Among the few tolerated modifications, Zask et al., (Bioorganic & Medicinal Chemistry Letters, 14:4353-4358, 2004) report that the addition of esterified cyclic amino acids at the carboxy-terminus yields tetrapeptide analogs with prolyl-like ester-containing termini, some of which exhibit potency comparable to parent compound in a tested cancer cell line.

While a wide variety of hemiasterlin analogs have been generated, many, including a wide variety of compounds with modifications at the carboxy terminus, exhibit reduced potency that limits utility in methods of medical treatment. However, certain hemiasterlin analogs modified by the addition of an N-acyl sulfonamide moiety at the carboxy terminus, such as those disclosed in International Application No. PCT/US14/29463 or U.S. Ser. No. 14/213,504, demonstrate potent anticancer activity across a broad range of cancer cell lines.

Accordingly, provided are compounds of Formula IV:

$$T\text{-}L^1\text{-}P^1 \qquad\qquad IV$$

wherein:
T is a targeting moiety comprising a VAR2CSA polypeptide;
L¹ is a linker, or L is absent; and
P¹ is a monovalent radical of a compound of Formula XIV:

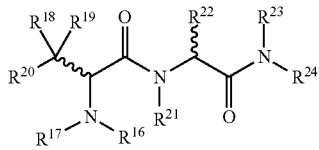

XIV wherein:
R¹⁶ and R¹⁷ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO₂H, —CHO, —COSH, or —NO₂; or R¹⁷ and R²⁰ are fused and form a ring;

$R^{18}$ and $R^{19}$ are independently selected from the group consisting of: H, $R^{25}$, and $ArR^{25}$—, or $R^{18}$ and $R^{19}$ are joined to form a ring;

$R^{20}$ is selected from the group consisting of: H, $R^{25}$, $ArR^{25}$—, and Ar; or $R^{20}$ and $R^{17}$ are fused and form a ring;

$R^{21}$ is selected from the group consisting of: H, $R^{25}$, and $ArR^{25}$—;

$R^{22}$ and $R^{23}$ are independently selected from the group consisting of: H, $R^{25}$, and $ArR^{25}$—;

$R^{24}$ is: —Y—(CO)NHSO$_2$—$R^{26}$ $R^{25}$ is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$^{28}$, —O$_2$CR$^{28}$, —SH, —SR$^{28}$, —SOCR$^{28}$, —NH$_2$, —NHR$^{28}$, —N(R$^{28}$)$_2$, —NHCOR$^{28}$, —NR$^{28}$COR$^{28}$, —I, —Br, —Cl, —F, —CN, —CO$_2$H, —CO$_2$R$^{28}$, —CHO, —COR$^{28}$, —CONH$_2$, —CONHR$^{28}$, —CON(R$^{28}$)$_2$, —COSH, —COSR$^{28}$, —NO$_2$, —SO$_3$H, —SOR$^{28}$, —SO$_2$R$^{28}$, wherein R$^{28}$ is a linear, branched or cyclic, one to ten carbon saturated or unsaturated alkyl group;

the ring formed by joining $R^{18}$ and $R^{19}$ is a three to seven member non-aromatic cyclic skeleton within the definition of $R^{25}$, Y is defined as a moiety selected from the group consisting of: a linear, saturated or unsaturated, one to six carbon alkyl group, optionally substituted with $R^{25}$, $ArR^{25}$—, or X; and, X is defined as a moiety selected from the group consisting of: —OH, —OR$^{25}$, =O, =S, —O$_2$CR$^{25}$, —SH, —SR$^{25}$, —SOCR$^{25}$, —NH$_2$, —NHR$^{25}$, —N(R$^{25}$)$_2$, —NHCOR$^{25}$, —NRCOR$^{25}$, —I, —Br, —Cl, —F, —CN, —CO$_2$H, —CO$_2$R$^{25}$, —CHO, —COR$^{25}$, —CONH$_2$, —CONHR$^{25}$, —CON(R$^{25}$)$_2$, —COSH, —COSR$^{25}$, —NO$_2$, —SO$_3$H, —SOR$^{25}$, and —SO$_2$R$^{25}$;

$R^{26}$ is selected from the group consisting of optionally substituted alkyl, optionally substituted alkylamino, optionally substituted cycloalkyl, optionally substituted aryl, optionally substituted heterocyclyl and optionally substituted heteroaryl, —COR$^{27}$, —CSR$^{27}$, —OR$^{27}$, and —NHR$^{27}$, wherein each R$^{27}$ is, independently, optionally substituted alkyl, optionally substituted alkylamino, optionally substituted cycloalkyl, optionally substituted aryl, optionally substituted heterocyclyl or optionally substituted heteroaryl;

or a stereoisomer, prodrug or pharmaceutically acceptable salt thereof.

In a preferred embodiment, $R^{26}$ is selected from the group consisting of optionally substituted alkyl, optionally substituted alkylamino, optionally substituted cycloalkyl, optionally substituted aryl, optionally substituted heterocyclyl and optionally substituted heteroaryl.

In one embodiment, Ar is an aromatic ring selected from the group consisting of: phenyl, naphthyl, anthracyl, pyrrolyl.

In some embodiments, $P^1$ is a monovalent radical of a compound of Formula XV:

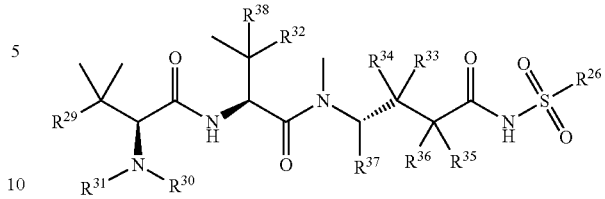

XV wherein:

$R^{26}$ is selected from the group consisting of optionally substituted alkyl, optionally substituted alkylamino, optionally substituted cycloalkyl, optionally substituted aryl, optionally substituted heterocyclyl, optionally substituted heteroaryl, —COR$^{27}$, —CSR$^{27}$, —OR$^{27}$, and —NHR$^{27}$, wherein each R$^{27}$ is, independently, alkyl optionally substituted with halogen, —OH or —SH;

$R^{29}$ is selected from the group consisting of optionally substituted alkyl, optionally substituted alkylamino, optionally substituted cycloalkyl, optionally substituted aryl, optionally substituted heterocyclyl and optionally substituted heteroaryl;

$R^{30}$ is selected from the group consisting of H and $C_{1-6}$ alkyl;

$R^{31}$ is selected from the group consisting of H and $C_{1-6}$ alkyl;

$R^{32}$ and $R^{38}$ are independently selected from the group consisting of H, $C_{1-6}$ alkyl and —SH, with the proviso that $R^{32}$ and $R^{38}$ cannot both be H;

$R^{33}$, $R^{34}$, $R^{35}$ and $R^{36}$ are independently H and $C_{1-6}$ alkyl, at least one of $R^{33}$ and $R^{34}$ is H; or $R^{34}$ and $R^{35}$ form a double bond, $R^{33}$ is H, and $R^{36}$ is H or $C_{1-6}$ alkyl; and $R^{37}$ is selected from the group consisting of H and $C_{1-6}$ alkyl;

or a stereoisomer, prodrug or pharmaceutically acceptable salt thereof.

In a preferred embodiment, $R^{26}$ is selected from the group consisting of optionally substituted alkyl, optionally substituted alkylamino, optionally substituted cycloalkyl, optionally substituted aryl, optionally substituted heterocyclyl and optionally substituted heteroaryl.

In a further embodiment, each optionally substituted alkyl, optionally substituted alkylamino, optionally substituted cycloalkyl, optionally substituted aryl, optionally substituted heterocyclyl and optionally substituted heteroaryl is, independently, optionally substituted with =O, =S, —OH, —OR$^{27}$, —O$_2$CR$^{27}$, —SH, —SR$^{27}$, —SOCR$^{27}$, —NH$_2$, —N$_3$, —NHR$^{27}$, —N(R$^{27}$)$_2$, —NHCOR$^{27}$, —NR$^{27}$COR$^{27}$, —I, —Br, —Cl, —F, —CN, —CO$_2$H, —CO$_2$R$^{27}$, —CHO, —COR$^{27}$, —CONH$_2$, —CONHR$^{27}$, —CON(R$^{27}$)$_2$, —COSH, —COSR$^{27}$, —NO$_2$, —SO$_3$H, —SOR$^{27}$ or —SO$_2$R$^{27}$ wherein each R$^{27}$ is, independently, alkyl optionally substituted with halogen, —OH or —SH.

In another further embodiment, each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

In another further embodiment, $R^{29}$ is selected from one of the following structures XVI, XVII, XVIII, and XIX:

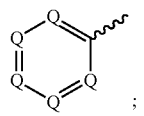

XVI

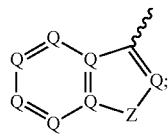

XVII

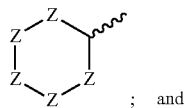

XVIII

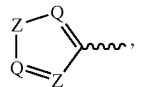

XIX wherein:

Q is $CR^{39}$ or N;

Z is $C(R^{39})_2$, $NR^{39}$, S, or O;

each $R^{39}$ is, independently, selected from the group consisting of H, —OH, —$R^{27}$, —$OR^{27}$, —$O_2CR^{27}$, —SH, —$SR^{27}$, —$SOCR^{27}$, —$NH_2$, —$N_3$, —$NHR^{27}$, —$N(R^{27})_2$, —$NHCOR^{27}$, —$NR^{27}COR^{27}$, —$R^{27}NH_2$, —I, —Br, —Cl, —F, —CN, —$CO_2H$, —$CO_2R^{27}$, —CHO, —$COR^{27}$, —$CONH_2$, —$CONHR^{27}$, —$CON(R^{27})_2$, —COSH, —$COSR^{27}$, —$NO_2$, —$SO_3H$, —$SOR^{27}$, and —$SO_2R^{27}$, wherein each $R^{27}$ is, independently, alkyl optionally substituted with halogen, —OH or —SH.

In another further embodiment, $R^{29}$ is selected from the group consisting of:

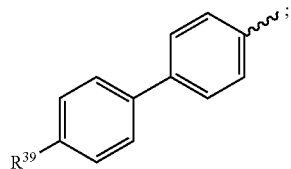

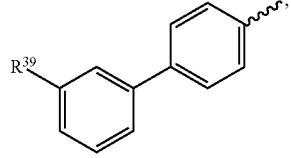

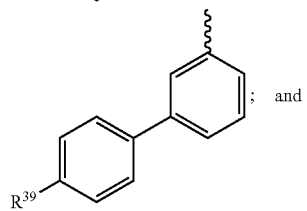

; and

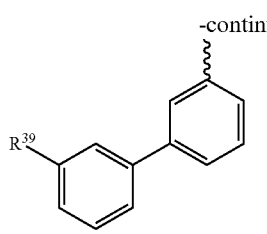

XVI wherein each $R^{39}$ is, independently, selected from the group consisting of H, —OH, —$R^{27}$, —$OR^{27}$, —$O_2CR^{27}$, —SH, —$SR^{27}$, —$SOCR^{27}$, —$NH_2$, —$N_3$, —$NHR^{27}$, —$N(R^{27})_2$, —$NHCOR^{27}$, —$NR^{27}COR^{27}$, —$R^{27}NH_2$, —I, —Br, —Cl, —F, —CN, —$CO_2H$, —$CO_2R^{27}$, —CHO, —$COR^{27}$, —$CONH_2$, —$CONHR^{27}$, —$CON(R^{27})_2$, —COSH, —$COSR^{27}$, —$NO_2$, —$SO_3H$, —$SOR^{27}$, and —$SO_2R^{27}$, wherein each $R^{27}$ is, independently, alkyl optionally substituted with halogen, —OH or —SH.

In another further embodiment, $R^{29}$ is selected from the group consisting of:

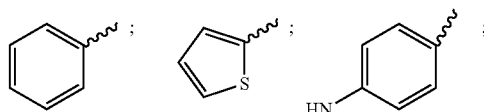

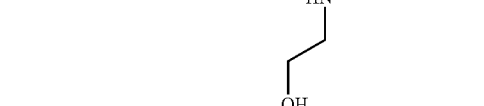

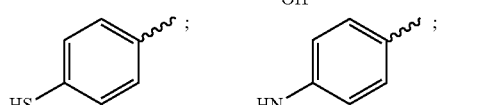

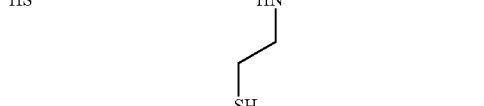

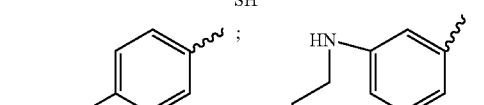

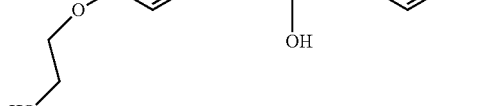

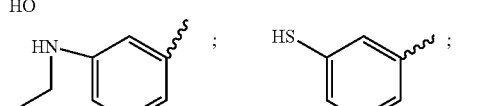

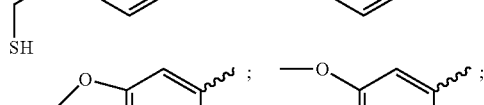

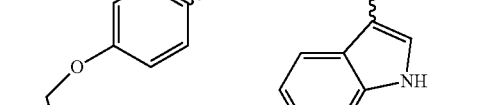

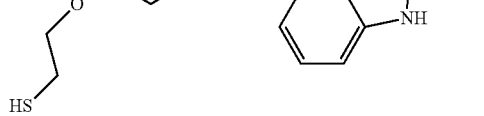

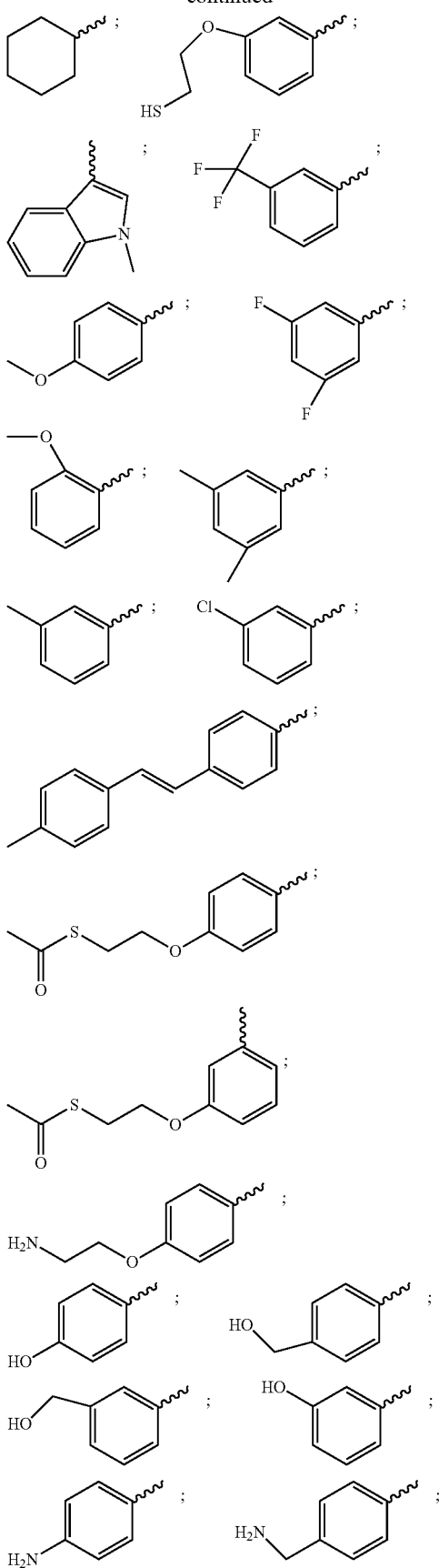
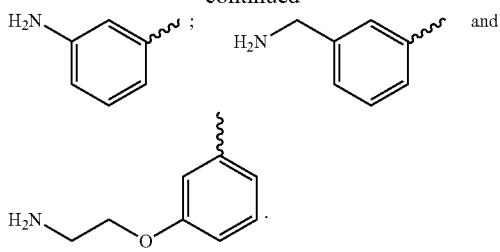
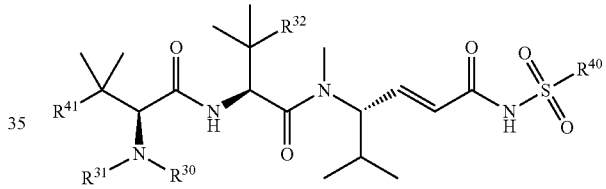

In another further embodiment, $R^{29}$ is:

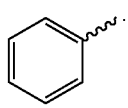

In another further embodiment, $R^{30}$, $R^{31}$, $R^{32}$, and $R^{38}$ are each methyl.

In another further embodiment, $R^{30}$ is H, $R^{31}$ is methyl, $R^{32}$ is methyl, and $R^{38}$ is methyl.

In some embodiments, $P^1$ is a monovalent radical of a compound of Formula XX:

XX wherein:

$R^{40}$ is selected from the group consisting of optionally substituted alkyl, optionally substituted alkylamino, optionally substituted cycloalkyl, optionally substituted aryl, optionally substituted heterocyclyl, optionally substituted heteroaryl, —COR$^{27}$, —CSR$^{27}$, —OR$^{27}$, and —NHR$^{27}$, wherein each $R^{27}$ is, independently, optionally substituted alkyl, optionally substituted alkylamino, optionally substituted cycloalkyl, optionally substituted aryl, optionally substituted heterocyclyl, optionally substituted heteroaryl;

$R^{41}$ is selected from the group consisting of optionally substituted alkyl, optionally substituted alkylamino, optionally substituted cycloalkyl, optionally substituted aryl, optionally substituted heterocyclyl and optionally substituted heteroaryl;

$R^{30}$ is selected from the group consisting of H and $C_{1-6}$ alkyl;

$R^{31}$ is selected from the group consisting of H and $C_{1-6}$ alkyl; and $R^{32}$ is selected from the group consisting of $C_{1-6}$ alkyl and —SH, or a stereoisomer, prodrug or pharmaceutically acceptable salt thereof.

In a preferred embodiment, $R^{40}$ is selected from the group consisting of optionally substituted alkyl, optionally substituted alkylamino, optionally substituted cycloalkyl, optionally substituted aryl, optionally substituted heterocyclyl and optionally substituted heteroaryl.

In a further embodiment, each optionally substituted alkyl, optionally substituted alkylamino, optionally substituted cycloalkyl, optionally substituted aryl, optionally substituted heterocyclyl and optionally substituted heteroaryl is, independently, optionally substituted with =O, =S, —OH, —OR$^{42}$, —O$_2$CR$^{42}$, —SH, —SR$^{42}$, —SOCR$^{42}$, —NH$_2$, —N$_3$, —NHR$^{42}$, —N(R$^{42}$)$_2$, —NHCOR$^{42}$, —NR$^{42}$COR$^{42}$, —I, —Br, —Cl, —F, —CN, —CO$_2$H, —CO$_2$R$^{42}$, —CHO, —COR$^{42}$, —CONH$_2$, —CONHR$^{42}$, —CON(R$^{42}$)$_2$, —COSH, —COSR$^{42}$, —NO$_2$, —SO$_3$H, —SOR$^{42}$ or —SO$_2$R$^{42}$, wherein each R$^{42}$ is, independently, alkyl optionally substituted with halogen, —OH or —SH.

In another further embodiment, each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

In another further embodiment, R$^{41}$ is selected from one of the following structures XVI, XVII, XVIII, and XIX:

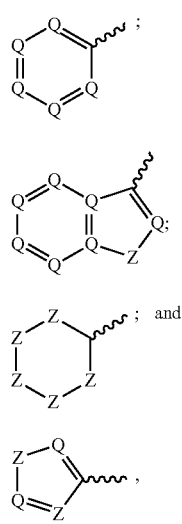

XVI

XVII

XVIII ; and

XIX wherein:

Q is CR$^{43}$ or N;

Z is C(R$^{43}$)$_2$, NR$^{43}$, S, or O;

each R$^{43}$ is, independently, selected from the group consisting of H, —OH, —OR$^{42}$, —O$_2$CR$^{42}$, —SH, —SR$^{42}$, —SOCR$^{42}$, —NH$_2$, —N$_3$, —NHR$^{42}$, —N(R$^{42}$)$_2$, —NHCOR$^{42}$, —NR$^{42}$COR$^{42}$, —I, —Br, —Cl, —F, —CN, —CO$_2$H, —CO$_2$R$^{42}$, —CHO, —COR$^{42}$, —CONH$_2$, —CONHR$^{42}$, —CON(R$^{42}$)$_2$, —COSH, —COSR$^{42}$, —NO$_2$, —SO$_3$H, —SOR$^{42}$, and —SO$_2$R$^{42}$, wherein each R$^{42}$ is, independently, alkyl optionally substituted with halogen, —OH or —SH.

In another further embodiment, R$^{41}$ is selected from the group consisting of:

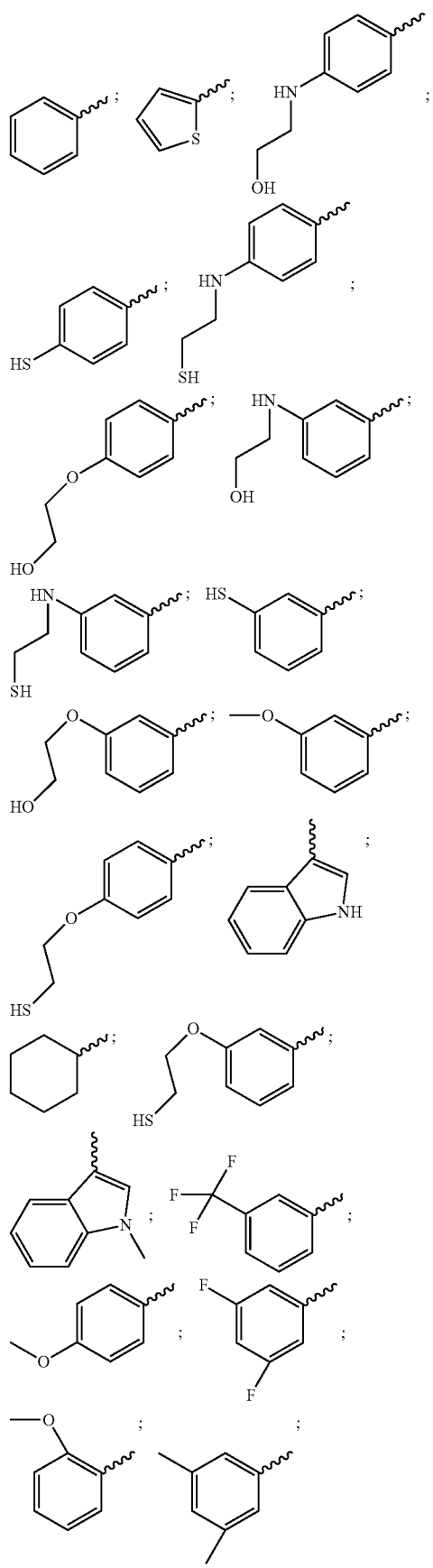

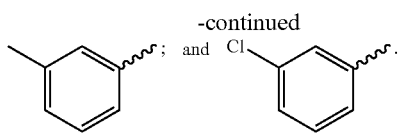; and

In another further embodiment, $R^{41}$ is:

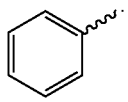

In another further embodiment, $R^{30}$, $R^{31}$ and $R^{32}$ are each methyl.

In another further embodiment, $R^{30}$ is H, $R^{31}$ is methyl, and $R^{32}$ is methyl.

In some embodiments, $P^1$ is a monovalent radical of a compound of Formula II:

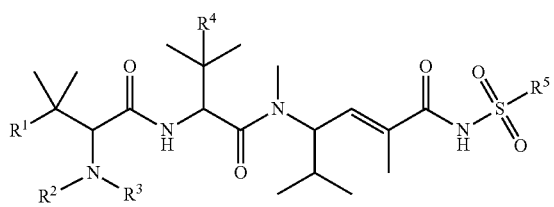

wherein:

$R^1$ is selected from: aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkoxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkoxy are further optionally substituted with one substituent selected from $C_1$-$C_4$ alkylaryl, hydroxyl, and thio;

$R^2$ and $R^3$ are each independently selected from: H and $C_1$-$C_6$ alkyl;

$R^4$ is selected from the group consisting of $C_1$-$C_6$ alkyl and thio; and $R^5$ is selected from: $C_1$-$C_6$ alkyl, aryl, aryl-$C_1$-$C_6$ alkyl, $C_3$-$C_7$ cycloalkyl, heteroaryl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, $C_3$-$C_7$ cycloalkyl, cyano, $C_1$-$C_6$ haloalkyl, $C_1$-$C_6$ haloalkoxy, halo, hydroxyl, nitro, thio, and thio-$C_1$-$C_6$ alkyl; and In some embodiments, $R^1$ is selected from: is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkoxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkoxy are further optionally substituted with one substituent selected from p-tolyl, hydroxyl, and thio.

In some embodiments, $R^1$ is selected from: H, aryl, $C_3$-$C_7$ cycloalkyl, and heteroaryl, each of which is optionally substituted with one or more substituents selected from: (2-hydroxyethyl)amino, (2-mercaptoethyl)amino, 2-(acetylthio)ethoxy, 2-aminoethoxy, 2-hydroxyethoxy, 2-mercaptoethoxy, 3-methoxy, 4-methylstyryl, amino, aminomethyl, chloro, fluoro, hydroxyl, hydroxymethyl, methyl, thio, trifluoromethyl.

In some embodiments, $R^1$ is selected from: H, cyclohexyl, 1H-indol-3-yl, phenyl, and thien-2-yl each of which is optionally substituted with one or more substituents selected from: (2-hydroxyethyl)amino, (2-mercaptoethyl)amino, 2-(acetylthio)ethoxy, 2-aminoethoxy, 2-hydroxyethoxy, 2-mercaptoethoxy, 3-methoxy, 4-methylstyryl, amino, aminomethyl, chloro, fluoro, hydroxyl, hydroxymethyl, methyl, thio, and trifluoromethyl.

In some embodiments, $R^1$ is selected from: H, 1H-indol-3-yl, 1-methyl-1H-indol-3-yl, 2-methoxyphenyl, 3-((2-hydroxyethyl)amino)phenyl, 3-((2-mercaptoethyl)amino)phenyl, 3-(2-(acetylthio)ethoxy)phenyl, 3-(2-hydroxyethoxy)phenyl, 3-(2-mercaptoethoxy)phenyl, 3-(4-methylstyryl)phenyl, 3-(aminomethyl)phenyl, 3-(hydroxymethyl)phenyl, 3-hydroxyphenyl, 3,5-difluorophenyl, 3,5-dimethylphenyl, 3-aminophenyl, 3-chlorophenyl, 3-mercaptophenyl, 3-methoxyphenyl, 3-trifluoromethylphenyl, 4-((2-hydroxyethyl)amino)phenyl, 4-((2-mercaptoethyl)amino)phenyl, 4-(2-(acetylthio)ethoxy)phenyl, 4-(2-aminoethoxy)phenyl, 4-(2-hydroxyethoxy)phenyl, 4-(2-mercaptoethoxy)phenyl, 4-(aminomethyl)phenyl, 4-(hydroxymethyl)phenyl, 4-aminophenyl, 4-hydroxyphenyl, 4-mercaptophenyl, 4-methoxyphenyl, cyclohexyl, thien-2-yl, m-tolyl, and phenyl.

In some embodiments, $R^1$ is selected from: H, 1H-indol-3-yl, 1-methyl-1H-indol-3-yl, 2-methoxyphenyl, 3-((2-hydroxyethyl)amino)phenyl, 3-((2-mercaptoethyl)amino)phenyl, 3-(2-hydroxyethoxy)phenyl, 3-(2-mercaptoethoxy)phenyl, 3,5-difluorophenyl, 3,5-dimethylphenyl, 3-chlorophenyl, 3-mercaptophenyl, 3-methoxyphenyl, 3-trifluoromethylphenyl, 4-((2-hydroxyethyl)amino)phenyl, 4-((2-mercaptoethyl)amino)phenyl, 4-4-(2-hydroxyethoxy)phenyl, 4-(2-mercaptoethoxy)phenyl, 4-mercaptophenyl, 4-methoxyphenyl, cyclohexyl, thien-2-yl, m-tolyl, and phenyl.

In some embodiments, $R^1$ is phenyl.
In some embodiments, $R^2$ is H.
In some embodiments, $R^2$ is methyl.
In some embodiments, $R^3$ is methyl.
In some embodiments, $R^4$ is methyl.
In some embodiments, $R^5$ is selected from: $C_1$-$C_6$ alkyl, aryl, aryl-$C_1$-$C_6$ alkyl, $C_3$-$C_7$ cycloalkyl, heteroaryl, and heterocyclyl, each optionally substituted with one or more substituents selected from: 1-aminocyclopropyl, 4-aminophenyl, amino, aminomethyl, bromo, tert-butyl, carboxamide, carboxyl, chloro, cyano, cyclopentyl, ethyl, fluoro, hydroxy, isopropyl, methoxy, methyl, nitro, phenyl, pyridin-3-yl, thio, thiomethyl, trifluoromethoxy, and trifluoromethyl.

In some embodiments, $R^5$ is selected from: 5,6,7,8-tetrahydronaphthalen-1-yl, benzyl, cyclohexyl, ethyl, hexan-2-yl, methyl, naphthalen-2-yl, piperidin-1-yl, phenyl, propyl, pyridin-3-yl, and thien-2-yl, each optionally substituted with one or more substituents selected from: 1-aminocyclopropyl, 4-aminophenyl, amino, aminomethyl, bromo, tert-butyl, carboxamide, carboxyl, chloro, cyano, cyclopentyl, ethyl, fluoro, hydroxy, isopropyl, methoxy, methyl, nitro, phenyl, pyridin-3-yl, thio, thiomethyl, trifluoromethoxy, and trifluoromethyl.

In some embodiments, $R^5$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, methyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, 4-aminophenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl.

In some embodiments, $R^5$ is selected from: aryl and aryl-$C_1$-$C_6$ alkyl, each optionally substituted with one or more substituents selected from: amino and amino-$C_1$-$C_6$ alkyl.

In some embodiments, $R^5$ is selected from: 4-aminobenzyl, 4-(aminomethyl)benzyl, 4-(aminomethyl)phenyl, 4-aminophenyl, and benzyl.

In some embodiments, $R^5$ is 4-aminobenzyl.
In some embodiments, $R^5$ is 4-(aminomethyl)benzyl.
In some embodiments, $R^5$ is 4-(aminomethyl)phenyl.
In some embodiments, $R^5$ is 4-aminophenyl.
In some embodiments, wherein $R^5$ is benzyl.

In some embodiments $P^1$ is a monovalent radical of a compound disclosed in International Application No. PCT/US14/29463 or U.S. Ser. No. 14/213,504.

It will be recognized by the artisan of reasonable skill that compounds of Formula XIV may be appropriately modified to facilitate a conjugation reaction with $L^1$, or if $L^1$ is not present, with T, and formation of a conjugate T-$L^1$-$P^1$ or T-$P^1$. Any point of attachment on $P^1$ may be used. In some embodiments, the C-terminus of $P^1$ forms the point of attachment in a T-$L^1$-$P^1$ conjugate. In another embodiment, the N-terminus of $P^1$ forms the point of attachment in a T-$L^1$-$P^1$ conjugate. In another embodiment, a side chain of $P^1$ forms the point of attachment in a T-$L^1$-$P^1$ conjugate.

In some embodiments, $P^1$ is a microtubule disrupting peptide toxin that covalently linked to $L^1$ through the side chain of the N-terminal amino acid of $P^1$, or if $L^1$ is not present, $P^1$ is covalently linked to T through the side chain of the N-terminal amino acid of $P^1$. In one embodiment, the microtubule disrupting peptide toxin is hemiasterlin or an analog thereof and the toxin is covalently linked in the conjugate through the indole moiety within the side chain of the N-terminal amino acid of the toxin peptide. In another embodiment, the microtubule disrupting peptide toxin is HTI-286 or an analog thereof and the toxin is covalently linked in the conjugate through the phenyl group within the side chain of the N-terminal amino acid of the toxin peptide. In one embodiment, the microtubule disrupting peptide toxin is tubulysin or an analog thereof and the toxin is covalently linked in the conjugate through the indole moiety within the side chain of the N-terminal amino acid of the toxin peptide. In one embodiment, the microtubule disrupting peptide toxin is auristatin or an analog thereof and the toxin is covalently linked in the conjugate through the indole moiety within the side chain of the N-terminal amino acid of the toxin peptide. In one embodiment, the microtubule disrupting peptide toxin is a compound having structure XIV, XV, or XX.

In some embodiments, the compound T-$L^1$-$P^1$ has antimitotic activity and the following structure (XXI):

$$T\text{-}L^1\text{-}PT \qquad\qquad XXI$$

wherein T is a targeting moiety as described herein, L is an optional linker as described herein, and PT is a microtubule disrupting peptide toxin that covalently linked to $L^1$ through the side chain of the N-terminal amino acid of PT, or if L is not present, PT is covalently linked to T through the side chain of the N-terminal amino acid of PT.

In one embodiment, VAR2CSA-drug conjugates comprising microtubule disrupting peptide toxins that are linked to the conjugate through the side chain of the N-terminal amino acid are provided.

In one embodiment, T-$L^1$-PT has the following structure (XXII):

XXII

T—L—$R^{44}$—[structure with $R^{18}$, $R^{19}$, $R^{17}$, $R^{16}$, $R^{21}$, $R^{22}$, $R^{23}$, $R^{45}$]

wherein, $R^{16}$ and $R^{17}$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —$CO_2$H, —CHO, —COSH, or —$NO_2$;

$R^{18}$ and $R^{19}$ are independently selected from the group consisting of: H, R, Ar$R^{25}$—, or $R^{18}$ and $R^{19}$ are joined to form a ring;

$R^{44}$ is selected from the group consisting of: H, $R^{46}$, Ar$R^{25}$—, Ar—$R^{25}$—Ar, $R^{25}$—Ar—Ar, Ar—Ar—$R^{25}$—, and Ar, wherein each $R^{25}$ and each Ar may be substituted, and zero to ten heteroatoms may replace carbon atoms in the chain, for example O or S or N may be incorporated into the carbon chain; and wherein $R^{46}$ is —($CH_2$—$CH_2$—O)$_m$—, wherein m is an integer from one to fifteen;

$R^{21}$ is selected from the group consisting of: H, $R^{25}$, and Ar$R^{25}$—;

$R^{22}$ and $R^{23}$ are independently selected from the group consisting of: H, R, and Ar$R^{25}$—; and $R^{45}$ is Z—C(O)—Y—; —Z—C(O)NHS(O)$_2$—$R^{26}$; or —Y—C(O)NHS(O)$_2$—$R^{26}$;

wherein,

Z is defined as a moiety selected from the group consisting of: —OH, —O$R^{25}$; —SH; —S$R^{25}$; —$NH_2$; —N$R^{25}$CH($R^{47}$)COOH; and —NHCH($R^{47}$)COOH, wherein $R^{47}$ is a moiety having the formula: $R^{25}$, or —($CH_2$)$_n$N$R^{48}$$R^{49}$, wherein n=1-4 and $R^{48}$ and $R^{49}$ are independently selected from the group consisting of: H; $R^{25}$; and —C(NH)(NH$_2$);

Y is defined as a moiety selected from the group consisting of: a linear, saturated or unsaturated, one to six carbon alkyl group, optionally substituted with $R^{25}$, Ar$R^{25}$—, or X; and, X is defined as a moiety selected from the group consisting of: —OH, —O$R^{25}$, =O, =S, —$O_2$C$R^{25}$, —SH, —SR$^{25}$, —SOCR$^{25}$, —NH$_2$, —NHR$^{25}$, —N(R$^{25}$)$_2$, —NHCOR$^{25}$, —NRCOR$^{25}$, —I, —Br, —Cl, —F, —CN, —CO$_2$H, —CO$_2$R$^{25}$, —CHO, —COR$^{25}$, —CONH$_2$, —CONHR$^{25}$, —CON(R$^{25}$)$_2$, —COSH, —COSR$^{25}$, —NO$_2$, —SO$_3$H, —SOR$^{25}$, and —SO$_2$R$^{25}$;

R$^{26}$ is selected from the group consisting of optionally substituted alkyl, optionally substituted alkylamino, optionally substituted cycloalkyl, optionally substituted aryl, optionally substituted heterocyclyl and optionally substituted heteroaryl, COR$^{27}$, —CSR$^{27}$, —OR$^{27}$, and —NHR$^{27}$, wherein each R$^{27}$ is, independently, optionally substituted alkyl, optionally substituted alkylamino, optionally substituted cycloalkyl, optionally substituted aryl, optionally substituted heterocyclyl or optionally substituted heteroaryl.

R$^{25}$ is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$^{28}$, —O$_2$CR$^{28}$, —SH, —SR$^{28}$, —SOCR$^{28}$, —NH$_2$, —NHR$^{28}$, —N(R$^{28}$)$_2$, —NHCOR$^{28}$, —NR$^{28}$COR$^{28}$, —I, —Br, —Cl, —F, —CN, —CO$_2$H, —CO$_2$R$^{28}$, —CHO, —COR$^{28}$, —CONH$_2$, —CONHR$^{28}$, —CON(R$^{28}$)$_2$, —COSH, —COSR$^{28}$, —NO$_2$, —SO$_3$H, —SOR$^{28}$, —SO$_2$R$^{28}$, wherein R$^{28}$ is a linear, branched or cyclic, one to ten carbon saturated or unsaturated alkyl group;

the ring formed by joining R$^{18}$ and R$^{19}$ is a three to seven member non-aromatic cyclic skeleton within the definition of R$^{25}$, Y is defined as a moiety selected from the group consisting of: a linear, saturated or unsaturated, one to six carbon alkyl group, optionally substituted with R, ArR$^{25}$—, or X; and, X is defined as a moiety selected from the group consisting of: —OH, —OR, =O, =S, —O$_2$CR$^{25}$, —SH, —SR$^{25}$, —SOCR$^{25}$, —NH$_2$, —NHR$^{25}$, —N(R$^{25}$)$_2$, —NHCOR$^{25}$, —NRCOR$^{25}$, —I, —Br, —Cl, —F, —CN, —CO$_2$H, —CO$_2$R$^{25}$, —CHO, —COR$^{25}$, —CONH$_2$, —CONHR$^{25}$, —CON(R$^{25}$)$_2$, —COSH, —COSR$^{25}$, —NO$_2$, —SO$_3$H, —SOR$^{25}$, and —SO$_2$R$^{25}$;

or a stereoisomer, prodrug or pharmaceutically acceptable salt thereof.

In a preferred embodiment, R$^{26}$ is selected from the group consisting of optionally substituted alkyl, optionally substituted alkylamino, optionally substituted cycloalkyl, optionally substituted aryl, optionally substituted heterocyclyl and optionally substituted heteroaryl.

In one embodiment, Ar is an aromatic ring selected from the group consisting of: phenyl, naphthyl, anthracyl, pyrrolyl.

In one embodiment, R$^{45}$ is Z—C(O)—Y—, wherein Z and Y are defined as above.

In one embodiment, R$_{45}$ is —Z—C(O)NHS(O)$_2$—R$^{26}$, wherein Z and R$^{26}$ are defined as above.

In one embodiment, R$_{45}$ is —Y—C(O)NHS(O)$_2$—R$^{26}$, wherein Y and R$^{26}$ are defined as above.

In another embodiment, T-L$^1$-PT has the following structure (XXIII):

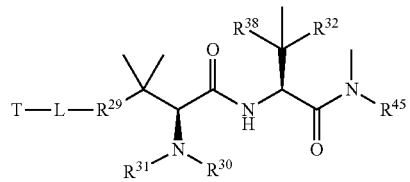

XXIII wherein,

R$^{29}$ is selected from the group consisting of optionally substituted alkyl, optionally substituted alkylamino, optionally substituted cycloalkyl, optionally substituted aryl, optionally substituted heterocyclyl and optionally substituted heteroaryl;

R$^{30}$ is selected from the group consisting of H and C$_{1-6}$ alkyl;

R$^{31}$ is selected from the group consisting of H and C$_{1-6}$ alkyl;

R$^{32}$ and R$^{38}$ are independently selected from the group consisting of H, C$_{1-6}$ alkyl and —SH, with the proviso that both the R$^{32}$ and R$^{38}$ substituents cannot be H;

R$^{45}$ is Z—C(O)—Y—; —Z—C(O)NHS(O)$_2$—R$^{26}$; or —Y—C(O)NHS(O)$_2$—R$^{26}$;

wherein Y and R$^{26}$ are defined as above;

Z is defined as a moiety selected from the group consisting of: —OH, —OR; —SH; —SR$^{25}$; —NH$_2$; —NR$^{25}$CH(R$^{47}$)COOH; and —NHCH(R$^{47}$)COOH, wherein R$^{47}$ is a moiety having the formula: R$^{25}$, or —(CH$_2$)$_n$NR$^{48}$R$^{49}$, wherein n=1-4 and R$^{48}$ and R$^{49}$ are independently selected from the group consisting of: H; R$^{25}$; and —C(NH)(NH$_2$), R$^{25}$ is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$^{28}$, —O$_2$CR$^{28}$, —SH, —SR$^{28}$, —SOCR$^{28}$, —NH$_2$, —NHR$^{28}$, —N(R$^{28}$)$_2$, —NHCOR$^{28}$, —NR$^{28}$COR$^{28}$, —I, —Br, —Cl, —F, —CN, —CO$_2$H, —CO$_2$R$^{28}$, —CHO, —COR$^{28}$, —CONH$_2$, —CONHR$^{28}$, —CON(R$^{28}$)$_2$, —COSH, —COSR$^{28}$, —NO$_2$, —SO$_3$H, —SOR$^{28}$, —SO$_2$R$^{28}$, wherein R$^{28}$ is a linear, branched or cyclic, one to ten carbon saturated or unsaturated alkyl group;

Y is defined as a moiety selected from the group consisting of: a linear, saturated or unsaturated, one to six carbon alkyl group, optionally substituted with R$^{25}$, ArR$^{25}$—, or X; and, X is defined as a moiety selected from the group consisting of: —OH, —OR$^{25}$, =O, =S, —O$_2$CR$^{25}$, —SH, —SR$^{25}$, —SOCR$^{25}$, —NH$_2$, —NHR$^{25}$, —N(R)$_2$, —NHCOR$^{25}$, —NRCOR$^{25}$, —I, —Br, —Cl, —F, —CN, —CO$_2$H, —CO$_2$R$^{25}$, —CHO, —COR$^{25}$, —CONH$_2$, —CONHR$^{25}$, —CON(R$^{25}$)$_2$, —COSH, —COSR$^{25}$, —NO$_2$, —SO$_3$H, —SOR$^{25}$, and —SO$_2$R$^{25}$;

or a stereoisomer, prodrug or pharmaceutically acceptable salt thereof.

In another embodiment, T-L$^1$-PT has the following structure (XXIV):

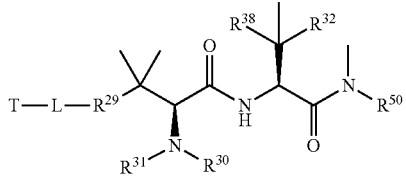

XXIV wherein,

R$^{29}$ is selected from the group consisting of optionally substituted alkyl, optionally substituted alkylamino, optionally substituted cycloalkyl, optionally substituted aryl, optionally substituted heterocyclyl and optionally substituted heteroaryl;

R$^{30}$ is selected from the group consisting of H and C$_{1-6}$ alkyl;

R$^{31}$ is selected from the group consisting of H and C$_{1-6}$ alkyl;

R$^{32}$ and R$^{38}$ are independently selected from the group consisting of H, C$_{1-6}$ alkyl and —SH, with the proviso that both the R$^{32}$ and R$^{38}$ substituents cannot be H;

R$^{50}$ is Z—C(O)—Y—, wherein Z is as defined above,

R$^{25}$ is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$^{28}$, —O$_2$CR$^{28}$, —SH, —SR$^{28}$, —SOCR$^{28}$, —NH$_2$, —NHR$^{28}$, —N(R$^{28}$)$_2$, —NHCOR$^{28}$, —NR$^{28}$COR$^{28}$, —I, —Br, —Cl, —F, —CN, —CO$_2$H, —CO$_2$R$^{28}$, —CHO, —COR$^{28}$, —CONH$_2$, —CONHR$^{28}$, —CON(R$^{28}$)$_2$, —COSH, —COSR$^{28}$, —NO$_2$, —SO$_3$H, —SOR$^{28}$, —SO$_2$R$^{28}$, wherein R$^{28}$ is a linear, branched or cyclic, one to ten carbon saturated or unsaturated alkyl group;

Y is defined as a moiety selected from the group consisting of: a linear, saturated or unsaturated, one to six carbon alkyl group, optionally substituted with R$^{25}$, ArR$^{25}$—, or X; and, X is defined as a moiety selected from the group consisting of: —OH, —OR$^{25}$, =O, =S, —O$_2$CR$^{25}$, —SH, —SR$^{25}$, —SOCR$^{25}$, —NH$_2$, —NHR$^{25}$, —N(R$^{25}$)$_2$, —NHCOR$^{25}$, —NRCOR$^{25}$, —I, —Br, —Cl, —F, —CN, —CO$_2$H, —CO$_2$R$^{25}$, —CHO, —COR$^{25}$, —CONH$_2$, —CONHR$^{25}$, —CON(R$^{25}$)$_2$, —COSH, —COSR$^{25}$, —NO$_2$, —SO$_3$H, —SOR$^{25}$, and —SO$_2$R$^{25}$;

or a stereoisomer, prodrug or pharmaceutically acceptable salt thereof.

In another embodiment, T-L$^1$-PT has the following structure (XXV):

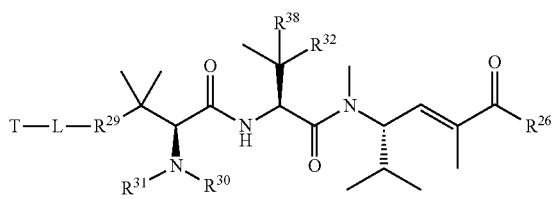

XXV wherein,

R$^{26}$ is selected from the group consisting of H, optionally substituted alkyl, optionally substituted alkylamino, optionally substituted cycloalkyl, optionally substituted aryl, optionally substituted heterocyclyl, optionally substituted heteroaryl, —COR$^{27}$, —CSR$^{27}$, —OR$^{27}$, —SR$^{27}$, and —NHR$^{27}$ wherein each R$^{27}$ is, independently, of optionally substituted alkyl, optionally substituted alkylamino, optionally substituted cycloalkyl, optionally substituted aryl, optionally substituted heterocyclyl, or optionally substituted heteroaryl;

R$^{29}$ is selected from the group consisting of optionally substituted alkyl, optionally substituted alkylamino, optionally substituted cycloalkyl, optionally substituted aryl, optionally substituted heterocyclyl and optionally substituted heteroaryl;

R$^{30}$ is selected from the group consisting of H and C$_{1-6}$ alkyl;

R$^{31}$ is selected from the group consisting of H and C$_{1-6}$ alkyl;

R$^{32}$ and R$^{38}$ are independently selected from the group consisting of H, C$_{1-6}$ alkyl and —SH, with the proviso that both the R$^{32}$ and R$^{38}$ substituents cannot be H;

or a stereoisomer, prodrug or pharmaceutically acceptable salt thereof.

In another embodiment, T-L$^1$-PT has the following structure (XXVI):

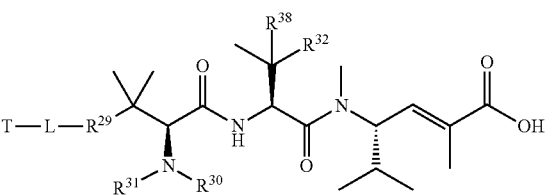

XXVI wherein,

R$^{29}$ is selected from the group consisting of optionally substituted alkyl, optionally substituted alkylamino, optionally substituted cycloalkyl, optionally substituted aryl, optionally substituted heterocyclyl and optionally substituted heteroaryl;

R$^{30}$ is selected from the group consisting of H and C$_{1-6}$ alkyl;

R$^{31}$ is selected from the group consisting of H and C$_{1-6}$ alkyl;

R$^{32}$ and R$^{38}$ are independently selected from the group consisting of H, C$_{1-6}$ alkyl and —SH, with the proviso that both the R$^{32}$ and R$^{38}$ substituents cannot be H;

or a stereoisomer, prodrug or pharmaceutically acceptable salt thereof.

In another embodiment, T-L$^1$-PT has the following structure (XXVII):

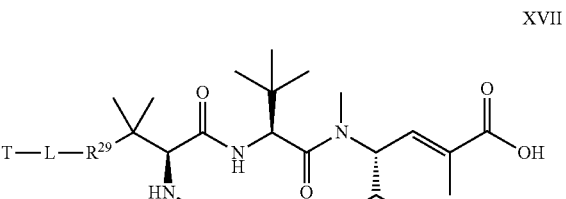

XVII wherein, $R^{29}$ is selected from the group consisting of optionally substituted alkyl, optionally substituted alkylamino, optionally substituted cycloalkyl, optionally substituted aryl, optionally substituted heterocyclyl and optionally substituted heteroaryl;

or a stereoisomer, prodrug or pharmaceutically acceptable salt thereof.

In another embodiment, T-L$^1$-PT has the following structure (XXVIII):

XXVIII wherein, $R^{25}$ is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$^{28}$, —O$_2$CR$^{28}$, —SH, —SR$^{28}$, —SOCR$^{28}$, —NH$_2$, —NHR$^{28}$, —N(R$^{28}$)$_2$, —NHCOR$^{28}$, —NR$^{28}$COR$^{28}$, —I, —Br, —Cl, —F, —CN, —CO$_2$H, —CO$_2$R$^{28}$, —CHO, —COR$^{28}$, —CONH$_2$, —CONHR$^{28}$, —CON(R$^{28}$)$_2$, —COSH, —COSR$^{28}$, —NO$_2$, —SO$_3$H, —SOR$^{28}$, —SO$_2$R$^{28}$, wherein R$^{28}$ is a linear, branched or cyclic, one to ten carbon saturated or unsaturated alkyl group, or a stereoisomer, prodrug or pharmaceutically acceptable salt thereof.

In another embodiment, T-L$^1$-PT has the following structure (XXIX):

XXIX wherein, $R^{25}$ is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$^{28}$, —O$_2$CR$^{28}$, —SH, —SR$^{28}$, —SOCR$^{28}$, —NH$_2$, —NHR$^{28}$, —N(R$^{28}$)$_2$, —NHCOR$^{28}$, —NR$^{28}$COR$^{28}$, —I, —Br, —Cl, —F, —CN, —CO$_2$H, —CO$_2$R$^{28}$, —CHO, —COR$^{28}$, —CONH$_2$, —CONHR$^{28}$, —CON(R$^{28}$)$_2$, —COSH, —COSR$^{28}$, —NO$_2$, —SO$_3$H, —SOR$^{28}$, —SO$_2$R$^{28}$, wherein R$^{28}$ is a linear, branched or cyclic, one to ten carbon saturated or unsaturated alkyl group, or a stereoisomer, prodrug or pharmaceutically acceptable salt thereof.

In a further embodiment of the invention, (PT) is a hemiasterlin analog, such as those disclosed in U.S. Pat. No. 7,579,323, which is hereby incorporated by reference in its entirety for all purposes. In a further embodiment of the invention, (PT) is a hemiasterlin analog, such as those disclosed in U.S. application Ser. No. 10/666,722 or U.S. application Ser. No. 10/911,300, each of which is hereby incorporated by reference in its entirety for all purposes.

Linker Moiety L$^2$

Provided are compounds of Formula VII:

T-L$^2$-P$^2$   VII wherein:

T is a targeting moiety comprising a VAR2CSA polypeptide;

L$^2$ is a linker, or L$^2$ is absent;

P$^2$ is a biologically active compound; and

L$^2$-P$^2$ has the following structure (III):

III wherein:

R is selected from the group consisting of optionally substituted alkyl, optionally substituted alkylamino, optionally substituted cycloalkyl, optionally substituted aryl, optionally substituted heterocyclyl, optionally substituted heteroaryl, —COR$^{27}$, —CSR$^{27}$, —OR$^{27}$, and —NHR$^{27}$, wherein each R$^{27}$ is, independently, optionally substituted alkyl, optionally substituted alkylamino, optionally substituted cycloalkyl, optionally substituted aryl, optionally substituted heterocyclyl, optionally substituted heteroaryl, or R is absent;

P$^3$ is the remaining portion of compound P$^2$; and

L$^3$ is optionally the remaining portion of linker L$^2$ when L$^2$ is present.

In a preferred embodiment, R is selected from the group consisting of optionally substituted alkyl, optionally substituted alkylamino, optionally substituted cycloalkyl, optionally substituted aryl, optionally substituted heterocyclyl and optionally substituted heteroaryl, or R is absent.

Also provided are compounds comprising a payload compound linked to a targeting moiety comprising a VAR2CSA polypeptide in a conjugate that is enzymatically cleavable and capable of releasing payload compound from targeting moiety upon enzymatic cleavage. In some embodiments, the payload compound is a biologically active compound. In some embodiments, the payload compound is a cytotoxic or cytostatic drug.

As disclosed herein, N-acyl sulfonamide-containing cleavable conjugates may be synthesized such that an N-acyl sulfonamide moiety is covalently linked to a chemical group, (R), which is covalently bonded to a nitrogen atom that forms an enzymatically cleavable peptide bond (the junction peptide bond (JPB)) with the carbonyl group of an amino acid that forms part of the amino acid sequence facilitating enzymatic cleavage of the JPB. Moieties similar to N-acyl sulfonamides, such as N-acyl sulfamamides, may also be used.

Accordingly, in one embodiment, the invention provides compounds of Formula VII:

T-L$^2$-P$^2$   VII wherein P$^2$ is a biologically active compound, L$^2$ is a linker, and T is a targeting moiety comprising VAR2CSA, wherein P$^2$ has the following structure (V):

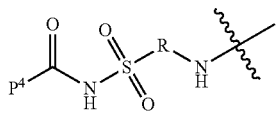

V and wherein L²-T has the following structure (VI):

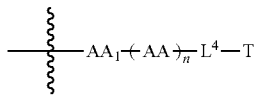

VI wherein P⁴ is the remaining portion of payload compound P², wherein the —NH— group bonded to R in Formula V forms a peptide bond (JPB) with AA₁ in formula VI, wherein said JPB is enzymatically cleavable, wherein R is selected from the group consisting of optionally substituted alkyl, optionally substituted alkylamino, optionally substituted cycloalkyl, optionally substituted aryl, optionally substituted heterocyclyl and optionally substituted heteroaryl, wherein each AA is independently an amino acid, wherein n is an integer from 0 to 25, wherein L⁴ is optionally the remaining portion of linker L², wherein T is said targeting moiety, and wherein AA₁-(AA)$_n$, taken together comprises an amino acid sequence capable of facilitating enzymatic cleavage of said JPB.

In some embodiments, R is selected from the group consisting of optionally substituted alkyl, optionally substituted alkylamino, optionally substituted cycloalkyl, optionally substituted aryl, optionally substituted heterocyclyl, optionally substituted heteroaryl, —COR²⁷, —CSR²⁷, —OR²⁷, and —NHR²⁷, wherein each R²⁷ is, independently, optionally substituted alkyl, optionally substituted alkylamino, optionally substituted cycloalkyl, optionally substituted aryl, optionally substituted heterocyclyl, and optionally substituted heteroaryl.

In some embodiments, R is selected from the group consisting of optionally substituted alkyl, optionally substituted alkylamino, optionally substituted cycloalkyl, optionally substituted aryl, optionally substituted heterocyclyl, and optionally substituted heteroaryl. In some embodiments, —R—NH— of Formula V is selected from:

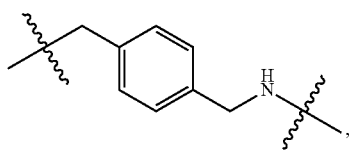

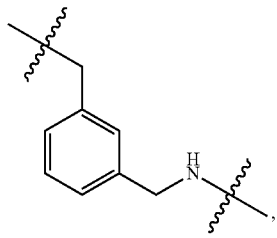

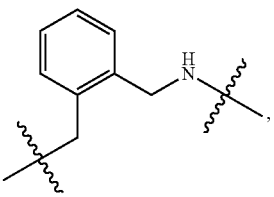

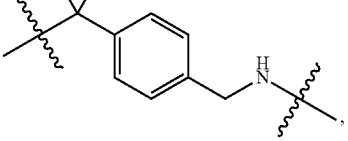

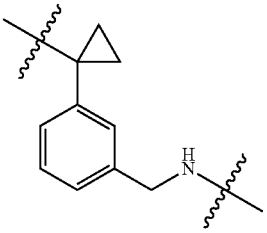

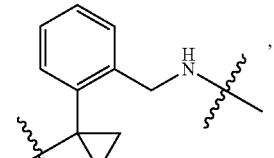

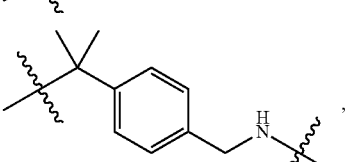

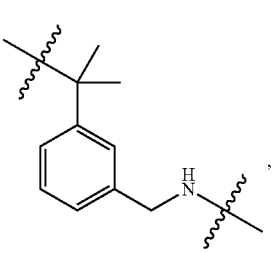

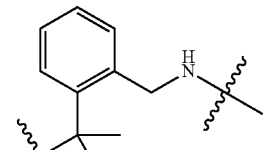

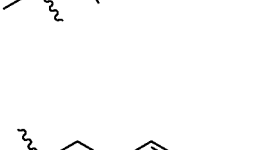

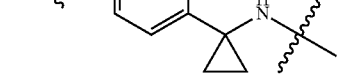

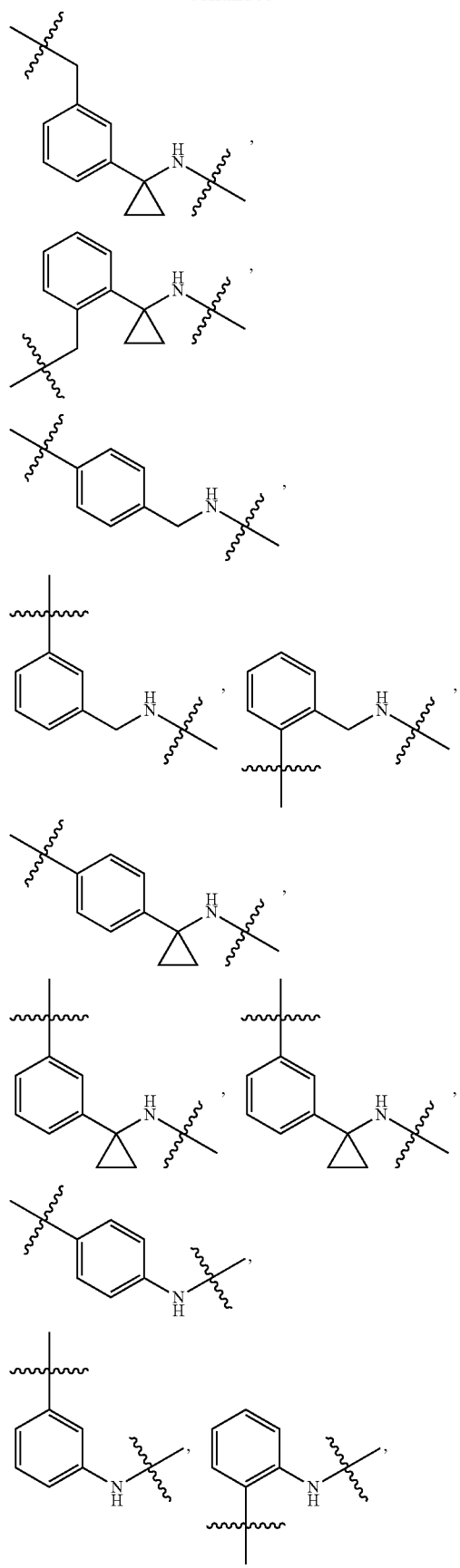
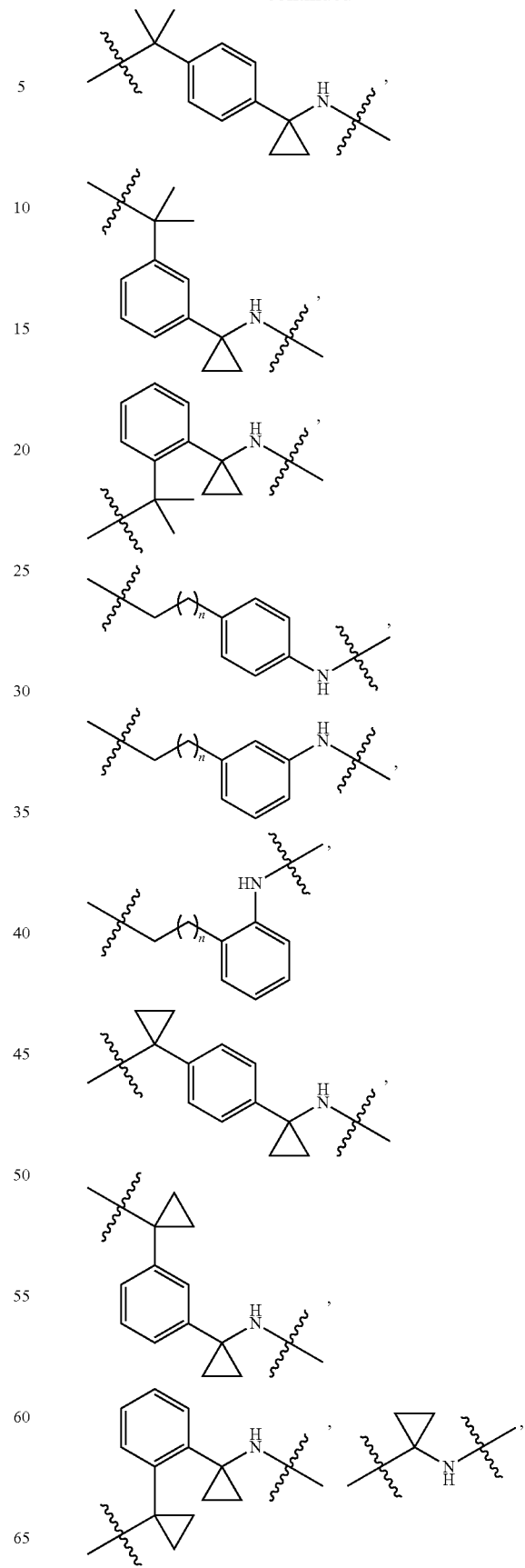

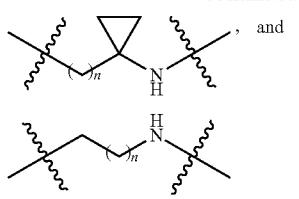, and
wherein each n is independently an integer from 0-10.
In some embodiments, —R—NH— of Formula V is selected from:
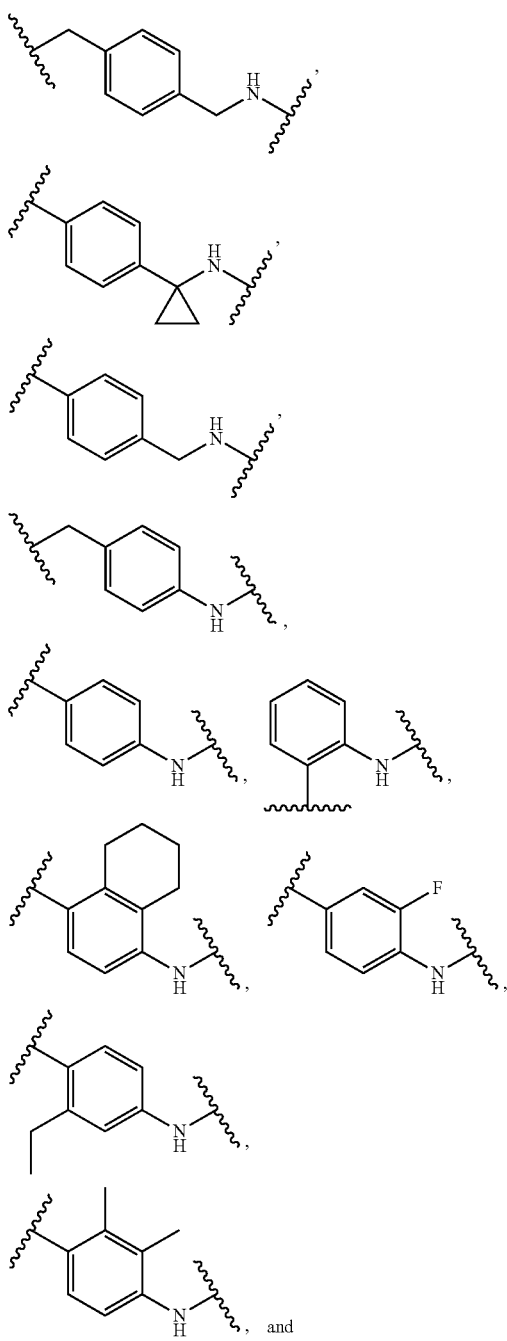
In some embodiments, —R—NH— of Formula V is selected from:
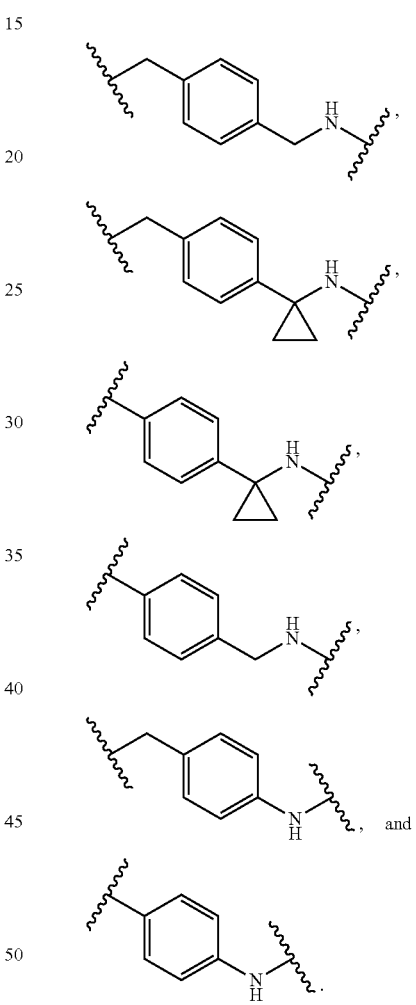
In one embodiment, cleavage of the JPB results in a compound of Formula VIII:
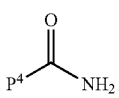
VIII
wherein P⁴ corresponds to P⁴ in Formula V.
In one embodiment, cleavage of the JPB results in a compound of Formula XXIX:

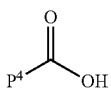

XXIX wherein $P^4$ corresponds to $P^4$ in Formula V.

In one embodiment, cleavage of the JPB results in a compound of Formula IX:

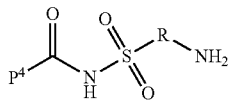

IX wherein $P^4$ corresponds to $P^4$ in Formula V.

In some embodiment, $P^2$ has the following structure (X):

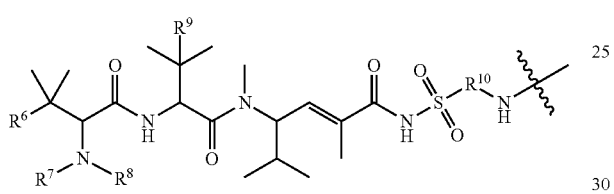

X or a stereoisomer, prodrug or pharmaceutically acceptable salt thereof, and $L^2$-T has the following structure (IV):

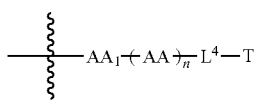

VI wherein:

$R^6$ is selected from: aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkoxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkoxy are further optionally substituted with one substituent selected from $C_1$-$C_4$ alkylaryl, hydroxyl, and thio;

$R^7$ and $R^8$ are each independently selected from: H and $C_1$-$C_6$ alkyl;

$R^9$ is selected from the group consisting of $C_1$-$C_6$ alkyl and thio; and wherein the —NH— group bonded to $R^{10}$ in Formula X forms the junction peptide bond (JPB) with $AA_1$ in Formula IV, wherein the JPB is enzymatically cleavable, wherein each AA is independently an amino acid, wherein n is an integer from 0 to 25, wherein $L^3$ is the remaining portion (if any) of linker $L^2$, wherein T is the targeting moiety, $AA_1$-$(AA)_n$, taken together comprises an amino acid sequence capable of facilitating enzymatic cleavage of said JPB.

In some embodiments, $R^{10}$ is selected from the group consisting of optionally substituted alkyl, optionally substituted alkylamino, optionally substituted cycloalkyl, optionally substituted aryl, optionally substituted heterocyclyl, optionally substituted heteroaryl, —COR$^{27}$, —CSR$^{27}$, —OR$^{27}$, and —NHR$^{27}$, wherein each $R^{27}$ is, independently, optionally substituted alkyl, optionally substituted alkylamino, optionally substituted cycloalkyl, optionally substituted aryl, optionally substituted heterocyclyl, and optionally substituted heteroaryl.

In some embodiments, $R^{10}$ is selected from the group consisting of optionally substituted alkyl, optionally substituted alkylamino, optionally substituted cycloalkyl, optionally substituted aryl, optionally substituted heterocyclyl, and optionally substituted heteroaryl. In some embodiments, —$R^{10}$—NH— of Formula X is selected from:

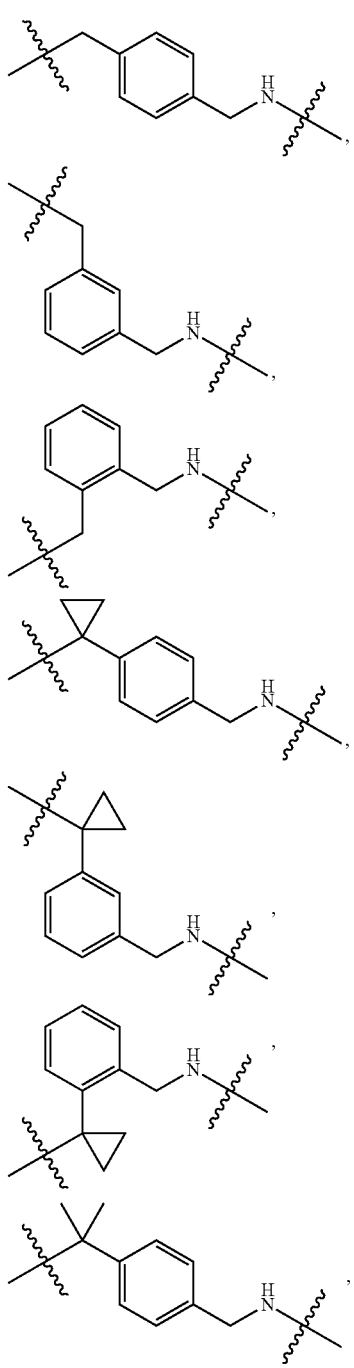

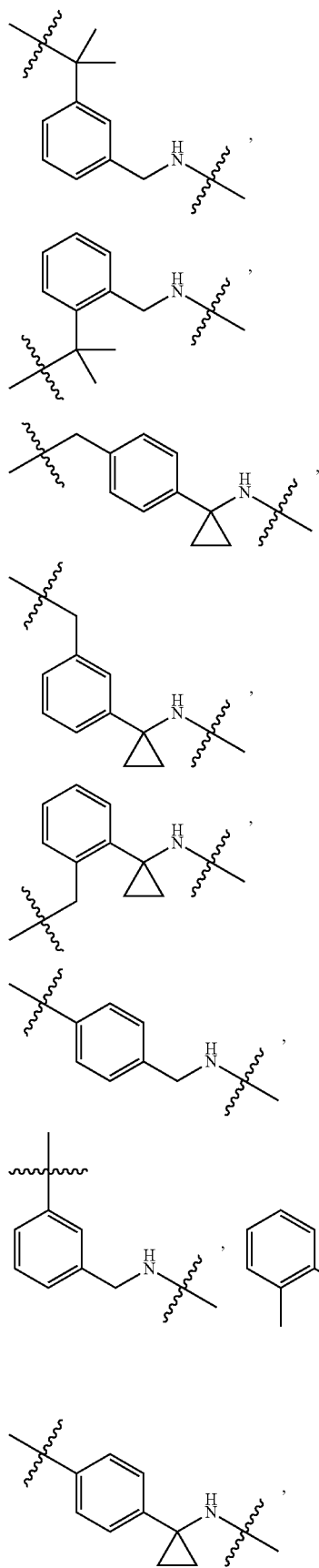
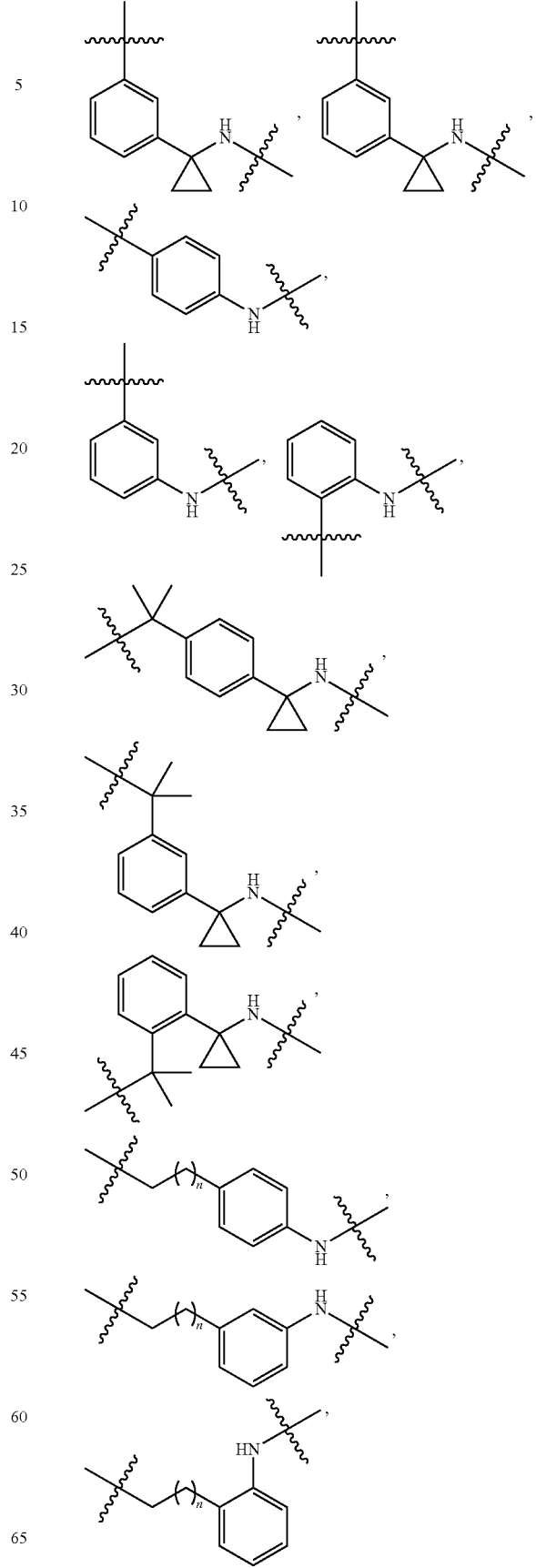

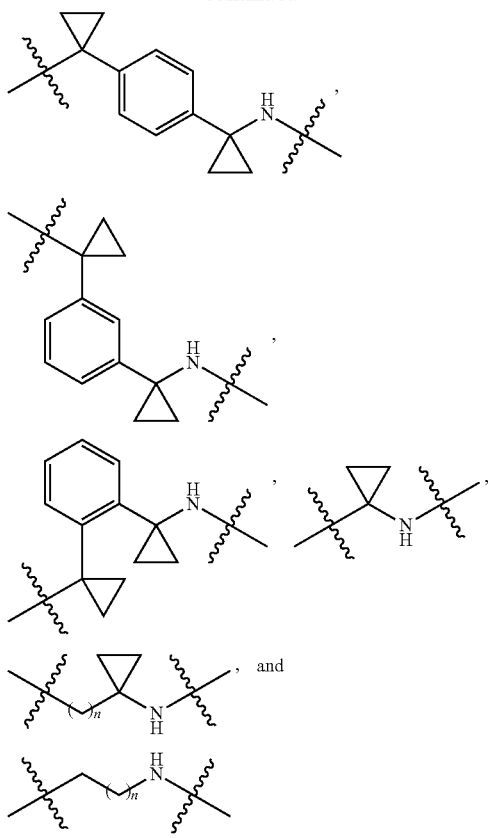
wherein each n is independently an integer from 0-10.
In some embodiments, —R$^{10}$—NH— of Formula X is selected from:
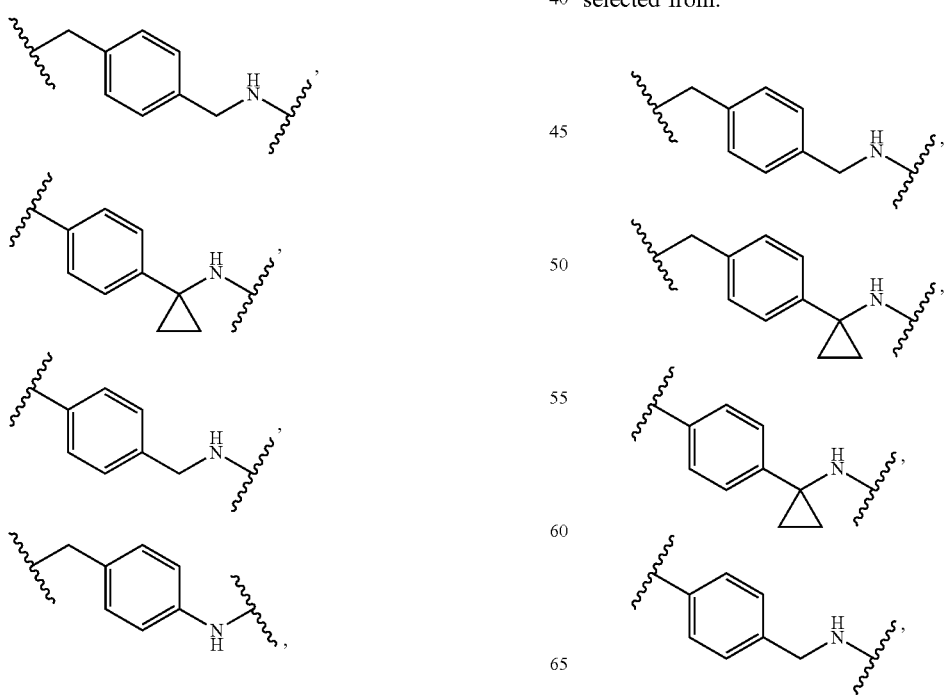
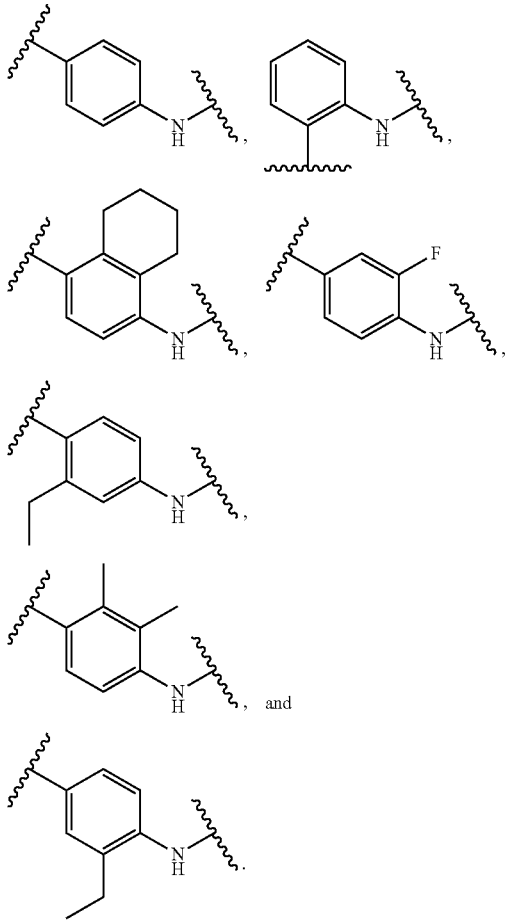
In some embodiments, —R$^{10}$—NH— of Formula X is selected from:

-continued

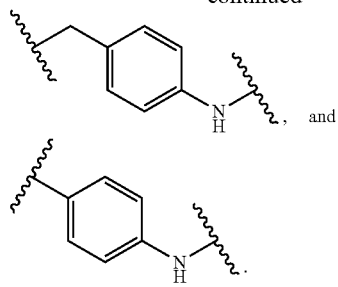

In one embodiment, cleavage of the JPB results in a compound of Formula VIII:

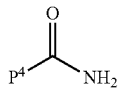
VIII wherein $P^4$ corresponds to $P^4$ in Formula V.

In one embodiment, cleavage of the JPB results in a compound of Formula XXIX:

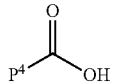
XXIX wherein $P^4$ corresponds to $P^4$ in Formula V.

In one embodiment, cleavage of the JPB results in a compound of Formula IX:

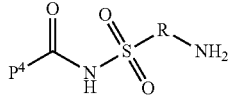
IX wherein $P^4$ corresponds to $P^4$ in Formula V.

The linker moiety $L^2$ is characterized from the perspective of an assembled conjugate described herein. Accordingly, $L^2$ as characterized herein does not necessarily but may correspond to a particular reactant used in the synthesis of a conjugate. The components of $L^2$ may be contributed by a number of reactants. Accordingly, $L^2$ is a bifunctional unit that links a payload compound ($P^2$) to a targeting moiety (T) to form a conjugate compound, T-$L^2$-$P^2$, that may be cleaved enzymatically at the junction peptide bond (JPB) between $P^2$ and $L^2$ to release $P^2$. Such conjugates allow the selective delivery of payload $P^2$ to target cells (e.g., tumor cells).

The linker $L^2$ and the targeting moiety T taken together have the following structure (VI):

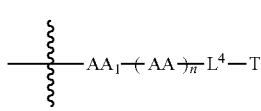
VI wherein the carbonyl of $AA_1$ forms a peptide bond referred to herein as the junction peptide bond (JPB) with the —NH— group bonded to R in Formula V, wherein the JPB is enzymatically cleavable, wherein each AA is independently an amino acid, wherein x is an integer from 0 to 25, wherein $L^3$ is the remaining portion (if any) of linker $L^2$, wherein T is the targeting moiety, and wherein $AA_1$-$(AA)_n$ comprises an amino acid sequence capable of facilitating enzymatic cleavage of the JPB.

The amino acid unit $AA_1$-$(AA)_n$, comprises a recognition sequence that provides for cleavage of the junction peptide bond (JPB) to release payload $P^2$ from the targeting moiety T. Any sequence capable of providing for such enzymatic cleavage may be used. Such sequences include, but are not limited to, applicable sequences described in U.S. Pat. No. 6,214,345. For example, amino acid sequences known in the art to direct cleavage of a peptide bond linking a PABC self-immolative unit directly to the amino acid sequence may be used in the present invention. Additional amino acid sequences useful in the present invention can be readily determined experimentally by the artisan of reasonable skill. In certain embodiments, an amino acid unit, $AA_1$-$(AA)_n$ allows for cleavage of the (JPB) by a protease, thereby facilitating release of payload $P^2$ from the conjugate upon exposure to such proteases. In certain embodiments, these include intracellular proteases, such as lysosomal enzymes.

In yet further embodiments, these include extracellular proteases.

Exemplary amino acid units $(AA)^1$-$(AA)_x$ include, but are not limited to, a dipeptide, a tripeptide, a tetrapeptide, and/or a pentapeptide. Exemplary dipeptides include: Val-Cit, Ala-Phe, Phe-Lys, Val-Ala, Val-Lys(Ac), Phe-Lys(Ac), or Me-Val-Cit. It is noted that while the naming convention for peptides and proteins is to list amino acid sequence from N-terminus to C-terminus, the configuration of the JPB is such that $(AA)^1$ is the C-terminus amino acid in the $(AA)^1$-$(AA)_x$ amino acid sequence. Accordingly, in an embodiment where the amino acid sequence facilitating enzymatic cleavage of the JPB was valine-citrulline, $(AA)^1$ in formula (III) would be citrulline and the carbonyl group of citrulline would form JPB with the —NH— group bonded to (R) in structure (II). In some embodiments, additional amino acids are linked to valine-citrulline through the N-terminus of valine and, accordingly, "x" for $(AA)_x$ is an integer greater than one.

Exemplary tripeptides include: Gly-Val-Cit, Pro-Pro-Pro, D-Ala-Phe-Lys, (D)-Val-Leu-Lys, Gly-Gly-Arg, and Ala-Ala-Asn. For illustration and clarity, when the tripeptide is (gly-val-cit), $(AA)^1$ of formula (III) is citrulline. An amino acid unit may comprise amino acid residues that occur naturally, as well as minor amino acids and non-naturally occurring amino acid analogs, such as citrulline. D-amino acids are included for use in the invention. Amino acid units can be designed and optimized in their selectivity for enzymatic cleavage by a particular enzyme, for example, a tumor-associated protease, cathepsin B, C and D, or a plasmin protease.

Exemplary tetrapeptides include: Lys-Ser-Gly-Arg, Gly-Phe-Leu-Gly, Leu-Ser-Gly-Arg, Ala-Leu-Ala-Leu, Gly-Gly-Gly-Arg-Arg, Gly-Lys-Ala-Phe-Arg-Arg, and Homo-Gly-Arg-Ser-Arg-Gly Exemplary amino acid sequences for use in linkers of the invention include the amino acid sequences within Phe-Lys, Val-Lys, Ala-Lys, Val-Cit, Phe-Cit, Leu-Cit, Ile-Cit, Trp-Cit, Phe-Arg. These sequences have been used for release of doxorubicin. See, for example, Table 1, Dubowchik, Firestone et al. *Bioconjugate Chem.* 2002, 13, 855-869 and references contained therein. Another exemplary amino acid sequence for use in linkers of the present invention is Pro-Pro (see, for example, Gianolio et al. *Cancer Chemother Pharmacol* 2012 70, 439-449). See also Firestone et al., U.S. Pat. No. 6,214,345 for amino acid sequences useful in the present invention. See also Miao et al., WO 2013/173392 for amino acid sequences useful in the present invention, including but not limited to amino acid sequences comprising non-natural amino acids. See also Dubowchik et al., Bioorganic & Med. Chem. Letters 8:3341-3346, 1998. See also Burke et al., Bioorganic & Med. Chem. Letters 19:2650-2653, 2009. See also Jeffrey et al., Bioorganic & Med. Chem. Letters 16:358-362, 2006. The artisan of reasonable skill will appreciate that additional amino acids may be included in the linker (L) to the N-terminus side of the amino acid sequence that is facilitating enzymatic cleavage of the JPB.

In one example, the JPB is cleavable by a protease that is associated with a disease. In another example, the JPB is cleavable by a protease that is up-regulated or associated with cancers in general. In still another example, the JPB is cleavable by a protease secreted by cancer-associated cells.

In another example, the JPB is cleavable by an enzyme that is up-regulated or associated with a specific cancer.

In certain embodiments, the remaining portion of linker ($L^3$) includes a stretcher moiety (S) between the amino acid unit, $AA_1$-$(AA)_n$ and the targeting moiety as shown in the following structures (XIa) and (XIb):

-$AA_1$-$(AA)_n$-S-$L^4$-T    XIa

-$AA_1$-$(AA)_n$-$L^4$-S-T    XIb wherein the carbonyl of $AA_1$ forms a peptide bond referred to herein as the junction peptide bond (JPB) with the —NH— group bonded to R in Formula V, wherein the JPB is enzymatically cleavable, wherein each AA is independently an amino acid, wherein n is an integer from 0 to 25, wherein $L^4$ is the remaining portion (if any) of $L^3$, wherein S is the stretcher unit, wherein T is the targeting moiety, and wherein $AA_1$-$(AA)_n$ comprises an amino acid sequence capable of facilitating enzymatic cleavage of the JPB. In particular embodiments, this stretcher is as described in U.S. Pat. Nos. 7,964,566 and 6,214,345.

Payload Moiety ($P^2$)

Provided are compounds of Formula VII:

T-$L^2$-$P^2$    VII wherein:
T is a targeting moiety comprising a VAR2CSA polypeptide;
$L^2$ is a linker, or $L^2$ is absent;
$P^2$ is a biologically active compound; and
$L^2$-$P^2$ has the following structure (III):

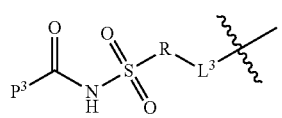
III wherein:
R is selected from the group consisting of optionally substituted alkyl, optionally substituted alkylamino, optionally substituted cycloalkyl, optionally substituted aryl, optionally substituted heterocyclyl and optionally substituted heteroaryl, or R is absent;

$P^3$ is the remaining portion of compound $P^2$; and
$L^3$ is optionally the remaining portion of linker $L^2$ when $L^2$ is present.

As with the linker moiety $L^2$, the payload $P^2$ is characterized from the perspective of an assembled conjugate described herein. Accordingly, the payload $P^2$ as characterized herein does not necessarily but may correspond to a particular reactant used in the synthesis of a conjugate. The components of the payload $P^2$ may be contributed by a number of reactants. Included within the scope of $P^2$ are precursors of biologically active compounds that may be converted to biologically active compounds in vivo.

A wide variety of compounds may be used to assemble desirable payload components of a conjugate described herein. Any compound that is functional as an amide as in Formula VIII or as a compound containing an N-acyl sulfonamide-R—$NH_2$ group as in Formula IX could be delivered to a target cell or tissue using the present conjugate technology. Any precursor compounds that can be used (directly, or following appropriate modification) to produce amides of Formula VIII or N-acyl sulfonamide-R—$NH_2$ compounds of Formula IX find use in the invention. Particularly preferred are amide containing drugs, carboxylic acid containing drugs that have active amide derivatives, carboxylic acid containing drugs, and drugs having the Formula IX. The route of synthesis and the particular reactants used to produce compounds of Formula VII are not limiting. It will be appreciated that in combination with the group "R", compounds of formula IX may be similar to N-acyl sulfonamides (e.g., sulfamamides).

In some embodiments, compounds of Formula VII can be used to deliver biologically active compounds of Formula VIII or IX. Suitable payload compounds $P^2$ that may be advantageously delivered by way of compositions described herein to targeted locations include, e.g., anti-inflammatory agents, cytotoxic agents, and anti-cancer drugs. In some embodiments, compounds of Formula VIII and IX show cytotoxic or cytostatic activity.

Non-limiting examples of cytotoxic payloads which may be fused or conjugated to targeting moieties comprising VAR2CSA polypeptides described herein, are chemotherapeutics selected from calicheamycin, cisplatin, adriamycin, auristatin, doxorubicin, maytansinoid, taxol, ecteinascidin, geldanamycin, methotrexate and their derivatives, and combinations thereof and the like suitable for cancer therapy. Examples of cytotoxic proteins fused to targeting moieties comprising VAR2CSA polypeptides are *Pseudomonas* exotoxin A, diphtheria toxin, ricin toxin, pokeweed antiviral protein, saporin, gelonin and variants hereof.

The payload molecule is preferably selectively guided to a cell, which expresses plCSA and includes anticancer agents, radioisotopes, toxins, cytostatic or cytolytic drugs, etc. Anticancer agents comprise, for example, anthracyclins (doxorubicin, daunorubicin, epirubicin, idarubicin, valrubicin, mitoxantrone), platinium and non-platinium based alkylating agents (cisplatin, carboplatin, oxaliplatin, mechlorethamine, cyclophosphamide, chlorambucil, ifosfamide, busulfan, carmustine, dacarbazine, lomustine, procarbazine), vinca alkaloids (vincristine, vinblastine, vinorelbine, vindesine), taxanes (taxol and decetaxel), topoisomerase I inhibitors (camptothecin, irinotecan, topotecan), topoisomerase II inhibitors (amsacrine, etoposide, etoposide phosphate, teniposide and other alkaloid-derivates naturally occurring in the root of American Mayapple (*Podophyllum peltatum*)), non-anthracycline cytotoxic antibiotics (dactinomycin, bleomycin, plicamycin and mitomycins), Anti-steroids (such as aminoglutethimide), nucleoside analogues (cytarabidine, fluorouracil and mercaptopurine), antimetabolites (methotrexate and thioguanine), dichlorodiphenyltrichloroethane analogues (like mitotane), and reactive oxygen species (ROS)-inducing compounds (including but not limited to piperlongumine, and beta-phenylethyl isothiocyanate). Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60. A VAR2CSA polypeptide conjugate may be used together with cell-penetrating peptides (CPP) to facilitate transport of the conjugate across cell plasma membranes. Cell-penetrating peptides have found numerous applications in medicine as drug delivery agents in the treatment of different diseases including cancer and virus inhibitors. Examples on CPP include but are not limited to: trans-activating transcriptional activator (Tat) from human immunodeficiency virus; pep-1 (Chariot™); R8, azo-R8; SMoC. (Okuyama M et al. Nat Methods. 2007 February; 4 (2): 153-9M; Soane L and Fiskum G J Neurochem. 2005 October; 95 (1):230-43; Loudet A et al. Org Biomol Chem. 2008 Dec. 21; 6 (24):4516-22).

In some embodiments, a targeting moiety comprising a VAR2CSA polypeptide is conjugated with an anti-inflammatory agent, including steroid hormones. Cartilage and scar tissue is known to contain CSPG in high amounts. Accordingly, it is useful to direct anti-inflammatory agents such as non-steroid anti-inflammatory compounds, disease modifying anti-rheumatic drugs (such as methotrexate, azathioprine, sulfasalazine, ciclosporine, pennicillamine, leflunomide, or gold), biological anti-rheumatic drugs (such as tumor necrosis factor inhibitors, interleukin-1-receptor antagonists, CD20-antibody, insulin growth factor 1) and steroid hormones or alternative compounds to such tissues.

In some embodiments, $P^2$ is a cytotoxic compound.

In some embodiments, $P^2$ is a cytotoxic compound, for example, a compound disclosed in U.S. Pat. No. 7,579,323; WO 2004/026293; U.S. Pat. No. 8,129,407; US 2014/0227295; WO 2013/068874; US 2013/0095123; US 2013/0190243; WO 2014/126198; EP 2740493; WO 2014086942; WO 2013072813; WO 2012166559; WO 2012166560; WO 2012123423; WO 2011154359; WO 2006063707; WO 2003008378; WO 2002000263; US 2013/224,228; WO 2013/085925; WO 2014/009774; U.S. Pat. No. 8,476,451; U.S. 2011/0027274; or related applications or patents, or Lundquist et al., Organic Letters, (3), pp. 781-783, 2001; Domling et al., Angew. Chem. Int. Ed. 2006, 45, 7235-7239; Kaur et al., Biochem J., (2006), 396:235-242; Steinmetz et al., Angew. Chem. Int. Ed. 2004, 43, 4888-4892; Khalil et al., ChemBioChem 2006, 7, 678-683; Peltier et al., J. Am. Chem. Soc. 2006, 128, 16018-16019.

In some embodiments, $P^2$ is a microtubule disrupting peptide toxin.

In some embodiments, $P^2$ is hemiasterlin or an analog thereof.

In some embodiments, $P^2$ is tubulysin or an analog thereof.

In some embodiments, $P^2$ is auristatin or an analog thereof.

In some embodiments, the cytotoxic compound is selected from: calicheamycin, auristatin, doxorubicin, maytansinoid, taxol, ecteinascidin, geldanamycin, methotrexate *Pseudomonas* exotoxin A, diphtheria toxin, ricin toxin, pokeweed antiviral protein, saporin, gelonin, pyrrolobenzodiazepines (PBDs) and functional variants, fragments, and combinations thereof.

In some embodiments, the cytotoxic compound is a polyketide from *Lithoplocamia lithistoides*. Examples of polyketides from *Lithoplocamia lithistoides* include those disclosed in Martin et al., J. Am. Chem. Soc. 2013, 135, 10164-10171. In some embodiments, the polyketide from *Lithoplocamia lithistoides* is selected from: PM050489 and PM060184.

In some embodiments, cytotoxic compound is a synthetic chemotoxin not derived from a naturally occurring compound.

In some embodiments, $P^2$ is an anti-inflammatory compound.

In some embodiments, $P^2$ is a microtubule disrupting peptide toxin. In one embodiment, the microtubule disrupting peptide toxin is hemiasterlin or an analog thereof. In another embodiment, the microtubule disrupting peptide toxin is HTI-286 or an analog thereof. In one embodiment, the microtubule disrupting peptide toxin is auristatin or an analog thereof. In one embodiment, the microtubule disrupting peptide toxin is a compound having structure XIII, XIV, or XIX.

In some embodiments, $P^2$ is a compound of Formula XIII

XIII or a stereoisomer, prodrug or pharmaceutically acceptable salt thereof, wherein:

$R^{11}$ is selected from: aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkoxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkoxy are further optionally substituted with one substituent selected from $C_1$-$C_4$ alkylaryl, hydroxyl, and thio;

$R^{12}$ and $R^{13}$ are each independently selected from: H and $C_1$-$C_6$ alkyl;

$R^{14}$ is selected from the group consisting of $C_1$-$C_6$ alkyl and thio; and $R^{15}$ has the same definition as $R^{10}$ in Formula X.

In one embodiment $R^{11}$ is selected from: phenyl, 1H-indol-3-yl, 1-methyl-1H-indol-3-yl, cyclohexyl, 4-methoxyphenyl, 2-methoxyphenyl, 3,5-dimethylphenyl, and m-tolyl.

In another further embodiment, $R^{12}$, $R^{13}$ and $R^{14}$ are each methyl.

In another further embodiment, $R^{12}$ is H, $R^{13}$ is methyl, and $R^{14}$ is methyl.

Methods of Preparing VAR2CSA-Drug Conjugates

Provided are methods of making compounds of Formula I. As will be appreciated by the artisan of reasonable skill, a wide variety of means are available to covalently link T-L-P. Any known method may be used to link the conjugate components. Any known linker technology may be used to link T to P. Further, T, L, and P may be modified in any suitable manner, as recognized by the artisan of reasonable skill, in order to facilitate conjugate formation.

Compounds of Formula I can be produced using a wide range of synthetic routes and a wide range of reactants. For example, the N-acyl sulfonamide moiety and the R group of Formula III may be present in the same reactant or different reactants. The N-acyl sulfonamide moiety may be present on a single reactant or may be formed by two reactants in a conjugation reaction step. The JPB may be intact within a reactant or may be formed by two reactants in a conjugation reaction step. The JPB may be intact within a single reactant that also contains the amino acid sequence facilitating enzymatic cleavage of the JPB, or the amino acid sequence facilitating enzymatic cleavage may be formed and brought together with the JPB by multiple reactants in a conjugation reaction step.

In some embodiments, compounds of Formula I are prepared by the conjugation of T with a precursor of L-P of Formula XII:

$$FG-L-P \qquad \text{XII}$$

wherein FG is a functional group that forms a covalent bond with one or more atoms of the targeting moiety. In further embodiments, FG forms a bond with a heteroatom of the targeting moiety. In particular embodiments, the FG group comprises a maleimide. As will be appreciated by the artisan of reasonable skill, additional moieties and bonding technologies may be used, including but not limited to transglutaminase sequences, 2-bromoacetamide chemistry, glycosylation chemistries, and others. See for example the linkage chemistry disclosed in WO2013173391, WO2013173392, WO2013173393, and U.S. Pat. No. 7,964,566.

Indications

The compounds described herein may be used in a wide range of indications associated with expression, such as inappropriate expression of plCSA, such as in various cancers, such as metastatic cancers including, but not limited to, melanomas, sarcomas, oligodendrocytomas, brain tumors, leukemias, lymphomas, and carcinomas of the lung, breast, urothelium, colon, pancreas, and liver. The compounds described herein may also be used for cancer stem cells and accordingly target the cells before development into a cancer. Other conditions associated with expression, such as inappropriate expression of plCSA are conditions of the cartilage and/or the development of scar tissue.

Accordingly, provided are methods for the treatment of any indication associated with expression, such as inappropriate expression of plCSA, such as in cancer, arthritis, arthrosis, multiple sclerosis, pathological conditions caused by neural damage, conditions of the cartilage and scar tissue, such as in rheumatism, cartilage repair or wound healing, or in psoriasis; the methods comprising administering a therapeutically or prophylactically effective amount of a compound described herein to a subject in need thereof.

Also provided are compounds for the treatment of any indications associated with a condition involving expression, such as inappropriate expression of plCSA, such as in cancer, arthritis, arthrosis, multiple sclerosis, pathological conditions caused by neural damage, conditions of the cartilage and scar tissue, such as in rheumatism, cartilage repair or wound healing, or in psoriasis.

The compounds described herein may be used in identifying, tracking and targeting distant micro-metastasis in vivo. Virtually all primary tumors, including cancers of the hematopoietic system, have the potential of developing into metastatic disease, which is highly associated with poor therapeutic outcome of the patients.

In some embodiments, the compounds described herein are useful in the treatment of malignant melanoma cancer including cutaneous, ocular and conjunctival melanoma having CSPG4 with plCSA chains on the surface of the melanoma cells. This GAG chain is believed to be involved in mitoses and metastases. However, CSPG4 is not only specific to melanoma. Micro- and tissue array analyses, performed on data from large panels of human tissue and cell lines, suggest that CSPG4 and other types of plCSA-containing proteoglycans may be present on a wide range of cancer types originating from all three cellular germ layers. These cancer types include carcinomas (breast carcinoma, pancreatic carcinoma, ovarian carcinoma, endometrial carcinoma, hepatocellular carcinoma, lung carcinoma, colon carcinoma, prostate carcinoma, cervix carcinoma, testis carcinoma, basal cell skin carcinoma, clear cell renal cell carcinoma, keratinized head and neck squamous cell carcinoma, skin squamous cell carcinoma, vulvar keratinized squamous cell carcinoma and vulvar basal cell carcinoma), sarcomas (breast liposarcoma, fibrosarcoma, dedifferentiated chondro- and liposarcoma, leiomyosarcoma, liposarcoma, myxoid liposarcoma, uterine corpus leiomyosarcoma, osteosarcoma, Ewing sarcoma and rhabdomyosarcoma), hematopoietic cancers (chronic lymphatic leukemia (CLL), acute lymphatic leukemia (ALL), acute myeloid leukemia (AML), B-cell, T-cell and large granular lymphoma), tumors of neuroepithelial tissue, such as astrocytomas (pleomorphic xanthoastrocytoma, fibrillary astrocytomas, anaplastic astrocytoma, glioblastoma multiforme), oligodrendroglioma, ependymoma, choroid plexus tumor, oligoastrocytoma, gliosarcoma, ganglioglioma, retinoblastoma, neurocytoma, neuroblastomas (esthesioneuroblastoma and ganglioneuroblastoma), medulloblastoma, atypical teratoid rhabdoid tumors and all types of neuroendocrine cancer.

Chondroitin sulfate proteoglycans (CSPG) also constitute an important component of the extracellular matrix of the central nervous system (CNS) including the eye, and of joint cartilage. Extra-cellular CSPG is critically involved in the pathogenesis of arthritis and the lack of regeneration after neural damage. Loss of extra-cellular CSPG is critical for the development of arthritis and arthrosis, and high local concentrations of extra-cellular CSPG prevents neural outgrowth after neural damage. Accordingly, the compounds described herein may be used not only in the treatment of indications associated with malignant growth, such as in cancers, but also to either increase or decrease CSPG presence in the extracellular environment in order to treat arthritis, arthrosis and to enhance neural recovery after neurite damage, including multiple sclerosis.

The compounds described herein may be used to target compounds that prevent degradation of or repair extracellular CSPG such as growth hormones, anti-inflammatory compounds or protein inhibitors, to cartilage tissue, joints, and neural tissue.

The compounds described herein may be used to target compounds that enhance degradation or prevent production of extracellular CSPG such as chondroitinase ABC, which cut the sugar chains of the protein core of CSPG molecules. Xylocides, which reduce CSPG production, or drugs that inhibit enzymes important for CSPG production such as chondroitin synthase or chondroitin polymerizing factor (such as 4-fluoro-glucosamine, p-nitrophenyl-beta-D-xyloxide, 4-methyl-umbelliferyl-beta-D-xylopyranoside), to damaged neural tissue.

In some embodiments, the cancer is selected from cutaneous, ocular or conjunctival melanoma; carcinomas (triple negative- and metaplastic breast carcinoma, pancreatic carcinoma, ovarian carcinoma, endometrial carcinoma, hepatocellular carcinoma, lung carcinoma, colon carcinoma, prostate carcinoma, cervix carcinoma, testis carcinoma, basal cell skin carcinoma, clear cell renal cell carcinoma, keratinized head and neck squamous cell carcinoma, skin squamous cell carcinoma, vulvar keratinized squamous cell carcinoma and vulvar basal cell carcinoma); sarcomas (breast liposarcoma, fibrosarcoma, dedifferentiated chondro- and liposarcoma, leiomyosarcoma, liposarcoma, myxoid liposarcoma, uterine corpus leiomyosarcoma, osteosarcoma, Ewing sarcoma and rhabdomyosarcoma); hematopoietic cancers (chronic lymphatic leukemia (CLL), acute lymphatic leukemia (ALL), acute myeloid leukemia (AML), B-cell, T-cell and large granular lymphoma); tumors of neuroepithelial tissue, such as astrocytomas (pleomorphic xanthoastrocytoma, fibrillary astrocytomas, anaplastic astrocytoma, glioblastoma multiforme), oligodrendroglioma, ependymoma, choroid plexus tumor, oligoastrocytoma, gliosarcoma, ganglioglioma, retinoblastoma, neurocytoma, neuroblastomas (esthesioneuroblastoma and ganglioneuroblastoma), medulloblastoma, and atypical teratoid rhabdoid tumors; and any other plCSA-expressing cancer subtype. In some embodiments, the cancer is selected from all plCSA-expressing malignancies including carcinomas (including but not limited to breast carcinoma, pancreatic carcinoma, ovarian carcinoma, endometrial carcinoma, hepatocellular carcinoma, lung carcinoma, colon carcinoma, prostate carcinoma, cervix carcinoma, testis carcinoma, basal cell skin carcinoma, clear cell renal cell carcinoma, head and neck squamous cell carcinoma, skin squamous cell carcinoma, vulvar keratinized squamous cell carcinoma and vulvar basal cell carcinoma); sarcomas (including but not limited to fibrosarcoma, dedifferentiated chondro- and liposarcoma, leiomyosarcoma, liposarcoma, myxoid liposarcoma, uterine corpus leiomyosarcoma, osteosarcoma, Ewing sarcoma and rhabdomyosarcoma, synovial sarcoma, solitary fibrous tumor), hematopoietic cancers (including but not limited to chronic lymphatic leukemia (CLL), acute lymphatic leukemia (ALL), acute myeloid leukemia (AML), b-cell, t-cell and large granular lymphoma); tumors of neuroepithelial tissue, such but not limited to astrocytomas (pleomorphic xanthoastrocytoma, fibrillary astrocytomas, anaplastic astrocytoma, glioblastoma multiforme), oligodrendroglioma, ependymoma, choroid plexus tumor, oligoastrocytoma, gliosarcoma, ganglioglioma, retinoblastoma, neurocytoma, neuroblastomas (esthesioneuroblastoma and ganglioneuroblastoma), medulloblastoma, atypical teratoid rhabdoid tumors; and all types of neuroendocrine cancer.

Solid tumors contemplated for treatment using the presently disclosed compounds include but are not limited to: sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer (e.g., gastrointestinal cancer), oral cancer, nasal cancer, throat cancer, squamous cell carcinoma (e.g., of the lung), basal cell carcinoma, adenocarcinoma (e.g., of the lung), sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, non-small cell lung cancer, epithelial carcinoma, glioma, glioblastoma, multiforme astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma. Blood-borne cancers contemplated for treatment using the presently disclosed compounds include but are not limited to: acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, and multiple myeloma. Acute and chronic leukemias contemplated for treatment using the presently disclosed compounds include but are not limited to: lymphoblastic, myelogenous, lymphocytic, and myelocytic leukemias. Lymphomas contemplated for treatment using the presently disclosed compounds include but are not limited to: Hodgkin's disease, non-Hodgkin's lymphoma, multiple myeloma, Waldenstrom's macroglobulinemia, heavy chain disease, and polycythemia vera. Other cancers contemplated for treatment using the presently disclosed compounds include but are not limited to: peritoneal cancer, hepatocellular cancer, hepatoma, salivary cancer, vulval cancer, thyroid, penile cancer, anal cancer, head and neck cancer, renal cell carcinoma, acute anaplastic large cell carcinoma, and cutaneous anaplastic large cell carcinoma.

Non-limiting examples of disorders to be treated herein include benign and malignant tumors; leukemia and lymphoid malignancies, in particular breast, ovarian, stomach, endometrial, salivary gland, lung, kidney, colon, thyroid, pancreatic, prostate or bladder cancer; neuronal, glial, astrocytal, hypothalamic and other glandular, macrophagal, epithelial, stromal and blastocoelic disorders, autoimmune disease, inflammatory disease, fibrosis, and infectious disease. Given the characteristics, and particularly the potency of the subject compounds, it will be apparent to the artisan of reasonable skill that the compounds described herein may be indicated for use to treat any disease where exertion of a cytotoxic or cytotoxic effect on a target cell is desirable. Cancers, including, but not limited to, a tumor, metastasis, or other disease or disorder characterized by uncontrolled or undesired cell growth, can be treated or prevented by administration of the presently disclosed compounds.

A therapeutically effective amount of compound in respect of cancer treatment may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; increase survival time; and/or relieve to some extent one or more of the symptoms associated with the cancer. To the extent the drug may prevent growth and/or kill existing cancer cells, it may be cytostatic and/or cytotoxic. Compounds of the present invention are preferably cytotoxic. For cancer therapy, efficacy can, for example, be measured by assessing the time to disease progression (TTP) and/or determining the response rate (RR).

The compounds described herein can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the animal's remaining bone-marrow cell population is then eradicated via the administration of a high dose of a compound described herein with or without accompanying high dose radiation therapy, and the stem cell graft is infused back into the animal. Supportive care is then provided while bone marrow function is restored and the animal recovers.

Combination Therapy

In other embodiments, methods for treating or preventing cancer are provided, including administering to a patient in need thereof an effective amount of a compound disclosed herein in combination with an additional method of treatment. In some embodiments, the additional method of treatment includes treatment with a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The compound described herein may be administered before, after, or at the same time as the chemotherapeutic agent.

Suitable anticancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, actinomycin D, dactinomycin, plicamycin, mitoxantrone, asparaginase, vinblastine, vincristine, vindesine, vinorelbine, paclitaxel, and docetaxel.

Other examples of chemotherapeutic agents include alkylating agents such as thiotepa and CYTOXAN® cyclosphosphamide; alkyl sulfonates such as busulfan, treosulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TEL-CYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopoletin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; triazines such as decarbazine; nitrosureas such as carmustine, chlorozotocin, fotemustine, lomustine, nimustine, and ranimustine; epipodophyllins, such as etoposide, teniposide, topotecan, 9-aminocamptothecin, camptothecin orcrisnatol; bisphosphonates, such as clodronate; antibiotics such as the enediyne antibiotics (e.g., calicheamicin, especially calicheamicin gamma1I and calicheamicin omega11 (see, e.g., Agnew, Chem. Intl. Ed. Engl., 33:183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins (e.g., A2 and B2), cactinomycin, carabicin, caminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; photodynamic therapies, such as vertoporfin (BPD-MA), phthalocyanine, photosensitizer Pc4, and demethoxy-hypocrellin A (2BA-2-DMHA); folic acid analogues such as denopterin, pteropterin, and trimetrexate; dpurine analogs such as fludarabine, 6-mercaptopurine, thiamiprine, and thioguanine; pyrimidine analogs such as ancitabine, azacitidine, 6-azauridine, carmofur, cytarabine, cytosine arabinoside, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate and trimetrexate; antimetabolites such as 5-fluorouracil (5-FU) and its prodrugs such as UFT, S-1 and capecitabine, floxuridine, doxifluridine and ratitrexed; and thymidylate synthase inhibitors and glycinamide ribonucleotide formyltransferase inhibitors such as raltitrexed (TOMUDEX®, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chlorambucil; gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); velcade; revlimid; thalidomide; IMiD3; lovastatin; verapamil; thapsigargin; 1-methyl-4-phenylpyridinium; cell cycle inhibitors such as staurosporine; novantrone; edatrexate; daunomycin; mitoxantrone; aminopterin; xeloda; ibandronate; topoisomerase inhibitor RFS 2000; difluoromethylornithine (DMFO); vitamin D3 analogs, such as EB 1089, CB 1093 and KH 1060; retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, megastrol, droloxifene, 4-hydroxytamoxifen, trioxifene, keoxifene, LYL17018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, bicalutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

In some embodiments, the additional method of treatment is radiation therapy. The compound described herein may be administered before, after, or at the same time as the radiation.

Compounds described herein may also be administered to a patient that has undergone or will undergo surgery as treatment for the cancer.

In a specific embodiment, the compound described herein is administered concurrently with the chemotherapeutic agent or with radiation therapy. In another specific embodiment, the chemotherapeutic agent or radiation therapy is administered prior or subsequent to administration of compound described herein, in one aspect at least an hour, five hours, 12 hours, a day, a week, a month, in further aspects several months (e.g., up to three months), prior or subsequent to administration of a compound described herein.

A chemotherapeutic agent can be administered over a series of sessions. Any one or a combination of the chemotherapeutic agents listed herein or otherwise known in the art can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, methods of treatment of cancer with a compound described herein are provided as an alternative to chemotherapy or radiation therapy where the chemotherapy or the radiation therapy has proven or can prove too toxic, e.g., results in unacceptable or unbearable side effects, for the subject being treated. Additionally, methods of treatment of cancer with a compound described herein are provided as an alternative to surgery where the surgery has proven or can prove unacceptable or unbearable for the subject being treated.

Provided are methods of treating cancer in a mammal comprising administering to a mammal in need thereof an effective amount of a compound or a pharmaceutical composition described herein.

Also provided are methods of increasing survival of a mammal having cancer, comprising administering to a mammal in need thereof an effective amount of a compound or a pharmaceutical composition described herein.

Also provided are methods of inhibiting tumor growth in a mammal comprising administering to a mammal in need thereof an effective amount of a compound or a pharmaceutical composition described herein.

Also provided are compounds and pharmaceutical compositions described herein for use in a method of treatment of the human or animal body by therapy.

Also provided are compounds and pharmaceutical compositions described herein for use in treating cancer in a mammal.

Also provided are compounds and pharmaceutical compositions described herein for use in increasing survival of a mammal having cancer.

Also provided are compounds and pharmaceutical compositions described herein for use in inhibiting tumor growth in a mammal.

Also provided are uses of a compound described herein in the manufacture of a medicament for treating cancer in a mammal.

Also provided are uses of a compound described herein in the manufacture of a medicament for increasing survival of a mammal having cancer.

Also provided are uses of a compound described herein in the manufacture of a medicament for inhibiting tumor growth in a mammal.

In some embodiments, the cancer is selected from: carcinomas, sarcomas, hematopoietic cancers, and tumors of neuroepithelial tissue.

Also provided are methods of treating an indication selected from: cancer, arthritis, arthrosis, multiple sclerosis, neural damage, cartilage damage, and psoriasis in a mammal comprising administering to a mammal in need thereof an effective amount of a compound or a pharmaceutical composition described herein.

Also provided are compounds and pharmaceutical compositions described herein for use in a method of treatment of an indication selected from: cancer, arthritis, arthrosis, multiple sclerosis, neural damage, cartilage damage, and psoriasis.

Also provided are uses of a compound described herein in the manufacture of a medicament for treating an indication selected from: cancer, arthritis, arthrosis, multiple sclerosis, neural damage, cartilage damage, and psoriasis.

Also provided are methods of treating an indication selected from: arthritis, multiple sclerosis, and psoriasis in a mammal comprising administering to a mammal in need thereof an effective amount of a compound or a pharmaceutical composition described herein.

Also provided are compounds and pharmaceutical compositions described herein for use in a method of treatment of an indication selected from: arthritis, multiple sclerosis, and psoriasis.

Also provided are uses of a compound described herein in the manufacture of a medicament for treating an indication selected from: arthritis, multiple sclerosis, and psoriasis.

Administration

Provided are pharmaceutical compositions comprising a compound described herein, and a pharmaceutically acceptable carrier, diluent or excipient.

For the purposes of administration, the compounds of the present disclosure may be administered as a raw chemical or may be formulated as pharmaceutical compositions. Pharmaceutical compositions of the present disclosure comprise a compound described herein and a pharmaceutically acceptable carrier, diluent or excipient. The compound described herein is present in the composition in an amount which is effective to treat a particular disease or condition of interest, e.g., in an amount sufficient to treat cancer or tumor cell growth, and preferably with acceptable toxicity to the patient. The activity of compounds described herein can be determined by one skilled in the art, for example, as described in the Examples below. Appropriate concentrations and dosages can be readily determined by one skilled in the art.

Administration of the compounds described herein, or their pharmaceutically acceptable salts, in pure form or in an appropriate pharmaceutical composition, can be carried out via any of the accepted modes of administration of agents for serving similar utilities. The pharmaceutical compositions of the disclosure can be prepared by combining a compound described herein with an appropriate pharmaceutically acceptable carrier, diluent or excipient, and may be formulated into preparations in solid, semi solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the disclosure are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound described herein in aerosol form may hold a plurality of dosage units. Actual methods of preparing such dosage forms are known, or will be apparent, to those skilled in this art; for example, see Remington: The Science and Practice of Pharmacy (22nd ed.) eds. Loyd V. Allen, Jr., et al., Pharmaceutical Press, 2012. The composition to be administered will, in any event, contain a therapeutically effective amount of a compound described herein, for treatment of a disease or condition of interest in accordance with the teachings of this disclosure.

A pharmaceutical composition described herein may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, pharmaceutical compositions of the present disclosure typically are either solid or liquid form, where semi solid, semi liquid, suspension and gel forms are included within the forms considered herein as either solid or liquid.

As a solid composition for oral administration, the pharmaceutical compositions may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

Pharmaceutical compositions described herein may be in the form of a liquid, for example, an elixir, syrup, solution, emulsion or suspension. The liquid may be for oral administration or for delivery by injection, as two examples. When intended for oral administration, pharmaceutical compositions described herein typically contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

Liquid pharmaceutical compositions described herein, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. Parenteral preparations can be enclosed in ampoules, disposable syringes or multiple dose vials made of glass or plastic. Physiological saline is a preferred adjuvant. An injectable pharmaceutical composition is preferably sterile.

A liquid pharmaceutical composition described herein intended for either parenteral or oral administration should contain an amount of a compound described herein such that a suitable dosage will be obtained.

Pharmaceutical compositions described herein may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

Pharmaceutical compositions described herein may be intended for rectal administration, in the form, for example, of a suppository, which will melt in the rectum and release the drug. Compositions for rectal administration may contain an oleaginous base as a suitable nonirritating excipient. Such bases include, without limitation, lanolin, cocoa butter and polyethylene glycol.

Pharmaceutical compositions described herein may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

Pharmaceutical compositions described herein may be prepared in dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds described herein may be delivered in single phase, bi phasic, or tri phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions described herein may be prepared by methodology well known in the pharmaceutical art. For example, a pharmaceutical composition intended to be administered by injection can be prepared by combining a compound described herein with sterile, distilled water so as to form a solution. A surfactant may be added to facilitate the formation of a homogeneous solution or suspension. Surfactants are compounds that non covalently interact with the compound described herein so as to facilitate dissolution or homogeneous suspension of the compound in the aqueous delivery system.

The compounds described herein, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds described herein, or pharmaceutically acceptable derivatives thereof, may also be administered simultaneously with, prior to, or after administration of one or more other therapeutic agents. Such combination therapy includes administration of a single pharmaceutical dosage formulation which contains a compound described herein and one or more additional active agents, as well as administration of the compound described herein and each active agent in its own separate pharmaceutical dosage formulation. For example, a compound described herein and the other active agent can be administered to the patient together in a single oral dosage composition such as a tablet or capsule, or each agent administered in separate oral dosage formulations. Where separate dosage formulations are used, the compounds described herein and one or more additional active agents can be administered at essentially the same time, i.e., concurrently, or at separately staggered times, i.e., sequentially; combination therapy is understood to include all these regimens.

EXAMPLES

The following Examples illustrate various methods of making compounds described herein, i.e., compounds of Formula I and related formulae. It is understood that one skilled in the art may be able to make these compounds by similar methods or by combining other methods known to one skilled in the art. It is also understood that one skilled in the art would be able to make, in a similar manner as described below, other compounds of Formula I not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

The following examples are provided for purposes of illustration, not limitation.

Example 1: Production of Truncated Recombinant VAR2CSA Proteins

All protein truncations are produced according to previously defined domain borders (Dahlbäck et al. J Biol Chem 286: 15908-17). The CIDRPAM domain is divided into two domains ID2a and ID2b, where ID2a is the N-terminal part of CIDRPAM not containing the CIDR-like sequence and ID2b corresponds to the CIDR-like sequence. There are two DBL2X borders—DBL2Xa and DBL2Xb. DBL2Xb incorporates 93 amino acids of ID2a. Primers used in cloning are listed in Table 5. Fragments are expressed in baculovirus-infected insect cells or C3029H *E. coli* cells as soluble proteins as described in Methods 1 and 2. Most proteins are produced based on the FCR3 genotype. Some FCR3 fragments do not express and these are instead made based on the 3D7 genotype. VAR2CSA polypeptides from both genotypes bind equally to plCSA.

TABLE 5

Cloning Primers

FCR3 Primers

| Protein | Forward Primer | Reverse Primer |
|---|---|---|
| ID1-ID2b | AACTACATCAAGGGCGAC (SEQ ID NO: 76) | CTTGTTGATATTGGTGTCGGT (SEQ ID NO: 77) |
| DBL1X-ID2a | CACAGCGATAGCGGCAAG (SEQ ID NO: 78) | GTCCAGCTTGCTGGAGTT (SEQ ID NO: 79) |
| ID1-ID2a | AACTACATCAAGGGCGAC (SEQ ID NO: 80) | GTCCAGCTTGCTGGAGTT (SEQ ID NO: 81) |
| ID1-DBL2Xa | AACTACATCAAGGGCGAC (SEQ ID NO: 82) | AGCGGCGTTGGTGGTGGA (SEQ ID NO: 83) |
| ID1-DBL2Xb | AACTACATCAAGGGCGAC (SEQ ID NO: 84) | GTACTI-GTACCGGTAGGG (SEQ ID NO: 85) |
| DBL1X-DBL2Xb | CACAGCGATAGCGGCAAG (SEQ ID NO: 86) | GTACTTGTACCGGTAGGG (SEQ ID NO: 87) |

TABLE 5-continued

Cloning Primers

3D7 Primers

| Protein | Forward Primer | Reverse Primer |
|---|---|---|
| DBL2X-DBL4E | CTGACCAACTGCTACAAG (SEQ ID NO: 88) | GGTCCAGAGGGTACAGCTT (SEQ ID NO: 89) |
| ID1-DBL3E | CTGTCCTTCATCCTGAAC (SEQ ID NO: 90) | TTCAGCGTTGTTGTACTCGTA (SEQ ID NO: 91) |
| ID1-DBL4E | CTGTCCTTCATCCTGAAC (SEQ ID NO: 92) | GTCCAGAGGGTACAGCTT (SEQ ID NO: 93) |
| DBL1X-ID2b | CACTCTGACTCTGGCACC (SEQ ID NO: 94) | AGAGGACTTCATCTTGTTGTTGGT (SEQ ID NO: 95) |
| ID1-ID2b | CTGTCCTTCATCCTGAAC (SEQ ID NO: 96) | AGAGGACTTCATCTTGTTGTTGGT (SEQ ID NO: 97) |
| DBL1X-ID2a | CACTCTGACTCTGGCACC (SEQ ID NO: 98) | GTCCAGCTTAGAGGAGTT (SEQ ID NO: 99) |
| ID1-ID2a | CTGTCCTTCATCCTGAAC (SEQ ID NO: 100) | GTCCAGCTTAGAGGAGTT (SEQ ID NO: 101) |
| DBL1X-DBL2Xa | CACTCTGACTCTGGCACC (SEQ ID NO: 102) | GGCGGCGTTGGTGGTAGA (SEQ ID NO: 103) |
| ID1-DBL2Xa | CTGTCCTTCATCCTGAAC (SEQ ID NO: 104) | GGCGGCGTTGGTGGTAGA (SEQ ID NO: 105) |
| DBL1X-DBL2Xb | CACTCTGACTCTGGCACC (SEQ ID NO: 106) | GTACTTGTATCCGTGGGG (SEQ ID NO: 107) |
| ID1-DBL2Xb | CTGTCCTTCATCCTGAAC (SEQ ID NO: 108) | GTACTTGTATCCGTGGGG (SEQ ID NO: 109) |

Mutating Putative pICSA Binding Sites

PCR1
Fragment 1

| Protein | Forward | Reverse |
|---|---|---|
| DBL1X-ID2a (DSM Deletion) | CACAGCGATAGCGGCAAG (SEQ ID NO: 110) | GGTGTCGAAGTTGATGTCGGGCAGATTGCCCAGGTA (SEQ ID NO: 111) |
| Alanine sub. K(626,629,630), R(631) | CACAGCGATAGCGGCAAG (SEQ ID NO: 112) | AGCTGCGGCCAGATTAGCGCCCTCGTGGAAGGACAC (SEQ ID NO: 113) |
| Alanine sub. K(459,460,461,464) | CACAGCGATAGCGGCAAG (SEQ ID NO: 114) | AGCGCATTCAGCTGCGGCGTTGGTCTTGATGGAGCT (SEQ ID NO: 115) |

Fragment 2

| Protein | Forward | Reverse |
|---|---|---|
| DBL1X-ID2a (DSM Deletion) | CACAGCGATAGCGGCAAG (SEQ ID NO: 116) | GTCCAGCTTGCTGGAGTT (SEQ ID NO: 117) |
| Alanine sub. K(626,629,630), R(631) | GCTAATCTGGCCGCAGCTTACCCCCAGAATAAGAAC (SEQ ID NO: 118) | GTCCAGCTTGCTGGAGTT (SEQ ID NO: 119) |
| Alanine sub. K(459,460,461,464) | GCCGCAGCTGAATGCGCTGACGTGAAGCTGGGCGTG (SEQ ID NO: 120) | GTCCAGCTTGCTGGAGTT (SEQ ID NO: 121) |

PCR2
Final Construct

| Protein | Forward | Reverse |
|---|---|---|
| DBL1X-ID2a (DSM Deletion) | CACAGCGATAGCGGCAAG (SEQ ID NO: 122) | GTCCAGCTTGCTGGAGTT (SEQ ID NO: 123) |
| Alanine sub. K(626,629,630), R(631) | CACAGCGATAGCGGCAAG (SEQ ID NO: 124) | GTCCAGCTTGCTGGAGTT (SEQ ID NO: 125) |
| Alanine sub. K(459,460,461,464) | CACAGCGATAGCGGCAAG (SEQ ID NO: 126) | GTCCAGCTTGCTGGAGTT (SEQ ID NO: 127) |

Method 1: Cloning and Protein Expression in Insect Cells.

VAR2CSA sequence fragments are amplified from codon optimized FCR3 (GenBank accession no. GU249598) or 3D7 (GenBank accession no. 3Q247428) VAR2CSA genes using specific primers (Table 5). Simple fragments are amplified in a one-step PCR. Amino acid substitution constructs are made in a two-step PCR. First PCR amplifies two fragments from the codon optimized FCR3 template, containing overlapping complimentary ends. Second PCR amplifies the total construct, using the two overlapping fragments as template with primers specific for the outer borders. All fragments are sequenced for verification. Fragments are cloned into the baculovirus vector pAcGP67-A (BD Biosciences), modified to contain a V5 and His tag at the C-terminal. The proteins are expressed in baculovirus-infected insect cells as soluble protein secreted into the cell culture supernatant. Briefly, linearized Bakpak6 Baculovirus DNA (BD Biosciences) is co-transfected with the pAcGP67-A plasmids, into Sf9 insect cells for generation of recombinant virus particles. 10 mL of the second amplification is used to infect High-Five cells in 400 mL serum-free medium (10486, GIBCO) at a density of $1 \times 10^6$ cells/mL. The secreted recombinant protein is harvested from the supernatant 3 days after initial infection. The supernatant is filtered (0.2 µm), dialyzed and concentrated before protein purification. The filtered supernatant containing the secreted recombinant protein is dialyzed using an AKTA cross-flow (GE Healthcare). The dialysis is performed in 10 mM $NaH_2PO_4$ (pH 7.4, Sigma-Aldrich) and 500 mM NaCl. The resulting solution is filtered (0.2 µm) and imidazole is added to a final concentration of 15 mM. The protein is then purified on a 1-mL HisSelect column (H8286, Sigma-Aldrich). Bound protein is eluted with 10 mM $NaH_2PO_4$ (pH 7.4), 500 mM NaCl, and 500 mM imidazole. The purity and structural integrity of the protein was verified by SDS-PAGE.

Method 2: Protein Expression in E. coli Cells

Recombinant VAR2CSA proteins were expressed in C3029H or C3030 E. coli SHuffle cells. 20 mL warm 2×YT

[+AMP] medium was inoculated with an *E. coli* clone bearing an appropriate plasmid and incubated overnight at 37° C. overnight with shaking (150 rpm). 800 mL of prewarmed 2×YT [+AMP] in a 5 L flask was next inoculated with 16 mL of the starter culture and incubated at 37° C. with shaking (100-150 rpm) until OD600 reached 0.5-0.8, after which time the temperature was adjusted to 20° C. After 20 minutes the culture was induced with 80 μL 1 M IPTG and incubated for a further 18-20 hours with shaking (100-150 rpm). Cells were harvested by centrifugation (10000×g, 10 min) and the pellet was resuspended in 40 mL lysis buffer (10 mM NaPO$_4$ (pH 7.2), 0.5 M NaCl, 60 mM imidazole+ CMPIT protease inhibitor tablet without EDTA per 20 mL buffer) and split equally into two 50 mL centrifuge tubes. Cells were lysed by sonication (2×5 mins.) on ice and the debris was removed by centrifugation (40000×g, 30 min, 4° C.). Supernatants were filtered (0.2 μm) into a tube on ice and either purified directly or frozen at −20° C.

Example 2: Preparation of T-L$^2$-P$^2$

Scheme 1

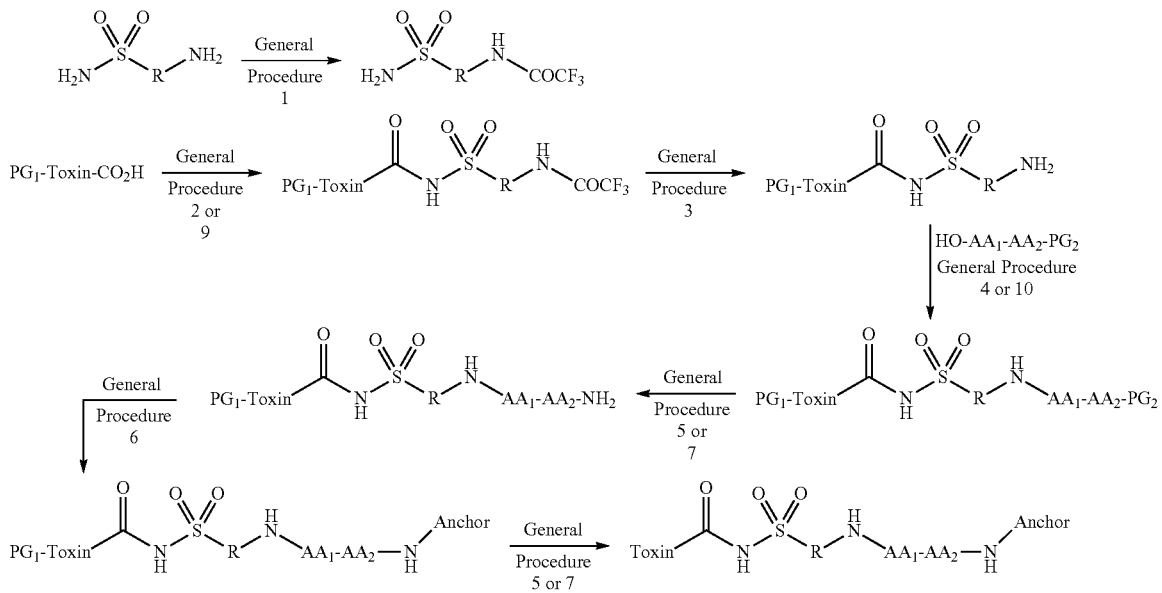

Scheme 1 illustrates a particular embodiment of a general scheme for the synthesis of L$^2$-P$^2$. In further embodiments, the protecting group (PG$_1$) is removed from the Toxin (P$^2$) before amino acid (e.g., AA$_1$-AA$_2$) addition. In certain embodiments, the Anchor includes a functional group that can form a covalent bond with the target moiety (T). In other embodiments, the Anchor comprises a Stretcher.

Scheme 2

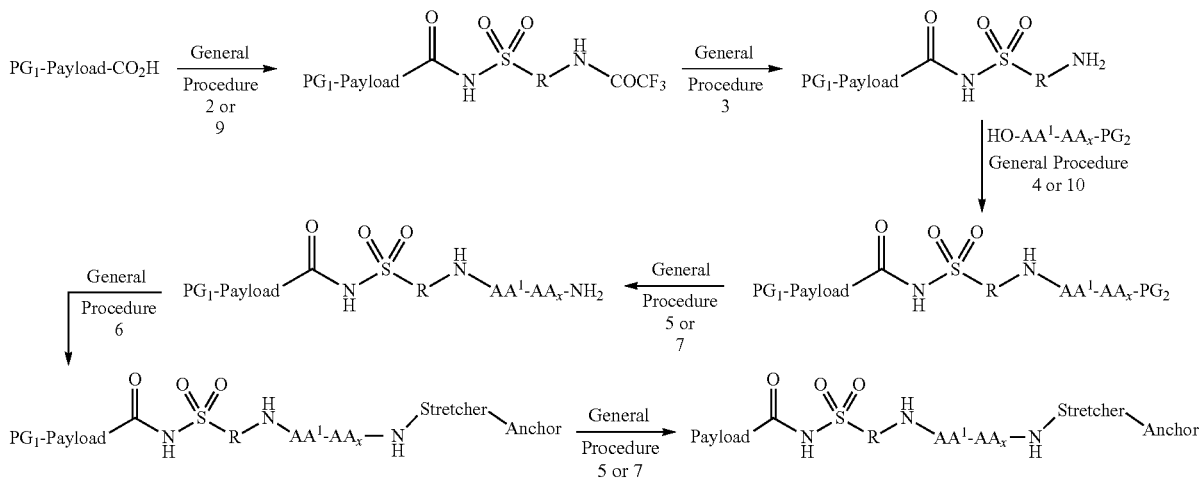

Scheme 2 illustrates a particular embodiment of a general scheme for the convergent synthesis of a P-L complex where the JPB between the payload and AA sequence is assembled prior to installation of stretcher and anchor moieties. This synthetic approach was used to generate the following compounds: Compound G, Compound H, Compound I, Compound J, Compound K, Compound L, Compound M, Compound N, Compound O, Compound P, Compound Q, Compound R, Compound U, Compound EE, Compound FF, Compound GG, Compound HH, Compound II, and Compound JJ.

tored by HPLC-MS (typically 16 h) and excess by-products could be precipitated by the addition of diethyl ether. Solids were removed by filtration and washed with 1:1 diethyl ether/dichloromethane. The combined organic layers were concentrated, and the residue was purified by silica gel chromatography to give the desired N-acyl sulfonamide.

Example 2.3: General Procedure 3—Trifluoroacetamide Saponification

To a solution of the trifluoroacetamide containing-construct in 1,4-dioxane or methanol was added lithium hydrox- Scheme 3

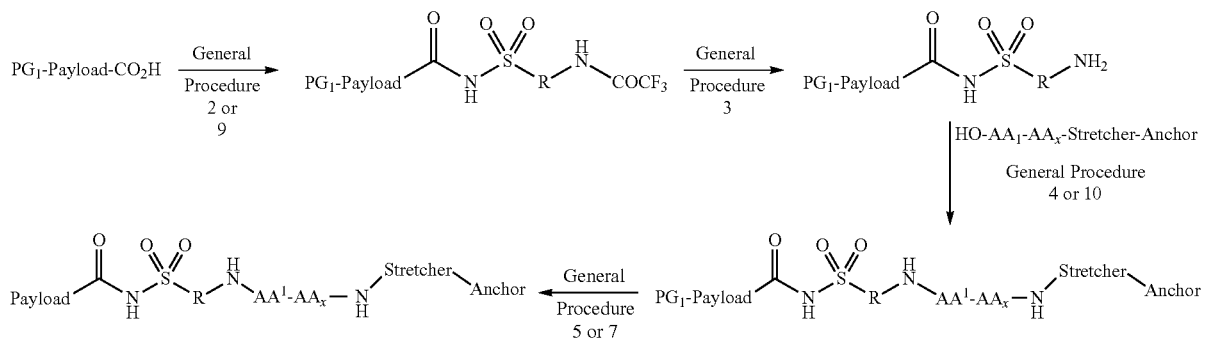

Scheme 3 illustrates a particular embodiment of a general scheme for the convergent synthesis of a P-L complex where the JPB is established between the payload and a proteolytic sequence that already contains a stretcher and anchor functionality. This synthetic approach was used to generate the following compounds: Compound S, Compound T, Compound W, Compound X, Compound Y, Compound Z, Compound AA, Compound BB, Compound CC, and Compound DD.

In certain embodiments, the general scheme comprises the procedures as discussed below. As will be understood by the reasonably skilled artisan, these procedures are illustrative of certain embodiments, and could be performed with alternative solvents, reagents and protecting groups known to be suitable in the art.

Example 2.1: General Procedure 1—Trifluoroacetamide Installation

To a stirred suspension of the amine in 1,4-dioxane was added trifluoroacetic anhydride (1.1 equivalents). The reaction mixture transitioned from a suspension to a solution and back to a suspension again. The progress of the reaction was monitored by TLC and/or HPLC-MS for completion. Once the starting material was fully consumed, the reaction was diluted with hexanes or diethyl ether, filtered on a Buchner funnel and the resulting solids were dried under reduced pressure to give the pure trifluoroacetamide.

Example 2.2: General Procedure 2—DCC/DMAP Mediated N-Acyl Sulfonamide Formation

To a stirred solution of the acid in dichloromethane was added a solution of the sulfonamide (1.3 equivalents, in dichloromethane, N,N-dimethylformamide, or a mixture thereof, as necessary). Dicyclohexylcarbodiimide (1.2 equivalents) was added and subsequently N,N-dimethylaminopyridine (1.2 equivalents). Reaction course was moniide (10 equivalents) and water (10% v/v). The reaction was allowed to stir at room temperature or optionally heated to 50° C. Reaction course was monitored by HPLC-MS. Upon completion, volatiles were removed under reduced pressure and the aqueous layer was quenched with an aqueous solution of 5% w/v citric acid or 1 M hydrochloric acid. The resulting aqueous solution was washed successively with dichloromethane or ethyl acetate and the organic phases were pooled, dried over MgSO$_4$, filtered and concentrated. The reaction product was either used "as is" or purified by silica gel chromatography as necessary.

Example 2.4: General Procedure 4—HATU Mediated Peptide Bond Formation

To a stirred solution of the carboxylic acid in a minimal amount of dichloromethane or N,N-dimethylformamide or mixture thereof, at 0° C. was added HATU (1.05-1.2 equivalents) and either N,N-diisopropylamine (2-4 equivalents) or 2,4,6-collidine (2-4 equivalents). Stirring was continued for a brief induction period (5-20 minutes) at which time the reaction was charged with a solution of the amine in dichloromethane. The reaction was allowed to warm to room temperature and monitored for progress by HPLC-MS. Upon completion, volatiles were removed under reduced pressure and the residual material was purified by silica gel chromatography or reverse phase HPLC to furnish amide in adequate purity.

Example 2.5: General Procedure 5—Fmoc Group Removal

The Fmoc-protected compound was dissolved in 20% piperidine in N,N-dimethylformamide. The reaction course was monitored by HPLC-MS. When complete, all volatiles were removed under reduced pressure to yield a residue that was either purified by silica gel chromatography or used directly in the next step.

Example 2.6: General Procedure 6—N-Acylation of Amines Using NHS-Activated Esters To a solution of the amine in a minimal amount of N,N-dimethylformamide was added the corresponding N-hydroxy succinimide containing ester (1.5 equivalents). The progress of the reaction was monitored by HPLC-MS (typically ~16 h) at which point all volatiles were removed under reduced pressure. The residue was then purified by either silica gel chromatography or reverse phase HPLC to give the desired amide product.

Example 2.7: General Procedure 7—Boc Group Removal

To a solution of the Boc-protected compound in dichloromethane was added 10% v/v trifluoroacetic acid. Reaction course was monitored by HPLC-MS. Upon reaction completion, all volatiles were removed under reduced pressure. The residual material was purified either by reverse phase HPLC, silica gel chromatography or precipitation from a mixture of cold methanol/dichloromethane/diethyl ether.

Example 2.7.1: General Procedure 8—4-Anilino Sulfonamide Synthesis

To a stirred suspension or solution of the starting aniline in $CH_2Cl_2$ (0.1 M) was added trifluoroacetic anhydride (1.1 equiv). The reaction was allowed to stir for ~1 h at which point it was concentrated under reduced pressure. The residue was twice dissolved in $CHCl_3$ and concentrated to give the desired trifluoroacetanilide in quantitative yield with the expected analytical results.

The trifluoroacetanilide (~8 mmol) was dissolved in $CHCl_3$ (10 mL). Chlorosulfonic acid (3 equiv) was added with stirring. The resulting solution was heated to 70° C. for 1 h, then cooled to room temperature at which time thionyl chloride (2 equiv) was added with stirring. The resulting biphasic mixture was re-heated to 70° C. for 15 minutes. The reaction mixture was then twice diluted with $CHCl_3$ and concentrated in vacuo to remove excess acids.

The resulting phenylchlorosulphonic acid was dissolved in 1,4-dioxane (~10 mL) and the resulting solution was added dropwise to a concentrated solution of aqueous ammonia (10 mL) at 0° C. with vigorous stirring. The reaction was quenched by addition of 1M citric acid and adjusted to pH=3. In most cases the sulfonamide precipitated and was filtered directly from the aqueous phase; in instances where the product did not precipitate, the reaction was diluted with ethyl acetate (~100 mL), transferred to a separatory funnel and the organic phase was washed with brine before being dried over $MgSO_4$ and concentrated to give the desired 4-trifluoroacetanilide substituted sulfonamides.

Example 2.7.2: General Procedure 9—Alternative Acyl Benzotriazole Mediated N-Acyl Sulfonamide Formation This procedure was adapted from the one described in ARKIVOC 2004 (xii), 14-22.

Example 2.7.3: General Procedure 10—EDCI/Cu(II) Mediated Peptide Bond Formation To a stirred solution of the carboxylic acid in a minimal amount of 30% N,N-dimethylformamide in dichloromethane was added 1-ethyl-3-(3-dimethylaminopropyl)carbodiimide (0.95 equiv), 1-hydroxy-7-azabenzotriazole (1.0 equiv), the amine (0.33 equiv) and anhydrous copper (II) chloride (1.0 equiv) in sequence with a brief pause between each additional reagent. Stirring was continued at room temperature and progress of the reaction was monitored by HPLC-MS. Upon completion, volatiles were removed under reduced pressure and the residual material was purified by silica gel chromatography or reverse phase HPLC to furnish the desired amide in adequate purity.

Example 2.7.4: General Procedure 11—Ester Saponification

To a solution of the ester containing compound in 1,4-dioxane or methanol was added lithium hydroxide (10 equivalents) and water (10% v/v). The reaction was allowed to stir at room temperature or optionally heated to 50° C. Reaction course was monitored by HPLC-MS. Upon completion, volatiles were removed under reduced pressure, the aqueous layer was pH adjusted if necessary and washed successively with dichloromethane or ethyl acetate. The organic phases were pooled, dried over $MgSO_4$, filtered and concentrated. The reaction product was either used "as is" or purified by silica gel chromatography as necessary.

Example 2.8.1: Fmoc-Val-Cit-OH: (R)-2-((R)-2-(((9H-Fluoren-9-yl-methoxy)carbonylamino)-3-methylbutanamido)-5-ureidopentanoic Acid, Fmoc-Valine-Citrulline-OH The title compound was prepared according to Dubowchik et al., Bioconjugate Chem., 2002, 13, 855-869. $^1$H NMR (400 MHz, DMSO-$d_6$) δ 12.56 (s, 1H), 8.21 (d, J=7.3 Hz, 1H), 7.90 (d, J=7.5 Hz, 2H), 7.76 (t, J=7.0 Hz, 2H), 7.49-7.39 (m, 3H), 7.38-7.23 (m, 2H), 5.96 (t, J=5.9 Hz, 1H), 5.40 (s, 2H), 4.34-4.09 (m, 4H), 3.93 (dd, J=9.1, 7.1 Hz, 1H), 3.39 (q, J=7.0 Hz, 3H), 2.96 (q, J=6.5 Hz, 2H), 1.97 (d, J=6.9 Hz, 1H), 1.86-1.63 (m, 1H), 1.57 (dtd, J=13.9, 9.0, 5.4 Hz, 1H), 1.41 (dhept, J=13.2, 6.9 Hz, 2H), 0.88 (dd, J=13.3, 6.7 Hz, 6H). $C_{26}H_{32}N_4O_6$ calcd. [M+H]$^+$ 497.23. found [M+H]$^+$ 497.19.

Example 2.8.2: Fmoc-Val-Cit-OH: (S)-2-((S)-2-(((9H-Fluoren-9-yl-methoxy)carbonylamino)-3-methylbutanamido)-5-ureidopentanoic Acid, Fmoc-Valine-Citrulline-OH The title compound was prepared according to Dubowchik et al., Bioconjugate Chem., 2002, 13, 855-869. $^1$H NMR (400 MHz, DMSO-$d_6$) δ 12.56 (s, 1H), 8.21 (d, J=7.3 Hz, 1H), 7.90 (d, J=7.5 Hz, 2H), 7.76 (t, J=7.0 Hz, 2H), 7.49-7.39 (m, 3H), 7.38-7.23 (m, 2H), 5.96 (t, J=5.9 Hz, 1H), 5.40 (s, 2H), 4.34-4.09 (m, 4H), 3.93 (dd, J=9.1, 7.1 Hz, 1H), 3.39 (q, J=7.0 Hz, 3H), 2.96 (q, J=6.5 Hz, 2H), 1.97 (d, J=6.9 Hz, 1H), 1.86-1.63 (m, 1H), 1.57 (dtd, J=13.9, 9.0, 5.4 Hz, 1H), 1.41 (dhept, J=13.2, 6.9 Hz, 2H), 0.88 (dd, J=13.3, 6.7 Hz, 6H).). $C_{26}H_{32}N_4O_6$ calcd. [M+H]$^+$ 497.23. found [M+H]$^+$ 497.19.

Example 2.9: MC-NHS: 2,5-Dioxopyrrolidin-1-yl 6-(2,5-Dioxo-2,5-dihydro-1H-pyrrol-1-yl)hexanoate To a stirred solution of 6-aminocaproic acid (10.0 g, 76.2 mmol, 1.0 eq) in acetic acid (75 mL), maleic anhydride (7.85 g, 80.0 mmol, 1.05 eq) was added. The solids took a few minutes to dissolve, then after ca. 5 min, white solids began to crash out. After an hour, the suspension thickened to a white cake. This material was scooped onto a fritted funnel and washed with toluene and dried in vacuo with heating to remove all traces of acetic acid. The intermediate powder was taken up in toluene (250 mL), triethylamine (21.3 mL, 152 mmol, 2.0 eq) was added, and the mixture heated to reflux with a Dean-Stark trap. After 5 h of reflux, the mixture was cooled and the clear toluene layer was decanted from the rest of the sticky residue in the flask. The toluene was removed in vacuo to yield a triethylamine salt of 6-(2,5-dioxo-2,5-dihydro-1H-pyrrol-1-yl)hexanoate. The salt was redissolved in toluene, and a small amount of acetic acid was added, then concentrated. Next, the mixture was taken up in 50% saturated sodium bicarbonate, and 1 M HCl was added to adjust the pH to 3, forming a milky precipitate. This was extracted three times with EtOAc, combined organics dried over sodium sulfate, filtered, and concentrated in vacuo to yield pure 6-(2,5-dioxo-2,5-dihydro-1H-pyrrol-1-yl) hexanoate (3.08 g, 19%). To a stirred solution of 6-(2,5-dioxo-2,5-dihydro-1H-pyrrol-1-yl)hexanoate (3.08 g, 14.6 mmol, 1.0 eq) and N-hydroxysuccinimide (1.76 g, 15.3 mmol, 1.05 eq) in EtOAc (30 mL) at 0° C., was added dicyclohexylcarbodiimide (3.16 g, 15.3 mmol, 1.05 eq). The reaction was then allowed to warm to rt. After 20 h, the reaction was filtered and washed with EtOAc and the filtrate concentrated. The residue was purified by flash chromatography to yield the title compound (2.16 g, 48%) as a clear oil that solidified slowly to a waxy white solid. $^1$H NMR (400 MHz, Chloroform-d) δ 6.71 (s, 2H), 3.56 (t, J=7.2 Hz, 2H), 2.86 (s, 4H), 2.63 (t, J=7.4 Hz, 2H), 1.80 (p, J=7.4 Hz, 2H), 1.73-1.57 (m, 2H), 1.50-1.35 (m, 2H). m/z calcd. for $C_{14}H_{16}N_2O_6$=308.10. Found [M+H]$^+$=309.13. $R_f$=0.28 (50% EtOAc/Hex).

Example 2.10: Fmoc-Phe-Lys(Boc)-OH: (R)-2((R)-2(((9H-Fluoren-9-yl-methoxy)carbonylamino)-3-phenylpropanamido)-6-(tert-butoxycarbonylamino) hexanoic Acid; Fmoc-Phenylalanine-Lysine(Boc)-OH The title compound was prepared according to Walker et al., Bioorganic Med Chem Lett, 2004, 14, 4323-4327. $^1$H NMR (400 MHz, DMSO-d$_6$) δ 8.28 (d, J=7.7 Hz, 1H), 7.89 (d, J=7.6 Hz, 2H), 7.71-7.57 (m, 2H), 7.41 (td, J=7.6, 3.8 Hz, 2H), 7.33 (t, J=7.5 Hz, 2H), 7.30-7.23 (m, 4H), 7.19 (t, J=7.3 Hz, 1H), 6.79 (t, J=5.6 Hz, 1H), 4.37-4.24 (m, 1H), 4.24-4.07 (m, 5H), 3.02 (dd, J=13.8, 3.5 Hz, 1H), 2.95-2.83 (m, 2H), 2.83-2.71 (m, 1H), 1.82-1.68 (m, 1H), 1.68-1.51 (m, 1H), 1.46-1.22 (m, 13H). m/z calcd. for $C_{35}H_{41}N_3O_7$=615.29. Found [M+H]$^+$=616.27, [M-Boc+2H]$^+$=516.16.

Example 2.11: MT-OH: 3-(2-(2-(2-(2,5-Dioxo-2,5-dihydro-1H-pyrrol-1-yl)ethoxy)ethoxy)ethoxy)propanoic Acid The title compound was prepared according to Warnecke, A., Kratz, F. Bioconjugate Chemistry 2003, 14, 377-387. $^1$H NMR (400 MHz, Chloroform-d) δ 6.74 (s, 2H), 3.87-3.72 (m, 4H), 3.72-3.62 (m, 10H), 2.73-2.64 (m, 2H). m/z calcd. for $C_{13}H_{29}NO_7$=301.12. Found [M+H]$^+$=302.14.

Example 2.12: MT-NHS: 2,5-Dioxopyrrolidin-1-yl 3-(2-(2-(2-(2,5-dioxo-2,5-dihydro-1H-pyrrol-1-yl) ethoxy)ethoxy)ethoxy)propanoate MT-OH (2.6 g, 8.6 mmol, 1.0 eq) was treated with dicyclohexylcarbodiimide (1.87 g, 9.06 mmol, 1.05 eq), and N-hydroxysuccinimide (1.04 g, 6.06 mmol, 1.05 eq) in 30 mL of 5:1 EtOAc/dioxane at rt. After 36 h, the mixture was filtered, washing with EtOAc, and the residue was purified by flash chromatography to yield the title compound (309 mg, 9.0%) as a clear oil along with starting material (1.31 g, 50% recovered). $^1$H NMR (400 MHz, Chloroform-d) δ 6.72 (s, 2H), 3.87 (t, J=6.4 Hz, 2H), 3.74 (t, J=5.6 Hz, 2H), 3.70-3.58 (m, 10H), 2.93 (t, J=6.4 Hz, 2H), 2.86 (s, 4H), 1.32-1.19 (m, 2H). m/z calcd. for $C_{17}H_{22}N_2O_9$=398.13. Found [M+H]$^+$=399.15, [M+Na]$^+$=421.14. $R_f$=0.59 (10% (5% AcOH/MeOH)/10% Hex/CH$_2$Cl$_2$).

Example 2.13: Boc-HTI-286-OH: (6S,9S,12S,E)-9-tert-Butyl-12-isopropyl-2,2,5,11,14-pentamethyl-4,7,10-trioxo-6-(2-phenylpropan-2-yl)-3-oxa-5,8,11-triazapentadec-13-en-15-oic Acid The title compound was prepared according to Nieman et al. J. Nat. Prod. 2003, 66, 183-199. $^1$H NMR (400 MHz, Methanol-d$_4$) δ 7.57 (d, J=7.3 Hz, 2H), 7.48 (t, J=7.8 Hz, 2H), 7.38 (t, J=7.3 Hz, 1H), 6.80 (dq, J=9.8, 1.6 Hz, 1H), 5.08 (t, J=10.2 Hz, 1H), 4.95 (s, 1H), 4.37 (s, 1H), 3.17 (s, 3H), 2.53 (s, 3H), 2.15-2.02 (m, 1H), 1.94 (d, J=1.5 Hz, 3H), 1.50 (s, 3H), 1.41 (s, 3H), 1.10 (s, 9H), 0.93 (d, J=6.6 Hz, 3H), 0.92 (d, J=6.6 Hz, 3H). $C_{32}H_{51}N_3O_6$ calcd. [M+H]$^+$ 574.38. found [M+Na]$^+$ 586.42, [M+H]$^+$ 574.46, [M-Boc+2H]$^+$ 474.39.

Example 2.14: Preparation of (S,E)-N-(4-(((S)-2-((S)-2-(6-(2,5-Dioxo-2,5-dihydro-1H-pyrrol-1-yl) hexanamido)-3-methylbutanamido)-5-ureidopentanamido)methyl)phenylsulfonyl)-2,5-dimethyl-4-((S)—N,3,3-trimethyl-2-((S)-3-methyl-2-(methylamino)-3-phenylbutanamido)butanamido) hex-2-enamide (Compound G)

Step 1: 4-(Azidomethyl)benzenesulfonamide

To a stirred solution of 4-(bromomethyl)benzenesulfonamide (0.50 g) in N,N-dimethylformamide (1 mL) was added sodium azide (0.20 g). The suspension was heated to 50° C. for 3 hours at which point the solvent was removed under reduced pressure. The residue was partitioned between ethyl acetate and water. The organic phase was washed with brine, dried over magnesium sulfate, filtered and concentrated to dryness to give the title compound as a syrup that solidified on standing. $^1$H NMR (400 MHz, Chloroform-d) δ 8.06-7.91 (m, 2H), 7.58-7.44 (m, 2H), 4.96 (s, 2H), 4.48 (s, 2H).

Step 2: 4-(Aminomethyl)benzenesulfonamide

To a solution of 4-(azidomethyl)benzenesulfonamide (0.354 g) in methanol (10 mL) in a round bottom flask equipped with a magnetic stirrer was added 10% Pd/C (0.05 g). The flask was evacuated of gases at reduced pressure and charged with hydrogen. This evacuation and charge was repeated three times at which point the suspension was left to stir overnight. At 16 h, TLC analysis indicated complete consumption of the starting material. The reaction was diluted with methanol (40 mL), Celite® was added and the mixture was filtered through a fritted glass funnel. The resulting solution was concentrated to dryness. $^1$H NMR suggested that the material was sufficiently clean at this stage for further use without purification. $^1$H NMR (400 MHz, DMSO-d$_6$) δ 7.77 (m, 2H), 7.53 (m, 2H), 5.76 (s, 2H), 3.76 (d, J=11.9 Hz, 2H).

Step 3: 2,2,2-Trifluoro-N-(4-sulfamoylbenzyl)acetamide

The title compound was synthesized by reaction of 4-(aminomethyl)benzenesulfonamide with TFAA according to General Procedure 1, with a $^1$H NMR spectrum that was complicated by rotamers. $^1$H NMR (400 MHz, DMSO-d$_6$) δ 7.91-7.75 (m, 2H), 7.55-7.31 (m, 4H), 4.72 (m, 2H), 4.47 (d, J=6.0 Hz, 1H), 3.18 (s, 2H).

Step 4: tert-Butyl (S)-1-((S)-1-(((S,E)-2,5-Dimethyl-6-oxo-6-(4-((2,2,2-trifluoroacetamido)methyl)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate)

The title compound was synthesized from Boc-HTI-286-OH according to General Procedure 2. $^1$H NMR (400 MHz, Methanol-d4) δ 8.11-7.99 (m, 2H), 7.50 (dd, J=18.3, 7.9 Hz, 4H), 7.39-7.07 (m, 7H), 6.43 (d, =9.0 Hz, 1H), 5.17 (s, 1H), 4.68 (d, J=8.9 Hz, 1H), 4.56 (s, 2H), 3.00 (d, J=33.9 Hz, 3H), 2.88 (d, J=7.6 Hz, 3H), 2.34 (s, 2H), 2.00 (d, J=13.6 Hz, 1H), 1.81 (d, J=6.4 Hz, 3H), 1.43 (s, 13H), 0.98-0.68 (m, 14H). C$_{41}$H$_{58}$F$_3$N$_5$O$_8$S calcd. [M+H]$^+$ 838.40; found [M+Na]$^+$ 860.48; [M+H]$^+$ 838.46; [M-Boc+2H]$^+$ 738.33.

Step 5: (S,E)-N-(4-(Aminomethyl)phenylsulfonyl)-2,5-dimethyl-4-((S)—N,3,3-trimethyl-2-((S)-3-methyl-2-(methylamino)-3-phenylbutanamido)butanamido)hex-2-enamide The title compound was prepared from tert-butyl (S)-1-((S)-1-((S,E)-2,5-dimethyl-6-oxo-6-(4-((2,2,2-trifluoroacetamido)methyl)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate) according to General Procedures 3 and 7. $^1$H NMR (400 MHz, Methanol-d4) δ 8.13 (d, J=8.3 Hz, 2H), 7.68 (d, J=8.4 Hz, 2H), 7.59-7.41 (m, 4H), 7.37 (t, J=7.3 Hz, 1H), 6.51 (dd, J=9.4, 1.7 Hz, 1H), 5.01 (t, J=9.9 Hz, 1H), 4.37 (s, 1H), 4.24 (s, 2H), 3.17 (s, 3H), 2.51 (s, 3H), 2.12-1.96 (m, 1H), 1.84 (d, J=1.5 Hz, 3H), 1.47 (s, 3H), 1.37 (s, 3H), 1.07 (s, 9H), 0.91 (m, 6H). C$_{34}$H$_{51}$N$_5$O$_5$S calcd. [M+H]$^+$ 642.38; found [M+H]$^+$ 642.40.

Step 6: (9H-Fluoren-9-yl)methyl (S)-1-((S)-1-(4-(N—(S,E)-2,5-dimethyl-4-((S)—N,3,3-trimethyl-2-((S)-3-methyl-2-(methylamino)-3-phenylbutanamido)butanamido)hex-2-enoyl)sulfamoyl)benzylamino)-1-oxo-5-ureidopentan-2-ylamino)-3-methyl-1-oxobutan-2-ylcarbamate Synthesized from (S,E)-N-(4-(aminomethyl)phenylsulfonyl)-2,5-dimethyl-4-((S)—N,3,3-trimethyl-2-((S)-3-methyl-2-(methylamino)-3-phenylbutanamido)butanamido)hex-2-enamide and Fmoc-Val-Cit-OH according to General Procedure 4 with minor contamination by DIPEA and AcOH. Material used "as is" in the subsequent step. C$_{60}$H$_{81}$N$_9$O$_{10}$S calcd. [M+H]$^+$ 1120.58; found [M+H]$^+$ 1120.68.

Step 7: (S,E)-N-(4-(((S)-2-((S)-2-Amino-3-methylbutanamido)-5-ureidopentanamido)methyl)phenylsulfonyl)-2,5-dimethyl-4-((S)—N,3,3-trimethyl-2-((S)-3-methyl-2-(methylamino)-3-phenylbutanamido)butanamido)hex-2-enamide The title compound was synthesized staring with (9H-fluoren-9-yl)methyl (S)-1-((S)-1-(4-(N—(S,E)-2,5-dimethyl-4-((S)—N,3,3-trimethyl-2-((S)-3-methyl-2-(methylamino)-3-phenylbutanamido)butanamido)hex-2-enoyl)sulfamoyl)benzylamino)-1-oxo-5-ureidopentan-2-ylamino)-3-methyl-1-oxobutan-2-ylcarbamate according to General Procedure 5.

Step 8: (S,E)-N-(4-(((S)-2-((S)-2-(6-(2,5-Dioxo-2,5-dihydro-1H-pyrrol-1-yl)hexanamido)-3-methylbutanamido)-5-ureidopentanamido)methyl)phenylsulfonyl)-2,5-dimethyl-4-((S)—N,3,3-trimethyl-2-((S)-3-methyl-2-(methylamino)-3-phenylbutanamido)butanamido)hex-2-enamide The title compound was synthesized from (S,E)-N-(4-(((S)-2-((S)-2-amino-3-methylbutanamido)-5-ureidopentanamido)methyl)phenylsulfonyl)-2,5-dimethyl-4-((S)—N,3,3-trimethyl-2-((S)-3-methyl-2-(methylamino)-3-phenylbutanamido)butanamido)hex-2-enamide and MC-NHS according to General Procedure 6. $^1$H NMR (600 MHz, Methanol-d4) δ 7.89 (d, J=8.0 Hz, 2H), 7.53-7.47 (m, 2H), 7.39 (t, J=7.5 Hz, 4H), 7.28 (t, J=7.3 Hz, 1H), 6.82 (s, 2H), 6.67 (d, J=9.3 Hz, 1H), 5.03 (t, J=10.0 Hz, 1H), 4.51-4.35 (m, 3H), 4.18 (d, J=7.4 Hz, 1H), 3.65 (s, 1H), 3.50 (t, J=7.1 Hz, 2H), 3.31 (s, 3H), 3.20-3.01 (m, 5H), 2.35-2.18 (m, 5H), 2.08 (dq, J=13.9, 6.9 Hz, 1H), 2.02-1.91 (m, 6H), 1.91-1.77 (m, 4H), 1.72 (dtd, J=14.0, 9.3, 5.2 Hz, 1H), 1.66-1.40 (m, 10H), 1.37 (s, 3H), 1.34-1.24 (m, 3H), 1.03 (s, 9H), 0.96 (dd, J=6.8, 4.0 Hz, 6H), 0.91-0.86 (m, 3H), 0.84 (d, J=6.6 Hz, 3H). C$_{55}$H$_{82}$N$_{10}$O$_{11}$S calcd. [M+H]$^+$ 1091.59; found [M+H]$^+$ 1091.67.

Example 2.15: Preparation of (S,E)-N-(4-(((R)-6-amino-2-((R)-2-(6-(2,5-dioxo-2,5-dihydro-1H-pyrrol-1-yl)hexanamido)-3-phenylpropanamido)hexanamido)methyl)phenylsulfonyl)-2,5-dimethyl-4-((S)—N,3,3-trimethyl-2-((S)-3-methyl-2-(methylamino)-3-phenylbutanamido)butanamido)hex-2-enamide (Compound H)

Step 1: tert-Butyl (S)-1-((S)-1-(((S,E)-6-(4-(Aminomethyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate The title compound was prepared from tert-butyl (S)-1-((S)-1-((S,E)-2,5-dimethyl-6-oxo-6-(4-((2,2,2-trifluoroacetamido)methyl)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate) according to General Procedure 3. See above for characterization.

Step 2: tert-Butyl (S)-1-(((S)-1-(((S,E)-6-(4-((5R,8R)-5-Benzyl-8-(4-((tert-butoxycarbonyl)amino)butyl)-1-(9H-fluoren-9-yl)-3,6,9-trioxo-2-xa-4,7,10-triazaudecan-11-yl)phenylsulfonamido)-2,5-dimethyl-6-oxohex-4-en-3-yl)(methyl)amino)-3,3-dimethyl-1-oxobutan-2-yl)amino)-3-methyl-1-oxo-3-phenylbutan-2-yl(methyl)carbamate (Compound H-1)

The title compound was prepared from tert-butyl (S)-1-(((S)-1-(((S,E)-6-(4-(aminomethyl)phenylsulfonamido)-2,5-dimethyl-6-oxohex-4-en-3-yl)(methyl)amino)-3,3-dimethyl-1-oxobutan-2-yl)amino)-3-methyl-1-oxo-3-phenylbutan-2-yl(methyl)carbamate and Fmoc-Phe-Lys(Boc)-OH according to General Procedure 4.

$C_{74}H_{98}N_8O_{13}S$ calcd. m/z=1338.70 amu; found [M+H]$^+$=1339.86, [M+Na]$^+$=1361.88, [M+K]$^+$=1377.95, [M-Boc+2H]$^+$=1239.83, [M−2Boc+3H]$^+$=1139.72.

Step 3: tert-Butyl (S)-1-(((S)-1-(((S,E)-6-(4-(((R)-2-((R)-2-Amino-3-phenylpropanamido)-6-((tert-butoxycarbonyl)amino)hexanamido)methyl)phenylsulfonamido)-2,5-dimethyl-6-oxohex-4-en-3-yl)(methyl)amino)-3,3-dimethyl-1-oxobutan-2-yl)amino)-3-methyl-1-oxo-3-phenylbutan-2-yl(methyl)carbamate (Compound H-2)

The title compound was prepared from Compound H-1 according to General Procedure 5. $C_{59}H_{88}N_8O_{11}S$ calcd. m/z=1116.63 amu; found [M+H]$^+$=1117.78, [M+Na]$^+$=1139.80, [M-Boc+2H]$^+$=1017.72, [M−2Boc+3H]$^+$=917.64.

Step 4: tert-Butyl (S)-1-(((S)-1-(((S,E)-6-(4-(((R)-6-((tert-Butoxycarbonyl)amino)-2-((R)-2-(6-(2,5-dioxo-2,5-dihydro-1H-pyrrol-1-yl)hexanamido)-3-phenylpropanamido)hexanamido)methyl)phenylsulfonamido)-2,5-dimethyl-6-oxohex-4-en-3-yl)(methyl)amino)-3,3-dimethyl-1-oxobutan-2-yl)amino)-3-methyl-1-oxo-3-phenylbutan-2-yl(methyl)carbamate (Compound H-3)

The title compound was prepared from Compound H-2 and MC-NHS according to General Procedure 6. $C_{69}H_{99}N_9O_{14}S$ calcd. m/z=1309.70 amu; found [M+H]$^+$=1310.89, [M+Na]$^+$=1332.91, [M-Boc+2H]$^+$=1210.86, [M−2Boc+3H]$^+$=1110.77.

Step 5: (S,E)-N-(4-(((R)-6-Amino-2-((R)-2-(6-(2,5-dioxo-2,5-dihydro-1H-pyrrol-1-yl)hexanamido)-3-phenylpropanamido)hexanamido)methyl)phenylsulfonyl)-2,5-dimethyl-4-((S)—N,3,3-trimethyl-2-((S)-3-methyl-2-(methylamino)-3-phenylbutanamido)butanamido)hex-2-enamide The title compound was prepared from Compound H-3 according to General Procedure 7. $C_{59}H_{83}N_9O_{10}S$ calcd. m/z=1109.60 amu; found [M+H]$^+$=1110.76, [M+Na]$^+$=1132.75, [(M+2H)/2]$^{2+}$=556.11.

Example 2.16: Preparation of (S,E)-N-(4-(((S)-2-((S)-2-(6-(2,5-Dioxo-2,5-dihydro-1H-pyrrol-1-yl)hexanamido)-3-methylbutanamido)-5-ureidopentanamido)methylbenzyl)sulfonyl)-2,5-dimethyl-4-((S)—N,3,3-trimethyl-2-((S)-3-methyl-2-(methylamino)-3-phenylbutanamido)butanamido)hex-2-enamide (Compound I)

Step 1: 2,2,2-Trifluoro-N-(4-(sulfamoylmethyl)benzyl)acetamide

The title compound was synthesized from commercially available (4-(aminomethyl)phenyl)methanesulfonamide and TFAA using General Procedure 1. $^1$H NMR (400 MHz, Acetone-d$_6$) δ 9.05 (s, 1H), 7.48-7.40 (m, 2H), 7.40-7.32 (m, 2H), 6.17 (s, 1H), 4.56 (d, J=6.1 Hz, 2H), 4.35 (s, 2H).

Step 2: (S,E)-2,5-Dimethyl-N-((4-((2,2,2-trifluoroacetamido)methyl)benzyl)sulfonyl)-4-((S)—N,3,3-trimethyl-2-((S)-3-methyl-2-((tert-butoxycarbonyl)(methyl)amino)-3-phenylbutanamido)butanamido)hex-2-enamide (Compound I-1)

The title compound was synthesized from Boc-HTI-286-OH and 2,2,2-trifluoro-N-(4-(sulfamoylmethyl)benzyl)acetamide according to General Procedure 2. $^1$H NMR (400 MHz, Methanol-d$_4$) δ 7.49 (d, J=7.7 Hz, 2H), 7.41-7.27 (m, 51H), 7.21 (d, J=8.0 Hz, 2H), 6.36 (d, J=9.4 Hz, 1H), 5.18 (s, 1H), 4.99 (s, 2H), 4.69 (s, 3H), 4.46 (s, 3H), 3.06-2.91 (m, 3H), 2.88 (d, J=4.7 Hz, 3H), 2.04 (d, J=1.8 Hz, 1H), 1.88 (d, J=13.5 Hz, 3H), 1.79-1.69 (m, 1H), 1.68-1.57 (m, 1H), 1.52 (d, J=8.2 Hz, 3H), 1.44 (s, 9H), 1.23-1.12 (m, 1H), 0.97 (t, J=7.4 Hz, 1H), 0.90 (d, J=6.0 Hz, 9H), 0.80 (d, J=6.8 Hz, 3H). $C_{42}H_{60}F_3N_5O_8S$ calcd. m/z=851.41 amu; found [M+H]$^+$=852.47, [M+Na]$^+$=874.47, [M-Boc+2H]$^+$=752.38.

Step 3: (S,E)-N-((4-(Aminomethyl)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound I-2)

The title compound was prepared from Compound I-1 according to General Procedure 3. $^1$H NMR (400 MHz, Methanol-d$_4$) δ 7.49 (t, J=8.0 Hz, 2H), 7.40-7.30 (m, 4H), 7.28 (d, J=7.9 Hz, 2H), 7.22 (q, J=7.9 Hz, 1H), 6.48 (d, J=9.4 Hz, 1H), 5.19 (s, 1H), 5.07-4.94 (m, 2H), 4.72 (s, 1H), 4.48 (s, 2H), 3.77 (s, 2H), 3.05-2.82 (m, 3H), 1.92-1.82 (m, 4H), 1.58-1.32 (m, 16H), 0.97-0.85 (m, 12H), 0.85-0.74 (m, 4H). $C_{40}H_{61}N_5O_7S$ calcd. m/z=755.43 amu; found [M+H]$^+$=756.46, [M+Na]$^+$=778.48, [M-Boc+2H]$^+$=656.39.

Step 4: (S,E)-N-((4-(((S)-2-((S)-2-(((9H-Fluoren-9-yl)methoxy)carbonyl)amino-3-methylbutanamido)-5-ureidopentanamido)methyl)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound I-3)

The title compound was prepared from Compound I-2 and Fmoc-Val-Cit-OH according to General Procedure 4. $C_{66}H_{91}N_9O_{12}S$ calcd. m/z=1233.65 amu; found [M+H]$^+$=1234.82, [M+Na]$^+$=1256.80, [M-Boc+2H]$^+$=1134.73.

Step 5: (S,E)-N-((4-(((S)-2-((S)-2-amino-3-methylbutanamido)-5-ureidopentanamido)methyl)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound I-4)

The title compound was prepared from Compound I-3 according to General Procedure 5. $C_{51}H_{81}N_9O_{10}S$ calcd. m/z=1011.58 amu; found [M+H]$^+$=1012.72, [M+Na]$^+$=1034.68, [M-Boc+2H]$^+$=912.66.

Step 6: (S,E)-N-((4-(((S)-2-((S)-2-((5-(2,5-Dioxo-2,5-dihydro-1H-pyrrol-1-yl)pentyl)amino)-3-methylbutanamido)-5-ureidopentanamido)methyl)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound I-5)

The title compound was prepared from Compound I-4 and MC-NHS according to General Procedure 6. $C_{61}H_{92}N_{10}O_{13}S$ calcd. m/z=1204.66 amu; found [M+H]$^+$=1205.84, [M+Na]$^+$ 1227.82, [M-Boc+2H]$^+$=1105.75.

Step 7: (S,E)-N-(4-(((S)-2-((S)-2-(6-(2,5-Dioxo-2,5-dihydro-1H-pyrrol-1-yl)hexanamido)-3-methylbutanamido)-5-ureidopentanamido)methylbenzyl)sulfonyl)-2,5-dimethyl-4-((S)—N,3,3-trimethyl-2-((S)-3-methyl-2-(methylamino)-3-phenylbutanamido)butanamido)hex-2-enamide The title compound was prepared from Compound I-5 according to General Procedure 7. $C_{56}H_{84}N_{10}O_{11}S$ calcd. m/z=1104.60 amu; found [M+H]$^+$=1105.78, [M+Na]$^+$=1127.76, [(M+2H)/2]$^{2+}$=553.60.

Example 2.17: Preparation of (S,E)-N-(4-(((R)-6-Amino-2-((R)-2-(6-(2,5-dioxo-2,5-dihydro-1H-pyrrol-1-yl)hexanamido)-3-phenylpropanamido)hexanamido)methyl)benzylsulfonyl)-2,5-dimethyl-4-((S)—N,3,3-trimethyl-2-((S)-3-methyl-2-(methylamino)-3-phenylbutanamido)butanamido)hex-2-enamide (Compound J)

Step 1: (S,E)-N-((4-(((R)-6-((tert-Butoxycarbonyl)amino)-2-((R)-2-(((((9H-Fluoren-9-yl)methoxy)carbonyl)amino)-3-phenylpropanamido)hexanamido)methyl)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound J-1)

The title compound was prepared from Compound I-2 and Fmoc-Phe-Lys(Boc)-OH according to General Procedure 4. $C_{75}H_{100}N_8O_{13}S$ calcd. m/z=1352.71 amu; found [M+H]$^+$=1353.96, [M+Na]$^+$=1375.83, [M-Boc+2H]$^+$=1253.78, [M−2Boc+H]$^+$=1153.70.

Step 2: (S,E)-N-((4-(((R)-6-((tert-Butoxycarbonyl)amino)-2-((R)-2-amino-3-phenylpropanamido)hexanamido)methyl)benzyl)sulfonyl)-2,5-dimethyl-4-((S)—N,3,3-trim ethyl-2-((S)-3-methyl-2-((tert-butoxycarbonyl)(methyl)amino)-3-phenylbutanamido)butanamido)hex-2-enamide (Compound J-2)

The title compound was prepared from Compound J-1 according to General Procedure 5. $C_{60}H_{90}N_8O_{11}S$ calcd. m/z=1130.64 amu; found [M+H]$^+$=1131.75, [M+Na]$^+$=1153.75, [M-Boc+2H]$^+$=1031.68, [M−2Boc+3H]$^+$=931.61.

Step 3: (S,E)-N-(4-(((R)-6-((tert-Butoxycarbonyl)amino)-2-((R)-2-(6-(2,5-dioxo-2,5-dihydro-1H-pyrrol-1-yl)hexanamido)-3-phenylpropanamido)hexanamido)methyl)benzylsulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound J-3)

The title compound was prepared from Compound J-2 and MC-NHS according to General Procedure 6. $C_{70}H_{101}N_9O_{14}S$ calcd. m/z=1323.72 amu; found [M+H]$^+$=1324.96, [M+Na]$^+$=1346.94, [M-Boc+2H]$^+$=1224.87, [M−2Boc+3H]$^+$=1124.79.

Step 4: (S,E)-N-(4-(((R)-6-Amino-2-((R)-2-(6-(2,5-dioxo-2,5-dihydro-1H-pyrrol-1-yl)hexanamido)-3-phenylpropanamido)hexanamido)methyl)benzylsulfonyl)-2,5-dimethyl-4-((S)—N,3,3-trimethyl-2-((S)-3-methyl-2-(methylamino)-3-phenylbutanamido)butanamido)hex-2-enamide (Compound J)

The title compound was prepared from Compound J-3 according to General Procedure 7. $C_{60}H_{85}N_9O_{10}S$ calcd. m/z=1123.61 amu; found [M+H]$^+$=1124.75, [M+Na]$^+$=1146.77, [(M+2H)/2]$^{2+}$=563.09.

Example 2.18: Preparation of (S,E)-N-(4-((R)-2-((R)-2-(6-(2,5-Dioxo-2,5-dihydro-1H-pyrrol-1-yl)hexanamido)-3-methylbutanamido)-5-ureidopentanamido)benzylsulfonyl)-2,5-dimethyl-4-((S)—N,3,3-trimethyl-2-((S)-3-methyl-2-(methylamino)-3-phenylbutanamido)butanamido)hex-2-enamide (Compound K)

Step 1: 2,2,2-Trifluoro-N-(4-(Sulfamoylmethylphenyl)acetamide

The title compound was synthesized from commercially available (4-aminophenyl)methanesulfonamide and TFAA using General Procedure 1. $^1$H NMR (400 MHz, DMSO-d$_6$) δ 11.31 (s, 1H), 7.79-7.51 (m, 2H), 7.51-7.23 (m, 2H), 6.85 (s, 2H), 4.27 (s, 2H).

Step 2: (S,E)-2,5-Dimethyl-N-((4-(2,2,2-trifluoroacetamido)benzyl)sulfonyl)-4-((S)—N,3,3-trimethyl-2-((S)-3-methyl-2-((tert-butoxycarbonyl)(methyl)amino)-3-phenylbutanamido)butanamido)hex-2-enamide (Compound K-1)

The title compound was synthesized from Boc-HTI-286-OH and 2,2,2-trifluoro-N-(4-(sulfamoylmethyl)phenyl)acetamide according to General Procedure 2. $^1$H NMR (400 MHz, Chloroform-d) δ 8.81 (s, 1H), 7.66-7.50 (m, 3H), 7.50-7.31 (m, 5H), 7.23 (t, J=7.7 Hz, 1H), 6.35 (dd, J=9.2, 1.6 Hz, 1H), 6.22 (d, J=8.8 Hz, 1H), 5.34 (s, 1H), 5.05-4.80 (m, 3H), 4.72-4.40 (m, 2H), 2.97-2.74 (m, 3H), 2.60 (s, 3H), 1.95 (m, 4H), 1.68-1.35 (m, 15H), 1.02-0.63 (m, 15H). $C_{41}H_{58}F_3N_5O_8S$ calcd. [M+H]$^+$ 838.40; found [M+Na]$^+$ 860.48; [M+H]$^+$ 838.52; [M-Boc+2H]$^+$ 738.39.

Step 3: (S,E)-N-((4-Aminobenzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound K-2)

The title compound was prepared from Compound K-2 according to General Procedure 3. $^1$H NMR (400 MHz, Chloroform-d) δ 7.63-7.39 (m, 2H), 7.35 (t, J=7.7 Hz, 2H), 7.22 (t, J=7.3 Hz, 1H), 7.16-7.03 (m, 2H), 6.73-6.54 (m, 2H), 6.36 (dd, J=9.2, 1.6 Hz, 1H), 6.07 (s, 1H), 5.00 (m, 2H), 4.60 (s, 3H), 2.98-2.75 (m, 6H), 1.97-1.71 (m, 4H), 1.68-1.34 (m, 15H), 0.97-0.63 (m, 15H). $C_{39}H_{59}N_5O_7S$ calcd. [M+H]$^+$ 742.41; found [M+H]$^+$ 742.47; [M-Boc+2H]$^+$ 642.40.

Step 4: (S,E)-N-((4-((R)-2-((R)-2-(((((9H-Fluoren-9-yl)methoxy)carbonyl)amino)-3-methylbutanamido)-5-ureidopentanamido)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound K-3)

The title compound was prepared from Compound K-2 and Fmoc-Val-Cit-OH according to General Procedure 4. $C_{65}H_{89}N_9O_{12}S$ calcd. [M+H]$^+$ 1220.64; found [M+H]$^+$ 1 220.97; [M-Boc+2H]$^+$ 1120.87.

Step 5: (S,E)-N-((4-((R)-2-((R)-2-Amino-3-methylbutanamido)-5-ureidopentanamido)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound K-4)

The title compound was prepared from Compound K-3 according to General Procedure 5. $C_{50}H_{79}N_9O_{10}S$ calcd. [M+Na]$^+$ 998.57; found [M+14]$^+$ 998.75; [M-Boc+H]$^+$ 898.69.

Step 6: (S,E)-N-(4-((R)-2-((R)-2-(6-(2,5-Dioxo-2,5-dihydro-1H-pyrrol-1-yl)hexanamido)-3-methylbutanamido)-5-ureidopentanamido)benzylsulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound K-5)

The title compound was prepared by reaction of Compound K-4 with MC-NHS according to General Procedure 6. $C_{60}H_{90}N_{10}O_{13}S$ calcd. [M+H]$^+$ 1191.64; found [M+H]$^+$ 1191.74; [M-Boc+2H]$^+$ 1091.67.

Step 7: (S,E)-N-(4-((R)-2-((R)-2-(6-(2,5-Dioxo-2,5-dihydro-1H-pyrrol-1-yl)hexanamido)-3-methylbutanamido)-5-ureidopentanamido)benzylsulfonyl)-2,5-dimethyl-4-((S)—N,3,3-trimethyl-2-((S)-3-methyl-2-(methylamino)-3-phenylbutanamido)butanamido)hex-2-enamide The title compound was prepared from Compound K-5 according to General Procedure 7. $C_{55}H_{82}N_{10}O_{11}S$ calcd. [M+H]$^+$ 1091.59; found [M+H]$^+$ 1091.67.

Example 2.19: Preparation of (S,E)-N-((4-((14R,17R)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)benzyl)sulfonyl)-2,5-dimethyl-4-((S)—N,3,3-trimethyl-2-((S)-3-methyl-2-(methylamino)-3-phenylbutanamido)butanamido)hex-2-enamide (Compound L)

Step 1: (S,E)-N-((4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound L-1)

To a stirred solution of Compound K-4 (40.0 mg, 0.040 mmol, 1.0 eq) in $CH_2Cl_2$ (0.5 mL) was added MT-OH (18.1 mg, 0.060 mmol, 1.5 eq). Next, triethylamine (0.017 mL, 0.120 mmol, 3.0 eq) then Mukiyama's reagent (15.4 mg, 0.060 mmol, 1.5 eq) were added. After 3 h, approximately one equivalent of acid, triethylamine, and Mukiyama's reagent was added, and after 30 more min, HPLC indicated consumption of starting material Compound K-4. The reaction mixture was diluted with 0.25 mL hexanes and loaded directly onto flash chromatography to yield the title compound (29.3 mg, 57%) as a clear yellow film. $C_{63}H_{96}N_{10}O_{16}S$ calcd. m/z=1280.67. Found [M+H]$^+$=1281.94, [M+Na]$^+$=1303.91, [M-Boc+2H]$^+$=1181.86. $R_f$=0.45 (10% (5% AcOH/MeOH)/10% Hex/$CH_2Cl_2$)

Step 2: (S,E)-N-((4-((14R,17R)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)benzyl)sulfonyl)-2,5-dimethyl-4-((S)—N,3,3-trimethyl-2-((S)-3-methyl-2-(methylamino)-3-phenylbutanamido)butanamido)hex-2-enamide The title compound was prepared according to General Procedure 7 from Compound L-1. $C_{58}H_{88}N_{10}O_{14}S$ calcd. m/z for=1180.62. Found [M+H]$^+$=1181.82, [(M+2H)/2]$^{2+}$= 591.60.

Example 2.20: (S,E)-N-(4-((R)-6-Amino-2-((R)-2-(6-(2,5-dioxo-2,5-dihydro-1H-pyrrol-1-yl)hexanamido)-3-phenylpropanamido)hexanamido)benzylsulfonyl)-2,5-dimethyl-4-((S)—N,3,3-trimethyl-2-((S)-3-methyl-2-(methylamino)-3-phenylbutanamido)butanamido)hex-2-enamide (Compound M)

Step 1: (S,E)-N-((4-((R)-6-((tert-Butoxycarbonyl)(methyl)amino)-2-((R)-2-((((9H-Fluoren-9-yl)methoxy)carbonyl)amino)-3-phenylpropanamido)hexanamido)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound M-1)

The title compound was prepared from Compound K-2 and Fmoc-Phe-Lys(Boc)-OH according to General Procedure 4. $C_{74}H_{98}N_8O_{13}S$ calcd. m/z=1338.70 amu; found [M+H]$^+$=1339.96, [M+Na]$^+$=1361.92, [M-Boc+2H]$^+$=1239.85, [M-2Boc+H]$^+$=1139.77.

Step 2: (S,E)-N-((4-((R)-6-((tert-Butoxycarbonyl)(methyl)amino)-2-((R)-2-amino-3-phenylpropanamido)hexanamido)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound M-2)

The title compound was prepared from Compound M-1 according to General Procedure 5. $C_{59}H_{88}N_8O_{11}S$ calcd. m/z=1116.63 amu; found [M+H]$^+$=1117.78, [M+Na]$^+$=1139.80, [M-Boc+H]$^+$=1017.72, [M-2Boc+3H]$^+$=917.64.

Step 3: (S,E)-N-(4-((R)-6-((tert-Butoxycarbonyl)(methyl)amino)-2-((R)-2-(6-(2,5-dioxo-2,5-dihydro-1H-pyrrol-1-yl)hexanamido)-3-phenylpropanamido)hexanamido)benzylsulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound M-3)

The title compound was prepared from Compound M-2 and MC-NHS according to General Procedure 6. $C_{69}H_{99}N_9O_{14}S$ calcd. m/z=1309.70 amu; found [M+H]$^+$=1310.93, [M+Na]$^+$=1332.89, [M-Boc+2H]$^+$=1210.84, [M-2Boc+3H]$^+$=1110.76.

Step 4: (S,E)-N-(4-((R)-6-Amino-2-((R)-2-(6-(2,5-dioxo-2,5-dihydro-1H-pyrrol-1-yl)hexanamido)-3-phenylpropanamido)hexanamido)benzylsulfonyl)-2,5-dimethyl-4-((S)—N,3,3-trimethyl-2-((S)-3-methyl-2-(methylamino)-3-phenylbutanamido)butanamido) hex-2-enamide The title compound was prepared from Compound M-3 according to General Procedure 7. $C_{59}H_{83}N_9O_{10}S$ calcd. m/z=1109.60 amu; found $[M+H]^+$=1110.71, $[M+Na]^+$= 1132.74, $[(M+2H)/2]^{2+}$=556.18.

Example 2.21: Preparation of (S,E)-N-(4-((S)-2-((S)-2-(6-(2,5-Dioxo-2,5-dihydro-1H-pyrrol-1-yl) hexanamido)-3-methylbutanamido)-5-ureidopentanamido)phenylsulfonyl)-2,5-dimethyl-4-((S)—N,3,3-trimethyl-2-((S)-3-methyl-2-(methylamino)-3-phenylbutanamido)butanamido)hex-2-enamide (Compound N)

Step 1: 2,2,2-Trifluoro-N-(4-sulfamoylphenyl)acetamide

The title compound was synthesized from commercially available sulfanilamide and TFAA using General Procedure 1.

Step 2: tert-Butyl (S)-1-((S)-1-(((S,E)-2,5-Dimethyl-6-oxo-6-(4-(2,2,2-trifluoroacetamido)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate The title compound was synthesized from Boc-HTI-286-OH and 2,2,2-trifluoro-N-(4-sulfamoylphenyl)acetamide according to General Procedure 2. $^1$H NMR (400 MHz, Methanol-d$_4$) δ 8.14-8.03 (m, 2H), 7.98-7.83 (m, 3H), 7.47 (d, J=7.6 Hz, 2H), 7.32 (d, J=7.6, 2H), 7.20 (q, J=7.4, 6.2 Hz, 2H), 6.44 (d, J=9.1 Hz, 1H), 5.16 (s, 1H), 4.68 (d, J=9.0 Hz, 1H), 3.08-2.95 (m, 3H), 2.87 (d, J=6.4 Hz, 3H), 2.01 (m, 6H), 1.80 (d, J=11.7 Hz, 3H), 1.62 (d, J=6.4 Hz, 1H), 1.52-1.36 (m, 14H), 1.26 (m, 1H), 0.98-0.72 (m, 15H). $C_{40}H_{56}F_3N_5O_8S$ calcd. $[M+H]^+$ 824.38; found $[M+Na]^+$ 846.43; $[M+H]^+$ 824.40; $[M-Boc+2H]^+$ 724.34.

Step 3: tert-Butyl (S)-1-((S)-1-(((S,E)-6-(4-Amino-phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl (methyl)carbamate (Compound N-1c)

The title compound was prepared from tert-butyl (S)-1-((S)-1-(((S,E)-2,5-dimethyl-6-oxo-6-(4-(2,2,2-trifluoroacetamido)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate according to General Procedure 3.

Step 4: tert-Butyl ((S)-1-(((S)-1-(((S,E)-6-(4-((S)-2-((S)-2-((((9H-Fluoren-9-yl)methoxy)carbonyl) amino)-3-methylbutanamido)-5-ureidopentanamido) phenylsulfonamido)-2,5-dimethyl-6-oxohex-4-en-3-yl)(methyl)amino)-3,3-dimethyl-1-oxobutan-2-yl) amino)-3-methyl-1-oxo-3-phenylbutan-2-yl)(methyl) carbamate (Compound N-1)

Synthesized from tert-butyl (S)-1-((S)-1-(((S,E)-6-(4-aminophenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate and Fmoc-Val-Cit-OH according to General Procedure 4. $C_{64}H_{87}N_9O_{12}S$ calcd. $[M+H]^+$ 1206.62; found $[M+Na]^+$ 1230.81; $[M+H]^+$ 1206.73; $[M-Boc+2H]^+$ 1106.63.

Step 5: tert-Butyl (S)-1-((S)-1-(((S,E)-6-(4-((S)-2-((S)-2-Amino-3-methylbutanamido)-5-ureidopentanamido)phenylsulfonamido)-2,5-dimethyl-6-oxo-hex-4-en-3-yl)(methyl)amino)-3,3-dimethyl-1-oxobutan-2-ylamino)-3-methyl-1-oxo-3-phenylbutan-2-yl(methyl)carbamate The title compound was prepared from Compound N-1 according to General Procedure 5. $C_{49}H_{77}N_9O_{10}S$ calcd. $[M+H]^+$ 984.55; found $[M+H]^+$ 984.63; $[M-Boc+2H]^+$ 884.57.

Step 6: tert-Butyl (S)-1-((S)-1-(((S,E)-6-(4-((S)-2-((S)-2-(6-(2,5-Dioxo-2,5-dihydro-1H-pyrrol-1-yl) hexanamido)-3-methylbutanamido)-5-ureidopentanamido)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate The title compound was prepared from tert-butyl (S)-1-((S)-1-(((S,E)-6-(4-((S)-2-((S)-2-amino-3-methylbutanamido)-5-ureidopentanamido)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl (methyl)carbamate and MC-NHS according to General Procedure 6. $C_{59}H_{88}N_{10}O_{13}S$ calcd. $[M+H]^+$ 1177.63; found $[M+Na]^+$ 1199.74; $[M+H]^+$ 1177.85; $[M-Boc+2H]^+$ 1077.68.

Step 7: (S,E)-N-(4-((S)-2-((S)-2-(6-(2,5-Dioxo-2,5-dihydro-1H-pyrrol-1-yl)hexanamido)-3-methylbutanamido)-5-ureidopentanamido)phenylsulfonyl)-2,5-dimethyl-4-((S)—N,3,3-trimethyl-2-((S)-3-methyl-2-(methylamino)-3-phenylbutanamido)butanamido) hex-2-enamide The title compound was prepared from tert-butyl (S)-1-((S)-1-(((S,E)-6-(4-((S)-2-((S)-2-(6-(2,5-dioxo-2,5-dihydro-1H-pyrrol-1-yl)hexanamido)-3-methylbutanamido)-5-ureidopentanamido)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl (methyl)carbamate according to General Procedure 7. $C_{54}H_{80}N_{10}O_{11}S$ calcd. $[M+H]^+$ 1077.63; found $[M+H]^+$ 1077.68.

Example 2.22: Preparation of (S,E)-N-((4-((14R, 17R)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)phenyl)sulfonyl)-2,5-dimethyl-4-((S)—N,3,3-trimethyl-2-((S)-3-methyl-2-(methylamino)-3-phenylbutanamido) butanamido)hex-2-enamide (Compound O)

Step 1: tert-Butyl ((S)-1-(((S)-1-(((S,E)-6-(4-((14R, 17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido) phenylsulfonamido)-2,5-dimethyl-6-oxohex-4-en-3-yl)(methyl)amino)-3,3-dimethyl-1-oxobutan-2-yl) amino)-3-methyl-1-oxo-3-phenylbutan-2-yl)(methyl) carbamate The title compound was prepared according to General Procedure 6 from tert-butyl (S)-1-((S)-1-(((S,E)-6-(4-((S)-

2-((S)-2-amino-3-methylbutanamido)-5-ureidopentanamido)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate and MT-NHS. m/z calcd. for $C_{62}H_{94}N_{10}O_{16}S$=1266.66. Found [M+H]$^+$=1267.87 [M+Na]$^+$=1289.86, [M-Boc+2H]$^+$=1167.82. $R_f$=0.49 (10% (5% AcOH/MeOH)/$CH_2Cl_2$).

Step 2: (S,E)-N-((4-((14R,17R)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)phenyl)sulfonyl)-2,5-dimethyl-4-((S)—N,3,3-trimethyl-2-((S)-3-methyl-2-(methylamino)-3-phenylbutanamido)butanamido)hex-2-enamide The title compound was prepared according to General Procedure 7 from tert-butyl ((S)-1-(((S)-1-(((S,E)-6-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonamido)-2,5-dimethyl-6-oxohex-4-en-3-yl)(methyl)amino)-3,3-dimethyl-1-oxobutan-2-yl)amino)-3-methyl-1-oxo-3-phenylbutan-2-yl)(methyl)carbamate. m/z calcd. for $C_{57}H_{86}N_{10}O_{14}S$=1166.60. Found [M+H]$^+$=1167.67, [(M+2H)/2]$^{2+}$=584.57.

Example 2.23: Preparation of (S,E)-N-(4-(1-((R)-2-((R)-2-(6-(2,5-Dioxo-2,5-dihydro-1H-pyrrol-1-yl)hexanamido)-3-methylbutanamido)-5-ureidopentanamido)cyclopropyl)benzylsulfonyl)-2,5-dimethyl-4-((S)—N,3,3-trimethyl-2-((S)-3-methyl-2-(methylamino)-3-phenylbutanamido)butanamido)hex-2-enamide (Compound P)

Step 1:4-(Tritylthiomethyl)benzonitrile

Tritylmercaptan (1.48 g, 5.36 mmol, 1.05 eq) in THF (5 mL) was added dropwise to a stirred suspension of sodium hydride (60% dispersion in mineral oil, 214 mg, 5.36 mmol, 1.05 eq) in THF (5 mL) under $N_2$ at 0° C. After 15 min, 4-(bromomethyl)benzonitrile (1.00 g, 5.10 mmol, 1.0 eq) in THF (5 mL) was added and the reaction was allowed to come to rt. After 1 h, TLC indicated complete conversion of starting material. The reaction was quenched by adding saturated ammonium chloride, then some $dH_2O$. The mixture was extracted three times with ether, washed with saturated brine, dried over sodium sulfate, and concentrated to a viscous yellow oil. Purification by flash chromatography gave the title compound (1.76 g, 88%) as a light white powder. $^1$H NMR (400 MHz, Chloroform-d) δ 7.52 (d, J=8.2 Hz, 2H), 7.47 (d, J=7.1 Hz, 6H), 7.33 (t, J=7.5 Hz, 6H), 7.26 (t, J=7.2 Hz, 3H), 7.19 (d, J=8.2 Hz, 2H), 3.40 (s, 2H). m/z calcd. for $C_{27}H_{21}NS$=391.14. Found [M+Na]$^+$=414.13. $R_f$=0.32 (10% EtOAc/Hex).

Step 2: 1-(4-(Tritylthiomethyl)phenyl)cyclopropanamine 4-(Tritylthiomethyl)benzonitrile (1.47 g, 3.75 mmol, 1.0 eq) was taken up in 40 mL THF, under $N_2$ atmosphere, then cooled to −78° C. To this solution was added $Ti(O-iPr)_4$ (1.21 mL, 4.13 mmol, 1.1 eq), then ethylmagnesium bromide (3 M, 2.75 mL, 8.26 mmol, 2.2 eq) was added dropwise over 5 min. The dry-ice bath was removed, allowing the solution to reach rt. After 45 min at rt, $BF_3.Et_2O$ (0.93 mL, 7.51 mmol, 2.0 eq) was added to the now very dark reaction mixture. After stirring for an additional 2.5 h, the reaction was quenched with 5 mL of 2 M HCl, followed by pH adjustment to strong base with about 15 mL 2 M NaOH. Some water was added to the mixture, then it was extracted three times with 75 mL EtOAc, washed once with $dH_2O$, once with saturated brine, dried over sodium sulfate, and concentrated to a clear oil. The material was purified by flash chromatography to afford the title compound (680 mg, 36%) as a clear oil. $^1$H NMR (400 MHz, Chloroform-d) δ 7.49 (d, J=7.8 Hz, 6H), 7.33 (t, J=7.7 Hz, 6H), 7.26 (t, J=7.2 Hz, 3H), 7.20 (d, J=8.2 Hz, 2H), 7.11 (d, J=8.2 Hz, 2H), 3.32 (s, 2H), 1.06 (dd, J=7.9, 5.0 Hz, 2H), 0.95 (dd, J=7.9, 4.7 Hz, 2H). m/z calcd. for $C_{29}H_{27}NS$=421.19. Found [M+H]$^+$=422.19. $R_f$=0.21 (50% EtOAc/Hex).

Step 3: 2,2,2-Trifluoro-N-(1-(4-(tritylthiomethyl)phenyl)cyclopropyl)acetamide

To a stirred solution of 1-(4-(tritylthiomethyl)phenyl)cyclopropanamine (680 mg, 1.61 mmol, 1.0 eq) in $CH_2Cl_2$ was added trifluoroacetic anhydride (0.448 mL, 3.22 mmol, 2.0 eq) and triethylamine (0.45 mL, 3.22 mmol, 2.0 eq). After two hours, TLC and HPLC indicated complete conversion of starting material. The reaction was quenched by the addition of 3 mL $NaHCO_3$, then some $dH_2O$ was added, and the mixture was extracted three times with $CH_2Cl_2$. The combined organics were washed with saturated brine, dried over sodium sulfate, and concentrated to a yellow foam, giving the title compound (715 mg, 86%) in sufficient purity to move to the next step. $^1$H NMR (400 MHz, Chloroform-d) δ 7.48 (d, J=7.7 Hz, 6H), 7.32 (t, J=7.6 Hz, 6H), 7.25 (t, J=7.2 Hz, 3H), 7.19 (d, J=8.2 Hz, 2H), 7.10 (d, J=8.3 Hz, 2H), 6.83 (s, 1H), 3.31 (s, 2H), 1.40-1.24 (m, 4H). m/z calcd. for $C_{31}H_{26}F_3NOS$=517.17. Found [M+Na]$^+$=540.25. $R_f$=0.71 (50% EtOAc/Hex).

Step 4: 2,2,2-Trifluoro-N-(1-(4-(mercaptomethyl)phenyl)cyclopropyl)acetamide 2,2,2-Trifluoro-N-(1-(4-(tritylthiomethyl)phenyl)cyclopropyl)acetamide (715 mg, 1.38 mmol, 1.0 eq) in 5 mL $CH_2Cl_2$ was treated with 2.5 mL TFA. After 1 min, TIPSH (0.42 mL, 2.1 mmol, 1.5 eq) was added, causing the yellow color to fade. After 30 min, TLC indicated the reaction to be complete. The mixture was concentrated, then co-evaporated once with CH2C12 and twice with toluene. The residue was purified by flash chromatography to afford the title compound (261 mg, 69%) as a white solid. $^1$H NMR (400 MHz, Chloroform-d) δ 7.35-7.23 (m, 4H), 6.87 (s, 1H), 3.74 (d, J=7.6 Hz, 2H), 1.77 (t, J=7.6 Hz, 1H), 1.36 (s, 4H). $R_f$=0.47 (20% EtOAc/Hex).

Step 5: 2,2,2-Trifluoro-N-(1-(4-(sulfamoylmethyl)phenyl)cyclopropyl)acetamide

To a stirred solution of 2,2,2-trifluoro-N-(1-(4-(mercaptomethyl)phenyl)cyclopropyl)acetamide (220 mg, 0.799 mmol, 1.0 eq) in acetonitrile were added $dH_2O$ (0.029 mL, 1.6 mmol, 2.0 eq), tetrabutylammonium chloride (110 mg, 0.40 mmol, 0.5 eq), then N-chlorosuccinimide (320 mg, 2.40 mmol, 3.0 eq). After 20 minutes, no starting material was visible by TLC. After 90 min, concentrated $NH_4OH$ (0.18 mL, 3.2 mmol, 4.0 eq) was added. After 10 minutes, 1 mL of $NH_4Cl$ was added, and the mixture was extracted three times with EtOAc. The combined organics were washed twice with $dH_2O$, once with saturated brine, dried over sodium sulfate, and concentrated to a clear oil. The residue was purified by flash chromatography to afford the title compound (192 mg, 74%) as a white solid. $^1$H NMR (400 MHz, DMSO-d$_6$) δ 10.21 (s, 1H), 7.31 (d, J=8.2 Hz, 2H), 7.16 (d, J=8.3 Hz, 2H), 6.85 (s, 2H), 4.23 (s, 2H), 1.27 (dt, J=6.1, 2.3 Hz, 4H). R$_f$=0.26 (50% EtOAc/Hex).

Step 6: (S,E)-2,5-Dimethyl-N-((4-(1-(2,2,2-trifluoroacetamido)cyclopropyl)benzyl)sulfonyl)-4-((S)—N,3,3-trimethyl-2-((S)-3-methyl-2-((tert-butoxycarbonyl)(methyl)amino)-3-phenylbutanamido)butanamido)hex-2-enamide (Compound P-1)

The title compound was prepared according to General Procedure 2 from 2,2,2-trifluoro-N-(1-(4-(sulfamoylmethyl)phenyl)cyclopropyl)acetamide and Boc-HTI-286-OH. $^1$H NMR (400 MHz, Chloroform-d) δ 8.54 (s, 1H), 7.78 (s, 1H), 7.36 (d, J=7.1 Hz, 2H), 7.31-7.23 (m, 2H), 7.23-7.11 (m, 5H), 6.33 (d, J=9.3 Hz, 1H), 6.28-6.14 (m, 1H), 5.35 (s, 1H), 4.97 (t, J=10.3 Hz, 1H), 4.84 (d, J=13.7 Hz, 1H), 4.70-4.56 (m, 1H), 4.50 (d, =8.9 Hz, 1H), 2.90 (s, 3H), 2.59 (s, 3H), 1.90 (s, 3H), 1.82-1.72 (m, 1H), 1.62-1.57 (m, 3H), 1.55 (s, 3H), 1.47 (s, 9H), 1.45-1.34 (m, 4H), 0.85 (d, J=6.5 Hz, 2H), 0.82-0.67 (m, 12H). m/z calcd. for C$_{44}$H$_{62}$F$_3$N$_5$O$_8$S=877.43. Found [M+Na]$^+$=900.67. R$_f$=0.34 (50% (2% AcOH/EtOAc)/Hex).

Step 7: (S,E)-N-((4-(1-Aminocyclopropyl)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound P-2)

The title compound was prepared according to General Procedure 3 in MeOH/H$_2$O from Compound P-1. $^1$H NMR (400 MHz, Chloroform-d) δ 7.62-7.48 (m, 4H), 7.35 (t, J=7.6 Hz, 2H), 7.31-7.12 (m, 3H), 6.51 (d, J=6.8 Hz, 1H), 6.36-6.18 (m, 1H), 5.29 (s, 1H), 5.00-4.86 (m, 1H), 4.67 (s, 2H), 4.60 (d, J=9.3 Hz, 1H), 3.07-2.73 (m, 6H), 2.02-1.84 (m, 4H), 1.68-1.51 (m, 6H), 1.47 (s, 9H), 1.45-1.38 (m, 2H), 1.16 (s, 2H), 0.89-0.81 (m, 12H), 0.80 (d, J=6.7 Hz, 3H). m/z calcd. for C$_{42}$H$_{63}$N$_5$O$_7$S=781.44. Found [M+H]$^+$=782.63.

Step 8: (S,E)-N-((4-(1-((R)-2-((R)-2-((((9H-Fluoren-9-yl)methoxy)carbonyl)amino)-3-methylbutanamido)-5-ureidopentanamido)cyclopropyl)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound P-3)

The title compound was prepared according to General Procedure 4 from Compound P-2 and Fmoc-Val-Cit-OH. m/z calcd. for C$_{68}$H$_{93}$N$_9$O$_{12}$S=1259.67. Found [M+H]$^+$=1261.11, [M+Na]$^+$=1283.06, [M-Boc+2H]$^+$=1160.97. R$_f$=0.54 (5% MeOH/(2% AcOH/EtOAc)).

Step 9: (S,E)-N-((4-(1-((R)-2-((R)-2-Amino-3-methylbutanamido)-5-ureidopentanamido)cyclopropyl)benzyl)sulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound P-4)

The title compound was prepared according to General Procedure 5 from Compound P-3. m/z calcd. for C$_{53}$H$_{83}$N$_9$O$_{10}$S=1037.60. Found [M+H]$^+$=1038.90, [M-Boc+2H]$^+$=938.78. R$_f$=0.1 (25% MeOH/CH$_2$Cl$_2$).

Step 10: (S,E)-N-(4-(1-((R)-2-((R)-2-(6-(2,5-Dioxo-2,5-dihydro-1H-pyrrol-1-yl)hexanamido)-3-methylbutanamido)-5-ureidopentanamido)cyclopropyl)benzylsulfonyl)-2,5-dimethyl-4-((S)—N,3,3-trimethyl-2-((S)-3-methyl-2-((tert-butoxycarbonyl)(methyl)amino)-3-phenylbutanamido)butanamido)hex-2-enamide (Compound P-5)

The title compound was prepared according to General Procedure 6 from Compound P-4 and MC-NHS. m/z calcd. for C$_{63}$H$_{94}$N$_{10}$O$_{13}$S=1230.67. Found [M+H]$^+$=1232.11, [M+Na]$^+$=1254.09, [M-Boc+2H]$^+$=1132.01. R$_f$=0.44 (10% (5% AcOH/MeOH)/CH$_2$Cl$_2$).

Step 11: (S,E)-N-(4-(1-((R)-2-((R)-2-(6-(2,5-Dioxo-2,5-dihydro-1H-pyrrol-1-yl)hexanamido)-3-methylbutanamido)-5-ureidopentanamido)cyclopropyl)benzylsulfonyl)-2,5-dimethyl-4-((S)—N,3,3-trimethyl-2-((S)-3-methyl-2-(methylamino)-3-phenylbutanamido)butanamido)hex-2-enamide The title compound was prepared according to General Procedure 7 from Compound P-5. m/z calcd. for C$_{58}$H$_{86}$N$_{10}$O$_{11}$S=1130.62. Found [M+H]$^+$=1131.95, [(M+2H)/2]$^{2+}$=566.69.

Example 2.24: (S,E)-N-(4-(1-((R)-2-((R)-2-(6-(2,5-Dioxo-2,5-dihydro-1H-pyrrol-1-yl)hexanamido)-3-methylbutanamido)-5-ureidopentanamido)cyclopropyl)phenylsulfonyl)-2,5-dimethyl-4-((S)—N,3,3-trimethyl-2-((S)-3-methyl-2-(methylamino)-3-phenylbutanamido)butanamido)hex-2-enamide (Compound Q)

Step 1: 1-Phenylcyclopropanamine

The title compound was prepared as described in Bertus, P., Szymoniak, J. J. Org. Chem., 2003, 68, 7133-7136 from benzonitrile (1.0 mL, 9.7 mmol) to give 270 mg (21%). $^1$H NMR (400 MHz, Chloroform-d) δ 7.44-7.28 (m, 4H), 7.27-7.15 (m, 1H), 1.18-1.06 (m, 2H), 1.07-0.95 (m, 2H). R$_f$=0.28 (5% (5% NH$_4$OH/MeOH)/CH$_2$Cl$_2$).

Step 2: 2,2,2-Trifluoro-N-(1-phenylcyclopropyl)acetamide

To a stirred solution of 1-phenylcyclopropanamine (270 mg, 2.03 mmol, 1.0 eq) in dioxane (5 mL), was added trifluoroacetic anhydride (0.310 mL, 2.23 mmol, 1.1 eq). After 5 min, TLC indicated complete conversion of starting material. The mixture was concentrated, then coevaporated once with CH$_2$Cl$_2$ and once with toluene to yield the title compound (453 mg, 97%) as a flaky white powder. $^1$H NMR (400 MHz, Chloroform-d) δ 7.47-7.15 (m, 5H), 6.88 (s, 1H), 1.65 (s, 4H). m/z calcd. for C$_{11}$H$_{10}$F$_3$NO=229.07. Found [M+H]$^+$=230.14. R$_f$=0.82 (5% (5% NH$_4$OH/MeOH)/CH$_2$Cl$_2$).

Step 3: 2,2,2-Trifluoro-N-(1-(4-sulfamoylphenyl)cyclopropyl)acetamide

To stirred chlorosulfonic acid (0.78 mL, 11.8 mmol, 6.0 eq) at 0° C., was added solid 2,2,2-trifluoro-N-(1-phenylcyclopropyl)acetamide (450 mg, 1.96 mmol, 1.0 eq) portionwise, keeping the temperature low. After complete addition, the mixture was heated to 50° C. After 1 minute, gas evolution ceased, and the reaction was allowed to cool. The mixture was added slowly to a beaker of ice, being mindful of splattering. The solid that was left in the ice was filtered off. This solid was dried in vacuo and then taken up in THF (4 mL). Concentrated $NH_4OH$ (0.44 mL, 7.85 mmol, 4.0 eq) was added, turning the solution green-black. After 2 min, TLC indicated complete consumption of the sulfonylchloride intermediate. 2M HCl was added until the color faded, then the mixture was extracted three times with EtOAc, washed once with saturated $NaHCO_3$, once with saturated brine, dried over sodium sulfate, and concentrated to a flaky solid. The crude material was purified by flash chromatography to yield the title compound (235 mg, 39%) as a white solid. $^1H$ NMR (400 MHz, DMSO-$d_6$) δ 10.28 (s, 1H), 7.76 (d, J=8.5 Hz, 2H), 7.32 (d, J=8.1 Hz, 2H), 7.31 (s, 2H), 1.42-1.35 (m, 2H), 1.35-1.27 (m, 2H). m/z calcd. for $C_{11}H_{11}F_3N_2O_3S$=308.04. Found [M+H]$^+$=309.07. $R_f$=0.27 (50% EtOAc/Hex).

Step 4: tert-Butyl (S)-1-((S)-1-(((S,E)-2,5-Dimethyl-6-oxo-6-(4-(1-(2,2,2-trifluoroacetamido)cyclopropyl)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate The title compound was prepared according to General Procedure 2 from 2,2,2-trifluoro-N-(1-(4-sulfamoylphenyl)cyclopropyl)acetamide and Boc-HTI-286-OH. $^1H$ NMR (400 MHz, Chloroform-d) δ 8.51 (s, 1H), 8.08 (d, J=8.6 Hz, 2H), 7.42-7.32 (m, 2H), 7.32-7.23 (m, 2H), 7.23-7.10 (m, 3H), 6.46 (d, J=9.0 Hz, 1H), 6.17-6.08 (m, 1H), 5.29 (s, 1H), 4.97-4.76 (m, 1H), 4.56 (d, J=8.8 Hz, 1H), 2.90 (d, J=10.4 Hz, 6H), 2.01-1.79 (m, 4H), 1.62 (s, 3H), 1.53 (s, 3H), 1.49 (s, 4H), 1.46 (s, 9H), 0.86 (t, J=6.9 Hz, 3H), 0.81 (d, =6.8 Hz, 3H), 0.77 (s, 9H). m/z calcd. for $C_{43}H_{60}F_3N_5O_8S$=863.41. Found [M+H]$^+$=864.56, [M+Na]$^+$=886.52, [M-Boc+2H]$^+$=764.44. $R_f$=0.34 (50% (2% AcOH/EtOAc)/Hex).

Step 5: tert-Butyl (S)-1-((S)-1-(((S,E)-6-(4-(1-Aminocyclopropyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate The title compound was prepared according to General Procedure 3 in dioxanes from compound tert-butyl (S)-1-((S)-1-(((S,E)-2,5-dimethyl-6-oxo-6-(4-(1-(2,2,2-trifluoroacetamido)cyclopropyl)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate. $^1H$ NMR (400 MHz, Methanol-d4) δ 7.97 (d, J=8.5 Hz, 2H), 7.52 (d, J=8.5 Hz, 2H), 7.51-7.43 (m, 2H), 7.32 (t, J=7.5 Hz, 2H), 7.20 (t, J=8.4 Hz, 1H), 6.55 (d, J=9.0 Hz, 1H), 5.17 (s, 1H), 5.03-4.94 (m, 1H), 4.70 (d, J=9.0 Hz, 1H), 2.94 (s, 3H), 2.88 (s, 3H), 1.94-1.89 (m, 1H), 1.80 (s, 3H), 1.53 (s, 3H), 1.51 (s, 3H), 1.43 (s, 9H), 1.40-1.37 (m, 21H), 1.36-1.32 (m, 2H), 0.87 (d, J=6.0 Hz, 12H), 0.82-0.76 (m, 3H). m/z calcd. for $C_{41}H_{61}N_5O_7S$=767.43. Found [M+H]$^+$=768.51 [M-Boc+2H]$^+$=668.38. $R_f$=0.32 (10% EtOAc/Hex).

Step 6: tert-Butyl ((S)-1-(((S)-1-(((S,E)-6-(4-(1-((R)-2-((R)-2-((((9H-Fluoren-9-yl)methoxy)carbonyl)amino)-3-methylbutanamido)-5-ureidopentanamido)cyclopropyl)phenylsulfonamido)-2,5-dimethyl-6-oxohex-4-en-3-yl)(methyl)amino)-3,3-dimethyl-1-oxobutan-2-yl)amino)-3-methyl-1-oxo-3-phenylbutan-2-yl)(methyl)carbamate (Compound Q-1)

The title compound was prepared according to General Procedure 4 from tert-butyl (S)-1-((S)-1-(((S,E)-6-(4-(1-aminocyclopropyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl (methyl)carbamate and Fmoc-Val-Cit-OH. m/z calcd. for $C_{67}H_{91}N_9O_{12}S$=1245.65. Found [M+H]$^+$=1246.89, [M+Na]$^+$=1268.88, [M-Boc+2H]$^+$=1146.82. $R_f$=0.52 (5% MeOH/(2% AcOH/EtOAc)).

Step 7: tert-Butyl (S)-1-((S)-1-(((S,E)-6-(4-(1-((R)-2-((R)-2-Amino-3-methylbutanamido)-5-ureidopentanamido)cyclopropyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate (Compound Q-2)

The title compound was prepared according to General Procedure 5 from Compound Q-1. m/z calcd. for $C_{52}H_{81}N_9O_{10}S$=1023.58. Found [M+H]$^+$=1024.72, [M-Boc+2H]$^+$=924.66.

Step 8: tert-Butyl (S)-1-((S)-1-(((S,E)-6-(4-(1-((R)-2-((R)-2-(6-(2,5-Dioxo-2,5-dihydro-1H-pyrrol-1-yl)hexanamido)-3-methylbutanamido)-5-ureidopentanamido)cyclopropyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate The title compound was prepared according to General Procedure 6 from tert-butyl (S)-1-((S)-1-(((S,E)-6-(4-(1-((R)-2-((R)-2-amino-3-methylbutanamido)-5-ureidopentanamido)cyclopropyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl (methyl)carbamate and MC-NHS. m/z calcd. for $C_{62}H_{92}N_{10}O_{13}S$=1216.66. Found [M+H]$^+$=1217.89, [M+Na]+=1239.94, [M-Boc+2H]$^+$=1117.82. $R_f$=0.39 (10% (5% AcOH/MeOH)/$CH_2Cl_2$).

Step 9: (S,E)-N-(4-(1-((R)-2-((R)-2-(6-(2,5-Dioxo-2,5-dihydro-1H-pyrrol-1-yl)hexanamido)-3-methylbutanamido)-5-ureidopentanamido)cyclopropyl)phenylsulfonyl)-2,5-dimethyl-4-((S)—N,3,3-trimethyl-2-((S)-3-methyl-2-(methylamino)-3-phenylbutanamido)butanamido)hex-2-enamide The title compound was prepared according to General Procedure 7 from compound tert-butyl (S)-1-((S)-1-(((S,E)-6-(4-(1-((R)-2-((R)-2-(6-(2,5-Dioxo-2,5-dihydro-1H-pyrrol-1-yl)hexanamido)-3-methylbutanamido)-5-ureidopentanamido)cyclopropyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl (methyl)carbamate. m/z calcd. for $C_{57}H_{84}N_{10}O_{11}S$=1116.60. Found [M+H]$^+$=1117.77, [(M+2H)/2]$^{2+}$=559.56.

Example 2.25: 2,5-Dioxopyrrolidin-1-yl 6-((R)-1-((R)-1-(4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)phenylamino)-1-oxo-5-ureidopentan-2-ylamino)-3-methyl-1-oxobutan-2-ylamino)-6-oxohexanoate (Compound KK)

Step 1:
2,2,2-Trifluoro-N-(4-sulfamoylphenyl)acetamide

The title compound was synthesized from commercially available sulfanilamide and TFAA using General Procedure 1.

Step 2: tert-Butyl (S)-1-((S)-1-(((S,E)-2,5-Dimethyl-6-oxo-6-(4-(2,2,2-trifluoroacetamido)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate The title compound was synthesized from Boc-HTI-286-OH and 2,2,2-trifluoro-N-(4-sulfamoylphenyl)acetamide according to General Procedure 2. $^1$H NMR (400 MHz, Methanol-d$_4$) δ 8.14-8.03 (m, 2H), 7.98-7.83 (m, 3H), 7.47 (d, J=7.6 Hz, 2H), 7.32 (d, J=7.6 Hz, 2H), 7.20 (q, J=7.4, 6.2 Hz, 2H), 6.44 (d, J=9.1 Hz, 1H), 5.16 (s, 1H), 4.68 (d, J=9.0 Hz, 1H), 3.08-2.95 (m, 3H), 2.87 (d, J=6.4 Hz, 3H), 2.01 (m, 6H), 1.80 (d, J=11.7 Hz, 3H), 1.62 (d, J=6.4 Hz, 1H), 1.52-1.36 (m, 14H), 1.26 (m, 1H), 0.98-0.72 (m, 15H). C$_{40}$H$_{56}$F$_3$N$_5$O$_8$S calcd. [M+H]$^+$ 824.38; found [M+Na]$^+$ 846.43; [M+H]$^+$ 824.40; [M-Boc+H]+724.34. MS found; 846.43 [M+Na]$^+$; 824.40 [M+H]$^+$; 724.34 [M-Boc+H]$^+$.

Step 3: tert-Butyl ((S)-1-(((S)-1-(((S,E)-6-(4-((R)-2-((R)-2-((tert-Butoxycarbonyl)amino)-3-methylbutanamido)-5-ureidopentanamido)phenylsulfonamido)-2,5-dimethyl-6-oxohex-4-en-3-yl)(methyl)amino)-3,3-dimethyl-1-oxobutan-2-yl)amino)-3-methyl-1-oxo-3-phenylbutan-2-yl)(methyl)carbamate The title compound was synthesized from tert-butyl (S)-1-((S)-1-(((S,E)-2,5-dimethyl-6-oxo-6-(4-(2,2,2-trifluoroacetamido)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate by first liberation of the aniline from the trifluoroacetanilide according to General Procedure 4, followed by coupling with Boc-Val-Cit-OH (synthesized according to US2010/0233190) according to General Procedure 5. A small sample was deprotected according to General Procedure 9 to resolve rotamers and facilitate NMR analysis. $^1$H NMR (400 MHz, Methanol-d$_4$) δ 8.00 (d, J=8.9 Hz, 2H), 7.83 (d, J=8.9 Hz, 2H), 7.55 (d, J=7.8 Hz, 2H), 7.47 (t, J=7.7 Hz, 2H), 7.38 (t, J=7.2 Hz, 1H), 6.51-6.44 (m, 1H), 5.05-4.97 (m, 1H), 4.64 (dd, J=9.3, 4.7 Hz, 1H), 4.35 (s, 1H), 3.77-3.70 (m, 1H), 3.30-3.20 (m, 1H), 3.21-3.08 (m, 4H), 2.51 (s, 3H), 2.30-2.20 (m, 1H), 2.13-1.99 (m, 1H), 1.99-1.71 (m, 4H), 1.72-1.54 (m, 2H), 1.47 (s, 3H), 1.37 (s, 3H), 1.16-0.99 (m, 15H), 0.91 (t, J=6.2 Hz, 6H). C$_{54}$H$_{85}$N$_9$O$_{12}$S calcd. [M+H]$^+$ 1083.60; found [M+Na]$^+$ 1106.8.

Step 4: 2,5-Dioxopyrrolidin-1-yl 6-((R)-1-((R)-1-(4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)phenylamino)-1-oxo-5-ureidopentan-2-ylamino)-3-methyl-1-oxobutan-2-ylamino)-6-oxohexanoate To a solution of tert-butyl ((S)-1-(((S)-1-(((S,E)-6-(4-((R)-2-((R)-2-((tert-butoxycarbonyl)amino)-3-methylbutanamido)-5-ureidopentanamido)phenylsulfonamido)-2,5-dimethyl-6-oxohex-4-en-3-yl)(methyl)amino)-3,3-dimethyl-1-oxobutan-2-yl)amino)-3-methyl-1-oxo-3-phenylbutan-2-yl)(methyl)carbamate (0.05 g, 0.046 mmol) in dichloromethane (2 mL) was added trifluoroacetic acid (1 mL). The reaction was monitored by HPLC-MS and upon completion, evaporated under reduced pressure and twice concentrated from toluene to remove excess TFA. The resulting residue was dissolved in N,N-dimethylformamide (2 mL). The solution was stirred, cooled to 0° C. and di-isopropylethylamine (0.008 mL, 1 equiv) and bis-N-Hydroxysuccinimidyl adipate (prepared according to Mishra et al., Molecular Pharmaceutics, 10, (10), 3903-3912, 2013, 0.062 g, 4 equiv) were added. The reaction was allowed to stir overnight at which time HPLC-MS indicated that the starting peptide had been converted to new product. The reaction was concentrated under reduced pressure, dissolved in acetone and the resulting solution purified by prep-scale HPLC to afford the title compound (0.0145 g) as a white powder after lyophilization. $^1$H NMR (400 MHz, DMSO-d$_6$ with D$_2$O exchange) δ 8.68 (d, J=8.1 Hz, 1H), 7.92-7.83 (m, 2H), 7.80 (d, J=8.8 Hz, 2H), 7.47 (d, J=7.8 Hz, 2H), 7.41 (t, J=7.6 Hz, 2H), 7.31 (dd, J=8.3, 6.1 Hz, 1H), 6.49 (d, J=9.1 Hz, 1H), 4.86 (t, J=9.9 Hz, 1H), 4.75 (d, J=8.1 Hz, 1H), 4.37 (d, J=7.3 Hz, 2H), 4.17 (d, J=6.9 Hz, 1H), 3.10-2.87 (m, 5H), 2.80 (s, 4H), 2.71-2.60 (m, 2H), 2.37-2.11 (m, 5H), 2.01-1.92 (m, 2H), 1.69 (s, 3H), 1.64-1.58 (m, 5H), 1.36 (s, 5H), 1.22 (s, 3H), 0.95 (s, 9H), 0.81 (m, 12H). C$_{54}$H$_{80}$N$_{10}$O$_{13}$S calcd. m/z=1108.56 found [M+H]$^+$=1109.54.

Example 3: Preparation of T-L$^1$-P$^1$

Example 3.1: General Procedure 8—Trifluoroacetamide Installation

To a stirred suspension of the amine in 1,4-dioxane was added trifluoroacetic anhydride (1.1 equivalents). The reaction mixture transitioned from a suspension to a solution and back to a suspension again. The progress of the reaction was monitored by TLC and/or HPLC-MS for completion. Once the starting material was fully consumed, the reaction was diluted with hexanes or diethyl ether, filtered on a Buchner funnel and the resulting solids were dried under reduced pressure to give the pure trifluoroacetamide.

Example 3.2: General Procedure 9—DCC/DMAP Mediated N-Acyl Sulfonamide Formation

To a stirred solution of the acid in dichloromethane was added a solution of the sulfonamide (1.3 equivalents, in dichloromethane, N,N-dimethylformamide, or a mixture thereof, as necessary). Dicyclohexylcarbodiimide (1.2 equivalents) was added and subsequently N,N-dimethylaminopyridine (1.2 equivalents). Reaction course was monitored by HPLC-MS (typically 16 h) and excess by-products could be precipitated by the addition of diethyl ether. Solids were removed by filtration and washed with 1:1 diethyl ether/dichloromethane. The combined organic layers were concentrated, and the residue was purified by silica gel chromatography or optionally prep-HPLC to give the desired N-acyl sulfonamide.

Example 3.3: General Procedure 10—General Saponification

To a solution of the trifluoroacetamide or ester containing construct in 1,4-dioxane or methanol was added lithium hydroxide (10 equivalents) and water (10% v/v). The reaction was allowed to stir at room temperature or optionally heated to 50° C. Reaction course was monitored by HPLC-MS. Upon completion, volatiles were removed under reduced pressure, the aqueous layer was pH adjusted if necessary and washed successively with dichloromethane or ethyl acetate. The organic phases were pooled, dried over $MgSO_4$, filtered and concentrated. The reaction product was either used "as is" or purified by silica gel chromatography as necessary.

Example 3.4: General Procedure 11—HATU Mediated Peptide Bond Formation

To a stirred solution of the carboxylic acid in a minimal amount of dichloromethane or N,N-dimethylformamide or mixture thereof, at 0° C. was added HATU (equivalents) and N,N-diisopropylethylamine (4 equivalents). Stirring was continued for a brief induction period (5-20 minutes) at which time the reaction was charged with a solution of the amine in dichloromethane. The reaction was allowed to warm to room temperature and monitored for progress by HPLC-MS. Upon completion, volatiles were removed under reduced pressure and the residual material was purified by silica gel chromatography or reverse phase HPLC to furnish amide in adequate purity.

Example 3.5: General Procedure 12—Boc Group Removal

To a solution of the Boc-protected construct in dichloromethane was added 10% v/v trifluoroacetic acid. Reaction course was monitored by HPLC-MS. Upon completion, all volatiles were removed under reduced pressure. The residual material was purified either by reverse phase HPLC, silica gel chromatography or precipitation from a mixture of cold methanol/dichloromethane/diethyl ether.

Example 3.6: General Procedure 13—Pd-Catalyzed Suzuki Cross Coupling

A suspension of aryl bromide, aryl (or alkenyl) boronic acid (1.5 eq), $Pd(OAc)_2$ (10 mol %), 2-(di-tert-butylphosphino)biphenyl (20 mol %), and $K_3PO_4$ (3 eq) in THF was stirred under $N_2$ at ambient temperature for 16 h (or 50° C. for 2 h). The resulting brown reaction mixture was dilute with ether and washed with 1 M NaOH (3×). The aqueous washes were combined and extracted with ether (2×). The organics were combined, dried over $MgSO_4$, filtered, concentrated in vacuo and purified via silica gel column chromatography (eluted with $MeOH/CH_2Cl_2$ mixtures) to afford the cross-coupled product.

Example 3.7: General Procedure 14—Cu-Catalyzed Ullman Cross Coupling (Methoxy Installation)

A mixture of aryl bromide, CuBr (20 mol %), NaOMe (20 eq, 4.9 M in MeOH), and EtOAc (1.5 eq) was stirred under $N_2$ at 95° C. for 16 h. The resulting mixture was diluted with $H_2O$ and poured into cold (0° C.) stirring 1 M citric acid. After stirring for 10 min, the mixture was extracted with EtOAc (4×). The organics were combined, washed with $H_2O$ (2×) and brine (1×), dried over $MgSO_4$, filtered and concentrated in vacuo. The product was used in the next step without further purification.

Example 3.8: General Procedure 15—Vinylogous Amino Ester Synthesis

The procedure for Weinreb amide synthesis, reduction and subsequent olefination thereof as described by Nieman J. A. et al. J. Nat. Prod. 2003, 66, 183-199 was employed to the desired commercially available amino acids with no modifications.

Example 3.9: General Procedure 16—Establishment of Boc-t-Leucine-(Me)-Vinylogous Amino Acid The vinylogous amino ester was deprotected and coupled to Boc-t-leucine according to procedures described by Nieman J. A. et al. J. Nat. Prod. 2003, 66, 183-199 with no modifications.

Example 3.10: General Procedure 17—Sulfonamide Formation from Alkyl Halide

To a suspension of the desired alkyl halide in 2:1 $H_2O$/EtOH was added sodium sulfite (1.2 equiv). The resulting mixture was heated to reflux for 6-24 h. The reaction was then cooled to room temperature, the solvents were removed at reduced pressure to remove ethanol and the product was precipitated. The sodium alkylsulfonate were filtered, collected and dried in vacuo. These solids were then suspended in dichloromethane and phosphorous pentachloride (2 equiv) was added with stirring. The resulting suspension was heated to reflux for 2 h and allowed to cool to room temperature. The reactions were then cooled to 0° C. and water was added dropwise to consume excess phosphorous pentachloride. The mixture was transferred to a separatory funnel and the organic phase was washed with brine, dried over $MgSO_4$, filtered and concentrated to give the desired sulfonyl chloride. The thusly derived chloride was subsequently dissolved in THF and added dropwise to a stirred aqueous solution of concentrated ammonium hydroxide at 0° C. Upon completion of the addition, the reaction was concentrated under reduced pressure and diluted with water and ethyl acetate. The organic phase was washed with brine, dried over $MgSO_4$, filtered and concentrated to give the desired sulfonamide in sufficient purity for further use.

Example 3.11: General Procedure 18—Sulfonamide Formation from Substituted Aryl Compounds To a stirred mixture of the desired aryl substituted compound in chloroform was added chlorosulfonic acid (4 equiv). The reaction was heated to 70° C. for 1 h and allowed to cool to room temperature. Thionyl chloride (2 equiv) was added and the reaction was again heated to 70° C. for 1 h. The contents of the reaction vessel were concentrated under reduced pressure to give an oil which was subsequently twice dissolved in toluene and concentrated under reduced pressure to remove residual acid. The remaining material was dissolved in THF and added dropwise to a concentrated, stirred solution of ammonium hydroxide at 0° C. Once the addition was complete, the reaction was concentrated under reduced pressure and the residue was partitioned between ethyl acetate and water. The organic phase was washed with brine, dried over $MgSO_4$, filtered and concentrated to give the desired phenylsulfonamide in adequate purity for further use.

Example 3.12: General Procedure
19—Sulfamamide Formation

The procedures used to generate the desired sulfamamides were adapted from Winum, J.-Y. et al., Org Lett, 2001, 3 (14), 2241-2243

Example 3.13: General Procedure 20—Preparation of MC-VC-PABC-Toxins ($L^1$-$P^1$)

The appropriate intermediate amine or aniline was taken up in DMF (~90 mg/mL), and to this was added 1-hydroxybenzotriazole hydrate (0.3 eq), then commercially obtained MC-VC-PABC-PNP (4-((R)-2-((R)-2-(6-(2,5-dioxo-2,5-dihydro-1H-pyrrol-1-yl)hexanamido)-3-methylbutanamido)-5-ureidopentanamido)benzyl 4-nitrophenyl carbonate) (1.3 eq) as described in Firestone, et al. U.S. Pat. No. 6,214,345 was added followed by pyridine (25 eq). The reaction was covered to protect from light and stirred at ambient temperature for 24 to 48 h. The reaction mixture could be purified by concentrating the mixture and performing flash chromatography directly on the crude, or alternatively, it could be diluted with DMSO to an appropriate volume and injected directly onto a preparatory HPLC to give the pure MC-VC-PABC-R construct.

All sulfonamides and sulfamamides or precursors to the materials used in the procedures below were purchased commercially and manipulated, if necessary, such that they were suitable for use. Specifically, General Procedures 8, 17, 18 and 19 were employed to manipulate commercially available starting materials unless otherwise noted below. Sulfamamide analogs of the N-acyl sulfonamide containing compounds disclosed herein may be synthesized by the artisan of reasonable skill based on the teachings herein and knowledge in the art, and are included within the scope of the invention.

Example 3.14: 3-Bromopropane-1-sulfonamide

To a stirred slurry of potassium bromide (1.904 g) in water (2.8 mL) was added 1,3-propanesultone. The reaction was heated to 60° C. with stirring for 1 h and allowed to cool to room temperature. Ethanol (~45 mL) was added with stirring and a precipitate formed. The suspension was filtered on a Buchner funnel and the solids were collected and dried at high vacuum over night to give potassium 3-bromopropane-1-sulfonate (2.90 g, 12.0 mmol) as a white solid. The above solid was added to a round bottom flask equipped with a stir bar. Phosphorous pentachloride (3.22 g, 1.3 equiv) was added in a single charge and the flask was gently shaken to mix the solids. A gas was observed to form and the solids became slightly molten. A singular drop of water was added to the mixture and a vigorous evolution of gas was observed, with more significant melting of the reaction mixture. The flask was submerged in an oil bath at 70° C. and the molten mixture manipulated to attempt to make it as uniform as possible. After 10 minutes of heating, the flask was allowed to cool to room temperature and was charged with ice (~60 mL) and diethyl ether (~80 mL) and stirred vigorously. The biphasic mixture was transferred to a separatory funnel, the organic layer washed with brine, then dried over $MgSO_4$, filtered and concentrated to a total volume of ~25 mL. The ethereal layer was added to a 100 mL round bottom flask, a stir bar was added and the flask was cooled to 0° C. in an ice bath. Ammonia ($NH_4OH$, 28% aq, 5 mL) was added with vigorous stirring and an emulsion formed. After the emulsion had subsided, brine (~20 mL) and diethyl ether (~20 mL) were added and the mixture transferred to a separatory funnel. The organic phase was separated, dried over $MgSO_4$ and concentrated to give the title compound as a stiff syrup that solidified on standing (0.782 g). $^1$H NMR (400 MHz, DMSO-$d_6$) δ (ppm)=2.24 (p, 2H, J=6.5 Hz), 3.12 (t, 2H, J=6.5 Hz), 3.66 (t, 2H, J=6.5 Hz), 6.91 (s, 2H).

Example 3.15: 3-(Tritylthio)propane-1-sulfonamide

To a stirred solution of triphenylmethanethiol (0.276 g) in N,N-dimethyl formamide at 0° C. was added sodium hydride (0.04 g, 1 equiv). After effervescence had ceased, 3-bromopropane-1-sulfonamide (0.100 g, 0.5 equiv) was added as a solid in a single portion and the reaction was allowed to warm to room temperature. Progress of the reaction was monitored by HPLC-MS and TLC (40% EtOAc in hexanes). After 2 h, the reaction was quenched with water (~0.5 mL) and concentrated on a rotovap at high-vacuum. The resulting oil was partitioned between ethyl acetate and brine, transferred to a separatory funnel and the organic phase was washed with brine, dried over $MgSO_4$, concentrated and purified by flash chromatography (5-50% EtOAc in hexanes) to give the title compound (0.135 g) as a white crystalline solid. $^1$H NMR (400 MHz, $CD_3OD$) δ (ppm)=1.77-1.85 (m, 2H), 2.35 (t, 2H, J=6.5 Hz), 2.95-2.99 (t, 2H, J=6.5 Hz), 7.22-7.33 (m, 9H), 7.40-7.45 (m, 6H).

Example 3.16: (6S,9S,12S,E)-9-tert-Butyl-12-isopropyl-2,2,5,11,14-pentamethyl-4,7,10-trioxo-6-(2-phenylpropan-2-yl)-3-oxa-5,8,11-triazapentadec-13-en-15-oic Acid Synthesized as per Nieman J. A. et al. J. Nat. Prod. 2003, 66, 183-199.

Example 3.17 (S,E)-N-(3-Mercaptopropylsulfonyl)-2,5-dimethyl-4-((S)—N,3,3-trimethyl-2-((S)-3-methyl-2-(methylamino)-3-phenylbutanamido)butanamido)hex-2-enamide (Compound A)

Example 3.17 was synthesized from Examples 3.15 and 3.16 according to General Procedures 9 and 12 with the inclusion of tri-isoproypsilane (2 equiv) to Procedure 14. $^1$H NMR (400 MHz, $CD_3OD$) δ (ppm)=0.88 (3H, d, J=6.2 Hz), 0.94 (3H, d, J=6.2 Hz), 1.08 (s, 9H), 1.40 (s, 3H), 1.48 (s, 3H), 1.94 (d, 3H, J=1.29 Hz), 2.03-2.16 (m, 3H), 2.41 (s, 3H), 2.67 (t, 2H, J=9.76 Hz), 3.16 (s, 3H), 3.46-3.50 (m, 2H), 4.08 (br s, 1H), 4.94 (s, 1H), 5.07 (t, 1H, J=10.0 Hz), 6.59 (d, 1H, J=9.5 Hz), 7.32-7.37 (m, 1H), 7.41-7.48 (m, 2H), 7.50-7.57 (m, 2H).

Methods described above were used to generate the following analogous compounds.

Example 3.18: 2,2'-Disulfanediyldiethanesulfonamide

Synthesized as described by Lemaire, H. and Rieger, M in J. Org. Chem., 1961, 1330-1331.

Example 3.19 (S,E)-N-(2-Mercaptoethylsulfonyl)-2,5-dimethyl-4-((S)—N,3,3-trimethyl-2-((S)-3-methyl-2-(methylamino)-3-phenylbutanamido)butanamido)hex-2-enamide (Compound B)

To a solution of (6S,9S,12S,E)-9-tert-butyl-12-isopropyl-2,2,5,11,14-pentamethyl-4,7,10-trioxo-6-(2-phenylpropan- 2-yl)-3-oxa-5,8,11-triazapentadec-13-en-15-oic acid (0.138 g, 2.4 equiv) in dichloromethane (4 mL) was added 2,2'-disulfanediyldiethanesulfonamide (0.028 g), di-isopropylcarbodiimide (0.044 mL, 2.4 equiv) and N,N-dimethylpyridine (0.034 g, 2.8 equiv). Stirring was continued for 16 h at which point TLC analysis (5% MeOH (with 5% AcOH) in 70/30 $CH_2Cl_2$/Hexanes) indicated complete consumption of the disulfanedisulfonamide. The reaction was diluted with hexanes (~5 mL), filtered to remove solids, concentrated and the resultant oil purified by flash chromatography. The chromatographically purified materials was then dissolved in dichloromethane (3 mL), a stir bar was added, then trifluoroacetic acid (0.60 mL) and tri-isopropylsilane (0.20 mL). The mixture immediately went yellow, with the color fading over 5 minutes and conversion of the material to the desired product was monitored by HPLC-MS. Upon complete conversion, the reaction was concentrated to dryness and the residue purified by flash chromatography (0-15% MeOH (containing 5% AcOH) in 80/20 $CH_2Cl_2$/hexanes). HPLC-MS showed this isolate to be a mixture of free thiol and disulfide. $^1$H NMR (400 MHz, $CD_3OD$) δ (ppm)=0.88 (3H, d, J=6.2 Hz), 0.93 (3H, d, J=6.2 Hz), 1.07 (s, 9H), 1.40 (s, 3H), 1.47 (s, 3H), 1.91-2.05 (m, 5H), 2.32 (s, 3H), 2.67 (t, 2H, J=9.76 Hz), 3.07-3.18 (m, 5H), 3.52-3.59 (m, 2H), 3.85 (s, 1H), HH 4.08 (br s, 1H), 4.93 (s, 1H), 5.09 (t, 1H, J=10.0 Hz), 6.76 (d, 1H, J=9.5 Hz), 7.29-7.35 (m, 1H), 7.39-7.46 (m, 2H), 7.49-7.55 (m, 2H). $C_{29}H_{48}N_4O_5S_2$ calcd. $[M+H]^+$=598.15 amu; found m/z=598.16.

Example 3.20:
4-(Tritylthiomethyl)benzenesulfonamide

To a stirred solution of triphenylmethanethiol (0.276 g, 2 equiv) in N,N-dimethylformamide (3 mL) at 0° C. was added sodium hydride (60% w/w dispersion in mineral oil, 0.04 g, 2 equiv). When the effervescence had ceased, 4-(bromomethyl)benzenesulfonamide (0.125 g, 1 equiv) was added in a single portion and the reaction was allowed to warm to room temperature. HPLC-MS at 20 minutes indicated that conversion was complete. The reaction was quenched with acetic acid (~0.2 mL), concentrated to dryness in vacuo and the subsequent residue partitioned between ethyl acetate and brine. The organic layer was separated, dried over $MgSO_4$, filtered, concentrated and purified by flash chromatography (0-50% ethyl acetate in hexanes). Fractions containing the desired material were concentrated to dryness to furnish the desired compound as a colorless solid (0.200 g). $^1$H NMR (400 MHz, DMSO-$d_6$) δ (ppm)=3.38 (s, 2H), 7.24-7.35 (m, 7H), 7.36-7.44 (m, 12H), 7.67-7.73 (m, 2H).

Example 3.21 (S,E)-N-(4-(Mercaptomethyl)phenylsulfonyl)-2,5-dimethyl-4-((S)—N,3,3-trimethyl-2-((S)-3-methyl-2-(methylamino)-3-phenylbutanamido)butanamido)hex-2-enamide (Compound C)

Title compound prepared from Examples 3.16 and 3.20 according to General Procedures 9 and 12 $^1$H NMR (400 MHz, $CD_3OD$) δ (ppm)=0.88 (d, 3H, J=6.2 Hz), 0.91 (d, 3H, J=6.2 Hz), 1.06 (s, 9H), 1.38 (s, 3H), 1.47 (s, 3H), 1.86 (s, 3H), 1.99-2.05 (m, 1H), 2.41 (s, 3H), 2.67 (t, 2H, J=9.76 Hz), 3.14 (s, 3H), 3.80 (s, 2H), HH 4.10 (br s, 1H), 4.93 (s, 1H), 5.00 (t, 1H, J=10.0 Hz), 6.54 (d, 1H, J=9.5 Hz), 7.30-7.51 (m, 5H), 7.52-7.58 (m, 2H), 7.90-7.97 (m, 2H). $C_{34}H_{50}N_4O_5S_2$ calcd. $[M+H]^+$=659.25 amu; found m/z=659.37.

Example 3.22 (S,E)-2,5-Dimethyl-N-tosyl-4-((S)—N,3,3-trimethyl-2-((S)-3-methyl-2-(methylamino)-3-phenylbutanamido)butanamido)hex-2-enamide (Compound D)

Title compound was prepared from Example 3.16 and tosylsulfonamide using General Procedures 9 and 12. $^1$H NMR (400 MHz, $CD_3OD$) δ (ppm)=0.88-0.94 (m, 6H), 1.06 (s, 9H), 1.35 (s, 3H), 1.45 (s, 3H), 1.86 (s, 3H), 2.02-2.11 (m, 1H), 2.44 (s, 3H), 2.51 (s, 3H), 3.17 (s, 3H), HH 4.35 (s, 1H), 4.89-4.99 (m, 2H), 6.48 (d, 1H, J=9.5 Hz), 7.30-7.43 (m, 4H), 7.43-7.50 (m, 2H), 7.51-7.57 (m, 2H). $C_{34}H_{50}N_4O_5S$ calcd. $[M+H]^+$=627.15 amu; found m/z=627.31.

Example 3.23 (S,E)-2,5-dimethyl-N-(methylsulfonyl)-4-((S)—N,3,3-trimethyl-2-((S)-3-methyl-2-(methylamino)-3-phenylbutanamido)butanamido)hex-2-enamide (Compound E)

Title compound was prepared from Example 3.16 and methanesulfonamide using General Procedures 9 and 12. $^1$H NMR (400 MHz, $CD_3OD$) δ (ppm)=0.87-0.98 (m, 6H), 1.09 (s, 9H), 1.40 (s, 3H), 1.49 (s, 3H), 1.97 (s, 3H), 2.03-2.13 (m, 1H), 2.52 (s, 3H), 2.67 (t, 2H, J=9.76 Hz), 3.18 (s, 3H), 3.31 (s, 3H), 4.38 (s, 1H), 4.94 (d, 1H, J=8.2 Hz), 5.07 (t, 1H, J=10.0 Hz), 6.54 (d, 1H, J=9.5 Hz), 7.30-7.40 (m, 1H), 7.40-7.51 (m, 2H), 7.51-7.59 (m, 2H). $C_{28}H_{46}N_4O_5S$ calcd. $[M+H]^+$=551.30 amu; found m/z=551.34.

Example 3.24 (S,E)-2,5-Dimethyl-4-((S)—N,3,3-trimethyl-2-((S)-3-methyl-2-(methylamino)-3-phenylbutanamido)butanamido)hex-2-enoic Acid (Compound F)

The title compound was synthesized using methods as described by Nieman et al. in J. Nat. Prod. 2003, 66, 183-199.

Example 3.25: (S,E)-N-(Mesitylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and mesitylsulfonamide using General Procedures 9 and 12. $^1$H NMR (400 MHz, Methanol-$d_4$) δ 7.60-7.55 (m, 2H), 7.47 (m, 2H), 7.37 (m, 1H), 7.03 (s, 2H), 6.50 (d, J=6 Hz, 1H), 5.06-4.91 (m, 3H), 4.34 (s, 1H), 3.17 (s, 3H), 2.68 (s, 6H), 2.51 (s, 3H), 2.31 (s, 3H), 2.07 (m, 6.6 Hz, 2H), 1.87 (s, 3H), 1.48 (s, 3H), 1.36 (s, 3H), 1.09-1.04 (m, J=16.8 Hz, 10H), 0.92 (t, J=6.3 Hz, 6H). $C_{36}H_{54}N_4O_5S$ calcd. m/z=654.38 found $[M+H]^+$=655.03.

Example 3.26: (S,E)-2,5-Dimethyl-N-(4-(trifluoromethoxy)phenylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 4-trifluoromethoxyphenylsulfonamide using General Procedures 9 and 12. $^1$H NMR (400 MHz, Methanol-$d_4$) δ 8.16 (dd, J=8.7, 1.4 Hz, 1H), 7.69-7.28 (m, 4H), 6.52 (d, J=9.2 Hz, 1H), 5.02-4.95 (m, 1H), 4.92 (s, 0H), 4.35 (s, 1H), 3.17 (s, 3H), 2.51 (s, 3H), 2.05 (ddd, J=15.9, 10.9, 3.7 Hz, 1H), 1.87 (s, 3H), 1.47 (s, 3H), 1.36 (s, 1H), 1.07 (s, 4H), 0.91 (t, J=6.1 Hz, 3H). $C_{34}H_{47}F_3N_4O_6S$ calcd. m/z=696.32 found $[M+H]^+$=697.26.

Figure 7:
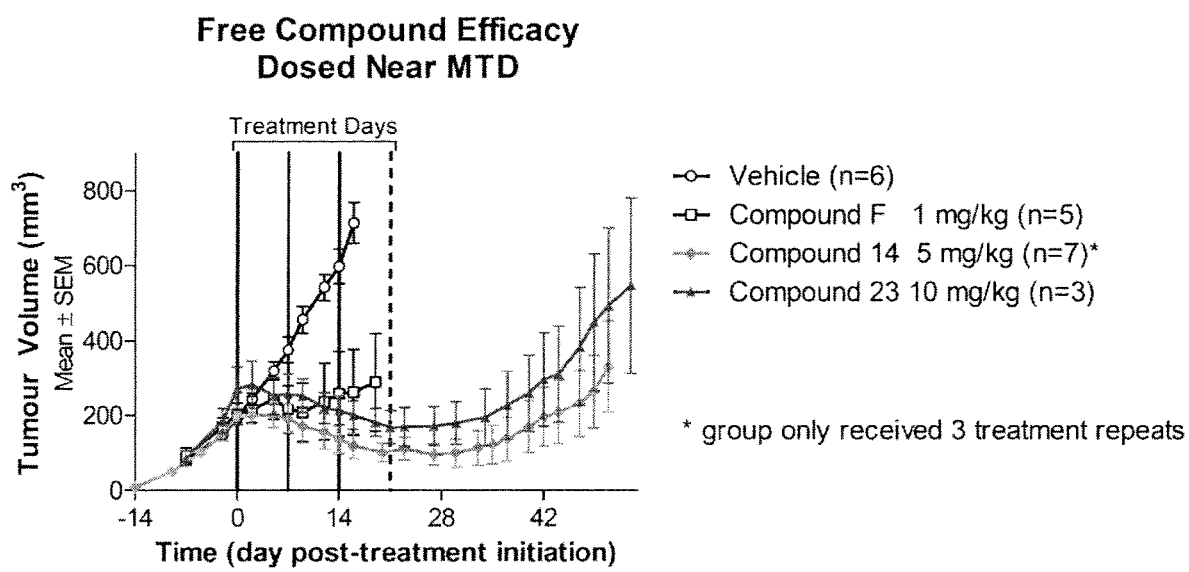
FIG. 7 shows the in vivo results of administration of Compound F, Compound 14, or Compound 23 on tumor volume in female athymic nude mice with established tumors.
Figure 8:
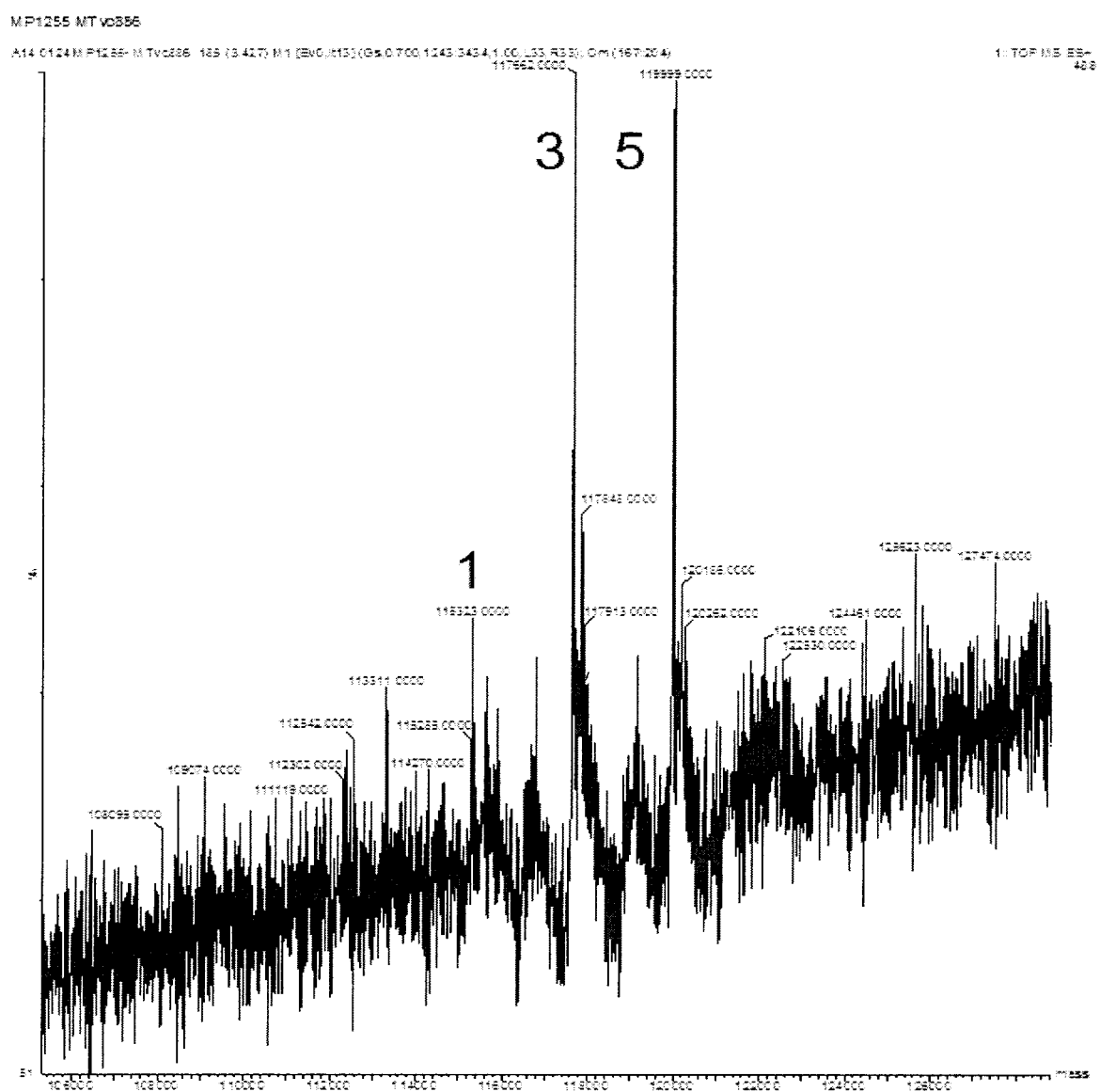
FIG. 8: shows the SEC-UPLC-QTof-MS MaxEnt1 processed intact mass of VAR2-Compound O. The MS signals at 115323 Da, 117662 Da and 119999 Da are consistent with conjugation of 1, 3 and 5 toxins, with a mean conjugation level of ~4 toxins per protein.
Figure 9:
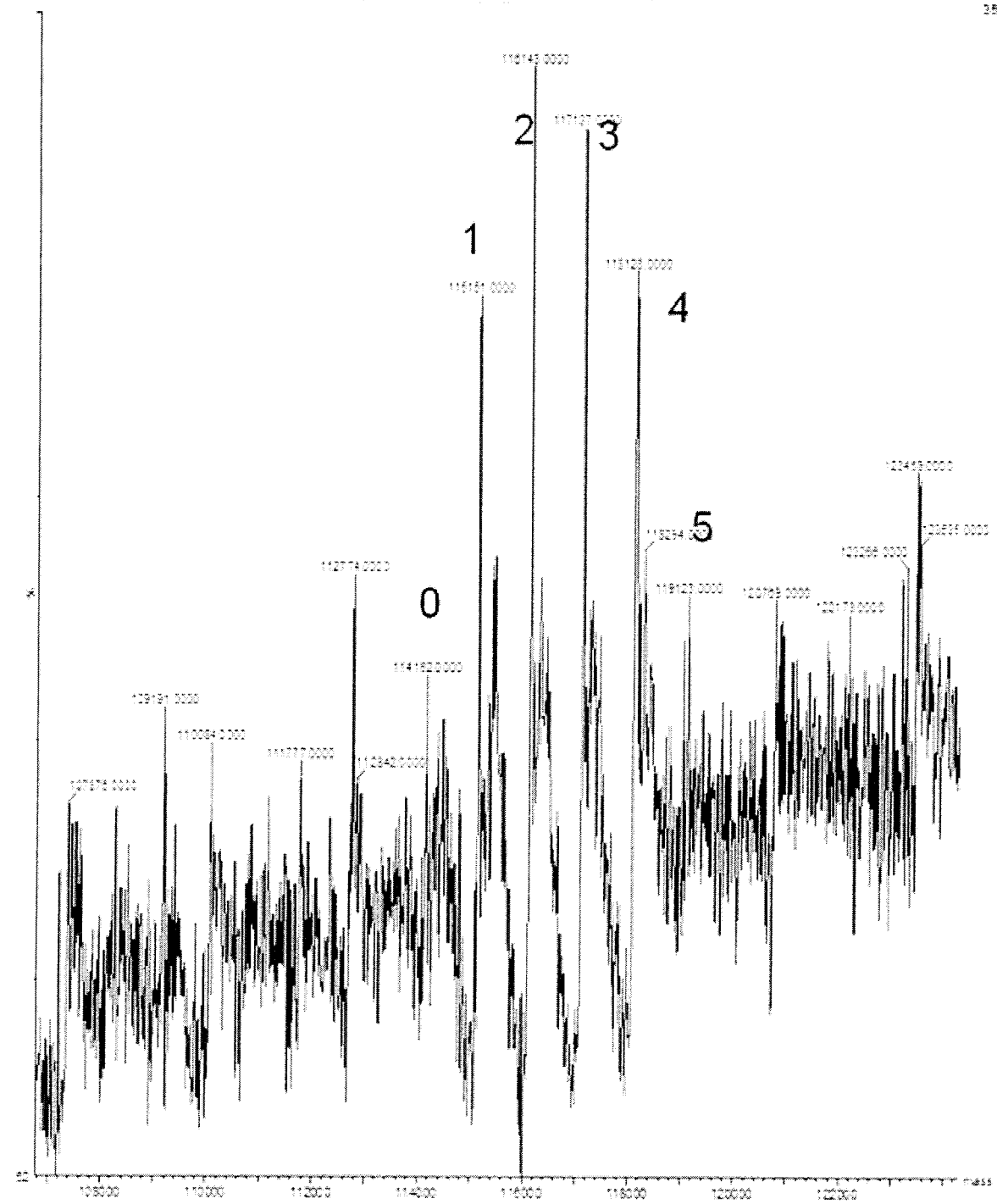
FIG. 9 shows the: SEC-UPLC-QTof-MS MaxEnt1 processed intact mass of VAR2-Compound KK. The profile of the deconvolved MS data is consistent with conjugation of up to 5 toxins (Compound KK), but with a mean drug load of ~2.5 drugs.
Figure 10:
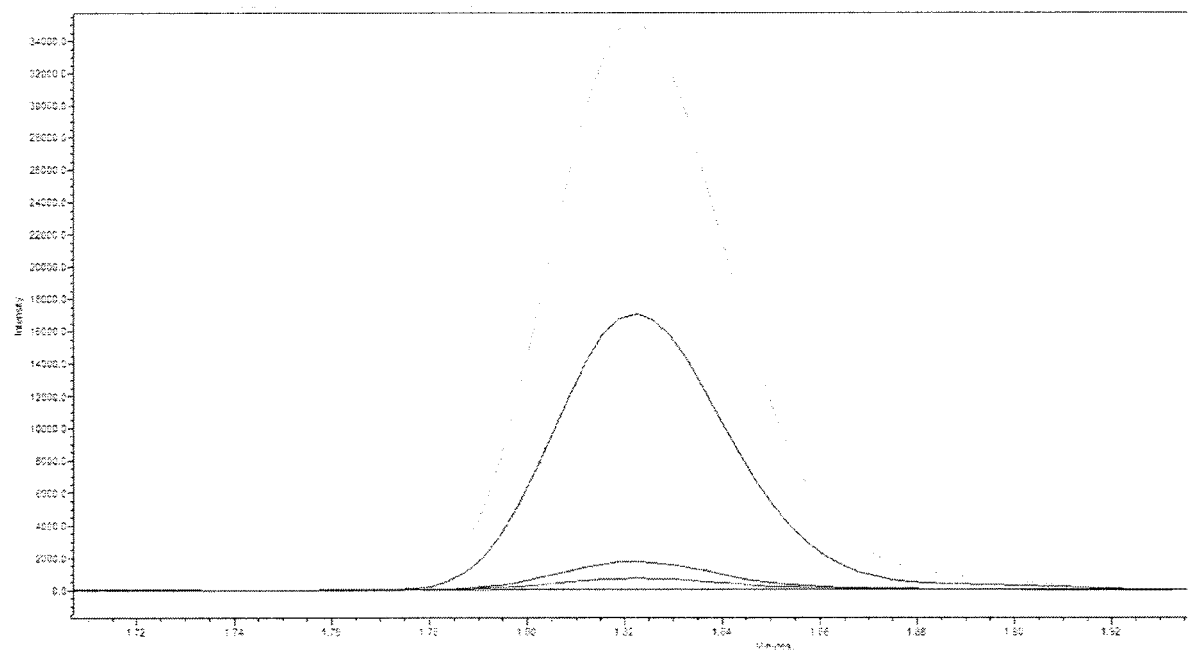
FIG. 10 shows the analysis of free unconjugated toxin-linker in VAR2CSA drug conjugate preparation. X-axis: Time. Y-axis: Intensity. Lines (based on decreasing height of apex) correspond to 20 nM drug-linker, 10 nM drug-linker, 1 nM drug linker, 0.5 nM drug linker, and analyte.

Example 3.27: (S,E)-N-(Benzylsulfonyl)-2,5-dimethyl-4-((S)—N,3,3-trimethyl-2-((S)-3-methyl-2-(methylamino)-3-phenylbutanamido)butanamido)hex-2-enamide (FIG. 7, Compound 14)

Title compound was prepared from Example 3.16 and benzylsulfonamide using General Procedures 9 and 12 $^1$H NMR (400 MHz, Methanol-$d_4$) δ 7.56 (d, J=7.9 Hz, 2H), 7.47 (t, J=7.3 Hz, 2H), 7.38 (brs, 6H), 6.39 (d, J=9.4 Hz, 1H), 5.06 (t, J=10.0 Hz, 1H), 4.93 (s, 1H), 4.75 (s, 2H), 4.36 (s, 1H), 3.13 (s, 3H), 2.51 (s, 3H), 2.06-1.95 (m, 4H), 1.48 (s, 3H), 1.39 (s, 3H), 1.09 (s, 9H), 0.90 (t, J=6.2 Hz, 6H). $C_{34}H_{47}F_3N_4O_6S$ calcd. m/z=626.35 found [M+H]$^+$=626.99.

Example 3.28: (S,E)-2,5-Dimethyl-N-(2,4,6-triisopropylphenylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 2,4,6-tri-isopropylphenylsulfonamide using General Procedures 9 and 12. $^1$H NMR (400 MHz, Methanol-$d_4$) δ 7.61-7.53 (m, 2H), 7.47 (t, J=7.8 Hz, 2H), 7.41-7.33 (m, 1H), 7.27 (s, 2H), 6.50 (dd, J=9.6, 1.8 Hz, 1H), 5.05 (t, J=10.0 Hz, 1H), 4.92 (s, 1H), 4.43-4.26 (m, 3H), 3.16 (s, 3H), 2.94 (dd, J=14.3, 7.4 Hz, 1H), 2.51 (s, 3H), 2.07-1.99 (m, 2H), 1.90 (d, J=1.4 Hz, 3H), 1.48 (s, 4H), 1.39 (s, 3H), 1.33-1.22 (m, 18H), 1.11 (s, 2H), 1.06 (s, 9H), 0.91 (t, J=6.0 Hz, 7H). $C_{42}H_{66}N_4O_5S$ calcd. m/z=738.48 found [M+H]$^+$=738.10.

Example 3.29: (S,E)-N-(4-tert-Butylphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 4-tert-butylphenylsulfonamide using General Procedures 9 and 12. $^1$H NMR (400 MHz, Methanol-$d_4$) δ 7.98 (d, J=8.6 Hz, 2H), 7.64 (d, J=8.6 Hz, 2H), 7.55 (d, J=7.9 Hz, 2H), 7.47 (t, J=7.7 Hz, 3H), 7.37 (t, J=7.1 Hz, 1H), 6.48 (dd, J=9.6, 1.8 Hz, 1H), 4.99 (t, J=10.0 Hz, 1H), 4.92 (s, 1H), 4.35 (s, 1H), 3.16 (s, 3H), 2.51 (s, 3H), 1.87 (d, J=1.4 Hz, 3H), 1.47 (s, 3H), 1.38 (s, 10H), 1.06 (s, 9H), 0.91 (t, J=6.2 Hz, 7H). $C_{42}H_{66}N_4O_5S$ calcd. m/z=668.40 found [M+H]$^+$=669.28.

Example 3.30: (S,E)-N-(4-Chlorophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 4-chlorophenylsulfonamide using General Procedures 9 and 12. $^1$H NMR (400 MHz, Methanol-$d_4$) δ 8.03 (d, J=8.7 Hz, 2H), 7.60 (d, J=8.7 Hz, 2H), 7.57-7.51 (m, 2H), 7.47 (dd, J=8.6, 6.9 Hz, 2H), 7.42-7.32 (m, 1H), 6.50 (dd, J=9.2, 1.7 Hz, 1H), 4.96 (dd, J=10.9, 9.1 Hz, 2H), 4.92 (s, 1H), 4.35 (s, 1H), 3.17 (s, 3H), 2.51 (s, 3H), 2.14-2.03 (m, 1H), 2.01 (s, 1H), 1.87 (d, J=1.4 Hz, 3H), 1.46 (s, 3H), 1.36 (s, 3H), 1.07 (s, 9H), 0.91 (dd, J=6.5, 4.6 Hz, 7H). $C_{33}H_{47}ClN_4O_5S$ calcd. m/z=646.30 found [M+H]$^+$=647.20.

Example 3.31: (S,E)-N-(3-Cyanophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 3-cyanophenylsulfonamide using General Procedures 9 and 12. $^1$H NMR (400 MHz, Methanol-$d_4$) δ 8.38 (s, 1H), 8.31 (dt, J=8.0, 1.5 Hz, 1H), 8.02-7.92 (m, 1H), 7.75 (t, J=7.9 Hz, 1H), 7.53 (d, J=1.2 Hz, 1H), 7.48 (dd, J=8.6, 6.9 Hz, 2H), 7.43-7.33 (m, 1H), 6.55 (dd, J=9.3, 1.7 Hz, 1H), 4.93 (d, J=5.4 Hz, 2H), 4.35 (s, 1H), 3.18 (s, 3H), 2.51 (s, 3H), 2.15-1.98 (m, 2H), 1.87 (d, J=1.4 Hz, 3H), 1.45 (s, 3H), 1.32 (s, 3H), 1.07 (s, 9H), 0.92 (dd, J=6.6, 3.9 Hz, 7H). $C_{34}H_{47}N_5O_5S$ calcd. m/z=637.33 found [M+H]$^+$=638.00.

Example 3.32: (S,E)-2,5-Dimethyl-N-(2-nitrophenylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 2-nitrophenylsulfonamide using General Procedures 9 and 12. $^1$H NMR (400 MHz, Methanol-$d_4$) δ 8.36-8.27 (m, 1H), 7.82 (dd, J=5.9, 3.8 Hz, 3H), 7.61-7.51 (m, 2H), 7.47 (dd, J=8.6, 6.9 Hz, 2H), 7.42-7.31 (m, 1H), 6.63 (dd, J=9.5, 1.7 Hz, 1H), 5.03 (t, J=10.0 Hz, 1H), 4.93 (s, 1H), 4.36 (s, 1H), 3.18 (s, 3H), 2.51 (s, 3H), 2.12-2.01 (m, 1H), 1.88 (d, J=1.4 Hz, 3H), 1.48 (s, 3H), 1.37 (s, 3H), 1.06 (s, 9H), 0.97-0.86 (m, 6H). C34H47N5O5S calcd. m/z=657.32 found [M+H]$^+$= 658.21.

Example 3.33: (S,E)-N-(4-Methoxy-2-nitrophenylsulfonyl)-2,5-dimethyl-4-((S)—N,3,3-trimethyl-2-((S)-3-methyl-2-(methylamino)-3-phenylbutanamido)butanamido)hex-2-enamide Title compound Was prepared from Example 3.16 and 2-nitro-4-methoxyphenylsulfonamide using General Procedures 9 and 12. $^1$H NMR (400 MHz, Methanol-$d_4$) δ 8.24 (d, J=8.9 Hz, 1H), 7.59-7.51 (m, 2H), 7.47 (t, J=7.6 Hz, 2H), 7.44-7.25 (m, 4H), 6.60 (dd, J=9.2, 1.7 Hz, 1H), 5.03 (t, J=10.0 Hz, 1H), 4.93 (s, 1H), 4.36 (s, 1H), 3.97 (s, 3H), 3.18 (s, 3H), 2.51 (s, 3H), 2.13-2.02 (m, 1H), 1.89 (d, J=1.4 Hz, 3H), 1.48 (s, 3H), 1.38 (s, 3H), 1.11 (s, 2H), 1.06 (s, 9H), 0.99-0.88 (m, 6H). $C_{34}H_{49}N_5O_8S$ calcd. m/z=687.33 found [M+H]$^+$=689.23.

Example 3.34: 4-(N—((S,E)-2,5-Dimethyl-4-((S)—N,3,3-trimethyl-2-((S)-3-methyl-2-(methylamino)-3-phenylbutanamido)butanamido)hex-2-enoyl)sulfamoyl)-3-nitrobenzamide Title compound was prepared from Example 3.16 and 3-nitro-4-sulfamoylbenzamide using General Procedures 9 and 12. $^1$H NMR (400 MHz, Methanol-$d_4$) δ 8.35 (d, J=8.0 Hz, 1H), 8.22 (d, J=8.0 Hz, 2H), 7.59-7.51 (m, 2H), 7.47 (t, J=7.6 Hz, 2H), 7.37 (t, J=7.3 Hz, 1H), 6.70-6.57 (m, 1H), 5.04 (t, J=10.0 Hz, 1H), 4.94 (s, 11H), 4.37 (s, 1H), 3.17 (s, 3H), 2.52 (s, 3H), 2.05 (ddd, J=10.3, 7.4, 5.5 Hz, 1H), 1.87 (d, J=1.4 Hz, 3H), 1.48 (s, 3H), 1.38 (s, 3H), 1.06 (s, 9H), 0.92 (dd, J=14.7, 6.8 Hz, 6H). $C_{34}H_{48}N_6O_8S$ calcd. m/z=700.33 found [M+H]$^+$=701.28.

Example 3.35: (S,E)-N-(4-Methoxyphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 4-methoxyphenylsulfonamide using General Procedures 9 and 12. $^1$H NMR (400 MHz, Methanol-$d_4$) δ 7.97 (d, J=9.0 Hz, 2H), 7.54 (d, J=7.5 Hz, 2H), 7.46 (t, J=7.6 Hz, 2H), 7.36 (t, J=7.2 Hz, 1H), 7.06 (d, J=9.0 Hz, 2H), 6.48 (dd, J=9.3, 1.9

Hz, 1H), 4.97 (t, J=9.9 Hz, 1H), 4.92 (s, 1H), 4.22 (s, 1H), 3.89 (s, 3H), 3.15 (s, 3H), 2.46 (s, 3H), 2.10-1.99 (m, 2H), 1.86 (d, J=1.4 Hz, 3H), 1.46 (s, 3H), 1.36 (s, 3H), 1.06 (s, 9H), 0.94-0.84 (m, 6H). $C_{34}H_{50}N_4O_6S$ calcd. m/z=642.35 found $[M+H]^+$=643.31.

Example 3.36: (S,E)-2,5-Dimethyl-N-(4-(2,2,2-trifluoroacetamido)phenylsulfonyl)-4-((S)—N,3,3-trimethyl-2-((S)-3-methyl-2-(methylamino)-3-phenylbutanamido)butanamido)hex-2-enamide (FIG. 7, Compound 23)

Title compound was prepared from Example 3.16 and 2,2,2-trifluoro-N-(4-sulfamoylphenyl)acetamide using General Procedures 9 and 12. $^1$H NMR (400 MHz, Methanol-$d_4$) δ 8.06 (d, J=8.9 Hz, 2H), 7.88 (d, J=8.9 Hz, 2H), 7.52 (d, J=7.1 Hz, 2H), 7.49-7.40 (m, 3H), 7.35 (dd, J=8.1, 6.1 Hz, 1H), 6.47 (dd, J=9.2, 1.8 Hz, 1H), 4.33 (s, 1H), 3.15 (s, 3H), 2.48 (s, 3H), 2.13-1.96 (m, 2H), 1.85 (d, J=1.4 Hz, 3H), 1.43 (s, 3H), 1.33 (s, 3H), 1.04 (s, 9H), 0.89 (dd, J=6.8, 4.7 Hz, 6H). $C_{35}H_{48}F_3N_5O_6S$ calcd. m/z=723.33 found $[M+H]^+$=724.08.

Example 3.37: (S,E)-N-(4-Aminophenylsulfonyl)-2,5-dimethyl-4-((S)—N,3,3-trimethyl-2-((S)-3-methyl-2-(methylamino)-3-phenylbutanamido)butanamido)hex-2-enamide (Compound 886)

Title compound was prepared from Example 3.16 and 2,2,2-trifluoro-N-(4-sulfamoylphenyl)acetamide using General Procedures 2, 3 and 7 $^1$H NMR (400 MHz, Methanol-$d_4$) δ 7.71 (d, J=8.8 Hz, 2H), 7.55 (d, J=7.6 Hz, 2H), 7.47 (d, J=6.9 Hz, 2H), 7.37 (t, J=6.8 Hz, 1H), 6.67 (d, J=8.8 Hz, 2H), 6.44 (dd, J=9.2, 1.6 Hz, 1H), 4.97 (t, J=9.7 Hz, 1H), 4.92 (s, 1H), 4.36 (s, 1H), 3.16 (s, 3H), 2.51 (s, 3H), 2.16-2.00 (m, 1H), 1.87 (d, J=1.4 Hz, 3H), 1.46 (s, 3H), 1.37 (s, 3H), 1.07 (s, 9H), 0.92 (d, J=6.4 Hz, 3H), 0.91 (d, J=6.3 Hz, 3H). $C_{33}H_{49}N_5O_5S$ calcd. m/z=627.35 found $[M+H]^+$=628.35.

Example 3.38: (S,E)-2,5-Dimethyl-N-(phenylsulfonyl)-4-((S)—N,3,3-trimethyl-2-((S)-3-methyl-2-(methylamino)-3-phenylbutanamido)butanamido)hex-2-enamide Title compound was prepared from Example 3.16 and phenylsulfonamide using General Procedures 2, and 7. $^1$H NMR (400 MHz, Methanol-$d_4$) δ 8.06-7.95 (m, 2H), 7.63-7.40 (m, 8H), 7.40-7.30 (m, 1H), 6.53 (dd, J=9.3, 1.6 Hz, 1H), 5.05-4.95 (m, 1H), 4.22 (s, 1H), 3.14 (s, 3H), 2.45 (s, 3H), 2.09-1.95 (m, 1H), 1.85 (d, J=1.4 Hz, 3H), 1.46 (s, 3H), 1.36 (s, 3H), 1.06 (s, 9H), 0.89 (dd, J=11.9, 6.5 Hz, 7H). $C_{33}H_{48}N_4O_5S$ calcd. m/z=612.33 found $[M+H]^+$=613.06.

Example 3.39: (S,E)-N—(N-(2-Fluorobenzyl)sulfamoyl)-2,5-dimethyl-4-((S)—N,3,3-trimethyl-2-((S)-3-methyl-2-(methylamino)-3-phenylbutanamido)butanamido)hex-2-enamide 2-Fluorobenzylsulfamamide was prepared from 2-fluorobenzylamine according to General Procedure 14; the title compound was prepared from Example 3.16 and 2-fluorobenzylsulfamamide using General Procedures 9 and 12. $^1$H NMR (400 MHz, Methanol-$d_4$) δ 7.63-7.41 (m, 6H), 7.41-7.26 (m, 3H), 7.14 (td, J=7.5, 1.2 Hz, 1H), 7.07 (ddd, J=9.5, 8.2, 1.1 Hz, 1H), 6.37 (dd, J=9.4, 1.7 Hz, 1H), 5.07-4.97 (m, 1H), 4.37 (s, 1H), 4.33 (s, 2H), 3.15 (s, 3H), 2.51 (s, 3H), 2.10-1.97 (m, 1H), 1.83 (d, J=1.4 Hz, 3H), 1.49 (s, 3H), 1.39 (s, 3H), 1.09 (s, 9H), 0.97-0.84 (m, 6H). $C_{34}H_{50}FN_5O_5S$ calcd. m/z=659.35 found $[M+H]^+$=660.28.

Example 3.40: (S,E)-2,5-Dimethyl-N-(piperidin-1-ylsulfonyl)-4-((S)—N,3,3-trimethyl-2-((S)-3-methyl-2-(methylamino)-3-phenylbutanamido)butanamido)hex-2-enamide Piperidine-1-sulfonamide was synthesized from piperidine according to General Procedure 14; the title compound was prepared from Example 3.16 and piperidine-1-sulfonamide using General Procedures 9 and 12. $^1$H NMR (400 MHz, Methanol-$d_4$) δ 7.55 (d, J=1.2 Hz, 1H), 7.47 (t, J=7.6 Hz, 3H), 7.42-7.29 (m, 1H), 6.48 (dd, J=9.7, 1.8 Hz, 1H), 5.05 (t, J=10.0 Hz, 1H), 4.39 (s, 1H), 3.18 (s, 3H), 2.52 (s, 3H), 2.07 (d, J=10.5 Hz, 1H), 1.96 (d, J=1.4 Hz, 3H), 1.61 (ddd, J=20.0, 10.3, 5.4 Hz, 9H), 1.49 (s, 4H), 1.39 (s, 3H), 1.09 (s, 9H), 0.99-0.84 (m, 9H). $C_{32}H_{53}N_5O_5S$ calcd. m/z=619.38 found $[M+H]^+$=620.38.

Example 3.41: (S,E)-2,5-Dimethyl-N-(o-tolylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 2-toluenesulfonamide using General Procedures 9 and 12. $^1$H NMR (400 MHz, Methanol-$d_4$) δ 8.10 (dd, J=8.0, 1.4 Hz, 1H), 7.60-7.33 (m, 11H), 6.52 (dd, J=9.6, 1.7 Hz, 1H), 5.04-4.90 (m, 2H), 4.35 (s, 1H), 3.18 (s, 3H), 2.67 (s, 3H), 2.51 (s, 3H), 2.15-2.03 (m, 2H), 2.01 (s, 1H), 1.87 (d, J=1.4 Hz, 3H), 1.46 (s, 3H), 1.35 (s, 3H), 1.07 (s, 9H), 0.92 (t, J=6.3 Hz, 6H). $C_{34}H_{50}N_4O_5S$ calcd. m/z=626.35 found $[M+H]^+$=627.05.

Example 3.42: (S,E)-N-(4-Bromophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 4-bromophenylsulfonamide using General Procedures 9 and 12. $^1$H NMR (400 MHz, Methanol-$d_4$) δ 7.95 (d, J=8.3 Hz, 2H), 7.76 (d, J=8.0 Hz, 2H), 7.55 (d, J=7.5 Hz, 2H), 7.47 (dd, J=8.6, 6.9 Hz, 2H), 7.41-7.29 (m, 1H), 6.51 (d, J=9.0 Hz, 1H), 4.35 (s, 1H), 3.16 (s, 3H), 2.50 (s, 3H), 2.06 (dt, J=10.7, 6.3 Hz, 1H), 1.87 (s, 3H), 1.46 (s, 3H), 1.36 (s, 3H), 1.07 (s, 9H), 0.91 (dd, J=6.9, 4.9 Hz, 8H). $C_{33}H_{47}BrN_4O_5S$ calcd. m/z=690.25 found $[M+H]^+$=691.17, 693.18.

Example 3.43: (S,E)-2,5-Dimethyl-N-(naphthalen-2-ylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 2-naphthylsulfonamide using General Procedures 9 and 12. $^1$H NMR (400 MHz, Methanol-$d_4$) δ 8.69-8.62 (m, 1H), 8.47 (d, J=8.2 Hz, 1H), 8.14-7.95 (m, 5H), 7.71 (dddd, J=18.4, 8.2, 6.9, 1.4 Hz, 2H), 7.57-7.50 (m, 2H), 7.46 (dd, J=8.6, 6.9 Hz, 2H), 7.42-7.33 (m, 1H), 6.50 (dd, J=9.3, 1.5 Hz, 1H), 4.92-4.87 (m, 1H), 4.34 (s, 1H), 3.16 (s, 3H), 2.50 (s, 3H), 2.13-1.99 (m, 1H), 1.85 (d, J=1.4 Hz, 3H), 1.44 (s, 3H), 1.34 (s, 3H), 1.04 (s, 9H), 0.90 (dd, J=6.6, 4.0 Hz, 6H). $C_{37}H_{50}N_4O_5S$ calcd. m/z=662.35 found $[M+H]^+$=663.32.

Example 3.44: Methyl 4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)benzoate Title compound was prepared from Example 3.16 and 4-carboxymethylphenylsulfonamide using General Procedures 9 and 12. $^1$H NMR (400 MHz, Methanol-d$_4$) δ 8.24-8.10 (m, 4H), 7.58-7.50 (m, 2H), 7.47 (dd, J=8.6, 6.9 Hz, 2H), 7.41-7.33 (m, 1H), 6.52 (dd, J=9.2, 1.6 Hz, 1H), 4.35 (s, 1H), 3.97 (s, 3H), 3.18 (s, 3H), 2.50 (s, 3H), 2.15-2.00 (m, 1H), 1.86 (d, J=1.4 Hz, 3H), 1.45 (s, 3H), 1.35 (s, 3H), 1.07 (s, 9H), 0.91 (dd, J=6.7, 3.8 Hz, 6H). C$_{35}$H$_{50}$N$_4$O$_7$S calcd. m/z=670.34 found [M+H]$^+$=671.10.

Example 3.45: (S,E)-2,5-Dimethyl-N—(N-(2-(trifluoromethyl)benzyl)sulfamoyl)-4-((S)—N,3,3-trimethyl-2-((S)-3-methyl-2-(methylamino)-3-phenylbutanamido)butanamido)hex-2-enamide Title compound was prepared from Example 3.16 and 2-trifluoromethylbenzylsulfonamide using General Procedures 9 and 12. $^1$H NMR (400 MHz, Methanol-d$_4$) δ 7.78 (d, J=7.9 Hz, 1H), 7.74-7.67 (m, 1H), 7.64 (dd, J=8.1, 6.7 Hz, 1H), 7.60-7.52 (m, 2H), 7.48 (dd, J=8.5, 6.8 Hz, 4H), 7.42-7.33 (m, 1H), 6.48-6.40 (m, 1H), 5.11-5.02 (m, 1H), 4.45 (s, 2H), 4.37 (s, 1H), 3.17 (s, 3H), 2.52 (s, 3H), 2.11-1.99 (m, 2H), 1.92 (d, J=1.4 Hz, 3H), 1.49 (s, 3H), 1.40 (s, 3H), 1.09 (s, 9H), 0.92 (dd, J=9.3, 6.7 Hz, 6H). C$_{35}$H$_{50}$F$_3$N$_5$O$_5$S calcd. m/z=709.35 found [M+H]$^+$=710.02.

Example 3.46: (4S,E)-N-(Hexan-2-ylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and hexane-2-sulfonamide using General Procedures 9 and 12. $^1$H NMR (400 MHz, Methanol-d$_4$) δ 7.56-7.48 (m, 2H), 7.42 (t, J=7.8 Hz, 2H), 7.31 (t, J=7.3 Hz, 1H), 6.58-6.50 (m, 1H), 5.05 (t, J=10.0 Hz, 1H), 4.92 (s, 1H), 3.84 (s, 1H), 3.65 (dt, J=10.8, 4.3 Hz, 1H), 3.14 (s, 3H), 2.32 (s, 3H), 2.09-1.96 (m, 2H), 1.93 (d, J=1.4 Hz, 3H), 1.61-1.27 (m, 3H), 1.06 (s, 9H), 0.98-0.90 (m, 6H), 0.87 (d, J=6.5 Hz, 3H). C$_{33}$H$_{56}$N$_4$O$_5$S calcd. m/z=620.40 found [M+H]$^+$=621.55.

Example 3.47: (S,E)-N-(2-Methoxyethylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2-methoxyethanesulfonamide using General Procedures 9 and 12. $^1$H NMR (400 MHz, Methanol-d$_4$) δ 7.56 (d, J=7.8 Hz, 2H), 7.47 (t, J=7.6 Hz, 2H), 7.37 (t, J=7.3 Hz, 1H), 6.51 (d, J=9.4 Hz, 1H), 5.07 (t, J=10.0 Hz, 1H), 4.95 (s, 1H), 4.33 (s, 1H), 3.82 (t, J=5.8 Hz, 2H), 3.70 (q, J=5.2 Hz, 2H), 3.18 (s, 3H), 2.50 (s, 3H), 2.18-2.00 (m, 1H), 1.95 (d, J=1.4 Hz, 3H), 1.49 (s, 3H), 1.39 (s, 3H), 1.09 (s, 9H), 0.93 (dd, J=14.8, 6.6 Hz, 6H). C$_{30}$H$_{50}$N$_4$O$_6$S calcd. m/z=594.35 found [M+H]$^+$=595.44.

Example 3.48: (S,E)-N-(Cyclopentylmethylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and cyclopentylmethanesulfonamide using General Procedures 9 and 12. $^1$H NMR (400 MHz, Methanol-d$_4$) δ 7.61-7.52 (m, 2H), 7.48 (dd, J=8.6, 6.9 Hz, 2H), 7.38 (t, J=7.4 Hz, 1H), 6.54 (dd, J=9.4, 1.7 Hz, 1H), 5.06 (t, J=10.0 Hz, 1H), 4.94 (s, 1H), 4.37 (s, 1H), 3.52 (dd, J=7.0, 5.4 Hz, 3H), 3.18 (s, 3H), 2.52 (s, 3H), 2.35 (p, J=8.1 Hz, 1H), 2.16-1.89 (m, 6H), 1.77-1.53 (m, 4H), 1.49 (s, 3H), 1.45-1.26 (m, 5H), 1.09 (s, 9H), 0.93 (dd, J=11.3, 6.7 Hz, 6H). C$_{33}$H$_{54}$N$_4$O$_5$S calcd. m/z=618.38 found [M+H]$^+$=619.54.

Example 3.49: (S)-Methyl 2-(tert-butoxycarbonyl(methyl)amino)-3-(4-cyanophenyl)-3-methylbutanoate To a mixture of the methyl ester of Example 3.51 (0.06 g, 0.15 mmol), tris(dibenzylideneacetone)dipalladium(0) (0.014 g, 0.015 mmol), 1,1'-bis(diphenylphosphino)ferrocene (0.02 g, 0.25 equiv), magnesium acetate (0.013 g, 0.06 mmol), zinc dust (0.004 g, 0.06 mmol) and zinc cyanide (0.0264 g, 0.225 mmol) under a bath of nitrogen was added N,N-dimethylformamide/water (0.8/0.08 mL). The reaction was sparged with nitrogen gas, then the vial was sealed and immersed in an oil bath at 105° C. The reaction was allowed to stir overnight and allowed to cool to room temperature. HPLC-MS analysis indicated good conversion to the desired product. The reaction was concentrated at reduced pressure, suspended in CH$_2$Cl$_2$ and the resulting suspension purified by silica gel chromatography (15-25% EtOAc in Hexanes) to yield the final compound as a colorless oil (0.036 g, 69%). $^1$H NMR (400 MHz, Chloroform-d) δ 7.69-7.35 (m, 4H), 5.24 (s, 1H), 3.54 (s, 3H), 2.74 (s, 3H), 1.51 (s, 3H), 1.45-1.25 (m, 12H).

Example 3.50: (S)-Methyl 2-(tert-butoxycarbonyl(methyl)amino)-3-(4-((tert-butoxycarbonylamino)methyl)phenyl)-3-methylbutanoate To a solution of the benzonitrile (0.300 g, 0.87 mmol) in methanol/acetic acid (10:1, 9 mL) in a shaker vessel was added palladium black. The flask was charged with hydrogen gas at 60 psi and the shaker turned on for 24 h. At that time, the vessel was purged of H2 under reduced pressure. The reaction was diluted with methanol and the suspension filtered through a Celite® pad. The filtrate was concentrated to a slightly yellow oil and re-dissolved in dichloromethane (5 mL). t-Butyl dicarbonate (0.524 g, 2.0 equiv) and triethylamine (0.846 mL, 5 equiv) were added to the solution at 0° C. with stirring. The reaction was allowed to stir for 3 h at which time HPLC-MS indicated complete consumption of the amine. The reaction was concentrated under reduced pressure and purified by silica gel chromatography (diethyl ether in hexanes, 15-30%) to yield the title compound as a colorless oil (0.232 g, 60%). $^1$H NMR (400 MHz, Chloroform-d) δ 7.38 (dd, J=16.6, 8.0 Hz, 2H), 7.23 (d, J=7.7 Hz, 2H), 5.27 (s, 1H), 4.31 (s, 2H), 3.61 (s, 3H), 2.78 (s, 3H), 1.50-1.61 (m, 6H), 1.47 (d, J=15.2 Hz, 18H).

Example 3.51: (S)-3-(4-Bromophenyl)-2-(tert-butoxycarbonyl(methyl)amino)-3-methylbutanoic Acid To a stirred solution of (S)-methyl 3-(4-bromophenyl)-2-(tert-butoxycarbonyl(methyl)amino)-3-methylbutanoate (0.710 g, 1.77 mmol) in 1,4 dioxane (4 mL) was added water (1mL) (2 mL) and lithium hydroxide monohydrate (0.367 g, 8.9 mmol). The reaction was heated to 50° C. and monitored by HPLC for completion. The reaction was cooled to room temperature, acidified to pH 3 with 1M citric acid and concentrated to near dryness under reduced pressure. The residue was taken up in ~20 mL ethyl acetate, washed with brine, dried over MgSO$_4$, filtered and concentrated to give analytically pure material that was used without further manipulation. $^1$H NMR (400 MHz, Chloroform-d) δ 7.44 (d, J=8.3 Hz, 2H), 7.33 (d, J=8.3 Hz, 2H), 5.18 (s, 1H), 2.71 (s, 3H), 1.60-1.42 (m, 15H).

Example 3.52: (S)-3-(4-Azidophenyl)-2-(tert-butoxycarbonyl(methyl)amino)-3-methylbutanoic Acid To an open pressure tube containing a magnetic stir bar was added Example 3.51 (0.690 g, 1.8 mmol), copper(I) iodide (0.034 g, 0.18 mmol), sodium azide (0.350 g, 5.4 mmol), N$^1$,N$^2$-dimethylethane-1,2-diamine (0.029 mL, 0.27 mmol), sodium ascorbate (0.036 g, 0.18 mmol), sodium hydroxide (0.072 g, 1.8 mmol), ethanol (6 mL) and water (1 mL). The suspension was sparged with nitrogen gas, the vessel was sealed and immersed in an oil bath at 105° C. with vigorous stirring. The course of reaction was monitored by HPLC-MS over the course of 24 h at which time little starting material remained. The reaction was diluted with ethyl acetate (~20 mL) and washed with brined. The aqueous layer was extracted 2× with ~20 mL ethyl acetate. The organic layers were combined, dried over MgSO$_4$, filtered and concentrated under reduced pressure. The residue was purified by silica gel chromatography (20-65% EtOAc (containing 2% v/v AcOH) in hexanes) to give the title compound as a colorless oil (0.475 g, 75%). $^1$H NMR (400 MHz, Chloroform-d) δ 7.44 (d, J=8.6 Hz, 2H), 6.99 (dd, J=9.0, 3.4 Hz, 2H), 5.24 (s, 1H), 2.71 (s, 3H), 1.63-1.38 (m, 18H).

Example 3.53: (S,E)-N-(Benzylsulfonyl)-4-((S)-2-((S)-3-(4-cyanophenyl)-3-methyl-2-(methylamino)butanamido)-N,3,3-trimethylbutanamido)-2,5-dimethylhex-2-enamide Title compound was prepared from Example 3.49 and (S,E)-4-((S)-2-amino-N,3,3-trimethylbutanamido)-N-(benzylsulfonyl)-2,5-dimethylhex-2-enamide using General Procedures 10, 11 and 12. $^1$H NMR (400 MHz, Methanol-d$_4$) δ 7.83 (d, J=8.2 Hz, 2H), 7.73 (d, J=8.4 Hz, 2H), 7.38 (d, J=2.6 Hz, 5H), 6.39 (dd, J=9.2, 1.8 Hz, 1H), 5.04 (t, J=10.1 Hz, 1H), 4.91 (s, 1H), 4.75 (s, 2H), 4.34 (s, 1H), 3.12 (s, 3H), 2.54 (s, 3H), 2.05-1.97 (m, 2H), 1.95 (d, J=1.5 Hz, 3H), 1.52 (s, 3H), 1.41 (s, 3H), 1.09 (s, 9H), 0.91 (dd, J=11.2, 4.8 Hz, 6H). C$_{35}$H$_{49}$N$_5$O$_5$S calcd. m/z=651.35 found [M+H]$^+$=652.4.

Example 3.54: (S,E)-4-((S)-2-((S)-3-(4-(Aminomethyl)phenyl)-3-methyl-2-(methylamino)butanamido)-N,3,3-trimethylbutanamido)-N-(benzylsulfonyl)-2,5-dimethylhex-2-enamide Title compound was prepared from Example 3.50 and (S,E)-4-((S)-2-amino-N,3,3-trimethylbutanamido)-N-(benzylsulfonyl)-2,5-dimethylhex-2-enamide using General Procedures 10, 11 and 12. $^1$H NMR (400 MHz, Methanol-d$_4$) δ 7.63 (t, J=8.8 Hz, 2H), 7.54 (d, J=8.3 Hz, 2H), 7.49-7.43 (m, 3H), 7.39 (m, 2H), 6.39 (d, J=9.4 Hz, 1H), 5.05-4.97 (m, 1H), 4.75 (s, 2H), 4.35 (s, 3H), 4.16 (s, 2H), 3.14 (s, 3H), 2.54 (s, 3H), 2.03 (m, 1H), 1.95 (s, 3H), 1.51 (s, 3H), 1.39 (s, 3H), 1.31 (s, 3H), 1.09 (s, 9H), 0.98-0.81 (m, 6H).

Example 3.55: (S,E)-4-((S)-2-((S)-3-(4-Azidophenyl)-3-methyl-2-(methylamino)butanamido)-N,3,3-trimethylbutanamido)-N-(benzylsulfonyl)-2,5-dimethylhex-2-enamide Title compound was prepared from Example 3.52 and (S,E)-4-((S)-2-amino-N,3,3-trimethylbutanamido)-N-(benzylsulfonyl)-2,5-dimethylhex-2-enamide using General Procedures 11 and 12. C$_{34}$H$_{49}$N$_7$O$_5$S calcd. m/z=667.35 amu; found [M+H]$^+$=668.4.

Example 3.56: (S,E)-4-((S)-2-((S)-3-(4-Aminophenyl)-3-methyl-2-(methylamino)butanamido)-N,3,3-trimethylbutanamido)-N-(benzylsulfonyl)-2,5-dimethylhex-2-enamide To a stirred solution of Boc protected Example 3.55 (0.035 g, 0.046 mmol) in ethanol (1.6 mL) and water (0.5 mL) was added zinc dust (0.015 g, 0.23 mmol) and ammonium chloride (0.025 g, 0.46 mmol). After 1 h HPLC-MS indicated complete consumption of the starting material. The reaction was quenched with ammonium hydroxide (~0.1 mL) and diluted with ethyl acetate (5 mL). The reaction was filtered, the solids washed with ethyl acetate (5 mL) and the biphasic filtrate transferred to a separatory funnel. The aqueous phase was washed twice with ethyl acetate (5 mL) and the organic phases were combined, washed with brine, dried over MgSO$_4$, filtered and concentrated. The reaction product was purified by silica gel chromatography (5-15% MeOH in CH$_2$Cl$_2$) to afford the Boc protected intermediate as a colorless glass (0.027 g, 66%). The intermediate was deprotected according to General Procedure 12 to give the title compound. C$_{34}$H$_{51}$N$_5$O$_5$S calcd. m/z=641.36 amu; found [M+H]$^+$=642.4.

Example 3.57: (S,E)-N-(Cyclohexylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and cyclohexylsulfonamide using General Procedures 9 and 12. $^1$H NMR (400 MHz, Methanol-d$_4$) δ 7.61-7.52 (m, 2H), 7.47 (dd, J=8.6, 6.9 Hz, 2H), 7.36 (t, J=7.5 Hz, 1H), 6.61-6.50 (m, 1H), 5.11-4.99 (m, 1H), 4.94 (s, 1H), 4.28 (s, 1H), 3.59-3.51 (m, 1H), 3.18 (s, 3H), 2.48 (s, 3H), 2.20-2.00 (m, 4H), 1.97-1.87 (m, 6H), 1.78-1.69 (m, 1H), 1.60 (td, J=14.2, 10.9 Hz, 2H), 1.48 (s, 3H), 1.44-1.23 (m, 6H), 1.09 (s, 9H), 0.93 (dd, J=13.7, 6.6 Hz, 7H). C$_{33}$H$_{54}$N$_4$O$_5$S calcd. m/z=618.38 found [M+H]$^+$=619.47.

Example 3.58: (S,E)-2,5-Dimethyl-N-(pyridin-3-ylmethylsulfonyl)-4-((S)—N,3,3-trimethyl-2-((S)-3-methyl-2-(methylamino)-3-phenylbutanamido)butanamido)hex-2-enamide Title compound was prepared from Example 3.16 and pyridin-3-ylmethanesulfonamide using General Procedures 9 and 12. $^1$H NMR (400 MHz, Methanol-d$_4$) δ 8.55 (d, J=1.7 Hz, 1H), 8.48 (dd, J=5.0, 1.6 Hz, 1H), 7.89 (d, J=8.0 Hz, 0H), 7.55 (d, J=7.6 Hz, 2H), 7.50-7.39 (m, 2H), 7.35 (s, 1H), 6.52 (dd, J=9.6, 2.0 Hz, 1H), 5.05 (s, 0H), 4.94 (s, 1H), 4.64 (s, 2H), 4.19 (s, 1H), 3.11 (s, 3H), 2.45 (s, 3H), 1.91 (d, J=1.5 Hz, 3H), 1.48 (s, 3H), 1.39 (s, 3H), 1.07 (s, 8H), 0.89 (dd, J=15.1, 6.5 Hz, 6H). C$_{33}$H$_{54}$N$_4$O$_5$S calcd. m/z=627.35 found [M+H]$^+$=628.35.

Example 3.59: 4-(N—((S,E)-2,5-Dimethyl-4-((S)—N,3,3-trimethyl-2-((S)-3-methyl-2-(methylamino)-3-phenylbutanamido)butanamido)hex-2-enoyl)sulfamoyl)benzoic Acid Title compound was prepared from Example 3.16 and methyl 4-sulfamoylbenzoate using General Procedures 9, 10 and 12. ¹H NMR (400 MHz, Methanol-$d_4$) δ 8.25-8.07 (m, 4H), 7.54 (d, J=7.8 Hz, 2H), 7.47 (t, J=7.6 Hz, 2H), 7.37 (t, J=7.3 Hz, 1H), 6.55 (d, J=9.3 Hz, 1H), 4.98 (t, J=9.9 Hz, 1H), 4.92 (s, 1H), 4.36 (s, 1H), 3.16 (s, 3H), 2.51 (s, 3H), 2.06 (q, J=9.0, 7.7 Hz, 1H), 1.88 (s, 3H), 1.46 (s, 3H), 1.36 (s, 3H), 1.06 (s, 9H), 0.91 (t, J=6.0 Hz, 6H).

Example 3.60: (S,E)-2,5-Dimethyl-N-(3-(2,2,2-trifluoroacetamido)phenylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 2,2,2-trifluoro-N-(3-sulfamoylphenyl)acetamide using General Procedures 9 and 12. ¹H NMR (400 MHz, Methanol-$d_4$) δ 8.49 (p, J=2.2 Hz, 1H), 7.90 (dtd, J=6.0, 4.8, 2.9 Hz, 2H), 7.64-7.56 (m, 1H), 7.53 (tt, J=5.4, 4.3, 1.8 Hz, 2H), 7.51-7.42 (m, 2H), 7.41-7.28 (m, 1H), 6.56-6.38 (m, 1H), 4.97 (s, 1H), 4.90 (d, J=3.3 Hz, 1H), 4.35 (s, 1H), 3.16 (d, J=15.5 Hz, 3H), 2.49 (d, J=14.2 Hz, 3H), 2.14-2.01 (m, 1H), 1.89-1.83 (m, 3H), 1.57-1.28 (m, 6H), 1.14-0.94 (m, 9H), 0.95-0.85 (m, 6H). ¹³C NMR (101 MHz, Methanol-$d_4$) δ 172.26, 168.81, 167.10, 167.00, 144.95, 141.82, 138.82, 138.47, 135.31, 130.71, 130.38, 128.91, 127.36, 126.65, 126.32, 121.39, 71.20, 66.92, 57.87, 57.78, 42.05, 35.83, 34.15, 32.66, 30.84, 29.79, 26.95, 21.39, 19.84, 19.82, 15.45, 14.03. ¹⁹F NMR (377 MHz, Methanol-$d_4$) δ−76.96, −77.07. $C_{35}H_{48}F_3N_5O_6S$ calcd. m/z=723.33 amu; found $[M+H]^+$=724.30, $[M+Na]^+$=746.30.

Example 3.61: (S,E)-N-(3-Aminophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2,2,2-trifluoro-N-(3-sulfamoylphenyl)acetamide using General Procedures 9, 10 and 12. ¹H NMR (400 MHz, Methanol-$d_4$) δ 7.55 (d, J=7.5 Hz, 2H), 7.51-7.45 (m, 2H), 7.43-7.20 (m, 4H), 6.97 (d, J=8.1 Hz, 1H), 6.48 (d, J=9.4 Hz, 1H), 5.02-4.89 (m, 2H), 4.36 (s, 1H), 3.17 (s, 3H), 2.50 (s, 3H), 2.14-2.00 (m, 1H), 1.88 (d, J=1.4 Hz, 3H), 1.46 (s, 3H), 1.35 (s, 3H), 1.07 (s, 9H), 0.92 (d, J=6.3 Hz, 3H), 0.90 (s, 3H). $C_{33}H_{49}N_5O_5S$ calcd. m/z=627.35 found $[M+H]^+$=628.36.

Example 3.62: (S,E)-2,5-Dimethyl-N-(pyridin-3-ylsulfonyl)-4-((S)—N,3,3-trimethyl-2-((S)-3-methyl-2-(methylamino)-3-phenylbutanamido)butanamido)hex-2-enamide Title compound was prepared from Example 3.16 and pyridine-3-sulfonamide using General Procedures 2, and 7. ¹H NMR (400 MHz, Methanol-$d_4$) δ 9.18 (s, 1H), 8.80 (s, 1H), 8.46 (dt, J=8.2, 1.8 Hz, 1H), 7.65 (dd, J=8.1, 4.9 Hz, 1H), 7.54 (d, J=7.3 Hz, 2H), 7.47 (t, J=7.8 Hz, 2H), 7.37 (t, J=7.3 Hz, 1H), 6.54 (d, J=9.3 Hz, 1H), 5.01-4.88 (m, 2H), 4.36 (s, 1H), 3.18 (s, 3H), 2.51 (s, 3H), 2.15-2.01 (m, 1H), 1.86 (d, J=1.4 Hz, 3H), 1.46 (s, 3H), 1.33 (s, 3H), 1.07 (s, 9H), 0.92 (d, J=3.3 Hz, 3H), 0.91 (d, J=3.5 Hz, 3H). $C_{32}H_{47}N_5O_5S$ calcd. m/z=613.33 found $[M+H]^+$=614.23.

Example 3.63: (S,E)-2,5-Dimethyl-N-(thiophen-2-ylsulfonyl)-4-((S)—N,3,3-trimethyl-2-((S)-3-methyl-2-(methylamino)-3-phenylbutanamido)butanamido)hex-2-enamide Title compound was prepared from Example 3.16 and thiophene-2-sulfonamide using General Procedures 9 and 12. ¹H NMR (400 MHz, Methanol-$d_4$) δ 7.93-7.82 (m, 2H), 7.55 (d, J=8.3 Hz, 1H), 7.48 (t, J=7.8 Hz, 2H), 7.37 (t, J=7.2 Hz, 1H), 7.15 (dd, J=5.0, 3.8 Hz, 1H), 6.51 (d, J=9.1 Hz, 1H), 5.02-4.93 (m, 2H), 4.36 (s, 1H), 3.18 (s, 3H), 2.51 (s, 3H), 2.15-2.01 (m, 1H), 1.89 (d, J=1.4 Hz, 3H), 1.46 (s, 3H), 1.34 (s, 3H), 1.08 (s, 9H), 0.93 (d, J=4.8 Hz, 3H), 0.91 (d, J=4.7 Hz, 3H). $C_{31}H_{46}N_4O_5S_2$ calcd. m/z=618.29 found $[M+H]^+$=619.24.

Example 3.64: (S,E)-N-(4-Hydroxyphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 4-(tert-butyldimethylsilyloxy)benzenesulfonamide using General Procedures 9 and 12. ¹H NMR (400 MHz, Methanol-$d_4$) δ 7.89 (d, J=8.8 Hz, 2H), 7.55 (d, J=7.0 Hz, 1H), 7.47 (t, J=7.6 Hz, 2H), 7.37 (t, J=7.3 Hz, 1H), 6.91 (d, J=8.9 Hz, 2H), 6.46 (d, J=9.2 Hz, 1H), 4.97 (d, J=10.2 Hz, 1H), 4.92 (s, 1H), 4.33 (s, 1H), 3.16 (s, 3H), 2.50 (s, 3H), 2.11-2.00 (m, 1H), 1.87 (d, J=1.4 Hz, 3H), 1.46 (s, 3H), 1.36 (s, 3H), 1.07 (s, 9H), 0.92 (d, J=6.5 Hz, 4H), 0.89 (d, J=6.7 Hz, 3H). $C_{33}H_{48}N_4O_6S$ calcd. m/z=628.33 found $[M+H]^+$=629.38.

Example 3.65: 4-(Tritylthiomethyl)benzonitrile

Tritylmercaptan (1.48 g, 5.36 mmol, 1.05 eq) in THF (5 mL) was added dropwise to a stirred suspension of sodium hydride (60% dispersion in mineral oil, 214 mg, 5.36 mmol, 1.05 eq) in THF (5 mL) under N2 at 0° C. After 15 min, 4-(bromomethyl)benzonitrile (1.00 g, 5.10 mmol, 1.0 eq) in THF (5 mL) was added and the reaction was allowed to come to rt. After 1 h, TLC indicated complete conversion of starting material. The reaction was quenched by adding saturated ammonium chloride, then some $dH_2O$. The mixture was extracted three times with ether, washed with saturated brine, dried over sodium sulfate, and concentrated to a viscous yellow oil. Purification by flash chromatography gave the title compound (1.76 g, 88%) as a light white powder. ¹H NMR (400 MHz, Chloroform-d) δ 7.52 (d, J=8.2 Hz, 2H), 7.47 (d, J=7.1 Hz, 6H), 7.33 (t, J=7.5 Hz, 6H), 7.26 (t, J=7.2 Hz, 3H), 7.19 (d, J=8.2 Hz, 2H), 3.40 (s, 2H). m/z calcd. for $C_{27}H_{21}NS$=391.14. Found $[M+Na]^+$=414.13. $R_f$=0.32 (10% EtOAc/Hex).

Example 3.66: 1-(4-(Tritylthiomethyl)phenyl)cyclopropanamine 4-(Tritylthiomethyl)benzonitrile (1.47 g, 3.75 mmol, 1.0 eq) was taken up in 40 mL THF, under N2 atmosphere, then cooled to −78° C. To this solution was added $Ti(O-iPr)_4$ (1.21 mL, 4.13 mmol, 1.1 eq), then ethylmagnesium bromide (3 M, 2.75 mL, 8.26 mmol, 2.2 eq) was added dropwise over 5 min. The dry-ice bath was removed, allowing the solution to reach rt. After 45 min at rt, $BF_3.Et_2O$ (0.93 mL, 7.51 mmol, 2.0 eq) was added to the now very dark reaction mixture. After stirring for an additional 2.5 h, the reaction was quenched with 5 mL of 2 M HCl, followed by pH adjustment to strong base with about 15 mL 2 M NaOH. Some water was added to the mixture, then it was extracted three times with 75 mL EtOAc, washed once with $dH_2O$, once with saturated brine, dried over sodium sulfate, and concentrated to a clear oil. The material was purified by flash chromatography to afford the title compound (680 mg, 36%) as a clear oil. ¹H NMR (400 MHz, Chloroform-d) δ 7.49 (d, J=7.8 Hz, 6H), 7.33 (t, J=7.7 Hz, 6H), 7.26 (t, J=7.2

Hz, 3H), 7.20 (d, J=8.2 Hz, 2H), 7.11 (d, J=8.2 Hz, 2H), 3.32 (s, 2H), 1.06 (dd, J=7.9, 5.0 Hz, 2H), 0.95 (dd, J=7.9, 4.7 Hz, 2H). m/z calcd. for $C_{29}H_{27}NS=421.19$. Found $[M+H]^+=422.19$. $R_f=0.21$ (50% EtOAc/Hex).

Example 3.67: 2,2,2-Trifluoro-N-(1-(4-(tritylthiomethyl)phenyl)cyclopropyl)acetamide To a stirred solution of 1-(4-(tritylthiomethyl)phenyl) cyclopropanamine (680 mg, 1.61 mmol, 1.0 eq) in $CH_2Cl_2$ was added trifluoroacetic anhydride (0.448 mL, 3.22 mmol, 2.0 eq) and triethylamine (0.45 mL, 3.22 mmol, 2.0 eq). After two hours, TLC and HPLC indicated complete conversion of starting material. The reaction was quenched by the addition of 3 mL NaHCO3, then some dH2O was added, and the mixture was extracted three times with $CH_2Cl_2$. The combined organics were washed with saturated brine, dried over sodium sulfate, and concentrated to a yellow foam, giving the title compound (715 mg, 86%) in sufficient purity to move to the next step. $^1H$ NMR (400 MHz, Chloroform-d) δ 7.48 (d, J=7.7 Hz, 6H), 7.32 (t, J=7.6 Hz, 6H), 7.25 (t, J=7.2 Hz, 3H), 7.19 (d, J=8.2 Hz, 2H), 7.10 (d, J=8.3 Hz, 2H), 6.83 (s, 1H), 3.31 (s, 2H), 1.40-1.24 (m, 4H). m/z calcd. for $C_{31}H_{26}F_3NOS=517.17$. Found $[M+Na]^+=540.25$. $R_f=0.71$ (50% EtOAc/Hex).

Example 3.68: 2,2,2-Trifluoro-N-(1-(4-(mercaptomethyl)phenyl)cyclopropyl)acetamide 2,2,2-Trifluoro-N-(1-(4-(tritylthiomethyl)phenyl)cyclopropyl)acetamide (715 mg, 1.38 mmol, 1.0 eq) in 5 mL $CH_2Cl_2$ was treated with 2.5 mL TFA. After 1 min, TIPSH (0.42 mL, 2.1 mmol, 1.5 eq) was added, causing the yellow color to fade. After 30 min, TLC indicated the reaction to be complete. The mixture was concentrated, then co-evaporated once with $CH_2Cl_2$ and twice with toluene. The residue was purified by flash chromatography to afford the title compound (261 mg, 69%) as a white solid. $^1H$ NMR (400 MHz, Chloroform-d) δ 7.35-7.23 (m, 4H), 6.87 (s, 1H), 3.74 (d, J=7.6 Hz, 2H), 1.77 (t, J=7.6 Hz, 1H), 1.36 (s, 4H). $R_f=0.47$ (20% EtOAc/Hex).

Example 3.69: 2,2,2-Trifluoro-N-(1-(4-(sulfamoylmethyl)phenyl)cyclopropyl)acetamide To a stirred solution of 2,2,2-trifluoro-N-(1-(4-(mercaptomethyl)phenyl)cyclopropyl)acetamide (220 mg, 0.799 mmol, 1.0 eq) in acetonitrile were added dH2O (0.029 mL, 1.6 mmol, 2.0 eq), tetrabutylammonium chloride (110 mg, 0.40 mmol, 0.5 eq), then N-chlorosuccinimide (320 mg, 2.40 mmol, 3.0 eq). After 20 minutes, no starting material was visible by TLC. After 90 min, concentrated $NH_4OH$ (0.18 mL, 3.2 mmol, 4.0 eq) was added. After 10 minutes, 1 mL of $NH_4Cl$ was added, and the mixture was extracted three times with EtOAc. The combined organics were washed twice with $dH_2O$, once with saturated brine, dried over sodium sulfate, and concentrated to a clear oil. The residue was purified by flash chromatography to afford the title compound (192 mg, 74%) as a white solid. $^1H$ NMR (400 MHz, DMSO-$d_6$) δ 10.21 (s, 1H), 7.31 (d, J=8.2 Hz, 2H), 7.16 (d, J=8.3 Hz, 2H), 6.85 (s, 2H), 4.23 (s, 2H), 1.27 (dt, J=6.1, 2.3 Hz, 4H). $R_f=0.26$ (50% EtOAc/Hex).

Example 3.70: (S,E)-2,5-Dimethyl-N-(4-(1-(2,2,2-trifluoroacetamido)cyclopropyl)benzylsulfonyl)-4-((S)—N,3,3-trimethyl-2-((S)-3-methyl-2-(methylamino)-3-phenylbutanamido)butanamido)hex-2-enamide Title compound was prepared from Example 3.16 and Example 3.69 using General Procedures 9 and 12. $^1H$ NMR (400 MHz, Methanol-$d_4$) δ 7.56 (d, J=8.4 Hz, 2H), 7.48 (t, J=7.7 Hz, 2H), 7.37 (t, J=7.4 Hz, 1H), 7.32 (d, J=8.5 Hz, 2H), 7.28 (d, J=8.5 Hz, 2H), 6.37 (d, J=9.6 Hz, 1H), 5.07 (t, J=10.0 Hz, 1H), 4.94 (s, 1H), 4.72 (s, 2H), 4.37 (s, 1H), 3.13 (s, 3H), 2.52 (s, 3H), 2.08-1.96 (m, 1H), 1.96 (d, J=1.5 Hz, 3H), 1.49 (s, 3H), 1.40 (s, 3H), 1.35-1.27 (m, 4H), 1.10 (s, 9H), 0.92 (d, J=7.1 Hz, 3H), 0.89 (d, J=6.8 Hz, 3H). $^{13}C$ NMR (101 MHz, MeOD) δ 170.93, 168.81, 165.64, 143.58, 142.24, 136.87, 134.19, 130.64, 129.00, 127.63, 127.53, 125.95, 125.61, 69.90, 57.10, 57.02, 56.39, 40.73, 34.55, 34.25, 32.80, 30.60, 29.33, 28.39, 25.57, 20.11, 18.38, 18.34, 16.21, 16.15, 14.04, 12.85. $C_{39}H_{54}F_3N_5O_6S$ calcd. m/z=777.37 found $[M+H]^+=778.55$.

Example 3.71: (S,E)-N-(4-(1-Aminocyclopropyl) benzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and Example 3.69 using General Procedures 9, 10 and 12. $^1H$ NMR (400 MHz, Methanol-$d_4$) δ 7.56 (d, J=8.7 Hz, 2H), 7.51 (s, 4H), 7.47 (t, J=7.6 Hz, 2H), 7.37 (t, J=7.3 Hz, 1H), 6.49 (d, J=9.5 Hz, 1H), 5.07 (t, J=10.0 Hz, 1H), 4.94 (s, 1H), 4.81 (d, J=14.0 Hz, 1H), 4.77 (d, J=13.8 Hz, 1H), 4.39 (s, 1H), 3.16 (s, 3H), 2.52 (s, 3H), 2.11-1.99 (m, 1H), 1.97 (d, J=1.5 Hz, 3H), 1.49 (s, 8H), 1.45-1.41 (m, 2H), 1.40 (s, 3H), 1.34-1.26 (m, 2H), 1.10 (s, 9H), 0.93 (d, J=6.2 Hz, 3H), 0.90 (d, J=6.3 Hz, 3H). $^{13}C$ NMR (101 MHz, MeOD) δ 170.94, 169.00, 165.69, 143.57, 137.54, 137.12, 134.38, 131.43, 129.66, 128.98, 127.51, 125.98, 69.85, 65.51, 57.68, 57.15, 56.39, 40.72, 36.16, 34.51, 32.80, 30.68, 29.42, 28.40, 25.61, 20.14, 18.42, 18.39, 14.05, 12.86, 11.80. $C_{37}H_{55}N_5O_5S$ calcd. m/z=681.39 found $[M+H]^+=682.49$.

Example 3.72: 1-Phenylcyclopropanamine

The title compound was prepared as described in Bertus, P., Szymoniak, J. J. Org. Chem., 2003, 68, 7133-7136 from benzonitrile (1.0 mL, 9.7 mmol) to give 270 mg (21%). $^1H$ NMR (400 MHz, Chloroform-d) δ 7.44-7.28 (m, 4H), 7.27-7.15 (m, 1H), 1.18-1.06 (m, 2H), 1.07-0.95 (m, 2H). $R_f=0.28$ (5% (5% $NH_4OH$/MeOH)/$CH_2Cl_2$).

Example 3.73: 2,2,2-Trifluoro-N-(1-phenylcyclopropyl)acetamide

To a stirred solution of 1-phenylcyclopropanamine (270 mg, 2.03 mmol, 1.0 eq) in dioxane (5 mL), was added trifluoroacetic anhydride (0.310 mL, 2.23 mmol, 1.1 eq). After 5 min, TLC indicated complete conversion of starting material. The mixture was concentrated, then coevaporated once with $CH_2Cl_2$ and once with toluene to yield the title compound (453 mg, 97%) as a flaky white powder. $^1H$ NMR (400 MHz, Chloroform-d) δ 7.47-7.15 (m, 5H), 6.88 (s, 1H), 1.65 (s, 4H). m/z calcd. for $C_{11}H_{10}F_3NO=229.07$. Found $[M+H]^+=230.14$. $R_f=0.82$ (5% (5% $NH_4OH$/MeOH)/$CH_2Cl_2$).

Example 3.74: 2,2,2-Trifluoro-N-(1-(4-sulfamoylphenyl)cyclopropyl)acetamide

To stirred chlorosulfonic acid (0.78 mL, 11.8 mmol, 6.0 eq) at 0° C., was added solid 2,2,2-trifluoro-N-(1-phenylcyclopropyl)acetamide (450 mg, 1.96 mmol, 1.0 eq) portionwise, keeping the temperature low. After complete addition, the mixture was heated to 50° C. After 10 minutes, gas evolution ceased, and the reaction was allowed to cool. The mixture was added slowly to a beaker of ice, being mindful of splattering. The solid that was left in the ice was filtered off. This solid was dried in vacuo and then taken up in THF (4 mL). Concentrated NH$_4$OH (0.44 mL, 7.85 mmol, 4.0 eq) was added, turning the solution green-black. After 2 min, TLC indicated complete consumption of the sulfonylchloride intermediate. 2M HCl was added until the color faded, then the mixture was extracted three times with EtOAc, washed once with saturated NaHCO$_3$, once with saturated brine, dried over sodium sulfate, and concentrated to a flaky solid. The crude material was purified by flash chromatography to yield the title compound (235 mg, 39%) as a white solid. $^1$H NMR (400 MHz, DMSO-d$_6$) δ 10.28 (s, 1H), 7.76 (d, J=8.5 Hz, 2H), 7.32 (d, J=8.1 Hz, 2H), 7.31 (s, 2H), 1.42-1.35 (m, 2H), 1.35-1.27 (m, 2H). m/z calcd. for C$_{11}$H$_{11}$F$_3$N$_2$O$_3$S=308.04. Found [M+H]$^+$=309.07. R$_f$=0.27 (50% EtOAc/Hex).

Example 3.75: (S,E)-2,5-dimethyl-N-(4-(1-(2,2,2-trifluoroacetamido)cyclopropyl) phenylsulfonyl)-4-((S)—N,3,3-trimethyl-2-((S)-3-methyl-2-(methylamino)-3-phenylbutanamido)butanamido)hex-2-enamide Title compound was prepared from Example 3.16 and Example 3.3.74 using General Procedures 9 and 12. $^1$H NMR (400 MHz, Methanol-d$_4$) δ 8.00 (d, J=8.6 Hz, 2H), 7.55 (d, J=7.6 Hz, 2H), 7.48 (t, J=7.7 Hz, 2H), 7.48-7.33 (m, 4H), 6.47 (dd, J=9.4, 1.6 Hz, 1H), 5.00 (t, J=10.0 Hz, 1H), 4.92 (s, 1H), 4.35 (s, 1H), 3.15 (s, 3H), 2.51 (s, 3H), 2.11-2.00 (m, 1H), 1.86 (d, J=1.4 Hz, 3H), 1.47 (d, J=6.2 Hz, 3H), 1.45 (s, 2H), 1.43 (s, 2H), 1.38 (s, 3H), 1.06 (s, 9H), 0.91 (d, J=6.1 Hz, 3H), 0.89 (d, J=6.2 Hz, 3H). C$_{37}$H$_{50}$F$_3$N$_5$O$_6$S calcd. m/z=763.36 found [M+H]$^+$=764.45.

Example 3.76: (S,E)-N-(4-(1-Aminocyclopropyl)phenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2,2,2-trifluoro-N-(1-(4-sulfamoylphenyl)cyclopropyl)acetamide using General Procedures 9, 10 and 12. $^1$H NMR (400 MHz, Methanol-d$_4$) δ 8.13 (d, J=8.5 Hz, 2H), 7.66 (d, J=8.6 Hz, 2H), 7.55 (d, J=7.2 Hz, 2H), 7.47 (t, J=7.6 Hz, 2H), 7.37 (t, J=7.2 Hz, 1H), 6.50 (dd, J=9.4, 1.7 Hz, 1H), 5.02 (t, J=10.0 Hz, 1H), 4.93 (d, J=4.9 Hz, 1H), 4.38 (s, 1H), 3.16 (s, 3H), 2.51 (s, 3H), 2.12-1.99 (m, 1H), 1.84 (d, J=1.4 Hz, 3H), 1.51-1.46 (m, 5H), 1.46-1.42 (m, 2H), 1.38 (s, 3H), 1.07 (s, 9H), 0.91 (dd, J=6.7, 1.7 Hz, 6H). C$_{36}$H$_{53}$N$_5$O$_5$S calcd. m/z=667.38 found [M+H]$^+$=668.40.

Example 3.77: (S,E)-2,5-Dimethyl-N-(2-methylbenzylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 2-methylbenzylsulfonamide using General Procedures 9 and 12. $^1$H NMR (400 MHz, Methanol-d$_4$) δ 7.61-7.52 (m, 2H), 7.48 (t, J=7.6 Hz, 2H), 7.37 (t, J=7.3 Hz, 1H), 7.30-7.23 (m, 3H), 7.22-7.14 (m, 1H), 6.48 (dd, J=9.3, 1.7 Hz, 1H), 5.08 (t, J=10.0 Hz, 1H), 4.94 (s, 1H), 4.81 (s, 2H), 4.34 (s, 1H), 3.15 (s, 3H), 2.51 (s, 3H), 2.48 (s, 3H), 2.08-2.00 (m, 1H), 1.98 (d, J=1.1 Hz, 3H), 1.49 (s, 3H), 1.40 (s, 3H), 1.10 (s, 9H), 0.93 (d, J=6.6 Hz, 3H), 0.91 (d, J=6.6 Hz, 3H). C$_{35}$H$_{52}$N$_4$O$_5$S calcd. m/z=640.37 found [M+H]+=641.41.

Example 3.78: (S,E)-2,5-Dimethyl-N-(4-nitrobenzylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 4-nitrobenzylsulfonamide using General Procedures 9 and 12. $^1$H NMR (400 MHz, Methanol-d$_4$) δ 8.18 (d, J=8.7 Hz, 2H), 7.64 (d, J=8.7 Hz, 2H), 7.52 (d, J=7.5 Hz, 2H), 7.42 (t, J=7.7 Hz, 2H), 7.31 (t, J=7.3 Hz, 1H), 6.55 (d, J=9.4 Hz, 1H), 5.04 (t, J=10.0 Hz, 1H), 4.92 (s, 1H), 4.63 (s, 2H), 3.08 (s, 3H), 2.32 (s, 3H), 1.95 (dt, J=11.4, 6.6 Hz, 4H), 1.89 (d, J=1.4 Hz, 3H), 1.46 (s, 3H), 1.38 (s, 3H), 1.05 (s, 9H), 0.89 (d, J=6.5 Hz, 3H), 0.85 (d, J=6.5 Hz, 3H). C$_{34}$H$_{49}$N$_5$O$_7$S calcd. m/z=671.34 found [M+H]$^+$=672.36.

Example 3.79: (S,E)-N-(4-Chlorobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 4-chlorobenzylsulfonamide using General Procedures 9 and 12. $^1$H NMR (400 MHz, Methanol-d$_4$) δ 7.56 (d, J=7.9 Hz, 2H), 7.48 (t, J=7.6 Hz, 2H), 7.44-7.34 (m, 5H), 6.39 (d, J=9.5 Hz, 1H), 5.06 (t, J=10.0 Hz, 1H), 4.94 (s, 1H), 4.75 (s, 2H), 4.35 (s, 1H), 3.13 (s, 3H), 2.51 (s, 3H), 2.06-1.95 (m, 1H), 1.95 (d, J=1.4 Hz, 3H), 1.49 (s, 3H), 1.39 (s, 3H), 1.09 (s, 9H), 0.91 (d, J=6.1 Hz, 3H), 0.89 (d, J=5.9 Hz, 3H). C$_{34}$H$_{49}$ClN$_4$O$_5$S calcd. m/z=660.31 found [M+H]$^+$=661.32.

Example 3.80: (S,E)-2,5-Dimethyl-N-(phenethylsulfonyl)-4-((S)—N,3,3-trimethyl-2-((S)-3-methyl-2-(methylamino)-3-phenylbutanamido)butanamido)hex-2-enamide Title compound was prepared from Example 3.16 and homobenzylsulfonamide using General Procedures 9 and 12. $^1$H NMR (400 MHz, Methanol-d$_4$) δ 7.56 (d, J=7.6 Hz, 2H), 7.48 (t, J=7.5 Hz, 2H), 7.38 (t, J=7.4 Hz, 1H), 7.34-7.28 (m, 2H), 7.28-7.20 (m, 3H), 6.47 (dd, J=9.2, 1.7 Hz, 1H), 5.03 (t, J=10.0 Hz, 1H), 4.94 (s, 1H), 4.36 (d, J=2.3 Hz, 2H), 3.78 (td, J=7.5, 4.1 Hz, 2H), 3.17 (s, 3H), 3.12 (t, J=7.8 Hz, 2H), 2.51 (s, 3H), 2.14-2.01 (m, 1H), 1.89 (d, J=1.4 Hz, 3H), 1.49 (s, 3H), 1.39 (s, 3H), 1.09 (s, 9H), 0.94 (d, J=6.6 Hz, 3H), 0.91 (d, J=6.6 Hz, 3H). C$_{35}$H$_{52}$N$_4$O$_5$S calcd. m/z=640.37 found [M+H]$^+$=641.36.

Example 3.81: (S,E)-N-(4-Bromobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 4-bromobenzylsulfonamide using General Procedures 9 and 12. $^1$H NMR (400 MHz, Methanol-d$_4$) δ 7.60-7.51 (m, 4H), 7.48 (t, J=7.7 Hz, 2H), 7.39 (s, 1H), 7.31 (d, J=8.3 Hz, 2H), 6.38 (d, J=9.3 Hz, 1H), 5.06 (t, J=10.0 Hz, 1H), 4.93 (s, 1H), 4.74 (s, 2H), 4.36 (s, 1H), 3.13 (s, 3H), 2.52 (s, 3H), 2.03-1.98 (m, 1H), 1.95 (d, J=1.4 Hz, 3H), 1.49 (s, 3H), 1.39 (s, 3H), 1.09 (s, 9H), 0.91 (d, J=6.1 Hz, 3H), 0.89 (d, J=6.3 Hz, 3H) C$_{34}$H$_{49}$BrN$_4$O$_5$S calcd. m/z=704.26 found [M+H]$^+$= 705.23.

Example 3.82: (S,E)-N-(4-Cyanobenzylsulfonyl)-2, 5-dimethyl-4-((S)—N,3,3-trimethyl-2-((S)-3-methyl-2-(methylamino)-3-phenylbutanamido)butanamido) hex-2-enamide Title compound was prepared from Example 3.16 and 4-cyanobenzylsulfonamide using General Procedures 9 and 12. $^1$H NMR (400 MHz, Methanol-$d_4$) δ 7.77 (d, J=8.3 Hz, 2H), 7.64-7.53 (m, 4H), 7.48 (t, J=7.7 Hz, 2H), 7.38 (t, J=7.3 Hz, 1H), 6.41 (dd, J=9.3, 1.7 Hz, 1H), 5.05 (t, J=10.0 Hz, 1H), 4.94 (s, 1H), 4.87 (s, 2H), 4.36 (s, 1H), 3.14 (s, 3H), 2.52 (s, 3H), 2.06-1.98 (m, 1H), 1.95 (d, J=1.4 Hz, 3H), 1.49 (s, 3H), 1.39 (s, 3H), 1.09 (s, 9H), 0.91 (d, J=4.0 Hz, 3H), 0.90 (d, J=4.0 Hz, 3H). $C_{35}H_{49}N_5O_5S$ calcd. m/z=651.35 found [M+H]$^+$=652.38.

Example 3.83: (S,E)-2,5-Dimethyl-N-(3-nitrobenzylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 3-nitrobenzylsulfonamide using General Procedures 9 and 12. $^1$H NMR (400 MHz, Methanol-$d_4$) δ 8.29 (d, J=8.0 Hz, 1H), 8.26 (s, 1H), 7.83 (d, J=7.8 Hz, 1H), 7.67 (t, J=8.0 Hz, 1H), 7.56 (d, J=7.2 Hz, 2H), 7.48 (t, J=7.7 Hz, 2H), 7.38 (t, J=7.3 Hz, 1H), 6.43 (dd, J=9.4, 1.7 Hz, 1H), 5.05 (t, J=10.0 Hz, 1H), 4.93 (s, 2H), 4.93 (s, 1H), 4.36 (s, 1H), 3.13 (s, 3H), 2.52 (s, 3H), 2.08-1.98 (m, 1H), 1.96 (d, J=1.4 Hz, 3H), 1.48 (s, 3H), 1.39 (s, 3H), 1.07 (s, 9H), 0.89 (d, J=6.6 Hz, 3H), 0.88 (d, J=6.6 Hz, 3H). $C_{34}H_{49}N_5O_7S$ calcd. m/z=671.34 found [M+H]$^+$=672.39.

Example 3.84: (S,E)-N-(4-tert-Butylbenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 4-t-butylbenzylsulfonamide using General Procedures 9 and 12. $^1$H NMR (400 MHz, Methanol-$d_4$) δ 7.56 (d, J=7.6 Hz, 2H), 7.48 (t, J=7.7 Hz, 2H), 7.43 (d, J=8.2 Hz, 2H), 7.38 (t, J=7.3 Hz, 1H), 7.30 (d, J=8.2 Hz, 2H), 6.39 (dd, J=9.4, 1.6 Hz, 1H), 5.07 (t, J=10.0 Hz, 1H), 4.93 (s, 1H), 4.72 (s, 2H), 4.37 (s, 1H), 3.13 (s, 3H), 2.52 (s, 3H), 2.06-1.98 (m, 1H), 1.96 (d, J=1.4 Hz, 3H), 1.49 (s, 3H), 1.39 (s, 3H), 1.33 (s, 9H), 1.10 (s, 9H), 0.92 (d, J=6.6 Hz, 3H), 0.89 (d, J=6.5 Hz, 3H). $C_{38}H_{58}N_4O_5S$ calcd. m/z=682.41 found [M+H]$^+$=683.47.

Example 3.85: (S,E)-2,5-Dimethyl-N-(2-nitrobenzylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 2-nitrobenzylsulfonamide using General Procedures 9 and 12. $^1$H NMR (400 MHz, Methanol-$d_4$) δ 8.03 (dd, J=8.0, 1.4 Hz, 1H), 7.72 (td, J=7.5, 1.5 Hz, 1H), 7.65 (td, J=7.7, 1.6 Hz, 1H), 7.60 (dd, J=7.6, 1.6 Hz, 1H), 7.56 (d, J=7.2 Hz, 2H), 7.48 (t, J=7.7 Hz, 2H), 7.38 (t, J=7.3 Hz, 1H), 6.43 (dd, J=9.4, 1.6 Hz, 1H), 5.31 (d, J=14.2 Hz, 1H), 5.26 (d, J=15.3 Hz, 1H), 5.06 (t, J=10.0 Hz, 1H), 4.94 (s, 1H), 4.37 (s, 1H), 3.15 (s, 3H), 2.52 (s, 3H), 2.08-1.98 (m, 1H), 1.96 (d, J=1.4 Hz, 3H), 1.49 (s, 3H), 1.39 (s, 3H), 1.10 (s, 9H), 0.92 (d, J=6.6 Hz, 3H), 0.90 (d, J=6.6 Hz, 3H). $C_{34}H_{49}N_5O_7S$ calcd. m/z=671.34 found [M+H]$^+$=672.39.

Example 3.86: (S,E)-2,5-Dimethyl-N-(4-nitrophenethylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 4-nitro-homobenzylsulfonamide using General Procedures 9 and 12. $^1$H NMR (400 MHz, Methanol-$d_4$) δ 8.19 (d, J=8.7 Hz, 2H), 7.58-7.51 (m, 4H), 7.47 (t, J=7.6 Hz, 2H), 7.37 (t, J=7.3 Hz, 1H), 6.47 (dd, J=9.5, 1.7 Hz, 1H), 5.00 (t, J=10.0 Hz, 1H), 4.93 (s, 1H), 4.36 (s, 1H), 3.91 (dd, J=14.9, 8.5 Hz, 1H), 3.84 (dd, J=12.9, 8.5 Hz, 1H), 3.28 (t, J=7.5 Hz, 2H), 3.16 (s, 3H), 2.51 (s, 3H), 2.12-1.98 (m, 1H), 1.87 (d, J=1.4 Hz, 3H), 1.48 (s, 3H), 1.39 (s, 3H), 1.08 (s, 9H), 0.91 (d, J=6.6 Hz, 3H), 0.91 (d, J=6.6 Hz, 3H). $C_{35}H_{51}N_5O_7S$ calcd. m/z=685.35 found [M+H]$^+$=686.38.

Example 3.87: Methyl 4-Chloro-3-(N—((S,E)-2,5-dimethyl-4-((S)—N,3,3-trimethyl-2-((S)-3-methyl-2-(methylamino)-3-phenylbutanamido)butanamido) hex-2-enoyl)sulfamoyl)benzoate Title compound was prepared from Example 3.16 and methyl 4-chloro-3-sulfamoylbenzoate using General Procedures 9 and 12. $^1$H NMR (400 MHz, Methanol-$d_4$) δ 8.80 (d, J=2.1 Hz, 1H), 8.20 (dd, J=8.3, 2.1 Hz, 1H), 7.71 (d, J=8.3 Hz, 1H), 7.59-7.52 (m, 2H), 7.47 (t, J=7.7 Hz, 2H), 7.40-7.32 (m, 1H), 6.63-6.56 (m, 1H), 5.02 (t, J=10.0 Hz, 1H), 4.37 (s, 1H), 3.98 (s, 3H), 3.18 (s, 3H), 2.51 (s, 3H), 2.13-2.00 (m, 1H), 1.86 (d, J=1.4 Hz, 3H), 1.47 (s, 3H), 1.37 (s, 3H), 1.06 (s, 9H), 0.96-0.87 (m, 6H). $^{13}$C NMR (101 MHz, Methanol-$d_4$) δ 170.87, 165.65, 164.87, 143.61, 137.01, 136.04, 134.29, 133.23, 131.81, 129.16, 128.98, 128.88, 127.50, 125.98, 69.81, 65.53, 57.39, 56.35, 56.15, 55.37, 51.86, 40.70, 34.51, 32.77, 30.80, 29.39, 28.44, 26.18, 25.56, 20.06, 18.40, 14.06, 12.74. $C_{35}H_{49}ClN_4O_7S$ calcd. m/z=704.30 amu; found [M+H]$^+$=705.25, [M+Na]+=727.25.

Example 3.88: 2,2,2-Trifluoro-N-(4-(sulfamoylmethyl)benzyl)acetamide

The title compound was synthesized from commercially available (4-(aminomethyl)phenyl)methanesulfonamide and TFAA using General Procedure 8. $^1$H NMR (400 MHz, Acetone-$d_6$) δ 9.05 (s, 1H), 7.48-7.40 (m, 2H), 7.40-7.32 (m, 2H), 6.17 (s, 1H), 4.56 (d, J=6.1 Hz, 2H), 4.35 (s, 2H).

Example 3.89: (S,E)-2,5-Dimethyl-N-(4-((2,2,2-trifluoroacetamido)methyl)benzylsulfonyl)-4-((S)—N,3,3-trimethyl-2-((S)-3-methyl-2-(methylamino)-3-phenylbutanamido)butanamido)hex-2-enamide Title compound was prepared from Example 3.16 and Example 3.88 using General Procedures 9 and 12. $^1$H NMR (400 MHz, Methanol-$d_4$) δ 7.57-7.49 (m, 2H), 7.45 (t, J=7.5 Hz, 2H), 7.33 (p, J=8.8, 7.9 Hz, 5H), 6.37 (d, J=9.7 Hz, 1H), 5.09-5.00 (m, 1H), 4.69 (s, 2H), 4.44 (s, 2H), 4.30 (s, 1H), 3.10 (s, 3H), 2.45 (d, J=17.5 Hz, 3H), 2.02-1.87 (m, 4H), 1.46 (s, 3H), 1.37 (s, 3H), 1.07 (s, 9H), 0.95-0.81 (m, 6H). $^{19}$F NMR (377 MHz, Methanol-$d_4$) δ −76.94, −77.24. $C_{37}H_{52}F_3N_5O_6S$ calcd. m/z=751.36 amu; found [M+H]$^+$=752.46, [M+Na]+=774.38.

Example 3.90: (S,E)-N-(4-(Aminomethyl)benzylsulfonyl)-2,5-dimethyl-4-((S)—N,3,3-trimethyl-2-((S)-3-methyl-2-(methylamino)-3-phenylbutanamido)butanamido)hex-2-enamide Prepared from Example 3.16 and Example 3.88 using General Procedures 9, 10 and 12 $^1$H NMR (400 MHz, Methanol-$d_4$) δ 7.60-7.54 (m, 2H), 7.54-7.50 (m, 4H), 7.47 (d, J=8.1 Hz, 2H), 7.37 (t, J=7.4 Hz, 1H), 6.49 (dd, J=9.5, 1.5 Hz, 1H), 5.07 (t, J=10.0 Hz, 1H), 4.94 (s, 1H), 4.83 (d, J=14.3 Hz, 1H), 4.79 (d, J=13.9 Hz, 1H), 4.38 (s, 1H), 4.16 (s, 2H), 3.16 (s, 3H), 2.52 (s, 3H), 2.10-2.00 (m, 1H), 1.97 (d, J=1.4 Hz, 3H), 1.49 (s, 3H), 1.40 (s, 3H), 1.10 (s, 9H), 0.93 (d, J=6.9 Hz, 3H), 0.91 (d, J=7.0 Hz, 3H). $C_{35}H_{53}N_5O_5S$ calcd. m/z=655.4; found [M+H]$^+$=656.3, [M+2H]2+=328.8.

Example 3.91: 2,2,2-Trifluoro-N-(4-(sulfamoylmethyl)phenyl)acetamide

The title compound was synthesized from commercially available (4-aminophenyl)methanesulfonamide and TFAA using General Procedure 8. $^1$H NMR (400 MHz, DMSO-$d_6$) δ 11.31 (s, 1H), 7.79-7.51 (m, 2H), 7.51-7.23 (m, 2H), 6.85 (s, 2H), 4.27 (s, 2H).

Example 3.92: (S,E)-2,5-Dimethyl-N-(4-(2,2,2-trifluoroacetamido)benzylsulfonyl)-4-((S)—N,3,3-trimethyl-2-((S)-3-methyl-2-(methylamino)-3-phenylbutanamido)butanamido)hex-2-enamide Title compound was prepared from Example 3.16 and Example 3.91 using General Procedures 9 and 12. $^1$H NMR (400 MHz, Methanol-$d_4$) δ 7.68 (d, J=8.6 Hz, 2H), 7.54 (d, J=7.1 Hz, 2H), 7.45 (t, J=7.6 Hz, 2H), 7.37 (dd, J=10.6, 5.0 Hz, 3H), 6.34 (d, J=9.4 Hz, 1H), 5.04 (t, J=10.1 Hz, 2H), 4.74 (s, 2H), 4.35 (s, 1H), 3.10 (s, 3H), 2.49 (s, 3H), 2.02-1.94 (m, 1H), 1.93 (d, J=1.4 Hz, 3H), 1.46 (s, 3H), 1.37 (s, 3H), 1.06 (s, 9H), 0.88 (d, J=6.3 Hz, 3H), 0.86 (s, 3H). $^{19}$F NMR (377 MHz, Methanol-$d_4$) δ−76.97, −77.05. $C_{36}H_{50}F_3N_5O_6S$ calcd. m/z=737.34 amu; found [M+H]$^+$=738.38, [M+Na]+=760.35.

Example 3.93: (S,E)-N-(4-Aminobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and Example 3.91 using General Procedures 9, 10 and 12. $^1$H NMR (400 MHz, Methanol-$d_4$) δ 7.56 (d, J=7.6 Hz, 2H), 7.48 (t, J=7.7 Hz, 2H), 7.37 (t, J=7.3 Hz, 1H), 7.20 (d, J=8.5 Hz, 2H), 6.87 (d, J=8.5 Hz, 2H), 6.39 (d, J=9.4 Hz, 1H), 5.07 (t, J=10.0 Hz, 1H), 4.95 (s, 1H), 4.64 (s, 2H), 4.38 (s, 1H), 3.14 (s, 3H), 2.52 (s, 3H), 2.07-1.98 (m, 1H), 1.96 (d, J=1.4 Hz, 3H), 1.49 (s, 3H), 1.39 (s, 3H), 1.10 (s, 9H), 0.92 (d, J=6.7 Hz, 3H), 0.90 (d, J=6.4 Hz, 3H). $C_{34}H_{51}N_5O_5S$ calcd. m/z=641.4; found [M+H]$^+$=642.3.

Example 3.94: 4-(Azidomethyl)benzenesulfonamide

To a stirred solution of 4-(bromomethyl)benzenesulfonamide (0.50 g) in N,N-dimethylformamide (1 mL) was added sodium azide (0.20 g). The suspension was heated to 50° C. for 3 hours at which points the solvent was removed under reduced pressure. The residue was partitioned between ethyl acetate and water. The organic phase was washed with brine, dried over magnesium sulfate, filtered and concentrated to dryness to give the title compound as a syrup that solidified on standing. $^1$H NMR (400 MHz, Chloroform-d) δ 8.06-7.91 (m, 2H), 7.58-7.44 (m, 2H), 4.96 (s, 2H), 4.48 (s, 2H).

Example 3.95: 4-(Aminomethyl)benzenesulfonamide

To a solution of 4-(azidomethyl)benzenesulfonamide (0.354 g) in methanol (10 mL) in a round bottom flask equipped with a magnetic stirrer was added 10% Pd/C (~0.05 g). The flask was evacuated of gases at reduced pressure and charged with hydrogen. This evacuation and charge was repeated three times at which point the suspension was left to stir overnight. At 16 h, TLC analysis indicated complete consumption of the starting material. The reaction was diluted with methanol (40 mL), Celite was added and the mixture was filtered through a fritted glass funnel. The resulting solution was concentrated to dryness. $^1$H NMR suggested that the material was sufficiently clean at this stage for further use without purification. $^1$H NMR (400 MHz, DMSO-$d_6$) δ 7.77 (m, 2H), 7.53 (m, 2H), 5.76 (s, 2H), 3.76 (d, J=11.9 Hz, 2H).

Example 3.96: 2,2,2-Trifluoro-N-(4-sulfamoylbenzyl)acetamide

The title compound was synthesized by reaction of 4-(aminomethyl)benzenesulfonamide with TFAA according to General Procedure 8, with a $^1$H NMR spectrum that was complicated by rotamers. $^1$H NMR (400 MHz, DMSO-$d_6$) δ 7.91-7.75 (m, 2H), 7.55-7.31 (m, 4H), 4.72 (m, 2H), 4.47 (d, J=6.0 Hz, 1H), 3.18 (s, 2H).

Example 3.97: (S,E)-2,5-Dimethyl-N-(4-((2,2,2-trifluoroacetamido)methyl)phenylsulfonyl)-4-((S)—N,3,3-trimethyl-2-((S)-3-methyl-2-(methylamino)-3-phenylbutanamido)butanamido)hex-2-enamide Title compound was prepared from Example 3.16 and Example 3.96 using General Procedures 9 and 12. $^1$H NMR (400 MHz, Methanol-$d_4$) δ 8.02 (d, J=8.5 Hz, 2H), 7.58-7.42 (m, 7H), 7.35 (t, J=7.3 Hz, 1H), 6.46 (d, J=8.5 Hz, 1H), 4.97 (d, J=10.4 Hz, 1H), 4.54 (s, 2H), 4.33 (s, 1H), 3.14 (s, 3H), 2.48 (s, 3H), 2.11-1.97 (m, 1H), 1.83 (d, J=1.4 Hz, 3H), 1.53 (s, 1H), 1.44 (s, 3H), 1.34 (s, 3H), 1.04 (s, 9H), 0.89 (d, J=3.9 Hz, 3H), 0.88 (d, J=4.1 Hz, 3H). $^{19}$F NMR (377 MHz, Methanol-$d_4$) δ−76.94, −77.26. $C_{36}H_{50}F_3N_5O_6S$ calcd. m/z=737.34 amu; found [M+H]$^+$=738.39, [M+Na]+=760.41

Example 3.98: (S,E)-N-(4-(Aminomethyl)phenylsulfonyl)-2,5-dimethyl-4-((S)—N,3,3-trimethyl-2-((S)-3-methyl-2-(methylamino)-3-phenylbutanamido)butanamido)hex-2-enamide Prepared from Example 3.16 and Example 3.96 using General Procedures 9, 10 and 12 $^1$H NMR (400 MHz, Methanol-$d_4$) δ 8.13 (d, J=8.3 Hz, 2H), 7.68 (d, J=8.3 Hz, 2H), 7.55 (d, J=7.6 Hz, 2H), 7.47 (t, J=7.7 Hz, 2H), 7.37 (t, J=7.3 Hz, 1H), 6.51 (dd, J=9.2, 1.8 Hz, 1H), 5.01 (t, J=10.0 Hz, 1H), 4.37 (s, 1H), 4.24 (s, 2H), 3.17 (s, 3H), 2.51 (s, 3H), 2.13-1.97 (m, 1H), 1.84 (d, J=1.4 Hz, 3H), 1.47 (s, 3H), 1.37 (s, 3H), 1.07 (s, 9H), 0.91 (dd, J=6.7, 2.0 Hz, 7H). $C_{34}H_{51}N_5OS$ calcd. m/z=641.36 amu; found [M+H]$^+$=642.4.

Example 3.99: (S,E)-N-(Benzylsulfonyl)-4-((S)-2-((S)-3-(4-bromophenyl)-3-methyl-2-(methylamino)butanamido)-N,3,3-trimethylbutanamido)-2,5-dimethylhex-2-enamide Title compound was prepared from Example 3.51 and (S,E)-4-((S)-2-amino-N,3,3-trimethylbutanamido)-N-(benzylsulfonyl)-2,5-dimethylhex-2-enamide using General Procedures 11 and 12. $^1$H NMR (400 MHz, Methanol-$d_4$) δ 7.62 (t, J=9.2 Hz, 2H), 7.50-7.43 (m, 2H), 7.38 (d, J=2.2 Hz, 5H), 6.38 (dd, J=9.5, 1.8 Hz, 1H), 5.05 (t, J=10.0 Hz, 1H), 4.92 (s, 1H), 4.75 (d, J=2.2 Hz, 2H), 4.30 (s, 1H), 3.12 (s, 3H), 2.53 (s, 3H), 2.06-1.97 (m, 1H), 1.95 (d, J=1.5 Hz, 3H), 1.47 (s, 3H), 1.39 (s, 3H), 1.09 (s, 9H), 0.94-0.86 (m, 6H). $C_{34}H_{49}BrN_4O_5S$ calcd. m/z=704.26 amu; found [M+H]$^+$=705.29, [M+Na]$^+$=727.36.

Example 3.100: (S,E)-4-((S)-2-((S)-3-(4'-Acetylbiphenyl-4-yl)-3-methyl-2-(methylamino)butanamido)-N,3,3-trimethylbutanamido)-N-(benzylsulfonyl)-2,5-dimethylhex-2-enamide Title compound was prepared according to General Procedure 13 from Boc protected Example 3.99 and 4-acetylphenylboronic acid. $^1$H NMR (400 MHz, Methanol-$d_4$) δ 8.15-8.08 (m, 2H), 7.86-7.76 (m, 4H), 7.66 (dd, J=14.7, 8.4 Hz, 2H), 7.38 (d, J=4.9 Hz, 5H), 6.39 (d, J=9.3 Hz, 1H), 5.05 (t, J=10.1 Hz, 1H), 4.94 (s, 1H), 4.75 (d, J=4.1 Hz, 2H), 4.37 (d, J=16.1 Hz, 1H), 3.13 (d, J=3.4 Hz, 3H), 2.67 (s, 3H), 2.53 (d, J=11.6 Hz, 3H), 2.01 (s, 1H), 1.96 (d, J=1.5 Hz, 3H), 1.54 (d, J=3.7 Hz, 3H), 1.44 (s, 3H), 1.09 (d, J=2.7 Hz, 9H), 0.96-0.83 (m, 6H). $C_{42}H_{56}N_4O_6S$ calcd. m/z=744.39 amu; found [M+H]$^+$=745.42, [M+Na]$^+$=767.36.

Example 3.101: (S,E)-N-(Benzylsulfonyl)-4-((S)-2-((S)-3-(4'-methoxybiphenyl-4-yl)-3-methyl-2-(methylamino)butanamido)-N,3,3-trimethylbutanamido)-2,5-dimethylhex-2-enamide Title compound was prepared according to General Procedure 13 from Boc protected Example 3.99 and 4-methoxyphenylboronic acid. $^1$H NMR (400 MHz, Methanol-$d_4$) δ 7.74-7.53 (m, 6H), 7.38 (d, J=4.7 Hz, 5H), 7.08-6.99 (m, 2H), 6.43-6.35 (m, 1H), 5.06 (s, 1H), 4.94 (s, 1H), 4.75 (d, J=4.1 Hz, 2H), 4.38 (s, 1H), 3.86 (s, 3H), 3.13 (s, 3H), 2.54 (s, 3H), 1.99 (d, J=11.0 Hz, 1H), 1.96 (d, J=1.5 Hz, 3H), 1.51 (s, 3H), 1.43 (s, 3H), 1.09 (s, 9H), 0.96-0.85 (m, J=6.0, 5.1 Hz, 6H). $C_{41}H_{56}N_4O_6S$ calcd. m/z=732.39 amu; found [M+H]$^+$=733.41, [M+Na]$^+$=755.40.

Example 3.102: (S,E)-N-(Benzylsulfonyl)-4-((S)-2-((S)-3-(biphenyl-4-yl)-3-methyl-2-(methylamino)butanamido)-N,3,3-trimethylbutanamido)-2,5-dimethylhex-2-enamide Title compound was prepared according to General Procedure 13 from Boc protected Example 3.99 and phenylboronic acid. $^1$H NMR (400 MHz, Methanol-$d_4$) δ 7.86-7.51 (m, 6H), 7.48 (t, J=7.6 Hz, 2H), 7.43-7.33 (m, 6H), 6.39 (d, J=9.5 Hz, 1H), 5.06 (t, J=10.1 Hz, 1H), 4.94 (s, 1H), 4.75 (d, J=3.3 Hz, 2H), 4.37 (d, J=14.4 Hz, 1H), 3.13 (d, J=3.7 Hz, 3H), 2.55 (d, J=4.5 Hz, 3H), 2.06-1.97 (m, 1H), 1.96 (d, J=1.5 Hz, 3H), 1.52 (s, 3H), 1.44 (s, J=4.5 Hz, 3H), 1.09 (d, J=5.6 Hz, 9H), 0.96-0.83 (m, 6H). $C_{40}H_{54}N_4O_5S$ calcd. m/z=702.38 amu; found [M+H]$^+$=703.40, [M+Na]$^+$=725.45.

Example 3.103: (S,E)-N-(Benzylsulfonyl)-2,5-dimethyl-4-((S)—N,3,3-trimethyl-2-((S)-3-methyl-2-(methylamino)-3-(4-(4-methylstyryl)phenyl)butanamido)butanamido)hex-2-enamide Title compound was prepared according to General Procedure 13 from Boc protected Example 3.99 and (E)-4-methylstyrylboronic acid. $^1$H NMR (400 MHz, Methanol-$d_4$) δ 7.65 (d, J=8.2 Hz, 2H), 7.54 (d, J=8.2 Hz, 2H), 7.47 (d, J=7.8 Hz, 2H), 7.38 (s, 5H), 7.26-7.11 (m, 4H), 6.39 (d, J=9.3 Hz, 1H), 5.06 (t, J=10.0 Hz, 1H), 4.97-4.91 (m, 1H), 4.76 (s, 2H), 4.36 (s, 1H), 3.12 (d, J=8.9 Hz, 3H), 2.54 (s, 3H), 2.37 (s, 3H), 2.05-1.97 (m, 1H), 1.97-1.93 (m, 3H), 1.49 (s, 3H), 1.41 (s, 3H), 1.09 (d, J=3.5 Hz, 9H), 0.91 (tq, J=10.8, 4.9 Hz, 6H). $C_{43}H_{58}N_4O_5S$ calcd. m/z=742.41 amu; found [M+H]$^+$=743.44, [M+Na]$^+$=765.41.

Example 3.104: (S,E)-N-(Benzylsulfonyl)-4-((S)-2-((S)-3-(4-methoxyphenyl)-3-methyl-2-(methylamino)butanamido)-N,3,3-trimethylbutanamido)-2,5-dimethylhex-2-enamide Title compound was prepared according to General Procedure 14 from Boc protected Example 3.99. Major diastereomer: $^1$H NMR (400 MHz, Methanol-$d_4$) δ 7.44 (dd, J=12.9, 8.6 Hz, 2H), 7.40-7.34 (m, 5H), 7.00 (t, J=8.4 Hz, 2H), 6.38 (d, J=9.2 Hz, 1H), 5.05 (t, J=9.9 Hz, 1H), 4.93 (s, 1H), 4.75 (d, J=1.8 Hz, 2H), 4.29 (s, 1H), 3.84 (s, 3H), 3.12 (s, 3H), 2.51 (s, 3H), 2.04-1.98 (m, 1H), 1.95 (d, J=1.4 Hz, 3H), 1.45 (s, 3H), 1.37 (s, 3H), 1.09 (s, 9H), 0.92-0.86 (m, 6H). Minor diastereomer: $^1$H NMR (400 MHz, Methanol-$d_4$) δ 7.44 (dd, J=12.9, 8.6 Hz, 2H), 7.40-7.34 (m, 5H), 7.00 (t, J=8.4 Hz, 2H), 6.38 (d, J=9.2 Hz, 1H), 4.99 (t, J=10.1 Hz, 1H), 4.93 (s, 1H), 4.75 (d, J=1.8 Hz, 2H), 4.26 (s, 1H), 3.82 (s, 3H), 3.11 (s, 3H), 2.47 (s, 3H), 2.04-1.98 (m, 1H), 1.92 (d, J=1.4 Hz, 3H), 1.53 (s, 3H), 1.48 (s, 3H), 0.94 (s, 9H), 0.92-0.86 (m, 6H). $C_{35}H_{52}N_4O_6S$ calcd. m/z=656.36 amu; found [M+H]$^+$=657.35, [M+Na]$^+$=679.25.

Example 3.105: (S,E)-N-(Benzylsulfonyl)-4-((S)-2-((R)-3-(3-methoxyphenyl)-3-methyl-2-(methylamino)butanamido)-N,3,3-trimethylbutanamido)-2,5-dimethylhex-2-enamide Title compound was prepared according to General Procedure 14 from Boc protected (S,E)-N-(benzylsulfonyl)-4-((S)-2-((S)-3-(3-bromophenyl)-3-methyl-2-(methylamino)butanamido)-N,3,3-trimethylbutanamido)-2,5-dimethylhex-2-enamide. The two diastereomeric products resulted from diastereomerically impure starting material and were separable by prep-scale HPLC. Major diastereomer: $^1$H NMR (400 MHz, Methanol-$d_4$) δ 7.51-7.32 (m, 6H), 7.14-7.07 (m, 1H), 7.06 (t, J=2.2 Hz, 1H), 6.98-6.90 (m, 1H), 6.38 (dd, J=9.6, 1.7 Hz, 1H), 4.99 (t, J=10.3 Hz, 1H), 4.93 (s, 1H), 4.75 (d, J=1.8 Hz, 2H), 4.32 (s, 1H), 3.85 (s, 3H), 3.11 (s, 3H), 2.47 (s, 3H), 2.04-1.96 (m, 1H), 1.93 (d, J=1.4 Hz, 3H), 1.54 (s, 3H), 1.47 (s, 3H), 0.96 (s, 9H), 0.89 (dd, J=6.6, 3.4 Hz, 6H). Minor diastereomer: refer to Example 3.106 (immediately following) for $^1$H NMR spectral data. $C_{35}H_{52}N_4O_6S$ calcd. m/z=656.36 amu; found [M+H]$^+$=657.36, [M+Na]$^+$=679.29.

Example 3.106: (S,E)-N-(Benzylsulfonyl)-4-((S)-2-((S)-3-(3-methoxyphenyl)-3-methyl-2-(methylamino)butanamido)-N,3,3-trimethylbutanamido)-2,5-dimethylhex-2-enamide Title compound was prepared according to Example 3.105. The two diastereomeric products resulted from diastereomerically impure starting material and were separable by prep-scale HPLC. ¹H NMR (400 MHz, Methanol-d₄) δ 7.39 (d, J=5.5 Hz, 6H), 7.11 (dd, J=4.9, 2.8 Hz, 3H), 6.38 (d, J=9.4 Hz, 1H), 5.06 (d, J=9.5 Hz, 1H), 4.93 (s, 1H), 4.76 (s, 2H), 4.35 (s, 1H), 3.86 (s, 3H), 3.13 (s, 3H), 2.52 (s, 3H), 2.05-1.97 (m, 1H), 1.95 (d, J=1.6 Hz, 3H), 1.46 (s, 3H), 1.38 (s, 3H), 1.09 (s, 9H), 0.90 (t, J=6.6 Hz, 6H). $C_{35}H_{52}N_4O_6S$ calcd. m/z=656.36 amu; found [M+H]⁺=657.36, [M+Na]⁺=679.32.

Example 3.107: (S,E)-N-(Benzylsulfonyl)-4-((S)-2-((S)-3-(4-(2-hydroxyethoxy)phenyl)-3-methyl-2-(methylamino)butanamido)-N,3,3-trimethylbutanamido)-2,5-dimethylhex-2-enamide Title compound was prepared as follows: a mixture of Boc protected Example 3.99, CuI (10 mol %), 3,4,7,8-tetramethyl-1,10-phenanthroline (20 mol %), Cs₂CO₃ (2.5 eq), and ethylene glycol (90 eq) was stirred under N₂ at 130° C. for 20 h. The resulting mixture was diluted with H₂O, carefully acidified with 1M citric acid and extracted with CH₂Cl₂ (5×). The organics were combined, washed with brine (1×), dried over MgSO₄, filtered, concentrated in vacuo and purified via silica gel column chromatography (eluted with AcOH/EtOAc/hexanes mixtures) to afford the cross-coupled product which was subsequently deprotected and purified according to General Procedure 12. ¹H NMR (400 MHz, Methanol-d₄) δ 7.46 (d, J=8.8 Hz, 2H), 7.38 (d, J=2.5 Hz, 5H), 7.05 (d, J=8.4 Hz, 2H), 6.38 (d, J=9.5 Hz, 1H), 5.05 (t, J=10.1 Hz, 1H), 4.93 (s, 1H), 4.76 (s, 2H), 4.28 (d, J=11.0 Hz, 1H), 4.13-4.04 (m, 2H), 3.90 (t, J=4.6 Hz, 2H), 3.12 (d, J=6.2 Hz, 3H), 2.50 (d, J=16.9 Hz, 3H), 2.05-1.97 (m, 1H), 1.94 (d, J=11.0 Hz, 3H), 1.56-1.34 (m, 6H), 1.09 (s, 9H), 0.90 (t, J=6.4 Hz, 6H). $C_{36}H_{54}N_4O_7S$ calcd. m/z=686.37 amu; found [M+H]⁺=687.42, [M+Na]⁺=709.37.

Example 3.108: S-2-(4-((S)-4-((S)-1-(((S,E)-2,5-Dimethyl-6-oxo-6-(benzylsulfonamido)hex-4-en-3-yl)(methyl)amino)-3,3-dimethyl-1-oxobutan-2-ylamino)-2-methyl-3-(methylamino)-4-oxobutan-2-yl)phenoxy)ethyl Ethanethioate Title compound was prepared as follows: Tributylphosphine (6 eq) was added to a cold (0° C.) stirring solution of di-tert-butyl azodicarboxylate (6 eq) in THF. After 0.5 h, a solution of the Boc protected Example 3.107 (1 eq) in THF was added, followed by a solution of AcSH (4.5 eq) in THF. The pale yellow mixture was stirred at 0° C. for 1 h then at ambient temperature for 23 h. The resulting mixture was concentrated in vacuo, dissolved in EtOAc and successively washed with 1M HCl (2×), sat'd NH₄Cl (1×) and brine (1×). The organics were dried over MgSO₄, filtered, concentrated in vacuo and purified via silica gel column chromatography (eluted with AcOH/EtOAc/hexanes mixtures) to afford the Boc-protected thioacetate product (HPLC/MS-[M+Na]⁺=867.47). The thioacetate was dissolved in CH₂Cl₂ and treated with TFA. After stirring for 1 h, the reaction mixture was concentrated in vacuo. The yellow/brown residue was dissolved in minimal amount of CH₂Cl₂, cooled to 0° C. and treated with ether to precipitate out the desired aminothioacetate as an off-white solid in 10% yield over two synthetic steps. ¹H NMR (400 MHz, Methanol-d₄) δ 7.46 (d, J=8.7 Hz, 2H), 7.38 (d, J=2.4 Hz, 5H), 7.03 (d, J=8.6 Hz, 2H), 6.38 (d, J=9.5 Hz, 1H), 5.05 (t, J=10.0 Hz, 1H), 4.93 (s, 1H), 4.75 (s, 2H), 4.27 (d, J=11.4 Hz, 1H), 4.14 (t, J=6.6 Hz, 2H), 3.28 (t, J=6.6 Hz, 2H), 3.11 (d, J=6.6 Hz, 3H), 2.49 (d, J=15.5 Hz, 3H), 2.38 (s, 3H), 2.05-1.97 (m, 1H), 1.95 (s, 3H), 1.45 (s, 3H), 1.37 (s, 3H), 1.08 (s, 9H), 0.96-0.85 (m, 6H). $C_{38}H_{56}N_4O_7S_2$ calcd. m/z=744.36 amu; found [M+H]⁺=745.39, [M+Na]⁺=777.32.

Example 3.109: (S,E)-4-((S)-2-((S)-3-(4-(2-Aminoethoxy)phenyl)-3-methyl-2-(methylamino)butanamido)-N,3,3-trimethylbutanamido)-N-(benzylsulfonyl)-2,5-dimethylhex-2-enamide Title compound was prepared as follows: Et₃N (4 eq) was added to a cold (0° C.) stirring solution of MsCl (3.7 eq) in CH₂Cl₂. After 2 min, a solution of the Boc protected Example 3.107 in CH₂Cl₂ was added. The pale yellow mixture was stirred cold for 5 min and then at ambient temperature for 72 h. The resulting mixture was dilute with EtOAc and successively washed with 1M citric acid (1×), 1M NaHCO₃ (1×) and brine (1×). The organics were dried over MgSO₄, filtered and concentrated in vacuo to afford the mesylated-alcohol (HPLC/MS-[M+Na]⁺=887.42) which was used in the next step without further purification.

The mesylate was dissolved in DMF and treated with NaN₃ (7 eq). The resulting suspension was stirred at ambient temperature for 18 h and then at 60° C. for 5 h. The reaction mix was diluted with H₂O, acidified with 1M HCl and extracted with CH₂Cl₂ (4×). The combined organics were dried over MgSO₄, filtered and concentrated in vacuo to afford the azido product (HPLC/MS-[M+Na]⁺=834.44) which was used in the next step without further purification.

The azide was dissolved in THF/H₂O (10:1) and treated with tributylphosphine (3.5 eq). The mixture was stirred at ambient temperature for 21 h and then concentrated in vacuo. The resulting residue was dissolved in EtOAc and successively washed with 1M HCl (3×), 1M NaHCO3 (3×), H2O (2×) and brine (2×). The organics were dried over MgSO₄, filtered, concentrated in vacuo and purified via silica gel column chromatography (eluted with MeOH/CH₂Cl₂ mixtures) to afford the primary amine as a white solid (HPLC/MS-[M+H]⁺=786.45).

The amine was dissolved in CH₂Cl₂ and treated with TFA. After stirring for 1 h, the reaction mixture was concentrated in vacuo. The off-white solid residue was dissolved in minimal amount of MeOH, cooled to 0° C. and treated with ether to precipitate out the desired diamine product as an off-white solid in 6% yield over four synthetic steps. ¹H NMR (400 MHz, Methanol-d₄) δ 7.50 (d, J=8.6 Hz, 2H), 7.37 (s, 5H), 7.09 (d, J=8.6 Hz, 2H), 6.41 (d, J=9.4 Hz, 1H), 5.02 (t, J=10.0 Hz, 1H), 4.91 (s, 1H), 4.70 (s, 2H), 4.27 (t, J=5.0 Hz, 2H), 3.40 (t, J=5.0 Hz, 2H), 3.37 (s, 1H), 3.12 (s, 3H), 2.47 (s, 3H), 2.06-1.95 (m, 1H), 1.94 (d, J=1.4 Hz, 3H), 1.45 (s, 3H), 1.37 (s, 3H), 1.08 (s, 9H), 0.89 (dd, J=9.7, 6.6 Hz, 6H). $C_{38}H_{55}N_5O_6S$ calcd. m/z=685.39 amu; found [M+H]⁺=686.32, [M+Na]⁺=708.27, [(M+2H)/2]²⁺=343.77.

Example 3.110: (S,E)-2,5-Dimethyl-N-(2-(2,2,2-trifluoroacetamido)phenylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 2,2,2-trifluoro-N-(2-sulfamoylphenyl)acetamide according to General Procedures 9 and 12. ¹H NMR (400 MHz, Methanol-d₄) δ 8.27 (d, J=8.4 Hz, 1H), 8.05 (d, J=7.8 Hz, 1H), 7.67 (t, J=7.9 Hz, 1H), 7.54 (d, J=8.1 Hz, 2H), 7.48 (t, J=7.7 Hz, 2H), 7.40 (dt, J=13.3, 7.4 Hz, 2H), 6.57 (d, J=9.2 Hz, 1H), 4.92 (s, 2H), 4.34 (s, 1H), 3.17 (s, 3H), 2.50 (s, 3H), 2.06 (m, 1H), 1.87 (d, J=1.3 Hz, 3H), 1.45 (s, 3H), 1.33 (s, 3H), 1.07 (s, 9H), 0.91 (dd, J=6.6, 3.5 Hz, 6H). $^{19}$F NMR (377 MHz, Methanol-d$_4$) δ −76.96, −77.73. C$_{35}$H$_{48}$F$_3$N$_5$O$_6$S calcd. m/z=723.33 amu; found [M+H]$^+$=723.34, [M+Na]+=746.23.

Example 3.111: (S,E)-N-(2-Aminophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2,2,2-trifluoro-N-(2-sulfamoylphenyl)acetamide according to General Procedures 9, 10 and 12. $^1$H NMR (400 MHz, Methanol-d$_4$) δ 7.75 (dd, J=8.2, 1.5 Hz, 1H), 7.55 (d, J=7.8 Hz, 2H), 7.48 (t, J=7.7 Hz, 2H), 7.38 (t, J=7.4 Hz, 1H), 7.33-7.27 (m, 1H), 6.81 (d, J=8.2 Hz, 1H), 6.69 (t, J=7.5 Hz, 1H), 6.49 (dd, J=9.1, 1.5 Hz, 1H), 4.97 (t, J=10.1 Hz, 1H), 4.92 (s, 1H), 4.35 (s, 1H), 3.17 (s, 3H), 2.51 (s, 3H), 2.07 (m, 1H), 1.88 (d, J=1.4 Hz, 3H), 1.46 (s, 3H), 1.36 (s, 3H), 1.06 (s, 9H), 0.92 (t, J=6.8 Hz, 6H). C$_{33}$H$_{49}$N$_5$O$_5$S calcd. m/z=627.35 amu; found [M+H]$^+$=628.36, [M+Na]+=650.37, [(M+2H)/2]$^{2+}$=314.76.

Example 3.112: (S,E)-N-(Biphenyl-4-ylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared using from Boc protected Example 3.69 with phenylboronic acid according to General Procedures 13 and 12. $^1$H NMR (400 MHz, Methanol-d$_4$) δ 8.12 (d, J=8.3 Hz, 2H), 7.83 (d, J=8.4 Hz, 2H), 7.71 (d, J=7.7 Hz, 2H), 7.52 (dd, J=11.6, 7.6 Hz, 4H), 7.45 (t, J=7.3 Hz, 3H), 7.36 (t, J=7.2 Hz, 1H), 6.52 (d, J=9.4 Hz, 1H), 4.96 (t, J=9.5 Hz, 1H), 4.92 (s, 1H), 4.33 (s, 1H), 3.18 (s, 3H), 2.50 (s, 3H), 2.14-2.03 (m, 1H), 1.88 (s, 3H), 1.45 (s, 3H), 1.35 (s, 3H), 1.07 (s, 9H), 0.92 (t, J=6.9 Hz, 6H). C$_{39}$H$_{52}$N$_4$O$_5$S calcd. m/z=688.37 amu; found [M+H]$^+$=689.10, [M+Na]$^+$=711.32.

Example 3.113: (S,E)-N-(4'-Aminobiphenyl-4-ylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Boc protected Example 3.81 with 4-(tert-butoxycarbonylamino)phenylboronic acid according to General Procedures 13 and 12. $^1$H NMR (400 MHz, Methanol-d$_4$) δ 8.05 (d, J=8.6 Hz, 2H), 7.75 (d, J=8.6 Hz, 2H), 7.59-7.51 (m, 4H), 7.45 (t, J=7.7 Hz, 2H), 7.36 (t, J=7.3 Hz, 1H), 6.91 (d, J=8.3 Hz, 2H), 6.50 (d, J=9.1 Hz, 1H), 4.98-4.92 (m, 1H), 4.91 (s, 1H), 4.34 (s, 1H), 3.18 (s, 3H), 2.50 (s, 3H), 2.13-2.03 (m, 1H), 1.88 (d, J=1.4 Hz, 3H), 1.45 (s, 3H), 1.35 (s, 3H), 1.06 (s, 9H), 0.92 (t, J=6.2 Hz, 6H). C$_{39}$H$_{53}$N$_5$O$_5$S calcd. m/z=703.38 amu; found [M+H]$^+$=704.26, [M+Na]+=726.41, [(M+2H)/2]$^{2+}$=352.77.

Example 3.114: (S,E)-N-(4-Fluorobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 4-fluorobenzylsulfonamide according to General Procedures 9 and 12. $^1$H NMR (400 MHz, Methanol-d$_4$) δ 7.60-7.52 (m, 2H), 7.48 (t, J=7.7 Hz, 2H), 7.44-7.34 (m, 3H), 7.18-7.05 (m, 2H), 6.41 (dd, J=9.5, 1.7 Hz, 1H), 5.06 (t, J=10.0 Hz, 1H), 4.94 (s, 1H), 4.74 (s, 2H), 4.35 (s, 1H), 3.13 (s, 3H), 2.51 (s, 3H), 2.07-1.97 (m, 1H), 1.95 (d, J=1.4 Hz, 3H), 1.48 (s, 3H), 1.39 (s, 3H), 1.09 (s, 9H), 0.90 (t, J=6.3 Hz, 6H). C$_{34}$H$_{49}$FN$_4$O$_5$S calcd. m/z=644.34 found [M+H]$^+$=645.32.

Example 3.115: (S,E)-2,5-Dimethyl-N-(3-(trifluoromethyl)benzylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 3-trifluorobenzylsulfonamide according to General Procedures 9 and 12. $^1$H NMR (400 MHz, Methanol-d$_4$) δ 7.74-7.64 (m, 3H), 7.61 (d, J=7.7 Hz, 1H), 7.60-7.54 (m, 2H), 7.48 (t, J=7.7 Hz, 2H), 7.38 (t, J=7.3 Hz, 1H), 6.42 (dd, J=9.4, 1.7 Hz, 1H), 5.06 (t, J=10.0 Hz, 1H), 4.93 (s, 1H), 4.36 (s, 1H), 3.13 (s, 3H), 2.51 (s, 3H), 2.07-1.97 (m, 1H), 1.95 (d, J=1.4 Hz, 3H), 1.48 (s, 3H), 1.39 (s, 3H), 1.08 (s, 9H), 0.89 (d, J=6.5 Hz, 6H). C$_{35}$H$_{49}$F$_3$N$_4$O$_5$S calcd. m/z=694.34 found [M+H]$^+$=695.38.

Example 3.116: (S,E)-2,5-Dimethyl-N-(3-(trifluoromethoxy)benzylsulfonyl)-4-((S)—N,3,3-trimethyl-2-((S)-3-methyl-2-(methylamino)-3-phenylbutanamido)butanamido)hex-2-enamide Title compound was prepared from Example 3.16 and 3-trifluoromethoxybenzylsulfonamide according to General Procedures 9 and 12. $^1$H NMR (400 MHz, Methanol-d$_4$) δ 7.56 (d, J=7.8 Hz, 2H), 7.48 (t, J=7.9 Hz, 3H), 7.43-7.36 (m, 2H), 7.32 (d, J=9.3 Hz, 2H), 6.43 (dd, J=9.4, 1.7 Hz, 1H), 5.06 (t, J=10.0 Hz, 1H), 4.93 (s, 1H), 4.82 (s, 2H), 4.35 (s, 1H), 3.13 (s, 3H), 2.51 (s, 3H), 2.07-1.97 (m, 1H), 1.95 (d, J=1.4 Hz, 3H), 1.48 (s, 3H), 1.39 (s, 3H), 1.08 (s, 9H), 0.90 (dd, J=6.6, 4.3 Hz, 6H). C$_{35}$H$_{49}$F$_3$N$_4$O$_6$S calcd. m/z=710.33 found [M+H]$^+$=711.38.

Example 3.117: (S,E)-N-(3,4-Dichlorobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 3,4-dichlorobenzylsulfonamide according to General Procedures 9 and 12. $^1$H NMR (400 MHz, Methanol-d$_4$) δ 7.56 (td, J=5.2, 4.5, 1.9 Hz, 4H), 7.48 (t, J=7.7 Hz, 2H), 7.38 (t, J=7.3 Hz, 1H), 7.33 (dd, J=8.4, 2.1 Hz, 1H), 6.41 (dd, J=9.5, 1.8 Hz, 1H), 5.06 (t, J=10.0 Hz, 1H), 4.93 (s, 1H), 4.77 (s, 2H), 4.36 (s, 1H), 3.14 (s, 3H), 2.52 (s, 3H), 2.07-1.97 (m, 1H), 1.95 (d, J=1.4 Hz, 3H), 1.49 (s, 3H), 1.39 (s, 3H), 1.08 (s, 9H), 0.90 (dd, J=6.6, 4.9 Hz, 6H). C$_{34}$H$_{48}$Cl$_2$N$_4$O$_5$S calcd. m/z=694.27 found [M+H]$^+$=695.32.

Example 3.118: (S,E)-N-(2-Cyanobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2-cyanobenzylsulfonamide according to General Procedures 9 and 12. $^1$H NMR (400 MHz, Methanol-d$_4$) δ 7.81 (dd, J=7.7, 1.3 Hz, 1H), 7.72 (td, J=7.7, 1.3 Hz, 1H), 7.66 (d, J=7.7 Hz, 1H), 7.62-7.59 (m, 1H), 7.58-7.53 (m, 2H), 7.48 (t, J=7.7 Hz, 2H), 7.38 (t, J=7.3 Hz, 1H), 6.50 (d, J=9.4 Hz, 1H), 5.08 (dd, J=10.6, 9.3 Hz, 1H), 4.99 (s, 2H), 4.95 (s, 1H), 4.36 (s, 1H), 3.16 (s, 3H), 2.52 (s, 3H), 2.09-1.99 (m, 1H), 1.98 (d, J=1.4 Hz, 3H), 1.49 (s, 3H), 1.39 (s, 3H), 1.10 (s, 9H), 0.94 (d, J=6.6 Hz, 3H), 0.91 (d, J=6.6 Hz, 3H). $C_{35}H_{49}N_5O_5S$ calcd. m/z=651.35 found [M+H]$^+$=652.38.

Example 3.119: (S,E)-N-(3-Chlorobenzylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 3-chlorobenzylsulfonamide according to General Procedures 9 and 12. $^1$H NMR (400 MHz, Methanol-d$_4$) δ 7.58-7.53 (m, 2H), 7.48 (t, J=7.6 Hz, 2H), 7.43-7.34 (m, 4H), 7.32 (d, J=7.5 Hz, 1H), 6.42 (d, J=9.5 Hz, 1H), 5.06 (t, J=10.0 Hz, 1H), 4.94 (s, 1H), 4.74 (s, 2H), 4.33 (s, 1H), 3.13 (s, 3H), 2.50 (s, 3H), 2.07-1.97 (m, 1H), 1.95 (d, J=1.4 Hz, 3H), 1.48 (s, 3H), 1.39 (s, 3H), 1.08 (s, 9H), 0.90 (t, J=7.2 Hz, 6H). $C_{34}H_{49}ClN_4O_5S$ calcd. m/z=660.31 found [M+H]$^+$= 661.32.

Example 3.120: (107) (S,E)-N-(4-Amino-2-ethylphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2-ethylbenzylsulfonamide according to General Procedures 9 and 12. $^1$H NMR (400 MHz, Methanol-d$_4$) δ 7.79 (d, J=8.7 Hz, 1H), 7.55 (d, J=7.9 Hz, 2H), 7.48 (t, J=7.6 Hz, 2H), 7.37 (t, J=7.4 Hz, 1H), 6.57 (d, J=2.3 Hz, 1H), 6.54 (dd, J=8.8, 2.4 Hz, 1H), 6.46 (d, J=9.4 Hz, 1H), 5.01 (t, J=10.0 Hz, 1H), 4.92 (s, 1H), 4.34 (s, 1H), 3.16 (s, 3H), 2.99-2.90 (m, 2H), 2.50 (s, 3H), 2.11-2.00 (m, 1H), 1.87 (d, J=1.4 Hz, 3H), 1.47 (s, 3H), 1.38 (s, 3H), 1.22 (t, J=7.5 Hz, 3H), 1.06 (s, 9H), 0.91 (dd, J=6.6 Hz, 6H). $C_{35}H_{53}N_5O_5S$ calcd. m/z=655.38 found [M+H]$^+$=656.4.

Example 3.121: (S,E)-N-(4-Amino-3-(trifluoromethoxy)phenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2,2,2-trifluoro-N-(4-sulfamoyl-2-(trifluoromethoxy)phenyl)acetamide according to General Procedures 9, 10 and 12. $^1$H NMR (400 MHz, Methanol-d$_4$) δ 7.81-7.75 (m, 1H), 7.71 (dd, J=8.7, 2.1 Hz, 1H), 7.55 (d, J=7.9 Hz, 2H), 7.47 (t, J=7.6 Hz, 2H), 7.37 (t, J=7.1 Hz, 1H), 6.89 (d, J=8.7 Hz, 1H), 6.51-6.42 (m, 1H), 4.98 (t, J=10.0 Hz, 1H), 4.92 (t, J=4.1 Hz, 1H), 4.37 (s, 1H), 3.16 (s, 3H), 2.51 (s, 3H), 2.12-2.01 (m, 1H), 1.88 (d, J=1.4 Hz, 3H), 1.47 (s, 3H), 1.37 (s, 3H), 1.07 (s, 9H), 0.92 (dd, J=6.6 Hz, 6H). $C_{34}H_{48}F_3N_5O_6S$ calcd. m/z=711.33 found [M+H]$^+$=712.4.

Example 3.122: (S,E)-N-(4-Amino-2,3-dimethylphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2,2,2-trifluoro-N-(4-sulfamoyl-2,3-dimethylphenyl)acetamide according to General Procedures 9, 10 and 12. $^1$H NMR (400 MHz, Methanol-d$_4$) δ 7.75 (d, J=8.8 Hz, 1H), 7.55 (d, J=7.9 Hz, 2H), 7.47 (t, J=7.7 Hz, 2H), 7.37 (t, J=6.9 Hz, 1H), 6.63 (d, J=8.8 Hz, 1H), 6.46 (d, J=9.7 Hz, 1H), 5.00 (t, J=10.0 Hz, 1H), 4.93 (s, 1H), 4.32 (s, 1H), 3.17 (s, 3H), 2.54 (s, 3H), 2.49 (s, 3H), 2.09 (s, 3H), 2.08-2.02 (m, 1H), 1.87 (d, J=1.4 Hz, 3H), 1.47 (s, 3H), 1.37 (s, 3H), 1.07 (s, 9H), 0.92 (dd, J=6.8, 6.5 Hz, 6H). $C_{35}H_{53}N_5O_5S$ calcd. m/z=655.38 found [M+H]$^+$=656.4.

Example 3.123: (S,E)-N-(4-Amino-5,6,7,8-tetrahydronaphthalen-1-ylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2,2,2-trifluoro-N-(4-sulfamoyl-5,6,7,8-tetrahydronaphthalen-1-yl)acetamide according to General Procedures 9, 10 and 12. $^1$H NMR (400 MHz, Methanol-d$_4$) δ 7.74 (d, J=8.7 Hz, 1H), 7.55 (d, J=7.9 Hz, 2H), 7.48 (t, J=7.6 Hz, 2H), 7.38 (t, J=7.2 Hz, 1H), 6.60 (d, J=8.7 Hz, 1H), 6.46 (d, J=9.2 Hz, 1H), 5.00 (t, J=10.0 Hz, 1H), 4.95-4.91 (m, 1H), 4.36 (s, 1H), 3.17 (s, 3H), 3.10-3.05 (m, 2H), 2.51 (s, 3H), 2.46 (t, J=6.5 Hz, 2H), 2.10-2.02 (m, 1H), 1.88 (s, 3H), 1.87-1.75 (m, 4H), 1.47 (s, 3H), 1.38 (s, 3H), 1.07 (s, 9H), 0.92 (dd, J=7.1 Hz, 6H). $C_{37}H_{55}N_5O_5S$ calcd. m/z=681.39 found [M+H]$^+$=682.4.

Example 3.124: (S,E)-N-(4-Amino-3-methylphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2,2,2-trifluoro-N-(2-methyl-4-sulfamoylphenyl)acetamide according to General Procedures 9, 10 and 12. $^1$H NMR (400 MHz, Methanol-d$_4$) δ 7.64 (s, 1H), 7.61 (dd, J=8.5, 2.3 Hz, 1H), 7.57-7.51 (m, 2H), 7.48 (t, J=7.7 Hz, 2H), 7.41-7.35 (m, 1H), 6.71 (d, J=8.5 Hz, 1H), 6.43 (dd, J=9.3, 1.6 Hz, 1H), 4.96 (t, J=10.0 Hz, 1H), 4.92 (s, 1H), 4.35 (s, 1H), 3.16 (s, 3H), 2.51 (s, 3H), 2.17 (s, 3H), 2.10-2.01 (m, 1H), 1.87 (d, J=1.4 Hz, 3H), 1.46 (s, 3H), 1.36 (s, 3H), 1.07 (s, 9H), 0.91 (dd, J=6.3 Hz, 6H). $C_{34}H_{51}N_5O_5S$ calcd. m/z=641.36 found [M+H]$^+$=642.4.

Example 3.125: (S,E)-N-(4-Amino-3-fluorophenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2,2,2-trifluoro-N-(2-fluoro-4-sulfamoylphenyl)acetamide according to General Procedures 9, 10 and 12. $^1$H NMR (400 MHz, Methanol-d$_4$) δ 7.62-7.55 (m, 3H), 7.54 (s, 1H), 7.48 (t, J=7.7 Hz, 2H), 7.37 (t, J=7.3 Hz, 1H), 6.85 (t, J=8.6 Hz, 1H), 6.45 (d, J=9.3 Hz, 1H), 4.98 (t, J=9.9 Hz, 1H), 4.92 (s, 1H), 4.34 (s, 1H), 3.16 (s, 3H), 2.50 (s, 3H), 2.12-2.00 (m, 1H), 1.88 (d, J=1.4 Hz, 3H), 1.46 (s, 3H), 1.37 (s, 3H), 1.07 (s, 9H), 0.91 (dd, J=6.8 Hz, 6H). $C_{33}H_{48}FN_5O_5S$ calcd. m/z=645.34 found [M+H]$^+$=646.4.

Example 3.126: (S,E)-N-(4-Amino-3-ethylphenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2,2,2-trifluoro-N-(2-ethyl-4-sulfamoylphenyl)acetamide according to General Procedures 9, 10 and 12. $^1$H NMR (400 MHz, Methanol-d$_4$) δ 7.66 (d, J=2.3 Hz, 1H), 7.61 (dd, J=8.6, 2.3 Hz, 1H), 7.55 (d, J=7.6 Hz, 2H), 7.48 (t, J=7.7 Hz, 2H), 7.37 (t, J=7.3 Hz, 1H), 6.71 (d, J=8.5 Hz, 1H), 6.43 (dd, J=9.3, 1.7 Hz, 1H), 4.96 (t, J=9.9 Hz, 1H), 4.92 (s, 1H), 4.35

(s, 1H), 3.16 (s, 3H), 2.54 (dd, J=7.4, 2.2 Hz, 2H), 2.51 (s, 3H), 2.12-1.99 (m, 1H), 1.87 (d, J=1.4 Hz, 3H), 1.46 (s, 3H), 1.36 (s, 3H), 1.27 (t, J=7.5 Hz, 3H), 1.07 (s, 9H), 0.91 (dd, J=6.4 Hz, 6H) $C_{35}H_{53}N_5O_5S$ calcd. m/z=655.38 found $[M+H]^+$=656.5.

Example 3.127: (S,E)-N-(4-Amino-3-(trifluoromethyl)phenylsulfonyl)-2,5-dimethyl-4-((S)—N,3,3-trimethyl-2-((S)-3-methyl-2-(methylamino)-3-phenylbutanamido)butanamido)hex-2-enamide Title compound was prepared from Example 3.16 and 2,2,2-trifluoro-N-(2-trifluoromethyl-4-sulfamoylphenyl)acetamide according to General Procedures 9, 10 and 12. $^1$H NMR (400 MHz, Methanol-$d_4$) δ 8.04 (s, 1H), 7.87 (d, J=8.8 Hz, 1H), 7.55 (d, J=7.6 Hz, 2H), 7.48 (t, J=7.3 Hz, 2H), 7.36 (dd, J=14.5, 7.4 Hz, 1H), 6.89 (d, J=8.9 Hz, 1H), 6.47 (d, J=9.3 Hz, 1H), 4.99 (t, J=10.2 Hz, 1H), 4.92 (s, 1H), 4.33 (s, 1H), 3.16 (s, 3H), 2.50 (s, 3H), 2.11-2.00 (m, 1H), 1.88 (s, 3H), 1.47 (s, 3H), 1.37 (s, 3H), 1.07 (s, 9H), 0.91 (dd, J=7.0 Hz, 6H). $C_{34}H_{48}F_3N_5O_5S$ calcd. m/z=695.33 found $[M+H]^+$= 696.4.

Example 3.128: (S)-1-Isopropyl-N—((S)-1-(((S,E)-6-(3-mercaptopropylsulfonamido)-2,5-dimethyl-6-oxohex-4-en-3-yl)(methyl)amino)-3,3-dimethyl-1-oxobutan-2-yl)piperidine-2-carboxamide To a solution of (S,E)-ethyl 4-((S)-2-(tert-butoxycarbonylamino)-N,3,3-trimethylbutanamido)-2,5-dimethylhex-2-enoate (0.373 g, 0.905 mmol) in $CH_2Cl_2$ (5 mL) was added trifluoroacetic acid (2 mL). The reaction was monitored by HPLC and upon complete conversion of the starting material concentrated under reduced pressure. N-isopropyl-pipecolic acid (0.200 g, 1.3 equiv) was dissolved in $CH_2Cl_2$ (5 mL) and stirred at 0° C., to which was added HBTU (0.450 g, 1.3 equiv) and N,N-di-isopropylethylamine (0.400 μL, 2.5 equiv). After 10 minutes, the above deprotected dipeptide was added as a solution in $CH_2Cl_2$ (~1 mL). The reaction was monitored by HPLC for complete consumption of the dipeptide at which time the entire reaction was concentrated under reduced pressure. The crude reaction mixture was dissolved in $CH_2Cl_2$ and purified by silica gel chromatography (1-20% MeOH (5% $NH_4OH$) in $CH_2Cl_2$).

The resulting ester was saponified with LiOH in 1,4-dioxane. The resulting carboxylic acid (0.128 g, 0.29 mmol) was dissolved in $CH_2Cl_2$ (5 mL) and to the stirred solution was added dicyclohexylcarbodiimide (0.084 g, 1.4 equiv), N,N-dimethylaminopyridine (0.05 g, 1.4 equiv) and 3-(tritylthio)propane-1-sulfonamide (0.174 g, 1.5 equiv). The resulting mixture was stirred overnight and monitored for reaction progress by HPLC-MS. When the reaction was complete, the mixture was concentrated under reduced pressure and the residue was purified by silica gel chromatography (5-30% MeOH in $CH_2Cl_2$) to give the S-trityl derivative of the parent compound as a colorless oil (0.056 g). $^1$H NMR (400 MHz, Methanol-$d_4$) δ 7.44-7.35 (m, 6H), 7.36-7.15 (m, 9H), 6.56 (dd, J=9.1, 1.7 Hz, 1H), 5.03 (dd, J=10.6, 9.3 Hz, 1H), 4.73 (s, 1H), 4.05 (dd, J=11.5, 3.3 Hz, 1H), 3.51-3.37 (m, 2H), 3.25-3.15 (m, 2H), 3.09 (s, 3H), 2.92 (td, J=12.5, 2.9 Hz, 1H), 2.31 (t, J=7.2 Hz, 2H), 2.18-1.70 (m, 15H), 1.61 (ddt, J=12.8, 8.4, 4.9 Hz, 1H), 1.28 (dd, J=30.1, 6.7 Hz, 7H), 1.04 (s, 9H), 0.88 (dd, J=37.3, 6.5 Hz, 6H).

Finally, the trityl protected thiol was dissolved in $CH_2Cl_2$ (3 mL) and trifluoroacetic acid was added (0.6 mL) with triisopropyl silane (0.1 mL). The reaction was monitored by HPLC-MS and upon completion, was concentrated to dryness under reduced pressure. The residue was taken up in $CH_2Cl_2$ (~0.8 mL) with a couple of drops of ethanol and cooled to 0° C. in an ice bath. Cold diethyl ether (~3 mL) was added with vigorous stirring to generate a white precipitate which was collected by filtration on a Buchner funnel at dried under high vacuum to yield the parent compound as an amorphous white solid. $^1$H NMR (400 MHz, Methanol-$d_4$) δ 6.52 (d, J=9.0 Hz, 1H), 5.06 (dd, J=10.7, 8.8 Hz, 1H), 4.73 (s, 1H), 4.16-4.04 (m, 1H), 3.69-3.56 (m, 2H), 3.48 (dd, J=13.3, 7.2 Hz, 2H), 3.15 (s, 3H), 3.03-2.94 (m, 1H), 2.68 (t, J=6.9 Hz, 1H), 2.24-1.77 (m, 11H), 1.61 (s, 1H), 1.31 (dd, J=27.2, 6.7 Hz, 6H), 1.06 (s, 9H), 0.91 (dd, J=34.1, 6.6 Hz, 6H).

Example 3.129: (S)—N—((S)-1-((S)-2-((E)-3-(3-Mercaptopropylsulfonamido)-2-methyl-3-oxoprop-1-enyl)pyrrolidin-1-yl)-3,3-dimethyl-1-oxobutan-2-yl)-3-methyl-2-(methylamino)-3-phenylbutanamide The title compound was synthesized from Boc-proline and Example 3.15 according to General Procedures 15, 16, 9, 10, 12 and others from Nieman J. A. et al. J. Nat. Prod. 2003, 66, 183-199. The compound was isolated as two diastereoisomers in an approximately 1:1 ratio. $^1$H NMR (400 MHz, Methanol-$d_4$) δ 7.57-7.12 (m, 5H), 6.39 (dd, J=9.4, 1.6 Hz, 0.5H), 6.31 (dd, J=8.2, 1.5 Hz, 0.5H), 4.72 (q, J=7.5 Hz, 0.5H), 4.66-4.56 (m, 0.5H), 4.40 (s, 0.5H), 4.28 (d, J=11.9 Hz, 1H), 3.81 (m, 0.5H), 3.76-3.56 (m, 3H), 2.77-2.64 (m, 2H), 2.59 (m, 3H), 2.39-2.22 (m, 1H), 2.18-1.72 (m, 7H), 1.61-1.33 (m, 6H), 1.15-0.85 (m, 11H). $C_{29}H_{46}N_4O_5S_2$ calcd. m/z=594.35 found $[M+H]^+$=595.3.

Example 3.130: (S)—N—((S)-1-(2-(3-(3-Mercaptopropylsulfonamido)-2-methyl-3-oxoprop-1-enyl)piperidin-1-yl)-3,3-dimethyl-1-oxobutan-2-yl)-3-methyl-2-(methylamino)-3-phenylbutanamide The title compound was synthesized from Boc-homoproline and Example 3.15 according to General Procedures 15, 16, 9, 10, 12 and others from Nieman J. A. et al. J. Nat. Prod. 2003, 66, 183-199. The compound was isolated as two diastereoisomers in an approximately 2:3 ratio. $^1$H NMR (600 MHz, Methanol-$d_4$) δ 7.55 (d, J=7.8 Hz, 1H), 7.46 (m, 3H), 7.38 (m, 1H), 6.81 (d, J=8.3 Hz, 0.6H), 6.79 (d, J=7.8 Hz, 0.4H), 5.66 (m, 0.6H), 5.12 (m, 0.4H), 5.05 (s, 0.6H), 4.86 (s, 0.4H), 4.42 (d, J=14.9 Hz, 0.4H), 4.35 (s, 0.6H), 4.26 (s, 0.4H), 4.12 (d, J=13.8 Hz, 0.6H), 3.64 (d, J=7.6 Hz, 1H), 3.63 (d, J=7.4 Hz, 1H), 3.39 (m, 0.6H), 2.94 (td, J=13.8, 2.6 Hz, 0.4H), 2.68 (t, J=6.7 Hz, 2H), 2.56 (m, 3H), 2.10 (m, 3.5H), 1.97 (s, 1.5H), 1.90-1.70 (m, 7H), 1.65-1.29 (m, 6H), 1.07 (s, 3.5H), 1.04 (s, 4.5H) ppm. $C_{30}H_{47}N_4O_5S_2$ calcd. m/z=608.31; found $[M+H]^+$=609.32.

Example 3.131: (S)—N—((S)-1-(2-(3-(4-(Mercaptomethyl)phenylsulfonamido)-2-methyl-3-oxoprop-1-enyl)piperidin-1-yl)-3,3-dimethyl-1-oxobutan-2-yl)-3-methyl-2-(methylamino)-3-phenylbutanamide The title compound was synthesized from Boc-homoproline and Example 3.20 according to General Procedures 15, 16, 9, 10, 12 and others from Nieman J. A. et al. J. Nat. Prod. 2003, 66, 183-199. The compound was isolated as two diastereoisomers in an approximately 2:3 ratio. $^1$H NMR (600 MHz, Methanol-$d_4$) δ 8.02 (d, J=8.4 Hz, 0.8H), 8.00 (d, J=8.5 Hz, 1.2H), 7.58 (d, J=8.5 Hz, 1H), 7.54 (d, J=8.5 Hz, 2H), 7.45 (t, J=8.2 Hz, 2H), 7.40 (d, J=7.2 Hz, 0.6H), 7.36 (m, 1H), 7.31 (t, J=7.1 Hz, 0.4H), 6.74 (d, J=8.2 Hz, 1H), 5.59 (m, 0.6H), 5.06 (m, 0.4H), 5.02 (s, 0.6H), 4.84 (s, 0.4H), 4.39 (d, J=12.5 Hz, 0.4H), 4.34 (s, 0.6H), 4.20 (s, 0.4H), 4.08 (d, J=12.0 Hz, 0.6H), 3.83 (s, 1.2H), 3.73 (s, 0.8H), 3.35 (m, 0.6H), 2.93 (td, J=13.6, 3.0 Hz, 0.4H), 2.55 (m, 3H), 2.00 (s, 1H), 1.90-1.51 (m, 7H), 1.51-1.30 (m, 4H), 1.30 (s, 1H), 1.15 (s, 1H), 1.04 (s, 3.5H), 1.01 (s, 4.5H) ppm. $C_{34}H_{47}N_4O_5S_2$ calcd. m/z=656.31; found [M+H]$^+$=657.30.

Example 3.132: MC-VC-PABC-3.90

The title compound was prepared by application of General Procedures 20 and 12 from Boc protected Example 3.90. $^1$H NMR (400 MHz, Methanol-d$_4$) δ 7.58 (d, J=8.2 Hz, 2H), 7.49 (d, J=7.5 Hz, 2H), 7.38 (t, J=7.7 Hz, 2H), 7.36-7.24 (m, 6H), 7.22 (d, J=7.8 Hz, 2H), 6.81 (s, 2H), 6.57 (d, J=9.1 Hz, 1H), 5.08 (s, 2H), 5.04 (t, J=10.0 Hz, 1H), 4.91 (s, 1H), 4.53 (dd, J=9.0, 5.1 Hz, 1H), 4.40 (s, 2H), 4.28 (s, 2H), 4.19 (d, J=7.4 Hz, 1H), 3.49 (t, J=7.1 Hz, 2H), 3.26-3.11 (m, 2H), 3.07-2.93 (m, 3H), 2.30 (t, J=7.4 Hz, 2H), 2.18 (s, 3H), 2.15-2.05 (m, 1H), 1.99-1.91 (m, 1H), 1.89 (s, 3H), 1.83-1.72 (m, 1H), 1.72-1.53 (m, 7H), 1.44 (s, 3H), 1.37 (s, 3H), 1.35-1.27 (m, 2H), 1.03 (s, 9H), 1.00 (d, J=6.8 Hz, 3H), 0.99 (d, J=6.7 Hz, 3H), 0.88 (d, J=6.5 Hz, 3H), 0.82 (d, J=6.6 Hz, 3H). $C_{64}H_{91}N_{11}O_{13}S$ calcd. m/z=1253.7; found [M+H]$^+$=1254.8.

Example 3.133: 4-((R)-2-((R)-2-(6-(2,5-Dioxo-2,5-dihydro-1H-pyrrol-1-yl)hexanamido)-3-methylbutanamido)-5-ureidopentanamido)benzyl 4-(N—((S, E)-2,5-dimethyl-4-((S)—N,3,3-trimethyl-2-((S)-3-methyl-2-(methylamino)-3-phenylbutanamido) butanamido)hex-2-enoyl)sulfamoyl)benzylcarbamate (MC-VC-PABC-3.98)

The title compound was prepared by application of General Procedures 20 and 12 to Boc protected Example 3.98. $C_{63}H_{89}N_{11}O_{13}S$ calcd. m/z=1239.6; found [M+H]$^+$=1240.9.

Example 3.134: MC-VC-PABC-3.93

The title compound was prepared by application of General Procedures 20 and 12 to Boc protected Example 3.93. $C_{63}H_{89}NO_{11}O_{13}S$ calcd. m/z=1239.6; found [M+H]$^+$=1240.9.

Example 3.135: MC-VC-PABC-3.54

The title compound was prepared by application of General Procedure 20 to Example 3.54. $C_{64}H_{91}N_{11}O_{13}S$ calcd. m/z=1253.65; found [M+H]$^+$=1254.75, [M+2H]$_{2+}$=628.20.

Example 3.136: (R)—N-(Benzylsulfonyl)-2,5-dimethyl-4-((S)—N,3,3-trimethyl-2-((S)-3-methyl-2-(methylamino)-3-phenylbutanamido)butanamido) hexanamide A suspension of the Example 3.27 and 10% palladium on carbon (25 mol % Pd) in glacial acetic acid was stirred under a H$_2$ atmosphere (1 atm) at ambient temperature. After 142 h, the reaction suspension was passed through a bed of Celite, rinsed with MeOH (5×) and concentrated in vacuo. The residual light brown crude film was dissolved and purified on the preparative HPLC (30-70% MeCN/H$_2$O with 0.1% TFA) and lyophilized to afford one diastereomer of the reduced product as a pale yellow solid in 15% yield $^1$H NMR (400 MHz, Methanol-d$_4$) δ 7.55 (d, J=7.2 Hz, 2H), 7.46 (t, J=7.8 Hz, 2H), 7.43-7.31 (m, 6H), 5.01 (s, 1H), 4.79 (d, J=14.1 Hz, 1H), 4.65 (d, J=14.1 Hz, 1H), 4.35 (s, 1H), 4.24 (s, 1H), 3.07 (s, 3H), 2.52 (s, 3H), 2.27 (m, J=10.3, 7.0, 3.2 Hz, 1H), 2.14 (ddd, J=13.5, 10.6, 2.7 Hz, 2H), 1.78 (d, J=8.6 Hz, 1H), 1.47 (s, 3H), 1.34 (s, 3H), 1.15 (d, J=6.9 Hz, 3H), 1.14 (s, 9H), 1.04 (d, J=6.6 Hz, 3H), 0.82 (d, J=6.6 Hz, 3H). $C_{34}H_{52}N_4O_5S$ calcd. m/z=628.37 amu; found [M+H]$^+$= 629.6, [M+Na]$^+$=651.

Example 3.137:
3-Methyl-3-(4-bromophenyl)-butanoic Acid

To a vigorously stirred solution of bromobenzene (4.70 g, 30.0 mmol) and 3,3-dimethylacrylic acid (1.00 g, 10.0 mmol) in 20 mL CH$_2$Cl$_2$ cooled to −10° C. in an NH$_4$Cl (aq)/ice bath, solid AlCl$_3$ was added portion-wise, keeping the internal temperature below −5° C. The solution turned yellow, then brown after addition. After one hour, analysis by LC and TLC indicated complete consumption of the limiting reagent. The reaction was then quenched by the addition of 1 M citric acid, causing the brown color to fade to yellow. The resulting sloppy suspension was extracted four times with 20 mL Et$_2$O, the combined organics washed with NaCl(sat), dried over Na$_2$SO$_4$(s), and concentrated in vacuo with heating to 45° C. to remove solvent and residual bromobenzene. The resulting oil solidified slowly. Recrystallization of the crude solid in hexanes afforded the title compound (1.29 g, 50%) as clusters of white prisms. $^1$H NMR (400 MHz, Chloroform-d) δ (ppm) 7.42 (d, J=8.6 Hz, 2H), 7.23 (d, J=8.6 Hz, 2H), 2.63 (s, 2H), 1.43 (s, 6H). $C_{11}H_{13}BrO_2$ calcd. [M+H]$^+$=257.02 amu; found m/z=257.03. R$_f$=0.21 (20% (2% AcOH/EtOAc)/Hex).

Example 3.138:
3-Methyl-3-(3-bromophenyl)-butanoic Acid

The title compound was prepared in the same manner as 3-methyl-3-phenylbutanoic acid in Nieman J. A., et al. J. Nat. Prod. 2003, 66, 183-199, using bromobenzene in place of benzene as the solvent, and substituting the acid-base workup with a simple extraction of the reaction mixture from 1 M citric acid and three successive recrystallizations from hexanes. From a crude product enriched in the desired meta isomer as a 2:1 mixture, the title compound could be obtained as white stubby needles in greater than 95% purity. $^1$H NMR (400 MHz, Chloroform-d) δ (ppm) 7.49 (t, J=1.9 Hz, 1H), 7.34 (ddd, J=7.9, 1.9, 1.0 Hz, 1H), 7.29 (ddd, J=7.9, 1.9, 1.0 Hz, 1H), 7.18 (t, J=7.9 Hz, 1H), 2.64 (s, 2H), 1.44 (s, 6H). $C_{11}H_{13}BrO_2$ calcd. [M+H]$^+$=257.02 amu; found m/z=257.01. R$_f$=0.21 (20% (2% AcOH/EtOAc)/Hex).

Example 3.139: (S)-Methyl 3-(4-bromophenyl)-2-(tert-butoxycarbonyl(methyl)amino)-3-methylbutanoate The title compound was synthesized from Example 3.137 according to the sequence of procedures described by Nieman et al. for the synthesis of(S)-methyl 2-(tert-butoxycarbonyl(methyl)amino)-3-methyl-3-phenylbutanoate.

Example 3.140: (S)-2-((tert-Butoxycarbonyl) (methyl)amino)-3-(4-((14-hydroxy-3,6,9,12-tetraoxatetradecyl)oxy)phenyl)-3-methylbutanoic Acid To a stirred solution of Example 3.81 (157 mg, 0.405 mmol) in pentaethylene glycol (1.5 mL) were added CsCO$_3$ (330 mg, 1.01 mmol), 3,4,7,8-tetramethyl-1,10-phenanthroline (57 mg, 0.24 mmol), and CuI (23 mg, 0.12 mmol).

Nitrogen was blown into the flask, then it was sealed and heated to 130° C., the solution quickly turning red to brown to black. After 40 h, the reaction looked to be nearly complete by HPLC analysis. Thus, the mixture was allowed to cool to ambient temperature, diluted with H$_2$O, and transferred to a larger Erlenmeyer with a stir bar. This mixture was carefully acidified to pH ~3 with 1 M citric acid, paying attention not to allow the foamy mixture to spill over. The mixture was then extracted five times with CH$_2$Cl$_2$, the combined organic extracts washed with NaCl (sat), dried over Na$_2$SO$_4$(s), and concentrated in vacuo to yield about 300 mg of crude oil. Purification by flash chromatography (1-10% MeOH/(2% AcOH/EtOAc)) yielded the title compound (66 mg, 30%) as a clear film which existed as a set of N-Boc rotamers an approximate 2:1 ratio. $^1$H NMR (400 MHz, Chloroform-d) δ (ppm) 7.35 (d, J=7.8 Hz, 1.3H), 7.30 (d, J=7.6 Hz, 0.7H), 6.87 (d, J=7.1 Hz, 2H), 5.07 (s, 0.7H), 4.93 (s, 0.3H), 4.14 (m, 2H), 3.86 (m, 2H), 3.70 (m, 16H), 2.83 (s, 1H), 2.72 (s, 2H), 1.54 (s, 3H), 1.49 (s, 3H), 1.45 (s, 9H). C$_{27}$H$_{45}$NO$_{10}$ calcd. [M+H]$^+$=544.31 amu; found m/z=544.36. R$_f$=0.36 (5% MeOH/(2% AcOH/EtOAc)).

Example 3.141: (S)-2-((tert-Butoxycarbonyl) (methyl)amino)-3-(4-(2-(2-(2-(2-hydroxyethoxy) ethoxy)ethoxy)ethoxy)phenyl)-3-methylbutanoic Acid The title compound was prepared according to the above method from Example 3.81 (132 mg, 0.341 mmol), CsCO$_3$ (278 mg, 0.853 mmol), 3,4,7,8-tetramethyl-1,10-phenanthroline (24 mg, 0.10 mmol), and CuI (10 mg, 0.051 mmol). Flash chromatography (1-10% MeOH/(2% AcOH/EtOAc)) gave the title compound (66 mg, 38%) as a clear oil in an approximate 2:1 ratio of N-Boc rotamers. $^1$H NMR (400 MHz, Chloroform-d) δ (ppm) 7.34 (d, J=8.4 Hz, 1.3H), 7.29 (d, J=8.1 Hz, 0.7H), 6.85 (d, J=8.4 Hz, 2H), 5.05 (s, 0.7H), 4.91 (s, 0.3H), 4.13 (t, J=4.6 Hz, 2H), 3.87-3.79 (m, 2H), 3.76-3.60 (m, 10H), 3.59 (t, J=4.1 Hz, 2H), 2.80 (s, 1H), 2.69 (s, 2H), 1.53 (s, 3H), 1.48 (s, 3H), 1.44 (s, 9H). C$_{25}$H$_{41}$NO$_9$ calcd. [M+H]$^+$=500.29 amu; found m/z=500.36. R$_f$=0.46 (5% MeOH/(2% AcOH/EtOAc)).

Example 3.142: (S)-3-(3-((14-Hydroxy-3,6,9,12-tetraoxatetradecyl)oxy)phenyl)-3-methyl-2-(methylamino)butanoic Acid The precursor to the title compound, (S)-3-(3-bromophenyl)-2-((tert-butoxycarbonyl)(methyl)amino)-3-methylbutanoic acid, was prepared from Example 3.138 by following the procedures in Neiman et al. Thus, following the procedures above, from (S)-3-(3-bromophenyl)-2-((tert-butoxycarbonyl)(methyl)amino)-3-methylbutanoic acid (166 mg, 0.43 mmol), CsCO$_3$ (330 mg, 1.01 mmol), 3,4,7,8-tetramethyl-1,10-phenanthroline (31 mg, 0.13 mmol), and CuI (12.3, 0.060 mmol) in 1.5 mL pentaethylene glycol heated to 130° C. for two days, the title compound (73 mg, 31%) was obtained as a clear oil after flash chromatography (1-10% MeOH/(2% AcOH/EtOAc)) in an approximate 2:1 ratio of N-Boc rotamers. $^1$H NMR (400 MHz, Chloroform-d) δ (ppm) 7.17 (t, J=7.8 Hz, 1H), 7.14-7.07 (m, 1H), 7.07-6.93 (m, 2H), 6.74 (d, J=8.0 Hz, 1H), 5.11 (s, 0.7H), 4.93 (s, 0.3H), 4.25-4.03 (m, 2H), 3.91-3.77 (m, 2H), 3.78-3.66 (m, 2H), 3.69-3.43 (s, 14H), 2.72 (s, 1H), 2.65 (s, 1H), 1.51 (s, 3H), 1.49 (s, 3H), 1.45 (s, 9H). C$_{27}$H$_{45}$NO$_{10}$ calcd. [M+H]$^+$=544.31 amu; found m/z=544.34.

Example 3.143: (6S,9S,12S,E)-Ethyl 9-(tert-butyl)-12-isopropyl-2,2,5,11,14-pentamethyl-4,7,10-trioxo-6-(2-(4-((16-oxo-3,6,9,12-tetraoxa-15-thiaheptadecyl)oxy)phenyl)propan-2-yl)-3-oxa-5,8,11-triazapentadec-13-en-15-oate (S)-2-((tert-Butoxycarbonyl)(methyl)amino)-3-(4-((14-hydroxy-3,6,9,12-tetraoxatetradecyl)oxy)phenyl)-3-methylbutanoic acid (65 mg, 0.120 mmol) was coupled to (S,E)-ethyl 4-((S)-2-amino-N,3,3-trimethylbutanamido)-2,5-dimethylhex-2-enoate with HATU and DIPEA following the same stoichiometry and procedure as described in the general coupling procedures in Nieman et al. to give an intermediate free alcohol after purification by flash chromatography (1-10% MeOH/(2% AcOH/EtOAc)). Next, to triphenylphosphine (40 mg, 0.15 mmol) in 0.75 mL THF under N2 at 0° C., di-tert-butylazodicarboxylate (35 mg, 0.15 mmol) was added in one portion. After 35 minutes, a white precipitate crashed out and the reaction became difficult to stir. To this suspension, a solution of the intermediate alcohol (42 mg, 0.050 mmol) in 0.75 mL THF was added diluting the precipitate enough to restore stirring. Five minutes later, thioacetic acid (5.7 mg, 0.075 mmol) in 0.05 mL THF was added causing all yellow color to fade from the mixture. After 30 min, the reaction was allowed to warm to ambient temperature. The precipitate disappeared after another 15 min, and analysis by TLC and LCMS showed nearly complete conversion. After another 40 minutes, the reaction mixture was concentrated in vacuo, then subjected directly to flash chromatography (40-100% EtOAc/Hex then to 10% MeOH/EtOAc) to yield the title compound (26 mg, 57%) as a clear film. $^1$H NMR (400 MHz, Chloroform-d) δ (ppm) 7.43 (d, J=8.4 Hz, 1.3H), 7.31 (d, J=8.3 Hz, 0.7H), 6.97-6.72 (m, 2H), 6.62 (dd, J=9.3, 1.6 Hz, 1H), 6.14 (d, J=9.6 Hz, 1H), 5.22 (s, 0.7H), 5.12-4.99 (m, 1H), 4.84 (s, 0.3H), 4.69 (d, J=9.3 Hz, 0.3H), 4.60 (d, J=8.9 Hz, 0.7H), 4.19 (q, J=7.2 Hz, 2H), 4.09 (td, J=4.6, 2.3 Hz, 2H), 3.84 (t, J=4.9 Hz, 2H), 3.77-3.70 (m, 2H), 3.70-3.61 (m, 10H), 3.59 (t, J=6.4 Hz, 2H), 3.07 (t, J=6.4 Hz, 2H), 2.97-2.91 (m, 3H), 2.84 (s, 3H), 2.32 (s, 3H), 1.87 (s, 3H), 1.49 (s, 3H), 1.43 (s, 9H), 1.35 (s, 3H), 1.30 (t, J=7.1 Hz, 3H), 0.87 (d, J=6.6 Hz, 3H), 0.80 (d, J=16.6 Hz, 3H), 0.77 (s, 9H). C$_{46}$H$_{77}$N$_3$O$_{12}$S calcd. [M+H]$^+$=896.53 amu; found m/z=896.77. R$_f$=0.56 (80% EtOAc/Hex).

Example 3.144: (6S,9S,12S,E)-Ethyl 9-(tert-butyl)-12-isopropyl-2,2,5,11,14-pentamethyl-4,7,10-trioxo-6-(2-(4-((13-oxo-3,6,9-trioxa-12-thiatetradecyl)oxy) phenyl)propan-2-yl)-3-oxa-5,8,11-triazapentadec-13-en-15-oate The title compound was prepared from (S)-2-((tert-butoxycarbonyl)(methyl)amino)-3-(4-(2-(2-(2-(2-hydroxyethoxy)ethoxy)ethoxy) ethoxy)phenyl)-3-methylbutanoic acid (66 mg, 0.065 mmol) following the same procedure described above to give 32 mg (57%) as a clear film after flash chromatography (20-100% EtOAc/Hex) $^1$H NMR (400 MHz, Chloroform-d) δ (ppm) 7.44 (d, J=8.5 Hz, 1.3H), 7.32 (d, J=8.5 Hz, 0.7H), 6.95-6.77 (m, 2H), 6.62 (dd, J=9.2, 1.7 Hz, 1H), 6.09 (d, J=9.1 Hz, 1H), 5.24 (s, 0.7H), 5.13-4.95 (m, 1H), 4.84 (s, 0.3H), 4.69 (d, J=9.6 Hz, 0.3H), 4.60 (d, J=9.0 Hz, 0.7H), 4.19 (q, J=7.1 Hz, 2H), 4.09 (td, J=4.7, 2.4 Hz, 2H), 3.84 (t, J=4.9 Hz, 2H), 3.72 (dd, J=5.7, 3.2 Hz, 2H), 3.70-3.65 (m, 2H), 3.66-3.62 (m, 4H), 3.60 (t, J=6.5 Hz, 2H), 3.09 (t, J=6.5 Hz, 2H), 2.96-2.88 (m, 3H), 2.84 (s, 3H), 2.33 (s, 3H), 1.88 (d, J=3.5 Hz, 3H), 1.49 (s, 2H), 1.43 (d, J=5.5 Hz, 11H), 1.35 (s, 2H), 1.30 (t, J=7.1 Hz, 2H), 0.87 (d, J=6.6 Hz, 3H), 0.80 (d, J=15.9 Hz, 3H), 0.76 (s, 9H). $C_{44}H_{73}N_3O_{11}S$ calcd. [M+H]$^+$=852.51 amu; found m/z=852.79. $R_f$=0.60 (60% EtOAc/Hex).

Example 3.145: (6S,9S,12S,E)-Ethyl 9-(tert-butyl)-12-isopropyl-2,2,5,11,14-pentamethyl-4,7,10-trioxo-6-(2-(3-((16-oxo-3,6,9-trioxa-12-thiatetradecyl)oxy)phenyl)propan-2-yl)-3-oxa-5,8,11-triazapentadec-13-en-15-oate The title compound was prepared from (S)-3-(3-((14-hydroxy-3,6,9,12-tetraoxatetradecyl)oxy)phenyl)-3-methyl-2-(methylamino)butanoic acid (73 mg, 0.080 mmol) following the same procedure described above to give 66 mg (47%) as a clear film after flash chromatography (20-100% EtOAc/Hex). $^1$H NMR (400 MHz, Chloroform-d) δ (ppm) 7.25-6.92 (m, 3H), 6.78-6.70 (m, 1H), 6.62 (d, J=8.9 Hz, 1H), 6.12 (d, J=8.9 Hz, 1H), 5.26 (s, 0.7H), 5.12-4.99 (m, 1H), 4.89 (s, 0.3H), 4.74-4.56 (m, 1H), 4.19 (q, J=7.2 Hz, 1H), 4.16-4.03 (m, 2H), 3.84 (td, J=5.0, 3.2 Hz, 2H), 3.77-3.61 (m, 14H), 3.60 (t, J=6.4 Hz, 2H), 3.09 (t, J=6.5 Hz, 2H), 2.97-2.75 (m, 6H), 2.33 (s, 3H), 1.91-1.83 (m, 3H), 1.52-1.35 (m, 16H), 1.26 (t, J=7.1 Hz, 3H), 0.87 (d, J=6.0 Hz, 3H), 0.81 (d, J=12.9 Hz, 3H), 0.77 (s, 9H). $C_{46}H_{77}N_3O_{12}S$ calcd. [M+H]$^+$=896.53 amu; found m/z=896.68. $R_f$=0.61 (75% EtOAc/Hex).

Example 3.146: (S,E)-4-((S)-2-((S)-3-(4-((14-Mercapto-3,6,9,12-tetraoxatetradecyl)oxy)phenyl)-3-methyl-2-(methylamino)butanamido)-N,3,3-trimethylbutanamido)-2,5-dimethylhex-2-enoic Acid Disulfide The title compound was prepared by saponification, then TFA promoted Boc removal, according to the exact methods described in Nieman et al. from (6S,9S,12S,E)-ethyl 9-(tert-butyl)-12-isopropyl-2,2,5,11,14-pentamethyl-4,7,10-trioxo-6-(2-(4-((16-oxo-3,6,9,12-tetraoxa-15-thiaheptadecyl)oxy)phenyl)propan-2-yl)-3-oxa-5,8,11-triazapentadec-13-en-15-oate (26 mg, 0.029 mmol) to afford the title compound (16 mg, 90%) as a clear glass after complete removal of excess TFA. $^1$H NMR (400 MHz, Methanol-d$_4$) δ (ppm) 8.43 (d, J=8.1 Hz, 1H), 7.47 (d, J=8.5 Hz, 2H), 7.08-6.94 (m, 2H), 6.80 (dq, J=9.9, 1.5 Hz, 1H), 5.08 (t, J=10.1 Hz, 1H), 4.94 (d, J=8.1 Hz, 1H), 4.32 (s, 1H), 4.21-4.12 (m, 2H), 3.93-3.81 (m, 3H), 3.76 (t, J=6.4 Hz, 2H), 3.76-3.72 (m, 2H), 3.72-3.62 (m, 10H), 3.17 (s, 3H), 2.92 (t, J=6.4 Hz, 2H), 2.61-2.47 (m, 1H), 2.14-2.00 (m, 1H), 1.94 (d, J=1.5 Hz, 3H), 1.46 (s, 3H), 1.40 (d, J=7.7 Hz, 3H), 1.09 (s, 9H), 0.94 (d, J=5.0 Hz, 3H), 0.92 (d, J=4.8 Hz, 3H). $C_{74}H_{124}N_6O_{18}S_2$ calcd. [M+H]$^+$=1449.85 amu; found m/z=1450.49.

Example 3.147: (S,E)-4-((S)-2-((S)-3-(4-((14-mercapto-3,6,9,12-tetraoxatetradecyl)oxy)phenyl)-3-methyl-2-(methylamino)butanamido)-N,3,3-trimethylbutanamido)-2,5-dimethylhex-2-enoic Acid Compound of Example 3.146 is reduced according to the methods below to produce the subject compound.

Example 3.148: (S,E)-4-((S)-2-((S)-3-(4-(2-(2-(2-(2-Mercaptoethoxy)ethoxy)ethoxy)phenyl)-3-methyl-2-(methylamino)butanamido)-N,3,3-trimethylbutanamido)-2,5-dimethylhex-2-enoic Acid Disulfide The title compound was prepared by saponification, then TFA promoted Boc removal, according to the exact methods described in Nieman et al. from (6S,9S,12S,E)-ethyl 9-(tert-butyl)-12-isopropyl-2,2,5,11,14-pentamethyl-4,7,10-trioxo-6-(2-(4-((13-oxo-3,6,9-trioxa-12-thiatetradecyl)oxy)phenyl)propan-2-yl)-3-oxa-5,8,11-triazapentadec-13-en-15-oate (32 mg, 0.037 mmol) to afford the title compound (29 mg, 86%) as a clear glass after complete removal of excess TFA. $^1$H NMR (400 MHz, Methanol-d$_4$) δ (ppm) 8.39 (d, J=8.2 Hz, 1H), 7.44 (d, J=8.9 Hz, 2H), 7.01 (d, J=8.5 Hz, 2H), 6.77 (d, J=7.9 Hz, 1H), 5.05 (t, J=10.1 Hz, 1H), 4.92 (d, J=8.3 Hz, 1H), 4.28 (s, 1H), 4.15 (dd, J=5.8, 3.4 Hz, 2H), 3.89-3.80 (m, 2H), 3.73 (t, J=6.4 Hz, 2H), 3.72-3.69 (m, 2H), 3.69-3.60 (m, 6H), 3.14 (s, 3H), 2.89 (t, J=6.4 Hz, 2H), 2.50 (s, 3H), 2.11-1.97 (m, 1H), 1.91 (d, J=1.4 Hz, 3H), 1.43 (s, 3H), 1.36 (s, 3H), 1.06 (s, 9H), 0.92-0.87 (m, 6H). $C_{70}H_{118}N_6O_{16}S_2$ calcd. [M+H]$^+$=1361.80 amu; found m/z=1362.26.

Example 3.149: (S,E)-4-((S)-2-((S)-3-(4-(2-(2-(2-(2-mercaptoethoxy)ethoxy)ethoxy)ethoxy)phenyl)-3-methyl-2-(methylamino)butanamido)-N,3,3-trimethylbutanamido)-2,5-dimethylhex-2-enoic Acid Compound of Example 3.148 is reduced according to the methods below to produce the subject compound.

Example 3.150: (S,E)-4-((S)-2-((S)-3-(3-((14-Mercapto-3,6,9,12-tetraoxatetradecyl)oxy)phenyl)-3-methyl-2-(methylamino)butanamido)-N,3,3-trimethylbutanamido)-2,5-dimethylhex-2-enoic Acid The title compound was prepared by saponification, then TFA promoted Boc removal, according to the exact methods described in Nieman et al. from (6S,9S,12S,E)-ethyl 9-(tert-butyl)-12-isopropyl-2,2,5,11,14-pentamethyl-4,7,10-trioxo-6-(2-(3-((16-oxo-3,6,9,12-tetraoxa-15-thiaheptadecyl)oxy)phenyl)propan-2-yl)-3-oxa-5,8,11-triazapentadec-13-en-15-oate (56 mg, 0.029 mmol) to afford the title compound (43 mg, 82%) as an off-white foam after complete removal of excess TFA. $^1$H NMR (400 MHz, Methanol-d$_4$) δ (ppm) 8.48 (d, J=8.3 Hz, 1H), 7.47-7.29 (m, 1H), 7.21-7.04 (m, 1H), 6.95 (t, J=9.4 Hz, 1H), 6.80 (d, J=9.7 Hz, 1H), 5.08 (t, J=10.1 Hz, 1H), 4.97-4.94 (m, 1H), 4.38 (s, 1H), 4.24-4.13 (m, 2H), 3.95-3.82 (m, 2H), 3.80-3.58 (m, 14H), 3.17 (s, 3H), 2.92 (t, J=6.4 Hz, 2H), 2.53 (s, 3H), 2.11-2.03 (m, 1H), 1.94 (d, J=1.4 Hz, 3H), 1.47 (s, 3H), 1.40 (s, 3H), 1.09 (s, 9H), 0.93 (dt, J=11.2, 3.4 Hz, 15H). $C_{74}H_{124}N_6O_{18}S_2$ calcd. [M+H]$^+$=1449.85 amu; found m/z=1450.06.

Example 3.151: (S,E)-4-((S)-2-((S)-3-(3-((14-mercapto-3,6,9,12-tetraoxatetradecyl)oxy)phenyl)-3-methyl-2-(methylamino)butanamido)-N,3,3-trimethylbutanamido)-2,5-dimethylhex-2-enoic Acid Compound of Example 3.150 is reduced according to the methods below to produce the subject compound.

Example 3.152: (S,E)-N-(Benzylsulfonyl)-4-((S)-2-((S)-3-cyclohexyl-3-methyl-2-(methylamino)butanamido)-N,3,3-trimethylbutanamido)-2,5-dimethylhex-2-enamide The title compound was synthesized from (S)-2-(tert-butoxycarbonyl(methyl)amino)-3-cyclohexyl-3-methylbutanoic acid as prepared by Zask et al., J. Med. Chem. 2004, 47, (19), 4774-4786 and (S,E)-4-((S)-2-amino-N,3,3-trimethylbutanamido)-N-(benzylsulfonyl)-2,5-dimethylhex-2-enamide, prepared using General Procedures 15, 16, 10 and 9 by application of General Procedures 11 and 12. $^1$H NMR (400 MHz, Methanol-d$_4$) δ 7.38 (s, 5H), 6.37 (dd, J=9.4, 1.7 Hz, 1H), 5.01 (t, J=10.0 Hz, 1H), 4.91 (s, 1H), 4.75 (s, 2H), 4.01 (s, 1H), 3.10 (s, 3H), 2.66 (s, 3H), 2.05-1.91 (m, 4H), 1.91-1.67 (m, 6H), 1.45-1.28 (m, 3H), 1.29-1.01 (m, 17H), 0.95-0.75 (m, 9H). C$_{34}$H$_{56}$N$_4$O$_5$S calcd. m/z=632.40 found [M+H]$^+$=633.35.

Example 3.153: MC-VC-PABC-3.71

The title compound was prepared by application of General Procedure 20 and 12 to Boc protected Example 3.58. $^1$H NMR (400 MHz, Methanol-d$_4$) δ 7.60 (d, J=8.1 Hz, 2H), 7.56 (d, J=7.8 Hz, 2H), 7.47 (t, J=7.6 Hz, 2H), 7.37 (t, J=7.3 Hz, 1H), 7.33 (d, J=8.2 Hz, 2H), 7.26 (d, J=8.0 Hz, 2H), 7.22 (d, J=7.9 Hz, 2H), 6.81 (s, 2H), 6.37 (d, J=9.3 Hz, 1H), 5.13-5.01 (m, 3H), 4.96 (s, 1H), 4.70 (s, 2H), 4.56-4.51 (m, 1H), 4.38 (s, 1H), 4.23-4.16 (m, 1H), 3.50 (t, J=7.1 Hz, 2H), 3.27-3.19 (m, 1H), 3.18-3.04 (m, 4H), 2.52 (s, 3H), 2.30 (t, J=7.4 Hz, 2H), 2.15-2.05 (m, 1H), 1.96 (s, 3H), 1.98-1.88 (m, 1H), 1.83-1.73 (m, 1H), 1.64 (dq, J=23.1, 7.3 Hz, 7H), 1.48 (s, 3H), 1.39 (s, 3H), 1.37-1.30 (m, 2H), 1.27 (s, 2H), 1.21 (s, 2H), 1.08 (s, 9H), 1.00 (d, J=6.7 Hz, 3H), 0.99 (d, J=6.8 Hz, 3H), 0.91 (d, J=6.6 Hz, 3H), 0.88 (d, J=6.5 Hz, 3H). C$_{66}$H$_{93}$N$_{11}$O$_{13}$S calcd. m/z=1279.7 found [M+H]$^+$=1281.0.

Example 3.154: MC-VC-PABC-3.76

The title compound was prepared by application of General Procedures 20 and 12 to Boc protected Example 3.76. C$_{65}$H$_{91}$N$_{11}$O$_{13}$S calcd. m/z=1265.7 found [M+H]$^+$=1266.7.

It is understood to those skilled in the art that it may be possible to carry out the chemical conversions shown in the schemes above with modifications of one or more parameters. As examples, alternate non-nucleophilic solvents may be suitable for the chemistry, such as THF, DMF, Toluene etc. Reaction temperatures may be varied. Alternate reagents may be suitable to act as dehydrating or acid-activating agents which are normally used in amide formation reactions, such as pentafluorophenyl esters, NHS esters, EDAC, HBTU, HOBT etc.

Example 3.155: Fmoc-Val-Lys(Boc)-OH: (S)-2-((S)-2-(((9H-Fluoren-9-yl)methoxy)carbonylamino)-3-methylbutanamido)-6-(tert-butoxycarbonylamino) hexanoic Acid The title compound was prepared based on the procedure from M. A. Walker, et al. *Bio. Org. Med. Chem. Lett.* 2004, 14, 4323-4327 starting with (S)-2,5-dioxopyrrolidin-1-yl 2-(((9H-fluoren-9-yl)methoxy)carbonylamino)-3-methylbutanoate. $^1$H NMR (400 MHz, Methanol-d$_4$) δ 8.28 (d, J=7.8 Hz, 1H), 7.82 (d, J=7.5 Hz, 2H), 7.69 (t, J=7.1 Hz, 2H), 7.41 (t, J=7.5 Hz, 2H), 7.33 (td, J=7.5, 1.2 Hz, 2H), 7.20 (d, J=8.5 Hz, 1H), 4.49-4.36 (m, 2H), 4.26 (t, J=7.0 Hz, 1H), 3.97 (t, J=8.0 Hz, 1H), 3.05-2.97 (m, 2H), 2.08 (dq, J=13.3, 6.6 Hz, 1H), 1.93-1.84 (m, 1H), 1.81-1.66 (m, 1H), 1.54-1.43 (m, 4H), 1.40 (s, 9H), 1.01 (d, J=6.8 Hz, 3H), 0.98 (d, J=6.8 Hz, 3H). m/z calcd. for C$_{31}$H$_{41}$N$_3$O$_7$=567.3 found [M-Boc+H$^+$]$^+$=468.8.

Example 3.156: Boc-Val-Cit-OH: (S)-2-((S)-2-(tert-Butoxycarbonylamino)-3-methylbutanamido)-5-ureidopentanoic Acid The title compound was synthesized according to US2010/0233190 A1 with matching spectroscopic data.

Example 3.157: H-Val-Cit-OH: (S)-2-((S)-2-Amino-3-methylbutanamido)-5-ureidopentanoic Acid The title compound was prepared from Boc-VC—OH according to General Procedure 7. $^1$H NMR (400 MHz, DMSO-d6) δ 8.69 (d, J=7.4 Hz, 1H), 8.21-7.97 (m, 3H), 4.24 (td, J=8.2, 4.9 Hz, 1H), 3.97 (s, OH), 3.63 (dd, J=9.2, 4.0 Hz, 1H), 2.98 (t, J=6.8 Hz, 2H), 2.60 (s, 1H), 2.10 (h, J=6.8 Hz, 1H), 1.85-1.69 (m, 1H), 1.61 (dtd, J=14.1, 9.0, 5.6 Hz, 1H), 1.45 (dtd, J=14.7, 8.2, 7.3, 3.7 Hz, 2H), 0.97 (dd, J=6.9, 5.0 Hz, 6H).

Example 3.158: Fmoc-Ala(D)-Phe-Lys(Boc)-OH: (5R,8S,11S)-8-Benzyl-1-(4-(tert-butoxycarbonylamino)butyl)-1-(9H-fluoren-9-yl)-5-methyl-3,6,9-trioxo-2-oxa-4,7,10-triazadodecan-12-oic Acid The title compound was prepared from Example 2.10 by general procedure 5, followed by treatment with (R)-2,5-dioxopyrrolidin-1-yl 2-(((9H-fluoren-9-yl)methoxy)carbonylamino)propanoate per general procedure 9. $^1$H NMR (400 MHz, DMSO-d$_6$) δ 12.57 (s, 1H), 8.20 (d, J=7.6 Hz, 1H), 8.12 (d, J=8.8 Hz, 1H), 7.89 (d, J=7.5 Hz, 2H), 7.71 (t, J=6.7 Hz, 2H), 7.48-7.37 (m, 3H), 7.33 (t, J=7.4 Hz, 2H), 7.30-7.13 (m, 5H), 6.77 (t, J=5.1 Hz, 1H), 4.59 (td, J=10.8, 10.3, 3.5 Hz, 1H), 4.33-4.10 (m, 4H), 4.02 (q, J=7.1 Hz, 1H), 3.10 (dd, J=13.8, 2.8 Hz, 1H), 2.94-2.87 (m, 2H), 2.79-2.67 (m, 1H), 1.75-1.70 (m, 1H), 1.62 (s, 1H), 1.37 (s, 4H), 1.36 (s, 9H), 0.96 (d, J=7.1 Hz, 3H). m/z calcd. for C$_{31}$H$_{41}$N$_3$O$_7$=686.3 found [M+Na]$^+$=709.9.

Example 3.159: Fmoc-Phe(D)-Phe-Lys-OH: (5R,8S,11S)-5,8-dibenzyl-11-(4-(tert-butoxycarbonylamino)butyl)-1-(9H-fluoren-9-yl)-3,6,9-trioxo-2-oxa-4,7,10-triazadodecan-12-oic Acid The title compound was prepared from Example 2.10 by general procedure 5, followed by treatment with (R)-2,5-dioxopyrrolidin-1-yl 2-(((9H-fluoren-9-yl)methoxy)carbonylamino)-3-phenylpropanoate per general procedure 9. $^1$H NMR (400 MHz, DMSO-d$_6$) δ 12.59 (s, 1H), 8.39 (d, J=8.7 Hz, 1H), 8.31 (d, J=7.6 Hz, 1H), 7.88 (d, J=7.5 Hz, 2H), 7.62 (t, J=8.2 Hz, 2H), 7.47 (d, J=8.7 Hz, 1H), 7.41 (t, J=7.1 Hz, 2H), 7.35-7.10 (m, 12H), 6.77 (t, J=5.7 Hz, 1H), 4.73-4.62 (m, 1H), 4.28-4.03 (m, 5H), 3.09 (dd, J=13.7, 3.8 Hz, 1H), 2.93-2.87 (m, 2H), 2.74 (dd, J=13.7, 10.4 Hz, 1H), 2.58 (dd, J=13.8, 3.4 Hz, 1H), 2.48-2.35 (m, 1H), 1.84-1.68 (m, 1H), 1.68-1.55 (m, 1H), 1.40-1.33 (m, 13H). ni/z calcd. for C$_{31}$H$_{41}$N$_3$O$_7$=762.4 found [M+Na]$^+$=785.9.

Example 3.160: (S,E)-N-(4-(1-((14S,17S)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)cyclopropyl)phenylsulfonyl)-2,5-dimethyl-4-((S)—N,3,3-trimethyl-2-((S)-3-methyl-2-(methylamino)-3-phenylbutanamido) butanamido)hex-2-enamide (Compound R)

Step 1: (S,E)-N-(4-(1-((S)-2-((S)-2-amino-3-methylbutanamido)-5-ureidopentanamido)cyclopropyl)phenylsulfonyl)-2,5-dimethyl-4-((S)—N,3,3-trimethyl-2-((S)-3-methyl-2-(methylamino)-3-phenylbutanamido)butanamido) hex-2-enamide (R-1) was synthesized from Compound Q-2 according to General Procedure 7. $^1$H NMR (400 MHz, Methanol-d$_4$) δ 7.97-7.90 (m, 2H), 7.59-7.51 (m, 2H), 7.47 (dd, J=8.5, 6.9 Hz, 2H), 7.44-7.34 (m, 3H), 6.46 (dd, J=9.4, 1.7 Hz, 1H), 5.02 (t, J=10.0 Hz, 1H), 4.93 (s, 1H), 4.43 (dd, J=8.6, 5.8 Hz, 1H), 4.35 (s, 1H), 3.71 (d, J=5.7 Hz, 1H), 3.23-3.09 (m, 5H), 2.51 (s, 3H), 2.22 (dt, J=13.4, 6.7 Hz, 1H), 2.04 (q, J=8.8, 7.8 Hz, 1H), 1.89-1.68 (m, 4H), 1.58 (dq, J=14.5, 8.7, 8.3 Hz, 2H), 1.48 (s, 4H), 1.36 (d, J=14.3 Hz, 5H), 1.15-0.99 (m, 16H), 0.90 (dd, J=6.6, 3.4 Hz, 6H). m/z calcd. for $C_{47}H_{73}N_9O_8S$=923.53. Found $[M+H]_+$=924.8.

Step 2: (S,E)-N-(4-(1-(((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)cyclopropyl)phenylsulfonyl)-2,5-dimethyl-4-((S)—N,3,3-trimethyl-2-((S)-3-methyl-2-(methylamino)-3-phenylbutanamido)butanamido)hex-2-enamide was synthesized from R-1 and MT-NHS according to General Procedure 6 prior to purification by preparative HPLC-MS. $^1$H NMR (400 MHz, Methanol-$d_4$) δ 7.99-7.91 (m, 2H), 7.60-7.52 (m, 2H), 7.48 (t, J=7.7 Hz, 2H), 7.44-7.31 (m, 3H), 6.84 (s, 2H), 6.45 (dd, J=9.3, 1.7 Hz, 1H), 5.00 (t, J=10.0 Hz, 1H), 4.94 (s, 1H), 4.35 (d, J=5.3 Hz, 2H), 4.21 (d, J=6.9 Hz, 1H), 3.81-3.67 (m, 4H), 3.67-3.54 (m, 10H), 3.25-3.05 (m, 5H), 2.64-2.47 (m, 5H), 2.20-1.99 (m, 2H), 1.85 (d, J=1.3 Hz, 4H), 1.73 (dq, J=9.5, 4.5 Hz, 1H), 1.66-1.28 (m, 11H), 1.12-0.94 (m, 16H), 0.90 (dd, J=6.6, 4.9 Hz, 6H). m/z calcd. for $C_{60}H_{90}N_{10}O_{14}S$=1206.64. Found $[M+H]^+$=1207.9.

Example 3.161: (R)—N-((2S,3S)-1-(((S,E)-6-(4-((14S,17S)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido) phenylsulfonamido)-2,5-dimethyl-6-oxohex-4-en-3-yl)(methyl)amino)-3-methyl-1-oxopentan-2-yl)-1-methylpiperidine-2-carboxamide (Compound S)

Step 1: (S,E)-Ethyl 4-(tert-Butoxycarbonyl(methyl) amino)-2,5-dimethylhex-2-enoate, Boc-ICD-OEt (S-1) was synthesized from (S,E)-ethyl 2,5-dimethyl-4-(methylamino) hex-2-enoate (synthesized according to U.S. Pat. No. 7,579,323 B1) and Boc-Isoleucine-OH and using General Procedure 4. NMR provided for a sample treated with TFA to remove the Boc group and resolve rotamers in the spectrum. $^1$H NMR (400 MHz, Chloroform-d) δ 6.68 (dd, J=9.5, 1.8 Hz, 1H), 5.33 (s, OH), 4.97 (t, J=9.9 Hz, 1H), 4.36 (d, J=4.1 Hz, 1H), 4.25 (q, J=7.1 Hz, 2H), 3.56 (s, 1H), 2.96 (s, 3H), 2.07-1.83 (m, 5H), 1.53 (s, 1H), 1.34 (t, J=7.1 Hz, 3H), 1.12 (d, J=7.0 Hz, 3H), 1.00-0.83 (m, 9H).

Step 2: (S,E)-4-((2S,3R)-2-(tert-Butoxycarbonylamino)-N,3-dimethylpentanamido)-2,5-dimethylhex-2-enoic acid (S-2) was generated from Boc-ICD-OEt using General Procedure 11. $^1$H NMR (400 MHz, Chloroform-d) δ 6.79 (dd, J=9.3, 1.7 Hz, 1H), 5.28 (d, J=9.7 Hz, 1H), 5.11 (dd, J=10.6, 9.2 Hz, 1H), 4.46-4.34 (m, 1H), 3.01 (s, 3H), 1.94 (s, 1.5 Hz, 4H), 1.77-1.54 (m, 2H), 1.44 (s, 9H), 1.14 (dt, J=15.8, 8.0 Hz, 1H), 0.97-0.81 (m, 12H).

Step 3: (S,E)-4-((2S,3S)—N,3-Dimethyl-2-((R)-1-methylpiperidine-2-carboxamido)pentanamido)-2,5-dimethylhex-2-enoic acid (S-3) was synthesized from Compound S-1 according to General Procedure 7 and reacting the liberated amine with D-(N-methyl)-pipecolic acid using General Procedure 4. Finally, the C-terminal carboxylate was liberated using General Procedure 11 prior to purification by preparative scale HPLC. $^1$H NMR (400 MHz, Methanol-$d_4$) δ 6.77 (dd, J=9.5, 1.4 Hz, 1H), 5.04 (t, J=10.1 Hz, 1H), 4.65-4.56 (m, 1H), 3.79-3.69 (m, 1H), 3.54-3.45 (m, 1H), 3.12 (s, 3H), 3.10-3.06 (m, 1H), 2.76 (s, 3H), 2.21-2.10 (m, 1H), 2.08-2.00 (m, 1H), 2.01-1.92 (m, 2H), 1.90 (d, J=1.5 Hz, 3H), 1.88-1.72 (m, 3H), 1.69-1.52 (m, 2H), 1.31-1.16 (m, 1H), 0.98-0.86 (m, 12H). $C_{22}H_{39}N_3O_4$ calcd. m/z=409.29 found $[M+H]^+$=410.91.

Step 4: (S,E)-4-((2S,3S)-2-Amino-N,3-dimethylpentanamido)-2,5-dimethyl-N-(4-(2,2,2-trifluoroacetamido)phenylsulfonyl)hex-2-enamide (S-4) was prepared from Compound S-2 according to General Procedure 11, followed by N-acyl sulfonamide generation with 2,2,2-trifluoro-N-(4-sulfamoylphenyl)acetamide according to General Procedure 1, followed by General Procedure 7. $^1$H NMR (400 MHz, Chloroform-d) δ 8.00-7.85 (m, 2H), 7.76 (d, J=8.8 Hz, 2H), 6.39 (dd, J=9.2, 1.8 Hz, 1H), 4.45-4.30 (m, 1H), 4.14 (d, J=4.1 Hz, 1H), 2.82 (s, 3H), 2.08-1.91 (m, 1H), 1.67 (s, J=1.5 Hz, 3H), 1.41-1.35 (m, J=13.3, 7.6, 3.2 Hz, 1H), 1.10-0.88 (m, 4H), 0.77 (ddd, J=17.2, 9.0, 5.4 Hz, 9H).

Step 5: (R)—N-((2S,3S)-1-(((S,E)-2,5-Dimethyl-6-oxo-6-(4-(2,2,2-trifluoroacetamido)phenylsulfonamido)hex-4-en-3-yl)(methyl)amino)-3-methyl-1-oxopentan-2-yl)-1-methylpiperidine-2-carboxamide (S-5) was prepared from Compound S-4 and N-methyl-D-pipecolic acid according to General Procedure 4. $^1$H NMR (400 MHz, Methanol-$d_4$) δ 7.97 (d, 2H), 7.77 (d, 2H), 7.67 (d, J=8.6 Hz, 0H), 6.60 (d, J=9.2 Hz, 1H), 4.96 (t, J=9.9 Hz, 1H), 4.61 (d, J=8.8 Hz, 1H), 3.75 (hept, J=6.6 Hz, 1H), 3.19-3.10 (m, 1H), 3.06 (s, 3H), 2.45 (s, 2H), 2.39 (s, 3H), 2.01-1.88 (m, 3H), 1.84 (d, J=1.4 Hz, 3H), 1.78-1.54 (m, 5H), 1.25-1.13 (m, 1H), 0.92 (s, 1H), 0.91-0.86 (m, 8H), 0.83 (d, J=6.6 Hz, 3H). $C_{30}H_{44}F_3N_5O_6S$ calcd. m/z=659.30 found $[M+H]^+$=660.88.

Step 6: (R)—N-((2S,3S)-1-(((S,E)-6-(4-Aminophenylsulfonamido)-2,5-dimethyl-6-oxohex-4-en-3-yl)(methyl) amino)-3-methyl-1-oxopentan-2-yl)-1-methylpiperidine-2-carboxamide (L-6) was prepared from Compound S-5 according to General Procedure 3. $^1$H NMR (400 MHz, Methanol-$d_4$) δ 7.72 (d, 2H), 6.69 (d, 2H), 6.42 (dd, J=9.2, 1.7 Hz, 1H), 4.61-4.55 (m, 1H), 3.72 (dd, J=12.2, 3.2 Hz, 1H), 3.52-3.44 (m, 1H), 3.37 (s, 3H), 3.12 (s, 3H), 3.09-3.03 (m, 1H), 2.71 (s, 3H), 2.20-1.92 (m, 3H), 1.84 (d, J=1.4 Hz, 3H), 1.80-1.72 (m, 2H), 1.67-1.53 (m, 2H), 1.29-1.16 (m, 1H), 0.96-0.85 (m, 12H). $C_{28}H_{45}N_5O_5S$ calcd. m/z=563.31 found $[M+H]^+$=564.93.

Step 7: (R)—N-((2S,3S)-1-(((S,E)-6-(4-((14S,17S)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonamido)-2,5-dimethyl-6-oxohex-4-en-3-yl)(methyl)amino)-3-methyl-1-oxopentan-2-yl)-1-methylpiperidine-2-carboxamide was prepared from Compound S-6 and MT-Val-Cit-OH according to General Procedure 10. $^1$H NMR (400 MHz, Methanol-$d_4$) δ 8.00 (d, 2H), 7.88 (d, 2H), 6.83 (s, 2H), 6.46 (dd, J=9.1, 1.6 Hz, 1H), 4.57 (d, J=8.3 Hz, 1H), 4.55-4.52 (m, 1H), 4.22 (d, J=6.9 Hz, 1H), 3.80-3.73 (m, 3H), 3.73-3.66 (m, 2H), 3.66-3.60 (m, 2H), 3.58 (d, J=2.2 Hz, 8H), 3.52-3.43 (m, 1H), 3.26-3.19 (m, 1H), 3.17-3.13 (m, 2H), 3.12 (s, 4H), 2.71 (s, 3H), 2.61-2.55 (m, 2H), 2.21-2.01 (m, 3H), 2.00-1.88 (m, 3H), 1.83 (d, J=1.4 Hz, 3H), 1.81-1.71 (m, 4H), 1.68-1.52 (m, 4H), 1.29-1.14 (m, 1H), 1.01 (t, J=6.8 Hz, 6H), 0.94-0.86 (m, 12H). $C_{52}H_{82}N_{10}O_{14}S$ calcd. m/z=1102.57 found $[M+H]^+$=1104.22.

Example 3.162: (R)—N—((S)-1-(((S,E)-6-(4-((14S,17S)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido) phenylsulfonamido)-2,5-dimethyl-6-oxohex-4-en-3-yl)(methyl)amino)-3,3-dimethyl-1-oxobutan-2-yl)-1-methylpiperidine-2-carboxamide (Compound T)

Step 1: (S,E)-2,5-Dimethyl-4-((S)—N,3,3-trimethyl-2-((R)-1-methylpiperidine-2-carboxamido)butanamido)hex- 2-enoic acid (T-1) was prepared from (S,E)-ethyl 4-((S)-2-amino-N,3,3-trimethylbutanamido)-2,5-dimethylhex-2-enoate (synthesized according to U.S. Pat. No. 7,579,323 B1) and D-N-methyl-pipecolic acid according to General Procedures 4 and 11. $^1$H NMR (400 MHz, Methanol-d$_4$) δ 6.60 (dd, J=9.4, 1.7 Hz, 1H), 5.04 (t, J=10.0 Hz, 1H), 4.77 (s, 1H), 4.62 (s, 1H), 3.30-3.23 (m, 1H), 3.10 (s, 3H), 2.68 (t, J=12.2 Hz, 1H), 2.52 (s, 3H), 2.04 (s, 1H), 2.02-1.93 (m, 2H), 1.90 (d, J=1.4 Hz, 3H), 1.88-1.79 (m, 1H), 1.77-1.62 (m, 2H), 1.56-1.43 (m, 1H), 1.04 (s, 9H), 0.92 (d, J=6.6 Hz, 3H), 0.85 (d, J=6.6 Hz, 3H). C$_{22}$H$_{39}$N$_3$O$_4$ calcd. m/z=409.29 found [M+H]$^+$=410.92.

Step 2: (R)—N—((S)-1-(((S,E)-2,5-Dimethyl-6-oxo-6-(4-(2,2,2-trifluoroacetamido)phenylsulfonamido)hex-4-en-3-yl)(methyl)amino)-3,3-dimethyl-1-oxobutan-2-yl)-1-methylpiperidine-2-carboxamide (T-2) was prepared from Compound T-1 and 2,2,2-trifluoro-N-(4-sulfamoylphenyl) acetamide using General Procedure 2. $^1$H NMR (400 MHz, Methanol-d$_4$) δ 8.08 (d, J=8.8 Hz, 2H), 7.92 (d, J=8.9 Hz, 2H), 6.47 (d, J=9.0 Hz, 1H), 5.01-4.92 (m, 1H), 4.70 (s, 1H), 3.82 (d, J=12.3 Hz, 1H), 3.53-3.43 (m, 1H), 3.13 (s, 3H), 2.72 (s, 3H), 2.22-1.90 (m, 4H), 1.85 (d, J=1.4 Hz, 5H), 1.60 (m, 1H), 1.40-1.22 (m, 4H), 1.03 (s, 9H), 0.89 (dd, J=17.1, 6.5 Hz, 6H). C$_{30}$H$_{44}$F$_3$N$_5$O$_6$S calcd. m/z=659.76 found [M+H]$^+$=660.95.

Step 3: (R)—N—((S)-1-(((S,E)-6-(4-Aminophenylsulfonamido)-2,5-dimethyl-6-oxohex-4-en-3-yl)(methyl)amino)-3,3-dimethyl-1-oxobutan-2-yl)-1-methylpiperidine-2-carboxamide (T-3) was prepared from Compound T-2 according to General Procedure 3. $^1$H NMR (400 MHz, Methanol-d$_4$) δ 7.76-7.66 (m, 2H), 6.74-6.64 (m, 2H), 6.42 (dd, J=8.9, 1.7 Hz, 1H), 4.94 (m, 1H), 4.70 (s, 1H), 3.82 (dd, J=12.2, 3.1 Hz, 1H), 3.54-3.42 (m, 1H), 3.13 (s, 4H), 2.70 (s, 3H), 2.16 (d, J=14.6 Hz, 1H), 2.11-2.01 (m, 1H), 1.96 (d, J=12.9 Hz, 2H), 1.89-1.51 (m, 6H), 1.03 (s, 9H), 0.89 (dd, J=16.3, 6.5 Hz, 6H). C$_{28}$H$_{45}$N$_5$O$_5$S calcd. m/z=563.31 found [M+H]$^+$=564.93.

Step 4: (R)—N—((S)-1-(((S,E)-6-(4-((14S,17S)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonamido)-2,5-dimethyl-6-oxohex-4-en-3-yl)(methyl)amino)-3,3-dimethyl-1-oxobutan-2-yl)-1-methylpiperidine-2-carboxamide was prepared from Compound T-3 and MT-Val-Cit-OH according to General Procedure 10. $^1$H NMR (400 MHz, Methanol-d$_4$) δ 8.00 (d, J=8.9 Hz, 2H), 7.88 (d, J=8.7 Hz, 2H), 6.83 (s, 1H), 6.46 (d, J=9.1 Hz, 1H), 4.96-4.91 (m, 1H), 4.72-4.68 (m, 1H), 4.58-4.51 (m, 1H), 4.22 (t, J=7.2 Hz, 1H), 3.83-3.73 (m, 3H), 3.72-3.67 (m, 2H), 3.65-3.61 (m, 2H), 3.61-3.55 (m, 8H), 3.52-3.46 (m, 1H), 3.27-3.19 (m, 1H), 3.13 (s, 3H), 3.09-3.03 (m, 1H), 2.69 (s, 3H), 2.58 (t, J=6.0 Hz, 2H), 2.19-2.01 (m, 4H), 2.00-1.90 (m, 3H), 1.84 (d, J=1.4 Hz, 3H), 1.83-1.72 (m, 3H), 1.61 (d, J=9.0 Hz, 3H), 1.03 (s, 11H), 1.00 (d, J=6.8 Hz, 4H), 0.91 (d, J=6.5 Hz, 3H), 0.87 (d, J=6.6 Hz, 3H). C$_{52}$H$_{82}$N$_{10}$O$_{14}$S calcd. m/z=1102.57 found [M+H]$^+$=1104.30.

Example 3.163: (R)—N—((S)-1-(((S,E)-6-(4-((14S,17S)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido) phenylsulfonamido)-2,5-dimethyl-6-oxohex-4-en-3-yl)(methyl)amino)-3,3-dimethyl-1-oxobutan-2-yl)-1-isopropylpiperidine-2-carboxamide (Compound U)

Step 1: (R)—N—((S)-1-(((S,E)-2,5-Dimethyl-6-oxo-6-(4-(2,2,2-trifluoroacetamido)phenylsulfonamido)hex-4-en-3-yl)(methyl)amino)-3,3-dimethyl-1-oxobutan-2-yl)-1-isopropylpiperidine-2-carboxamide (U-1) was prepared from (S,E)-4-((S)-2-((R)-1-isopropylpiperidine-2-carboxamido)-N,3,3-trimethylbutanamido)-2,5-dimethylhex-2-enoic acid (prepared according to US 2012/0309938 A1) and 2,2,2-trifluoro-N-(4-sulfamoylphenyl)acetamide using General Procedure 3. $^1$H NMR (400 MHz, Methanol-d$_4$) δ 8.00 (d, J=8.8 Hz, 2H), 7.83 (d, J=8.8 Hz, 2H), 6.56 (d, J=9.1 Hz, 1H), 4.69 (s, 1H), 4.12 (dd, J=11.6, 3.3 Hz, 1H), 3.95 (hept, J=6.2 Hz, 1H), 3.54-3.41 (m, 2H), 3.37 (s, 3H), 3.08 (s, 3H), 3.04-2.89 (m, 1H), 2.13 (dd, J=17.2, 6.4 Hz, 1H), 2.00-1.88 (m, 4H), 1.84 (d, J=1.5 Hz, 4H), 1.71-1.52 (m, 1H), 1.29 (dd, J=28.0, 6.7 Hz, 8H), 1.17 (d, J=6.1 Hz, 6H), 1.01 (s, 10H), 0.86 (dd, J=28.2, 6.5 Hz, 7H). C$_{32}$H$_{48}$F$_3$N$_5$O$_6$S calcd. m/z=687.33 found [M+H]$^+$=688.9.

Step 2: (R)—N—((S)-1-(((S,E)-6-(4-Aminophenylsulfonamido)-2,5-dimethyl-6-oxohex-4-en-3-yl)(methyl)amino)-3,3-dimethyl-1-oxobutan-2-yl)-1-isopropylpiperidine-2-carboxamide (U-2) was prepared from Compound U-1 according to General Procedure 3. $^1$H NMR (400 MHz, Methanol-d$_4$) δ 7.75-7.62 (m, 2H), 6.74-6.62 (m, 2H), 6.59-6.35 (m, 1H), 4.70 (s, 1H), 4.09 (dd, J=11.7, 3.3 Hz, 1H), 3.52-3.38 (m, 2H), 3.10 (s, 3H), 3.02-2.87 (m, 1H), 2.12 (d, J=11.9 Hz, 1H), 2.06-1.73 (m, 11H), 1.70-1.50 (m, 1H), 1.28 (dd, J=28.8, 6.7 Hz, 6H), 1.02 (s, 9H), 0.87 (dd, J=27.7, 6.5 Hz, 6H). C$_{30}$H$_{49}$N$_5$O$_5$S calcd. m/z=591.35 found [M+H]$^+$=593.0.

Step 3: tert-Butyl (S)-1-((S)-1-(4-(N—((S,E)-4-((S)-2-((R)-1-Isopropylpiperidine-2-carboxamido)-N,3,3-trimethylbutanamido)-2,5-dimethylhex-2-enoyl)sulfamoyl)phenylamino)-1-oxo-5-ureidopentan-2-ylamino)-3-methyl-1-oxobutan-2-ylcarbamate (U-3) was synthesized from Compound U-2 and Boc-Val-Cit-OH according to General Procedure 10. C$_{46}$H$_{77}$N$_9$O$_{10}$S calcd. m/z=947.55 found [M+H]$^+$=949.2.

Step 4: (R)—N—((S)-1-(((S,E)-6-(4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonamido)-2,5-dimethyl-6-oxohex-4-en-3-yl)(methyl)amino)-3,3-dimethyl-1-oxobutan-2-yl)-1-isopropylpiperidine-2-carboxamide was prepared from Compound U-3 and MT-NHS according to General Procedures 7 and 6 and purified by preparative HPLC-MS. C$_{54}$H$_{86}$N$_{10}$O$_{14}$S calcd. m/z=1130.60 found [M+H]$^+$=1132.5.

Example 3.164: (S)—N-(4-((N-((2R,3R)-3-((S)-1-((3R,4S,5R)-4-((S)-2-((S)-2-(Dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)methyl) phenyl)-2-((S)-1-(2,5-dioxo-2,5-dihydro-1H-pyrrol-1-yl)-14-isopropyl-12-oxo-3,6,9-trioxa-13-azapentadecanamido)-5-ureidopentanamide (Compound W)

Step 1: tert-Butyl (S)-1-(((3R,4S,5R)-3-Methoxy-1-((S)-2-((1R,2R)-1-methoxy-2-methyl-3-oxo-3-((4-(2,2,2-trifluoroacetamido)phenyl)methylsulfonamido)propyl)pyrrolidin-1-yl)-5-methyl-1-oxoheptan-4-yl)(methyl)amino)-3-methyl-1-oxobutan-2-ylcarbamate (W-1) was prepared from commercially available Boc-Val-Dil-Dap-OH and 2,2,2-trifluoro-N-(4-(sulfamoylmethyl)phenyl)acetamide through General Procedure 2. C$_{38}$H$_{60}$F$_3$N$_5$O$_{10}$S calcd. m/z=835.40 found [M+H]$^+$=836.7.

Step 2: (S)-2-((S)-2-(Dimethylamino)-3-methylbutanamido)-N-((3R,4S,5R)-3-methoxy-1-((S)-2-((1R,2R)-1- methoxy-2-methyl-3-oxo-3-((4-(2,2,2-trifluoroacetamido)phenyl)methylsulfonamido)propyl)pyrrolidin-1-yl)-5-methyl-1-oxoheptan-4-yl)-N,3-dimethylbutanamide (W-2) was prepared from Compound W-1 and N,N-dimethylvaline according to General Procedure 4. $C_{40}H_{65}F_3N_6O_9S$ calcd. m/z=862.45 found [M+H]$^+$=863.2.

Step 3: (S)—N-((3R,4S,5R)-1-((S)-2-((1R,2R)-3-((4-Aminophenyl)methylsulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (W-3) was prepared from Compound W-2 by following General Procedure 3. $C_{38}H_{66}N_6O_8S$ calcd. m/z=766.47 found [M-$C_7H_8O_2S$+H]$^+$= 599.0. (Quinone methide fragmentation and loss of 4-aminobenzylsulfonate).

Step 4: (S)—N-(4-((N-((2R,3R)-3-((S)-1-((3R,4S,5R)-4-((S)-2-((S)-2-(Dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)methyl)phenyl)-2-((S)-1-(2,5-dioxo-2,5-dihydro-1H-pyrrol-1-yl)-14-isopropyl-12-oxo-3,6,9-trioxa-13-azapentadecanamido)-5-ureidopentanamide. was synthesized using General Procedure 10 from MT-VAL-CIT-OH and Compound W-3 and purified by preparative HPLC chromatography. $C_{61}H_{101}N_{11}O_{17}S$ calcd. m/z=1305.73 found [M+H]$^+$=1306.9.

Example 3.165: (S)—N-(4-(N—((S)-2-((2R,3R)-3-((S)-1-((3R,4S,5R)-4-((S)-2-((S)-2-(Dimethylamino)-3-methylbutanamido)-N,3-dimethylbutanamido)-3-methoxy-5-methylheptanoyl)pyrrolidin-2-yl)-3-methoxy-2-methylpropanamido)-3-phenylpropanoyl)sulfamoyl)phenyl)-2-((S)-1-(2,5-dioxo-2,5-dihydro-1H-pyrrol-1-yl)-14-isopropyl-12-oxo-3,6,9-trioxa-13-azapentadecanamido)-5-ureidopentanamide (Compound X)

Step 1: (S)-2-Amino-3-phenyl-N-(4-(2,2,2-trifluoroacetamido)phenylsulfonyl)propanamide (X-1) was prepared from Boc-phenylalanine and 2,2,2-trifluoro-N-(4-sulfamoylphenyl)acetamide according to General Procedures 2 and 7. $^1$H NMR (400 MHz, DMSO-d$_6$) δ 11.42 (s, 1H), 7.84 (d, J=8.7 Hz, 2H), 7.73-7.64 (m, 1H), 7.69 (d, J=8.7 Hz, 2H), 7.24-7.14 (m, 3H), 7.13-7.06 (m, 2H), 3.65-3.60 (m, 1H), 3.06 (dd, J=14.2, 5.1 Hz, 1H), 2.91 (dd, J=14.1, 7.1 Hz, 1H). $C_{17}H_{16}F_3N_3O_4S$ calcd. m/z=415.08 found [M+H]$^+$=416.5.

Step 2: tert-Butyl (S)-1-(((3R,4S,5R)-3-Methoxy-1-((S)-2-((1R,2R)-1-methoxy-2-methyl-3-oxo-3-((S)-1-oxo-3-phenyl-1-(4-(2,2,2-trifluoroacetamido)phenylsulfonamido)propan-2-ylamino)propyl)pyrrolidin-1-yl)-5-methyl-1-oxoheptan-4-yl)(methyl)amino)-3-methyl-1-oxobutan-2-ylcarbamate (X-2) was synthesized from commercially available Boc-Val-Dip-Dap-OH (0.07 g) and Compound X-1 using General Procedure 4. $C_{46}H_{67}F_3N_6O_{11}S$ calcd. m/z=968.45 found [M+Na]$^+$=992.1.

Step 3: (S)-2-((S)-2-(Dimethylamino)-3-methylbutanamido)-N-((3R,4S,5R)-3-methoxy-1-((S)-2-((1R,2R)-1-methoxy-2-methyl-3-oxo-3-((S)-1-oxo-3-phenyl-1-(4-(2,2,2-trifluoroacetamido)phenylsulfonamido)propan-2-ylamino)propyl)pyrrolidin-1-yl)-5-methyl-1-oxoheptan-4-yl)-N,3-dimethylbutanamide (X-3) was prepared from Compound X-2 (110 mg) and N,N-dimethyl valine using General Procedures 7 and 4. $C_{48}H_{72}F_3N_7O_{10}S$ calcd. m/z=995.50 found [M+H]$^+$ 997.3.

Step 4: (S)—N-((3R,4S,5R)-1-((S)-2-((1R,2R)-3-((S)-1-(4-Aminophenylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (X-4) was prepared from Compound X-3 (100 mg) using General Procedure 3. $C_{46}H_{73}N_7O_9S$ calcd. m/z=899.52 found [M+H]$^+$ 901.3.

Step 5: (S)—N-(4-(N—((S)-2-((2R,3R)-3-((S)-1-((3R,4S,5R)-4-((S)-2-((S)-2-(Dimethylamino)-3-methylbutanamido)-N,3-dimethylbutanamido)-3-methoxy-5-methylheptanoyl)pyrrolidin-2-yl)-3-methoxy-2-methylpropanamido)-3-phenylpropanoyl)sulfamoyl)phenyl)-2-((S)-1-(2,5-dioxo-2,5-dihydro-1H-pyrrol-1-yl)-14-isopropyl-12-oxo-3,6,9-trioxa-13-azapentadecanamido)-5-ureidopentanamide was prepared from Compound X-4 (25 mg) and MT-Val-Cit-OH (63 mg) using General Procedure 10. $C_{70}H_{110}N_{12}O_{18}S$ calcd. m/z=1438.8 amu; found [M+H]$^+$=1440.2, [(M+2H)/2]$^{2+}$=720.5.

Example 3.166: (S)—N-((3R,4S,5R)-1-((S)-2-((1R,2R)-3-((S)-1-(4-Amino phenylmethylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound Y)

Step 1: (S)-2-Amino-3-phenyl-N-(4-(2,2,2-trifluoroacetamido)benzylsulfonyl)propanamide (Y-1) was prepared from Boc-phenylalanine and 2,2,2-trifluoro-N-(4-sulfamoylphenyl)acetamide according to General Procedures 9 and 7 (S)-tert-butyl 1-oxo-3-phenyl-1-(phenylmethylsulfonamido)propan-2-ylcarbamate $^1$H NMR (400 MHz, DMSO-d$_6$) δ 7.76-7.71 (m, 2H), 7.58 (d, J=8.4 Hz, 2H), 7.36-7.21 (m, 8H), 4.34 (d, J=13.1 Hz, 1H), 4.30 (d, J=13.1 Hz, 1H), 3.62 (dd, J=8.2, 4.6 Hz, 1H), 3.21-3.09 (m, 1H), 2.89 (dd, J=14.3, 8.3 Hz, 1H). $C_{18}H_{18}F_3N_3O_4S$ calcd. m/z=429.10 found [M+H]$^+$=430.7.

Step 2: tert-Butyl (S)-1-(((3R,4S,5R)-3-methoxy-1-((S)-2-((1R,2R)-1-methoxy-2-methyl-3-oxo-3-((S)-1-oxo-3-phenyl-1-(4-(2,2,2-trifluoroacetamido)phenylmethylsulfonamido)propan-2-ylamino)propyl)pyrrolidin-1-yl)-5-methyl-1-oxoheptan-4-yl)(methyl)amino)-3-methyl-1-oxobutan-2-ylcarbamate (Y-2) was prepared from commercially available Boc-Val-Dil-Dap-OH and Compound Y-1 by following General Procedure 4. $C_{47}H_{69}F_3N_6O_{11}S$ calcd. m/z=982.47 found [M+Na]$^+$= 1006.2.

Step 3: (S)-2-((S)-2-(Dimethylamino)-3-methylbutanamido)-N-((3R,4S,5R)-3-methoxy-1-((S)-2-((1R,2R)-1-methoxy-2-methyl-3-oxo-3-((S)-1-oxo-3-phenyl-1-(4-(2,2,2-trifluoroacetamido)phenylmethylsulfonamido)propan-2-ylamino)propyl)pyrrolidin-1-yl)-5-methyl-1-oxoheptan-4-yl)-N,3-dimethylbutanamide (Y-3) was prepared from Compound Y-2 and N,N-dimethylvaline according to General Procedures 7 and 4. $C_{49}H_{74}F_3N_7O_{10}S$ calcd. m/z=1009.52 found [M+H]$^+$=1011.0.

Step 4: (S)—N-((3R,4S,5R)-1-((S)-2-((1R,2R)-3-((S)-1-(4-Aminophenylmethylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Y-4) was prepared from Compound Y-3 according to General Procedure 3. $C_{47}H_{75}N_7O_9S$ calcd. m/z=913.53 found [M-$C_7H_8O_2S$+Na]$^+$=768.1. (Quinone methide fragmentation and loss of 4-aminobenzylsulfonate).

Step 5: (S)—N-((3R,4S,5R)-1-((S)-2-((1R,2R)-3-((S)-1-(4-Amino phenylmethylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide was prepared from Compound Y-4 and MT-Val-Cit-OH according to General Procedure 10, followed by purification by preparative HPLC. $C_{71}H_{112}N_{12}O_{18}S$ calcd. m/z=1452.8 found $[M+H^+]^+$= 1454.6.

Example 3.167: (S,E)-N-(4-((14R,17R)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)-2,3-dimethylphenylsulfonyl)-2,5-dimethyl-4-((S)—N,3,3-trimethyl-2-((S)-3-methyl-2-(methylamino)-3-phenylbutanamido)butanamido)hex-2-enamide (Compound Z)

Step 1: N-(2,3-Dimethyl-4-sulfamoylphenyl)-2,2,2-trifluoroacetamide (Z-1) synthesized from 2,3-dimethylaniline according to General Procedure 8. $^1$H NMR (400 MHz, DMSO-$d_6$) δ 11.25 (s, 1H), 7.79 (d, J=8.5 Hz, 1H), 7.48 (s, 2H), 7.29 (d, J=8.5 Hz, 1H), 2.55 (s, 3H), 2.14 (s, 3H).

Step 2: (S,E)-N-(4-Amino-2,3-dimethylphenylsulfonyl)-2,5-dimethyl-4-((S)—N,3,3-trimethyl-2-((S)-3-methyl-2-(methylamino)-3-phenylbutanamido)butanamido)hex-2-enamide (Z-2) synthesized from Boc-HTI-286-OH and Compound Z-1 using General Procedures 2, 3 and 7.

$^1$H NMR (400 MHz, Methanol-$d_4$) δ 7.75 (d, J=8.8 Hz, 1H), 7.55 (d, J=7.9 Hz, 2H), 7.47 (t, J=7.7 Hz, 2H), 7.37 (t, J=6.9 Hz, 1H), 6.63 (d, J=8.8 Hz, 1H), 6.46 (d, J=9.7 Hz, 1H), 5.00 (t, J=10.0 Hz, 1H), 4.93 (s, 1H), 4.32 (s, 1H), 3.17 (s, 3H), 2.54 (s, 3H), 2.49 (s, 3H), 2.09 (s, 3H), 2.08-2.02 (m, 1H), 1.87 (d, J=1.4 Hz, 3H), 1.47 (s, 3H), 1.37 (s, 3H), 1.07 (s, 9H), 0.92 (dd, J=6.8, 6.5 Hz, 6H). $C_{35}H_{53}N_5O_5S$ calcd. m/z=655.38 found $[M+H]^+$=656.4.

Step 3: (S,E)-N-(4-((14R,17R)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)-2,3-dimethylphenylsulfonyl)-2,5-dimethyl-4-((S)—N,3,3-trimethyl-2-((S)-3-methyl-2-(methylamino)-3-phenylbutanamido)butanamido)hex-2-enamide synthesized from Compound Z-2 and MT-NHS according to General Procedure 6. $^1$H NMR (400 MHz, Methanol-$d_4$) δ 8.01 (dd, J=11.0, 8.2 Hz, 2H), 7.60-7.51 (m, 2H), 7.47 (dd, J=8.5, 6.8 Hz, 3H), 7.41-7.31 (m, 1H), 6.83 (s, 2H), 6.50 (dd, J=9.5, 1.8 Hz, 1H), 5.01 (t, J=10.0 Hz, 1H), 4.93 (t, J=4.1 Hz, 1H), 4.60 (m, 1H), 4.36 (s, 1H), 4.30-4.17 (m, 1H), 3.80-3.67 (m, 4H), 3.64 (td, J=5.5, 1.2 Hz, 2H), 3.60 (d, J=3.2 Hz, 7H), 3.29-3.13 (m, 5H), 2.67-2.46 (m, 9H), 2.24 (s, 3H), 2.20-1.92 (m, 4H), 1.93-1.75 (m, 3H), 1.65 (dp, J=16.0, 7.8 Hz, 2H), 1.43 (d, J=38.9 Hz, 6H), 1.14-0.96 (m, 16H), 0.92 (t, J=6.8 Hz, 6H). $C_{59}H_{90}N_{10}O_{14}S$ calcd. m/z=1194.64 found $[M+H]^+$ 1195.51; $[M+2H/2]^+$ 599.09.

Example 3.168: (S,E)-N-(4-((14R,17R)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)-5,6,7,8-tetrahydronaphthalen-1-ylsulfonyl)-2,5-dimethyl-4-((S)—N,3,3-trimethyl-2-((S)-3-methyl-2-(methylamino)-3-phenylbutanamido)butanamido)hex-2-enamide (Compound AA)

Step 1: 2,2,2-trifluoro-N-(4-sulfamoyl-5,6,7,8-tetrahydronaphthalen-1-yl)acetamide (AA-1) synthesized from 5,6,7,8-tetrahydronaphthalen-1-amine according to General Procedure 8. $^1$H NMR (400 MHz, DMSO-$d_6$) δ 11.04 (s, 1H), 7.79 (d, J=8.4 Hz, 1H), 7.46 (s, 2H), 7.30 (d, J=8.4 Hz, 1H), 3.14 (s, 1H), 2.77 (d, J=15.4 Hz, 1H), 2.72-2.57 (m, 4H), 1.73 (p, J=3.3 Hz, 4H).

Step 2: (S,E)-N-(4-amino-5,6,7,8-tetrahydronaphthalen-1-ylsulfonyl)-2,5-dimethyl-4-((S)—N,3,3-trimethyl-2-((S)-3-methyl-2-(methylamino)-3-phenylbutanamido)butanamido)hex-2-enamide (AA-2) synthesized from Boc-HTI-286-OH and Compound AA-1 using General Procedures 2, 3 and 7. $^1$H NMR (400 MHz, Methanol-$d_4$) δ 7.74 (d, J=8.7 Hz, 1H), 7.55 (d, J=7.9 Hz, 2H), 7.48 (t, J=7.6 Hz, 2H), 7.38 (t, J=7.2 Hz, 1H), 6.60 (d, J=8.7 Hz, 1H), 6.46 (d, J=9.2 Hz, 1H), 5.00 (t, J=10.0 Hz, 1H), 4.95-4.91 (m, 1H), 4.36 (s, 1H), 3.17 (s, 3H), 3.10-3.05 (m, 2H), 2.51 (s, 3H), 2.46 (t, J=6.5 Hz, 2H), 2.10-2.02 (m, 1H), 1.88 (s, 3H), 1.87-1.75 (m, 4H), 1.47 (s, 3H), 1.38 (s, 3H), 1.07 (s, 9H), 0.92 (dd, J=7.1 Hz, 6H). $C_{37}H_{55}N_5O_5S$ calcd. m/z=681.39 found $[M+H]^+$=682.4.

Step 3: (S,E)-N-(4-((14R,17R)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)-5,6,7,8-tetrahydronaphthalen-1-ylsulfonyl)-2,5-dimethyl-4-((S)—N,3,3-trimethyl-2-((S)-3-methyl-2-(methylamino)-3-phenylbutanamido)butanamido)hex-2-enamide synthesized from Compound AA-2 and MT-NHS according to General Procedure 6. $^1$H NMR (400 MHz, Methanol-$d_4$) δ 7.98 (d, J=8.7 Hz, 1H), 7.62 (d, J=8.7 Hz, 1H), 7.59-7.51 (m, 2H), 7.47 (dd, J=8.5, 6.8 Hz, 2H), 7.42-7.30 (m, 1H), 6.83 (s, 2H), 6.50 (dd, J=9.5, 1.8 Hz, 1H), 5.01 (t, J=10.0 Hz, 1H), 4.93 (t, J=4.1 Hz, 1H), 4.62 (td, J=8.1, 7.5, 5.0 Hz, 1H), 4.37 (s, 1H), 4.29-4.18 (m, 1H), 3.75 (t, J=6.0 Hz, 2H), 3.72-3.67 (m, 2H), 3.64 (td, J=5.9, 1.5 Hz, 2H), 3.29-3.08 (m, 7H), 2.74 (d, J=6.0 Hz, 2H), 2.62-2.46 (m, 5H), 2.20-1.94 (m, 4H), 1.91-1.75 (m, 7H), 1.70-1.58 (m, 2H), 1.48 (s, 3H), 1.38 (s, 3H), 1.07 (s, 9H), 1.00 (dd, J=6.8, 3.4 Hz, 6H), 0.92 (t, J=6.6 Hz, 6H). $C_{61}H_{92}N_{10}O_{14}S$ calcd. m/z=1220.65 found $[M+H]^+$ 1221.48; $[(M+2H)/2]^+$ 611.39.

Example 3.169: (S,E)-N-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)-3-fluorophenylsulfonyl)-2,5-dimethyl-4-((S)—N,3,3-trimethyl-2-((S)-3-methyl-2-(methylamino)-3-phenylbutanamido)butanamido)hex-2-enamide (Compound BB)

Step 1: 2,2,2-trifluoro-N-(2-fluoro-4-sulfamoylphenyl)acetamide (BB-1) synthesized from 2-fluoroaniline according to General Procedure 8. $^1$H NMR (400 MHz, DMSO-$d_6$) δ 11.58 (s, 1H), 7.85-7.66 (m, 3H), 7.56 (s, 2H).

Step 2: (S,E)-N-(4-amino-3-fluorophenylsulfonyl)-2,5-dimethyl-4-((S)—N,3,3-trimethyl-2-((S)-3-methyl-2-(methylamino)-3-phenylbutanamido)butanamido)hex-2-enamide (BB-2) synthesized from Boc-HTI-286-OH and Compound BB-1 using General Procedures 2, 3 and 7.

$^1$H NMR (400 MHz, Methanol-$d_4$) δ 7.62-7.55 (m, 3H), 7.54 (s, 1H), 7.48 (t, J=7.7 Hz, 2H), 7.37 (t, J=7.3 Hz, 1H), 6.85 (t, J=8.6 Hz, 1H), 6.45 (d, J=9.3 Hz, 1H), 4.98 (t, J=9.9 Hz, 1H), 4.92 (s, 1H), 4.34 (s, 1H), 3.16 (s, 3H), 2.50 (s, 3H), 2.12-2.00 (m, 1H), 1.88 (d, J=1.4 Hz, 3H), 1.46 (s, 3H), 1.37 (s, 3H), 1.07 (s, 9H), 0.91 (dd, J=6.8 Hz, 6H).

$C_{33}H_{48}FN_5O_5S$ calcd. m/z=645.34 $[M+H]^+$=646.4

Step 3: (S,E)-N-(4-((14R,17R)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)-3-fluorophenylsulfonyl)-2,5-dimethyl-4-((S)—N,3,3-trimethyl-2-((S)-3-methyl-2-(methylamino)-3-phenylbutanamido)butanamido)hex-2-enamide synthesized from Compound BB-2 and MT-NHS according to General Procedure 6. ¹H NMR (400 MHz, Methanol-d₄) δ 8.42-8.28 (m, 1H), 7.91-7.77 (m, 2H), 7.58-7.51 (m, 2H), 7.47 (t, J=7.8 Hz, 2H), 7.42-7.32 (m, 1H), 6.84 (s, 2H), 6.50 (dd, J=9.3, 1.8 Hz, 1H), 5.02-4.90 (m, 2H), 4.67 (td, J=7.9, 7.2, 4.8 Hz, 1H), 4.35 (s, 1H), 4.26 (t, J=7.5 Hz, 1H), 3.76 (t, J=6.1 Hz, 2H), 3.70 (td, J=5.5, 1.2 Hz, 2H), 3.67-3.53 (m, 10H), 3.28-3.06 (m, 5H), 2.61-2.47 (m, 5H), 2.19-2.01 (m, 2H), 2.01-1.71 (m, 4H), 1.61 (dt, J=15.2, 7.1 Hz, 2H), 1.46 (s, 3H), 1.36 (s, 3H), 1.13-0.95 (m, 16H), 0.91 (dd, J=6.6, 4.9 Hz, 6H). C₅₇H₈₅FN₁₀O₁₄S calcd. m/z=1184.60 found [M+H]⁺ 1185.47; [(M+2H)/2]⁺ 593.41.

Example 3.170: (S,E)-N-(4-((14R,17R)-1-(2,5-di-oxo-2,5-dihydro-1H-pyrrol-1-yl)-14-isopropyl-12,15-dioxo-17-(3-ureidopropyl)-3,6,9-trioxa-13,16-diazaoctadecanamido)-2-ethylphenylsulfonyl)-2,5-dimethyl-4-((S)—N,3,3-trimethyl-2-((S)-3-methyl-2-(methylamino)-3-phenylbutanamido)butanamido)hex-2-enamide (Compound CC)

Step 1: N-(3-Ethyl-4-sulfamoylphenyl)-2,2,2-trifluoroacetamide (CC-1) synthesized from 3-ethylaniline according to General Procedure 8. ¹H NMR (400 MHz, DMSO-d₆) δ 11.48 (s, 1H), 7.89 (d, J=8.5 Hz, 1H), 7.75-7.63 (m, 2H), 7.45 (s, 2H), 3.02 (q, J=7.5 Hz, 2H), 1.24 (t, J=7.4 Hz, 3H).

Step 2: (S,E)-N-(4-Amino-2-ethylphenylsulfonyl)-2,5-dimethyl-4-((S)—N,3,3-trimethyl-2-((S)-3-methyl-2-(methylamino)-3-phenylbutanamido)butanamido)hex-2-enamide (CC-2) synthesized from Boc-HTI-286-OH and Compound CC-1 using General Procedures 2, 3 and 7.

¹H NMR (400 MHz, Methanol-d₄) δ 7.79 (d, J=8.7 Hz, 1H), 7.55 (d, J=7.9 Hz, 2H), 7.48 (t, J=7.6 Hz, 2H), 7.37 (t, J=7.4 Hz, 1H), 6.57 (d, J=2.3 Hz, 1H), 6.54 (dd, J=8.8, 2.4 Hz, 1H), 6.46 (d, J=9.4 Hz, 1H), 5.01 (t, J=10.0 Hz, 1H), 4.92 (s, 1H), 4.34 (s, 1H), 3.16 (s, 3H), 2.99-2.90 (m, 2H), 2.50 (s, 3H), 2.11-2.00 (m, 1H), 1.87 (d, J=1.4 Hz, 3H), 1.47 (s, 3H), 1.38 (s, 3H), 1.22 (t, J=7.5 Hz, 3H), 1.06 (s, 9H), 0.91 (dd, J=6.6 Hz, 6H). C₃₅H₅₃N₅O₅S calcd. m/z=655.38 [M+H]⁺=656.4.

Step 3: (S,E)-N-(4-((14R,17R)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)-2-ethylphenylsulfonyl)-2,5-dimethyl-4-((S)—N,3,3-trimethyl-2-((S)-3-methyl-2-(methylamino)-3-phenylbutanamido)butanamido)hex-2-enamide synthesized from Compound CC-2 and MT-NHS according to General Procedure 6. ¹H NMR (400 MHz, Methanol-d₄) δ 8.04 (d, J=8.8 Hz, 1H), 7.77 (d, J=2.2 Hz, 1H), 7.67 (dd, J=8.8, 2.2 Hz, 1H), 7.54 (d, J=7.6 Hz, 2H), 7.46 (t, J=7.7 Hz, 2H), 7.36 (t, J=7.3 Hz, 1H), 6.83 (s, 2H), 6.51 (dd, J=9.5, 1.9 Hz, 1H), 5.01 (t, J=10.0 Hz, 1H), 4.92 (d, J=8.4 Hz, 2H), 4.60-4.47 (m, 1H), 4.37 (s, 1H), 4.23 (d, J=6.9 Hz, 1H), 3.82-3.72 (m, 2H), 3.69 (dd, J=6.0, 4.5 Hz, 2H), 3.66-3.52 (m, 10H), 3.28-3.10 (m, 5H), 3.06 (q, J=7.4 Hz, 2H), 2.58 (t, J=6.0 Hz, 2H), 2.52 (s, 3H), 2.20-1.90 (m, 3H), 1.87 (s, 3H), 1.84-1.72 (m, 1H), 1.64-1.55 (m, 2H), 1.47 (s, 3H), 1.37 (s, 3H), 1.26 (t, J=7.5 Hz, 3H), 1.10-0.96 (m, 15H), 0.91 (dd, J=6.6, 4.0 Hz, 6H). C₅₉H₉₀N₁₀O₁₄S calcd. m/z=1194.64 found [M+H]⁺ 1195.57; [(M+2H)/2]⁺ 599.12.

Example 3.171: (S,E)-N-(4-((14R,17R)-1-(2,5-di-oxo-2,5-dihydro-1H-pyrrol-1-yl)-14-isopropyl-12,15-dioxo-17-(3-ureidopropyl)-3,6,9-trioxa-13,16-diazaoctadecanamido)-3-ethylphenylsulfonyl)-2,5-dimethyl-4-((S)—N,3,3-trimeth-2-((S)-3-methy-2-(methylamino)-3-phenylbutanamido)butanamido)hex-2-enamide (Compound DD)

Step 1: N-(2-ethyl-4-sulfamoylphenyl)-2,2,2-trifluoroacetamide (DD-1) synthesized from 2-ethylaniline according to general procedure 1. ¹H NMR (400 MHz, DMSO-d₆) δ 11.21 (s, 1H), 7.80 (d, J=2.1 Hz, 1H), 7.72 (dd, J=8.2, 2.2 Hz, 1H), 7.48 (d, J=8.3 Hz, 1H), 7.41 (s, 2H), 2.64 (q, J=7.6 Hz, 2H), 1.16 (t, J=7.5 Hz, 3H).

Step 2: (S,E)-N-(4-amino-3-ethylphenylsulfonyl)-2,5-dimethyl-4-((S)—N,3,3-trimethyl-2-((S)-3-methyl-2-(methylamino)-3-phenylbutanamido)butanamido)hex-2-enamide (DD-2) synthesized from Boc-HTI-286-OH and Compound DD-1 using General Procedures 2, 3 and 7. ¹H NMR (400 MHz, Methanol-d₄) δ 7.66 (d, J=2.3 Hz, 1H), 7.61 (dd, J=8.6, 2.3 Hz, 1H), 7.55 (d, J=7.6 Hz, 2H), 7.48 (t, J=7.7 Hz, 2H), 7.37 (t, J=7.3 Hz, 1H), 6.71 (d, J=8.5 Hz, 1H), 6.43 (dd, J=9.3, 1.7 Hz, 1H), 4.96 (t, J=9.9 Hz, 1H), 4.92 (s, 1H), 4.35 (s, 1H), 3.16 (s, 3H), 2.54 (dd, J=7.4, 2.2 Hz, 2H), 2.51 (s, 3H), 2.12-1.99 (m, 1H), 1.87 (d, J=1.4 Hz, 3H), 1.46 (s, 3H), 1.36 (s, 3H), 1.27 (t, J=7.5 Hz, 3H), 1.07 (s, 9H), 0.91 (dd, J=6.4 Hz, 6H). C₃₅H₅₃N₅O₅S calcd. mt/z=655.38 [M+H]⁺=656.5.

Step 3: (S,E)-N-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)-3-ethylphenylsulfonyl)-2,5-dimethyl-4-((S)—N,3,3-trimethyl-2-((S)-3-methyl-2-(methylamino)-3-phenylbutanamido)butanamido)hex-2-enamide synthesized from Compound DD-2 and MT-NHS according to General Procedure 6. ¹H NMR (400 MHz, Methanol-d₄) δ 7.97 (d, J=2.3 Hz, 1H), 7.87 (dd, J=8.5, 2.3 Hz, 1H), 7.77 (d, J=8.5 Hz, 1H), 7.59-7.51 (m, 2H), 7.51-7.42 (m, 2H), 7.41-7.34 (m, 1H), 6.84 (s, 2H), 6.48 (dd, J=9.4, 1.8 Hz, 1H), 4.98 (t, J=9.9 Hz, 1H), 4.92 (d, J=8.4 Hz, 1H), 4.64 (td, J=8.4, 7.6, 3.7 Hz, 1H), 4.36 (s, 1H), 4.25 (d, J=7.0 Hz, 1H), 3.82-3.67 (m, 4H), 3.67-3.53 (m, 10H), 3.29-3.09 (m, 5H), 2.77 (q, J=7.5 Hz, 2H), 2.62-2.46 (m, 5H), 2.20-1.95 (m, 4H), 1.91-1.74 (m, 4H), 1.72-1.60 (m, 2H), 1.47 (s, 3H), 1.37 (s, 3H), 1.27 (t, J=7.5 Hz, 3H), 1.12-0.95 (m, 16H), 0.91 (dd, J=6.6, 4.6 Hz, 6H). C₅₉H₉₀N₁₀O₁₄S calcd. m/z=1194.64 found [M+H]⁺ 1195.54; [(M+2H)/2]⁺ 599.09.

Example 3.172: (S)—N-(4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)phenyl)-1-((S)-1-(2,5-dioxo-2,5-dihydro-1H-pyrrol-1-yl)-14-methyl-12-oxo-3,6,9-trioxa-13-azapentadecane)pyrrolidine-2-carboxamide (Compound EE)

Synthesized from Compound N-1c and Boc-Ala-Pro-OH according to General Procedure 10, followed by Boc-removal according to General Procedure 7 and MT-NHS installation according to General Procedure 6 prior to purification by preparative HPLC. ¹H NMR (400 MHz, Methanol-d₄) δ 7.99 (d, J=8.9 Hz, 2H), 7.81 (d, J=8.5 Hz, 2H), 7.55 (d, J=7.5 Hz, 2H), 7.48 (t, J=7.7 Hz, 2H), 7.38 (t, J=7.3 Hz, 1H), 6.84 (s, 2H), 6.54-6.42 (m, 1H), 5.07-4.95 (m, 2H), 4.67 (t, J=6.8 Hz, 1H), 4.57 (dd, J=8.4, 4.6 Hz, 1H), 4.35 (s, 1H), 3.95-3.83 (m, 1H), 3.80-3.66 (m, 5H), 3.61 (dd, J=18.6, 4.6 Hz, 10H), 3.16 (s, 3H), 2.58-2.42 (m, 5H), 2.36 (d, J=18.0 Hz, 1H), 2.23-1.98 (m, 4H), 1.86 (d, J=1.4 Hz, 3H), 1.46 (s, 3H), 1.43-1.31 (m, 6H), 1.07 (s, 10H), 0.91 (t, J=6.3 Hz, 6H). C₅₉H₉₀N₁₀O₁₄S calcd. m/z=1078.54 found [M+H]⁺ 1079.48; [(M+2H)/2]⁺ 540.27.

Example 3.173: (S,E)-N-(4-((S)-6-Amino-2-((S)-2-(3-(2-(2,5-dioxo-2,5-dihydro-1H-pyrrol-1-yl)ethoxy)propanamido)-3-phenylpropanamido)hexanamido)phenylsulfonyl)-2,5-dimethyl-4-((S)—N,3,3-trimethyl-2-((S)-3-methyl-2-(methylamino)-3-phenylbutanamido)butanamido)hex-2-enamide (Compound FF)

The title compound was prepared from Compound N-1c and Fmoc-Phe-Lys(Boc)-OH according to General Procedure 10, followed by Fmoc removal according to General Procedure 5, acylation with MT-NHS according to General Procedure 6 and deprotection according to General Procedure 7 prior to purification by preparative HPLC. $C_{61}H_{87}N_9O_{13}S$ calcd. m/z=1185.6 found $[M+H^+]^+=1186.6$ and $[(M+2H^+)/2]^{2+}=593.9$.

Example 3.174: (S,E)-N-((4-((14S,17S)-17-(4-Aminobutyl)-1-(2,5-dioxo-2,5-dihydro-1H-pyrrol-1-yl)-14-isopropyl-12,15-dioxo-3,6,9-trioxa-13,16-diazaoctadecanamido)phenyl)sulfonyl)-2,5-dimethyl-4-((S)—N,3,3-trimethyl-2-((S)-3-methyl-2-(methylamino)-3-phenylbutanamido)butanamido)hex-2-enamide (Compound GG)

The title compound was prepared from Compound N-1c and Fmoc-Val-Lys(Boc)-OH according to General Procedure 10, followed by Fmoc removal according to General Procedure 5, acylation with MT-NHS according to General Procedure 6 and deprotection according to General Procedure 7 prior to purification by preparative HPLC. $C_{57}H_{87}N_9O_{13}S$ calcd. m/z=1137.6 found $[M+H^+]^+=1138.5$ and $[(M+2H^+)/2]^{2+}=569.8$.

Example 3.175: (S,E)-N-(4-((2S,5S,8R)-2-(4-Aminobutyl)-5-benzyl-15-(2,5-dioxo-2,5-dihydro-1H-pyrrol-1-yl)-8-methyl-4,7,10-trioxo-13-oxa-3,6,9-triazapentadecanamido)phenylsulfonyl)-2,5-dimethyl-4-((S)—N,3,3-trimethyl-2-((S)-3-methyl-2-(methylamino)-3-phenylbutanamido)butanamido)hex-2-enamide (Compound HH)

The title compound was prepared from Compound N-1c and Fmoc-Ala-Phe(D)-Lys(Boc)-OH according to General Procedure 10. The resulting material, purified by flash chromatography was then subject to General Procedure 5 to remove the Fmoc protecting group, followed by treatment with MT-NHS according to General Procedure 6 and deprotection according to General Procedure 7 prior to purification by preparative HPLC. $C_{64}H_{92}N_{10}O_{14}S$ calcd. m/z=1256.7 found $[M+H^+]^+=1258.3$ and $[(M+2H^+)/2]^{2+}=630.2$.

Example 3.176: (S,E)-N-(4-((2S,5S,8R)-2-(4-Aminobutyl)-5,8-dibenzyl-15-(2,5-dioxo-2,5-dihydro-1H-pyrrol-1-yl)-4,7,10-trioxo-13-oxa-3,6,9-triazapentadecanamido)phenylsulfonyl)-2,5-dimethyl-4-((S)—N,3,3-trimethyl-2-((S)-3-methyl-2-(methylamino)-3-phenylbutanamido)butanamido)hex-2-enamide (Compound II)

The title compound was prepared from Compound N-1c and Fmoc-Phe-Phe(D)-Lys(Boc)-OH according to General Procedure 10, Fmoc-removal via General Procedure 5, reaction with MT-NHS according to General Procedure 6 and deprotection according to General Procedure 7, followed by prep HPLC purification. $C_{69}H_{94}N_{10}O_{14}S$ calcd. m/z=1332.7 found $[M+H^+]^+=1334.3$ and $[(M+2H^+)/2]^{2+}=668.2$.

Example 3.177: (S,E)-N-(2-((14S,17S)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonyl)-2,5-dimethyl-4-((S)—N,3,3-trimethyl-2-((S)-3-methyl-2-(methylamino)-3-phenylbutanamido)butanamido)hex-2-enamide (Compound JJ)

Step 1: 2,2,2-Trifluoro-N-(2-sulfamoylphenyl)acetamide (JJ-1) was made from 2-aminobenzenesulfonamide according to General Procedure 1.

Step 2: (S,E)-N-(2-Aminophenylsulfonyl)-2,5-dimethyl-4-((S)—N,3,3-trimethyl-2-((S)-3-methyl-2-(methylamino)-3-phenylbutanamido)butanamido)hex-2-enamide (JJ-2) was made from Compound JJ-1 and Boc-HTI-286-OH according to General Procedures 2 and 3. $^1$H NMR (400 MHz, Methanol-$d_4$) δ 7.75 (dd, J=8.2, 1.5 Hz, 1H), 7.55 (d, J=7.8 Hz, 2H), 7.48 (t, J=7.7 Hz, 2H), 7.38 (t, J=7.4 Hz, 1H), 7.33-7.27 (m, 1H), 6.81 (d, J=8.2 Hz, 1H), 6.69 (t, J=7.5 Hz, 1H), 6.49 (dd, J=9.1, 1.5 Hz, 1H), 4.97 (t, J=10.1 Hz, 1H), 4.92 (s, 1H), 4.35 (s, 1H), 3.17 (s, 3H), 2.51 (s, 3H), 2.07 (m, 1H), 1.88 (d, J=1.4 Hz, 3H), 1.46 (s, 3H), 1.36 (s, 3H), 1.06 (s, 9H), 0.92 (t, J=6.8 Hz, 6H). $C_{33}H_{49}N_5O_5S$ calcd. m/z=627.35 amu; found $[M+H]^+=628.36$, $[M+Na]^+=650.37$, $[(M+2H)/2]^{2+}=314.76$.

Step 3: tert-Butyl ((S)-1-(((S)-1-((2-(N—((S,E)-2,5-dimethyl-4-((S)—N,3,3-trimethyl-2-((S)-3-methyl-2-((tert-butoxycarbonyl)methylamino)-3-phenylbutanamido)butanamido)hex-2-enoyl)sulfamoyl)phenyl)amino)-1-oxo-5-ureidopentan-2-yl)amino)-3-methyl-1-oxobutan-2-yl)carbamate (JJ-3) was generated from Compound JJ-2 and Boc-Val-Cit-OH according to General Procedure 10. $C_{54}H_{85}N_9O_{12}S$ calcd. m/z=1083.60 amu; found $[M+H]^+=1084.8$, $[M+Na]^+=1106.7$.

Step 4: (S,E)-N-(2-((S)-2-((S)-2-Amino-3-methylbutanamido)-5-ureidopentanamido)phenylsulfonyl)-2,5-dimethyl-4-((S)—N,3,3-trimethyl-2-((S)-3-methyl-2-(methylamino)-3-phenylbutanamido)butanamido)hex-2-enamide (JJ-4) was generated from Compound JJ-3 according to General Procedure 7. $C_{44}H_{69}N_9O_8S$ calcd. m/z=883.50 amu; found $[M+H]^+=884.6$, $[M+Na]^+=906.6$, $[(M+2H)/2]^{2+}=442.8$.

Step 5: (S,E)-N-(2-((14S,17S)-1-(2,5-Dioxo-2,5-dihydro-H-pyrrol-1-yl)-14-isopropyl-12,15-dioxo-17-(3-ureidopropyl)-3,6,9-trioxa-13,16-diazaoctadecanamido)phenylsulfonyl)-2,5-dimethyl-4-((S)—N,3,3-trimethyl-2-((S)-3-methyl-2-(methylamino)-3-phenylbutanamido)butanamido)hex-2-enamide was generated from Compound JJ-4 and MT-NHS according to General Procedure 6 before purification by preparative HPLC-MS. $^1$H NMR (400 MHz, Methanol-$d_4$) δ 8.16 (d, J=8.3 Hz, 1H), 7.95 (dd, J=8.0, 1.6 Hz, 1H), 7.50 (d, J=7.9 Hz, 2H), 7.42 (dt, J=15.5, 7.8 Hz, 3H), 7.29 (t, J=7.3 Hz, 1H), 7.19 (t, J=7.5 Hz, 1H), 6.85 (s, 2H), 6.62 (d, J=9.3 Hz, 1H), 4.66 (s, 1H), 4.61 (dd, J=9.1, 4.5 Hz, 1H), 4.37 (d, J=6.9 Hz, 1H), 3.76 (dd, J=7.5, 5.7 Hz, 2H), 3.73-3.67 (m, 2H), 3.67-3.56 (m, 10H), 3.29-3.13 (m, 4H), 3.11 (s, 3H), 2.70 (s, 6H), 2.65-2.49 (m, 2H), 2.22 (s, 3H), 2.11 (d, J=7.5 Hz, 2H), 2.00 (dt, J=17.2, 6.2 Hz, 2H), 1.86 (d, J=1.4 Hz, 3H), 1.66 (dt, J=14.5, 7.8 Hz, 2H), 1.01 (d, J=13.3 Hz, 15H), 0.87 (dd, J=21.4, 6.6 Hz, 6H). $C_{57}H_{86}N_{10}O_{14}S$ calcd. m/z=1166.60 amu; found $[M+H]^+=1167.8$, $[M+Na]^+=1189.9$, $[(M+2H)/2]^{2+}=584.4$.

Example 3.178: MT-Val-Cit-OH: (14R,17R)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecan-18-oic Acid The title compound was prepared from H—VC—OH (0.50 g, 1.287 mmol)) and MT-NHS (0.512 g, 1.287 mmol) with N,N-di-isopropylethylamine (0.448 mL, 2 equiv) in dioxanes (0.50 mL). Upon consumption of the starting material (~16 h, evaluated by HPLC-MS), the reaction was concentrated in vacuo and the resulting oil was purified by preparative HPLC-MS. Lyophilization of the desired fractions afforded the title compound as a white powder (0.351 g, 63%). $^1$H NMR (400 MHz, Chloroform-d) δ 6.76 (s, 2H), 4.54-4.59 (m, 1H), 4.33-4.38 (m, J=7.6 Hz, 1H), 3.85-3.70 (m, 5H), 3.60-3.68 (m, 10H), 3.18-3.22 (m, 2H), 2.55-2.62 (m, 2H), 2.10-2.18 (m, 1H), 1.90-2.05 (m, 1H), 1.72-1.85 (m, 1H), 1.54-1.65 (m, 2H), 0.98 (t, J=6.6 Hz, 6H).

Example 3.179: Other Representative Compounds (P$^1$)

The following representative compounds may be prepared according to the foregoing procedures. As recognized by the artisan of reasonable skill, the following compounds are synthetically accessible using the disclosure of WO 2004/026293 to achieve the precursor reactant and applying General Procedures with the appropriate sulfonamide.

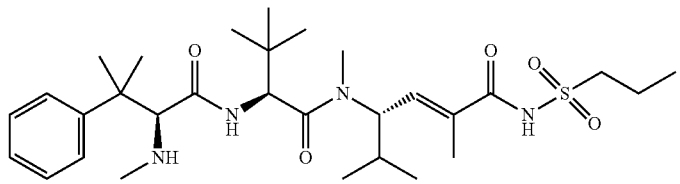

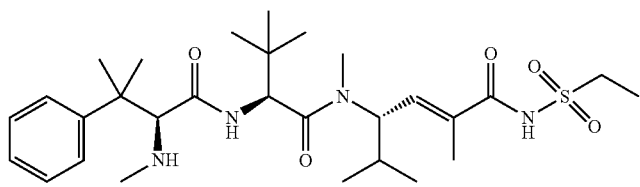

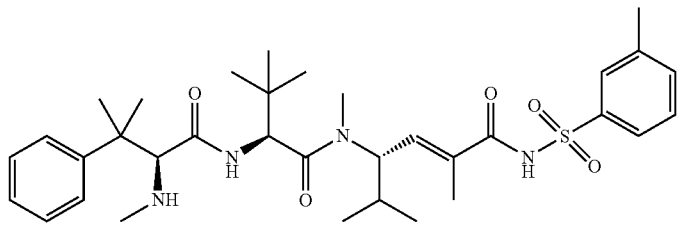

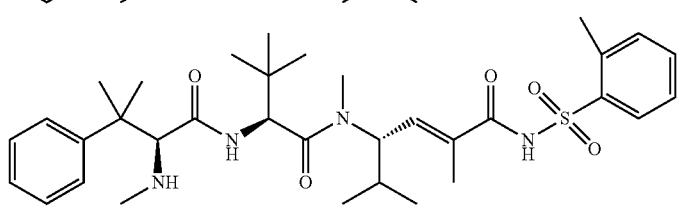

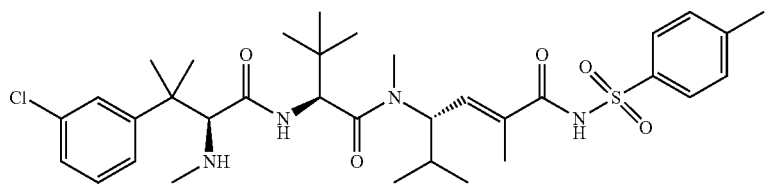

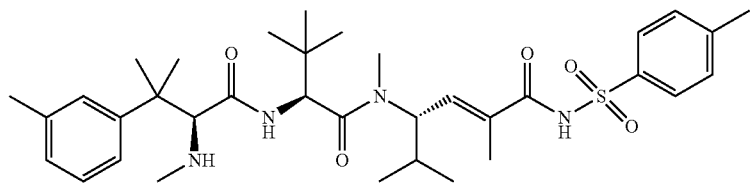

-continued
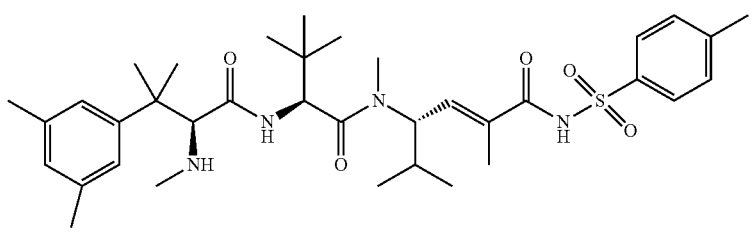
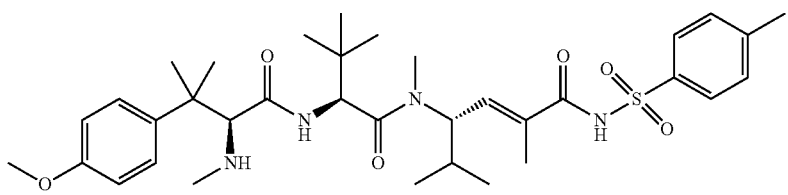
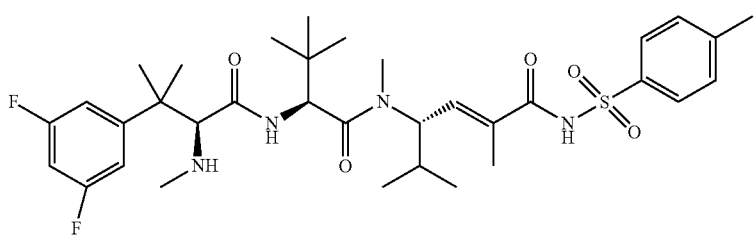
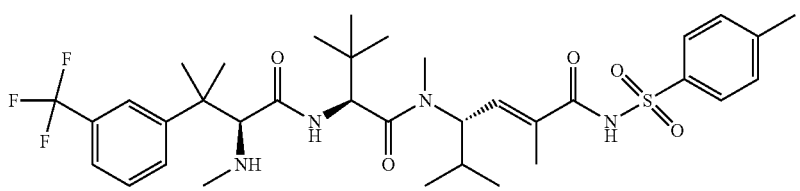
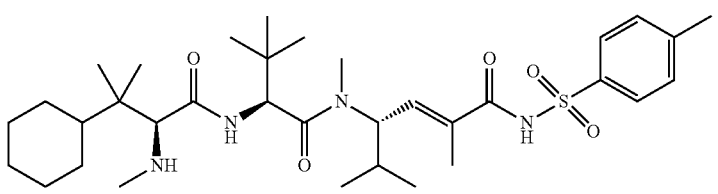
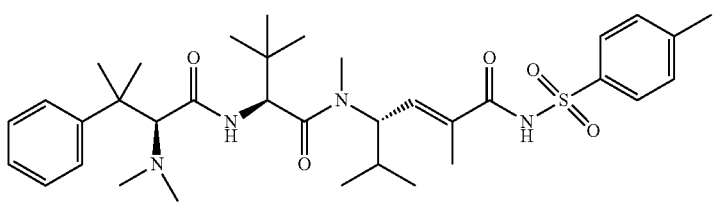
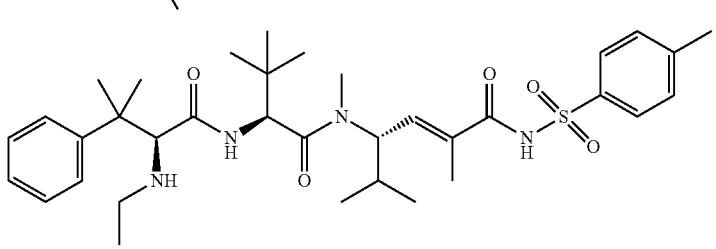
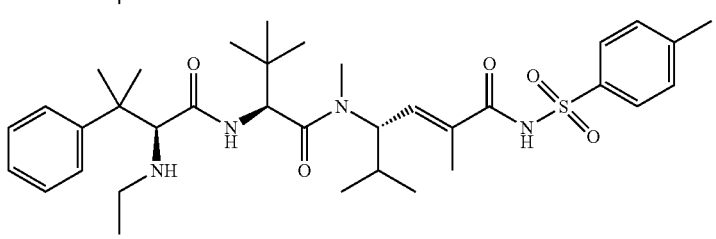

-continued
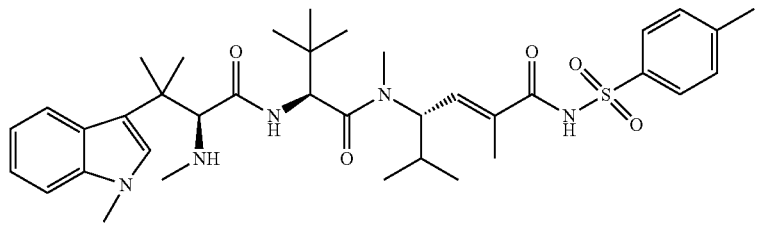
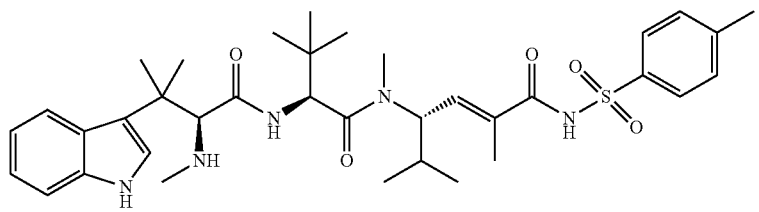
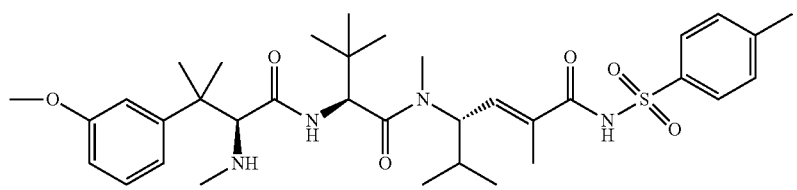
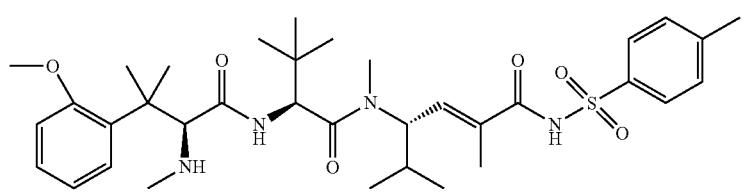
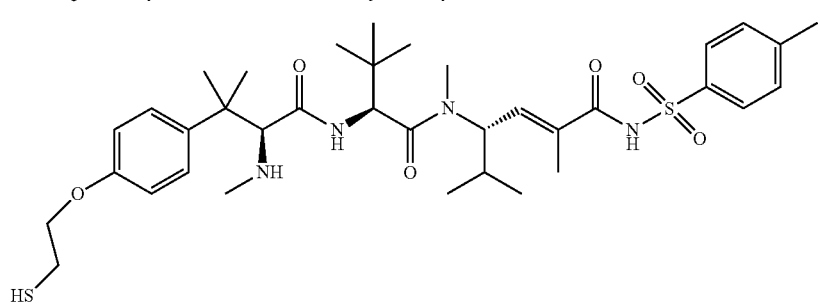
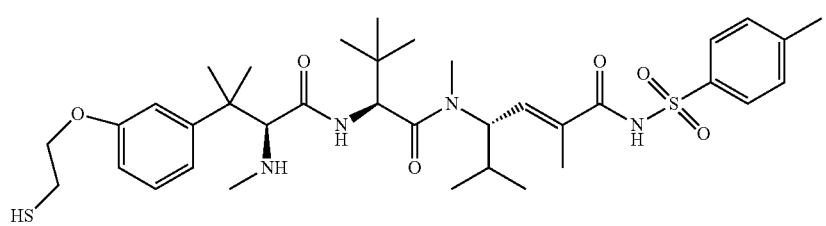
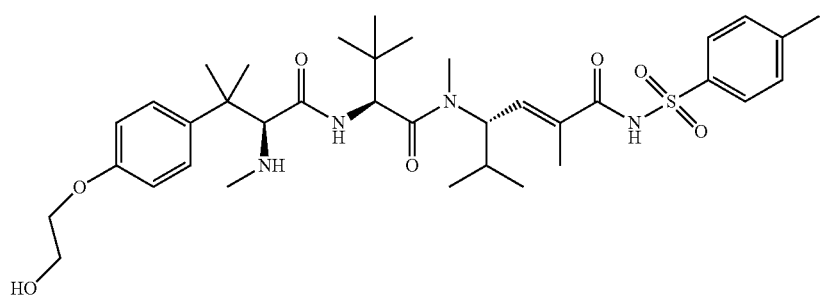

-continued
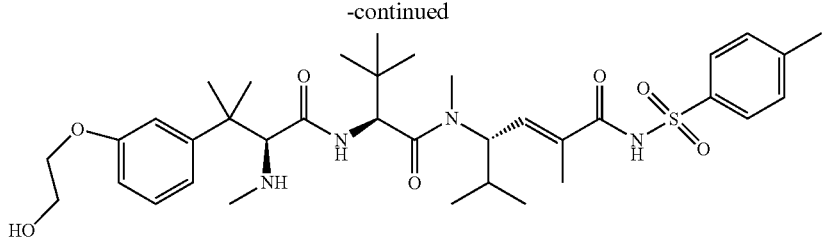
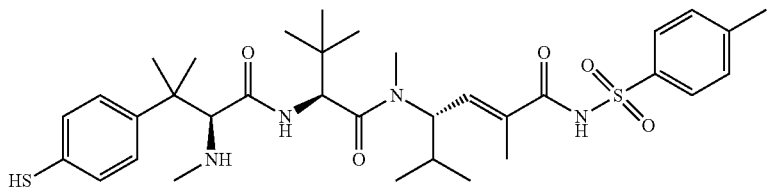
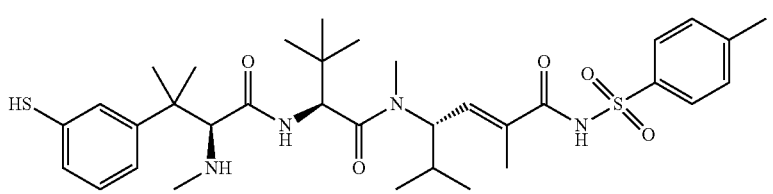
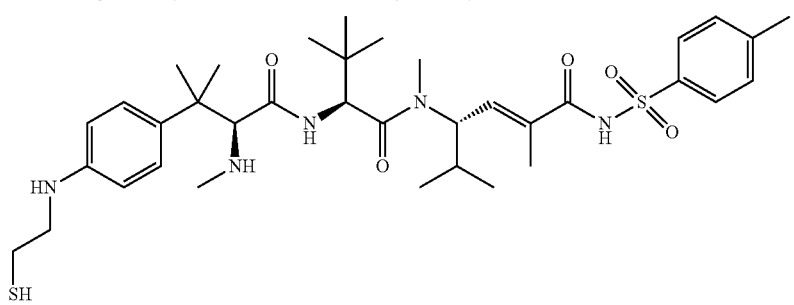
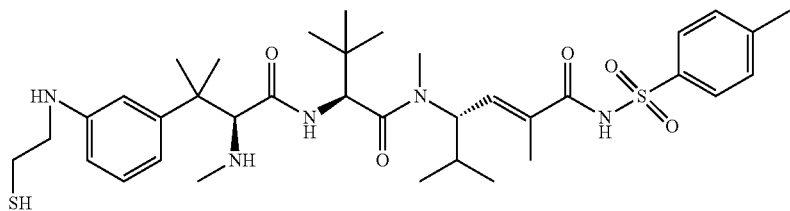
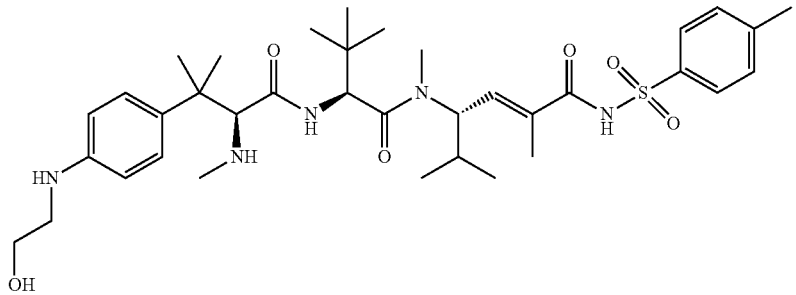
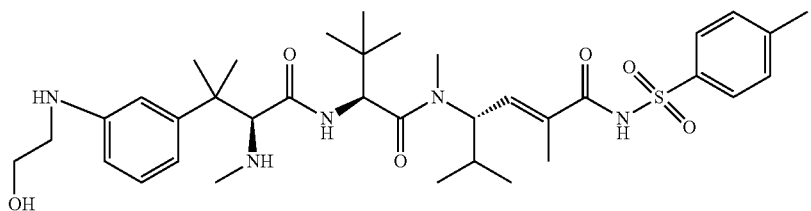

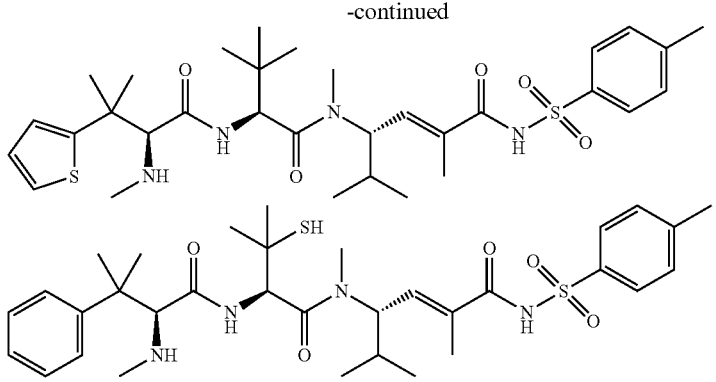

Example 4: Preparation of Certain Compounds of Formula I

Proteins:

Truncated recombinant VAR2CSA proteins (see Dahlbäck et al. for domain boundaries—J. Biol. Chem. 286: 15908-15917) were expressed in E. coli or eukaryotic expression systems and purified according to the general methods below.

General Purification Methods for Recombinant VAR2CSA Proteins

Recombinant DBL1-ID2a and ID1-ID2a were produced in stable transfected Drosophila Schneider-2 (S2) cells or in baculovirus transfected insect cells. Harvested culture supernatants were diafiltrated using an Äcta Crossflow. HIS tagged versions of the two proteins were purified on Ni++ 5 mL HisTrap HP columns and eluted with 350 mM imidazole. The eluted fractions were further purified on a Superdex200 GF column (in: 1×PBS, 0.5M NaCl, pH 7.2 with 1 CMPIT protease inhibitor tablet per 300 mL buffer) and monomeric fractions were selected for further analyses and toxin coupling. The VAR2CSA recombinant proteins with or without poly histidine tag were also purified using standard ion exchange columns (negative and positive selection) and further purified on columns utilizing a hydrophobic interaction as well as ionic interaction. The proteins were also purified on columns with bound nanobody or antibody specific to VAR2CSA relying on a specific interaction between the VAR2CSA specific antibody reagents and the VAR2CSA protein. The proteins were eluted in a NaCl gradient or a pH gradient going from 7.4 down to 2, followed by immediate neutralization in a basic buffer. To stabilize protein during purification we used (each alone or in combination) the following compounds: Hydroxyectoine, Sucrose, EDTA, D-Sorbitol, Xylitol, D-(+)-Trehalose dehydrate, Betaine monohydrate, Tryptone, Gly-gly-gly, Gly-gly, 6-Aminohexanoic acid, L-Serine, β-Alanine, L-Histidine, Glycine, L-Arginine, L-Arginine+L-Glutamic acid, Taurine, Non Detergent Sulfobetaine 211 (NDSB-211)

Recombinant VAR2CSA proteins expressed in C3029H or C3030H E. coli cells were purified from cell lysates produced by sonication. Polyhistidine tagged proteins were purified on Ni++ 5 mL HisTrap HP columns and eluted with 350 mM imidazole. The eluted fractions were further purified on a Superdex200 GF column (in: 1×PBS, 0.5M NaCl, pH 7.2 with 1 CMPIT protease inhibitor tablet per 300 mL buffer) and monomeric fractions were selected for further analyses and toxin coupling.

Cell Binding Panel:

Numerous cancer cell lines were screened for binding to VAR2CSA by FACS. Table 6 summarizes the binding of recombinant DBL1-ID2a to a panel of cancer cell lines. Signal from VAR2CSA staining (mean fluorescence intensity of bound V5-tagged VAR2CSA detected by mIgG2ak anti-V5-FITC) is compared to background (mean fluorescence intensity of bound V5-tagged VAR2CSA detected by mIgG2a-FITC isotype control antibody).

General Method: Binding of Recombinant VAR2CSA to Cancer Cells by FACS

Cells were established in logarithmic growth in their respective growth medium prior to the assay. On the day staining was performed, culture medium was aspirated and discarded. 5 mL of PBS was added to the culture vessel to rinse cells and PBS was then removed by aspiration. At this point cell dissociation buffer (3 mL; Sigma C5914) was added to adherent cell lines and the cells were incubated until detachment was observed under a microscope. The cell dissociation reagent was neutralized with 7 mL of serum containing culture medium and cell viability was determined using Trypan Blue exclusion assay. Alternatively, suspension cells were assayed for viability directly after washing with PBS. Cells were added to the bottom of 96 well V-bottomed plates (50,000 cells/well) and pelleted by centrifugation (400×g, 3 min). After removal of supernatant, 15 µL of V5-tagged recombinant VAR2CSA (400 nM) or FACS buffer (PBS+1% FBS) was added to resuspend the cell pellet. After incubation on ice for a period of one hour, plates were washed by addition of 200 µL FACS buffer, centrifugation (400×g, 3 min), removal of supernatant, resuspension of the cell pellet in 200 µL of FACS buffer with disruption of the pellet, centrifugation (400×g, 3 min), and finally removal of supernatant. Cell pellets were resuspended in 25 µL of either mIgG2ak anti-V5-FITC (1:100 dilution), or mIgG2a-FITC (2 µg/mL dilution) and 7A.A.D (2.5 µg/mL). Plates were incubated on ice for 0.5 hours before washing cells as described above. The cell pellets were then resuspended in 75 µL FACS buffer and analyzed by flow cytometry. Data are represented as live cell (7-AAD negative population) geometric mean fluorescence in the FITC channel

TABLE 6

Cell line binding by recombinant VAR2CSA as assessed by FACS.

| Cell Line | VAR2CSA Staining MFI | Signal:Background Ratio | Background Controls MFI (Secondary alone/Isotype) |
|---|---|---|---|
| Ramos | 4044 | 7 | 584 |
| A-172 | 52938 | 30 | 1766 |
| NCI-H358 | 45991 | 26 | 1800 |
| HT-29 | 16405 | 9 | 1845 |
| HCT-15 | 6470 | 8 | 800 |
| A549 | 81032 | 52 | 1561 |
| MDA-MB-231 | 49745 | 43 | 1149 |
| HCC-1954 | 61444 | 18 | 3353 |
| OE19 | 51471 | 9 | 5565 |
| OVCAR-3 | 32114 | 11 | 2796 |
| OV-90 | 20503 | 6 | 3644 |
| BxPC-3 | 33962 | 7 | 4778 |
| MIA PaCa-2 | 9031 | 4 | 2277 |
| HPAF-II | 11745 | 3 | 3540 |
| PANC-1 | 18348 | 5 | 3586 |
| AsPc-1 | 30015 | 11 | 2856 |
| CCRF-CEM | 6395 | 17 | 367 |
| AML-193 | 2943 | 4 | 741 |
| Jurkat | 9363 | 24 | 389 |
| PC-3 | 32925 | 19 | 1775 |
| DU145 | 21069 | 11 | 1854 |
| RT112/84 | 38410 | 21 | 1820 |
| CaOV3 | 19852 | 5 | 3724 |
| SKOV3 | 61831 | 29 | 2144 |
| MCF7 | 18259 | 10 | 1879 |
| A-431 | 54090 | 21 | 2592 |
| NCI-N87 | 4487 | 5 | 995 |
| Colo-205 | 449061 | 233 | 1926 |
| T47-D | 83146 | 52 | 1595 |
| MDA-MB-231 | 82323 | 53 | 1566 |
| MDA-MB-468 | 70162 | 31 | 2287 |
| Colo-205 | 108367 | 73 | 1479 |
| 253JB-V | 32875 | 24 | 1398 |
| Myla 2059 | 89669 | 94 | 958 |
| K562 wt | 20211 | 15 | 1315 |
| K562 #16 | 2018 | 1 | 1773 |
| K562 #14 | 2215 | 2 | 1386 |
| PC-3 | 46023 | 29 | 1603 |
| UM-UC3 | 73627 | 47 | 1553 |
| A549 | 109308 | 33 | 3312 |
| MG-63 | 75389 | 28 | 2729 |
| T47-D | 74285 | 59 | 1257 |
| HUVEC | 9703 | 5 | 2024 |
| MDA-MB-231 | 27663 | 14 | 1950 |
| MDA-MB-231 | 91666 | 46 | 1986 |
| U2OS | 96707 | 55 | 1761 |
| RH-30 | 43355 | 11 | 4058 |

Exemplary Conjugation Conditions:

General Method: Coupling at Cysteine Residues with Maleimide Functionalized Toxins An aliquot of truncated recombinant VAR2CSA protein DBL1-ID2a (lot MP1255; 197 µL; 181 µg) was thawed on ice and handled on ice thereafter. To the protein solution was added maleimide functionalized toxin (2.4 µL of a 10 mM DMSO stock solution; 15.0 equivalents to protein) with thorough and immediate mixing. The reaction was allowed to proceed for a period of 90 minutes after which time the solution was applied to a Zeba spin desalting column (Pierce, product #87766, lot #198863) preconditioned with PBS. The recovered eluate was aliquoted and frozen at −80° C. prior to use.

Examples of Maleimide Functionalized Toxins

Compound O

MCvcPABC-3.90

General Method: Coupling at Lysine Residues with NHS-Ester Functionalized Toxins An aliquot of truncated recombinant VAR2CSA protein DBL1-ID2a (197 μL; 181 μg) was thawed on ice and handled on ice thereafter. To the protein solution was added an NHS ester functionalized toxin (3.2 μL of a 5 mM DMSO stock solution; 10.0 equivalents to protein) with thorough and immediate mixing. The reaction was allowed to proceed for a period of 90 minutes after which time the solution was applied to a Zeba spin desalting column (Pierce, product #87766, lot #198863) preconditioned with PBS. The recovered eluate was aliquoted and frozen at −80° C. prior to use.

Example of N-Hydroxysuccinimidyl Ester Functionalized Toxins gas: Nitrogen, and collision gas: Argon. The summed TIC mass spectra of the sample peak were deconvoluted by the MaxEnt1 algorithm to generate the neutral mass data of the sample component.

Exemplary Data for Average Drug to VAR2CSA Ratio Determination:

VAR2CSA (DBL1-ID2a) conjugates prepared by modification of cysteine and lysine residues with maleimide functionalized toxin (Compound O) or NHS functionalized toxin (Compound KK) were evaluated for toxin loading by SEC-MS as described in the General Method. The estimated mass obtained for the unmodified precursor protein was 114162 Da.

Compound KK

Standard Characterization Procedures:

1. Purified drug conjugates were assessed for total protein content (BCA assay, Pierce microBCA protocol).

2. VAR2CSA conjugates were evaluated alongside unmodified VAR2CSA for degradation and or oligomerization via SDS-PAGE under both reducing and non-reducing conditions, using Coomassie Blue staining and appropriate protein standards.

3. Purified VAR2CSA drug conjugates were evaluated (alongside unmodified VAR2CSA) to assess drug loading by Size Exclusion Ultra High Performance Liquid Chromatography-Mass Spectrometry (SEC-UPLC-QTof-MS). An average drug to VAR2CSA ratio (DVR) was estimated from the deconvolved mass spectrum via evaluation of peak intensities corresponding to VAR2CSA+1 drug, 2 drugs, 3 drugs, etc.

General Method: SEC-UPLC-ESI-ToF-MS Analysis of VAR2CSA Conjugates for DVR Determination Frozen aliquots of VAR2CSA conjugates were thawed prior to SEC-EsiTofMS analysis. The SEC analysis was performed with a WATERS Acquity UPLC BEH200 SEC 1.7 μm 4.6×150 mm column and mobile phase composed of Acetonitrile/Water/Trifluoroacetic acid/Formic acid, (30/70/0.1/0.1, v/v/v/v %—trifluoroacetic acid was omitted in some instances), and a column temperature of 30° C. 10 μL of sample was injected onto the SEC column. The elution time was 11.0 min. VAR2CSA and the VAR2CSA conjugates eluted at ~3.4 min. The MS total ion current (TIC) data was acquired on a Quatro-Premier QToF mass spectrometer with an electrospray ion source (WATERS 20 Corporation) over 500-4500 m/z range using MassLynx data acquisition software (Waters Corporation). Sample component mass data was acquired in the positive ion V-mode, and the Esi source was operated at a source temperature: 150° C., desolvation temperature: 350° C., desolvation gas: 800 L/hr, Sample cone voltage: 60 V, Capillary voltage: 3.0 kV, desolvation FIG. 8 shows the SEC-UPLC-QTof-MS MaxEnt1 processed intact mass of VAR2-Compound O. The MS signals at 115323 Da, 117662 Da and 119999 Da are consistent with conjugation of 1, 3 and 5 toxins, with a mean conjugation level of ~4 toxins per protein.

FIG. 9 shows the: SEC-UPLC-QTof-MS MaxEnt1 processed intact mass of VAR2-Compound KK. The profile of the deconvolved MS data is consistent with conjugation of up to 5 toxins (Compound KK), but with a mean drug load of ~2.5 drugs.

4. Conjugates were evaluated for the presence of unconjugated linker-toxin or free toxin by UPLC-ESI-Triple quadrupole mass spectrometry. Any unconjugated-drug in the purified product was extracted by protein precipitation with 0.1% formic acid in acetonitrile. The extract was filtered through a 3 KDa molecular weight cutoff filter (Amicon). The resulting filtrate was analyzed by RP-UPLC-MSMS to quantify the amount of unconjugated-drug. The amount of unconjugated-drug was quantified against a free drug (and free drug-linker) calibration curve. The UPLC-MSMS equipment used consists of an Ultra Performance Liquid Chromatograph (Waters Acquity™ UPLC) with tandem Waters Acquity™ PDA and TQD detectors. Control of the equipment and data acquisition were performed by PC computer and Waters Empower-2™ chromatography software.

Detection of Compound O in VAR2-Compound O Sample Prepared by General Conjugation Method, Above.

Exemplary data for free ESI-MS based free drug analysis is shown in FIG. 10. A similar result was obtained for free drug Compound 886 alone.

5. VAR2CSA drug conjugates were assessed by flow cytometry +/−CSA (Sigma C9819) for binding to “benchmark” Myla 2059 cutaneous T cell lymphoma cell line in order to estimate the specificity of binding. The binding of tumor-cell plCSA can be inhibited by incubating the VAR2CSA with excess soluble CSA. This sequesters VAR2CSA in solution and inhibits plCSA-binding on the cell-surface. It is assumed that cell surface staining observed in the presence of excess soluble CSA would indicate non-specific binding of the VAR2CSA to the cells.

General Method: Flow Cytometry Based Determination of VAR2CSA-Drug Conjugate Binding Specificity Cells were established in logarithmic growth in their respective growth medium prior to the assay. On the seeding day, cells were aspirated, resuspended in PBS+2% FBS, counted and cell viability was determined using Trypan Blue exclusion assay. Cells were added to the bottom of 96 well V-bottomed plates (50,000 cells/well) and pelleted by centrifugation (400×g, 3 min). After removal of supernatant, 62.5 µL of VAR2CSA or VAR2CSA conjugates (+/−400 µg/mL CSA) or FACS buffer were added at one or more concentrations (400 nM to obtain saturated binding; titration down to ~1 nM) and the cell pellets were resuspended. After incubation on ice for a period of 0.5 hours, plates were washed by addition of 200 µL FACS buffer, centrifugation (400×g, 3 min), removal of supernatant, resuspension of the cell pellet in 200 µL of FACS buffer with disruption of the pellet, centrifugation (400×g, 3 min), and finally removal of supernatant. Cell pellets were resuspended in 25 µL of either mIgG2ak anti-V5-FITC (1:100 dilution), or mIgG2a-FITC (2 gtg/mL dilution) and 7A.A.D (2.5 µg/mL). Plates were incubated on ice for 0.5 hours before washing cells as described above. The cell pellets were then resuspended in 50 µL FACS buffer and analyzed by flow cytometry. Data are represented as live cell (7-AAD negative population) geometric mean fluorescence in the FITC channel.

Figure 11:
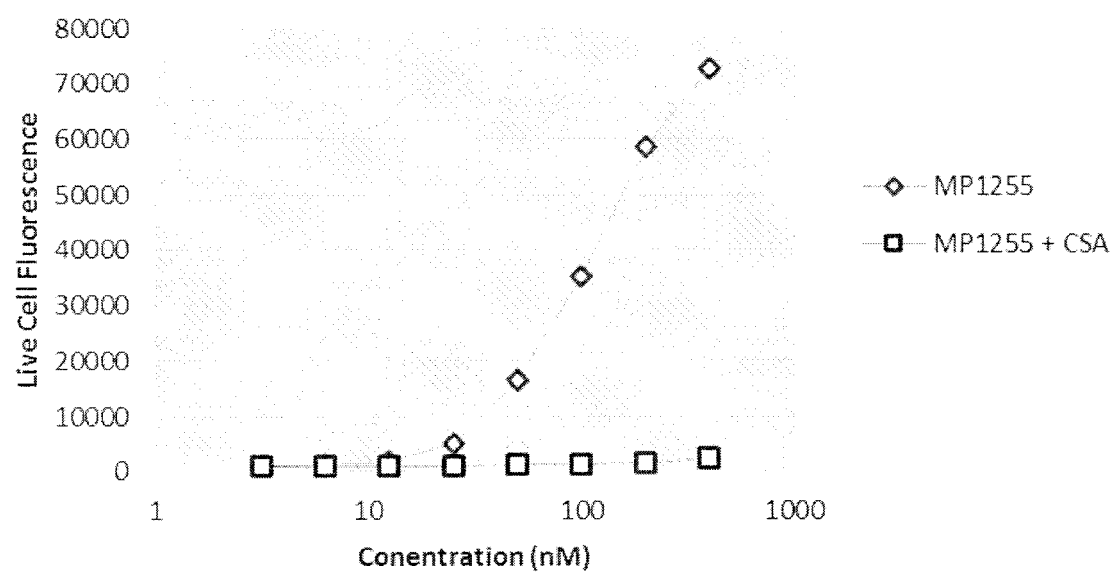
FIG. 11 shows the specificity of non-modified DBL1-ID2a (MP1255) binding to Myla2059 cell line in the presence and absence of CSA (Sigma C9819).
Figure 12:
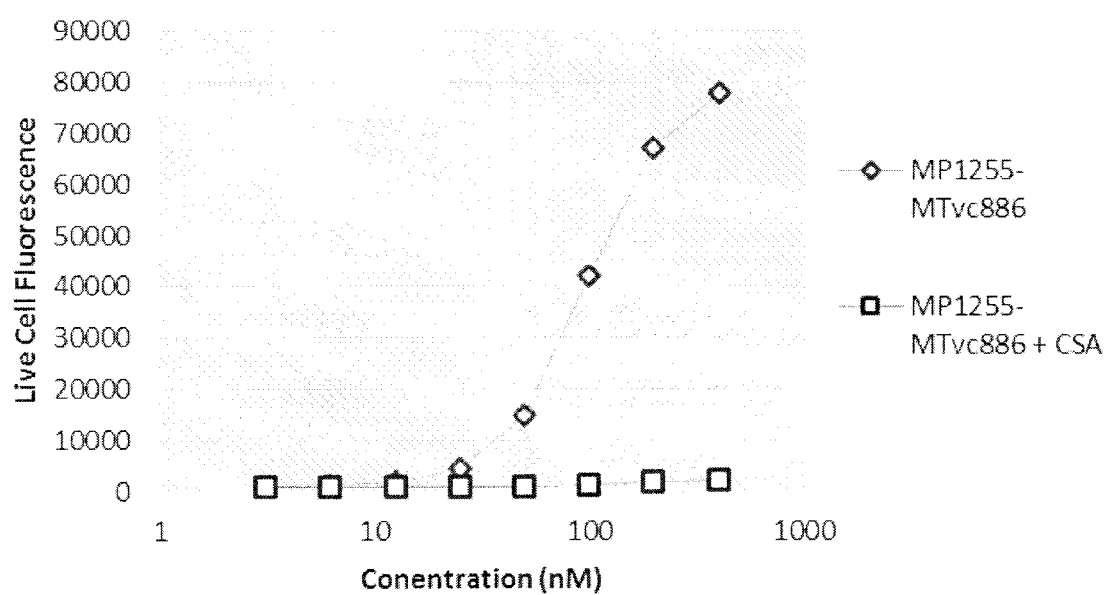
FIG. 12 shows the specificity of VAR2-Compound O (Cysteine conjugate) binding to the Myla2059 cell line in the presence and absence of CSA (Sigma C9819).
Figure 13:
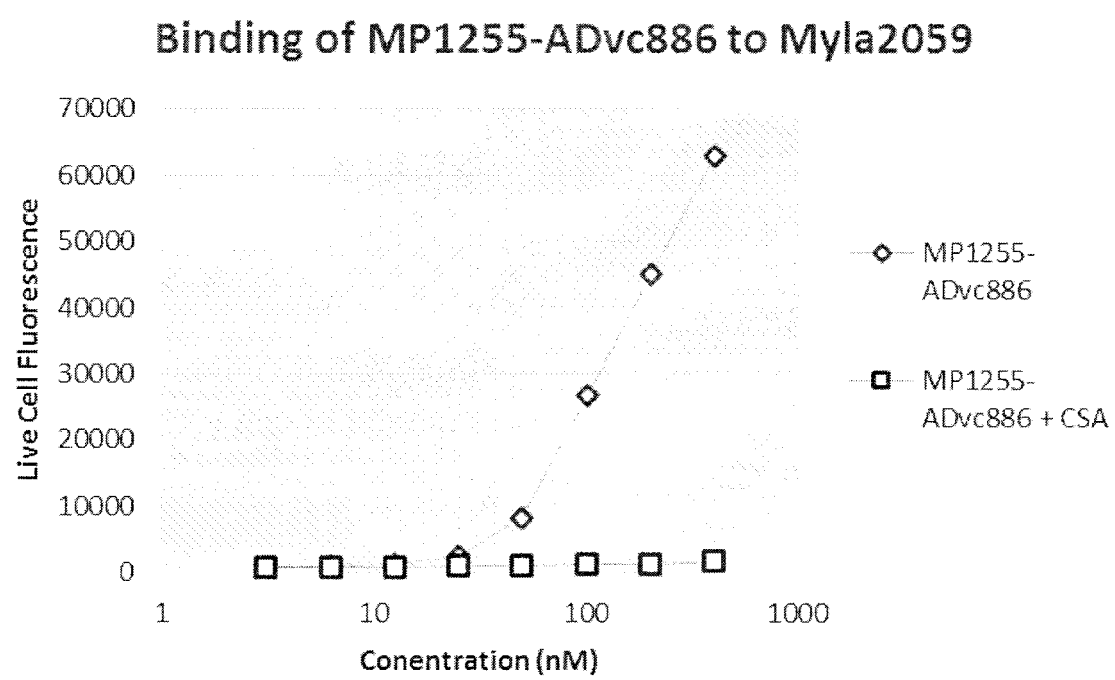
FIG. 13 shows the specificity of VAR2-Compound KK (Lysine conjugate) binding to the Myla2059 cell line in the presence and absence of CSA (Sigma C9819).
Figure 15:
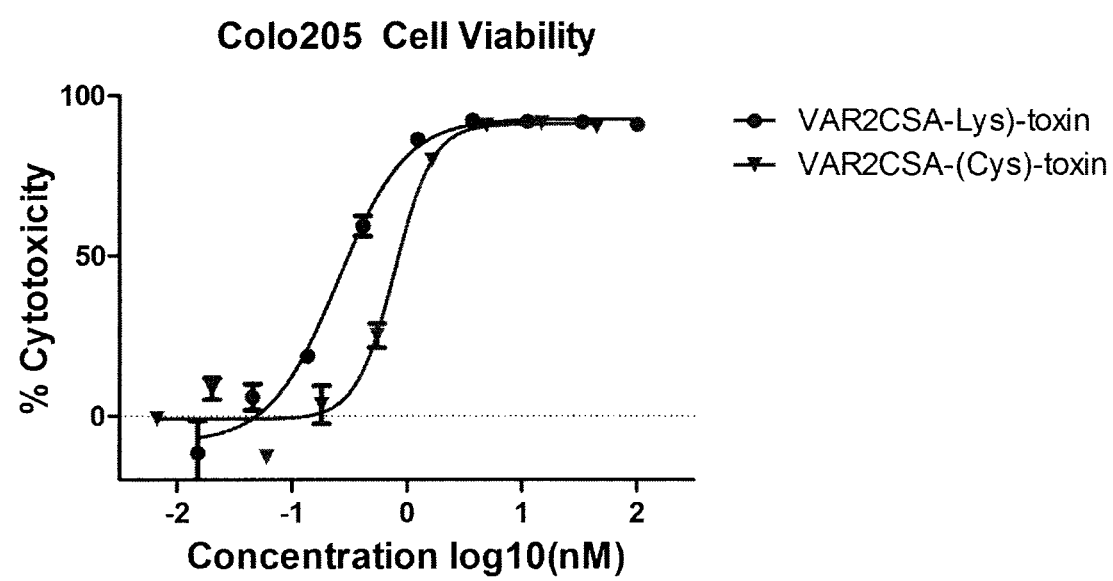
FIG. 15 shows the cytotoxicity of VAR2CSA drug conjugates against Colo205 cells. VAR2-Compound O prepared by cysteine conjugation—triangles. VAR2-Compound KK prepared by lysine conjugation—circles.
Figure 17:
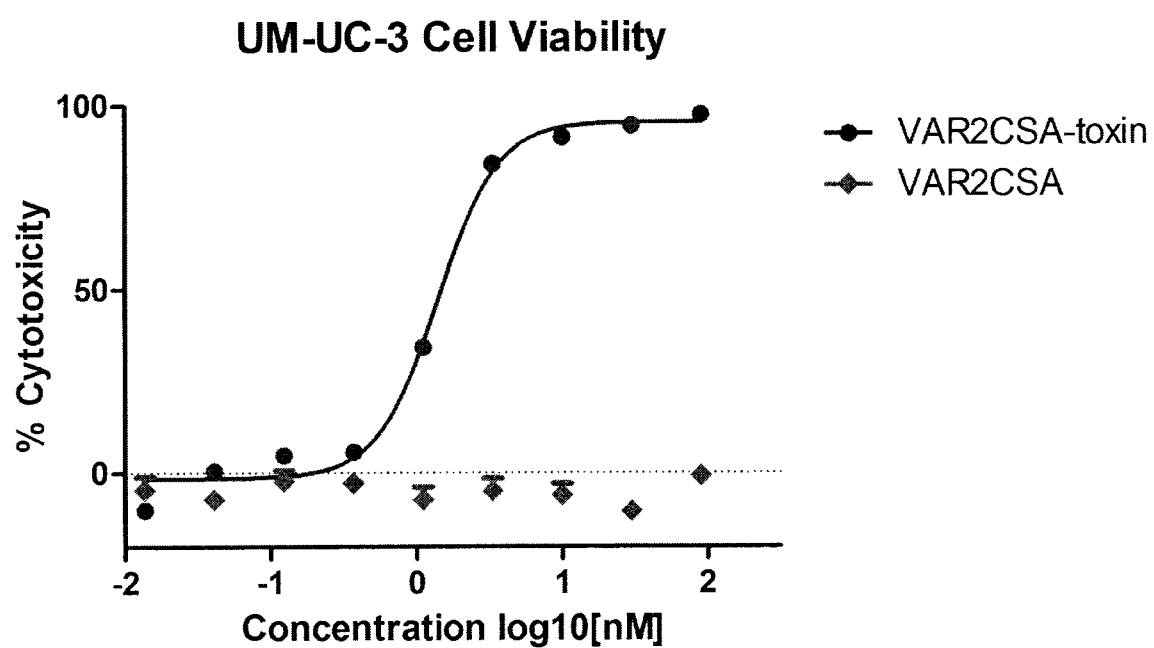
FIG. 17 shows the cytotoxicity of VAR2CSA drug conjugates against UM-UC 3 Cells. VAR2-Compound O—circles. VAR2CSA alone—diamonds.
Figure 19:
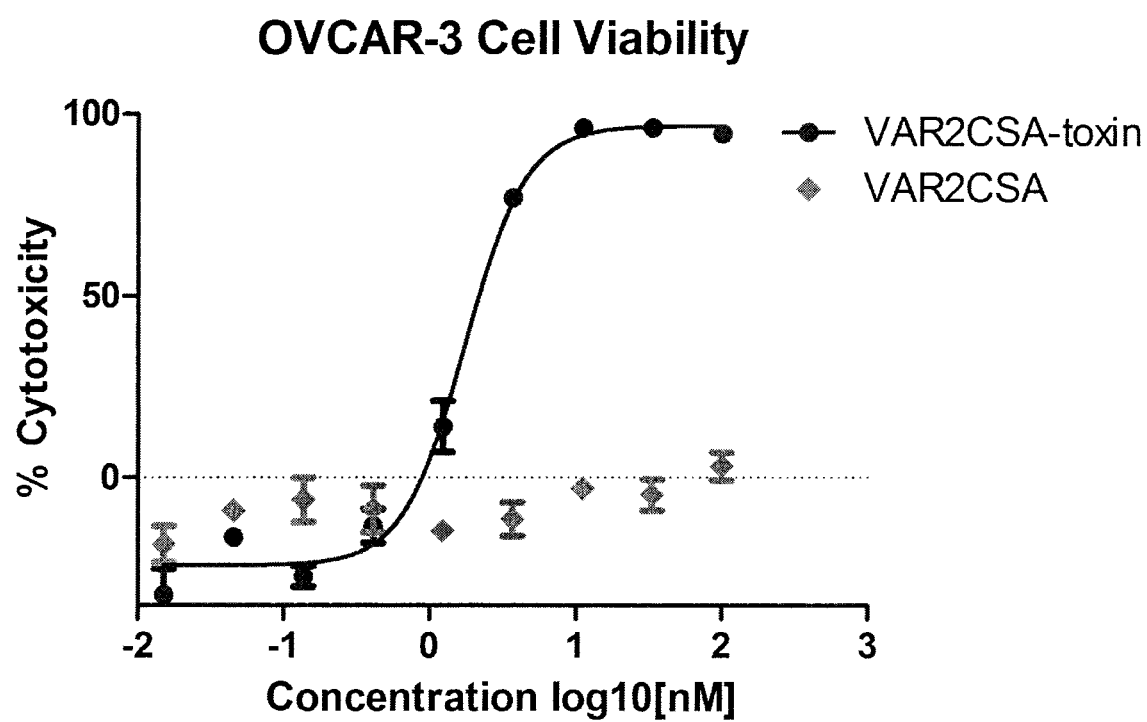
FIG. 19 shows the cytotoxicity of VAR2CSA drug conjugates against OVCAR-3 Cells. VAR2-Compound O—circles. VAR2CSA alone—diamonds.

FIGS. 11-13 show the specificity of certain compounds of Formula I binding to the Myla2059 cell line.

6. VAR2CSA drug conjugates were evaluated for in vitro potency against a broad array of cancer cell lines. Cells were incubated with variable concentrations of each conjugate, incubated under growth conditions and assessed for cell viability at a predetermined time point. Table 7 summarizes the cytotoxic activity of a representative drug conjugate against 34 human cancer cell lines. As a negative control, CSA "knockout" cell lines K562#14 (or K562#16) could also be treated with VAR2CSA drug conjugates. K562#14 and #16 showed low binding to VAR2CSA by FACS, thus suggesting that significant cytotoxic effect of the conjugates on this cell line would arise only in the presence of excess free toxin.

General Method: Cellular Cytotoxicity Assay of VAR2CSA-Drug Conjugates

On the day prior to adding test articles, adherent cells were added to opaque-walled 96-well tissue culture-treated microtiter plates using complete growth medium at a density of 2500 cells/100 microliter (µL) of medium (Colo205 cells were added at a density of 5000 cells/100 µL of medium). The cells were incubated for one night at 37° C./5% $CO_2$ to allow the cells to attach to the microtiter plate surface. On the day that test articles were added, suspension cell lines were added to separate 96-well microtiter plates at 2500 cells/100 µL using the recommended growth medium. Drug conjugates were diluted directly in growth medium at five-times the desired final concentration and were then titrated 1:3, eight steps. A control with no test article present (growth medium alone) was included on each microtiter plate in sextuplicate. The prepared compound/protein-drug conjugate titrations were added (twenty-five µL/well) in triplicate to cells. The cells and titrations were incubated at 37° C./5% $CO_2$ for five nights. After the incubation, cell viability is measured using CellTiter-Glo® reagent by adding thirty µL of prepared CellTiter-Glo® to each assay well. The assay is incubated for at least twenty minutes in the dark prior to measuring emitted luminescence using a microplate luminometer (500 ms integration time). The collected relative luminescence units (RLU) are converted to % cytotoxicity using the Growth medium alone control mentioned above (% Cytotoxicity=1−[Well RLU/average medium alone control RLU]).

Exemplary cytotoxicity data is shown in FIGS. 14-19.

TABLE 7

Collected Cytotoxicity Data for DBL1-ID2a-toxin conjugates on a Panel of Human Cancer Cell Lines. Average Loading of ~4 toxins per DBL1-ID2a molecule.

| Cell Line | Cancer Tissue Type | $EC_{50}$ (nM) Toxin Compound O | MCvcPABC-3.90 |
|---|---|---|---|
| BxPC-3 | Pancreas | 5.8 | |
| NCI-N87 | Stomach | 6.8 | |
| HCC1954 | Breast | 1.7 | |
| Capan-2 | Pancreas | ~100 | |
| AsPC-1 | Pancreas | 5.2 | |
| Jurkat | T cell leukemia | ~11 | |
| MiaPaCa | Pancreas | 30.9 | |
| OVCAR-3 | Ovary | 1.7 | |
| Karpas 299 | T Cell Lymphoma | 1 | |
| H1975 | Non-small cell Lung | 1.7 | |
| NCI-H358 | Non-small cell Lung | 6.6 | |
| SK-Br-3 | Breast | 1.1 | |
| MCF-7 | Breast | 6 | |
| NCI-H1437 | Non-small cell Lung | 3.3 | |
| HPAF-II | Pancreas | 10.8 | |
| Colo205 | Colon | 0.43-2.2* | 0.2 |
| Myla 2059 | T cell Lymphoma | 0.5 | |
| MG63 | Bone | 0.6 | 0.3 |
| PC-3 | Prostate | 0.8 | 0.8 |
| T47D | Breast | 0.79-2.53 | |
| MDA-MB-231 | Breast | 10.9 | |
| MDA-MB-468 | Breast | 1.1 | |
| A549 | Lung | 3.5 | 1.8 |
| 253J B-V | Bladder | 8.6 | |
| UM-UC-3 | Bladder | 1.4 | 1.8 |
| K562 | Bone | 8.8 | |
| Rh30 | Bone | 0.6 | |
| U2OS | Bone | 10.3 | |
| U138MG | Brain | 0.2 | |
| A172 | Brain | 1.9 | |
| K562 #14 | Control (Bone) | <100 nM | |
| K562 #16 | Control (Bone) | <100 nM | |
| DU-145 | Prostate | 1.6 | |
| MCF-7 | Breast | 2.4 | |
| HepG2 | Liver | 15.1 | |
| SK-OV-3 | Ovary | 4.4 | |
| JIMT-1 | Breast | 2.3 | |
| OE19 | Oesophagus | 3.7 | |

*$EC_{50}$ is larger since these cells are used at 2× the density of the others. $EC_{50}$ ranged from 0.5-1 at 2500 cells/well.

Example 5: Tolerability Study

Study Outline

Female CD-1 mice (Harlan Laboratories) were injected with the test article VAR2-Compound O at a dose of 1.0 mg/kg q2dx3. Dose escalation or reductions following assessment of tolerability as outlined in the Study Grouping Table 8. Mice were weighed 3× weekly for 12 days.

TABLE 8

Study Grouping

| Group # | Group Name | n | Admin. Route | Dose (mg/kg) | Dose Volume (mL/kg) | Dosing Schedule | Injection day |
|---|---|---|---|---|---|---|---|
| 1 | 1.0 | 3 | IV | 1.0 | 10 | q2dx3 | 1, 3, 5 |
| 2 | 0.3 or 3.0 | 3 | IV | 0.3 or 3.0* | 10 | q2dx3 | 1, 3, 5 |
| 3 | 0.1 or 9.0 | 3 | IV | 0.1 or 9.0** | 10 | q2dx3 | 1, 3, 5 |
| 4 | 6.0 or 15 | 3 | IV | 6.0 or 15*** | 10 | q2dx3 | 1, 3, 5 |

*Dose to be determined after tolerability of group 1 is determined. If 1 mg/kg is well tolerated after 3 administrations, then 3 mg/kg will be tested. If 1 mg/kg is not well tolerated, then 0.3 mg/kg will be tested.
**Dose to be determined after tolerability of group 1 and group 2 is determined. If groups 1 and 2 are tolerated after 3 administrations, then 9 mg/kg will be tested. If groups 1 and 2 are not well tolerated after 3 administrations, then 0.1 mg/kg is tested. Otherwise, this group will be abandoned or an alternate dose will be selected.
***Dose to be determined after tolerability of group 3 at 9 mg/kg is determined. If group 3 is tolerated after 3 administrations, then 15 mg/kg will be tested. If group 3 is not well tolerated after 3 administrations, then 6 mg/kg is tested.

Results
Treatment

All animals received their doses as indicated in the Injection Record.

Body Weights

Figure 20:
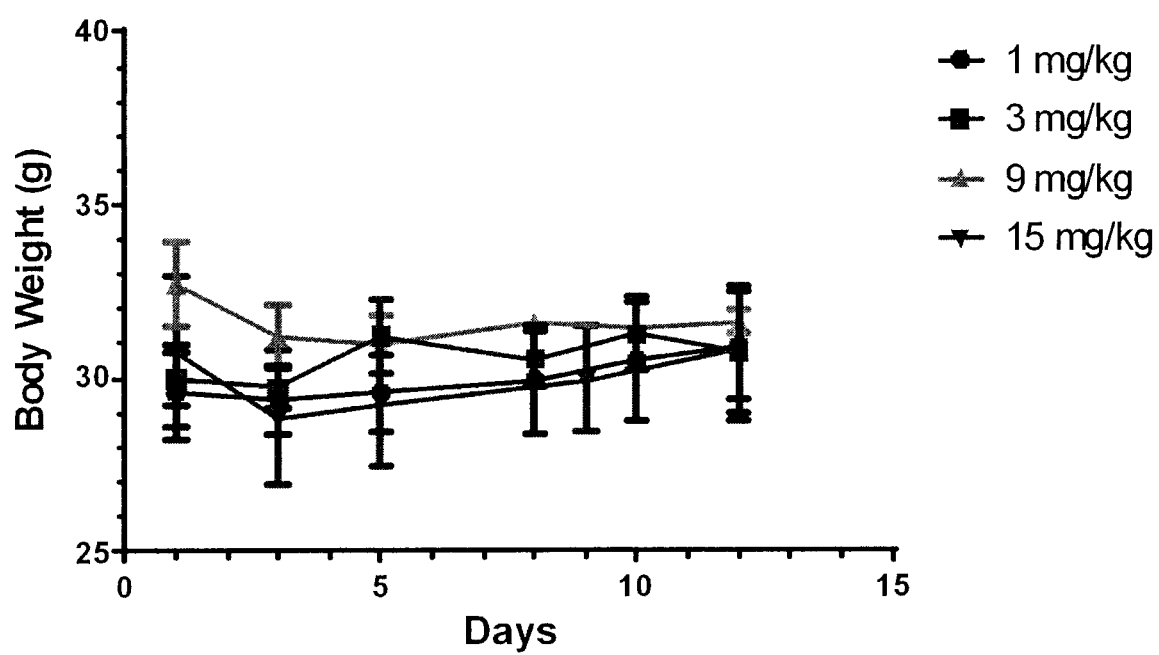
FIG. 20 shows the body weights of mice in a tolerability study with VAR2-Compound O.

No significant body weight loss was observed in any groups. Body Weights (Means±S.D.) are shown in FIG. 20.

Conclusions

For VAR2-Compound O experiments, no mice were terminated prior to scheduled sacrifice Day 12, indicating that the doses tested (up to 15 mg/kg) were tolerated.

Example 6: Karpas 299 Xenograft Efficacy Study

Study Overview

Female C.B-17/IcrHsd-Prkdcscid mice (Harlan Laboratories) were implanted subcutaneously in the back with the Karpas 299 human T cell lymphoma tumor cell line. Karpas 299 was established from the peripheral blood of a 25-year-old man with T cell non-Hodgkin's lymphoma in 1986; now classed as CD30+ anaplastic large cell lymphoma (ALCL). The lab stocks were *mycoplasma* negative. Tumors established over a period of 19 days, and test subjects were then grouped according to tumor volume such that each group (n=7) had an equal distribution of tumor volumes. The mean tumor volume on treatment day (day 21) was greater than 150 mm$^3$. Test articles were administered intravenously on Day 1, 3, and 6 (total of three injections) at the doses indicated in the study grouping table. Body weights and tumor volumes were measured every Monday, Wednesday, and Friday. Animals remained on study until their tumors reached 800 mm$^3$ in size or they otherwise required euthanasia due to achieving a humane endpoint.

TABLE 9

Study Grouping

| Group # | Group Name | n | Admin. Route | Dose (mg/kg) | Dose Volume (mL/kg) | Schedule | Injection Days |
|---|---|---|---|---|---|---|---|
| 1 | Vehicle | 7 | IV | n/a | 10 | q2dx3 | Wed, Fri, Mon |
| 2 | VAR2-Compound O | 7 | IV | 12 | 10 | q2dx3 | Wed, Fri, Mon |
| 3 | VAR2 | 7 | IV | 12 | 10 | q2dx3 | Wed, Fri, Mon |
| 4 | Compound 886 | 7 | IV | 0.312 | 10 | q2dx3 | Wed, Fri, Mon |

Results

Figure 21:
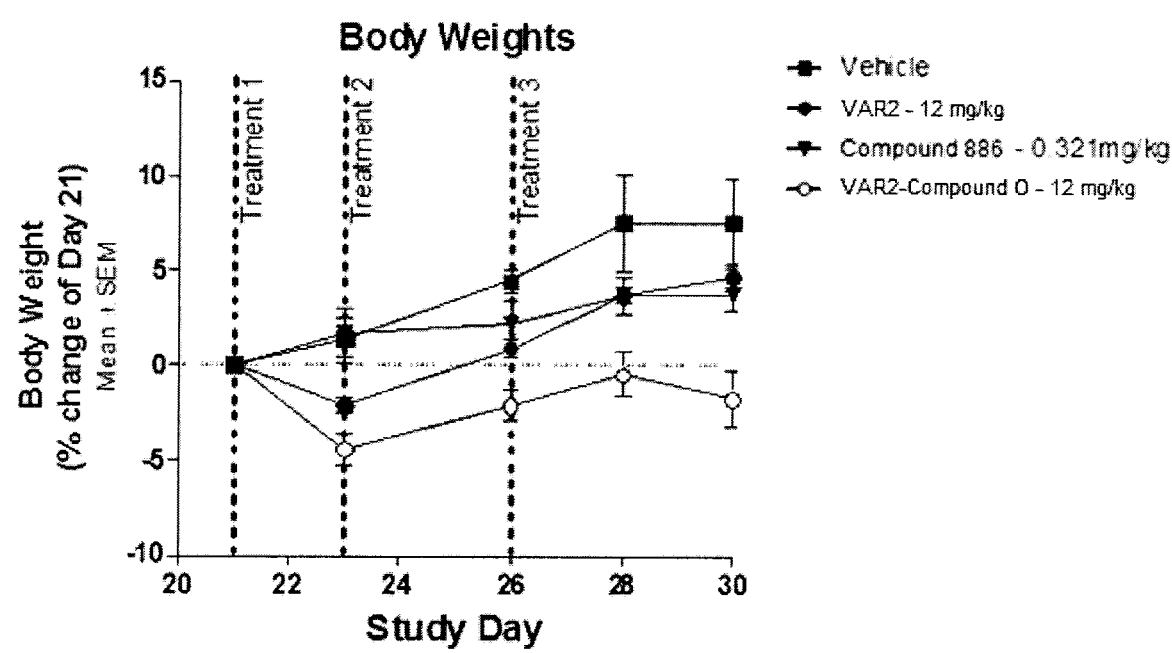
FIG. 21 shows the body weights of mice in a Karpas 299 xenograft efficacy study following three IV doses of test articles.
Figure 22:
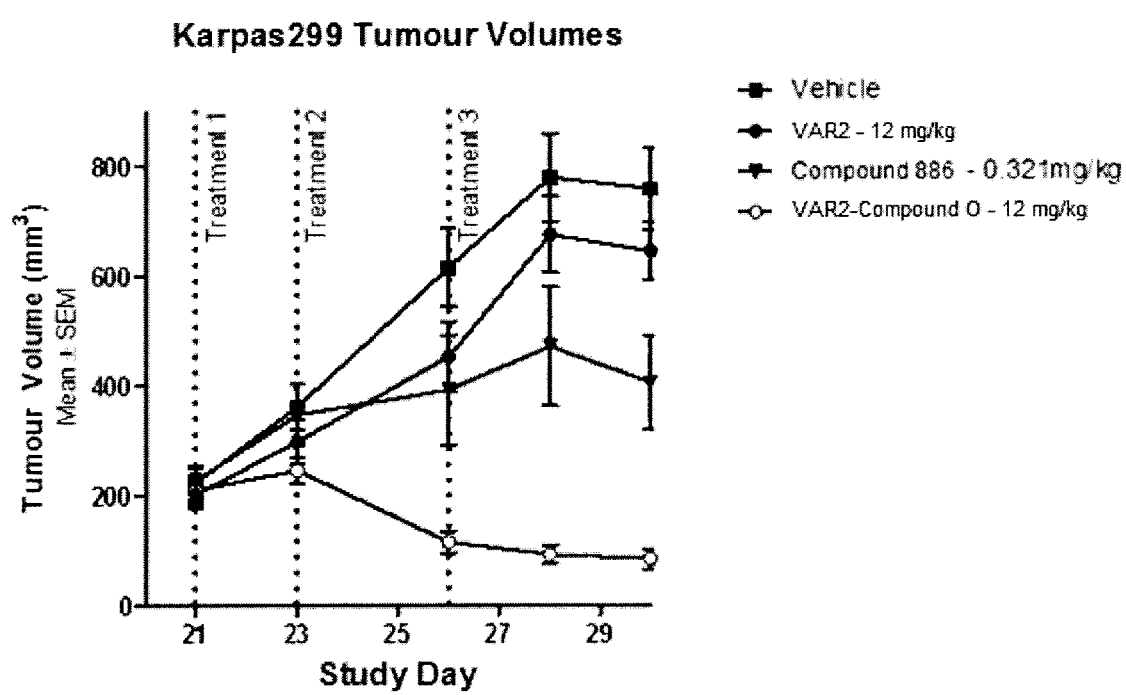
FIG. 22 shows tumor volumes of mice in a Karpas 299 xenograft efficacy study following three IV doses of test articles.

Body weights of study mice following three IV doses of test articles are shown in FIG. 21. Tumor volumes of study mice following three IV doses of test articles are shown in FIG. 22. Statistical analysis of tumor volume by two-way ANOVA Bonferroni posttests are shown in Table 10.

TABLE 10

| | Vehicle versus | | |
|---|---|---|---|
| Study Day | VAR2-Compound O | VAR2 | Compound 886 |
| 21 | ns | ns | ns |
| 23 | ns | ns | ns |
| 26 | *** | ns | * |
| 28 | *** | ns | *** |
| 30 | *** | ns | *** |

| | VAR2 versus | | |
|---|---|---|---|
| Study Day | VAR2-Compound O | VAR2 | Compound 886 |
| 21 | ns | — | ns |
| 23 | ns | — | ns |
| 26 | * | — | ns |
| 28 | *** | — | * |
| 30 | *** | — | ** |

$P > 0.05$ = ns (not significant),
$P < 0.05$ = *,
$P < 0.01$ = **,
$P < 0.001$ = ***

Conclusion

In conclusion, VAR2-Compound O inhibited the Karpas 299 tumor growth.

Example 7: PC3 Prostate Cancer Efficacy Study

Study Overview

Male nude nu/nu mice (Harlan Laboratories) were implanted subcutaneously in the back with the PC3 prostate cancer cell line in 100 μl of Matrigel® in both right and left flanks. The lab stocks were *mycoplasma* negative. Tumors established over a period of 28 days, and test subjects were grouped according to tumor volume such that each group had an equal distribution of tumor volumes. The mean tumor volume on treatment day was greater than 200 mm³. Test articles were administered intravenously on Day 1, 3, and 6 (total of three injections) at the doses indicated in the study grouping table. Body weights and tumor volumes were measured every Monday, Wednesday, and Friday. Animals remained on study until their tumors reached 1000 mm³ in size or they otherwise required euthanasia due to achieving a humane endpoint.

TABLE 11

Study Grouping

| Group # | Group Name | N: Mice, Tumors | Admin. Route | Dose (mg/kg) | Dose Volume (mL/kg) | Schedule | Injection Days |
|---|---|---|---|---|---|---|---|
| 1 | Vehicle | 7M (14T) | IV | n/a | 10 | q2dx3 | Mon, Wed, Sat |
| 2 | VAR2-Compound O | 8M (16T) | IV | 12 | 10 | q2dx3 | Mon, Wed, Sat |
| 3 | VAR2 | 8M (15T) | IV | 12 | 10 | q2dx3 | Mon, Wed, Sat |
| 4 | Compound 886 | 8M (16T) | IV | 0.312 | 10 | q2dx3 | Mon, Wed, Sat |

Results

Body Weights

Figure 23:
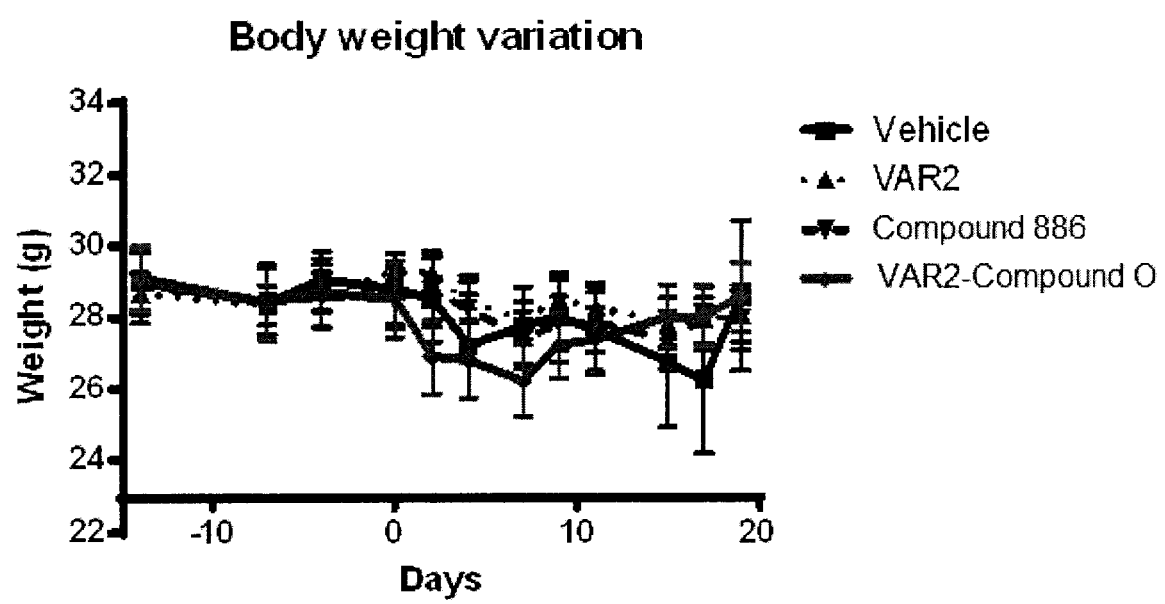
FIG. 23 shows the body weights of mice in a PC3 prostate cancer efficacy study.

The body weights of study mice are shown in FIG. 23. No difference in body weight loss between the different arms of treatment. The observed body weight loss is due to tumor volume increase. No clinical toxicity signs were observed.

Tumor Volumes

Figure 24:
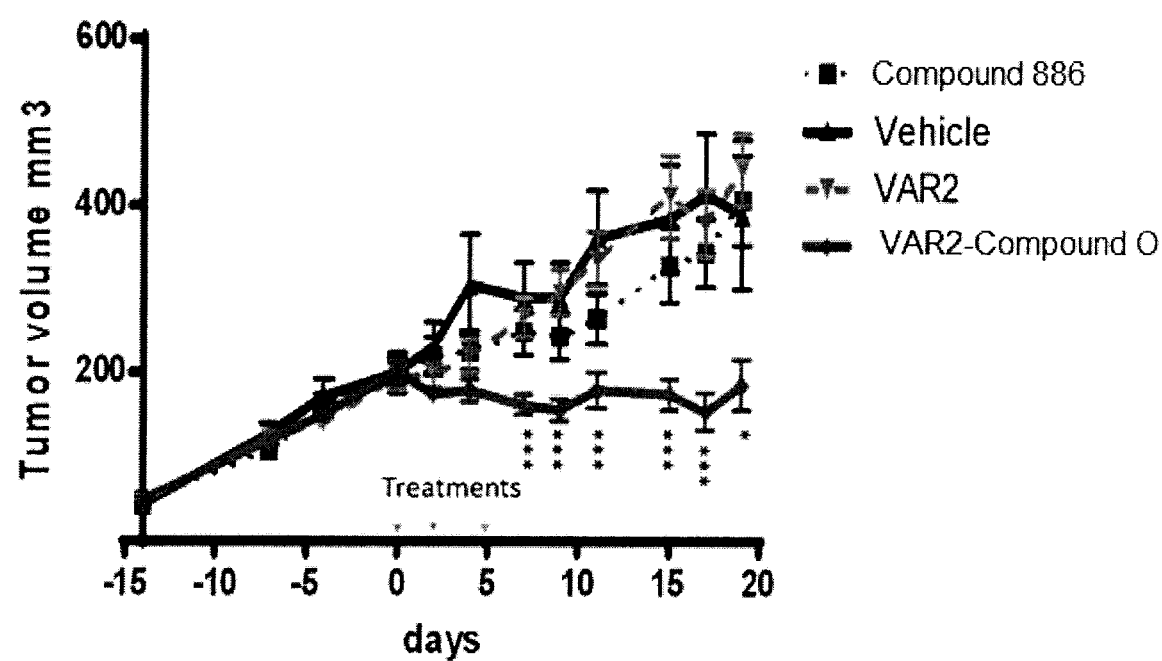
FIG. 24 shows tumor volumes of mice in a PC3 prostate cancer efficacy study.

Tumor volumes of study mice are shown in FIG. 24. Data shows mean tumor volume and SEM (Tumor volume was calculated using the formula V=0.5×W×L×1. Statistical evaluation performed using T-test as shown in Table 12.

TABLE 12

| | T-test p-values | | |
|---|---|---|---|
| Time (days) | Vehicle/ VAR2-Compound O | Compound 886/ VAR2-Compound O | VAR2/ VAR2-Compound O |
| −14 | 0.2931 (ns) | 0.9583 (ns) | 0.7097 (ns) |
| −7 | 0.5034 (ns) | 0.3604 (ns) | 0.6627 (ns) |
| −4 | 0.3161 (ns) | 0.4445 (ns) | 0.3808 (ns) |
| 0 | 0.9817 (ns) | 0.8854 (ns) | 0.7867 (ns) |
| 2 | 0.0812 (ns) | 0.0801 (ns) | 0.2466 (ns) |
| 4 | 0.0394* | 0.0918 (ns) | 0.0961 (ns) |
| 7 | 0.0036*** | 0.0065*** | 0.0004*** |
| 9 | 0.0026*** | 0.0060*** | 0.0001*** |
| 11 | 0.0025*** | 0.0228*** | 0.0003*** |
| 15 | 0.0016*** | 0.0035*** | 0.0001*** |
| 17 | 0.0007*** | 0.0003*** | 2.0626 × 10⁻⁵*** |
| 19 | 0.0136* | 0.0013*** | 3.20276 × 10⁻⁵*** |

P > 0.05 = ns (not significant),
P < 0.05 =*,
P < 0.001 =***

Necropsy

Mice were sacrificed when total tumor volume reached 1000 mm3 or when clinical signs were observed as body weight loss. Necropsy didn't show any toxicity or abnormality signs. The number of mice reaching endpoint is shown in Table 13

TABLE 13

| Time | Mice Reaching End Point | | |
|---|---|---|---|
| (days) | Vehicle | VAR2 | VAR2-Compound O |
| −14 | — | — | — |
| −7 | — | — | — |
| −4 | — | — | — |
| 0 | — | — | — |
| 2 | — | — | — |
| 4 | 1 | — | — |
| 7 | — | — | — |
| 9 | — | — | — |
| 11 | — | — | — |
| 15 | — | — | — |

TABLE 13-continued

| Time | Mice Reaching End Point | | |
|---|---|---|---|
| (days) | Vehicle | VAR2 | VAR2-Compound O |
| 17 | 2 | — | — |
| 19 | 1 | 2 | 1 |

Conclusions

In conclusion, VAR2-Compound O inhibited the PC3 tumor growth. Twenty days after the last treatment, tumor volume average in VAR2-Compound O arm was still stable and was significantly lower than Vehicle, VAR2 and Compound 886 arms.

All of the U.S. patents, U.S. patent application publications, U.S. patent applications, foreign patents, foreign patent applications and non-patent publications referred to in this specification are incorporated herein by reference, in their entirety to the extent not inconsistent with the present description. From the foregoing it will be appreciated that, although specific embodiments described herein have been described herein for purposes of illustration, various modifications may be made without deviating from the spirit and scope described herein. Accordingly, the disclosure is not limited except as by the appended claims.

It is contemplated that the different parts of the present description may be combined in any suitable manner. For instance, the present examples, methods, aspects, embodiments or the like may be suitably implemented or combined with any other embodiment, method, example or aspect of the invention.

Unless defined otherwise, all technical and scientific terms used herein have the same meaning as is commonly understood by one of ordinary skill in the art to which this invention belongs.

Use of examples in the specification, including examples of terms, is for illustrative purposes only and is not intended to limit the scope and meaning of the embodiments of the invention herein. Numeric ranges are inclusive of the numbers defining the range. In the specification, the word "comprising" is used as an open-ended term, substantially equivalent to the phrase "including, but not limited to," and the word "comprises" has a corresponding meaning.

What is claimed is:

1. A compound of Formula I:

T-L-P    I wherein:
T is a targeting moiety comprising a VAR2CSA polypeptide, and
L-P is $L^1$-$P^1$ or $L^2$-$P^2$;

wherein:
$L^1$ is a linker, or $L^1$ is absent;
$P^1$ is a monovalent radical of a compound of Formula XV:

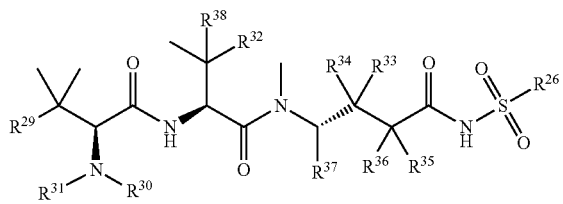

XV wherein:
$R^{26}$ is selected from the group consisting of optionally substituted alkyl, optionally substituted alkylamino, optionally substituted cycloalkyl, optionally substituted aryl, optionally substituted heterocyclyl, optionally substituted heteroaryl, $-COR^{27}$, $-CSR^{27}$, $-OR^{27}$, and $-NHR^{27}$, wherein each $R^{27}$ is, independently, alkyl optionally substituted with halogen, $-OH$ or $-SH$;
$R^{29}$ is selected from the group consisting of optionally substituted alkyl, optionally substituted alkylamino, optionally substituted cycloalkyl, optionally substituted aryl, optionally substituted heterocyclyl and optionally substituted heteroaryl;
$R^{30}$ is selected from the group consisting of H and $C_{1-6}$ alkyl;
$R^{31}$ is selected from the group consisting of H and $C_{1-6}$ alkyl;
$R^{32}$ and $R^{38}$ are each independently selected from the group consisting of H, $C_{1-6}$ alkyl and $-SH$, with the proviso that $R^{32}$ and $R^{38}$ cannot both be H;
$R^{33}$, $R^{34}$, $R^{35}$ and $R^{36}$ are each independently H or $C_{1-6}$ alkyl, wherein at least one of $R^{33}$ and $R^{34}$ is H; or $R^{34}$ and $R^{35}$ form a double bond, $R^{33}$ is H, and $R^{36}$ is H or $C_{1-6}$ alkyl; and
$R^{37}$ is selected from the group consisting of H and $C_{1-6}$ alkyl; and wherein:
$L^2$ is a linker;
$P^2$ is a cytotoxic compound; and $L^2$-$P^2$ has the following structure (III):

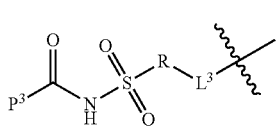

III wherein:
R is selected from the group consisting of optionally substituted alkyl, optionally substituted alkylamino, optionally substituted cycloalkyl, optionally substituted aryl, optionally substituted heterocyclyl, optionally substituted heteroaryl, $-COR^{27}$, $-CSR^{27}$, $-OR^{27}$, and $-NHR^{27}$, wherein each $R^{27}$ is, independently, optionally substituted alkyl, optionally substituted alkylamino, optionally substituted cycloalkyl, optionally substituted aryl, optionally substituted heterocyclyl and optionally substituted heteroaryl, or R is absent;
$P^3$ is the remaining portion of compound $P^2$; and
$L^3$ is the remaining portion of linker $L^2$ or is absent.

2. The compound of claim 1, wherein said VAR2CSA polypeptide comprises a sequential amino acid sequence of
   a. ID1; and
   b. DBL2Xb.

3. The compound of claim 1, wherein said VAR2CSA polypeptide binds chondroitin sulfate A (CSA) on proteoglycans (CSPG) with an affinity as measured by a $K_D$ lower than 100 nM.

4. The compound of claim 1, wherein said VAR2CSA polypeptide comprises an amino acid sequence having at least 70% sequence identity with an amino acid sequence selected from: amino acids 1-577 of SEQ ID NO: 1; amino acids 1-592 of SEQ ID NO:3; amino acids 1-579 of SEQ ID NO:4; amino acids 1-576 of SEQ ID NO:5; amino acids 1-586 of SEQ ID NO: 10; amino acids 1-579 of SEQ ID NO: 11; amino acids 1-565 of SEQ ID NO:29; amino acids 1-584 of SEQ ID NO:34; amino acids 1-569 of SEQ ID NO:36; amino acids 1-575 of SEQ ID NO:37; amino acids 1-592 of SEQ ID NO:38; amino acids 1-603 of SEQ ID NO:41; amino acids 1-588 of SEQ ID NO:43; amino acids 1-565 of SEQ ID NO:44; amino acids 1-589 of SEQ ID NO:45; amino acids 1-573 of SEQ ID NO:48; amino acids 1-583 of SEQ ID NO:53; amino acids 1-569 of SEQ ID NO:54; amino acids 578-640 of SEQ ID NO:1; amino acids 593-656 of SEQ ID NO:3; amino acids 580-643 of SEQ ID NO:4; amino acids 577-640 of SEQ ID NO:5; amino acids 587-650 of SEQ ID NO: 10; amino acids 580-643 of SEQ ID NO: 11; amino acids 566-628 of SEQ ID NO:29; amino acids 585-647 of SEQ ID NO:34; amino acids 570-632 of SEQ ID NO:36; amino acids 576-639 of SEQ ID NO:37; amino acids 593-655 of SEQ ID NO:38; amino acids 604-667 of SEQ ID NO:41; amino acids 589-652 of SEQ ID NO:43; amino acids 566-628 of SEQ ID NO:44; amino acids 590-653 of SEQ ID NO:45; amino acids 574-637 of SEQ ID NO:48; amino acids 584-646 of SEQ ID NO:53; amino acids 570-632 of SEQ ID NO:54; SEQ ID NO:2; SEQ ID NO:6; SEQ ID NO:7; SEQ ID NO:8; SEQ ID NO:9; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:30; SEQ ID NO:31; SEQ ID NO:32; SEQ ID NO:33; SEQ ID NO:35; SEQ ID NO:39; SEQ ID NO:40; SEQ ID NO:42; SEQ ID NO:46; SEQ ID NO:47; SEQ ID NO:49; SEQ ID NO:50; SEQ ID NO:51; SEQ ID NO:52; SEQ ID NO: 1; SEQ ID NO:3; SEQ ID NO:4; SEQ ID NO:5; SEQ ID NO: 10; SEQ ID NO:11; SEQ ID NO:29; SEQ ID NO:34; SEQ ID NO:36; SEQ ID NO:37; SEQ ID NO:38; SEQ ID NO:41; SEQ ID NO:43; SEQ ID NO:44; SEQ ID NO:45; SEQ ID NO:48; SEQ ID NO:53; and SEQ ID NO:54.

5. The compound of claim 1, wherein said VAR2CSA polypeptide comprises an amino acid sequence having at least 70% sequence identity with an amino acid sequence selected from: amino acids 1-577 of SEQ ID NO: 1; amino acids 1-592 of SEQ ID NO:3; amino acids 1-579 of SEQ ID NO:4; amino acids 1-576 of SEQ ID NO:5; amino acids 1-586 of SEQ ID NO: 10; amino acids 1-579 of SEQ ID NO:11; amino acids 1-565 of SEQ ID NO:29; amino acids 1-584 of SEQ ID NO:34; amino acids 1-569 of SEQ ID NO:36; amino acids 1-575 of SEQ ID NO:37; amino acids 1-592 of SEQ ID NO:38; amino acids 1-603 of SEQ ID NO:41; amino acids 1-588 of SEQ ID NO:43; amino acids 1-565 of SEQ ID NO:44; amino acids 1-589 of SEQ ID NO:45; amino acids 1-573 of SEQ ID NO:48; amino acids 1-583 of SEQ ID NO:53; amino acids 1-569 of SEQ ID NO:54; SEQ ID NO: 1; SEQ ID NO:3; SEQ ID NO:4; SEQ ID NO:5; SEQ ID NO:10; SEQ ID NO:11; SEQ ID NO:29; SEQ ID NO:34; SEQ ID NO:36; SEQ ID NO:37; SEQ ID NO:38; SEQ ID NO:41; SEQ ID NO:43; SEQ ID NO:44; SEQ ID NO:45; SEQ ID NO:48; SEQ ID NO:53; and SEQ ID NO:54.

6. The compound of claim 1, wherein said VAR2CSA polypeptide consists of an amino acid sequence having a length of less than 700 amino acids.

7. The compound of claim 1, wherein said VAR2CSA polypeptide is a recombinant protein.

8. The compound of claim 1, wherein L-P is $L^2$-$P^2$.

9. The compound of claim 8, wherein:
$P^2$ is a compound of Formula V:

V $L^2$-T has the following structure (VI):

VI wherein
$P^4$ is the remaining portion of compound $P^2$;
the —NH— group bonded to R in Formula V forms a peptide bond (JPB) with $AA_1$ in formula VI, wherein said JPB is enzymatically cleavable;
R is selected from the group consisting of optionally substituted alkyl, optionally substituted alkylamino, optionally substituted cycloalkyl, optionally substituted aryl, optionally substituted heterocyclyl, optionally substituted heteroaryl, —$COR^{27}$, —$CSR^{27}$, —$OR^{27}$, and —$NHR^{27}$, wherein each $R^{27}$ is, independently, optionally substituted alkyl, optionally substituted alkylamino, optionally substituted cycloalkyl, optionally substituted aryl, optionally substituted heterocyclyl or optionally substituted heteroaryl;
each AA is independently an amino acid;
n is an integer from 0 to 25;
$L^4$ is the remaining portion of linker $L^2$ or is absent;
T is said targeting moiety, and
$AA_1$-$(AA)_n$, taken together comprises an amino acid sequence capable of facilitating enyzmatic cleavage of said JPB.

10. The compound of claim 9, wherein $AA_1$-$(AA)_n$ is selected from: Phe-Lys, Val-Lys, Ala-Lys, Val-Cit, Phe-Cit, Leu-Cit, Ile-Cit, Trp-Cit, Phe-Arg, (D)Phe-Phe-Lys and (D)Ala-Phe-Lys.

11. The compound of claim 8, wherein said cytotoxic compound is a microtubule disrupting peptide toxin.

12. The compound of claim 8, wherein said cytotoxic compound is a hemiasterlin or an analog thereof; a tubulysin or an analog thereof; or an auristatin or an analog thereof.

13. The compound of claim 1, wherein L-P is $L^1$-$P^1$.

14. The compound of claim 13, wherein $L^1$ comprises: SPDP, SMCC, vcPABC, MCvcPABC, MTvc, ADvc, maleimide, NHS, biotin, streptavidin, NeutrAvidin, a glycoside, or a combination thereof.

15. The compound of claim 13, wherein $L^1$ comprises vcPABC, MCvcPABC, MTvc or ADvc.

16. The compound of claim 13, wherein each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

17. The compound of claim 13, wherein $R^{29}$ is selected from one of the following structures XVI, XVII, XVIII, and XIX:

XVI

XVII

-continued

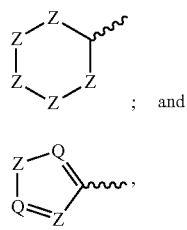

wherein:
Q is $CR^{39}$ or N;
Z is $C(R^{39})_2$, $NR^{39}$, S, or O;
wherein in structure XIX, one instance of Z is $CR^{39}$ or N, and the other instance is $(CR^{39})_2$, $NR^{39}$, S or O; and
each $R^{39}$ is, independently, selected from the group consisting of H, —OH, —$R^{27}$, —$OR^{27}$, —$O_2CR^{27}$, —SH, —$SR^{27}$, —$SOCR^{27}$, —$NH_2$, —$N_3$, —$NHR^{27}$, —$N(R^{27})_2$, —$NHCOR^{27}$, —$NR^{27}COR^{27}$, —$R^{27}NH_2$, —I, —Br, —Cl, —F, —CN, —$CO_2H$, —$CO_2R^{27}$, —CHO, —$COR^{27}$, —$CONH_2$, —$CONHR^{27}$, —$CON(R^{27})_2$, —COSH, —$COSR^{27}$, —$NO_2$, —$SO_3H$, —$SOR^{27}$, and —$SO_2R^{27}$, wherein each $R^{27}$ is, independently, alkyl optionally substituted with halogen, —OH or —SH.

18. The compound of claim 13, wherein $R^{29}$ is selected from the group consisting of:

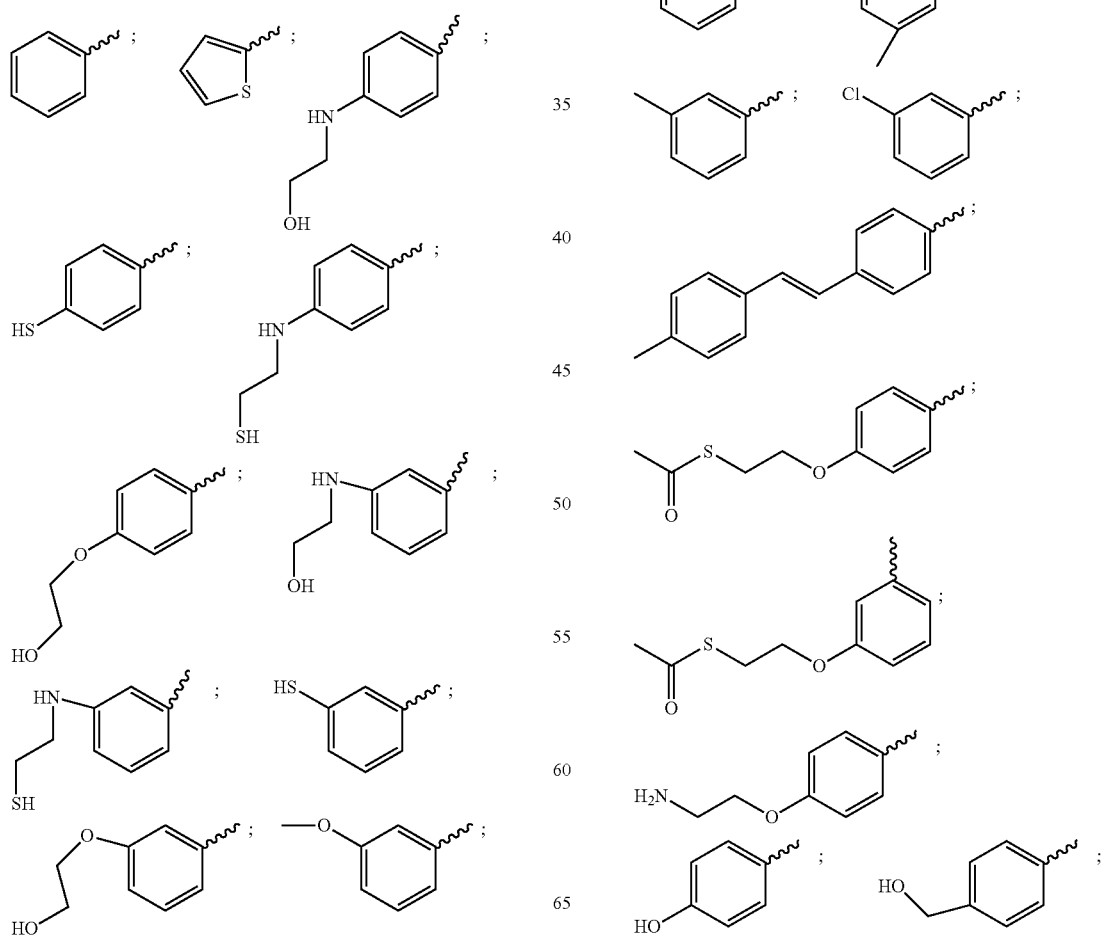

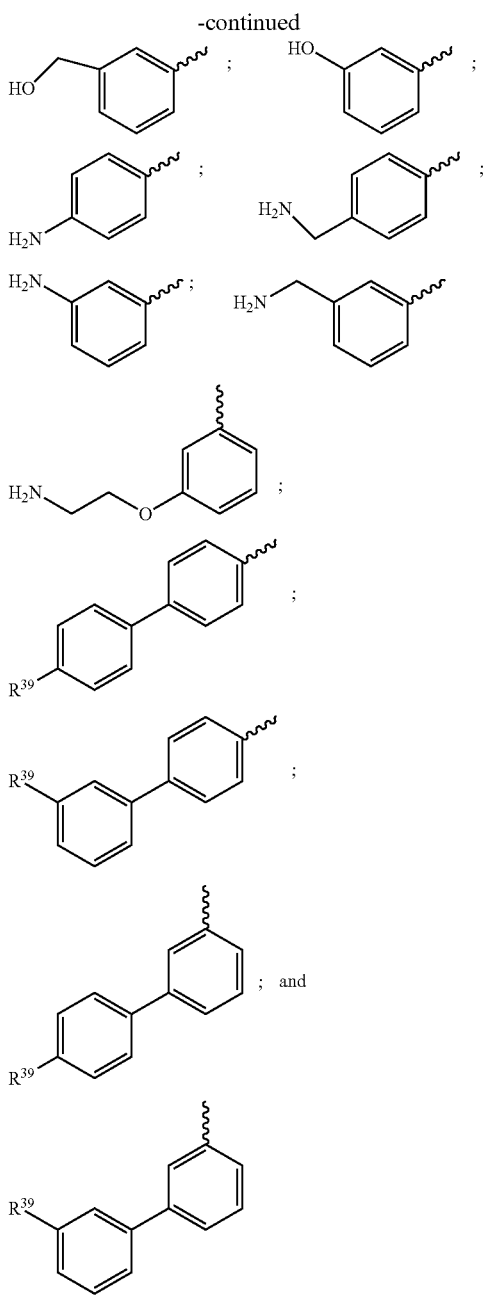

wherein each $R^{39}$ is independently selected from the group consisting of H, —OH, —$R^{27}$, —$OR^{27}$, —$O_2CR^{27}$, —SH, —$SR^{27}$, —$SOCR^{27}$, —$NH_2$, —$N_3$, —$NHR^{27}$, —$N(R^{27})_2$, —$NHCOR^{27}$, —$NR^{27}COR^{27}$, —$R^{27}NH_2$, —I, —Br, —Cl, —F, —CN, —$CO_2H$, —$CO_2R^{27}$, —CHO, —$COR^{27}$, —$CONH_2$, —$CONHR^{27}$, —$CON(R^{27})_2$, —COSH, —$COSR^{27}$, —$NO_2$, —$SO_3H$, —$SOR^{27}$, and —$SO_2R^{27}$, wherein each $R^{27}$ is, independently, alkyl optionally substituted with halogen, —OH or —SH.

19. The compound of claim 13, wherein $R^{30}$ is H or methyl, and $R^{31}$, $R^{32}$, and $R^{38}$ are each methyl.

20. The compound of claim 13, wherein $P^1$ is a monovalent radical of a compound of Formula II:

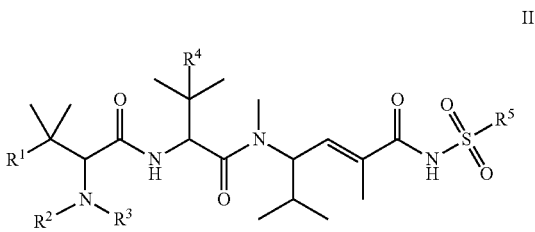

wherein:
$R^1$ is selected from: aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkoxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkoxy are further optionally substituted with one substituent selected from $C_1$-$C_4$ alkylaryl, hydroxyl, and thio;
$R^2$ and $R^3$ are each independently H or $C_1$-$C_6$ alkyl;
$R^4$ is $C_1$-$C_6$ alkyl or thio; and
$R^5$ is selected from: $C_1$-$C_6$ alkyl, aryl, aryl-$C_1$-$C_6$ alkyl, $C_3$-$C_7$ cycloalkyl, heteroaryl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, $C_3$-$C_7$ cycloalkyl, cyano, $C_1$-$C_6$ haloalkyl, $C_1$-$C_6$ haloalkoxy, halo, hydroxyl, nitro, thio, and thio-$C_1$-$C_6$ alkyl.

21. The compound of claim 20, wherein $R^1$ is selected from: 1H-indol-3-yl, 1-methyl-1H-indol-3-yl, 2-methoxyphenyl, 3-((2-hydroxyethyl)amino)phenyl, 3-((2-mercaptoethyl)amino)phenyl, 3-(2-(acetylthio)ethoxy)phenyl, 3-(2-hydroxyethoxy)phenyl, 3-(2-mercaptoethoxy)phenyl, 3-(4-methylstyryl)phenyl, 3-(aminomethyl)phenyl, 3-(hydroxymethyl)phenyl, 3-hydroxyphenyl, 3,5-difluorophenyl, 3,5-dimethylphenyl, 3-aminophenyl, 3-chlorophenyl, 3-mercaptophenyl, 3-methoxyphenyl, 3-trifluoromethylphenyl, 4-((2-hydroxyethyl)amino)phenyl, 4-((2-mercaptoethyl)amino)phenyl, 4-(2-(acetylthio)ethoxy)phenyl, 4-(2-aminoethoxy)phenyl, 4-(2-hydroxyethoxy)phenyl, 4-(2-mercaptoethoxy)phenyl, 4-(aminomethyl)phenyl, 4-(hydroxymethyl)phenyl, 4-aminophenyl, 4-hydroxyphenyl, 4-mercaptophenyl, 4-methoxyphenyl, cyclohexyl, thien-2-yl, m-tolyl, and phenyl.

22. The compound of claim 20, wherein $R^2$ is H, or methyl.

23. The compound of claim 20, wherein $R^3$ is methyl and/or $R^4$ is methyl.

24. The compound of claim 20, wherein $R^5$ is selected from: $C_1$-$C_6$ alkyl, aryl, aryl-$C_1$-$C_6$ alkyl, $C_3$-$C_7$ cycloalkyl, heteroaryl, and heterocyclyl, each optionally substituted with one or more substituents selected from: 1-aminocyclopropyl, 4-aminophenyl, amino, aminomethyl, bromo, tert-butyl, carboxamide, carboxyl, chloro, cyano, cyclopentyl, ethyl, fluoro, hydroxy, isopropyl, methoxy, methyl, nitro, phenyl, pyridin-3-yl, thio, thiomethyl, trifluoromethoxy, and trifluoromethyl.

25. The compound of claim 20, wherein $R^5$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, methyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, 4-aminophenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl.

26. A pharmaceutical composition comprising the compound of claim 1, and a pharmaceutically acceptable carrier, diluent or excipient.

27. A method of treating cancer in a mammal, or increasing survival of a mammal having cancer, or inhibiting tumor growth in a mammal, comprising administering to a mammal in need thereof an effective amount of the compound of claim 1.

28. The method of claim 27, wherein said cancer is a carcinoma, a sarcoma, an hematopoietic cancer, or a tumor of neuroepithelial tissue.

29. A method of treating an indication selected from: cancer, arthritis, arthrosis, multiple sclerosis, neural damage, cartilage damage, and psoriasis in a mammal comprising administering to a mammal in need thereof an effective amount of the compound of claim 8.

30. The compound of claim 1, wherein said VAR2CSA polypeptide comprises a sequential amino acid sequence of:
  a. ID1;
  b. DBL2Xb; and
  c. ID2a.

31. The compound of claim 30, wherein the VAR2CSA polypeptide further comprises an amino acid sequence at the N- or C-terminus of 100 amino acids or less derived from a part of SEQ ID NO: 55 or SEQ ID NO: 56, wherein said part is not ID1, DBL2Xb or ID2a.

32. The compound of claim 1, wherein said VAR2CSA polypeptide is non-glycosylated.

33. The compound of claim 9, wherein $L^4$ comprises repeating alkoxy units, a diacid amide, a diacid ester, or a combination thereof.

34. The compound of claim 9, wherein said cytotoxic compound is a hemiasterlin or an analog thereof; a tubulysin or an analog thereof, or an auristatin or an analog thereof.

35. The compound of claim 8, wherein $P^2$ has the following structure (X):

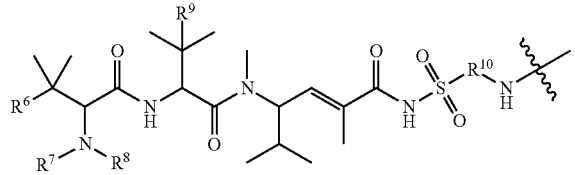

and $L^2$-T has the following structure (IV):

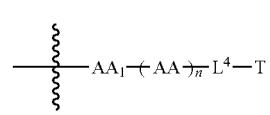

wherein:
  $R^6$ is selected from: aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkoxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkoxy are further optionally substituted with one substituent selected from $C_1$-$C_4$ alkylaryl, hydroxyl, and thio;
  $R^7$ and $R^8$ are each independently H or $C_1$-$C_6$ alkyl;
  $R^9$ is $C_1$-$C_6$ alkyl or thio;
  $R^{10}$ is selected from optionally substituted alkyl, optionally substituted alkylamino, optionally substituted cycloalkyl, optionally substituted aryl, optionally substituted heterocyclyl, optionally substituted heteroaryl, —$COR^{27}$, —$CSR^{27}$, —$OR^{27}$, and —$NHR^{27}$, wherein each $R^{27}$ is independently optionally substituted alkyl, optionally substituted alkylamino, optionally substituted cycloalkyl, optionally substituted aryl, optionally substituted heterocyclyl, or optionally substituted heteroaryl; and
  each AA is independently an amino acid;
  n is an integer from 0 to 25;
  $L^4$ is the remaining portion of linker $L^2$ or is absent;
  T is said targeting moiety;
  wherein the —NH— group bonded to $R^{10}$ in Formula X forms a junction peptide bond (JPB) with $AA_1$ in Formula VI, wherein the JPB is enzymatically cleavable, and
  wherein $AA_1$-(AA), taken together comprises an amino acid sequence capable of facilitating enyzmatic cleavage of said JPB.

36. The compound of claim 35, wherein —$R^{10}$—NH— of Formula X is selected from:

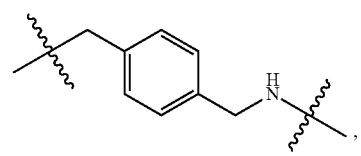

377
-continued
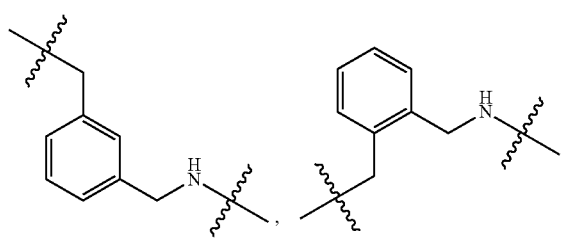
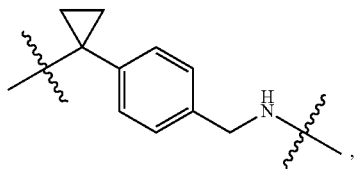
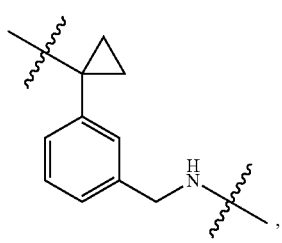
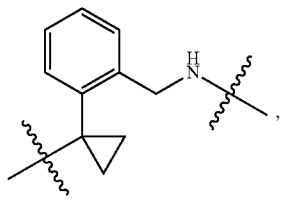
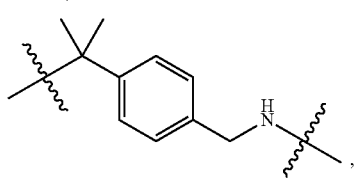
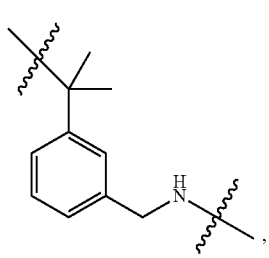
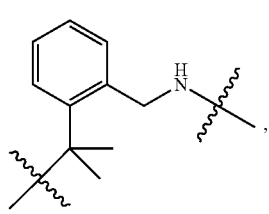
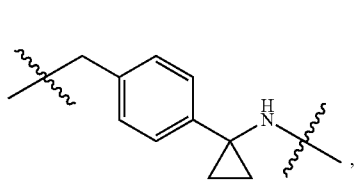
378
-continued
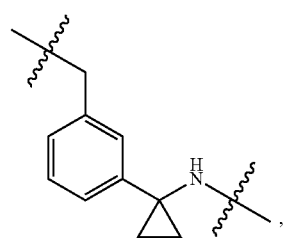
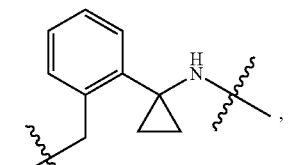
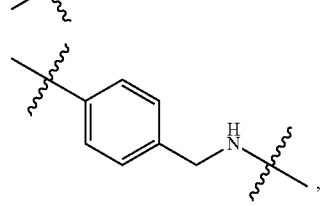
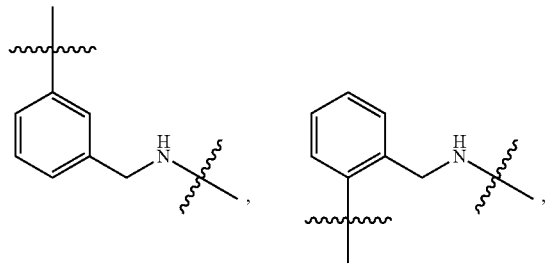
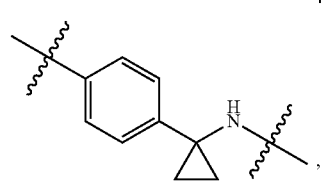
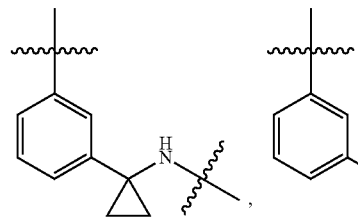
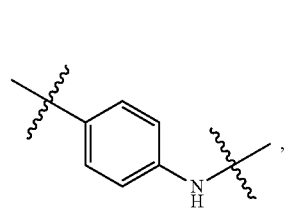
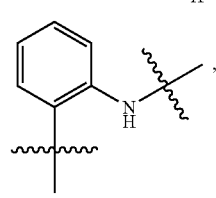

-continued

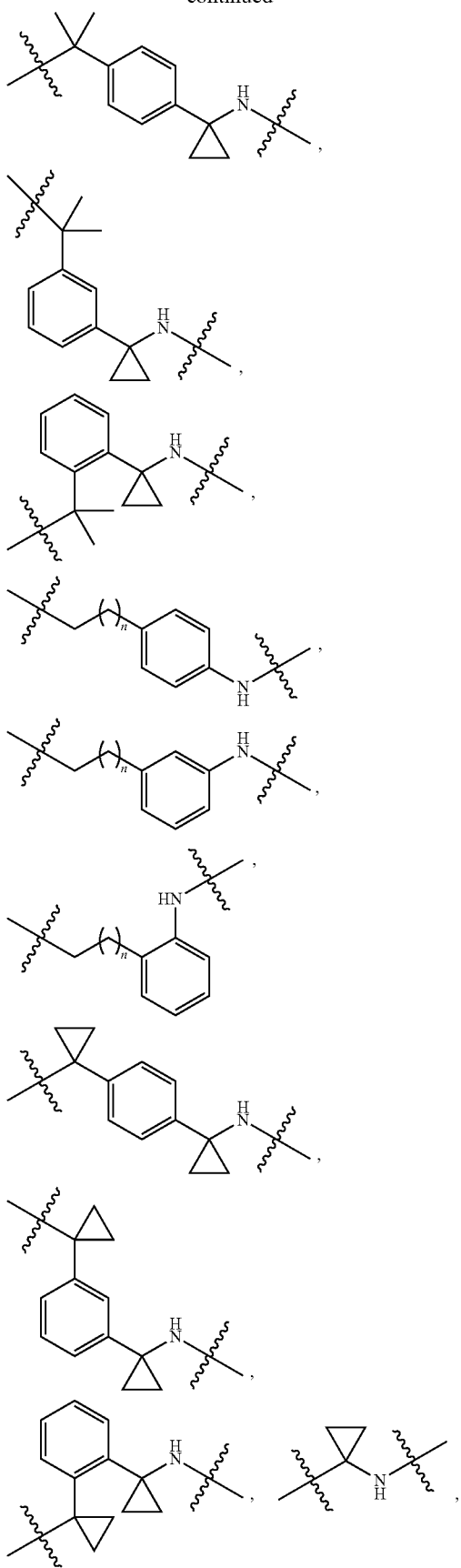

-continued

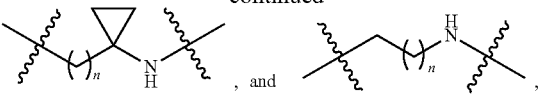

wherein each n is independently an integer from 0-10.

37. The compound of claim 35, wherein $AA_1$-$(AA)_n$ is selected from: Phe-Lys, Val-Lys, Ala-Lys, Val-Cit, Phe-Cit, Leu-Cit, Ile-Cit, Trp-Cit, Phe-Arg, (D)Phe-Phe-Lys and (D)Ala-Phe-Lys.

38. The compound of claim 8, wherein $P^2$ is a monovalent radical of one of the following compounds:

a) (S,E)-N-(3-Mercaptopropylsulfonyl)-2,5-dimethyl-4-((S)—N,3,3-trimethyl-2-((S)-3-methyl-2-(methylamino)-3-phenylbutanamido)butanamido)hex-2-enamide (Compound A);

b) (S,E)-N-(2-Mercaptoethylsulfonyl)-2,5-dimethyl-4-((S)—N,3,3-trimethyl-2-((S)-3-methyl-2-(methylamino)-3-phenylbutanamido)butanamido)hex-2-enamide (Compound B);

c) (S,E)-N-(4-(Mercaptomethyl)phenylsulfonyl)-2,5-dimethyl-4-((S)—N,3,3-trimethyl-2-((S)-3-methyl-2-(methylamino)-3-phenylbutanamido)butanamido)hex-2-enamide (Compound C);

d) (S,E)-2,5-Dimethyl-N-tosyl-4-((S)—N,3,3-trimethyl-2-((S)-3-methyl-2-(methylamino)-3-phenylbutanamido)butanamido)hex-2-enamide (Compound D);

e) (S,E)-2,5-dimethyl-N-(methylsulfonyl)-4-((S)—N,3,3-trimethyl-2-((S)-3-methyl-2-(methylamino)-3-phenylbutanamido)butanamido)hex-2-enamide (Compound E);

f) (S,E)-N-(Mesitylsulfonyl)-2,5-dimethyl-4-((S)—N,3,3-trimethyl-2-((S)-3-methyl-2-(methylamino)-3-phenylbutanamido)butanamido)hex-2-enamide;

g) (S,E)-2,5-Dimethyl-N-(4-(trifluoromethoxy)phenylsulfonyl)-4-((S)—N,3,3-trimethyl-2-((S)-3-methyl-2-(methylamino)-3-phenylbutanamido)butanamido)hex-2-enamide;

h) (S,E)-N-(Benzylsulfonyl)-2,5-dimethyl-4-((S)—N,3,3-trimethyl-2-((S)-3-methyl-2-(methylamino)-3-phenylbutanamido)butanamido)hex-2-enamide (Compound 14);

i) (S,E)-2,5-Dimethyl-N-(2,4,6-triisopropylphenylsulfonyl)-4-((S)—N,3,3-trimethyl-2-((S)-3-methyl-2-(methylamino)-3-phenylbutanamido)butanamido)hex-2-enamide;

j) (S,E)-N-(4-tert-Butylphenylsulfonyl)-2, 5-dimethyl-4-((S)—N,3,3-trimethyl-2-((S)-3-methyl-2-(methylamino)-3-phenylbutanamido)butanamido)hex-2-enamide;

k) (S,E)-N-(4-Chlorophenylsulfonyl)-2,5-dimethyl-4-((S)—N,3,3-trimethyl-2-((S)-3-methyl-2-(methylamino)-3-phenylbutanamido)butanamido)hex-2-enamide;

l) (S,E)-N-(3-Cyanophenylsulfonyl)-2,5-dimethyl-4-((S)—N,3,3-trimethyl-2-((S)-3-methyl-2-(methylamino)-3-phenylbutanamido)butanamido)hex-2-enamide;

m) (S,E)-2,5-Dimethyl-N-(2-nitrophenylsulfonyl)-4-((S)—N,3,3-trimethyl-2-((S)-3-methyl-2-(methylamino)-3-phenylbutanamido)butanamido)hex-2-enamide;

n) (S,E)-N-(4-Methoxy-2-nitrophenylsulfonyl)-2,5-dimethyl-4-((S)—N,3,3-trimethyl-2-((S)-3-methyl-2-(methylamino)-3-phenylbutanamido)butanamido)hex-2-enamide;

o) 4-(N—((S,E)-2,5-Dimethyl-4-((S)—N,3,3-trimethyl-2-((S)-3-methyl-2-(methylamino)-3-phenylbutanamido)butanamido)hex-2-enoyl)sulfamoyl)-3-nitrobenzamide;

p) (S,E)-N-(4-Methoxyphenylsulfonyl)-2,5-dimethyl-4-((S)—N,3,3-trimethyl-2-((S)-3-methyl-2-(methylamino)-3-phenylbutanamido)butanamido)hex-2-enamide;

q) (S,E)-2,5-Dimethyl-N-(4-(2,2,2-trifluoroacetamido)phenylsulfonyl)-4-((S)—N,3,3-trimethyl-2-((S)-3-methyl-2-(methylamino)-3-phenylbutanamido)butanamido)hex-2-enamide (Compound 23);

r) (S,E)-N-(4-Aminophenylsulfonyl)-2,5-dimethyl-4-((S)—N,3,3-trimethyl-2-((S)-3-methyl-2-(methylamino)-3-phenylbutanamido)butanamido)hex-2-enamide (Compound 886);

s) (S,E)-2,5-Dimethyl-N-(phenylsulfonyl)-4-((S)—N,3,3-trimethyl-2-((S)-3-methyl-2-(methylamino)-3-phenylbutanamido)butanamido)hex-2-enamide;

t) (S,E)-N—(N-(2-Fluorobenzyl)sulfamoyl)-2,5-dimethyl-4-((S)—N,3,3-trimethyl-2-((S)-3-methyl-2-(methylamino)-3-phenylbutanamido)butanamido)hex-2-enamide;

u) (S,E)-2,5-Dimethyl-N-(piperidin-1-ylsulfonyl)-4-((S)—N,3,3-trimethyl-2-((S)-3-methyl-2-(methylamino)-3-phenylbutanamido)butanamido)hex-2-enamide;

v) (S,E)-2,5-Dimethyl-N-(o-tolylsulfonyl)-4-((S)—N,3,3-trimethyl-2-((S)-3-methyl-2-(methylamino)-3-phenylbutanamido)butanamido)hex-2-enamide;

w) (S,E)-N-(4-Bromophenylsulfonyl)-2,5-dimethyl-4-((S)—N,3,3-trimethyl-2-((S)-3-methyl-2-(methylamino)-3-phenylbutanamido)butanamido)hex-2-enamide;

x) (S,E)-2,5-Dimethyl-N-(naphthalen-2-ylsulfonyl)-4-((S)—N,3,3-trimethyl-2-((S)-3-methyl-2-(methylamino)-3-phenylbutanamido)butanamido)hex-2-enamide;

y) Methyl 4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)benzoate;

z) (S,E)-2,5-Dimethyl-N—(N-(2-(trifluoromethyl)benzyl)sulfamoyl)-4-((S)—N,3,3-trimethyl-2-((S)-3-methyl-2-(methylamino)-3-phenylbutanamido)butanamido)hex-2-enamide;

aa) (4S,E)-N-(Hexan-2-ylsulfonyl)-2,5-dimethyl-4-((S)—N,3,3-trimethyl-2-((S)-3-methyl-2-(methylamino)-3-phenylbutanamido)butanamido)hex-2-enamide;

bb) (S,E)-N-(2-Methoxyethylsulfonyl)-2,5-dimethyl-4-((S)—N,3,3-trimethyl-2-((S)-3-methyl-2-(methylamino)-3-phenylbutanamido)butanamido)hex-2-enamide;

cc) (S,E)-N-(Cyclopentylmethylsulfonyl)-2,5-dimethyl-4-((S)—N,3,3-trimethyl-2-((S)-3-methyl-2-(methylamino)-3-phenylbutanamido)butanamido)hex-2-enamide;

dd) (S,E)-N-(Benzylsulfonyl)-4-((S)-2-((S)-3-(4-cyanophenyl)-3-methyl-2-(methylamino)butanamido)-N,3,3-trimethylbutanamido)-2,5-dimethylhex-2-enamide;

ee) (S,E)-4-((S)-2-((S)-3-(4-(Aminomethyl)phenyl)-3-methyl-2-(methylamino)butanamido)-N,3,3-trimethylbutanamido)-N-(benzylsulfonyl)-2,5-dimethylhex-2-enamide;

ff) (S,E)-4-((S)-2-((S)-3-(4-Azidophenyl)-3-methyl-2-(methylamino)butanamido)-N,3,3-trimethylbutanamido)-N-(benzylsulfonyl)-2,5-dimethylhex-2-enamide;

gg) (S,E)-4-((S)-2-((S)-3-(4-Aminophenyl)-3-methyl-2-(methylamino)butanamido)-N,3,3-trimethylbutanamido)-N-(benzylsulfonyl)-2,5-dimethylhex-2-enamide;

hh) (S,E)-N-(Cyclohexylsulfonyl)-2,5-dimethyl-4-((S)—N,3,3-trimethyl-2-((S)-3-methyl-2-(methylamino)-3-phenylbutanamido)butanamido)hex-2-enamide;

ii) (S,E)-2,5-Dimethyl-N-(pyridin-3-ylmethylsulfonyl)-4-((S)—N,3,3-trimethyl-2-((S)-3-methyl-2-(methylamino)-3-phenylbutanamido)butanamido)hex-2-enamide;

jj) 4-(N—((S,E)-2,5-Dimethyl-4-((S)—N,3,3-trimethyl-2-((S)-3-methyl-2-(methylamino)-3-phenylbutanamido)butanamido)hex-2-enoyl)sulfamoyl)benzoic acid;

kk) (S,E)-2,5-Dimethyl-N-(3-(2,2,2-trifluoroacetamido)phenylsulfonyl)-4-((S)—N,3,3-trimethyl-2-((S)-3-methyl-2-(methylamino)-3-phenylbutanamido)butanamido)hex-2-enamide;

ll) (S,E)-N-(3-Aminophenylsulfonyl)-2,5-dimethyl-4-((S)—N,3,3-trimethyl-2-((S)-3-methyl-2-(methylamino)-3-phenylbutanamido)butanamido)hex-2-enamide;

mm) (S,E)-2,5-Dimethyl-N-(pyridin-3-ylsulfonyl)-4-((S)—N,3,3-trimethyl-2-((S)-3-methyl-2-(methylamino)-3-phenylbutanamido)butanamido)hex-2-enamide;

nn) (S,E)-2,5-Dimethyl-N-(thiophen-2-ylsulfonyl)-4-((S)—N,3,3-trimethyl-2-((S)-3-methyl-2-(methylamino)-3-phenylbutanamido)butanamido)hex-2-enamide;

oo) (S,E)-N-(4-Hydroxyphenylsulfonyl)-2,5-dimethyl-4-((S)—N,3,3-trimethyl-2-((S)-3-methyl-2-(methylamino)-3-phenylbutanamido)butanamido)hex-2-enamide;

pp) (S,E)-2,5-dimethyl-N-(4-(1-(2,2,2-trifluoroacetamido)cyclopropyl)phenylsulfonyl)-4-((S)—N,3,3-trimethyl-2-((S)-3-methyl-2-(methylamino)-3-phenylbutanamido)butanamido)hex-2-enamide;

qq) (S,E)-N-(4-(1-Aminocyclopropyl)phenylsulfonyl)-2,5-dimethyl-4-((S)—N,3,3-trimethyl-2-((S)-3-methyl-2-(methylamino)-3-phenylbutanamido)butanamido)hex-2-enamide;

rr) (S,E)-2,5-Dimethyl-N-(2-methylbenzylsulfonyl)-4-((S)—N,3,3-trimethyl-2-((S)-3-methyl-2-(methylamino)-3-phenylbutanamido)butanamido)hex-2-enamide;

ss) (S,E)-2,5-Dimethyl-N-(4-nitrobenzylsulfonyl)-4-((S)—N,3,3-trimethyl-2-((S)-3-methyl-2-(methylamino)-3-phenylbutanamido)butanamido)hex-2-enamide;

tt) (S,E)-N-(4-Chlorobenzylsulfonyl)-2,5-dimethyl-4-((S)—N,3,3-trimethyl-2-((S)-3-methyl-2-(methylamino)-3-phenylbutanamido)butanamido)hex-2-enamide;

uu) (S,E)-2,5-Dimethyl-N-(phenethylsulfonyl)-4-((S)—N,3,3-trimethyl-2-((S)-3-methyl-2-(methylamino)-3-phenylbutanamido)butanamido)hex-2-enamide;

vv) (S,E)-N-(4-Bromobenzylsulfonyl)-2,5-dimethyl-4-((S)—N,3,3-trimethyl-2-((S)-3-methyl-2-(methylamino)-3-phenylbutanamido)butanamido)hex-2-enamide;

ww) (S,E)-N-(4-Cyanobenzylsulfonyl)-2,5-dimethyl-4-((S)—N,3,3-trimethyl-2-((S)-3-methyl-2-(methylamino)-3-phenylbutanamido)butanamido)hex-2-enamide;

xx) (S,E)-2,5-Dimethyl-N-(3-nitrobenzylsulfonyl)-4-((S)—N,3,3-trimethyl-2-((S)-3-methyl-2-(methylamino)-3-phenylbutanamido)butanamido)hex-2-enamide;

yy) (S,E)-N-(4-tert-Butylbenzylsulfonyl)-2,5-dimethyl-4-((S)—N,3,3-trimethyl-2-((S)-3-methyl-2-(methylamino)-3-phenylbutanamido)butanamido)hex-2-enamide;

zz) (S,E)-2,5-Dimethyl-N-(2-nitrobenzylsulfonyl)-4-((S)—N,3,3-trimethyl-2-((S)-3-methyl-2-(methylamino)-3-phenylbutanamido)butanamido)hex-2-enamide;

aaa) (S,E)-2,5-Dimethyl-N-(4-nitrophenethylsulfonyl)-4-((S)—N,3,3-trimethyl-2-((S)-3-methyl-2-(methylamino)-3-phenylbutanamido)butanamido)hex-2-enamide;

bbb) Methyl 4-Chloro-3-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)benzoate;

ccc) (S,E)-N-(4-(Aminomethyl)benzylsulfonyl)-2,5-dimethyl-4-((S)—N,3,3-trimethyl-2-((S)-3-methyl-2-(methylamino)-3-phenylbutanamido)butanamido)hex-2-enamide;

ddd) (S,E)-N-(4-Aminobenzylsulfonyl)-2,5-dimethyl-4-((S)—N,3,3-trimethyl-2-((S)-3-methyl-2-(methylamino)-3-phenylbutanamido)butanamido)hex-2-enamide;

eee) (S,E)-N-(4-(Aminomethyl)phenylsulfonyl)-2,5-dimethyl-4-((S)—N,3,3-trimethyl-2-((S)-3-methyl-2-(methylamino)-3-phenylbutanamido)butanamido)hex-2-enamide;

fff) (S,E)-N-(Benzylsulfonyl)-4-((S)-2-((S)-3-(4-bromophenyl)-3-methyl-2-(methylamino)butanamido)-N,3,3-trimethylbutanamido)-2,5-dimethylhex-2-enamide;

ggg) (S,E)-4-((S)-2-((S)-3-(4'-Acetylbiphenyl-4-yl)-3-methyl-2-(methylamino)butanamido)-N,3,3-trimethylbutanamido)-N-(benzylsulfonyl)-2,5-dimethylhex-2-enamide;

hhh) (S,E)-N-(Benzylsulfonyl)-4-((S)-2-((S)-3-(4'-methoxybiphenyl-4-yl)-3-methyl-2-(methylamino)butanamido)-N,3,3-trimethylbutanamido)-2,5-dimethylhex-2-enamide;

iii) (S,E)-N-(Benzylsulfonyl)-4-((S)-2-((S)-3-(biphenyl-4-yl)-3-methyl-2-(methylamino)butanamido)-N,3,3-trimethylbutanamido)-2,5-dimethylhex-2-enamide;

jjj) (S,E)-N-(Benzylsulfonyl)-2,5-dimethyl-4-((S)—N,3,3-trimethyl-2-((S)-3-methyl-2-(methylamino)-3-(4-(4-methylstyryl)phenyl)butanamido)butanamido)hex-2-enamide;

kkk) (S,E)-N-(Benzylsulfonyl)-4-((S)-2-((S)-3-(4-methoxyphenyl)-3-methyl-2-(methylamino)butanamido)-N,3,3-trimethylbutanamido)-2,5-dimethylhex-2-enamide;

lll) (S,E)-N-(Benzylsulfonyl)-4-((S)-2-((R)-3-(3-methoxyphenyl)-3-methyl-2-(methylamino)butanamido)-N,3,3-trimethylbutanamido)-2,5-dimethylhex-2-enamide;

mmm) (S,E)-N-(Benzylsulfonyl)-4-((S)-2-((S)-3-(3-methoxyphenyl)-3-methyl-2-(methylamino)butanamido)-N,3,3-trimethylbutanamido)-2,5-dimethylhex-2-enamide;

nnn) (S,E)-N-(Benzylsulfonyl)-4-((S)-2-((S)-3-(4-(2-hydroxyethoxy)phenyl)-3-methyl-2-(methylamino)butanamido)-N,3,3-trimethylbutanamido)-2,5-dimethylhex-2-enamide;

ooo) S-2-(4-((S)-4-((S)-1-(((S,E)-2,5-Dimethyl-6-oxo-6-(benzylsulfonamido)hex-4-en-3-yl)(methyl)amino)-3,3-dimethyl-1-oxobutan-2-ylamino)-2-methyl-3-(methylamino)-4-oxobutan-2-yl)phenoxy)ethyl ethanethioate;

ppp) (S,E)-4-((S)-2-((S)-3-(4-(2-Aminoethoxy)phenyl)-3-methyl-2-(methylamino)butanamido)-N,3,3-trimethylbutanamido)-N-(benzylsulfonyl)-2,5-dimethylhex-2-enamide;

qqq) (S,E)-N-(2-Aminophenylsulfonyl)-2,5-dimethyl-4-((S)—N,3,3-trimethyl-2-((S)-3-methyl-2-(methylamino)-3-phenylbutanamido)butanamido)hex-2-enamide;

rrr) (S,E)-N-(Biphenyl-4-ylsulfonyl)-2,5-dimethyl-4-((S)—N,3,3-trimethyl-2-((S)-3-methyl-2-(methylamino)-3-phenylbutanamido)butanamido)hex-2-enamide;

sss) (S,E)-N-(4'-Aminobiphenyl-4-ylsulfonyl)-2,5-dimethyl-4-((S)—N,3,3-trimethyl-2-((S)-3-methyl-2-(methylamino)-3-phenylbutanamido)butanamido)hex-2-enamide;

ttt) (S,E)-N-(4-Fluorobenzylsulfonyl)-2,5-dimethyl-4-((S)—N,3,3-trimethyl-2-((S)-3-methyl-2-(methylamino)-3-phenylbutanamido)butanamido)hex-2-enamide;

uuu) (S,E)-2,5-Dimethyl-N-(3-(trifluoromethyl)benzylsulfonyl)-4-((S)—N,3,3-trimethyl-2-((S)-3-methyl-2-(methylamino)-3-phenylbutanamido)butanamido)hex-2-enamide;

vvv) (S,E)-2,5-Dimethyl-N-(3-(trifluoromethoxy)benzylsulfonyl)-4-((S)—N,3,3-trimethyl-2-((S)-3-methyl-2-(methylamino)-3-phenylbutanamido)butanamido)hex-2-enamide;

www) (S,E)-N-(3,4-Dichlorobenzylsulfonyl)-2,5-dimethyl-4-((S)—N,3,3-trimethyl-2-((S)-3-methyl-2-(methylamino)-3-phenylbutanamido)butanamido)hex-2-enamide;

xxx) (S,E)-N-(2-Cyanobenzylsulfonyl)-2,5-dimethyl-4-((S)—N,3,3-trimethyl-2-((S)-3-methyl-2-(methylamino)-3-phenylbutanamido)butanamido)hex-2-enamide;

yyy) (S,E)-N-(3-Chlorobenzylsulfonyl)-2,5-dimethyl-4-((S)—N,3,3-trimethyl-2-((S)-3-methyl-2-(methylamino)-3-phenylbutanamido)butanamido)hex-2-enamide;

zzz) (S,E)-N-(4-Amino-2-ethylphenylsulfonyl)-2,5-dimethyl-4-((S)—N,3,3-trimethyl-2-((S)-3-methyl-2-(methylamino)-3-phenylbutanamido)butanamido)hex-2-enamide;

aaaa) (S,E)-N-(4-Amino-3-(trifluoromethoxy)phenylsulfonyl)-2,5-dimethyl-4-((S)—N,3,3-trimethyl-2-((S)-3-methyl-2-(methylamino)-3-phenylbutanamido)butanamido)hex-2-enamide;

bbbb) (S,E)-N-(4-Amino-2,3-dimethylphenylsulfonyl)-2,5-dimethyl-4-((S)—N,3,3-trimethyl-2-((S)-3-methyl-2-(methylamino)-3-phenylbutanamido)butanamido)hex-2-enamide;

cccc) (S,E)-N-(4-Amino-5,6,7,8-tetrahydronaphthalen-1-ylsulfonyl)-2,5-dimethyl-4-((S)—N,3,3-trimethyl-2-((S)-3-methyl-2-(methylamino)-3-phenylbutanamido)butanamido)hex-2-enamide;

dddd) (S,E)-N-(4-Amino-3-methylphenylsulfonyl)-2,5-dimethyl-4-((S)—N,3,3-trimethyl-2-((S)-3-methyl-2-(methylamino)-3-phenylbutanamido)butanamido)hex-2-enamide;

eeee) (S,E)-N-(4-Amino-3-fluorophenylsulfonyl)-2,5-dimethyl-4-((S)—N,3,3-trimethyl-2-((S)-3-methyl-2-(methylamino)-3-phenylbutanamido)butanamido)hex-2-enamide;

ffff) (S,E)-N-(4-Amino-3-ethylphenylsulfonyl)-2,5-dimethyl-4-((S)—N,3,3-trimethyl-2-((S)-3-methyl-2-(methylamino)-3-phenylbutanamido)butanamido)hex-2-enamide;

gggg) (S,E)-N-(4-Amino-3-(trifluoromethyl)phenylsulfonyl)-2,5-dimethyl-4-((S)—N,3,3-trimethyl-2-((S)-3-methyl-2-(methylamino)-3-phenylbutanamido)butanamido)hex-2-enamide;

hhhh) (S)-1-Isopropyl-N—((S)-1-(((S,E)-6-(3-mercaptopropylsulfonamido)-2,5-dimethyl-6-oxohex-4-en-3-yl)(methyl)amino)-3,3-dimethyl-1-oxobutan-2-yl)piperidine-2-carboxamide;

iiii) (S)—N—((S)-1-((S)-2-((E)-3-(3-Mercaptopropylsulfonamido)-2-methyl-3-oxoprop-1-enyl)pyrrolidin-1-yl)-3,3-dimethyl-1-oxobutan-2-yl)-3-methyl-2-(methylamino)-3-phenylbutanamide;

jjjj) (S)—N—((S)-1-(2-(3-(3-Mercaptopropylsulfonamido)-2-methyl-3-oxoprop-1-enyl)piperidin-1-yl)-3,3-dimethyl-1-oxobutan-2-yl)-3-methyl-2-(methylamino)-3-phenylbutanamide;

kkkk) (S)—N—((S)-1-(2-(3-(4-(Mercaptomethyl)phenylsulfonamido)-2-methyl-3-oxoprop-1-enyl)piperidin-1-yl)-3,3-dimethyl-1-oxobutan-2-yl)-3-methyl-2-(methylamino)-3-phenylbutanamide;

llll) (R)—N-(Benzylsulfonyl)-2,5-dimethyl-4-((S)—N,3,3-trimethyl-2-((S)-3-methyl-2-(methylamino)-3-phenylbutanamido)butanamido)hexanamide; or mmmm) (S,E)-N-(Benzylsulfonyl)-4-((S)-2-((S)-3-cyclohexyl-3-methyl-2-(methylamino)butanamido)-N,3,3-trimethylbutanamido)-2, 5-dimethylhex-2-enamide.

39. The compound of claim 8, wherein $P^2$ is a monovalent radical of one of the following compounds:

a) (S,E)-N-(4-Aminophenylsulfonyl)-2,5-dimethyl-4-((S)—N,3,3-trimethyl-2-((S)-3-methyl-2-(methylamino)-3-phenylbutanamido)butanamido)hex-2-enamide (Compound 886);

b) (S,E)-N-(4-(1-Aminocyclopropyl)benzylsulfonyl)-2,5-dimethyl-4-((S)—N,3,3-trimethyl-2-((S)-3-methyl-2-(methylamino)-3-phenylbutanamido)butanamido)hex-2-enamide;

c) (S,E)-N-(4-(1-Aminocyclopropyl)phenylsulfonyl)-2,5-dimethyl-4-((S)—N,3,3-trimethyl-2-((S)-3-methyl-2-(methylamino)-3-phenylbutanamido)butanamido)hex-2-enamide;

d) (S,E)-N-(4-(Aminomethyl)benzylsulfonyl)-2,5-dimethyl-4-((S)—N,3,3-trimethyl-2-((S)-3-methyl-2-(methylamino)-3-phenylbutanamido)butanamido)hex-2-enamide;

e) (S,E)-N-(4-Aminobenzylsulfonyl)-2,5-dimethyl-4-((S)—N,3,3-trimethyl-2-((S)-3-methyl-2-(methylamino)-3-phenylbutanamido)butanamido)hex-2-enamide, or f) (S,E)-N-(4-(Aminomethyl)phenylsulfonyl)-2,5-dimethyl-4-((S)—N,3,3-trimethyl-2-((S)-3-methyl-2-(methylamino)-3-phenylbutanamido)butanamido)hex-2-enamide.

40. The compound of claim 39, wherein $L^2$ comprises Phe-Lys, Val-Lys, Ala-Lys, Val-Cit, Phe-Cit, Leu-Cit, Ile-Cit, Trp-Cit, Phe-Arg, (D)Phe-Phe-Lys or (D)Ala-Phe-Lys.

41. The compound of claim 8, wherein $L^2$-$P^2$ is a monovalent radical of one of the following compounds:

a) (S,E)-N-(4-((S)-2-((S)-2-(6-(2,5-Dioxo-2,5-dihydro-1H-pyrrol-1-yl)hexanamido)-3-methylbutanamido)-5-ureidopentanamido)phenylsulfonyl)-2,5-dimethyl-4-((S)—N,3,3-trimethyl-2-((S)-3-methyl-2-(methylamino)-3-phenylbutanamido)butanamido)hex-2-enamide (Compound N);

or b)

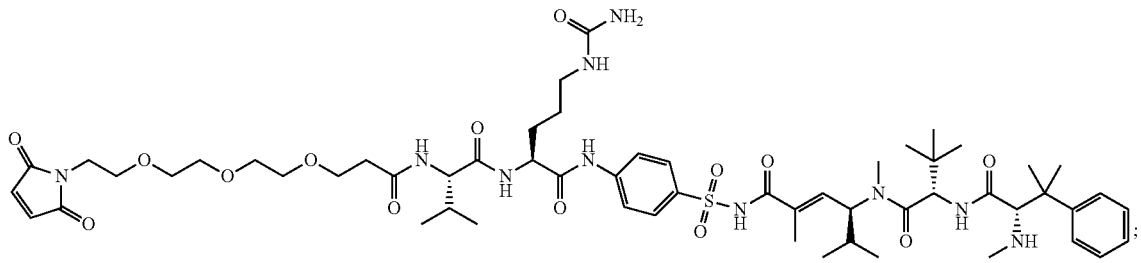

Compound O c)

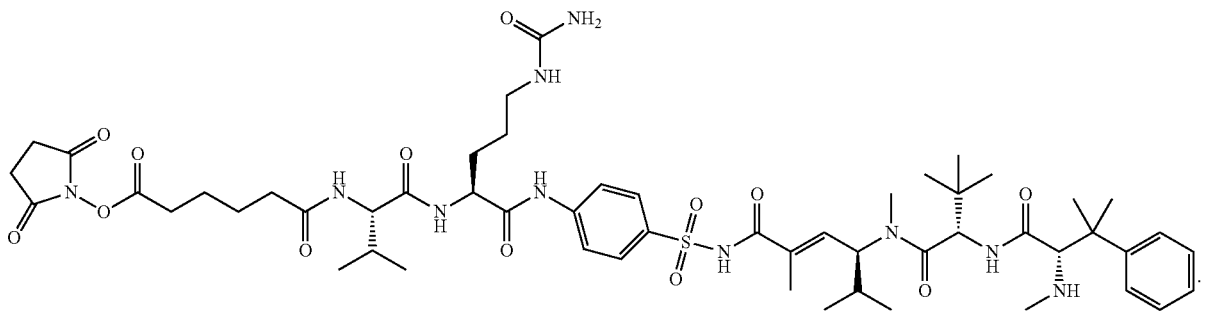

Compound KK

42. The compound of claim 13, wherein $P^1$ is a monovalent radical of one of the following compounds:
a) (S,E)-N-(3-Mercaptopropylsulfonyl)-2,5-dimethyl-4-((S)—N,3,3-trimethyl-2-((S)-3-methyl-2-(methylamino)-3-phenylbutanamido)butanamido)hex-2-enamide (Compound A);
b) (S,E)-N-(2-Mercaptoethylsulfonyl)-2,5-dimethyl-4-((S)—N,3,3-trimethyl-2-((S)-3-methyl-2-(methylamino)-3-phenylbutanamido)butanamido)hex-2-enamide (Compound B);
c) (S,E)-N-(4-(Mercaptomethyl)phenylsulfonyl)-2,5-dimethyl-4-((S)—N,3,3-trimethyl-2-((S)-3-methyl-2-(methylamino)-3-phenylbutanamido)butanamido)hex-2-enamide (Compound C);
d) (S,E)-2,5-Dimethyl-N-tosyl-4-((S)—N,3,3-trimethyl-2-((S)-3-methyl-2-(methylamino)-3-phenylbutanamido)butanamido)hex-2-enamide (Compound D);
e) (S,E)-2,5-dimethyl-N-(methylsulfonyl)-4-((S)—N,3,3-trimethyl-2-((S)-3-methyl-2-(methylamino)-3-phenylbutanamido)butanamido)hex-2-enamide (Compound E);
f) (S,E)-N-(Mesitylsulfonyl)-2,5-dimethyl-4-((S)—N,3,3-trimethyl-2-((S)-3-methyl-2-(methylamino)-3-phenylbutanamido)butanamido)hex-2-enamide;
g) (S,E)-2,5-Dimethyl-N-(4-(trifluoromethoxy)phenylsulfonyl)-4-((S)—N,3,3-trimethyl-2-((S)-3-methyl-2-(methylamino)-3-phenylbutanamido)butanamido)hex-2-enamide;
h) (S,E)-N-(Benzylsulfonyl)-2,5-dimethyl-4-((S)—N,3,3-trimethyl-2-((S)-3-methyl-2-(methylamino)-3-phenylbutanamido)butanamido)hex-2-enamide (Compound 14);
i) (S,E)-2,5-Dimethyl-N-(2,4,6-triisopropylphenylsulfonyl)-4-((S)—N,3,3-trimethyl-2-((S)-3-methyl-2-(methylamino)-3-phenylbutanamido)butanamido)hex-2-enamide;
j) (S,E)-N-(4-tert-Butylphenylsulfonyl)-2,5-dimethyl-4-((S)—N,3,3-trimethyl-2-((S)-3-methyl-2-(methylamino)-3-phenylbutanamido)butanamido)hex-2-enamide;
k) (S,E)-N-(4-Chlorophenylsulfonyl)-2,5-dimethyl-4-((S)—N,3,3-trimethyl-2-((S)-3-methyl-2-(methylamino)-3-phenylbutanamido)butanamido)hex-2-enamide;
l) (S,E)-N-(3-Cyanophenylsulfonyl)-2,5-dimethyl-4-((S)—N,3,3-trimethyl-2-((S)-3-methyl-2-(methylamino)-3-phenylbutanamido)butanamido)hex-2-enamide;
m) (S,E)-2,5-Dimethyl-N-(2-nitrophenylsulfonyl)-4-((S)—N,3,3-trimethyl-2-((S)-3-methyl-2-(methylamino)-3-phenylbutanamido)butanamido)hex-2-enamide;
n) (S,E)-N-(4-Methoxy-2-nitrophenylsulfonyl)-2,5-dimethyl-4-((S)—N,3,3-trimethyl-2-((S)-3-methyl-2-(methylamino)-3-phenylbutanamido)butanamido)hex-2-enamide;
o) 4-(N—((S,E)-2,5-Dimethyl-4-((S)—N,3,3-trimethyl-2-((S)-3-methyl-2-(methylamino)-3-phenylbutanamido)butanamido)hex-2-enoyl)sulfamoyl)-3-nitrobenzamide;
p) (S,E)-N-(4-Methoxyphenylsulfonyl)-2,5-dimethyl-4-((S)—N,3,3-trimethyl-2-((S)-3-methyl-2-(methylamino)-3-phenylbutanamido)butanamido)hex-2-enamide;
q) (S,E)-2,5-Dimethyl-N-(4-(2,2,2-trifluoroacetamido)phenylsulfonyl)-4-((S)—N,3,3-trimethyl-2-((S)-3-methyl-2-(methylamino)-3-phenylbutanamido)butanamido)hex-2-enamide (Compound 23);
r) (S,E)-N-(4-Aminophenylsulfonyl)-2,5-dimethyl-4-((S)—N,3,3-trimethyl-2-((S)-3-methyl-2-(methylamino)-3-phenylbutanamido)butanamido)hex-2-enamide (Compound 886);
s) (S,E)-2,5-Dimethyl-N-(phenylsulfonyl)-4-((S)—N,3,3-trimethyl-2-((S)-3-methyl-2-(methylamino)-3-phenylbutanamido)butanamido)hex-2-enamide;
t) (S,E)-N—(N-(2-Fluorobenzyl)sulfamoyl)-2,5-dimethyl-4-((S)—N,3,3-trimethyl-2-((S)-3-methyl-2-(methylamino)-3-phenylbutanamido)butanamido)hex-2-enamide;
u) (S,E)-2,5-Dimethyl-N-(piperidin-1-ylsulfonyl)-4-((S)—N,3,3-trimethyl-2-((S)-3-methyl-2-(methylamino)-3-phenylbutanamido)butanamido)hex-2-enamide;
v) (S,E)-2,5-Dimethyl-N-(o-tolylsulfonyl)-4-((S)—N,3,3-trimethyl-2-((S)-3-methyl-2-(methylamino)-3-phenylbutanamido)butanamido)hex-2-enamide;
w) (S,E)-N-(4-Bromophenylsulfonyl)-2,5-dimethyl-4-((S)—N,3,3-trimethyl-2-((S)-3-methyl-2-(methylamino)-3-phenylbutanamido)butanamido)hex-2-enamide;
x) (S,E)-2,5-Dimethyl-N-(naphthalen-2-ylsulfonyl)-4-((S)—N,3,3-trimethyl-2-((S)-3-methyl-2-(methylamino)-3-phenylbutanamido)butanamido)hex-2-enamide;
y) Methyl 4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)benzoate;
z) (S,E)-2,5-Dimethyl-N—(N-(2-(trifluoromethyl)benzyl)sulfamoyl)-4-((S)—N,3,3-trimethyl-2-((S)-3-methyl-2-(methylamino)-3-phenylbutanamido)butanamido)hex-2-enamide;
aa) (4S,E)-N-(Hexan-2-ylsulfonyl)-2,5-dimethyl-4-((S)—N,3,3-trimethyl-2-((S)-3-methyl-2-(methylamino)-3-phenylbutanamido)butanamido)hex-2-enamide;
bb) (S,E)-N-(2-Methoxyethylsulfonyl)-2,5-dimethyl-4-((S)—N,3,3-trimethyl-2-((S)-3-methyl-2-(methylamino)-3-phenylbutanamido)butanamido)hex-2-enamide;
cc) (S,E)-N-(Cyclopentylmethylsulfonyl)-2,5-dimethyl-4-((S)—N,3,3-trimethyl-2-((S)-3-methyl-2-(methylamino)-3-phenylbutanamido)butanamido)hex-2-enamide;
dd) (S,E)-N-(Benzylsulfonyl)-4-((S)-2-((S)-3-(4-cyanophenyl)-3-methyl-2-(methylamino)butanamido)-N,3,3-trimethylbutanamido)-2, 5-dimethylhex-2-enamide;
ee) (S,E)-4-((S)-2-((S)-3-(4-(Aminomethyl)phenyl)-3-methyl-2-(methylamino)butanamido)-N,3,3-trimethylbutanamido)-N-(benzylsulfonyl)-2, 5-dimethylhex-2-enamide;
ff) (S,E)-4-((S)-2-((S)-3-(4-Azidophenyl)-3-methyl-2-(methylamino)butanamido)-N,3,3-trimethylbutanamido)-N-(benzylsulfonyl)-2,5-dimethylhex-2-enamide;
gg) (S,E)-4-((S)-2-((S)-3-(4-Aminophenyl)-3-methyl-2-(methylamino)butanamido)-N,3,3-trimethylbutanamido)-N-(benzylsulfonyl)-2,5-dimethylhex-2-enamide;
hh) (S,E)-N-(Cyclohexylsulfonyl)-2,5-dimethyl-4-((S)—N,3,3-trimethyl-2-((S)-3-methyl-2-(methylamino)-3-phenylbutanamido)butanamido)hex-2-enamide;

ii) (S,E)-2,5-Dimethyl-N-(pyridin-3-ylmethylsulfonyl)-4-((S)—N,3,3-trimethyl-2-((S)-3-methyl-2-(methylamino)-3-phenylbutanamido)butanamido)hex-2-enamide;

jj) 4-(N—((S,E)-2,5-Dimethyl-4-((S)—N,3,3-trimethyl-2-((S)-3-methyl-2-(methylamino)-3-phenylbutanamido)butanamido)hex-2-enoyl)sulfamoyl)benzoic acid;

kk) (S,E)-2,5-Dimethyl-N-(3-(2,2,2-trifluoroacetamido)phenylsulfonyl)-4-((S)—N,3,3-trimethyl-2-((S)-3-methyl-2-(methylamino)-3-phenylbutanamido)butanamido)hex-2-enamide;

ll) (S,E)-N-(3-Aminophenylsulfonyl)-2,5-dimethyl-4-((S)—N,3,3-trimethyl-2-((S)-3-methyl-2-(methylamino)-3-phenylbutanamido)butanamido)hex-2-enamide;

mm) (S,E)-2,5-Dimethyl-N-(pyridin-3-ylsulfonyl)-4-((S)—N,3,3-trimethyl-2-((S)-3-methyl-2-(methylamino)-3-phenylbutanamido)butanamido)hex-2-enamide;

nn) (S,E)-2,5-Dimethyl-N-(thiophen-2-ylsulfonyl)-4-((S)—N,3,3-trimethyl-2-((S)-3-methyl-2-(methylamino)-3-phenylbutanamido)butanamido)hex-2-enamide;

oo) (S,E)-N-(4-Hydroxyphenylsulfonyl)-2, 5-dimethyl-4-((S)—N,3,3-trimethyl-2-((S)-3-methyl-2-(methylamino)-3-phenylbutanamido)butanamido)hex-2-enamide;

pp) (S,E)-2, 5-dimethyl-N-(4-(1-(2,2,2-trifluoroacetamido)cyclopropyl) phenylsulfonyl)-4-((S)—N,3,3-trimethyl-2-((S)-3-methyl-2-(methylamino)-3-phenylbutanamido)butanamido)hex-2-enamide;

qq) (S,E)-N-(4-(1-Aminocyclopropyl)phenylsulfonyl)-2, 5-dimethyl-4-((S)—N,3,3-trimethyl-2-((S)-3-methyl-2-(methylamino)-3-phenylbutanamido)butanamido) hex-2-enamide;

rr) (S,E)-2,5-Dimethyl-N-(2-methylbenzylsulfonyl)-4-((S)—N,3,3-trimethyl-2-((S)-3-methyl-2-(methylamino)-3-phenylbutanamido)butanamido)hex-2-enamide;

ss) (S,E)-2,5-Dimethyl-N-(4-nitrobenzylsulfonyl)-4-((S)—N,3,3-trimethyl-2-((S)-3-methyl-2-(methylamino)-3-phenylbutanamido)butanamido)hex-2-enamide;

tt) (S,E)-N-(4-Chlorobenzylsulfonyl)-2, 5-dimethyl-4-((S)—N,3,3-trimethyl-2-((S)-3-methyl-2-(methylamino)-3-phenylbutanamido)butanamido)hex-2-enamide;

uu) (S,E)-2,5-Dimethyl-N-(phenethylsulfonyl)-4-((S)—N,3,3-trimethyl-2-((S)-3-methyl-2-(methylamino)-3-phenylbutanamido)butanamido)hex-2-enamide;

vv) (S,E)-N-(4-Bromobenzylsulfonyl)-2, 5-dimethyl-4-((S)—N,3,3-trimethyl-2-((S)-3-methyl-2-(methylamino)-3-phenylbutanamido)butanamido)hex-2-enamide;

ww) (S,E)-N-(4-Cyanobenzylsulfonyl)-2, 5-dimethyl-4-((S)—N,3,3-trimethyl-2-((S)-3-methyl-2-(methylamino)-3-phenylbutanamido)butanamido)hex-2-enamide;

xx) (S,E)-2,5-Dimethyl-N-(3-nitrobenzylsulfonyl)-4-((S)—N,3,3-trimethyl-2-((S)-3-methyl-2-(methylamino)-3-phenylbutanamido)butanamido)hex-2-enamide;

yy) (S,E)-N-(4-tert-Butylbenzylsulfonyl)-2, 5-dimethyl-4-((S)—N,3,3-trimethyl-2-((S)-3-methyl-2-(methylamino)-3-phenylbutanamido)butanamido)hex-2-enamide;

zz) (S,E)-2,5-Dimethyl-N-(2-nitrobenzylsulfonyl)-4-((S)—N,3,3-trimethyl-2-((S)-3-methyl-2-(methylamino)-3-phenylbutanamido)butanamido)hex-2-enamide;

aaa) (S,E)-2,5-Dimethyl-N-(4-nitrophenethylsulfonyl)-4-((S)—N,3,3-trimethyl-2-((S)-3-methyl-2-(methylamino)-3-phenylbutanamido)butanamido)hex-2-enamide;

bbb) Methyl 4-Chloro-3-(N—((S,E)-2, 5-dimethyl-4-((S)—N,3,3-trimethyl-2-((S)-3-methyl-2-(methylamino)-3-phenylbutanamido)butanamido)hex-2-enoyl)sulfamoyl)benzoate;

ccc) (S,E)-N-(4-(Aminomethyl)benzylsulfonyl)-2, 5-dimethyl-4-((S)—N,3,3-trimethyl-2-((S)-3-methyl-2-(methylamino)-3-phenylbutanamido)butanamido)hex-2-enamide;

ddd) (S,E)-N-(4-Aminobenzylsulfonyl)-2, 5-dimethyl-4-((S)—N,3,3-trimethyl-2-((S)-3-methyl-2-(methylamino)-3-phenylbutanamido)butanamido)hex-2-enamide;

eee) (S,E)-N-(4-(Aminomethyl)phenylsulfonyl)-2, 5-dimethyl-4-((S)—N,3,3-trimethyl-2-((S)-3-methyl-2-(methylamino)-3-phenylbutanamido)butanamido)hex-2-enamide;

fff) (S,E)-N-(Benzylsulfonyl)-4-((S)-2-((S)-3-(4-bromophenyl)-3-methyl-2-(methylamino)butanamido)-N,3,3-trimethylbutanamido)-2, 5-dimethylhex-2-enamide;

ggg) (S,E)-4-((S)-2-((S)-3-(4'-Acetylbiphenyl-4-yl)-3-methyl-2-(methylamino)butanamido)-N,3,3-trimethylbutanamido)-N-(benzylsulfonyl)-2, 5-dimethylhex-2-enamide;

hhh) (S,E)-N-(Benzylsulfonyl)-4-((S)-2-((S)-3-(4'-methoxybiphenyl-4-yl)-3-methyl-2-(methylamino)butanamido)-N,3,3-trimethylbutanamido)-2, 5-dimethylhex-2-enamide;

iii) (S,E)-N-(Benzylsulfonyl)-4-((S)-2-((S)-3-(biphenyl-4-yl)-3-methyl-2-(methylamino)butanamido)-N,3,3-trimethylbutanamido)-2, 5-dimethylhex-2-enamide;

jjj) (S,E)-N-(Benzylsulfonyl)-2, 5-dimethyl-4-((S)—N,3,3-trimethyl-2-((S)-3-methyl-2-(methylamino)-3-(4-(4-methylstyryl)phenyl)butanamido)butanamido)hex-2-enamide;

kkk) (S,E)-N-(Benzylsulfonyl)-4-((S)-2-((S)-3-(4-methoxyphenyl)-3-methyl-2-(methylamino)butanamido)-N,3,3-trimethylbutanamido)-2, 5-dimethylhex-2-enamide;

lll) (S,E)-N-(Benzylsulfonyl)-4-((S)-2-((R)-3-(3-methoxyphenyl)-3-methyl-2-(methylamino)butanamido)-N,3,3-trimethylbutanamido)-2, 5-dimethylhex-2-enamide;

mmm) (S,E)-N-(Benzylsulfonyl)-4-((S)-2-((S)-3-(3-methoxyphenyl)-3-methyl-2-(methylamino)butanamido)-N,3,3-trimethylbutanamido)-2, 5-dimethylhex-2-enamide;

nnn) (S,E)-N-(Benzylsulfonyl)-4-((S)-2-((S)-3-(4-(2-hydroxyethoxy)phenyl)-3-methyl-2-(methylamino)butanamido)-N,3,3-trimethylbutanamido)-2, 5-dimethylhex-2-enamide;

ooo) S-2-(4-((S)-4-((S)-1-(((S,E)-2,5-Dimethyl-6-oxo-6-(benzylsulfonamido)hex-4-en-3-yl)(methyl)amino)-3, 3-dimethyl-1-oxobutan-2-ylamino)-2-methyl-3-(methylamino)-4-oxobutan-2-yl)phenoxy)ethyl ethanethioate;

ppp) (S,E)-4-((S)-2-((S)-3-(4-(2-Aminoethoxy)phenyl)-3-methyl-2-(methylamino)butanamido)-N,3,3-trimethylbutanamido)-N-(benzylsulfonyl)-2, 5-dimethylhex-2-enamide;

qqq) (S,E)-N-(2-Aminophenylsulfonyl)-2,5-dimethyl-4-((S)—N,3,3-trimethyl-2-((S)-3-methyl-2-(methylamino)-3-phenylbutanamido)butanamido)hex-2-enamide;

rrr) (S,E)-N-(Biphenyl-4-ylsulfonyl)-2,5-dimethyl-4-((S)—N,3,3-trimethyl-2-((S)-3-methyl-2-(methylamino)-3-phenylbutanamido)butanamido)hex-2-enamide;

sss) (S,E)-N-(4'-Aminobiphenyl-4-ylsulfonyl)-2,5-dimethyl-4-((S)—N,3,3-trimethyl-2-((S)-3-methyl-2-(methylamino)-3-phenylbutanamido)butanamido)hex-2-enamide;

ttt) (S,E)-N-(4-Fluorobenzylsulfonyl)-2,5-dimethyl-4-((S)—N,3,3-trimethyl-2-((S)-3-methyl-2-(methylamino)-3-phenylbutanamido)butanamido)hex-2-enamide;

uuu) (S,E)-2,5-Dimethyl-N-(3-(trifluoromethyl)benzylsulfonyl)-4-((S)—N,3,3-trimethyl-2-((S)-3-methyl-2-(methylamino)-3-phenylbutanamido)butanamido)hex-2-enamide;

vvv) (S,E)-2,5-Dimethyl-N-(3-(trifluoromethoxy)benzylsulfonyl)-4-((S)—N,3,3-trimethyl-2-((S)-3-methyl-2-(methylamino)-3-phenylbutanamido)butanamido)hex-2-enamide;

www) (S,E)-N-(3,4-Dichlorobenzylsulfonyl)-2, 5-dimethyl-4-((S)—N,3,3-trimethyl-2-((S)-3-methyl-2-(methylamino)-3-phenylbutanamido)butanamido)hex-2-enamide;

xxx) (S,E)-N-(2-Cyanobenzylsulfonyl)-2,5-dimethyl-4-((S)—N,3,3-trimethyl-2-((S)-3-methyl-2-(methylamino)-3-phenylbutanamido)butanamido)hex-2-enamide;

yyy) (S,E)-N-(3-Chlorobenzylsulfonyl)-2,5-dimethyl-4-((S)—N,3,3-trimethyl-2-((S)-3-methyl-2-(methylamino)-3-phenylbutanamido)butanamido)hex-2-enamide;

zzz) (S,E)-N-(4-Amino-2-ethylphenylsulfonyl)-2,5-dimethyl-4-((S)—N,3,3-trimethyl-2-((S)-3-methyl-2-(methylamino)-3-phenylbutanamido)butanamido)hex-2-enamide;

aaaa) (S,E)-N-(4-Amino-3-(trifluoromethoxy)phenylsulfonyl)-2,5-dimethyl-4-((S)—N,3,3-trimethyl-2-((S)-3-methyl-2-(methylamino)-3-phenylbutanamido)butanamido)hex-2-enamide;

bbbb) (S,E)-N-(4-Amino-2,3-dimethylphenylsulfonyl)-2,5-dimethyl-4-((S)—N,3,3-trimethyl-2-((S)-3-methyl-2-(methylamino)-3-phenylbutanamido)butanamido)hex-2-enamide;

cccc) (S,E)-N-(4-Amino-5,6,7,8-tetrahydronaphthalen-1-ylsulfonyl)-2,5-dimethyl-4-((S)—N,3,3-trimethyl-2-((S)-3-methyl-2-(methylamino)-3-phenylbutanamido)butanamido)hex-2-enamide;

dddd) (S,E)-N-(4-Amino-3-methylphenylsulfonyl)-2,5-dimethyl-4-((S)—N,3,3-trimethyl-2-((S)-3-methyl-2-(methylamino)-3-phenylbutanamido)butanamido)hex-2-enamide;

eeee) (S,E)-N-(4-Amino-3-fluorophenylsulfonyl)-2,5-dimethyl-4-((S)—N,3,3-trimethyl-2-((S)-3-methyl-2-(methylamino)-3-phenylbutanamido)butanamido)hex-2-enamide;

ffff) (S,E)-N-(4-Amino-3-ethylphenylsulfonyl)-2,5-dimethyl-4-((S)—N,3,3-trimethyl-2-((S)-3-methyl-2-(methylamino)-3-phenylbutanamido)butanamido)hex-2-enamide;

gggg) (S,E)-N-(4-Amino-3-(trifluoromethyl)phenylsulfonyl)-2,5-dimethyl-4-((S)—N,3,3-trimethyl-2-((S)-3-methyl-2-(methylamino)-3-phenylbutanamido)butanamido)hex-2-enamide;

hhhh) (R)—N-(Benzylsulfonyl)-2,5-dimethyl-4-((S)—N,3,3-trimethyl-2-((S)-3-methyl-2-(methylamino)-3-phenylbutanamido)butanamido)hexanamide; or iiii) (S,E)-N-(Benzylsulfonyl)-4-((S)-2-((S)-3-cyclohexyl-3-methyl-2-(methylamino)butanamido)-N,3,3-trimethylbutanamido)-2, 5-dimethylhex-2-enamide.

43. The compound of claim 13, wherein $P^1$ is a monovalent radical of one of the following compounds:

a) (S,E)-4-((S)-2-((S)-3-(4-(Aminomethyl)phenyl)-3-methyl-2-(methylamino)butanamido)-N,3,3-trimethylbutanamido)-N-(benzylsulfonyl)-2, 5-dimethylhex-2-enamide;

b) (S,E)-N-(4-(1-Aminocyclopropyl)benzylsulfonyl)-2,5-dimethyl-4-((S)—N,3,3-trimethyl-2-((S)-3-methyl-2-(methylamino)-3-phenylbutanamido)butanamido)hex-2-enamide;

c) (S,E)-N-(4-(1-Aminocyclopropyl)phenylsulfonyl)-2,5-dimethyl-4-((S)—N,3,3-trimethyl-2-((S)-3-methyl-2-(methylamino)-3-phenylbutanamido)butanamido)hex-2-enamide;

d) (S,E)-N-(4-(Aminomethyl)benzylsulfonyl)-2,5-dimethyl-4-((S)—N,3,3-trimethyl-2-((S)-3-methyl-2-(methylamino)-3-phenylbutanamido)butanamido)hex-2-enamide, or e) (S,E)-N-(4-Aminobenzylsulfonyl)-2,5-dimethyl-4-((S)—N,3,3-trimethyl-2-((S)-3-methyl-2-(methylamino)-3-phenylbutanamido)butanamido)hex-2-enamide.

\* \* \* \* \*